US005942662A

United States Patent [19]
Ryals et al.

[11] Patent Number: 5,942,662
[45] Date of Patent: *Aug. 24, 1999

[54] INDUCIBLE HERBICIDE RESISTANCE

[75] Inventors: John A. Ryals, Cary, N.C.; Christian T. Harms, Bad Krozingen, Germany; Leslie B. Friedrich, Apex, N.C.; James J. Beck, Cary, N.C.; Scott J. Uknes, Apex, N.C.; Eric R. Ward, Durham, N.C.

[73] Assignee: Novartis Finance Corporation, New York, N.Y.

[*] Notice: This patent is subject to a terminal disclaimer.

[21] Appl. No.: 08/971,217

[22] Filed: Nov. 14, 1997

Related U.S. Application Data

[60] Continuation of application No. 08/457,364, May 31, 1995, Pat. No. 5,847,258, which is a division of application No. 08/181,271, Jan. 13, 1994, Pat. No. 5,614,395, which is a continuation-in-part of application No. 08/093,301, Jul. 16, 1993, abandoned, which is a continuation of application No. 07/973,197, Nov. 6, 1992, abandoned, which is a continuation of application No. 07/678,378, Apr. 1, 1991, abandoned, which is a continuation of application No. 07/305,566, Feb. 6, 1989, abandoned, which is a continuation-in-part of application No. 07/165,667, Mar. 8, 1988, abandoned, application No. 08/181,271, Jan. 13, 1994, Pat. No. 5,614,395, which is a continuation-in-part of application No. 08/042,847, Apr. 6, 1993, abandoned, which is a continuation of application No. 07/632,441, Dec. 21, 1990, abandoned, which is a continuation of application No. 07/425,504, Oct. 20, 1989, abandoned, and a continuation-in-part of application No. 07/165,667, Mar. 8, 1988, abandoned, application No. 08/181,271, Jan. 13, 1994, Pat. No. 5,614,395, which is a continuation-in-part of application No. 07/848,506, Mar. 6, 1992, abandoned, which is a continuation-in-part of application No. 07/768,122, Sep. 27, 1991, abandoned, which is a continuation-in-part of application No. 07/580,431, Sep. 7, 1990, abandoned, which is a continuation-in-part of application No. 07/425,504, Oct. 20, 1989, abandoned, which is a continuation-in-part of application No. 07/368,672, Jun. 20, 1989, abandoned, which is a continuation-in-part of application No. 07/329,018, Mar. 24, 1989, abandoned, application No. 08/181,271, Jan. 13, 1994, Pat. No. 5,614,395, which is a continuation-in-part of application No. 08/045,957, Apr. 12, 1993, abandoned.

[51] Int. Cl.$^6$ .......................... C12N 15/29; C12N 15/56; C12N 15/82; A01H 5/00

[52] U.S. Cl. .......................... 800/300; 800/278; 800/298; 435/6; 435/69.1; 435/70.1; 435/200; 435/206; 435/209; 435/320.1; 435/418; 435/419; 435/468; 536/23.6; 536/24.1

[58] Field of Search ................................ 536/23.6, 24.1; 435/69.1, 6, 70.1, 172.3, 320.1, 418, 419, 200, 206, 209, 468; 800/205, 250, 278, 298, 300; 47/58

[56] References Cited

U.S. PATENT DOCUMENTS

| | | | |
|---|---|---|---|
| 4,394,443 | 7/1983 | Weissman et al. | 435/6 |
| 4,399,216 | 8/1983 | Axel et al. | 438/68 |
| 4,634,665 | 1/1987 | Axel et al. | 435/6 |
| 4,810,648 | 3/1989 | Stalker | 435/191 |
| 4,886,753 | 12/1989 | Marcker et al. | 435/172.3 |
| 4,940,840 | 7/1990 | Suslow et al. | 800/205 |
| 5,654,414 | 8/1997 | Ryals et al. | 536/24.1 |
| 5,689,044 | 11/1997 | Ryals et al. | 800/205 |
| 5,789,214 | 8/1998 | Ryals et al. | 435/172.3 |

FOREIGN PATENT DOCUMENTS

| | | |
|---|---|---|
| 232845 | 6/1987 | European Pat. Off. . |
| 244598 | 11/1987 | European Pat. Off. . |
| 249676 | 12/1987 | European Pat. Off. . |
| 292435 | 11/1988 | European Pat. Off. . |
| 0307841 | 3/1989 | European Pat. Off. . |
| 0332104A3 | 3/1989 | European Pat. Off. . |
| 332104 | 9/1989 | European Pat. Off. . |
| 0353191 | 1/1990 | European Pat. Off. . |
| 0360750 | 3/1990 | European Pat. Off. . |
| 0392225A3 | 3/1990 | European Pat. Off. . |
| 388186 | 9/1990 | European Pat. Off. . |
| 418695 | 3/1991 | European Pat. Off. . |
| 1176799 | 1/1970 | United Kingdom . |
| 21976535 | 5/1988 | United Kingdom . |
| US83/01240 | 3/1984 | WIPO . |
| WO8800976 | 2/1988 | WIPO . |
| WO8807585 | 10/1988 | WIPO . |
| WO90/07001 | 6/1990 | WIPO . |
| WO97/06269 | 2/1997 | WIPO . |

OTHER PUBLICATIONS

Kaulen et al. EMBO J 5(1):1–8, Jan. 1986.

Abel et al., "Delay of Disease Development in Transgenic Plants that Express the Tobacco Mosaic Virus Coat Protein Gene", *Science*, 232:738–743 (1986).

(List continued on next page.)

*Primary Examiner*—David T. Fox
*Attorney, Agent, or Firm*—J. Timothy Meigs; Larry W. Stults

[57] ABSTRACT

The present invention provides chemically regulatable DNA sequences capable of regulating transcription of an associated DNA sequence in plants or plant tissues, chimeric constructions containing such sequences, vectors containing such sequences and chimeric constructions, and transgenic plants and plant tissues containing these chimeric constructions. In one aspect, the chemically regulatable DNA sequences of the invention are derived from the 5' region of genes encoding pathogenisis-related (PR) proteins. The present invention also provides anti-pathogenic sequences derived from novel cDNAs coding for PR proteins which can be genetically engineered and transformed into plants to confer enhanced resistance to disease. Also provided is a method for the exogenous regulation of gene expression in plants, which comprises obtaining a plant incapable of regulating at least one gene or gene family, or at least one heterologous gene, due to the deactivation of at least one endogenous signal transduction cascade which regulates the gene in the plant, and applying a chemical regulator to the plant at a time when expression of the gene is desired A novel signal peptide sequence and corresponding DNA coding sequence is also provided. Further provided are assays for the identification and isolation of additional chemically regulatable DNA sequences and cDNAs encoding PR proteins and assays for identifying chemicals capable of exogenously regulating the chemically regulatable DNA sequences of the invention.

46 Claims, 40 Drawing Sheets

OTHER PUBLICATIONS

Alexander et al., "Increased tolerance to two comycete pathogens in transgenic tobacco expressing pathogenesis–related protein 1a", *Proc. Natl. Acad. Sci., USA*, 90:7327–7331 (1993).

Antoniw et al., "The role of pathogenesis–related proteins", *Plant Resistance to Viruses*, 57–91 Ciba Foundation Symposium 133, Wiley and Sons (1987).

Asselin et al., "Light–influenced extracellular accumulation of b (pathogenesis–related) proteins in Nicotiana green tissue induced by various chemicals or prolonged floating on water" *Can. J. Bot.*, 63:1276–1283 (1985).

Beilmann et al., "Functional analysis of the PR–1a promoter by transient and by stable transfections", Abstract *International Meeting on Biology*, Valencia, Spain, Oct. 11–26, 1989.

Bell et al., "Differential Accumulation of Plant Defence Gene." *Mol. Cell. Biol.*, 6:1615–1623 (1986).

Bol et al., "The synthesis and possible functions of virus–induced proteins in plants", *Microbiol. Sci.*, 5:47–52 (1988).

Bol et al., "Characterization of pathogenesis–related proteins and genes", *CIBA Symp.*, 133:72–91 (1987).

Bol et al., "Plant defense genes induced by virus infection", *J. Cell. Biochem.*, 12C:244 (1988).

Broglie et al., "Ethylene–regulated gene expression: Molecular cloning of the genes encoding an endochitinase from *Phaseolus vulgaris*", *Proc. Natl. Acad. Sci. USA*, 83:6820–6824 (1986).

Carr et al., "Synthesis of pathogenesis–related proteins in tobacco is regulated at the level of mRNA accumulation and occurs on membrane–bound polysomes", *Proc. Natl. Acad. Sci., USA* 82:7999–8003 (1985).

Comai et al., "Novel and useful properties of a chimeric plant promoter combining CaMV 35S and MAS elements", *Pl Molec Biol 15*: 373–381 (1990).

Cornelissen et al., "Molecular characterization of messenger RNAs for 'pathogenesis–related' proteins 1a, 1b and 1c, induced by TMV infection of tobacco", *The EMBO Journal*, 5:37–40 (1986).

Cornelissen et al., "A tobacco mosaic virus–induced tobacco protein is homologous to the sweet–tasting protein thaumatin", *Nature*, 321:531–532 (1986).

Cornelissen et al., "Structure of tobacco genes encoding pathogenesis–related proteins from the PR–1 group", *Nucleic Acids Research*, 15:6799–6811 (1987).

Cutt et al., "Pathogenesis–Related Proteins of *Nicotiana tabacum*" *J. Cell. Biochem.* Suppl. 12C, Y210 (1988).

Duguid et al., "Isolation of cDNAs of scrapie–modulated RNAs by subtractive hybridization of a cDNA library", *Proc. Natl. Acad. Sci. USA*, 85:5738–5742 (1988).

Ellis et al., "Maize Adh–1 promoter sequences control anaerobic regulation: addition of upstream promoter elements from constitutive genes is necessary for expression in tobacco", *EMBO J.*, 6:11–16 (1987).

Fraser, "Are 'Pathogenesis–related' Proteins Involved in Acquired Systemic Resistance of Tobacco Plants to Tobacco Mosaic Virus?", *Virol.*, 58:305–313 (1982).

Gelvin et al., "Use of a $T_R$ T–DNA promoter to express genes in plants and bacteria", *Mol. Gen Genet*, 199:240–248 (1985).

Gianinazzi, "Genetic and Molecular Aspects of Resistance Induced by Infections or Chemicals", *Plant Response to the Environment* 321–342 (MacMillan Publishing Company, London, 1984).

Gianinazzi et al., "The genetic and molecular basis of b–proteins in the genus Nicotiana", *Neth. J. Pl. Path.*, 89: 275–281 (1983).

Hamilton et al., "The complete nucleotide sequence of tobacco rattle virus RNA–1", *J. Gen. Virol.*, 68(10): 2563–75 (1987) Chemical Abstract, vol. 108 (9), Abstract No. 69776y.

Hedrick et al., "Chitinase cDNA Cloning and mRNA Induction" *Plant Physiol.*, 86:182–186 (1988).

Høj et al., "Purification of (1→3)–β–glucan endohydrolase isoenzyme II from germinated barley and determination of its primary structure from a cDNA clone", *Plant Molecular Biology*, 13:31–42 (1989).

Hooft van Huijsduijnen et al, "Virus–induced synthesis of messenger RNAs for precursors of pathogenesis–related proteins in tobacco", *The EMBO Journal* 4:2167–2171 (1985).

Hooft van Huijsduijnen et al., "cDNA cloning of six mRNAs induced by TMV infection of tobacco and a characterization of their translation products", *EMBO J.*, 5:2057–2061 (1986).

Hooft van Huijsduijnen et al., "Homology between chitinases that are induced by TMV infection of tobacco", *Plant Molecular Biology*, 9:411–420 (1987).

Horowitz et al., "TMV induced gene expression in tobacco", *Journal of Cellular Biochemistry*, 11B:37 Abstract F320, UCLA Symposia on Molecular & Cellular Biology, (Feb. 2–27, 1987).

Jackson et al., "Construction of a yeast vector directing the synthesis and release of barley (1→3), 1→4)–β–glucanase.", *Biochem. Genetics*, 107:187 Abstract 107:18833M (1987).

Jamet et al., "Purification and characterization of 8 of the pathogenesis–related proteins in tobacco leaves reacting hypersensitively to tobacco mosaic virus", *Plant Molecular Biology* 6:69–80 (1986).

Jefferson et al., "Beta–glucuronidase (GUS) as a sensitive and versatile gene fusion marker in plants", *J. Cell. Biol.*,, 11B:57 (1987).

Jefferson et al., "GUS fusions: β–glucuronidase as a sensitive and versatile gene fusion marker in higher plants", *The EMBO Journal*, 6:3901–3907 (1987).

Kauffmann et al., "Biological function of 'pathogenesis–related' proteins: four PR proteins of tobacco have 1,3–β–glucanase activity", *The EMBO Journal 6*: 3209–3212 (1987).

Kay, et al., "Duplication of CaMV 35S Promoter Sequences Creates a Strong Enhancer for Plant Genes", *Science*, 236:1299–1302 (1987).

Koncz et al., "The promoter of $T_L$–DNA gene 5 controls the tissue–specific expression of chimaeric genes carried by a novel type of Agrobacterium binary vector", *Mol Gen Genet 104*: 383–396 (1986).

Kowalski et al., "Vectors for the direct selection of cDNA clones corresponding to mammalian cell mRNA of low abundance", *Gene*, 35:45–54 (1985).

Lamb et al., "Signals and Transduction Mechanisms for Activation of Plant Defenses against Microbial Attack", *Cell*, 56:215–224 (1989).

Lawton et al., "The Molecular Biology of Systemic Acquired Resistance", *Development in Plant Pathology*, 2: 422–432 (1993).

Legrand et al., "Biological function of pathogenesis–related proteins: Four tobacco pathogenesis–related proteins are chitinases", *Proc. Natl. Acad. Sci. USA* 84: 6750–6754 (1987).

Linthorst et al., "Constitutive Expression of Pathogenesis–Related Proteins PR–1, GRP, and PR–S in Tobacco Has No Effect on Virus Infection", *The Plant Cell*, 1:285–291 (1989).

Lucas et al., "Amino acid sequence of the 'pathogenesis–related' leaf protein p14 from viroid–infected tomato reveals a new type of structurally unfamiliar proteins", *The EMBO Journal* 4:2745–2749 (1985).

McGeoch et al., "The complete DNA sequence of the long unique region in the genome of herpes simplex virus type 1", *J. Gen. Virol.* 69(7):1531–74 (1988) Chemical Abstracts, vol. 110 (5), Abstract No. 34475p.

McKnight et al., "Transcriptional Control Signals of a Eukaryotic Protein–Coding Gene", *Science*, 217:316–324 (1982).

Matsuoka et al., "Classification and Structural Comparison of Full–Length cDNAs for Pathogenesis–Related Proteins", *Plant Physiol.*, 85:942–946 (1987).

Memelink et al., "Cytokinin stress changes the developmental regulation of several defence–related genes in tobacco", *The EMBO Journal*, 6:3579–3583 (1987).

Metraux et al., "Isolation of a complementary DNA encoding a chitinase with structural homology to a bifunctional lysozyme/chitinase", *Proc. Natl. Acad. Sci.*, 86:896–900 (1989).

Metzler et al., "Isolation and Characterization of a Gene Encoding a PR–1–Like Protein from *Arabidopsis thaliana*", *Plant Physiol.*, 96:346–348 (1991).

Mohnen et al., "Hormonal regulation of β1,3–glucanase messenger RNA levels in cultured tobacco tissues", *EMBO J.*, 4:1631–1635 (1985).

Mohnen et al., "Hormonal regulation of of β1,3–glucanase messenger RNA levels in cultured tobacco tissues", *Plant Biochem.*, 103:453, Abstract 138890s (1985).

Morelli et al., "A short conserved sequence is involved in the light–inducibility of a gene encoding ribulose 1,5–bisphosphate carboxylase small subunit of pea", *Nature*, 315:200–204 (1985).

Morgens et al., "Cloning and Sequencing of a cDNA Clone Encoding an Ethylene–Induced Peroxidase from Cucumber Cotyledons", *J. Cell. Biochem*, 13D:283, M232 (1989).

O'Neal et al. "Isolation of tobacco SSU genes: characterization of a transcriptionally active pseudogene" *Nucl. Acids Res.*, 15(21):8661–8677 (1987).

Ohsako et al., "Arylamine N–acetyltransferase from chicken liver. II. Cloning of cDNA and expression in Chinese hamster ovary cells", *J. Biol. Chem.* 263(16): 7534–8 (1988) Chemical Abstracts, vol. 109(13), Abstract No. 105831u.

Oshima et al., "Nucleotide sequence of the PR–1 gene of *Nicotiana tabacum*", *FEBS Lett.*, 225:243–246 (1987).

Payne et al., "Isolation of the genomic clone for pathogenesis–related protein 1a from *Nicotiana tabacum* cv. Xanthi–nc" *Plant Molecular Biology*, 11:89–94 (1988).

Payne et al., "Isolation and nucleotide sequence of a novel cDNA clone encoding the major form of pathogenesis–related protein R", *Plant Molecular Biology* 11: 223–224 (1988).

Perry et al., "The DNA sequences of the long repeat region and adjoining parts of the long unique region in the genome of herpes simplex virus type 1", *J. Gen. Virol.* 69(11) 1831–46 (1988) Chemical Abstracts, vol. 111 (7), Abstract No. 51292 q.

Pfitzner et al., "DNA sequence analysis of a PR–1a gene from tobacco: Molecular relationship of heat shock and pathogen responses in plants", *Mol. Gen. Genet.*, 211:290–295 (1988).

Pfitzner et al., "Structure and promoter analysis of PR–1 genes from tobacco", *J. Cell Biochem.*, 12C:271 (1988).

Pfitzner et al., *UCLA Symposia on Molecular & Cellular Biology*, abstract Y233, p. 291 (Feb. 28–Apr. 10, 1988).

Pfitzner et al. "Isolation and characterization of cDNA clones encoding pathogenesis–related proteins from tobacco mosaic virus infected tobacco plants", *Nucleic Acids Research*, 15:4449–4465 (1987).

Pfitzner et al., *Workshop on Pathogenesis–Related Proteins in Plants*, Abstract (Oct. 22–26, 1989).

Pierpoint, "The Pathogenesis–Related Proteins of Tobacco Leaves", *Phytochemistry*, 25:1595–1601 (1986).

Pierpoint et al., "Identification of the virus–induced protein of tobacco leaves that resembles the sweet–protein thaumatin", *Physiological and Molecular Plant Physiology*, 31:291–298 (1987).

Pruitt, "Expression vectors permitting cDNA cloning and enrichment for specific seqences by hybridization/selection", *Gene*, 66:121–134 (1988).

Rothstein, et al., "Studies of Antisense Inhibition of Gene Expression in Tobacco: Nopaline Synthase and Peroxidase", *J. Cell. Biochem.*, Suppl. 13D #M014 (1989).

Sanchez et al., Wound–induced expression of potato proteinase inhibitor II gene in Transgenic tobacco plants:, *EMBO Journal*, 6:303–306 (1987).

Shinshi et al., "Regulation of a plant pathogenesis–related enzyme: Inhibition of chitinase and chitinase mRNA accumulation in cultured tobacco tissues by auxin and cytokinin", *Proc. Natl. Acad. Sci, USA 84*: 89–93 (1987).

Shinshi et al., "Evidence for N–and C–terminal processing of a plant defense–related enzyme: Primary structure of tobacco prepro–⊕–1,3–glucanase", *Proc. Natl. Acad. Sci, USA 85*: 5541–5545 (1988).

Twell et al., *Pl Molec Biol 9*: 345–375 (1987).

Uknes et al., "Acquired Resistance in Arabidopsis", *The Plant Cell*, 4:645–656 (1992).

Uknes et al., "Regulation of Pathogenesis–Related Protein–1a Gene Expression in Tobacco", *The Plant Cell*, 5: 159–169 (1993).

Van de Rhee et al., "Analysis of Regulatory Elements Involved in the Induction of Two Tobacco Genes by Salicylate Treatment and Virus Infection", *The Plant Cell*, 2:357–366 (1990).

van Kan et al, "A Virus–Inducible Tobacco Gene Encoding a Glycine–Rich Protein Shares Putative Regulatory Elements with the Ribulose Bisphosphate Carboxylase Small Subunit Gene", *Molecular Plant–Microbe Interactions 1*: 107–112 (1988).

van Loon, "Pathogenesis–related proteins", *Plant Molecular Biology*, 4:111–116 (1985).

van Loon et al., "Identification, purification, and characterization of pathogenesis–related proteins from virus–infected Samsun NN tobacco leaves", *Plant Molecular Biology*, 9:593–609 (1987).

Vera et al., "Pathogenesis–Related Proteins of Tomato", *Plant Physiol.*, 87:58–63 (1988).

Ward et al., "Coordinate Gene Activity in Response to Agents That Induce Systemic Acquired Resistance", *The Plant Cell*, 3: 1085–1094 (1991).

Wenzler et al., *Pl Molec Biol 12*: 347–354 (1989).

Collinge et al., *Plant Mol. Biol.*, 9:389–410 (1987).

Bjourson et al., *Applied Environ. Microbiol.*, 54:2852–2855 (1988).
Jefferson et al., *J. Cell. Biol.*, 11B:57 (Abstract F434) (1987).
Stintzi et al., *Biochimie*, 75:687–706 (1993).
Walden et al., *Eur. J. Biochem.*, 192:543–576 (1990).
Walter et al., *Mol. Gen. Genet.*, 222:353–360 (1990).
Willmitzer, *Trends in Genetics*, 4(1):13–18 (Jan. 1988).

5' deletion of PR-1A promoter sequence (AluI-NcoI) in front of the Gus gene in pCIB200.

5' deletion of PR-1A promoter sequence (HaeIII-NcoI) in front of the Gus gene in pCIB200.

PR-1A Promoter in front of truncated Bacillus thuringensis endotoxin gene cloned into SalI/BamHI digested pCI Promoter sequence from PR-1A gene in front of a truncated Bacillus thuringensis endotoxin gene PR-1A promoter in front of a wild type Arabidopsis AHAS gene cloned into Bluescript Promoter sequence from PR-1A gene in front of a wild type Arabidopsis AHAS gene cloned into pCIB200

Promoter sequence from b-1,3 Glucuronidase clone pBSGluc39.1 in front of the GUS gene from pBSGUS1.2

Promoter sequence from b-1,3 Glucuronidase clone pBSGluc39.1 in front of a truncated Bacillus thuringens Glucanase 39.1 promoter in front of a wild type Arabidopsis AHAS gene cloned into Bluescript Promoter sequence from b-1,3 Glucuronidase clone pBSGluc39.1 in front of a wild type Arabidopsis AHAS gene Promoter sequence from b-1,3 Glucuronidase clone pBSGluc39.3 in front of the GUS gene from pBSGUS1.2

Promoter sequence from b-1,3 Glucuronidase clone pBSGluc39.3 in front of a truncated Bacillus th Glucanase 39.3 promoter in front of a wild type Arabidopsis AHAS gene cloned into Bluescript Promoter sequence from b-1,3 Glucuronidase clone pBSGluc39.3 in front of a wild type Arabidopsis AHAS gene Herbicide resistant Arabidopsis AHAS gene in Bluescript PR-1A promoter in front of a herbicide resistant Arabidopsis AHAS gene cloned into Bluescript Promoter sequence from PR-1A gene in front of the herbicide resistant Arabidopsis AHAS gene cloned into pCIB200

Promoter sequence from b-1,3 Glucuronidase clone pBSGluc39.1 in front of the herbicide resistant Arabidopsis AHAS gene Glucanase 39.3 promoter in front of herbicide resistant Arabidopsis AHAS gene cloned into Bluescript Promoter sequence from b-1,3 Glucuronidase clone pBSGluc39.3 in front of the herbicide resistant Arabidopsis AHAS gene

Figure 39

```
     10        20        30        40        50        60        70        80        90
MFSKTNLFLCLSLAILVIVISSQVDAREMSKAPASITQAMNSNIITDQKMGAGITRKIPGWIRKGAKPGGKIIGKACKICSCKYQICSKCPKCHD*
8.2a
8.2b ...I...F...........M............A....QI....A.P....H....N..N..T..I......................N..VA......................*
8.2c ...............L............A.......A.P....H....N..N..T..I.........................VA...................*
8.2d ...............L............A......AVP.........N..N..T..I......------KR-P.........N.F...........P.......D.>
8.2e ...............L............A......T.P....E......NT....T.......QN.A..F............T.........NQN*
```

Figure 40

SEQUENCE LISTING (1) GENERAL INFORMATION:

(iii) NUMBER OF SEQUENCES: 111

(2) INFORMATION FOR SEQ ID NO:1:

(i) SEQUENCE CHARACTERISTICS:
      (A) LENGTH: 2038 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 932..1435

(xi) SEQUENCE DESCRIPTION: SEQ ID NO:1:

```
CTCGAGGATT TCAAACTCTA GCTTCACTAA AACTTGAGCT TTCTTTTCCA CTAATGTCGA     60

AAAACGAAAT AAACATAAGC TATTTACAAA AAATAAAAAA ATACTCCATT TGAATCTAAA    120

GTCAAGTCGT GATTGGGATA AGAAAATAGA AATTTATTTA TACTCCAGAT CAAGCCGTGA    180

TTGGAATGAG ATAATAGAAA AGTATGATAG TACATGAGTA ACATCAAGTT GGAAATTAAG    240

GGAAGGAAAT TAGAGAAAGA ACTGAAGAAT ATCCAAATAT TCTTTACGTC CAAATTTGAT    300

AGTTATTTAA CGTCATCGAG ATGACGGCCA TGTTCAAGTT TTCCACAAAT ATTGAGAAAA    360

GAAAGAAGAA GACACAAACT GTGTTTGGTA TTATTATAGT TTTTTCTTTT AGAGAATTGA    420

TTGTACATAT AAGAAATATA ATATAAGATT TAGAAATAAG ATTATTAGAA AAATCAAACA    480

TCAAAGTATT TATTTTAAAT TCTTTTTCCA ATGGACATTC CCATTCTGAA AAAAAAGAGA    540

TATAAATATG GAAGTAAAAA TTAATCAGAT CGTTAAATGT AGAAAATATT AATTAACACA    600

TTAACCATAA CCAGTCTACT TTATTTAACA AAAAGCACAT CTGATAGATC AAAAAAGTGT    660

TTAACTTCAT GCATTGACAA TTTAAAATTA TTTTGCAACA TCGGGTAAAA CTATTTTACA    720

ACAATTGGTA ACTGCATATA TAAGTTTAAT ATGGTAACCT AGAAAATAGG ATAAATTATC    780

TATAACAGGA TATATTACAT TGATATTACC ATGTCAAAAA ATTTAGTAAG TACATGAATA    840

ATCACCGTGA AATCTTCAAG ATTTCTCCTA TAAATACCCT TGGTAGTAAA TCTAGTTTTT    900

CCATTCAAGA TACAACATTT CTCCTATAGT C ATG GGA TTT GTT CTC TTT TCA     952
                                    Met Gly Phe Val Leu Phe Ser
                                      1               5

CAA TTG CCT TCA TTT CTT CTT GTC TCT ACA CTT CTC TTA TTC CTA GTA    1000
Gln Leu Pro Ser Phe Leu Leu Val Ser Thr Leu Leu Leu Phe Leu Val
        10                  15                  20

ATA TCC CAC TCT TGC CGT GCC CAA AAT TCT CAA CAA GAC TAT TTG GAT    1048
Ile Ser His Ser Cys Arg Ala Gln Asn Ser Gln Gln Asp Tyr Leu Asp
 25                  30                  35

GCC CAT AAC ACA GCT CGT GCA GAT GTA GGT GTA GAA CCT TTG ACC TGG    1096
Ala His Asn Thr Ala Arg Ala Asp Val Gly Val Glu Pro Leu Thr Trp
 40                  45                  50                  55

GAC GAC CAG GTA GCA GCC TAT GCG CAA AAT TAT GCT TCC CAA TTG GCT    1144
Asp Asp Gln Val Ala Ala Tyr Ala Gln Asn Tyr Ala Ser Gln Leu Ala
             60                  65                  70

GCA GAT TGT AAC CTC GTA CAT TCT CAT GGT CAA TAC GGC GAA AAC CTA    1192
Ala Asp Cys Asn Leu Val His Ser His Gly Gln Tyr Gly Glu Asn Leu
         75                  80                  85

GCT GAG GGA AGT GGC GAT TTC ATG ACG GCT GCT AAG GCT GTT GAG ATG    1240
Ala Glu Gly Ser Gly Asp Phe Met Thr Ala Ala Lys Ala Val Glu Met
     90                  95                 100

TGG GTC GAT GAG AAA CAG TAT TAT GAC CAT GAC TCA AAT ACT TGT GCA    1288
Trp Val Asp Glu Lys Gln Tyr Tyr Asp His Asp Ser Asn Thr Cys Ala
 105                 110                 115

CAA GGA CAG GTG TGT GGA CAC TAT ACT CAG GTG GTT TGG CGT AAC TCG    1336
Gln Gly Gln Val Cys Gly His Tyr Thr Gln Val Val Trp Arg Asn Ser
```

```
                       120              125              130              135
GTT CGT GTT GGA TGT GCT AGG GTT CAG TGT AAC AAT GGA GGA TAT GTT         1384
Val Arg Val Gly Cys Ala Arg Val Gln Cys Asn Asn Gly Gly Tyr Val
                140              145              150

GTC TCT TGC AAC TAT GAT CCT CCA GGT AAT TAT AGA GGC GAA AGT CCA         1432
Val Ser Cys Asn Tyr Asp Pro Pro Gly Asn Tyr Arg Gly Glu Ser Pro
            155              160              165

TAC TAATTGAAAC GACCTACGTC CATTTCACGT TAATATGTAT GGATTGTTCT              1485
Tyr

GCTTGATATC AAGAACTTAA ATAATTGCTC TAAAAAGCAA CTTAAAGTCA AGTATATAGT       1545

AATAGTACTA TATTTGTAAT CCTCTGAAGT GGATCTATAA AAAGACCAAG TGGTCATAAT       1605

TAAGGGGAAA AATATGAGTT GATGATCAGC TTGATGTATG ATCTGATATT ATTATGAACA       1665

CTTTTGTACT CATACGAATC ATGTGTTGAT GGTCTAGCTA CTTGCGATAT TACGAGCAAA       1725

ATTCTTAACT ACATGCCTTA GGAACAAGCT TACACAGTTC ATATAATCTA CTAGAGGGCC       1785

AAAAACATGA AAATTACCAA TTTAGATGGT AGGAGGATAT TGAAAGTGGA GCAGCTAGTT      1845

TTAATAACTG ACCGTTAGTC TTAAAATTGA CGGTATAAAA ATATTTACAT AATCAGGTCA       1905

TTTATAAGGT AATTATAGGT AAATATTTAT GACGAATTCT CAATAGTAAT CTGAAAAAAA      1965

ATTGTAACTA ACCTATTATA CTAAAACTAC TATAATAGGT TAGATTACAT TAATCATGTC      2025

ATTAGAAGAT CTT                                                          2038

(2) INFORMATION FOR SEQ ID NO:2:

(i) SEQUENCE CHARACTERISTICS:
        (A) LENGTH: 2256 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 716..1246

(xi) SEQUENCE DESCRIPTION: SEQ ID NO:2:

TTACTGTTAA AGTATTCGTA CTCGTAGATA TTTCAAAAAT TAGATAGCGA TTTTATCATC        60

TAATCAACTA TAGATCTAAG TCGAAAATAT ACCTTGAGTA TAGATTTTTA CTTACCAGCC       120

TTTCATCTTC TTCCAGAAAT AAGAGTGGAA ATCAACGGTA GCAGATAACG TTGAGATATG       180

ATCTTGTAGT AATTGACACC TAACGGGACT GCTTTCCTTT AAAATATAGA CGATAATATC       240

AGTTATAAGG ATGCTTTCAC TTTCTAATTA AAGCATATTC TGATTCGGTT TTATAGAATT       300

TGATAGAAGT TAGACAGCAT CCCTCCAATT GAACAGGTTC GATTACTCAA CTTCCCGTCT       360

ACTTAAACAA ATTCAACTCT TTTCGCGTAC TATATTTATG TTAAAATACA CTGGTAATAA       420

TGTATAAAAC TATATGTATG TATATAATAT AACTTCATGA TTTATCAAAG TTGGTCAAAT       480

TATGATCATG GCTATAATAG TTGTTCATCA ATAGATAGAA TTTTTTAATG GCGGCTTTTG       540

TTTCTTTAAC GAATATGATC TAACGTTCTT TGAATTAACG GAGCTATAAT TTTATACTAT       600

TCTTTTCAAA TATGGCTAAA GAGTTTGCTA CAAGTTGCA AACTTTGTAA CTCAGCTATA       660

TTCTTCCCTA TAAAAATCAT CCTTACTATG CTTTGTTTCT CACCAAAACA CAAAA ATG        718
                                                                  Met
                                                                   1

GGA TTC TTA ACA ACA ATA GTT GCT TGT TTC ATT ACC TTT GCA ATA TTA         766
Gly Phe Leu Thr Thr Ile Val Ala Cys Phe Ile Thr Phe Ala Ile Leu
        5                  10                  15
```

| | | | | | | | | | | | | | | |
|---|---|---|---|---|---|---|---|---|---|---|---|---|---|---|
| ATT | CAC | TCA | TCC | AAA | GCT | CAA | AAC | TCC | CCC | CAA | GAT | TAT | CTT | AAC | CCT | 814
| Ile | His | Ser | Ser | Lys | Ala | Gln | Asn | Ser | Pro | Gln | Asp | Tyr | Leu | Asn | Pro |
| | | 20 | | | | 25 | | | | 30 | | | | | |

```
ATT CAC TCA TCC AAA GCT CAA AAC TCC CCC CAA GAT TAT CTT AAC CCT    814
Ile His Ser Ser Lys Ala Gln Asn Ser Pro Gln Asp Tyr Leu Asn Pro
        20              25              30

CAC AAT GCA GCT CGT AGA CAA GTT GGT GTT GGC CCC ATG ACA TGG GAC    862
His Asn Ala Ala Arg Arg Gln Val Gly Val Gly Pro Met Thr Trp Asp
 35              40              45

AAT AGG CTA GCA GCC TAT GCC CAA AAT TAT GCC AAT CAA AGA ATT GGT    910
Asn Arg Leu Ala Ala Tyr Ala Gln Asn Tyr Ala Asn Gln Arg Ile Gly
 50              55              60                           65

GAC TGC GGG ATG ATC CAC TCT CAT GGC CCT TAC GGC GAA AAC CTA GCC    958
Asp Cys Gly Met Ile His Ser His Gly Pro Tyr Gly Glu Asn Leu Ala
                 70              75                      80

GCC GCC TTC CCT CAA CTT AAC GCT GCT GGT GCT GTA AAA ATG TGG GTC    1006
Ala Ala Phe Pro Gln Leu Asn Ala Ala Gly Ala Val Lys Met Trp Val
             85              90              95

GAT GAG AAG CGT TTC TAT GAT TAC AAT TCA AAT TCT TGT GTA GGA GGA    1054
Asp Glu Lys Arg Phe Tyr Asp Tyr Asn Ser Asn Ser Cys Val Gly Gly
            100             105             110

GTA TGT GGA CAC TAT ACT CAG GTG GTG TGG CGT AAC TCA GTA CGT CTC    1102
Val Cys Gly His Tyr Thr Gln Val Val Trp Arg Asn Ser Val Arg Leu
        115             120             125

GGT TGT GCT AGG GTT CGA AGC AAC AAT GGT TGG TTT TTC ATA ACT TGC    1150
Gly Cys Ala Arg Val Arg Ser Asn Asn Gly Trp Phe Phe Ile Thr Cys
130             135             140                     145

AAT TAT GAT CCA CCA GGT AAT TTT ATA GGA CAA CGT CCC TTT GGC GAT    1198
Asn Tyr Asp Pro Pro Gly Asn Phe Ile Gly Gln Arg Pro Phe Gly Asp
                150             155                 160

CTT GAG GAG CAA CCC TTT GAT TCC AAA TTG GAA CTT CCA ACT GAT GTC    1246
Leu Glu Glu Gln Pro Phe Asp Ser Lys Leu Glu Leu Pro Thr Asp Val
            165             170                 175
```

TAATGAGTGC ACGTACATGA ACAAATTATC ATGAATAAAG GAAAATAAAA TGCAGTGCTA    1306

TGCTATGTGA TTTTAGCTTC CCAGTTGGAT AATAATCTGA TGGTGTAGTA ACTGGCCGAG    1366

TGTTTGGACC CTACCTTGCA TGTTGGTAGA TGGAATCAGT TTATATATGA GTTTTCTGTT    1426

GGCTATGTT ATTTTTATTA AAATCTTATT CTAGTTTTAC AGTTTTTTAT TCGCACTATA    1486

TGTGTATGGG TCCAAATTTG ATCGACCACG ACCTATGACG AGTACAACAA ACGACCGGGT    1546

ACCTTCGAAT CGGCGTCCCA AGGGAAACGA CCCTAGGGCG AAAGAAGAGA CTGTATGACT    1606

CTTGTAGTAG TGTAAGCCCA TTAGGGAACA TTAAGAATAT TCCGCCGAAT ACTAATTGTA    1666

TTTTGTTTCT TACAATTCGG AAGGGTTTCT CTCTAGTATA TAAAGGGGAC AAAAAACCTT    1726

GTAAGTGGCG GTGGATACTC TGAGAAGCTT ACTAATCTTG GATGAAAAGA AAAACTCTCT    1786

TCTCTTTATC TATTATTATT CTAGAGATTA TTATCTTCAG CTACGATTTA CCCCTTCATC    1846

TTTGATTGAT TTGTTCAAAA AGGTTTTAAC ATCTTTTGAG TCAAACAATT TGGCNCCGTC    1906

TATGGGGATT TCTATAGCTG AAATCATAGT TCTCATCTAG ATTTCTGAAG TGATAATTAC    1966

TTTTCTTCAA ACCTCATAAA AATCAACAAT GGCSGGAAAG GAAGTGAAGC TAAAGGCGGT    2026

ASAGATCGTC TCGAATAACT CCTGAACTCC CTCAACGAAG ACGGCAGAGA AGACAATGAG    2086

AATACAACAC CAAGCGCTAC ACCGGAGGGA AGATCTCACC TCTTCCACAC GGGGATCTAA    2146

CGATCTTGCG CGAAAGGGGA GTCTCGACAT CCACAGCAGG GGAAGCACCA CCAACACTCA    2206

AAAGGTTACT AGAATAATGG TTAACGAGTG CTTGGAGCAA CATGCTTGAG              2256

(2) INFORMATION FOR SEQ ID NO:3:

(i) SEQUENCE CHARACTERISTICS:
        (A) LENGTH: 1103 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:3:

```
AAAGAAAGCT CTTTAAGCAA TGGCTGCCCA CAAAATAACT ACAACCCTTT CCATCTTCTT      60

CCTCCTTTCC TCTATTTTCC GCTCTTCCGA CGCGGCTGGA ATCGCCATCT ATTGGGGTCA     120

AAACGGCAAC GAGGGCTCTC TTGCATCCAC CTGCGCAACT GGAAACTACG AGTTCGTCAA     180

CATAGCATTT CTCTCATCCT TTGGCAGCGG TCAAGCTCCA GTTCTCAACC TTGCTGGTCA     240

CTGCAACCCT GACAACAACG GTTGCGCTTT TTTGAGCGAC GAAATAAACT CTTGCAAAAG     300

TCAAAATGTC AAGGTCCTCC TCTCTATCGG TGGTGGCGCG GGGAGTTATT CACTCTCCTC     360

CGCCGACGAT GCGAAACAAG TCGCAAACTT CATTTGGAAC AGCTACCTTG GCGGGCAGTC     420

GGATTCCAGG CCACTTGGCG CTGCGGTTTT GGATGGCGTT GATTTCGATA TCGAGTCTGG     480

CTCGGGCCAG TTCTGGGACG TACTAGCTCA GGAGCTAAAG AATTTTGGAC AAGTCATTTT     540

ATCTGCCGCG CCGCAGTGTC CAATACCAGA CGCTCACCTA GACGCCGCGA TCAAAACTGG     600

ACTGTTCGAT TCCGTTTGGG TTCAATTCTA CAACAACCCG CCATGCATGT TTGCAGATAA     660

CGCGGACAAT CTCCTGAGTT CATGGAATCA GTGGACGGCG TTTCCGACAT CGAAGCTTTA     720

CATGGGATTG CCAGCGGCAC GGGAGGCAGC GCCGAGCGGG GGATTTATTC CGGCGGATGT     780

GCTTATTTCT CAAGTTCTTC CAACCATTAA AGCTTCTTCC AACTATGGAG GAGTGATGTT     840

ATGGAGTAAG GCGTTTGACA ATGGCTACAG CGATTCCATT AAAGGCAGCA TCGGCTGAAG     900

GAAGCTCCTA AGTTTAATTT TAATTAAAGC TATGAATAAA CTCCAAAGTA TTATAATAAT     960

TAAAAAGTGA GACTTCATCT TCTCCATTTA GTCTCATATT AAATTAGTGT GATGCAATAA    1020

TTAATATCCT TTTTTTCATT ACTATACTAC CAATGTTTTA GAATTGAAAA GTTGATGTCA    1080

ATAAAAACAT TCCAAGTTTA TTT                                            1103
```

(2) INFORMATION FOR SEQ ID NO:4:

(i) SEQUENCE CHARACTERISTICS:
        (A) LENGTH: 900 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
AAAAAGAAAA AAAAAATGAA CTTCCTCAAA AGCTTCCCCT TTTTTGCCTT CCTTTATTTT      60

GGCCAATACT TTGTAGCTGT TACTCATGCT GCCACTTTTG ACATTGTCAA CAAATGCACC     120

TACACAGTCT GGGCCGCGGC CTCTCCAGGT GGAGGCAGGC GGCTCGACTC AGGCCAATCT     180

TGGAGCATTA ATGTGAACCC AGGAACAGTC CAGGCTCGCA TTTGGGGTCG AACCAATTGC     240

AACTTCGATG GCAGTGGCCG AGGTAATTGT GAGACTGGAG ACTGTAACGG GATGTTAGAG     300

TGTCAAGGCT ATGGAAAAGC ACCTAACACT TTAGCTGAAT TTGCACTTAA TCAACCCAAT     360

CAGGACTTTG TCGACATCTC TCTTGTTGAT GGATTTAACA TCCCCATGGA ATTCAGCCCG     420

ACCAATGGAG GATGTCGTAA TCTCAGATGC ACAGCACCTA TTAACGAACA ATGCCCAGCA     480

CAGTTGAAAA CACAAGGTGG ATGTAACAAC CCATGTACTG TGATAAAAAC CAATGAATAT     540

TGTTGTACAA ATGGGCCTGG ATCATGTGGG CCTACTGATT TGTCGAGATT TTTTAAGGAA     600

AGATGCCCTG ATGCTTATAG TTATCCACAG GATGATCCAA CCAGTTTGTT TACGTGTCCT     660
```

```
TCTGGTACTA ATTACAGGGT TGTCTTCTGC CCTTGAAATT GAAGCCTGCA AAATTATGAC      720

TATGTAATTT GTAGTTTCAA ATATATAAGC TACACAAGTA GTACTAAGCA CTATTAAATA      780

AAAAAGAGAG TGACAAAGAG GAGAGGCTGT GGGTCAGATT CTCTTGTTCG CTGTTGTCGT      840

TGTTGTAGCA TTCTGGTTTT AAGAAATAAA GAAGATATAT ATCTGCTAAA TTATTAAATG      900

(2) INFORMATION FOR SEQ ID NO:5:

(i) SEQUENCE CHARACTERISTICS:
        (A) LENGTH: 4483 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GAGCTCCTCT AGGGGGCCAA GGCAAACCTT TTTGCTAATG GGAAAAAAAT ATTAGACCAA       60

GAGTTTGTAA TAGCTACTCA ATTTCAATTT ACAAAGGGGA AAATTTAACT GTTTTGCCCT      120

TATATCTTTT GGTCCCGAAA CATAAAATAT CCCATCCGAA ATTCCAAATG GTCCATTATC      180

GGCAAGTAGC TTTCTTTTAT TATAGTTAGT TGACAAAACA CTATCGAGAT ATCATTAGTA      240

TAATAATAAC TTCAAAGTCC ATCTTCTTAG CTGCCTCCTC ATTAGAGCCG CCACTAAAAT      300

AAGACCGATC AAATAAAAGC CGCCATTAAA ATAATGAATT TTAGGACTCT CAATTGTCAC      360

GTAAGTGCCA AAACTCTTCC AATACTTTGC TGCAACTTGG GGCTGCTAGC TTCTGAGCTT      420

CCTGGGATAT TTCTATGTTT ATCTCTTAAT TTACATCTCA ACTAATATCA AGAAATTAAA      480

CAGGTGCAGC AAATCATAAA ATTTTCCTCT AAAGAAGAAA ATGACTCCGG TTACTGATTC      540

ATTGGCCTTT TCAGAGTCTG CGTGCCATAT TCACTAATGG GTCGTTTGGT ACAAGAAATA      600

ATGATAATAA TTTCGAAATA GAATTTGGGA TTTCATTTAT TTCATATTTA ATTATAAATA      660

TTAGCTAATT TCGAAATAAA TTTTACATTA AAATAGTGAA ATCAACTATC TCATATATAA      720

GGTGGAATAG CTAATCTCAT AGCCACCTCA GTTAGAATCC AGTTTCCTCT AATAAATGCA      780

GCGAAATATT AGAAGACTTT CATTAAATCA ATTCATATAA TTTAAAAATA CTAGACATGG      840

AAAAAAAAAA CGATTCGAGA CTGTTATGGA AGGCGTTGCC TTCGATGTAG ATTCTCATCC      900

ATTGCTTTCG TGCAATAGCA ATATGACATC TTATTCTTAG AACTACTTTT AAATGAAAGT      960

CATATAGAAC TTTAAAATCT CTCAACTAGT TTTAAGGGAA TTCAAAATAC GACCAATATT     1020

TATTACTTAC TTATGGATAA ATTTAAATAA TATGTATTTT ATCTTGAAAT TGAATTGAAA     1080

ATATTAAATT ACTTGGTTTA ATATAAACAA TAGATATCGT TAAGTATTTA CCACAAACAT     1140

TTTATTAGTT GTAACGATGA TTAAGCAGGA ATTCCTCTGG TTGTGCAGGA TGAAAGAAAC     1200

TAACTAGCTA TAATTTCTTT TGTAAAGTCA AGATAGTACG GCACCTTATG GAGAAAATAA     1260

ATAACTTTAC ATCATCAAAC TCATCTTCTT TTTTCCACAA AATGATCAAG TTGACATGTT     1320

AATAGCCAGG TCACCGGGGG CGGCTCTTAA CTTCATTAGC CTACGAATAA CAAATCCAAT     1380

ATTATATTTA CACAAGGCTA TATATATATC TCAATATAAA TAGCTCGTTG TTCATCTTAA     1440

TTCTCCCAAC AAGTCTTCCC ATCATGTCTA CCTCACATAA ACATAATACT CCTCAAATGG     1500

CTGCTATCAC ACTCCTAGGA TTACTACTTG TTGCCAGCAG CATTGACATA GCAGGTTTCT     1560

GGTCAAATAT TTGAACTTCC CAGCCAAAAA TATTGTCTTA TAATTTTGTG TGCGCAAAAT     1620

TTTAATTTAG TTGATAGTTA TTTGCTTATT TTTCTTTTCA AATTGCTTGT GTTTTTTTCT     1680

CAAATTAACT TGCACCGTAT TCATTTAGCG ATAGTTATTT GCTCTATTTT TGTGTAACAC     1740

TCACTCACAA ACTTTTCAAT TTGAGGGGAG GACAGTGAAT CTAAGATTGA AATTTATGAG     1800
```

```
TTTAATTAGA CTAATTCCCA TTTGATTTAT TGGCTAGAAG TCAATTATTT GCATAGTGAG    1860

TCTTTTAACA CACAGATTTG AGTTAAAGCT ACTACGTTCG TATTAACCCA TAACATATAC    1920

ACCTTCTGTT CTAATTTCTT TGACACTTTT TGTTAGTTTG TTCCAAAAAG GACGGACATA    1980

TTTGATATTT GAGAATACTT TACCTTAACC TTAATAGAAT TTTTTATGAC ATCACATATA    2040

TTATGGAATA TATACGACCA TAATTTTCAA ATATCTTATA GTCGTACAAA TATTATAGCA    2100

TGTTTAATAC CACAACTTTC AAATTCTTCT TTTCCTTAAA AACAAAATAT GTCACATAAA    2160

TTAAAATAGA GGAAGTATAC TACATCAATC AGCCCCTAGT GGAGGGGACC CTACTGTAAG    2220

TTTTTAAGTT TTCAAGAATT CAGTAATTGA TTAGGAGCCC GTCTGGACAT AAAAAAAAAT    2280

TCCTTTTTTT CCAAAAAATG CCCACTAAAT TTCTAACACT ATTTTGTAAT TCTTATTGAG    2340

CAGGGGCTC AATCGATAGG TGTTTGCTAT GGAATGCTAG GCAACAACTT GCCAAATCAT    2400

TGGGAAGTTA TACAGCTCTA CAAGTCAAGA ACATAGGAA GACTGAGGCT TTATGATCCA    2460

AATCATGGAG CTTTACAAGC ATTAAAAGGC TCAAATATTG AAGTTATGTT AGGACTTCCC    2520

AATTCAGATG TGAAGCACAT TGCTTCCGGA ATGGAACATG CAAGATGGTG GGTACAGAAA    2580

AATGTTAAAG ATTTCTGGCC AGATGTTAAG ATTAAGTATA TTGCTGTTGG GAATGAAATC    2640

AGCCCTGTCA CTGGCACATC TTACCTAACC TCATTTCTTA CTCCTGCTAT GGTAAATATT    2700

TACAAAGCAA TTGGTGAAGC TGGTTTGGGA AACAACATCA AGGTCTCAAC TTCTGTAGAC    2760

ATGACCTTGA TTGAAACTC TTATCCACCA TCACAGGGTT CGTTTAGGAA CGATGCTAGG    2820

TGGTTTGTTG ATCCCATTGT TGGCTTCTTA AGGGACACAC GTGCACCTTT ACTCGTTAAC    2880

ATTTACCCCT ATTTCAGTTA TTCTGGTAAT CCAGGCCAGA TTTCTCTCCC CTATTCTCTT    2940

TTTACAGCAC CAAATGTGGT GGTACAAGAT GGTTCCCGCC AATATAGGAA CTTATTTGAT    3000

GCAATGCTGG ATTCTGTGTA TGCTGCCCTC GAGCGATCAG GAGGGGCATC TGTAGGGATT    3060

GTTGTGTCCG AGAGTGGCTG GCCATCTGCT GGTGCATTTG GAGCCACATA TGACAATGCA    3120

GCAACTTACT TGAGGAACTT AATTCAACAC GCTAAAGAGG GTAGCCCAAG AAAGCCTGGA    3180

CCTATTGAGA CCTATATATT TGCCATGTTT GATGAGAACA ACAAGAACCC TGAACTGGAG    3240

AAACATTTTG GATTGTTTTC CCCCAACAAG CAGCCCAAAT ATAATATCAA CTTTGGGGTC    3300

TCTGGTGGAG TTTGGGACAG TTCAGTTGAA ACTAATGCTA CTGCTTCTCT CGTAAGTGAG    3360

ATGTGAGCTG ATGAGACACT TGAAATCTCT TTACATACGT ATTCCTTGGA TGGAAAACCT    3420

AGTAAAAACA AGAGAAATTT TTTCTTTATG CAAGATACTA AATAACATTG CATGTCTCTG    3480

TAAGTCCTCA TGGATTGTTA TCCAGTGACG ATGCAACTCT GAGTGGTTTT AAATTCCTTT    3540

TCTTTGTGAT ATTGGTAATT TGGCAAGAAA CTTTCTGTAA GTTGTGAAT TTCATGCATC    3600

ATTAATTATA CATCAGTTCC ATGTTTGATC AGATTGGGAT TTGGTAACTT CAATGTTTAG    3660

TTATTTATTA ATTAGTGTCT TTATCATTTG ACTATCAATT AATCTTTATT TGGCAAGGCT    3720

TGATATATTT GAGTTACTCT TAGGTATTTG CAAGCAACTG ATCTTTCTTT TATCCCGTTT    3780

CTCCGTTAAA CCTCATTAGA AATATATTAT AATGTCACCT ACTCTGTGGT TTAAGACATT    3840

CCCTTACATT ATAAGGTATT TCACGTCGTA TCAGGTCGAA AAAAATAATG GTACGCTCTT    3900

TCTTATCACA AATTTCTCTC AACTTCTAGA CCAATTGAAT CTTGTCTCCA ATAAGCATTG    3960

CTTTTACTGT ATGTTTCTCT CTATCAATTC AAGGCTCAAG CCATCAAATC GCTTGGTATT    4020

TCTCGCTCCC ATTTAACCAA TCGAGCTGTT AGCTCTGCTA AAGTCTCATT CTTCAGCTTC    4080

TCAAACCACT CAGAGCTTCT CCAACCAAAA ATGTAGAAAA AATCTTTGAT CCACATGTAA    4140

AACCCCAGAA TTGTCATTCG AGTGAAGGAA GGTGCTGGAA ACGCGACATC AAACACGGAT    4200
```

```
TTGCCAGCTG ATTGTCATAG GAAAAAGAAA AGTTGATCAG ATAGTTCGTC CGGGGTATTT     4260

CCTACCTCGC CTTTGATCAT AGCTCTAGGC TTGCGAAACT AAGTTATGCA CGAGGCCCCC     4320

TGCGAATCCA TAAATCTAAG AAGCATGCCA CAACAAACGA GATAACTTCC AGCTAAGAGA     4380

TCTATTTTGA TCTTACCCAC AAACTAGCTC CGTGTGAATT GTCCATTTCA TCAACTCCAA     4440

AGGCAGGAAA AAGACTCTA TTCAGAGAGC AGCAAAAGAG CTC                        4483

(2) INFORMATION FOR SEQ ID NO:6:

(i) SEQUENCE CHARACTERISTICS:
        (A) LENGTH: 4699 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GAGCTCCCTT GGGGGGCAAG GGCAAAACTT TTTGCTAAAT GGAAAAATAT TATACCAAGT       60

GTTTGTAATA GTTACTCAAT TTGAATTAAC AAAGGGGCAA ATTTGACTAT TTTGCCCTTA      120

TATCTTTTGG TCACAAAAAC ATAAAATATC CCATCCGAAA TTCCAAATGG TCCATTATCG      180

GCAAGTAGCT TTCTTTAATT ATAGTTAGTT GACAAAACAC TATCAAGATA TCATTATTAT      240

AATAATAACT TCAAAGTCCA TCATCTTAGC TGCCTCCTCA GTAGAGCCGC CAGTAAAATA      300

AGACCGATCA AATAAAAGCC GCCATTAAAA TAATGAATTT TAGGACTCTC GATTGGCACG      360

TAAGTGCCAA AACTCTTCCA ATACTTTGCT GCAACTTGGG GCTGCTAGGT TCTGAGCTTC      420

CAGATATGGG ATATTTCTAA GTTTATCTCC TAATTTACAT CTCAACTAAT ATTAAGAAAT      480

TAAACAGGTA CAGCAAATCA TAAAATTTTC CTCTAAAGAA GACAATGAAT CCGGTTACTG      540

ATTCATTGGC CTTTTCAGAG TCTGCATGCC ATATTCACTA AGGGGTCGTT TGGTACAAGA      600

AATAATAATA ATAATTTCGG GATAGAATTT GAGATTGCAT TTATCTTGTG TTTAATTATA      660

AGTATTAGCT AATTTCAGAA TAAATTTTAC ACTAAAATAG TAAAATCAAC TATCACATGT      720

AGAAGGTGGA ATGGAATAGC TAATCCCATA GCCACTCACA TAGAATATCC TTATTTATCT      780

CACTATTTTA CCAAATGATC GGTTAGTCTT CATGAGAATC CAGTATCCTC AATAAATGCA      840

GTAAGAAGTT AGAAAATTTT CATTAAATCA ATTCATATAA TTTAAAAATA TTAGATATGG      900

AGCACTTAAG ATACAATAAA AGATGTACCG TTAATAATAA AAGATAAGAT AGAGTTTTAA      960

ATAGGAAAAA AAAAACGGTT CGAGACACTC TTATGGAAGG CGTTGTCTTC AAAGTAGATT     1020

CTCATTCATT GCTCTGGTGC AATAGCAAAA TGACATCTTA CTCTTAAGAT ACAGCGAGCC     1080

ACTCTACAAT CTTCTATTGT ATACTCAAAT GAAAGTTTTA GAGAACTTTC AAATCTCTCA     1140

ACTACTTTTA AGGGAATTCA AAATACGACC AATATTTATT ACTTACTTAC TTATAGTTAA     1200

ATGATATGAA TTTTATTTTA AATTTGAATT GAAAATATTA AATTACTTGA TTTAATATAA     1260

ACAATAGATA TCGCTAAGTA TTTACCACAA ACATGGAGAT ACTACAGAAG ATTTTATTAT     1320

TTGTAACGAT GATTAAGCAG CTATTCATCT GGTTGTGCAG GATGAAAGAA AGTAACTAGC     1380

TATAATTTCT TTTGTAAAGT CAAGATAGTA CGGCACCTTT GGANNAAATA TAAAACTTGT     1440

ACATCATCAA ACTCATTTTC TTTTTTCCAC AAAATGATCA AGTTGACATG TTAATAGCCA     1500

GGTCAGCCGG GGCGGCTCTT AACTTCATTA GCCTACGAAT AACAAATACT CCAATAATAT     1560

TCCACTCGAA TATTTACATT TACACAAGGC TATCTCAATA TAAATAGCTC ATTGTTCATC     1620

TTAATTCTTC CAACAAGTCT TCTCATCATG TCTACCTCAG ATAAACATAA TACTCCTCAA     1680
```

```
ATGGCTGCTA TCACACTGCT AGGATTACTA CTTGTTGCCA GCACCATTGA GATAGCAGGT      1740

TTCTGGTCAA ATATTTGAAC TTCCGAGCCA AAAATATTGT CTTATAATTT TGTTGGTGCA      1800

AAATCTTAAT TTAGTTGATA GTTATTTGCT TATTTTTCTT ATCAAATTGC TTGTGTTTTT      1860

TTCTCAAATT TACTTGCACT ATATTCATTT AGCGATAGTT ATTTGCTCTT TTTTCGGGTA      1920

ACACTCACTC ACAAGCTTTT CAAATTTGAG GGGAGGGCGG TGAATCTAAA ATTTGAAATT      1980

TATGAGTTTA GACTAGTGTC CATTTGATTT ATTGGCTAGA CGTCTATTAG TTGTATAGTA      2040

AATCTTTTAA CACATACACC GACCTGAGTC AAAGCTATTA GGTTCGTATT AACACATAAC      2100

ACATATTCCC TCTGTTCTAA TTTATGTGAC ACACTTTCTG TTAGTTTCTT CCAAAGAGAA      2160

TGACATATTT GATATTTAAA AATATTTTAA CTTTAAACTT TTTATTCTCA ACCTTTTATA      2220

ACATCACAAA TATTATGGAA CATATTAGAC TACAAGTTCC AAATATCTTA TAGTCTGTAC      2280

AAATATTATA GCATGTTTAA TAACACAATT TTCACATTCT TCTTTTTCTT AAACTTTGTG      2340

CCGAATTAAA TTATGTCACA TAAATTAAAA TGGTTACATC ATCCCCTAGT GGAGGGACCT      2400

ACCATGTCTA CTGTAAGTTT TTAACTTTTC AAGAATTACA TAATTGATTT AGTTTCTAAC      2460

ACTAATTCTA ATTCTTATTG AGCAGGGGCT CAATCAATAG GTGTTTGCTA TGGAATGCTA      2520

GGCAACAACT TGCCAAATCA TTGGGAAGTT ATACAGCTCT ACAAGTCAAG AAACATAGGA      2580

AGACTGAGGC TTTATGATCC AAATCATGGA GCTTTACAAG CATTAAAAGG CTCAAACATT      2640

GAAGTTATGT TAGGACTTCC CAATTCAGAT GTCAAGCACA TTGCTTCCGG AATGGAACAT      2700

GCAAGATGGT GGGTACAAAA AAATGTTAAA GATTTCTGGC CAGATGTTAA GATTAAGTAT      2760

ATTGCTGTTG GGAATGAAAT CAGCCCTGTC ACAGGCACAT CTTACCTTAC CTCATTTCTT      2820

ACTCCTGCCA TGGTAAATAT TTACAAAGCA ATTGGTGAAG CTGGTTTAGG AAACAACATC      2880

AAGGTCTCAA CTTCTGTAGA CATGACCTTG ATTGGAAACT CTTATCCACC ATCACAGGGT      2940

TCGTTTAGGA ACGATGCTAG GTGGTTTACT GATCCAATTG TTGGGTTCTT AAGGGACACA      3000

CGTGCACCTT TACTCGTTAA CATTTACCCC TATTTCAGCT ATTCTGGTAA TCCAGGGCAG      3060

ATTTCTCTCC CCTATTCTCT TTTTACAGCA CCAAATGTGG TAGTACAAGA TGGTTCACGC      3120

CAATATAGGA ACTTATTTGA TGCAATGCTG GATTCTGTGT ATGCTGCCCT CGAGCGATCA      3180

GGAGGGGCAT CTGTAGGGAT TGTTGTGTCC GAGAGTGGCC GGCCATCTGC TGGTGCATTT      3240

GGAGCTACAT ATGACAATGC AGCAACTTAC TTGAGGAACT TAATTCAACA CGCTAAAGAG      3300

GGTAGCCCAA GAAAGCCTGG ACCTATTGAG ACCTATATAT TGCCATGTT TGATGAGAAC      3360

AACAAGAACC CTGAACTGGA GAAACATTTT GGATTGTTTT CCCCCAACAA GCAGCCCAAA      3420

TATAATCTCA ACTTTGGGGT CTCTGGTGGT GTTTGGGACA GTTCAGTTGA AACTAATGCT      3480

ACTGCTTCTC TCATAAGTGA GATGTGAGAT GAGACACTTG AAATCTCTTT ACATAAGTAT      3540

TGCTTAGATG GAAAGCTTAG TAAAAACAAG AGAAATTTAT TCTTCATGCA AGACACTAAA      3600

TAACATTGCA CGTCTCTGTA AGTCCTCATG GATTGTTATC CAGAGACGAT GCAACTCTGA      3660

GTGGTTTTAA ATCCCTTTTC TTTGTGATGT TGGTAATTTG GCAAGAAACT TTCTGTAAGT      3720

TTGTGAATTT CATGACTTTC TGTAAGTTTG TGAATTTCAT GCACCATCAA TTATACATCT      3780

TTTCCATGTT TGATCACATT AGGATTTGGT AATTGCAAAG TTTAGTTATT TATTAATTAG      3840

TGTCTTTATC ATTTGACTCG ATCAATTAAT CTTTAATTGG TAAGGCTTGA TATATCGGAG      3900

CGACTCTTAG GTAGTGGCAT TCAACTGATC TTTCTGTTAT CCCATGTCTC CGTTAACCCT      3960

CATTAGAAAT ATATTATAAT GTCACCTAAA TCAGAGGTTT TAGAGCTTCA AAATCGATTG      4020

ACAACAGTTT TGGAGTTACA CTGTGGTTTA GGACATTCTG TTACATTATA AGGTATTTCA      4080
```

| | | |
|---|---|---|
| CGTCGTATCA AGGTCGAATA AAATAATGGT ACGCTCTTTC TTATCACAAA TTTCTCTCAA | | 4140 |
| CTTCTAGACC AATTGAATCT TGTCTCCAAT AAGTATTGCT TTTACTCTAT GTTTCTCTCT | | 4200 |
| ATCAATTCAA GGCTCAAGCC ATCAAATCGC TTGGTATTTC TCGCTCTCAA TTAACCAATC | | 4260 |
| GAGCTGTTAA CTCTGCTAAA GTCTCATTCT TCAGCTTCTC AAACCACTCA AAGCTTCTCC | | 4320 |
| AACAAAAAAA GTAGAAAAAA ACTTTGATCC ACATGTAAAA CCCCATAACC ATGTCATTCG | | 4380 |
| AGTGAAGGAA GGTGCTTGAA ATGCAACGAA CAAACACGGC TTTGCCACTG CTTGTGATAG | | 4440 |
| GTAAAAGAAA ACTTGATTAG ATAGTTCGTG CGGGGCATTT CCTACCTCGC CTTTGATCTT | | 4500 |
| AGCTTTAGGC TTGCGAAACT AAGTAGAACC TAAGGCCCCA GCGAATCCGT AAATCTGAGG | | 4560 |
| AGCATGCCAC AGCAAAAAGG TTAGCTTTCA GATAAGAGAT CTATTTGATC TTACCCACTA | | 4620 |
| ACTAGCTCTG TGTGAATTGT CCATTTCATC AACTCCAAAG GCAGGAAAGA AGACTATTGA | | 4680 |
| GAGAGCAGCA AAAGAGCTC | | 4699 |

(2) INFORMATION FOR SEQ ID NO:7:

(i) SEQUENCE CHARACTERISTICS:
        (A) LENGTH: 1020 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

| | | |
|---|---|---|
| AAAAAAAAAA AAAAACATAA GAAAGTACAG AGGAAAATGG AGTTTTCTGG ATCACCAATG | | 60 |
| GCATTGTTTT GTTGTGTGTT TTTCCTGTTC TTAACAGGGA GCTTGGCACA AGGCATTGGT | | 120 |
| TCTATTGTAA CGAGTGACTT GTTCAACGAG ATGCTGAAGA ATAGGAACGA CGGTAGATGT | | 180 |
| CCTGCCAATG GCTTCTACAC TTATGATGCA TTCATAGCTG CTGCCAATTC CTTTCCTGGT | | 240 |
| TTTGGAACTA CTGGTGATGA TACTGCCCGT AGGAAAGAAA TTGCTGCCTT TTTCGGTCAA | | 300 |
| ACTTCTCACG AAACTACTGG TGGATCCCTG AGTGCAGAAC CATTTACAGG AGGGTATTGC | | 360 |
| TTTGTTAGGC AAAATGACCA GAGTGACAGA TATTATGGTA GAGGACCCAT CCAATTGACA | | 420 |
| AACCGAAATA ACTATGAGAA AGCTGGAACT GCAATTGGAC AAGAGCTAGT TAACAACCCT | | 480 |
| GATTTAGTGG CCACAGATGC TACTATATCA TTCAAAACAG CTATATGGTT TTGGATGACA | | 540 |
| CCACAGGACA ACAAGCCATC TTCCCACGAC GTTATCATCG GTCGTTGGAC TCCGTCTGCC | | 600 |
| GCGGATCAGG CGGCGAATCG AGTACCAGGT TACGGTGTAA TTACCAACAT CATTAACGGT | | 660 |
| GGAATTGAAT GTGGCATAGG ACGGAATGAC GCAGTGGAAG ATCGAATTGG ATACTACAGG | | 720 |
| AGGTATTGTG GTATGTTAAA TGTTGCTCCG GGGGAAAACT TGGACTGTTA CAACCAAAGG | | 780 |
| AACTTCGGCC AGGGCTAGGC TTCGTTACAT AGAATGCAGA TCATGTTATG TATACAAGTT | | 840 |
| ATATTTGTAT TAATTAATGA ATAAGGGGAT TGTGTATCCA TTAAGAATTA GGTGAAATAT | | 900 |
| TTCTGTTATT TGTCTTCTTG GGAAGAACCA ATAGCTCCTA TATATGAGGC GCTTTTAAGT | | 960 |
| GATGAGGCTA CTGCATTGAT GAAAACGAAA TTTCTATCCA GAAATAAAAG TTCCTTGTCT | | 1020 |

(2) INFORMATION FOR SEQ ID NO:8:

(i) SEQUENCE CHARACTERISTICS:
        (A) LENGTH: 1107 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

| | | | | | |
|---|---|---|---|---|---|
| CAGGTGCTCA | AGCAGGAGTT | TGTTATGGAA | GGCAAGGGAA | TGGATTACCA | TCTCCAGCAG | 60 |
| ATGTTGTGTC | GCTATGCAAC | CGAAACAACA | TTCGTAGGAT | GAGAATATAT | GATCCTGACC | 120 |
| AGCCAACTCT | CGAAGCGCTT | AGAGGCTCCA | ACATTGAGCT | CATGCTAGGT | GTCCCGAATC | 180 |
| CGGACCTTGA | GAATGTTGCT | GCTAGCCAAG | CCAATNCAGA | TACTTGGGTC | CAAAACAATG | 240 |
| TTAGGAACTA | TGGTAATGTC | AAGTTCAGGT | ATATAGCAGT | TGGAAATGAA | GTTAGTCCCT | 300 |
| TAAATGAAAA | CTCTAAGTAT | GTACCTGTCC | TTCTCAACGC | CATGCGAAAC | ATTCAAACTG | 360 |
| CCATATCTGG | TGCTGGTCTT | GGAAACCAGA | TCAAAGTCTC | CACAGCTATT | GAAACTGGAC | 420 |
| TTACTACAGA | CACTTCTCCT | CCATCAAATG | GGAGATTCAA | AGATGATGTT | CGACAGTTTA | 480 |
| TAGAGCCTAT | CATCAACTTC | CTAGTGACCA | ATCGCGCCCC | TTTGCTTGTC | AACCTTTATC | 540 |
| CTTACTTTGC | AATAGCAAAC | AATGCAGATA | TTAAGCTTGA | GTATGCACTT | TTTACATCCT | 600 |
| CTGAAGTTGT | TGTAAATGAT | AACGGAAGAG | GATACCGAAA | CCTTTTTGAT | GCCATCTTAG | 660 |
| ATGCCACATA | CTCGGCCCTT | GAAAAGGCTA | GTGGCTCGTC | TTTGGAGATT | GTTGTATCAG | 720 |
| AGAGTGGTTG | GCCTTCAGCT | GGAGCAGGAC | AATTAACATC | CATTGACAAT | GCCAGGACTT | 780 |
| ATAACAACAA | CTTGATTAGT | CACGTGAAGG | GAGGGAGTCC | CAAAAGGCTT | CCGGTCCAAT | 840 |
| AGAGACCTAC | GTTTTCGCTC | TGTTTGATGA | AGATCAGAAA | GACCCTGAAA | TTGAGAAGCA | 900 |
| TTTTGGACTA | TTTTCAGCAA | ACATGCAACC | AAAGTACCAG | ATCAGTTTTA | ACTAGTTAAA | 960 |
| AGCAAGAGGA | GAGCATTAAT | AGGAATAAGG | ACTTTCCTTT | GTATGAAGAG | AAAGTAGTCC | 1020 |
| ATTGGCACTA | TGTACTGAAA | CTATATATCA | TGCTCATAAA | GAAAGCAGTT | ATTACAATAA | 1080 |
| TGAAACACTT | ACAAGAAAAG | CCATCAA | | | | 1107 |

(2) INFORMATION FOR SEQ ID NO:9:

(i) SEQUENCE CHARACTERISTICS:
        (A) LENGTH: 809 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

| | | | | | |
|---|---|---|---|---|---|
| ATTCAAGATA | CAACATTTCT | CCTATAGTCA | TGGGATTTGT | TCTCTTTTCA | CAATTGCCTT | 60 |
| CATTTCTTCT | TGTCTCTACA | CTTCTCTTAT | TCCTAGTAAT | ATCCCACTCT | TGCCGTGCCC | 120 |
| AAAATTCTCA | ACAAGACTAT | TTGGATGCCC | ATAACACAGC | TCGTGCAGAT | GTAGGTGTAG | 180 |
| AACCTTTGAC | CTGGGACGAC | CAGGTAGCAG | CCTATGCGCA | AAATTATGCT | TCCCAATTGG | 240 |
| CTGCAGATTG | TAACCTCGTA | CATTCTCATG | GTCAATACGG | CGAAAACCTA | GCTGAGGGAA | 300 |
| GTGGCGATTT | CATGACGGCT | GCTAAGGCTG | TTGAGATGTG | GGTCGATGAG | AAACAGTATT | 360 |
| ATGACCATGA | CTCAAATACT | TGTGCACAAG | GACAGGTGTG | TGGACACTAT | ACTCAGGTGG | 420 |
| TTTGGCGTAA | CTCGGTTCGT | GTTGGATGTG | CTAGGGTTCA | GTGTAACAAT | GGAGGATATG | 480 |
| TTGTCTCTTG | CAACTATGAT | CCTCCAGGTA | ATTATAGAGG | CGAAAGTCCA | TACTAATTGA | 540 |
| AACGACCTAC | GTCCATTTCA | CGTTAATATG | TATGGATTGT | TCTGCTTGAT | ATCAAGAACT | 600 |
| TAAATAATTG | CTCTAAAAAG | CAACTTAAAG | TCAAGTATAT | AGTAATAGTA | CTATATTTGT | 660 |
| AATCCTCTGA | AGTGGATCTA | TAAAAAGACC | AAGTGGTCAT | AATTAAGGGG | AAAAATATGA | 720 |
| GTTGATGATC | AGCTTGATGT | ATGATCTGAT | ATTATTATGA | ACACTTTTGT | ACTCATACGA | 780 |
| ATCATGTGTT | GATGGTCTAG | CTACTTGCG | | | | 809 |

(2) INFORMATION FOR SEQ ID NO:10:

(i) SEQUENCE CHARACTERISTICS:
        (A) LENGTH: 771 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
GTTCAAAATA AAACATTTCT CCTATAGTCA TGGGATTTTT TCTCTTTTCA CAAATGCCCT      60
CATTTTTTCT TGTCTCTACA CTTCTCTTAT TCCTAATAAT ATCTCACTCT TCTCATGCCC     120
AAAACTCTCA ACAAGACTAT TTGGATGCCC ATAACACAGC TCGTGCAGAT GTAGGCGTGG     180
AACCATTAAC TTGGGACAAC GGGGTAGCAG CCTATGCACA AAATTATGTT TCTCAATTGG     240
CTGCAGACTG CAACCTCGTA CATTCTCATG GCCAATACGG CGAAAACCTA GCTCAGGGAA     300
GTGGCGATTT TATGACGGCT GCTAAGGCCG TCGAGATGTG GGTCGATGAG AAACAGTACT     360
ATGACCATGA CTCAAATACT TGTGCACAAG GACAGGTGTG TGGACACTAT ACTCAGGTGG     420
TTTGGCGTAA CTCGGTTCGT GTTGGATGTG CTAGGGTTAA GTGCAACAAT GGAGGATATG     480
TTGTCTCTTG CAACTATGAT CCTCCAGGTA ATGTCATAGG CCAAAGTCCA TACTAATTGA     540
AATGAATGTC CATTTCACGT TATATATGTA TGGACTTCTG CTTGATATAT ATAAACAACT     600
TAAATAATTG CACTAAAAAG CAACTTATAG TTAAAAGTAT ATAATATTTG TAATCCTCTG     660
AAGAACTGGA TCTGTAAAAA GTCCAAGTGG TCTTAATTAA GGGGGGGAGG ATATATGAAT     720
TCAGCTTGAT GTATGATCTG ATATTATTAT GAACTCTTTA GTACTCTTAC G             771
```

(2) INFORMATION FOR SEQ ID NO:11:

(i) SEQUENCE CHARACTERISTICS:
        (A) LENGTH: 696 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
GTTCAAAATA AAACATTTCT CCTATAGTCA TGGAATTTGT TCTCTTTTCA CAAATGTCTT      60
CATTTTTTCT TGTCTCTACG CTTCTCTTAT TCCTAATAAT ATCCCACTCT TGTCATGCTC     120
AAAACTCTCA ACAAGACTAT TTGGATGCCC ATAACACAGC TCGTGCAGAT GTAGGTGTAG     180
AACCTTTGAC CTGGGACGAC CAGGTAGCAG CCTATGCACA AAATTATGCT TCCCAATTGG     240
CTGCAGATTG TAACCTCGTA CATTCTCATG GTCAATACGG CGAAAACCTA GCTTGGGGAA     300
GTGGCGATTT CTTGACGGCC GCTAAGGCCG TCGAGATGTG GGTCAATGAG AAACAGTATT     360
ATGCCCACGA CTCAAACACT TGTGCCCAAG GACAGGTGTG TGGACACTAT ACTCAGGTGG     420
TTTGGCGTAA CTCGGTTCGT GTTGGATGTG CTAGGGTTCA GTGTAACAAT GGAGGATATA     480
TTGTCTCTTG CAACTATGAT CCTCCAGGTA ATGTTATAGG CAAAAGCCCA TACTAATTGA     540
AAACATATGT CCATTTCACG TTATATATGT GTGGACTTCT GCTTGATATA TATCAAGAAC     600
TTAAATAATT GCGCTAAAAA GCAACTTATA GTTAAGTATA TAGTACTATA TTTGTAATTC     660
TCTGAAGTGG ATATATAATA AGACCTAGTG CTCTTG                                696
```

(2) INFORMATION FOR SEQ ID NO:12:

(i) SEQUENCE CHARACTERISTICS:
    (A) LENGTH: 968 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:12:

| | | | | | |
|---|---|---|---|---|---|
| GAAAATGGAG | TTTTCTGGAT | CACCACTGAC | ATTGTTTTGT | TGTGTGTTTT | TCCTGTTCCT | 60 |
| AACAGGGAGC | TTGGCACAAG | GCATTGGCTC | AATTGTAACG | AATGACTTGT | TCAACGAGAT | 120 |
| GCTGAAGAAT | AGGAACGACG | GTAGATGTCC | TGCCAATGGC | TTCTATACTT | ATGATGCATT | 180 |
| CATAGCTGCT | GCCAATTCCT | TTCCTGGTTT | TGGAACTAGT | GGTGATGATA | CTGCCCGTAG | 240 |
| GAAAGAAATT | GCTGCCTTTT | TCGGTCAAAC | TTCTCATGAA | ACTACAGGTG | GTTCCCTGAG | 300 |
| TGCAGAACCT | TTTACAGGAG | GATATTGCTT | TGTTAGGCAA | AATGACCAGA | GTGACAGATA | 360 |
| TTATGGTAGA | GGACCCATCC | AATTGACAAA | CCAAAATAAC | TATGAGAAAG | CTGGAAATGC | 420 |
| AATTAGACAA | GACCTAGTTA | ACAACCCAGA | TTTAGTAGCT | ACAGATGCTA | CTATATCATT | 480 |
| CAAAACAGCT | ATATGGTTCT | GGATGACACC | ACAGGATAAT | AAGCCATCAA | GCCACGACGT | 540 |
| TATCATCGGT | AGTTGGACTC | CGTCCGCCGC | TGATCAGTCG | GCGAATCGAG | CACCTGGTTG | 600 |
| CGGTGTAATT | ACCAACATTA | TTAACGGTGG | AATTGAATGT | GGCGTAGGTC | CGAATGCCGC | 660 |
| AGTGGAAGAT | CGAATTGGAT | ACTACAGGAG | GTATTGTGGT | ATGTTGAATG | TTGCTCCTGG | 720 |
| GGACAACTTG | GACTGTTACA | ACCAAAGGAA | CTTCGCCCAA | GGCTAGGATT | CGTTAGATCA | 780 |
| TGTTATGTGT | ACACAAGTTA | TATTTGTATG | TAATGAATAA | GGGGATTGTG | TACCCATTTA | 840 |
| GAATAAGGGG | AAATATTTCT | GTTATTTGTC | TTCTTCGAAA | GAATAACCAG | TAGTTCCTAT | 900 |
| ATATCTGGTG | CTTCGAGTGA | AAACGAATAT | TCTATCCGGA | AATAAATACT | GTATGTTTCT | 960 |
| TGTCTTAT | | | | | | 968 |

(2) INFORMATION FOR SEQ ID NO:13:

(i) SEQUENCE CHARACTERISTICS:
       (A) LENGTH: 1108 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:13:

| | | | | | |
|---|---|---|---|---|---|
| CAGGTGCTCA | AGCAGGAGTT | TGTTATGGAA | GGCAAGGGAA | TGGATTACCA | TCTCCAGCAG | 60 |
| ATGTTGTGTC | GCTATGCAAC | CGAAACAACA | TTCGTAGGAT | GAGAATATAT | GATCCTGACC | 120 |
| AGCCAACTCT | CGAAGCGCTT | AGAGGCTCCA | ACATTGAGCT | CATGCTAGGT | GTCCCGAATC | 180 |
| CGGACCTTGA | GAATGTTGCT | GCTAGCCAAG | CCAATGCAGA | TACTTGGGTC | CAAAACAATG | 240 |
| TTAGGAACTA | TGGTAATGTC | AAGTTCAGGT | ATATAGCAGT | TGGAAATGAA | GTTAGTCCCT | 300 |
| TAAATGAAAA | CTCTAAGTAT | GTACCTGTCC | TTCTCAACGC | CATGCGAAAC | ATTCAAACTG | 360 |
| CCATATCTGG | TGCTGGTCTT | GGAAACCAGA | TCAAAGTCTC | CACAGCTATT | GAAACTGGAC | 420 |
| TTACTACAGA | CACTTCTCCT | CCATCAAATG | GGAGATTCAA | AGATGATGTT | CGACAGTTTA | 480 |
| TAGAGCCTAT | CATCAACTTC | CTAGTGACCA | ATCGCGCCCC | TTTGCTTGTC | AACCTTTATC | 540 |
| CTTACTTTGC | AATAGCAAAC | AATGCAGATA | TTAAGCTTGA | GTATGCACTT | TTTACATCCT | 600 |
| CTGAAGTTGT | TGTAAATGAT | AACGGAAGAG | GATACCGAAA | CCTTTTTGAT | GCCATCTTAG | 660 |
| ATGCCACATA | CTCGGCCCTT | GAAAAGGCTA | GTGGCTCGTC | TTTGGAGATT | GTTGTATCAG | 720 |

```
AGAGTGGTTG GCCTTCAGCT GGAGCAGGAC AATTAACATC CATTGACAAT GCCAGGACTT     780

ATAACAACAA CTTGATTAGT CACGTGAAGG GAGGGAGTCC CAAAAGGCCT TCCGGTCCAA     840

TAGAGACCTA CGTTTTCGCT CTGTTTGATG AAGATCAGAA AGACCCTGAA ATTGAGAAGC     900

ATTTTGGACT ATTTTCAGCA AACATGCAAC CAAAGTACCA GATCAGTTTT AACTAGTTAA     960

AAGCAAGAGG AGAGCATTAA TAGGAATAAG GACTTTCCTT TGTATGAAGA GAAAGTAGTC    1020

CATTGGCACT ATGTACTGAA ACTATATATC ATGCTCATAA AGAAAGCAGT TATTACAATA    1080

ATGAAACACT TACAAGAAAA GCCATCAA                                      1108
```

(2) INFORMATION FOR SEQ ID NO:14:

(i) SEQUENCE CHARACTERISTICS:
        (A) LENGTH: 1195 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
CTCAATTCTT GTTTTCCTTA CAAATGGCAC ATTTAATTGT CACACTGCTT CTCCTTAGTG      60

TACTTACATT AGCTACCCTG GATTTTACAG GTGCTCAAGC AGGAGTTTGT TATGGAAGGC     120

AAGGGAATGG ATTACCATCT CCAGCAGATG TTGTGTCGCT ATGCAACCGA ACAACATTC     180

GTAGGATGAG AATATATGAT CCTGACCAGC CAACTCTCGA AGCGCTTAGA GGCTCCAACA    240

TTGAGCTCAT GCTAGGTGTC CCGAATCCGG ACCTTGAGAA TGTTGCTGCT AGCCAAGCCA    300

ATGCAGATAC TTGGGTCCAA AACAATGTTA GGAACTATGG TAATGTCAAG TTCAGGTATA    360

TAGCAGTTGG AAATGAAGTT AGTCCCTTAA ATGAAAACTC TAAGTATGTA CCTGTCCTTC    420

TCAACGCCAT GCGAAACATT CAAACTGCCA TATCTGGTGC TGGTCTTGGA AACCAGATCA    480

AAGTCTCCAC AGCTATTGAA ACTGGACTTA CTACAGACAC TTCTCCTCCA TCAAATGGGA    540

GATTCAAAGA TGATGTTCGA CAGTTTATAG AGCCTATCAT CAACTTCCTA GTGACCAATC    600

GCGCCCCTTT GCTTGTCAAC CTTTATCCTT ACTTTGCAAT AGCAAACAAT GCAGATATTA    660

AGCTTGAGTA TGCACTTTTT ACATCCTCTG AAGTTGTTGT AAATGATAAC GGAAGAGGAT    720

ACCGAAACCT TTTTGATGCC ATCTTAGATG CCACATACTC GGCCCTTGAA AAGGCTAGTG    780

GCTCGTCTTT GGAGATTGTT GTATCAGAGA GTGGTTGGCC TTCAGCTGGA GCAGGACAAT    840

TAACATCCAT TGACAATGCC AGGACTTATA ACAACAACTT GATTAGTCAC GTGAAGGGAG    900

GGAGTCCCAA AAGGCCTTCC GGTCCAATAG AGACCTACGT TTTCGCTCTG TTTGATGAAG    960

ATCAGAAAGA CCCTGAAATT GAGAAGCATT TTGGACTATT TCAGCAAAC ATGCAACCAA    1020

AGTACCAGAT CAGTTTTAAC TAGTTAAAAG CAAGAGGAGA GCATTAATAG GAATAAGGAC    1080

TTTCCTTTGT ATGAAGAGAA AGTAGTCCAT TGGCACTATG TACTGAAACT ATATATCATG    1140

CTCATAAAGA AAGCAGTTAT TACAATAATG AAACACTTAC AAGAAAGCC ATCAA          1195
```

(2) INFORMATION FOR SEQ ID NO:15:

(i) SEQUENCE CHARACTERISTICS:
        (A) LENGTH: 584 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: CDS
      (B) LOCATION: 37..321

(xi) SEQUENCE DESCRIPTION: SEQ ID NO:15:

ACATCAAAAA CTTGAAACTC CAAATAGCTC ATCAAA ATG TTT TCC AAA ACT AAT      54
                                       Met Phe Ser Lys Thr Asn
                                         1               5

CTT TTT CTT TGC CTT TCT TTG GCT ATT TTG GTA ATA GTA ATA TCC TCA     102
Leu Phe Leu Cys Leu Ser Leu Ala Ile Leu Val Ile Val Ile Ser Ser
             10                  15                  20

CAA GTT GAT GCA AGG GAG ATG TCT AAG GCG CCT GCT TCA ATA ACC CAA     150
Gln Val Asp Ala Arg Glu Met Ser Lys Ala Pro Ala Ser Ile Thr Gln
         25                  30                  35

GCA ATG AAT TCA AAC ATC ATT ACT GAT CAG AAG ATG GGT GCA GGA ATC     198
Ala Met Asn Ser Asn Ile Ile Thr Asp Gln Lys Met Gly Ala Gly Ile
     40                  45                  50

ACC CGT AAG ATA CCG GGT TGG ATA CGA AAA GGT GCA AAA CCT GGA GGC     246
Thr Arg Lys Ile Pro Gly Trp Ile Arg Lys Gly Ala Lys Pro Gly Gly
 55                  60                  65                  70

AAA ATC ATT GGC AAA GCT TGC AAA ATT TGC TCA TGT AAA TAC CAG ATT     294
Lys Ile Ile Gly Lys Ala Cys Lys Ile Cys Ser Cys Lys Tyr Gln Ile
             75                  80                  85

TGC AGC AAA TGT CCT AAA TGT CAT GAC TAATGTACTT GTGCTGGTGT           341
Cys Ser Lys Cys Pro Lys Cys His Asp
         90                  95

GAGTCTAGTT TTGAGGATAA AGGGAAAGCT ATGAATAGCC TAATATAATT CTATTCACTT   401

TCCTCTAGTT AATTTCTCTT AGTTTGTGTT TTGTTTTGTT AATAGTTATT ATATTGTTGG   461

AACTTGCAAC AAGTCTTGGG TCAATATATA TTCTTGTTTT CTAGTCTTTA TATTGTATGG   521

TATTGTATTG TATTGTATTT TTCTTTAGTC ACGTGATATT TGAAACCAAA TCTGATTAAA   581

TCT                                                                584

(2) INFORMATION FOR SEQ ID NO:16:

(i) SEQUENCE CHARACTERISTICS:
        (A) LENGTH: 502 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 39..320

(xi) SEQUENCE DESCRIPTION: SEQ ID NO:16:

AGCAAAAAAT TAAAACTCGA TATAGCTCAT CTTTCAAA ATG TTT TCC AAA ACT        53
                                         Met Phe Ser Lys Thr
                                           1               5

ATT CTT TTT CTT TGC TTT TCT TTG GCT ATT TTG GTA ATG GTA ATA TCC    101
Ile Leu Phe Leu Cys Phe Ser Leu Ala Ile Leu Val Met Val Ile Ser
             10                  15                  20

TCA CAA GCT GAT GCA AGG GAG ATG TCT AAG GCG GCT GCT CCA ATT ACC    149
Ser Gln Ala Asp Ala Arg Glu Met Ser Lys Ala Ala Ala Pro Ile Thr
         25                  30                  35

CAA GCA ATG AAT TCA AAC ATC ATT ACT GAT CAG AAG ACG GGT GCA GGA    197
Gln Ala Met Asn Ser Asn Ile Ile Thr Asp Gln Lys Thr Gly Ala Gly
     40                  45                  50

ATC ATC CGT AAG ATA CCG GGT TGG ATA CGA AAA GGT GCA AAA GGA GGC    245
Ile Ile Arg Lys Ile Pro Gly Trp Ile Arg Lys Gly Ala Lys Gly Gly
 55                  60                  65

```
AAC ATC ATT GGC AAA GCT TGC AAA ATT TGC TCA TGT AAA TAC CAG ATT     293
Asn Ile Ile Gly Lys Ala Cys Lys Ile Cys Ser Cys Lys Tyr Gln Ile
 70              75                  80                  85

TGC AGC AAA TGT CCT AAA TGT CAT GAC TAATGTACTT GTGTTGGTGT           340
Cys Ser Lys Cys Pro Lys Cys His Asp
             90

GAGTCTAGTT TTGAGAATAA AGGGAAAGCT ATGAATAGCC TAATATAATT CTATCACTTT   400

CCTCTAGTTA ATTTCTCTTA GTTTGTGTTT TGTTAATAGT TATTATATTG TTGGAACTTG   460

CAACAAGTCT TGGGTCAATA TATATCTTGT TTTCTAGTCT TT                      502

(2) INFORMATION FOR SEQ ID NO:17:

(i) SEQUENCE CHARACTERISTICS:
        (A) LENGTH: 560 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 38..322

(xi) SEQUENCE DESCRIPTION: SEQ ID NO:17:

GACAGTAAAA AACTGAAACT CCAAATAGCT CATCAAA ATG TTT TCC AAA ACT AAC     55
                                         Met Phe Ser Lys Thr Asn
                                          1               5

CTT TTT CTT TGC CTT TCT TTG GCT ATT TTG CTA ATT GTA ATA TCC TCA    103
Leu Phe Leu Cys Leu Ser Leu Ala Ile Leu Leu Ile Val Ile Ser Ser
             10                  15                  20

CAA GCT GAT GCA AGG CAG ATT TCT AAG GCG GCT GCT CCA ATT ACC CAT    151
Gln Ala Asp Ala Arg Gln Ile Ser Lys Ala Ala Ala Pro Ile Thr His
         25                  30                  35

GCA ATG AAT TCA AAC AAC ATT ACT AAT CAG AAG ACG GGT GCC GGA ATC    199
Ala Met Asn Ser Asn Asn Ile Thr Asn Gln Lys Thr Gly Ala Gly Ile
 40                  45                  50

ATC CGT AAG ATA CCG GGT TGG ATA CGA AAA GGT GCA AAA CCA GGA GGC    247
Ile Arg Lys Ile Pro Gly Trp Ile Arg Lys Gly Ala Lys Pro Gly Gly
 55                  60                  65                  70

AAA GTC GCC GGC AAA GCT TGT AAA ATT TGC TCA TGT AAA TAC CAG ATT    295
Lys Val Ala Gly Lys Ala Cys Lys Ile Cys Ser Cys Lys Tyr Gln Ile
             75                  80                  85

TGC AGC AAA TGT CCT AAA TGT CAT GAC TAAAGTTAGG CCTTGAGACT          342
Cys Ser Lys Cys Pro Lys Cys His Asp
             90                  95

ATGTACTTGT GCTGGTGTGA GTTTAATTTT GAGAGTAAAG GGAAAGTTAT GAATAGCCTA  402

ATATAATTCT ATTCACTATG TTTTCTTAGT AATTCTTATT GTTGAAACTT GGAACAGGTC  462

TTTGGGTCAA AATGTACCTC TTGTCTTGTA GTCTTTCAAC TGTATGGTAT TGTACTGTAT  522

CTTTCTTTAG CCACTTGATA TCAAATCCGA TTAAATCT                          560

(2) INFORMATION FOR SEQ ID NO:18:

(i) SEQUENCE CHARACTERISTICS:
        (A) LENGTH: 529 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
```

(B) LOCATION: 37..321

(xi) SEQUENCE DESCRIPTION: SEQ ID NO:18:

```
ACAGTAAAAA ACTGAAACTC CAAATAGCTC ATCAAA ATG TTT TCC AAA ACT AAC        54
                                        Met Phe Ser Lys Thr Asn
                                                            5

CTT TTT CTT TGC CTT TCT TTG GCT ATT TTG CTA ATT GTA ATA TCC TCA       102
Leu Phe Leu Cys Leu Ser Leu Ala Ile Leu Leu Ile Val Ile Ser Ser
            10                  15                  20

CAA GCT GAT GCA AGG GAG ATG TCT AAG GCG GCT GTT CCA ATT ACC CAA       150
Gln Ala Asp Ala Arg Glu Met Ser Lys Ala Ala Val Pro Ile Thr Gln
        25                  30                  35

GCA ATG AAT TCA AAC AAC ATT ACT AAT CAG AAG ACG GGT GCC GGA ATC       198
Ala Met Asn Ser Asn Asn Ile Thr Asn Gln Lys Thr Gly Ala Gly Ile
    40                  45                  50

ATC CGT AAG ATA CCG GGT TGG ATA CGA AAA GGT GCA AAA CCA GGA GGC       246
Ile Arg Lys Ile Pro Gly Trp Ile Arg Lys Gly Ala Lys Pro Gly Gly
55                  60                  65                  70

AAA GTC GCC GGC AAA GCT TGT AAA ATT TGC TCA TGT AAA TAC CAG ATT       294
Lys Val Ala Gly Lys Ala Cys Lys Ile Cys Ser Cys Lys Tyr Gln Ile
                75                  80                  85

TGC AGC AAA TGT CCT AAA TGT CAT GAC TAAAGTTAGG CCTTGAGACT             341
Cys Ser Lys Cys Pro Lys Cys His Asp
            90                  95

ATGTACTTGT GCTGGTGTGA GTTTAGTTTT GAGAGTAAAG GGAAAGTTAT GAATAGCCTA     401

ATATAATTGT ATTCACTATG TTTTCTTAGT AATTCTTATT GTTGAAACTT GGAACAGGTC     461

TTTGGGTCAA AATGTACCTC TTGTCTTGTA GTCTTTCAAC TGTATAGTAT TGTACTGTAT     521

TTTTCTTT                                                              529
```

(2) INFORMATION FOR SEQ ID NO:19:

(i) SEQUENCE CHARACTERISTICS:
        (A) LENGTH: 607 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 32..364

(xi) SEQUENCE DESCRIPTION: SEQ ID NO:19:

```
AAAAAATTGA AACTCCAAAT AGCTCATCAA A ATG TTT TCC AAA ACT AAC CTT         52
                                  Met Phe Ser Lys Thr Asn Leu
                                  1               5

TTT CTT TGC CTT TCT TTG GCT ATT TTG CTA ATT GTA ATA TCC TCA CAA       100
Phe Leu Cys Leu Ser Leu Ala Ile Leu Leu Ile Val Ile Ser Ser Gln
            10                  15                  20

GCT GAT GCA AGG GAG ACG TCT AAG GCA ACT GCT CCA ATT ACC CAA GAA       148
Ala Asp Ala Arg Glu Thr Ser Lys Ala Thr Ala Pro Ile Thr Gln Glu
        25                  30                  35

ATG AAT TCA AAC AAC ACT ACT GAT CAG AAG ATA CCA AAA CGT CCA AAA       196
Met Asn Ser Asn Asn Thr Thr Asp Gln Lys Ile Pro Lys Arg Pro Lys
    40                  45                  50                  55

CCA GGA GGC AAT ATC TTC GGC AAA GCT TGT AAA ATT TGC CCA TGT AAA       244
Pro Gly Gly Asn Ile Phe Gly Lys Ala Cys Lys Ile Cys Pro Cys Lys
                60                  65                  70

TAC CAG ATT TGC AGC AAA TGT CCT AAA TGT GAT GAC CAA AAT ATC GCC       292
Tyr Gln Ile Cys Ser Lys Cys Pro Lys Cys Asp Asp Gln Asn Ile Ala
            75                  80                  85
```

```
GGC AAA TTT TGT AAA ATT TGC TCA TGT AAG ACT CAG ATT TGC AGT AAA        340
Gly Lys Phe Cys Lys Ile Cys Ser Cys Lys Thr Gln Ile Cys Ser Lys
         90                  95                 100

TGT CCT AAA TGT CAT AAC CAA AAT TAGGCCTCAG AGACTATGTA CTTGTGCTGG        394
Cys Pro Lys Cys His Asn Gln Asn
        105                 110

TGTGAGTTTA GTTTTGAGAA TAAAAGGAAA GTTATGAATA GCCTAATATA ATTCTATTCA       454

CTTTCCTCTA GTTAATTTCT CTTAGTTTGT GTTTTGTTTT GTTAGTAGTT CCTATTGTTG       514

CAACTTGCAA CAAGTCTTGG GGTCAACATG TACCTCTTGT CTTGTAGTCT TTCGACTGTA       574

TGATATTGTA CCGTATTGTA TTGTATTTTC TTT                                    607

(2) INFORMATION FOR SEQ ID NO:20:

(i) SEQUENCE CHARACTERISTICS:
        (A) LENGTH: 1358 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 7..1086

(xi) SEQUENCE DESCRIPTION: SEQ ID NO:20:

CCTCAA ATG GCT GCT ATC ACA CTC CTA GGA TTA CTA CTT GTT GCC AGC         48
       Met Ala Ala Ile Thr Leu Leu Gly Leu Leu Leu Val Ala Ser
        1               5                  10

AGC ATT GAC ATA GCA GGG GCT CAA TCG ATA GGT GTT TGC TAT GGA ATG         96
Ser Ile Asp Ile Ala Gly Ala Gln Ser Ile Gly Val Cys Tyr Gly Met
 15              20                  25                  30

CTA GGC AAC AAC TTG CCA AAT CAT TGG GAA GTT ATA CAG CTC TAC AAG        144
Leu Gly Asn Asn Leu Pro Asn His Trp Glu Val Ile Gln Leu Tyr Lys
                 35                  40                  45

TCA AGA AAC ATA GGA AGA CTG AGG CTT TAT GAT CCA AAT CAT GGA GCT        192
Ser Arg Asn Ile Gly Arg Leu Arg Leu Tyr Asp Pro Asn His Gly Ala
             50                  55                  60

TTA CAA GCA TTA AAA GGC TCA AAT ATT GAA GTT ATG TTA GGA CTT CCC        240
Leu Gln Ala Leu Lys Gly Ser Asn Ile Glu Val Met Leu Gly Leu Pro
         65                  70                  75

AAT TCA GAT GTG AAG CAC ATT GCT TCC GGA ATG GAA CAT GCA AGA TGG        288
Asn Ser Asp Val Lys His Ile Ala Ser Gly Met Glu His Ala Arg Trp
     80                  85                  90

TGG GTA CAG AAA AAT GTT AAA GAT TTC TGG CCA GAT GTT AAG ATT AAG        336
Trp Val Gln Lys Asn Val Lys Asp Phe Trp Pro Asp Val Lys Ile Lys
 95                 100                 105                 110

TAT ATT GCT GTT GGG AAT GAA ATC AGC CCT GTC ACT GGC ACA TCT TAC        384
Tyr Ile Ala Val Gly Asn Glu Ile Ser Pro Val Thr Gly Thr Ser Tyr
                115                 120                 125

CTA ACC TCA TTT CTT ACT CCT GCT ATG GTA AAT ATT TAC AAA GCA ATT        432
Leu Thr Ser Phe Leu Thr Pro Ala Met Val Asn Ile Tyr Lys Ala Ile
            130                 135                 140

GGT GAA GCT GGT TTG GGA AAC AAC ATC AAG GTC TCA ACT TCT GTA GAC        480
Gly Glu Ala Gly Leu Gly Asn Asn Ile Lys Val Ser Thr Ser Val Asp
        145                 150                 155

ATG ACC TTG ATT GGA AAC TCT TAT CCA CCA TCA CAG GGT TCG TTT AGG        528
Met Thr Leu Ile Gly Asn Ser Tyr Pro Pro Ser Gln Gly Ser Phe Arg
    160                 165                 170

AAC GAT GCT AGG TGG TTT GTT GAT CCC ATT GTT GGC TTC TTA AGG GAC        576
Asn Asp Ala Arg Trp Phe Val Asp Pro Ile Val Gly Phe Leu Arg Asp
```

```
     175                 180                 185                 190
ACA CGT GCA CCT TTA CTC GTT AAC ATT TAC CCC TAT TTC AGT TAT TCT      624
Thr Arg Ala Pro Leu Leu Val Asn Ile Tyr Pro Tyr Phe Ser Tyr Ser
                    195                 200                 205

GGT AAT CCA GGC CAG ATT TCT CTC CCC TAT TCT CTT TTT ACA GCA CCA      672
Gly Asn Pro Gly Gln Ile Ser Leu Pro Tyr Ser Leu Phe Thr Ala Pro
                210                 215                 220

AAT GTG GTG GTA CAA GAT GGT TCC CGC CAA TAT AGG AAC TTA TTT GAT      720
Asn Val Val Val Gln Asp Gly Ser Arg Gln Tyr Arg Asn Leu Phe Asp
            225                 230                 235

GCA ATG CTG GAT TCT GTG TAT GCT GCC CTC GAG CGA TCA GGA GGG GCA      768
Ala Met Leu Asp Ser Val Tyr Ala Ala Leu Glu Arg Ser Gly Gly Ala
        240                 245                 250

TCT GTA GGG ATT GTT GTG TCC GAG AGT GGC TGG CCA TCT GCT GGT GCA      816
Ser Val Gly Ile Val Val Ser Glu Ser Gly Trp Pro Ser Ala Gly Ala
255                 260                 265                 270

TTT GGA GCC ACA TAT GAC AAT GCA GCA ACT TAC TTG AGG AAC TTA ATT      864
Phe Gly Ala Thr Tyr Asp Asn Ala Ala Thr Tyr Leu Arg Asn Leu Ile
                    275                 280                 285

CAA CAC GCT AAA GAG GGT AGC CCA AGA AAG CCT GGA CCT ATT GAG ACC      912
Gln His Ala Lys Glu Gly Ser Pro Arg Lys Pro Gly Pro Ile Glu Thr
                290                 295                 300

TAT ATA TTT GCC ATG TTT GAT GAG AAC AAC AAG AAC CCT GAA CTG GAG      960
Tyr Ile Phe Ala Met Phe Asp Glu Asn Asn Lys Asn Pro Glu Leu Glu
            305                 310                 315

AAA CAT TTT GGA TTG TTT TCC CCC AAC AAG CAG CCC AAA TAT AAT ATC     1008
Lys His Phe Gly Leu Phe Ser Pro Asn Lys Gln Pro Lys Tyr Asn Ile
        320                 325                 330

AAC TTT GGG GTC TCT GGT GGA GTT TGG GAC AGT TCA GTT GAA ACT AAT     1056
Asn Phe Gly Val Ser Gly Gly Val Trp Asp Ser Ser Val Glu Thr Asn
335                 340                 345                 350

GCT ACT GCT TCT CTC GTA AGT GAG ATG TGAGCTGATG AGACACTTGA           1103
Ala Thr Ala Ser Leu Val Ser Glu Met
                    355                 360

AATCTCTTTA CATACGTATT CCTTGGATGG AAAACCTAGT AAAAACAAGA GAAATTTTTT   1163

CTTTATGCAA GATACTAAAT AACATTGCAT GTCTCTGTAA GTCCTCATGG ATTGTTATCC   1223

AGTGACGATG CAACTCTGAG TGGTTTTAAA TTCCTTTTCT TTGTGATATT GGTAATTTGG   1283

CAAGAAACTT TCTGTAAGTT TGTGAATTTC ATGCATCATT AATTATACAT CAGTTCCATG   1343

TTTGATCAAA AAAAA                                                    1358

(2) INFORMATION FOR SEQ ID NO:21:

(i) SEQUENCE CHARACTERISTICS:
        (A) LENGTH: 1204 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

GTGTTTCTTA CTCTCTCATT TCCATTTTAG CTATGACTTT ATGCATTAAA AATGGCTTTC     60

TTGCAGCTGC CCTTGTACTT GTTGGGCTGT TAATTTGCAG TATCCAAATG ATAGGGGCAC    120

AATCTATTGG AGTATGCTAT GGAAAACATG CAAACAATTT ACCATCAGAC CAAGATGTTA    180

TAAACCTATA CGATGCTAAT GGCATCAGAA AGATGAGAAT CTACAATCCA GATACAAATG    240

TCTTCAACGC TCTCAGAGGA AGTAACATTG AGATCATTCT CGACGTCCCA CTTCAAGATC    300

TTCAATCCCT AACTGATCCT TCAAGAGCCA ATGGATGGGT CCAAGATAAC ATAATAAATC    360
```

```
ATTTCCCAGA TGTTAAATTT AAATATATAG CTGTTGGAAA TGAAGTCTCT CCCGGAAATA        420

ATGGTCAATA TGCACCATTT GTTGCTCCTG CCATGCAAAA TGTATATAAT GCATTAGCAG        480

CAGCAGGGTT GCAAGATCAA ATCAAGGTCT CAACTGCAAC ATATTCAGGG ATCTTAGCGA        540

ATACCAACCC GCCCAAAGAT AGTATTTTTC GAGGAGAATT CAATAGTTTC ATTAATCCCA        600

TAATCCAATT TCTAGTACAA CATAACCTTC CACTCTTAGC CAATGTCTAT CCTTATTTTG        660

GTCACATTTT CAACACTGCT GATGTCCCAC TTTCTTATGC TTTGTTCACA CAACAAGAAG        720

CAAATCCTGC AGGATATCAA AATCTTTTTG ATGCCCTTTT GGATTCTATG TATTTTGCTG        780

TAGAGAAAGC TGGAGGACAA AATGTGGAGA TTATTGTATC TGAAAGTGGC TGGCCTTCTG        840

AAGGAAACTC TGCAGCAACT ATTGAAAATG CTCAAACTTA CTATGAAAAT TTGATTAATC        900

ATGTGAAAAG CGGGGCAGGA ACTCCAAAGA AACCTGGAAA TGCTATAGAA ACTTATTTAT        960

TTGCCATGTT TGATGAAAAT AATAAGGAAG GAGATATCAC AGAGAAACAC TTTGGACTCT       1020

TTTCTCCTGA TCAGAGGGCA AAATATCAAC TCAATTTCAA TTAATTAATG CATGGTAACA       1080

TTTATTGATA TATATAGTGA TATGAGTAAT AAGGAGAAGT AGAACTGCTA TGTTTTTCTC       1140

TTCAATTGAA AATGTAACTC TGGTTTCACT TTGATATTTA TATGACATGT TTATTGAGAT       1200

CTAA                                                                   1204

(2) INFORMATION FOR SEQ ID NO:22:

(i) SEQUENCE CHARACTERISTICS:
        (A) LENGTH: 1131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

ACCAGAGAAG ACCCCATTTG CAGTATCAAA AATGGGTTTA CCTAAAATGG CAGCCATTGT         60

TGTGGTGGTG GCTTTGATGC TATCACCCTC TCAAGCCCAG YTTTCTCCTT TCTTCTACGC        120

CACCACATGC CCTCAGCTGC CTTTCGTTGT TCTCAACGTG GTTGCCCAAG CCCTACAGAC        180

TGATGACCGA GCTGCTGCTA AGCTCATTCG CCTCCATTTT CATGATTGCT TTGTCAATGG        240

GTGTGATGGA TCGATTCTAT TGGTAGACGT ACCGGGCGTT ATCGATAGTG AACTTAATGG        300

ACCTCCAAAT GGTGGAATCC AAGGAATGGA CATTGTGGAC AACATCAAAG CAGCAGTTGA        360

GAGTGCTTGT CCAGGAGTTG TTTCTTGCGC TGATATCTTA GCCATTTCAT CTCAAATCTC        420

TGTTTTCTTG TCGGGAGGAC CAATTTGGGT TGTACCAATG GGAAGAAAAG ACAGCAGAAT        480

AGCCAATAGA ACTGGAACCT CAAACTTACC TGGTCCCTCA GAAACTCTAG TGGGACTTAA        540

AGGCAAGTTT AAAGATCAAG GGCTTGATTC TACAGATCTC GTGGCTCTAT CAGGAGCCCA        600

CACGTTTGGA AAATCAAGAT GCATGTTCTT CAGTGACCGC CTCATCAACT TCAACGGCAC        660

AGGAAGACCC GACACAACGC TTGACCCAAT ATACAGGGAG CAGCTTCGAA GACTTTGTAC        720

TACTCAACAA ACACGAGTAA ATTTCGACCC AGTCACACCC ACTAGATTTG ACAAGACCTA        780

TTACAACAAT TTGATTAGCT TAAGAGGGCT CTCTCCAAAGC GACCAAGAGC TCTTCTCAAC        840

TCCCAGAGCT GATACCACAG CCATTGTCAR AACTTTTGCT GCCAACGAAC GTGCCTTCTT        900

TAAACAATTT GTGAAATCAA TGATCAAAAT GGGCAACCTC AAGCCTCCCC CTGGCATTGC        960

ATCAGAAGTT AGATTGGACT GTAAGAGGGT CAACCCAGTC AGAGCCTACG ACGTTATGTA       1020

ATAACTTTAT CCCACTTCAT CCCTTCTACT TTTGCTGTCT CTTGTACTAC TTTGTTGATG       1080
```

TATTAGTTCA ACCGGTTAAG ATATATATAT CGTTGACCTA AATAATAGAT C       1131

(2) INFORMATION FOR SEQ ID NO:23:

(i) SEQUENCE CHARACTERISTICS:
        (A) LENGTH: 627 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

AATAGTTTCA TTAATCCCAT AATCCAATTT CTAGCACGAA ATAACCTTCC ACTCTTAGCC       60
AATGTCTATC CTTATTTTGG TCACATTTAC AACACTGCTG ATGTCCCACT TTCTTATGCA      120
TTGTTCACAC AACAAGAAGC AAATCCTGCA GGATATCAAA ATCTTTTTGA TGCCCTTTTG      180
GATTCTATGT ATTTTGCTGT AGAGAAAGCT GGAGGACCAA ATGTGGAGAT TATTGTATCT      240
GAAAGTGGCT GGCCTTCTGA AGGAAACTCT GCAGCAACTA TTGAAAATGC TCAAACTTAT      300
TACAGAAATT TGATTGATCA TGTGAAAAGA GGGGCAGGAA CCCCAAAGAA ACCTGGAAAG      360
ACTATAGAAA CTTATTTATT TGCCATGTTT GATGAAAATG ATAAGAAAGG AGAAATTACA      420
GAGAAACACT TTGGACTCTT TTCTCCTGAT CAGAGGGCAA AATATCAACT CAATTTCAAT      480
TAATTAATGG CAATATATAT TGATATATAT ATATAGTGAT ATGAGTAATA AGGAGAACTG      540
CTATGTTTTT CTCTTCAATT GAAAATGYAA TTCTGGTTTC ACTTTGATAT CTATATGTCA      600
TTTATTGAAA TCTCGTCTTT TGGTTTT                                         627

(2) INFORMATION FOR SEQ ID NO:24:

(i) SEQUENCE CHARACTERISTICS:
        (A) LENGTH: 966 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

AATGTCTTCA ACGCTCTCAG AGGAAGTAAC ATTGAGATCA TTCTCGACGT CCCACTTCAA       60
GATCTTCAAT CCCTAACTGA TCCTTCAAGA GCCAATGGAT GGGTCCAAGA TAACATAATA      120
AATCATTTCC CAGATGTTAA ATTTAAATAT ATAGCTGTTG GAAATAAAGT CTCTCCCGGA      180
AATAATGGTC AATATGCACC ATTTGTTGCT CCTGCCATGC AAAATGTATA TAATGCATTA      240
GCAGCAGCAG GGTTGCAAGA TCAAATCAAG GTCTCAACTG CAACATATTC AGGGATCTTA      300
GCGAATACCT ACCCGCCCAA AGATAGTATT TTTCGAGGAG AATTCAATAG TTTCATTAAT      360
CCCATAATCC AATTTCTAGT ACAACATAAC CTTCCACTCT TAGCCAATGT CTATCCTTAT      420
TTTGGTCACA TTTTCAACAC TGCTGATGTC CCACTTTCTT ATGCTTTGTT CACACAACAA      480
GAAGCAAATC CTGCAGGATA TCAAAATCTT TTTGATGCCC TTTTGGATTC TATGTATTTT      540
GCTGTAGAGA AAGCTGGAGG ACAAAATGTG GAGATTATTG TATCTGAAAG TGGCTGGCCT      600
TCTGAAGGAA ACTCTGCAGC AACTATTGAA AATGCTCAAA CTTACTATGA AAATTTGATT      660
AATCATGTGA AAGCGGGGC AGGAACTCCA AAGAAACCTG GAAGGCTAT AGAAACTTAT       720
TTATTTGCCA TGTTTGATGA AAATAATAAG GAAGGAGATA TCACAGAGAA ACACTTTGGA      780
CTCTTTTCTC CTGATCAGAG GGCAAAATAT CAACTCAATT TCAATTAATT AATGCATGGT      840
AACATTTATT GATATATATA GTGATATGAG TAATAAGGAG AAGTAGAACT GCTATGTTTT      900

```
TCTCTTCAAT TGAAAATGTA ACTCTGGTTT CACTTTGATA TTTATATGAC ATATTTATTG      960

AGATCT                                                                 966
```

(2) INFORMATION FOR SEQ ID NO:25:

(i) SEQUENCE CHARACTERISTICS:
        (A) LENGTH: 1099 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
ATGGCTTTCT TGCAGCTGCC CTTGTACTTG TTGGGCTRAT AATGTGCAGT ATCCAAATCA       60

TAGGGGCACA GTCTATTGGA GTATGCTATG GAAAAGCTGC CAACAATTTA CCATCAGACC      120

AAGATGTTAT AAACCTATAC AATGCTAATG GCATCAGAAA GTTGAGAATT TACTATCCTG      180

ATAAAAACAT TTTCAAAGCT CTCAATGGAA GTAACATTGA GATCATTCTT GGTGTCCCAA      240

ATCAAGACCT TGAAGCCCTA GCCAATTCTT CAATAGCCAA TGGTTGGGTT CAAGATAACA      300

TAAGAAGTCA TTTCCCATAT GTTAAATTCA AGTACATATC TATAGGAAAT AAAGTATCTC      360

CCACAAATAA TGATCAATAT TCAGAATTTC TTCTTCAAGC AATGAAAAAT GTGTACAATG      420

CTTTAGCAGC AGCAGGGTTG CAAGATATGA TCAAGGTCTC AACTGTGACA TATTCAGGGG      480

TCTTAGCGAA TACCTACCCA CCTGAACGTA GTATTTTTCG CGAAGAATTC AAGAGTTTCA      540

TTAATCCGAT AATCCAATTT CTAGCACGAA ATAACCTTCC ACTCTTAGCC AATGTCTATC      600

CTTATTTTGT TCACGTTTCC AACACTGCTG ATGTTTCACT TTCTTATGCA TTGTTCACAC      660

AGCAAGGAAC AAATTCAGCA GGGTATCAAA ATCTTTTTGA TGCTATTTTG GATTCTATGT      720

ATTTTGCTGT AGAGAAAGCT GGAGGACCAA ATGTGGAGAT TATTGTATCT GAAAGTGGAT      780

GGCCTTCTGA AGGAAGCTCT GCAGCAACTA TTGAAAACGC TCAAACTTAT TACAGAAATT      840

TGATTAATCA TGTGAAAAGC GGGGCAGGAA CTCCAAAGAA ACCTGGAAAG ACTATAGAAA      900

CTTATTTGTT TGCCATGTTT GATGAAAATG ATAAGATAGG AGAAATCACA GAGAAACACT      960

TTGGACTGTT TTCTCCTGAT CAAAGGGCAA AATATCAACT CAATTTCAAT TATTTGCCAA     1020

TATATATATT GAGATGAGTA ATAAGGACAA CTGTTATGTT TTTCTCTTCA ATTGAAAATG     1080

TAACTCTGGT TTCACTTTG                                                 1099
```

(2) INFORMATION FOR SEQ ID NO:26:

(i) SEQUENCE CHARACTERISTICS:
        (A) LENGTH: 1201 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

```
GAAACTTCTC TCATTTCCAT TTTAGCTATG GCTTTGTGCA TTAAAAATGG CTTTCTTGCG       60

GCTGCCCTTG TACTTGTTGG GCTGTTAATG TGCAGCATCC AAATGATAGG GGCACAATCT      120

ATTGGAGTAT GCTATGGAAA AATTGCCAAC AATTTACCAT CAGAACAAGA TGTCATAAAC      180

CTATACAAGG CTAATGGCAT TAGAAAGATG AGAATCTACT ATCCAGATAA AAACATCTTC      240

AAAGCTCTCA AAGGAAGTAA CATTGAGATC ATTCTTGATG TTCCAAATCA AGATCTTGAA      300

GCCCTAGCCA ATTCTTCAAT AGCCAATGGT TGGGTTCAAG ATAACATAAG AAGTCATTTC      360
```

```
CCATATGTTA AATTCAAGTA CATATCTATA GGAAATGAAG TATCTCCCAT AAATAATGGT      420

CAATATTCAC AATTTCTTCT TCATGCAATG GAAAATGTGT ACAATGCATT AGCAGCATCA      480

GGGTTGCAAG ATAAGATCAA GGTCACAACT GCAACATATT CAGGGCTCTT AGCAAACACC      540

TACCCACCCA AAGCTAGTAT ATTTCGAGGA GAATTCAATA GTTTCATTAA TCCCATAATC      600

CAATTTCTAG CACAAAATAA CCTTCCACTC TTAGCCAATG TCTACCCTTA TTTTGTTCAC      660

ATTTCCAACA CTGCTGATGT CCCACTTTCT TATGCATTGT TCACACAACG AGGAAAAAAT      720

TCAGCAGGGT ATCAAAATCT TTTTGATGCC ATTTTGGATT CTATGTATTT TGCTGTAGAG      780

AAAGCTGGAG GACCAAATGT GGAGATTATT GTATCTGAAA GTGGCTGGCC TTCTGAAGGA      840

AACTCTGCAG CAACTATTGA AAATGCTCAA ACTTATTACA GAAATTTGAT TGATCATGTT      900

AAAAGAGGGG CAGGAACTCC AAAGAAACCT GGAAAGTCTA TAGAAACTTA TTTATTTGCC      960

ATGTTTGATG AAAATGTTAA GAAAGGAGAA ATCACAGAGA AACACTTTGG GCTCTTTTCT     1020

CCTGATCAGA GGGCAAAATA TCAACTCAAT TTCAATTCTT TGATGCCAAT ATATATTGAT     1080

ATATCTAGAG TGATATGAGT AATAAGGAGA ACTGTTATGT TTTTCTCCAA TTGAAAATGT     1140

AACTATGGTT TCACTTTGAT ATCTATATGT CATATTTATT GAAATCACGT CTTTTGGTTT     1200

T                                                                    1201

(2) INFORMATION FOR SEQ ID NO:27:

(i) SEQUENCE CHARACTERISTICS:
        (A) LENGTH: 1181 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

GGTTTTTTTT TTTTTTTTTT TTTTTTTTT TTTTTTTTT TTTTTTAGGA AGCAAGGAAG        60

ATTTACTCTT ATTATACAGT AGTATGGAGA TCACATTCTA TTAAACTGAT ACAGACTATG     120

TTTTCACAGG CACCAACACC ATTAGTTTGT TCCAAGTACA GGGCTGAGCT TAACGGATAG     180

AACTCTCTCT GGAAATGAAG ATGACAGCAG ATGACAGTCG AATTCGGAGT CAAAAGAGCT     240

ATCGAAACTG ATATTCGTGC TGGTGCTAAA CTCATTCGCT TCCATTTCCA CGATTGTTTC     300

GTCCAAGGCT GCGATGGGTC TGTTTTGCTA GAGGATCCTC CTGGCTTCGA GACCGAGCTC     360

AACGGACTTG GAAACTTAGG AATCCAAGGA ATCGAGATTA TCGACGCTAT CAAAGCTGCC     420

GTCGAGATAG AATGCCCTGG CGTTGTCTCC TGTGCCGACA TCCTAGCTCA AGCCTCTAAG     480

GACTCTGTCG ACGTGCAAGG AGGACCCAGT TGGAGAGTTC TATACGGCAG AAGAGATAGC     540

AGAACAGCCA ATAAAACAGG GGCTGATAAC CTCCCAAGCC CCTTCGAAAA TCTTGACCCA     600

CTCGTAAAAA AATTTGCAGA CGTTGGTTTA AATGAAACCG ACCTTGTTGC TCTATCAGGG     660

GCACATACGT TTGGTCGGTC CAGATGCGTG TTCTTCAGTG GTCGTTTGTC CAACTTCAGT     720

GGCAGTGGGC AACCAGATCC AACGCTGGAT CCAACTTACA GCAAGAACT  TCTAAGCGCT     780

TGTACAAGCC AAGACACACG AGTGAATTTC GATCCAACAA CACCTGATAA ATTTGATAAG     840

AATTACTTCA CCAATCTTCG AGCCAATAAA GGGCTGTTAC AGAGTGACCA AGTTCTGCAT     900

TCAACGGAAG GGGCTAAAAC AGTTGAAATT GTTAGACTTA TGGCGTTGAA ACAAGAAACT     960

TTCTTTAGAC AATTTCGGTT GTCGATGATT AAGATGGGCC ACATTAAACC ATTAACTGGA    1020

AGCCAAGGGC CAATTAGAAG AAACTGCAGG AGGGTTAATG ACTTGGGAAG TGAAACAGGG    1080

CATGATGTTA TGTAAATTTT GTCTTCCCTC TTACGTTTGT TTGTTTCTCT CTTCCACTTC    1140
```

CATCTCCTTT CTATAATAAA TTAGCTCCAC TACATCACCT C        1181

(2) INFORMATION FOR SEQ ID NO:28:

(i) SEQUENCE CHARACTERISTICS:
        (A) LENGTH: 686 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

AATACACAGA TTAATATATG TATCTAAAGA AGATGATGAA TGGAGGCTAT AGTTTATTTT        60
TTATTTTAAA AAAAAAAAAT TCAGCCACCG ATTTGCGAAT TCAACAATA CAGGAAGGCC        120
AGACCAATCA TTGAACCCAG ACTACAGGAG CTTTCTTGAA GGGGTTTGTT CAGCAGGAGC        180
AGACACAAGA GCGAATTTCG ATCCAGTAAC ACCGGATGTG TTTGACAAAA ATTACTACAC        240
AAATCTTCAA GTGGGGAAGG GGCTTTTGCA GAGCGATCAA GAGCTGATCT CAACACCTGG        300
AGCTGACACC ATCGTCATTG TTAACAGCTT TGCAGAAAGA GAAGGAACAT TCTTCAAGGA        360
GTTCAGACAG TCGATGATCA ATATGGGAAA TATAAAGCCA TTGACTGGTG ACAAGGGGA        420
AATTAGAAGA AACTGCAGGC GGGTTAATTC AAACTCTGGT TTGTTGGGTG GAGAAGGAGA        480
AGGATCAGAA GGCCACGATG TTATGTAAAA CTAAAAAAAT GAGCTGCCTG TTTCTGCATA        540
TGTGGTGTTC ATCATATCCA TAACTTATAA TTAAGCATAA TGTGTGTGTT AATTTAGTTG        600
GGTGTTTGTG CTTTCTTCCA TGAATAAAAA TGCAGGGGTA GGCTCATCTT TTGTTTTGAT        660
TAAGCTTACT TATTATGTTG TCGGAT        686

(2) INFORMATION FOR SEQ ID NO:29:

(i) SEQUENCE CHARACTERISTICS:
        (A) LENGTH: 1064 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

AAACAATGAA CATTAAGGTA TCATTACTTT TCATTCTACC AATATTCTTG CTTCTCCTAA        60
CCAGCAAAGT AAAAGCTGGA GATATTGTAG TCTATTGGGG CCAAGATGTA GGAGAAGGTA        120
AATTGATTGA CACATGCAAC TCTGGTCTCT ACAATATTGT CAACATTGCC TTTTTATCTT        180
CTTTTGGCAA TTTCCAAACT CCTAAACTTA ACTTAGCTGG CCATTGTGAA CCATCTTCTG        240
GTGGTTGCCA ACAGTTGACA AAAAGCATCA GACATTGTCA AAGCATAGGC ATTAAAATCA        300
TGCTCTCCAT TGGAGGTGGA ACTCCTACCT ACACATTATC CTCAGTTGAT GATGCCAGAC        360
AAGTTGCTGA TTACCTGTGG AACAATTTTC TCGGCGGCCA ATCATCTTTT AGGCCACTTG        420
GAGATGCTGT ATTAGATGGC ATAGATTTTG ATATTGAACT TGGCCAACCA CATTATATTG        480
CACTTGCCAG GAGACTTTCA GAACATGGCC AACAAGGTAA AAAATTATAC TTAACTGCAG        540
CACCACAATG TCCTTTTCCT GATAAACTTC TTAATGGTGC ATTGCAAACT GGTTTATTTG        600
ACTATGTTTG GGTCCAATTT TACAACAATC CCGAGTGCGA GTTCATGAGC AATTCAGAAA        660
ATTTCAAGAG GAGGTGGAAT CAGTGGACAT CAATCCCTGC AAAGAAGTTG TATATTGGAC        720
TTCCAGCAGC CAAGACAGCC GCGGGTAATG GCTATATTCC AAAGCAAGTG CTAATGTCAC        780
AAGTTTTACC ATTTCTAAAG GGGTCTTCAA AATATGGAGG TGTCATGCTT TGGAATAGAA        840

```
AATTTGATGT CCAATGTGGC TATAGCTCTG CTATCAGGGG TGCTGTTTAA GTTCTGAATG      900

AACAAGGCGC CCCTGAATCG CTATAAGCCA TCGTTAAGGC CTAAATAAAG CAAGTTAATT      960

TGCTGTTATC TGCCTAGAAA GTACTTAAGT TTTAATTTGT ACTGATGAAA ATGTGAAGGT     1020

CATCTTGTTT CCTTCTTGAT AATAGTAGTA CTATGGTTCT CTTT                     1064
```

(2) INFORMATION FOR SEQ ID NO:30:

(i) SEQUENCE CHARACTERISTICS:
        (A) LENGTH: 1018 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

```
TGAAGTGTTA GCACACACAC ACAAAAAAAA CTTAAAGTTA TGATCAAATA TAGTTTTCTT       60

TTGACAGCAT TAGTGCTATT TCTTCGAGCA TTAAAACTAG AAGCAGGGGA TATAGTAATA      120

TATTGGGGCC AAAATGGGAA TGAAGGTAGC TTAGCTGACA CTTGTGCAAC AAATAACTAT      180

GCCATTGTCA ATATTGCTTT CCTTGTAGTT TTTGGGAATG GCCAAAATCC AGTGCTAAAT      240

TTAGCTGGTC ATTGTGATCC AAATGCTGGT GCATGCACTG GCTTAAGCAA TGACATTAGA      300

GCTTGTCAAA ACCAAGGCAT CAAAGTTATG CTTTCTCTTG GTGGTGGTGC TGGAAGCTAT      360

TTTCTTTCTT CTGCTGATGA TGCTAGGAAT GTGGCAAATT ATTTGTGGAA CAATTATCTT      420

GGAGGTCAAT CAAACACACG TCCACTAGGA GATGCAGTTC TAGATGGAAT TGATTTTGAT      480

ATAGAAGGCG GACAACACA ACATTGGGAT GAATTAGCAA AAACTCTATC ACAATTTAGC      540

CAACAAAGGA AGTATACTT AACTGCAGCT CCACAATGTC CATTCCCAGA TACATGGTTA      600

AATGGGCAC TTTCCACTGG CTTATTTGAT TATGTTTGGG TTCAATTTTA CAATAATCCA      660

CCGTGTCAAT ACTCCGGTGG GAGCGCGGAC AATTTAAAAA ATTACTGGAA TCAGTGGAAC      720

GCGATTCAAG CTGGAAAAAT TTTTCTGGGA TTGCCAGCAG CTCAAGGAGC AGCTGGAAGT      780

GGTTTTATAC CATCTGATGT TCTTGTTTCT CAGGTTTTAC CATTAATTAA TGGTTCACCA      840

AAGTATGGGG TGTTATGCT TTGGTCTAAA TTTTATGACA ATGGTTATAG CTCTGCTATT      900

AAGGCTAATG TTTGAGATAT ATGATCATAG CTAGTCAGCT TGTATTAATA TGATGACGTC      960

AATAATGTTA TATTATAAAC TATATAGTAC TCAATAATAA GGCTTTGAAA GTTACTTA      1018
```

(2) INFORMATION FOR SEQ ID NO:31:

(i) SEQUENCE CHARACTERISTICS:
        (A) LENGTH: 645 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

```
AAAATGGAGA GAGTTAATAA TTATAAGTTG TGCGTGGCAT TGTTGATCAT CAGCATGGTG       60

ATGGCAATGG CGGCGGCACA GAGCGCCACA AACGTGAGAT CGACGTATCA TTTATATAAC      120

CCACAGAACA TTAACTGGGA TTTGAGAGCA GCAAGTGCTT TCTGCGCTAC TTGGGATGCC      180

GACAAGCCTC TCGCATGGCG CCAGAAATAT GGCTGGACTG CTTTCTGTGG TCCTGCTGGA      240

CCTCGAGGCC AAGATTCCTG TGGTAGATGC TTGAGGGTGA CGAACACAGG AACAGGAACT      300

CAAACAACAG TGAGAATAGT AGATCAATGC AGCAATGGAG GGCTTGATTT AGATGTAAAC      360
```

```
GTCTTTAACC AATTGGACAC AAATGGAGTG GGCTATCAGC AAGGCCACCT TACTGTCAAC      420

TATGAATTTG TCAACTGCAA TGACTAATTA ATCTGCTTCC AGATATATAA GTACCATCAT      480

AAAAAACCAC AATAATTCAT ATATACTGGC ATATCTTATT TTTAAGAGCC GTTTAGAATA      540

AGAAGGGGCT GAGCTAGCTT TTAATGTGTA TGGTATTATC TGAAGCTCTA CATGCCCTTC      600

ACTATTATAG ATAAAAGCTT GTTCTTGTTG TTAAAAAAAA AAAAA                       645

(2) INFORMATION FOR SEQ ID NO:32:

(i) SEQUENCE CHARACTERISTICS:
        (A) LENGTH: 635 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

AAAATGGAGA GAGTTAATAA TTATAAGTTG TGCGTGGCAT TGTTGATCAT GAGCGTGATG       60

ATGGCAATGG CGGCGGCACA GAGCGCCACA AACGTGAGAT CGACGTATCA TTTATATAAC      120

CCACAGAACA TTAACTGGGA TTTGAGAGCA GCAAGTGCTT TCTGCGCTAC TTGGGATGCC      180

GACAAGCCTC TCGCATGGCG CCAGAAATAT GGCTGGACTG CTTTCTGTGG TCCTGCTGGA      240

CCTCGAGGCC AAGATTCCTG TGGTAGATGC TTGAGGGTGA CGAACACAGG AACAGGAACT      300

CAAGCAACAG TGAGAATAGT AGATCAATGC AGCAATGGAG GGCTTGATTT AGATGTAAAC      360

GTCTTTAACC AATTGGACAC AAATGGATTG GGCTATCAGC AAGGCCACCT TATTGTCAAC      420

TATGAATTTG TCAACTGCAA TGACTAATTA ATCTGCTTCC AGAAAATAAG TAGCTACTGT      480

AGTATCTTAT TTTTCAGAGC TGCGCTGTTT AGAATAAGAA GGGGCTGAG ATTGCTTTTA       540

ATAGTATACT GTAGGTATTA TCTGAAGCTC TACATGTTTG GTTGCCCTTC ACGATTATAG      600

ATAAAAGCTT GTTCTTAGTA CTAAAAAAAA AAAAA                                  635

(2) INFORMATION FOR SEQ ID NO:33:

(i) SEQUENCE CHARACTERISTICS:
        (A) LENGTH: 860 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

GGGAACAAAA GCTGGAGCTC CACCGCGGTG GCGCCGCTCT AGAACTAGTG GATCCCCCGG       60

GCTGCAGGAA TTCGGCACGA GCAACTTAGA AAAATGAATT TTACTGGCTA TTCTCGATTT      120

TTAATCGTCT TTGTAGCTCT TGTAGGTGCT CTTGTTCTTC CCTCGAAAGC TCAAGATAGC      180

CCACAAGATT ATCTAAGGGT TCACAACCAG GCACGAGGAG CGGTAGGCGT AGGTCCCATG      240

CAGTGGGACG AGAGGGTTGC AGCCTATGCT CGGAGCTACG CAGAACAACT AAGAGGCAAC      300

TGCAGACTCA TACACTCTGG TGGGCCTTAC GGGGAAAACT TAGCCTGGGG TAGCGGTGAC      360

TTGTCTGGCG TCTCCGCCGT GAACATGTGG GTTAGCGAGA AGGCTAACTA CAACTACGCT      420

GCGAACACGT GCAATGGAGT TTGTGGTCAC TACACTCAAG TTGTTTGGAG AAAGTCAGTG      480

AGACTCGGAT GTGCCAAAGT GAGGTGTAAC AATGGTGGAA CCATAATCAG TTGCAACTAT      540

GATCCTCGTG GGAATTATGT GAACGAGAAG CCATACTAAT GAAGTAATGA TGTGATCATG      600

CATACACACG TACATAAAGG ACGTGTATAT GTATCAGTAT TTCAATAAGG AGCATCATAT      660
```

```
GCAGGAYGTA TCAATATTTA TCAAATAATA CAAATAAGAG CTGAGATTAC GAGAATCTAT    720

TTAAATTAAA AGTTACATAC TTAATTATTA TAGTTATATA TGTAAAATAT GTGGCCTTTT    780

TAAAAGTTAC ATAATTAATT ATTATAGTTA ATGTCTTTCA AAAAAAAAAA AAAAAAAACT    840

CGAGGGGGGG CCCGGTACCC                                                860
```

(2) INFORMATION FOR SEQ ID NO:34:

(i) SEQUENCE CHARACTERISTICS:
    (A) LENGTH: 783 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:34:

```
GAAGATCAGA CTTAGCATAA CCATCATACT TTTATCATAC ACAGTGGCTA CGGTGGCCGG     60

ACAACAATGC GGTCGTCAAG GCGGTGGTCG AACTTGTCCC GGTAACATCT GCTGCAGTCA    120

GTACGGTTAC TGTGGTACCA CCGCGGACTA CTGTTCTCCG ACCAACAACT GTCAGAGCAA    180

TTGTTGGGGA AGTGGGCCTA GCGGACCAGG GGAGAGCGCG TCGAACGTAC GCGCCACCTA    240

CCATTTCTAT AATCCGGCGC AGAATAATTG GGATTTGAGA GCCGTGAGTG CTTATTGCTC    300

CACGTGGGAT GCTGATAAGC CGTACGCATG GCGGAGCAAG TATGGCTGGA CCGCCTTCTG    360

CGGGCCGGCA GGACCTCGTG GTCAAGCTTC TTGCGGCAAG TGTTTAAGGG TGAAGAACAC    420

AAGAACAAAT GCTGCAGTAA CTGTGAGAAT AGTGGACCAA TGCAGCAACG GAGGCTTGGA    480

TTTGGATGTA GCAATGTTCA ATCAAATAGA CACCGATGGT TTTGGCTATC AACAAGGCCA    540

TCTCATTGTT GACTACCAAT TTGTCGACTG TTGGCAATGA GCTCATTGGG CAGCCTGATT    600

CCAGAAACAT GCTTGTTTCG GCCATTGATC GCGTTTGATA TTATGTAATG ATTTTGAGGT    660

CAATATCGAT CGGTCTACAT AAAAATAATA AAGACCGCTA TATATGTATT GTCGAGGGAT    720

ATATGTTTCG TATCAATAAG GAAATTTTAA ATATTATTAT CAAAAAAAAA AAAAAAAAA    780

CTC                                                                  783
```

(2) INFORMATION FOR SEQ ID NO:35:

(i) SEQUENCE CHARACTERISTICS:
    (A) LENGTH: 979 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:35:

```
GGCACGAGCT CGTGCAATTC GGCCGAATTC GGCACGAGAA AATATGGCAA ATATCTCCAG     60

TATTCACATT CTCTTCCTCG TGTTCATCAC AAGCGGCATT GCTGTTATGG CCACAGACTT    120

CACTCTAAGG AACAATTGCC CTACCACCGT CTGGGCCGGA ACTCTCGCCG GTCAAGGACC    180

CAAGCTCGGC GATGGAGGAT TGAATTGAC TCCAGGTGCT TCCCGACAGC TCACGGCTCC     240

TGCAGGATGG TCAGGCCGGT TCTGGGCTCG TACAGGCTGC AACTTTGACG CCTCCGGAAA    300

CGGTAGATGT GTAACCGGAG ACTGTGGCGG TCTAAGATGT AACGGCGGCG GAGTTCCTCC    360

CGTCACTCTG GCTGAATTCA CTCTAGTAGG CGATGGCGGC AAAGATTTCT ACGATGTGAG    420

CCTCGTAGAT GGTTACAATG TCAAGCTGGG GATAAGACCA TCCGGAGGAT CGGGAGATTG    480

CAAATACGCA GGCTGTGTCT CTGACCTCAA CGCGGCTTGC CCCGACATGC TTAAGGTCAT    540
```

```
GGATCAGAAC AATGTCGTGG CCTGCAAGAG TGCCTGTGAG AGGTTTAATA CGGATCAATA       600

TTGCTGCCGT GGAGCTAACG ATAAGCCGGA AACTTGTCCT CCCACGGACT ACTCGAGGAT       660

TTTCAAGAAC GCTTGCCCTG ACGCCTATAG CTACGCTTAT GACGACGAAA CGAGCACCTT       720

CACTTGTACC GGAGCTAACT ACGAAATCAC TTTCTGCCCT TAAAAACCGA AGCTTCGAGT       780

TAGATACAGT CGGGTTTAAT TATCTCTCAC GTTTCTTTTG CTTATTATGT ACGGAAAGAT       840

AAATAAGGAA AGCTGATGAC TATGAATCAT CGTCTTCCAC TTTTAAGCTT TTTTAGTGAG       900

TATTAGTCAG TTGTTACACT CAGCTGATTT GTTTACAAAG AAATAAAACA AAATGATTGA       960

TCTAAAAAAA AAAAAAAA                                                    979

(2) INFORMATION FOR SEQ ID NO:36:

(i) SEQUENCE CHARACTERISTICS:
        (A) LENGTH: 12124 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Cucumis sativus
        (C) INDIVIDUAL ISOLATE: Cucumber Chitinase Genomic DNA (vii) IMMEDIATE SOURCE:
        (B) CLONE: pBScucchrcht5

(xi) SEQUENCE DESCRIPTION: SEQ ID NO:36:

GAATTCTCTT TTTACAATTA CAAAACTAAA ACGAACATTG TATTTTAAAA TTTAAATAAT        60

TAAAATGAAT ACATTACAAG TATAGATATC AAAATAAAAA AATCAAAATA GGATTAAAAT       120

TGCTCAGCTT ACATAAACTT ATATTGTAGA CTTTAGAGTT GAGGTTCGAT ATCTCACGTT       180

ACATGCTGTG GTGTATATAT ATATTTATGA AGCATATTTT GTCACTATTA TAAGCTTTTT       240

ATTTTTGAGG CTAAATATTG CAAGTGGAGG AGGAAATTAG TTAAGCACAT AACAAAATCG       300

TAGTTGGCCA TTACATGTTG CGAGAAATTC GATGTGAAGA TCATTATTAT ATATTCAACT       360

CTTCAAATTA TTATAGATTC CTTGACTATT TCTCTTTCTA TTTTATATTA TTACATCAAT       420

CCCTCAACAA ATAAATCATT CAACTATACA AATTTAATAA TATGTGTATG GAAATGATCA       480

TCTCATCATA ATTAAATTAA ATTTAAAACT ATGAACACCA ACACCAATCA ATAAACCGTA       540

CATAACTCAA ACTATTATTA TTAAATCACT TAATTTAGTC ACAAACTAAC GTTTATAGAC       600

ATGGTTGGAT TCACAAGGAA TAACATTCTT CCTATTTTAA AAAAAGTTA GTACTTATGT       660

TTGCTTGTAT ACCAAACACG TGTATTAATT AATGTCAAAT TACTTACATA ACAGCTATAA       720

ATAATACTTA CGATCGACTA ATTAATAATT AAAAATAATA TAATGGTATC TAGAAATAGA       780

TCGATTATAG ATGTTATGTC TAGAGTTGGT CCTTATAGGT GATTGGGTGA TCGAGGTATT       840

CACACATTAC ACATAAGTAA TGAGTGGACA AAAGTTGGTC CTTGAGGTGG TCGTCGATTG       900

TTTAGAGTTG ATTGGGCACA AAGGTTTCAC CTAAAGTATG GGTTTACCAA AGATGTGACC       960

TAAAACGATG GGTGTTGGTA GCCATCACTC AAACCATTTT AGTAAACTTA ATAATTATA      1020

TAAATTAGGT TAACATCAAG CAATCAAAAA TCGTGCTTTG TATTTTAAGT GAATTCTTG      1080

AAATGATTAT CTCTTATCAA CGTATTTCAT GACAAACTCA TTTTTCTTAT AAATTATTTC      1140

TCTATTAGTT ACCTCACACT TTAACGTGTT TAAAATAATT TTTCTCACAC AATTAAATAC      1200

TTAAAATCCT AAGCTAAATA CAATTAAATA TAATCTTGCA ATTTCAAAAT AATTAAAATC      1260

ACTGGAAAAA AAAAAGGAGA AACTATTGAT AGTCCACATT AATCATAAAT TTAACTATAT      1320
```

```
GAAATTAAAA AGTTATTATA AAATATCCTT CAAATTACCT CATGCATAGT AAATTTTTTT    1380

TATAATTTTC TTTCAGAAAG TTCGATCAAG TCATAAGATT ATCTCTACAA AATAAGTATA    1440

AGTTAATGAG TAACCTAAAA TGCAGATTTG TTGAAGAAAA AACAAAATTA CTGTACTGTG    1500

TGTTTGTAAA CTTTTCCACA TATATATACA GCTATTTGTG ACAATGATAT AATGTGAACG    1560

TGTGGAATAA TTTGTTTTTG ATAGAAGTTG GAGTTTGAAA TGTCTAACTT TTAACCAAAT    1620

AAATTCCGTT AATTACGGTG ACTTAGGACT CACCTTAACT ATATAGTCAA TAGGTATTTT    1680

CTTTTGTTCA CACAACTTTT TTAATATACT CTTTTACGTA AGTAATGTAA CATAAACTAT    1740

CGCTGCAAAA AGAACAGGCT TTGCTCGCCT AAAAGCACGT CGGCATATTC ATCTCTGTCA    1800

GTAGACAAAA ATTCTGTCAG CAGAAACTCG TCGGAGTTGA TCTTCCAACA ACAAGACGAG    1860

GTCGTCCGCT GTTAGAAAAA ATGTTGATGG TTTAAATATA TTGTCTGCAG TAGTGATAAG    1920

CAGACTAATT GTTATTAGAG GGTTATAGAG GTTGAAATTC TTACAAATTT TCTAATCGTC    1980

AAACTAATTG AGAGTTTAAA GAGTTTCTCA TAATCTTCAA AGGATGGGTA GGAATTTTTT    2040

GAGTACCTAA TAAGTTATAA GCAAAGATGG TTGATTGTGC TGGGATTAAA TTACAAATTT    2100

AGTACAAAAA TATTCATATT AAAGTATAGT TCCATTTGGT TCTTTCACCT TTAGTTTTGT    2160

GTCATAATCT TCAAACTTTT AACAATCCAA GGCAACTACT AAACAAAATT TAATCTGTTG    2220

AATAACAAAA CTACAAATTT TTTTAAAAAA TATCGGAGAA TAAACTTATA ACTATCACAA    2280

AACTCTCGTA CTTAACACCA CATAATCATA ATCGTATTCT CCATGAAAAT TTCAAATCAA    2340

CCATTTTTTT CTCTCTTCAA TTAGAATGAT CGAACAAGCC AATTCATTAC ATAATTTGTA    2400

ACATTTTTTT CCAAACCCAA ATGACACTCT ACAAATACTT TGATTTGATC AACAATAACC    2460

CTACGTGATT ACCTTTTCCC TTCCCAATAA ATTCACTTCA TATTTTCCAC TGTTTAAACA    2520

CATAATCTCA AAGGAAAAAG CTCTTTAAGA AATGGCTGCC CACAAAATAA TAACTACAAC    2580

CCTCTCCATC TTCTTCCTCC TCTCCTCTAT TTTCCGCTCT TCCAACGCGG CTGGAATCGC    2640

CATCTATTGG GGCCAAAACG GCAACGAAGG CTCTCTTGCA TCCACCTGCG CCACTGGAAA    2700

CTACGAGTTC GTCAACATAG CATTTCTCTC ATCCTTCGGC AGCGGTCAAA CTCCGGTCCT    2760

CAACCTTGCC GGTCACTGCA ACCCTGACAA CAACGGTTGC GCCTTTGTGA GCGACGAAAT    2820

AAACTCTTGC CAAAGTCAAA ATGTCAAGGT TCTCCTCTCT ATTGGAGGCG GCGTAGGGAG    2880

ATATTCACTC TCCTCCGCCA ACAATGCGAA ACAAGTCGCA GGCTTCCTCT GGAACAACTA    2940

CCTCGGCGGG CAGTCGGATT CCAGGCCACT CGGCGATGCG GTTTTGGATG GCGTTGATTT    3000

TGTTATCGGG TTTGGCTCGG GCCAGTTCTG GGATGTACTA GCTCGGGAGC TAAAGAGTTT    3060

TGGACAAGTC ATTTTATCTG CCGCGCCACA GTGTCCGTTC CCAGACGCTC AGCTAGACGC    3120

CGCGATCAGA ACTGGACTGT TCGATTCCGT CTGGGTTCAA TTCTACAACA ACCCGCCATG    3180

CATGTATGCA GATAACGCGG ACAACCTCCT GAGTTCATGG AATCAGTGGG CGGCGTATCC    3240

GATATCGAAG CTTTACATGG GATTGCCAGC GGCACCGGAG GCAGCGCCGA GCGGGGGATT    3300

TATTCCGGCG GATGTTCTTA TTTCTCAAGT TCTTCCAACC ATTAAAACTT CTTCCAACTA    3360

TGGAGGAGTG ATGTTATGGA GTAAGGCGTT TGACAATGGC TACAGCGATG CCATTAAAGG    3420

CAGGATCCTA TTGAAAAAGA GTAGCTATTG TTATGGAGTA AGGCGTTTGA CAATGGCTAC    3480

ACACCTGCCT CTCTCACTTG AAATAGAGCA GGTATTGGTT TGAAATCAAT TATAACCAGA    3540

GCCCATCAGT ATACTCCGTC CTAATTAATC TCAAGTTGTC AAAATTATTA GAAGCAAATT    3600

TCTAATCAAA CAACAATATT ACTCTATCCT TACACGGAAG AATGCTCAAG GAGTTTACCG    3660

GAACTATCTT TTACTCTGAA ACCGTCTCCA AACCACTACT ACATCAATAA AACCATCTCT    3720
```

```
AACTCTAGAA AACAACAGAA TTGCCCATTC AACTCTACAG TGAACGAATC CAAGACATAG    3780

TTTCCAAAAA GTTCAAGAGT TAATTAATTA AAGATTTGGT CAAGTCCAAT CAAAATAGAG    3840

CTTGAATATA TAAAAGAAAA TAATCATACC CTTGATATTG TTGTATTCAA GAAGGGAAAC    3900

GTAGACGGCC ATATCAACCT TTGGGTACTT GGCAAAAGAA AAGAAAATAT AGTAGACTAG    3960

ATAATTGAAT TTGTAGTTAG ACTTGTAAAA TAGTAAGGAG CAACTTTGTA GATATATCTT    4020

TACAAAGGTG TGGTAGAGGC AACAACCATT TCTTTATCTT CTTATAAATC AACTTGTGGA    4080

TCGAAGTTTA ATATCTTGAA CCGTAATAAA ATCATAAGTT TAACTATTTG AAGTCTTAAA    4140

AAACTTATTA TAAAATATCC TTCAATTTAT CTAATGCATA GTAGAAGTTA TAAGATTCTC    4200

TCTAAAAATA AGTATATAAA TTAATGAGTA CCCTAAAATG CAGGTTTGTT GAAGAAAAAA    4260

TAAAATTAGT ACTGTTTGTA AACTTTTCCA CATATATACG CAGCTACAAT GTTAACGTGT    4320

GGAATAATTT GTTTTGGATA GAATTTGGAG TTTGAAATGT CTAACTATAA TCAAACAAAT    4380

TCCATTAATT ATGATGACTT AGACTCACTT TAACTATATG TAGTCAATAG ATATTTCTAG    4440

ATTTCACGGC TAATTTAATT GAATTTTGGA CTTTTTTAAT GTACTCTTTT ACATATGTAC    4500

GTAATGCATA ACTATTGCTA CAAAAAATAG GTTTCTCTCG CTGCACAAAA CAGTCGATAA    4560

ATACCTAAAA GCAGTGGATA AAAACTTGTT GGGAGTTCAG TTGGAAGAAA CTCGTCGGGA    4620

CTTGATCTCC TGACAACAAA GCAAGGTCAT CAGTTGTTAG AAAAATTGCA AATGGTGTAA    4680

ATACGTTGTC GACGGTAGTG ATATATCGTC CAACCCTTAC ATTACGTCGT TGGCGGTTGT    4740

ACTATCTCCA GTGCACCCCT TGACCGGTTG ACAATTATCC ACAAAACACA CCAATGTTAT    4800

TCTAGCTAGT TAAATCTCCC AACATTACAT AAAAACAAA ATGTGTTTGA CACAAATGTG    4860

AAAATAAAGA TTAATTGAAC AGTACATATG ATCTTAAATC AAATTCAAGA GACGATATGT    4920

ATAGTCATAT AAACTCTATA CGTAACATAG CTATACACTT TTTCGGCTAA CTTGAACTTA    4980

GTTAAACAAG TAAAATAAGT TGATCATGTA CCATGCTTAC TATTTAGAAG GTCACAGAGG    5040

TTCAAATACT TGCAAAAAAT TTTAACGTTG AACTTTTAAA ATAAATAAAT TTCATTGTTA    5100

TACCTTAAAC TAATTGGAGT TAAAGTGTGA TCTCTAGGTT AAATTACAAT TTTAGTACAA    5160

AAAAAAATTA TATTCGAGTC CAGCCATCTA GTTCTTCCAT TTTAGTTTTG TGTCATAATC    5220

CTAAACTTTC AATTTTATAT TTAATAAATT ATTGTATTGG ACTTAACAAA TCATAACTCA    5280

ATTATTGTTT TATCAACTTC AAAATTAACG TTTGGTTTTC CTATCACACA TTATCAAAAA    5340

GAGAAACGTT CACGTTCAAC AACACAATTA TAATAATAAC ATGCATCAAT TATTAAAATT    5400

TCACAAACCC ACAAAAGAAA AAACAACAAC AACAAAATTG AAATTAAGTC CAGAGGTCCT    5460

TCCATATACC TAAACCTCAA TTTTACTTAT AAACATTAGT TAACATTTTA AATATCTAAT    5520

AATCCAACCA TATGACATAT TAGAGATTTA TGGACTTATT AAGCACATGT TTAACAATAG    5580

TTCAAAGGCC GCCCTACTAA TAACATATAC AAATTTAATT TGTTGAACAT AACTACAATT    5640

TTTTTTAAAA AAATATTAGA GAATAAACTT ATAATTTAAC AATATTTTAA TCACATAGCT    5700

TATAATAAAC TTAATTATAA TCACAAAAGT CTAGTACTTA TATATAATTT GTAGAGATAT    5760

GTTTACTTTG ACCTTGACTC CACGTAATCG TATTTCCATG GAAATTCAAA TTAATCAACC    5820

ACTTTTTTTC TCTCTTCAAT TAGAACACGG CAATTGATTA ATAATTTGT AACATTTTT    5880

CCAAATCCAA ATGACACTTC CAAAATTATA TTATATGATC TTATACTTTG ATTTGATCAA    5940

CAATAACCCT TCGTGATTGC CTTTTCCCTT CCCTATAAAT TCACTTCACA TTTTCCATTG    6000

TTTAGACACA CAAACTCAAA GAAAGCTCTT TAAGCAATGG CTGCCCACAA AATAACTACA    6060

ACCCTTTCCA TCTTCTTCCT CCTTTCCTCT ATTTTCCGCT CTTCCGACGC GGCTGGAATC    6120
```

-continued

```
GCCATCTATT GGGGTCAAAA CGGCAACGAG GGCTCTCTTG CATCCACCTG CGCAACTGGA    6180

AACTACGAGT TCGTCAACAT AGCATTTCTC TCATCCTTTG GCAGCGGTCA AGCTCCAGTT    6240

CTCAACCTTG CTGGTCACTG CAACCCTGAC AACAACGGTT GCGCTTTTTT GAGCGACGAA    6300

ATAAACTCTT GCAAAAGTCA AAATGTCAAG GTCCTCCTCT CTATCGGTGG TGGCGCGGGG    6360

AGTTATTCAC TCTCCTCCGC CGACGATGCG AAACAAGTCG CAAACTTCAT TTGGAACAGC    6420

TACCTTGGCG GGCAGTCGGA TTCCAGGCCA CTTGGCGCTG CGGTTTTGGA TGGCGTTGAT    6480

TTCGATATCG AGTCTGGCTC GGGCCAGTTC TGGGACGTAC TAGCTCAGGA GCTAAAGAAT    6540

TTTGGACAAG TCATTTTATC TGCCGCGCCG CAGTGTCCAA TACCAGACGC TCACCTAGAC    6600

GCCGCGATCA AAACTGGACT GTTCGATTCC GTTTGGGTTC AATTCTACAA CAACCCGCCA    6660

TGCATGTTTG CAGATAACGC GGACAATCTC CTGAGTTCAT GGAATCAGTG ACGGCGTTT    6720

CCGACATCGA AGCTTTACAT GGGATTGCCA GCGGCACGGG AGGCAGCGCC GAGCGGGGGA    6780

TTTATTCCGG CGGATGTGCT TATTTCTCAA GTTCTTCCAA CCATTAAAGC TTCTTCCAAC    6840

TATGGAGGAG TGATGTTATG GAGTAAGGCG TTTGACAATG GCTACAGCGA TTCCATTAAA    6900

GGCAGCATCG GCTGAAGGAA GCTCCTAAGT TTAATTTTAA TTAAAGCTAT GAATAAACTC    6960

CAAAGTATTA TAATAATTAA AAAGTGAGAC TTCATCTTCT CCATTTAGTC TCATATTAAA    7020

TTAGTGTGAT GCAATAATTA ATATCCTTTT TTTCATTACT ATACTACCAA TGTTTTAGAA    7080

TTGAAAAGTT GATGTCAATA AAAACATTCC AAGTTTATTT AAATTTTGTG TAAACTGTTT    7140

GAAGTTTAAA TACAATATAA TCTCATTAAC GTAAGAATTT GATATTTTAG CCAAATTTTT    7200

AAATCGATCC TCTGTCTTCT TTCTAGTTAA TTATATATCA ATTTTATTTC TTACTTGGGT    7260

GAAATTTTTT TCTAATTAAA AACAATAGTA CATACAATAA GTTTGATATA ATCACTAATT    7320

CAATCTTAAG CTTTAATAGA TGAAGTTAAA TTTGATATTA AATCTAACAA TTTATGTTAT    7380

CGGTTACTGT TGAAAGAGAT GAAATTATCA AAATAAATGG AGTTGAAGAT TAATTAATCA    7440

AATCATTGAC GTAGACGTTA CTGTGATTGT TTTAAGTTTA CAAATATATT GACAGTCAAC    7500

TATTTTCCTA ATTCTAAGAT AATCAAACTT GTTTAATTCC TAAAGAATCG AAAGAAAAGA    7560

AGTAATAAAA AAACTTGTTT AATTCAATCT TTAAATTGGT TTTATTTTCC AACTAGCTAA    7620

ATTATTCATC TTATTATCAT TTGTATTTGT AGTCATATTA ATATTAACAT GTGATTTTTT    7680

TTTAAAAAAA AATGTTTTGT TGTGTATTTA TAGAAATTGA TGCTTGAATC TTTATGATTT    7740

ATACATATGT GGATAGATAG TTAAATTATT ATCTATCAAA GTTAATATAC AGAATATGAA    7800

AATATGAGAT GTATTTATTT ATTGTGCAAA TGTAAATCTC GTATCTAGTT TATTAATTTC    7860

TACATTCACT TTTTAGTTAA AGGGTGCAAC GAAGGATGTT TTGAGATTTC TCGAATGGTT    7920

ATCATATACT TAAACTCCAT TTCCATGAAC GTACAAAGTA AATTTGAGGT AGATTGTCAC    7980

TATATTCATT ATGGTTCTCA AGATAGCACA TGCATTGTGC TACATGTCAT GTTGTTACT    8040

AAGGAGCAAC TTTGTAGATG CAACAATCAT ATGATTTGTA TATATTTCAT ATTTATTTAT    8100

GTTCATATGT ATTTTCCATG AAAAGTTGGA AGAACCTGAG ACTTAAGCAC GTTGGCCGGA    8160

GTAAAACCAC CGCTCGGTGA AGCTGCAGAT GCCGCCTGTC GCCCCATGTA CAGCTTCTCA    8220

ACCGGAAGCC CCGTCCACCA AGTTCCAAGA ATAATTCCGG AGATTGTTGA CGTTTCCATT    8280

TGCATACATA CAGGGCGGAT TGTTGTAGGA TATTGAACCC AAACGAAATC AAACAAACCT    8340

GTTTTAATGG CAGAAAATGG ATATGCTCTC TTCCTCACGA GGAATTTCAT TCAATAACCT    8400

ATCTGCCTCA TCAAGGACCT GCTCGACATG CAAAACAGGG TAGCCAGTGT ACAAGCTTAT    8460

TGTCTCTCTA TACCAAAAAA ATTTAGCCAC GGCAACATTC GATAAGGAGA TAATGATAAT    8520
```

```
GTATAGAAAT TTAGATGATG TAATTAACAA AAGTACTTTA GGGAGAATCA CATGATTGTA    8580

GAGGAATAAG GTGATGTGCT AAACATTATT GTATGTCATT TTCAGTACAA CTTGGGATAA    8640

TATATATTTT TTATCAATGT TGAATTGTTT ATTATTGATC TTGAGATCCA TTGACGATTT    8700

GTTATAATGT TTTTATTTGC TCTTTTTGAA TTGAGATCGA TTGACCCATA AACCCAAAGC    8760

ATCGATAATT TTTTTTACTT GGTGGAGTCT TGGTAAAAAA GAAAATCAAG AAAATTGTAT    8820

AAACTAATAT AAAAATATTT ATCTTATAAA TTAATTACTT CAAATTTGGG AGAAACTGAA    8880

GATTACATAG AGGATATTTT AATGTATGGA TCTAGAATTG AAGATTACAT AGAGGATTTT    8940

TTTAGTGTAT GGATGTAAAA TGTGTTGGTG TACTTAAGTT GAATTATGAA TAGAAAATTT    9000

GGAGAAAGAT TATAAAAGAT TGCATAAGAT CGATTTTCGG AAAAGAGATA TTACTTAGCT    9060

TGCAATTTCA ATCTTGCATT TTTATATATA TATACTTCTA AATAGACTAT CATAAGTAGA    9120

ATCAATTAAC CTTTTTTTTT TTTTCATTTA GAACATTACC ATTCATTTAA ATAATTTGTA    9180

ACATTTTTTC CAAATCCAAA TGACACTTAC AAAATTATAT TATATGATCT ACTTTGATTT    9240

GATCAACAAT AACCCTTCGT GATTCATTTC CCTTCCCTAT AAATTCACTT CACATTTTCC    9300

ATTGTTTAGA TACACGAACT CAAAGAAAGC TCTTTAAGCA ATGGCTGCCC ACAAAATAAC    9360

TACAACCCTT TCCATCTTCT TCCTCCTTTC CTCTATTTTC CACTCATCCG ACGCGGCTGG    9420

AATCGGCATC TATTGGGGCC AAAACGGCAA CGAAGGCTCT CTTGCATCCA CCTGCGCTAC    9480

TGGAAACTAC GAGTTCGTCA ACATAGCATT TCTCTCATCC TTCGGCGGCG GTCAAACTCC    9540

GGTCCTCAAC CTTGCCGGTC ACTGCAACCC TGACAACAAC GGTTGCACCA TCTTGAGCAA    9600

CGAAATAAAC TCCTGCCAAA GTCAAAATGT CAAAGTCCTC CTCTCTATTG GCGGTGGCAC    9660

GGGGAGTTAT TCACTCTACT CCGCCGACGA TGCGAAAGAA GTCGCAAACT TCATTTGGAA    9720

CAGCTACCTC GGCGGGCAGT CGGATTCCCG GCCACTGGGC GATGCGGTTT TGGATGGCGT    9780

TGATTTCGAT ATCGAGTTTG GCTCGGACCA GTTCTGGGAC GTACTAGCTC AGGAGCTAAA    9840

GAGTTTTGGA CAAGTCATTT TATCTGCCGC GCCGCAGTGT CCGATCCCAG ACGCTCACCT    9900

AGACGCCGCG ATCAGAACTG GACTGTTCGA TTCCGTCTGG GTTCAATTCT ACAACAACCC    9960

GTCATGCATG TATGCAGATA ACACGGACGA TATCCTGAGT TCATGGAATC AGTGGGCGGC    10020

TTATCCGATA TTGAAGCTTT ACATGGGATT GCCAGCGGCA CCGGAGGCAG CGCCGAGCGG    10080

GGGATTTATT CCGGTGGATG AGCTTATTTC TGAAGTTCTT CCAACCATTA AGCTTATTC     10140

CAACTATGGA GGAGTGATGT TATGGAGTAA GGCGTTTGAC AATGGCTACA GCGATGCCAT    10200

TAAAGACAGC ATATATCAGC TGAAGGGAAG CTCCTAAGTT TAGTTTTAAT TAAAGCTATG    10260

AATAAACTCC AAAGTATTGT AATAATTAAA AAGTGAGACT TCATCTTCTC CATTTAGTCA    10320

TGCTACAATT AAAATCCTTT ATTTTTACTA CAATACTATC AATGTTTTAG AATTAAAGTT    10380

GATATCAATA AAAATATTCC AAGTTTATTT CAATTGTGCA AAATGTTTGA AGTACTTTAA    10440

AAACAATATA ATCTCATTAA CATGAGAATT TTATATTTTA GCCATTATGT AAGAATAATA    10500

TTTCTTATTT GGAAGCAATT ATGTGAGAAT TTTACTTCTT ATTTGGTTGG AATTTTTTCT    10560

AATAAAAATA ATAGTATACA GGTATGTTGA TATAATCACC AATTCAATCC AAATTAAAGC    10620

TTAAGTTTAA TAGATGAAGT TAAATTTTAT ATTAAATCTA ACAATTCATG TTGAACTCAT    10680

AAACATATGT GATTATACAG CAAAAAAAAA AAAATTGCAA GGGTTGAGTA CCATTGTCAT    10740

AGATGTCAAT ATATATATAT ATATATATAT ATATTCCATC AATATAAAAA ATTGAAAATC    10800

TTTAAAATAA TATACAGAGA TGAAATTAAA CTAAATAGTA ATTAGAAGTT TTAATTTTAT    10860

CCTAATGTTC TAATTTTGAT TATAAAAAAA CAACCTTGTG ACATAGCTCA ATAGTAAATA    10920
```

-continued

```
AAACTGATCT CTCCATAATG TAATTAGTTG TGTTTTTAAG TCAAATAGTG ATATTCACAT    10980

AACACCAAAA CACAAGAACT CATATTTTCT GATTTTTTTT TTTCTTCTCA TCAATGTTAA    11040

TGTCTATTAT TACTCTTTTT TTAAGTATAA AATGTCTATG TTTGATATGA TATTCTTGAC    11100

CCATTATACA CCCATAAAAA AATATATGTT TTCTAACAAC GGCAAAACTT GGAAGTATGG    11160

AGTTGAGGAT TAAATTAAAT TAAAGTGTTG ATGTTGATGT TACTGTCACT ATTTTAATTT    11220

TACAAATATT TGACTGACAA CTACTTTCCT TCTAAGATAA TAAACTTTTG TTTAATTGAT    11280

CAATCTTCAA ATTGGTTTTA TTTAATTTCC AACTAGATTA TTCATCCTAT TCTTTGTATT    11340

TGTAGTCATA TTACATATGA TTTTTATAAA AGATATATTA GAGATATCAA TAGACATTGT    11400

TGAACCTTTA TGATTTATAG ATATATATGG ATAGATATTT CAAGAGTGCT CATCATATAC    11460

TTAAGAATCC ATTTTTTTTA TGAACGTTCA AGTATTGAG TAGAGATTGT CATTATATTC     11520

ATTATTGTTC AAGATGGCAC CATTGTGCTA CATGTCATGT TTTTACTAAG GTTACGTTGC    11580

AGATATATCT TTACAAAGGT GTGTGTTAGG GCAACAACCA TCTTTGTTAT CTTCTTCACG    11640

AATTAATTGG GAGGGAGCTG GTATTAAAAA ATATGTTTTC ATGTATGATT TGTATATATA    11700

TTTCCAATTC ATTATTTATG TTCATATGTA TTTTCCATGA AAAGTTATAC TCTAATAAAA    11760

AGTAATTTTA TTGCATCAAA GTGATGACAT ATAGATATAT AAGATGGGCC AACAAATCCC    11820

ATTTTTGTTT CCATTTCTTA TAGTTTACTT ATTCATGGAT TTATAATAAC TAATTACTAA    11880

ATAAGTTTAT TGAAGAGAAG AAGCTCAAAG ACTTCCTTTA ATGGCGTTGC TGTACCCATT    11940

ATCAAATGCC TTACTCCACA GCATAATTCC TCCATACTTG GAAGAACTTT TAATCCTTGG    12000

AAGAACCTTA GACTTAAGCA CGTTGGCCGG AATAAAACCA CCGCTGGGTG CAGCTGCAGA    12060

TGCCGCCGGT AGCCCCATGT ACAGCTTCCC AACTGGAAAC CCCGTCCACC GGTTCCAAGA    12120

ATTC                                                                12124
```

(2) INFORMATION FOR SEQ ID NO:37:

(i) SEQUENCE CHARACTERISTICS:
        (A) LENGTH: 1079 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

```
ACAAACCAAT AACACAAAAC ATGGCTTTCA CAAAAATCTC CTTAGTCCTT CTTCTCTGCC       60

TCTTAGGTTT CTTTTCTGAA ACTGTCAAGT CTCAAAACTG CGGTTGCGCT CCAAACCTCT      120

GTTGCAGTCA GTTCGGTTAC TGTGGTACCG ACGATGCATA CTGCGGTGTT GGATGCCGAT      180

CAGGTCCTTG TAGAGGTAGT GGAACCCCGA CCGGAGGGTC GGTCGGTAGC ATTGTGACAC      240

AAGGTTTCTT TAACAATATT ATCAACCAAG CTGGTAATGG TTGCGCGGGG AAAAGATTCT      300

ACACCCGTGA CTCTTTCGTT AACGCCGCTA ATACTTTCCC CAACTTTGCC AATTCTGTTA      360

CCAGACGTGA AATTGCTACC ATGTTTGCTC ATTTCACTCA CGAGACCGGA CATTTCTGCT      420

ACATAGAAGA GATTAACGGA GCAACACGTA ACTACTGCCA GAGCAGCAAC ACACAATACC      480

CATGTGCACC GGGAAAAGGC TACTTCGGTC GTGGTCCGAT CCAACTATCA TGGAACTACA      540

ACTACGGAGC GTGTGGTCAA AGTCTCGGTC TTGACCTTCT ACGCCAGCCC GAACTTGTGG      600

GTAGCAACCC AACTGTAGCT TTCAGGTCGG GTTTGTGGTT TTGGATGAAT AGCGTAAGGC      660

CGGTTCTGAA CCAAGGGTTT GGAGCCACCA TTAGAGCTAT TAATGGAATG GAATGTAACG      720
```

-continued

| | |
|---|---|
| GTGGTAATTC CGGTGCAGTC AACGCAAGGA TTGGATACTA TAGAGACTAT TGTGGACAGC | 780 |
| TTGGTGTGGA CCCTGGTCCT AACCTTAGTT GCTAAAAAAC CTTTGAACCC AAACACGGAC | 840 |
| ATATGTGACG TGGCATGTAA TAAGTGAGAT ATACTAAAAT TTCACACGTA TGTACTTTAT | 900 |
| GTCGGGTCTC GGTGTTCCCT GCGTCACAAG CAAAAAATTG TTGTAATAAA CTTGTGAAAG | 960 |
| TGATTTTCTT TTCTTATGTG ACTTCTTATG AAAGAGAATT TTAAGATTGA TAGATGTTTG | 1020 |
| AGTTTGACAC TTGCAGTATC TGATTTTGGG ATACTCGCAT AAAAAAAAAA AAAAAAAA | 1079 |

(2) INFORMATION FOR SEQ ID NO:38:

(i) SEQUENCE CHARACTERISTICS:
        (A) LENGTH: 952 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

| | |
|---|---|
| AAAACAACAT AACATGGCTT CCACCAAAAT TTCCTTAGTC TTTTTCCTTT GCCTCGTAGG | 60 |
| TCCTTGTATA GGCGCTGGAA CCACAAGCGC TGCCGAATCA GTCAGTAGCA TTGTGACACA | 120 |
| AGGTTTCTTT AACAACATTA TCAACCAAGC CGGTAATGGC TGCACGAGAA AAAGATTCAA | 180 |
| CACCCGCGAC TCTTTCATTG ACGCTGCTAA TAATTTTCCA AACTTTGCAA GTTCCGTTAC | 240 |
| AAGACGTGAA ATTGCAAGCA TGTTTGCTCA TGTCACTCAC GAGACCGGAC ACTTCTGCTA | 300 |
| CATAGAAGAA ATAAAGAAAA GGTCACGTGG TAGGTGCGAC GAGAACGTAG AGCAGAGACC | 360 |
| ATGTCCATCA CAGAGTAAAG GTCACTCCGG TCGTGGTCAT CAGAGTCTCG GTCTCGACCT | 420 |
| TCTACGCCAG CCTGAGCTTG TGGGTAGCAA CCCAACTGTA GCTTTCAGGA AGGGTTTGTC | 480 |
| GTTTTGGATT AATAGCGTAA GGCCGGTGCT GAACCAAGGA TTTGGAGCCA CTATAAGAGC | 540 |
| CATCAATGGG ATGGAATGTA ACGGTGGGAA TTCAGGTGCG GTCAAGGCAA GGATTGGGTA | 600 |
| CTATAGAGAC TATTGTAGAC AGCTTGGTGT GGATCCTGGT CATAACCTTA GTTGCTAAAA | 660 |
| CGTTTTACAA ACGCATACAA CGTGACGTGT CACGTGATAA TGCGGAATAA GAAGTTACAT | 720 |
| TTCAAACAGG GCAAGGATTC AGAATCGCAA GTACATGAAT TAACATTCTG TAACTGTTAA | 780 |
| TTGTATCAAG TTGTGTTAAT ATATAAGAGC TAGGAGAATT GGTCTTTCTT ATGTCTAGCT | 840 |
| AGTAACCATC TATGTTTGTA GCTAGGAGCT ACTTGTTGTT TCTAGTTGTT TGTCTATCTA | 900 |
| AGCCAATCAT ACAAAATCTA TGCTTATTCA CAAAAAAAAA AAAAAAAAA AA | 952 |

(2) INFORMATION FOR SEQ ID NO:39:

(i) SEQUENCE CHARACTERISTICS:
        (A) LENGTH: 1250 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

| | |
|---|---|
| GAATTCGGCA CGAGCACACA CAATCCTGCC TATAGCCACC ATGTCTCCTC AGCCTACCTT | 60 |
| AGCCACCACC ACCACGCCTG CTACTGGGCC TAACCCTTCC TATTACCAAA CAGCTCCTGT | 120 |
| TAGCCAAGAG AGTATCCAGC GAACGGAGGT TCTTCTCCAC CTGTACGCCT ACCAGCACAC | 180 |
| CCAAGGAAAA CCAAATGCTA ACCAGACTGT CATAGTGGAT CCAAAGCTCC CCGCGTGTTT | 240 |
| CGGTGCCCTT GCTGCTAATG ACTGGACCAT ATATGATGGC ACTTGCACCA ATGCAAACCT | 300 |

```
TGTTGCGCAC GCTCAAGGTT TGCACATTGG TGCTGGTATG ACCAAAGAAA ATTGGTTCAT      360

TTGTTTCAAC ATGGTGTTTG TGGACCGAAG GTTTATGGGT TCCAGCTTCA AGGTGATGGG      420

AGATTTTCGA GGAAACGAAG GTGAATGGGC AATTGTTGGT GGGACGGGAG AGTTTGCATA      480

TGCACAAGGT GTCATAACCT TTAACAAGAC CTGGTCGGCC CAGGCAAATG TCAGGGAGCT      540

TCATGTTCGT GCTTTGTGTC TGTCCTTCTC AAAAGCACCG GAAACACCGT GCTCAAGGAC      600

ACCACGGGAG AGCTCTGTCA CCAAGATCGG CCCATGGGGT AAAATAAGTG GAGAATTTCT      660

TGACGTTCCC ACGACACCAC AACGTCTAGA GTGTGTGACC ATTCGCCATG GAGTTGTCAT      720

TGATTCACTT GCATTTTCCT TCGTCGACCA AGCTGGTGGA CAACATAACG TTGGCCCATG      780

GGGTGGGCCA TGCGGGGACA CAAGGACAC GATTAAACTT GGTCCATCGG AGATTGTGAC       840

AGAAGTCTCT GGAACGATTG GTGTATTTGG AGCAGCCAAT GTCGAGTACA ATGCCATAAC      900

ATCACTAACC ATTACCACAA ATGTCCGCAC GTACGGGCCC TTTGGAGAAC CGCAGTGTAC      960

TCGTTTCAGT GTTCCCGTGC AGGACAAAAG CAGCATCGTG GGTTTCTTCG TGTGCGCTAG     1020

GAAATACGTG GAGGCGCTCG GGGTTTACGT GTGTCCACCT ATTTCAAACT AGTCCCGAAG     1080

TGCTTCACAC TCGGTGTGCC TTCCACCTTT CTATGTTGTG CCAATAAAGT AGGTTATATA     1140

CTTTTGGTGT AATGCTATGC CCCCCCCCAA GTGTGATGGT TTTCATATCA GCAAGAAGTT     1200

TCTCTTGCTA CTATATGCAA AATAAAAAAA AAAAAAAAAA AAAACTCGAG                1250

(2) INFORMATION FOR SEQ ID NO:40:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

AGCTCGNGTG GCGAACGGAC GAGGAGTTCG CCCGGGAGAT GCTCGCCGGN CTCAACCCAC       60

ACATCATCAC CCGCCTGAAC GTGTTCCCTC CGAGGAGCAC GNTTGAAGGG TACGGTGACC      120

AGACGAGCAA GATCACGGTG GAGCACATCC AACACAACCT CGGNAAGCTC AACGTCGACA      180

AGGCAATCGA CGCCAAGAGG CTCTTCATCC TAGACCACCA CGACAACTTC ATGCCTCACC      240

TGCTAAAGAT CAACAGTCTC CCAAACACAT TCCGTCTTAC GNCACCAGGA CGCTGCTCTT      300

CCTGCAAGAT GACGGGACTC TCAAGNCAAT CGNCATCGAG                           340

(2) INFORMATION FOR SEQ ID NO:41:

(i) SEQUENCE CHARACTERISTICS:
        (A) LENGTH: 436 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

ACATCGAGAA GGGATCATGA ATTGACCCGA TCCCCAACTC AAGAACCGGA ATGGGCCACC       60

AAAATCCCCT AATGCTACTC TACCCCAACA CATCTGACAT CGATGGTGAG AGCGCCACCG      120

GGATCACAGC CAAGGGCATC CCCAACAGCA TCTCCATCTG ATCGATGTTA TGCCGTTTTA      180

TGTTATTGTT GTATGTTTCC CATTGCAAAT AAGGAACGCT GCATGTGCAC GTTTCATGAG      240

TGGCCAGAAG CGTGCTCGTT CACGTTGAGG CGAGTTGTGT TTATTTTCGT GTTGATGAAG      300
```

```
TGTTTTGGCC GCAATGGAAA GCCCGTGGGA TGGCACGGAT GAAGGGTTGT GGTCGGCCAG    360

TGTGTTGAGC TGGACATATA TACGGAAAAA AATTGTATGA GACCGGGTCT CATAGACCCA    420

AAAAAAAAAA AAAAAA                                                    436
```

(2) INFORMATION FOR SEQ ID NO:42:

(i) SEQUENCE CHARACTERISTICS:
        (A) LENGTH: 1162 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

```
AAGACACAAC CTTATTTTGC ATATAGTAGC AAGAGAAACT TCTTGCTGAT ATGAAAACCA     60

TCACACTTGG GGGGGGGCA TAGCATTACA CCAAAAGTAT ATAACCTACT TTATTGGCAC    120

AACATAGAAA GGTGGAAGGC ACACCGAGTG TGAAGCACTT CGGGACTAGT TTGAAATAGG    180

TGGACACACG TAAACCCCGA GCGCCTCCAC GTATTCCTAG CGCACACGAA GAAACCCACG    240

ATGCTGCTTT TGTCCTGCAC GGGAACACTG AAACGAGTAC ACTGCGGTTC TCCAAAGGGC    300

CCGTACGTGC GGACATTTGT GGTAATGGTT AGTGATGTTA TGGCATTGTA CTCGACATTG    360

GCTGCTCCAA ATACACCAAT CGTTCCAGAG ACTTCTGTCA CAATCTCCGA TGGACCAAGT    420

TTAATCGTGT CCTTGTTGTC CCCGCATGGC CCACCCCATG GGTCAACAGC CCACAGCTTC    480

ACAAGCCAAT ACACACACCA ATATAGTCTC CTTTCCAGAG CTAGCTAGCA TCAATGGCTT    540

CTGGTGCTCA GATGAAGATG GTTGCCGTCG GCATGATGCT GGCCATCATG TTCATCGCTG    600

CAGCTCATGC AGAACCAGCG CCTGCAGAAA CTTGCATCGA CAAGACCGAA AAAGTTGGTC    660

TTGCCACTGA CTGCATCTGC TCCAAGAACT GTGCTTGTGC AGGAAAGTGC ATCTTAGAAG    720

GCGGCGAGGG TGGCGAAATC CAGAAGTGCT TTGTCGAATG CGTGCTGAAA AATGACTGCA    780

ACTGCAATGC TAAGCACCAC AGTGCCGCAG CCCCTCAGTA AGGAGACTCC TGATTGGAGC    840

TTCTTCAGCC ATGCTATGAG GTCTGCGTCC ACAAGTCCAC AGTCAACATT TGAGTAAATT    900

AATAAACCTC TTATACCTGC GTTCTTGGCA TGCGCTTATT GCTTGCAGCG AATGTATGTT    960

GAGAGTTGGT TTCCCGGTCA CAGCTCATAT ATATGCTGCC AGTCACGTGT ACGACGACTG   1020

CCACATGTAT TGCTGGAAAT GAATATGTAT GTGTATTTGT CCTTTTCGTC ATTTGGGTCA   1080

TTTTAAAAAT AAGTTGTATG CTGGAGCATG ACAACAAGTG TATTTGGCTA CTATAATATT   1140

ATTAATGATA TGATGTCTTG TT                                           1162
```

(2) INFORMATION FOR SEQ ID NO:43:

(i) SEQUENCE CHARACTERISTICS:
        (A) LENGTH: 1371 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

```
ATCCACCTCG ATCCAGCCAT GCTGTCCTCC AAGTCTTCTT TAGCTGTTGC TCTAATCCTT     60

GTGGTCACCC TGACAGATGT GCTACCGCTG GTATCTTCTT CACGTGGCCT CGTTGGGGTA    120

CCCACTGATG GGGCACTGGA GGACTCTCTG TTGATGATGG AGAGATTCCA TGGCTGGATG    180

GCAAAGCATG GCAAGTCGTA TGCGGGAGTC GAGGAGAAAC TGCGGCGGTT TGACATATTC    240
```

```
CGCAGGAACG TAGAGTTCAT CGAGGCGGCG AACCGAGATG GCAGGCTCTC GTACACCCTC      300

GGGGTGAACC AGTTCGCCGA CCTCACCCAC GAGGAGTTCC TTGCCACGCA CACCAGCCGC      360

CGTGTGGTGC CGTCAGAGGA GATGGTGATT ACAACTCGCG CTGGCGTTGT TGTCGAGGGT      420

GCCAATTGTC AGCCGGCGCC AAATGCTGTG CCTCGTAGCA TCAATTGGGT GAATCAAAGC      480

AAAGTCACCC CAGTCAAAAA TCAAGGAAAA GTATGCGGGG CTTGCTGGGC TTTTTCTGCC      540

GTGGCCACGA TCGAAAGCGC CTACGCGGTC GCCAAGCGAG GCGAGCCGCC GGTTCTGTCC      600

GAGCAGGAGC TCATCGACTG TGACACAATC GACAGAGGCT GCACGAGCGG CGAGATGTAC      660

AATGCCTACT TCTGGGTCTT GAGGAACGGC GGCATCGCCA ACAGCTCAAC GTACCCCTAC      720

AAAGAGACTG ACGGCAAGTG CGAGAGAGGG AAACTGCAGG AACACGCGGC CACGATCAGG      780

GACTACAAAT TCGTCAAACC CAACTGCGAG GAGAAGCTCA TGGCAGCCGT GGCGGTGCGA      840

CCCGTCGCCG TCGGGTTCGA CTCCAACGAC GAATGCTTCA AGTTCTACCA AGCTGGTTTG      900

TACGACGGCA TGTGCATCAT GCACGGGGAA TACTTTGGCC CGTGCTCGTC CAACGACCGC      960

ATCCACTCCT TGGCCATTGT CGGGTACGCC GGCAAGGGGG GCGACAGGGT CAAGTACTGG     1020

ATCGCCAAGA ACTCGTGGGG CGAGAAGTGG GGAAAGAAGG GCTACGTCTG GCTGAAGAAG     1080

GATGTTGATG AGCCGGAAGG CCTCTGCGGC CTTGCAATTC AGCCGGTATA TCCTATAGTC     1140

TGATCTGATC TGACGAGATC GACTGCACTG GGCGTGCATG AAACCTACGG AAATGGCATT     1200

CACCTATATT TTGGGTTGCT CTGTATGCAT GGATGCGCCT ACTATATTTT ACTACATATA     1260

TATTCATCTC CCGCTAATAA AACTACATGT CCTTGTATCC ATTTATGCAC GTTTATCCAT     1320

ATCTTGAATA AATTGGATGG ATTGGTTATC CAAAAAAAAA AAAAAAAAA A              1371

(2) INFORMATION FOR SEQ ID NO:44:

(i) SEQUENCE CHARACTERISTICS:
        (A) LENGTH: 723 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

CAACCGGGAA CCGGAGGCCT CCGACCCCTC ACCTCGCTGT GGTTGACAAC ATCGACCTGT       60

GCCCAAGACC TCGGGGAACG CTACCAACTC CGAACCCAAG TATGTCCCCG CCTTCGACGA      120

GGCCGACGTC AAAGAAGGAG GTGAAGGGCG TTCTGTACCC ACGAGGCGAC GCACGTGTGT      180

CAGTGGAACG GGCAGGCCAG GTCAAACGGC GGGCTCATCG AGGGGATCGC CGACTACGTG      240

CGGCTCAAGG CCGACCTCGC GCCGACGCAC TGGCGCCCGC AGGGGAGCGG CGACCGTTGG      300

GACGAGGGGT ACGACGTGAC GGCCAAGTTC CTGGACTACT GCGACTCCCT CAAGGCCGGG      360

TTCGTGTCGG AGATGAACAG CAAGCTCAAG GACGGATACA GCGACGACTA CTTCGTGCAG      420

ATCCTGGGGA AGAGCGTGGA CCAGCTGTGG AACGACTACA AGGCCAAGTA CCCCCCAGCC      480

CCAGGGCTGA TCGACGATGC ATGCAGTTTG TTGTTGTATG TGTACCGGTC TTCGTCTACA      540

TACAGATACA TTATAGTACT TGTATTACTG TACAATTTAT GTACTGCCTG GAATGGAATA      600

AATCAGCGTT GGCACGGTGT GTGTTAACGA ATTGACGAGA CAAAGGGACC GTCTATAGGT      660

CATGTCATCG GTTGCCTGAA ATACATTGAA CATCATCACT TTCTTTACAG CAAAAAAAAA      720

AAA                                                                   723

(2) INFORMATION FOR SEQ ID NO:45:
```

(i) SEQUENCE CHARACTERISTICS:
    (A) LENGTH: 168 amino acids
    (B) TYPE: amino acid
    (D) TOPOLOGY: linear (ii) MOLECULE TYPE: protein (xi) SEQUENCE DESCRIPTION: SEQ ID NO:45:

```
Met Gly Phe Val Leu Phe Ser Gln Leu Pro Ser Phe Leu Leu Val Ser
 1               5                  10                  15

Thr Leu Leu Phe Leu Val Ile Ser His Ser Cys Arg Ala Gln Asn
                20                  25                  30

Ser Gln Gln Asp Tyr Leu Asp Ala His Asn Thr Ala Arg Ala Asp Val
                35                  40                  45

Gly Val Glu Pro Leu Thr Trp Asp Asp Gln Val Ala Ala Tyr Ala Gln
 50                  55                  60

Asn Tyr Ala Ser Gln Leu Ala Ala Asp Cys Asn Leu Val His Ser His
 65                  70                  75                  80

Gly Gln Tyr Gly Glu Asn Leu Ala Glu Gly Ser Gly Asp Phe Met Thr
                85                  90                  95

Ala Ala Lys Ala Val Glu Met Trp Val Asp Glu Lys Gln Tyr Tyr Asp
               100                 105                 110

His Asp Ser Asn Thr Cys Ala Gln Gly Gln Val Cys Gly His Tyr Thr
               115                 120                 125

Gln Val Val Trp Arg Asn Ser Val Arg Val Gly Cys Ala Arg Val Gln
130                 135                 140

Cys Asn Asn Gly Gly Tyr Val Val Ser Cys Asn Tyr Asp Pro Pro Gly
145                 150                 155                 160

Asn Tyr Arg Gly Glu Ser Pro Tyr
                165
```

(2) INFORMATION FOR SEQ ID NO:46:

(i) SEQUENCE CHARACTERISTICS:
        (A) LENGTH: 177 amino acids
        (B) TYPE: amino acid
        (D) TOPOLOGY: linear (ii) MOLECULE TYPE: protein (xi) SEQUENCE DESCRIPTION: SEQ ID NO:46:

```
Met Gly Phe Leu Thr Thr Ile Val Ala Cys Phe Ile Thr Phe Ala Ile
 1               5                  10                  15

Leu Ile His Ser Ser Lys Ala Gln Asn Ser Pro Gln Asp Tyr Leu Asn
                20                  25                  30

Pro His Asn Ala Ala Arg Arg Gln Val Gly Val Gly Pro Met Thr Trp
                35                  40                  45

Asp Asn Arg Leu Ala Ala Tyr Ala Gln Asn Tyr Ala Asn Gln Arg Ile
 50                  55                  60

Gly Asp Cys Gly Met Ile His Ser His Gly Pro Tyr Gly Glu Asn Leu
 65                  70                  75                  80

Ala Ala Ala Phe Pro Gln Leu Asn Ala Ala Gly Ala Val Lys Met Trp
                85                  90                  95

Val Asp Glu Lys Arg Phe Tyr Asp Tyr Asn Ser Asn Ser Cys Val Gly
               100                 105                 110

Gly Val Cys Gly His Tyr Thr Gln Val Val Trp Arg Asn Ser Val Arg
               115                 120                 125

Leu Gly Cys Ala Arg Val Arg Ser Asn Asn Gly Trp Phe Phe Ile Thr
130                 135                 140
```

```
Cys Asn Tyr Asp Pro Pro Gly Asn Phe Ile Gly Gln Arg Pro Phe Gly
145                 150                 155                 160

Asp Leu Glu Glu Gln Pro Phe Asp Ser Lys Leu Glu Leu Pro Thr Asp
                165                 170                 175

Val
```

(2) INFORMATION FOR SEQ ID NO:47:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

GGGATCCCTG CA                                              12

(2) INFORMATION FOR SEQ ID NO:48:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

ATAGTCTTGT TGAGAGTT                                    18

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

TCACGGGTTG GGGTTTCTAC                                20

(2) INFORMATION FOR SEQ ID NO:50:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:50:

AGGAGATGGT TTGGTGGA                                    18

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:51:

ATACGTTCTA CTATCATAGT                                      20

(2) INFORMATION FOR SEQ ID NO:52:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:52:

Ala Thr Phe Asp Ile Val Asn Lys Cys Thr Tyr Thr Val Trp Ala Ala
1               5                   10                  15

Ala Ser Pro Gly Gly Gly Arg Arg
            20

(2) INFORMATION FOR SEQ ID NO:53:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

Ala Thr Phe Asp Ile Val Asn Gln Cys Thr Tyr Thr Val Trp Ala Ala
1               5                   10                  15

Ala Ser Pro Gly Gly Gly Arg Gln Leu Asn
            20                  25

(2) INFORMATION FOR SEQ ID NO:54:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:54:

GGGATCCCTG CA                                              12

(2) INFORMATION FOR SEQ ID NO:55:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

AATCCCATGG CTATAGGA                                        18

(2) INFORMATION FOR SEQ ID NO:56:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:56:

CCGGTACCGG CATG                                                                14

(2) INFORMATION FOR SEQ ID NO:57:

(i) SEQUENCE CHARACTERISTICS:
             (A) LENGTH: 38 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:57:

GTTTATGTGA GGTAGCCATG GTGGGAAGAC TTGTTGGG                                       38

(2) INFORMATION FOR SEQ ID NO:58:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:58:

GATCGCGGTA CCGAGCTCCT CTAGGGGCC AAGG                                            34

(2) INFORMATION FOR SEQ ID NO:59:

(i) SEQUENCE CHARACTERISTICS:
             (A) LENGTH: 38 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:59:

GTTTATCTGA GGTAGCCATG GTGAGAAGAC TTGTTGGA                                       38

(2) INFORMATION FOR SEQ ID NO:60:

(i) SEQUENCE CHARACTERISTICS:
             (A) LENGTH: 32 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:60:

GATCGCGGTA CCGAGCTCCC TTGGGGGCA AG                                              32

(2) INFORMATION FOR SEQ ID NO:61:

(i) SEQUENCE CHARACTERISTICS:
             (A) LENGTH: 38 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:61:

```
AATTTCCCGG GCCCTCTAGA CTGCAGTGGA TCCGAGCT                              38
```

(2) INFORMATION FOR SEQ ID NO:62:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:62:

```
CCGATCCACT GCAGTCTAGA GGGCCCGGGA                                       30
```

(2) INFORMATION FOR SEQ ID NO:63:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:63:

```
CAAAACTCTC AACAAGACTA TTTGGATGCC C                                     31
```

(2) INFORMATION FOR SEQ ID NO:64:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:64:

```
GAACTTCCTA AAAGCTTCCC CTTTTATGCC                                       30
```

(2) INFORMATION FOR SEQ ID NO:65:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:65:

```
CAGCAGCTAT GAATGCAT                                                    18
```

(2) INFORMATION FOR SEQ ID NO:66:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:66:

```
GGCAGGGATA TTCTGGC                                                     17
```

(2) INFORMATION FOR SEQ ID NO:67:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:67:

TGCAAAGCTT GCATGCC                                                          17

(2) INFORMATION FOR SEQ ID NO:68:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:68:

ATGTTYGAYG ARAAYAA                                                          17

(2) INFORMATION FOR SEQ ID NO:69:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:69:

AACATCTTGG TCTGATGG                                                         18

(2) INFORMATION FOR SEQ ID NO:70:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:70:

GGYTTRTCNG CRTCCCA                                                          17

(2) INFORMATION FOR SEQ ID NO:71:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:71:

SCWTTCTRNC CCCAGTA                                                          17

(2) INFORMATION FOR SEQ ID NO:72:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:72:

GGRTKAKTMT AAAATTGNAC CCA                                             23

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:73:

ACRAARCART CRTGRAARTG                                                 20

(2) INFORMATION FOR SEQ ID NO:74:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:74:

ATGTTYGAYG ARAAYAA                                                    17

(2) INFORMATION FOR SEQ ID NO:75:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

Met Phe Asp Glu Asn Asn
1               5

(2) INFORMATION FOR SEQ ID NO:76:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:76:

AAYAAYTGYC CNACNAC                                                    17

(2) INFORMATION FOR SEQ ID NO:77:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

Asn Asn Cys Pro Thr Thr
1               5

(2) INFORMATION FOR SEQ ID NO:78:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:78:

ACRTCRTARA ARTCYTT                                                17

(2) INFORMATION FOR SEQ ID NO:79:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:79:

Lys Asp Phe Tyr Asp Val
1               5

(2) INFORMATION FOR SEQ ID NO:80:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:80:

CKRCARCART AYTGRTC                                                17

(2) INFORMATION FOR SEQ ID NO:81:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:81:

Asp Gln Tyr Cys Cys Arg
1               5

(2) INFORMATION FOR SEQ ID NO:82:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:82:

GCCTCGAGGA TCCTATTGAA AAAG                                        24

(2) INFORMATION FOR SEQ ID NO:83:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:83:

GCCTCGAGTG CTTAAAGAGC TTTC                                            24

(2) INFORMATION FOR SEQ ID NO:84:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:84:

CTATGAATGC ATCATAAGTG                                                20

(2) INFORMATION FOR SEQ ID NO:85:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:85:

GCGGAATTCA AAAAAAAAAA AAAACATAAG                                30

(2) INFORMATION FOR SEQ ID NO:86:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:86:

CCATAACAAA CTCCTGCTTG GGCACGGCAA GAGTGGGATA                      40

(2) INFORMATION FOR SEQ ID NO:87:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:87:

TATCCCACTC TTGCCGTGCC CAAGCAGGAG TTTGTTATGG                      40

(2) INFORMATION FOR SEQ ID NO:88:

(i) SEQUENCE CHARACTERISTICS:

```
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:88:

GATCGAATTC ATTCAAGATA CAACATTTCT                                    30

(2) INFORMATION FOR SEQ ID NO:89:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:89:

CATTCTCAAG GTCCGG                                                   16

(2) INFORMATION FOR SEQ ID NO:90:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:90:

CATCTGAATT CTCCCAACAA GTCTTCCC                                      28

(2) INFORMATION FOR SEQ ID NO:91:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:91:

AACACCTATC GATTGAGCCC CTGCTATGTC AATGCTGGTG GC                      42

(2) INFORMATION FOR SEQ ID NO:92:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:92:

GGATCCGTTT GCATTTCACC AGTTTACTAC TACATTAAAA TGAGGCTTTG              50

TAAATTCACA GCTCTCTCTT CTCTACTATT T                                  81

(2) INFORMATION FOR SEQ ID NO:93:

(i) SEQUENCE CHARACTERISTICS:
        (A) LENGTH: 33 base pairs
        (B) TYPE: nucleic acid
        (C) STRANDEDNESS: single
```

(D) TOPOLOGY: linear (ii) MOLECULE TYPE: DNA (xi) SEQUENCE DESCRIPTION: SEQ ID NO:93:

GTGACCGAGC TCAAAGAAAA ATACAGTACA ATA                                     33

(2) INFORMATION FOR SEQ ID NO:94:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:94:

ACCGTGGGAT CCACAGTAAA AAACTGAAAC TCC                                     33

(2) INFORMATION FOR SEQ ID NO:95:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:95:

GTGACCGGAT CCAAAGAAAA ATACAGTACA ATA                                     33

(2) INFORMATION FOR SEQ ID NO:96:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:96:

ACCGTGGAGC TCACAGTAAA AAACTGAAAC TCC                                     33

(2) INFORMATION FOR SEQ ID NO:97:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:97:

GAACTCCAGG ACGAGGC                                                       17

(2) INFORMATION FOR SEQ ID NO:98:

(i) SEQUENCE CHARACTERISTICS:
        (A) LENGTH: 359 amino acids
        (B) TYPE: amino acid
        (D) TOPOLOGY: linear (ii) MOLECULE TYPE: protein (xi) SEQUENCE DESCRIPTION: SEQ ID NO:98:

```
Met Ala Ala Ile Thr Leu Leu Gly Leu Leu Val Ala Ser Ser Ile
  1               5                    10                  15

Asp Ile Ala Gly Ala Gln Ser Ile Gly Val Cys Tyr Gly Met Leu Gly
             20                  25                  30

Asn Asn Leu Pro Asn His Trp Glu Val Ile Gln Leu Tyr Lys Ser Arg
             35                  40                  45

Asn Ile Gly Arg Leu Arg Leu Tyr Asp Pro Asn His Gly Ala Leu Gln
         50                  55                  60

Ala Leu Lys Gly Ser Asn Ile Glu Val Met Leu Gly Leu Pro Asn Ser
 65                  70                  75                  80

Asp Val Lys His Ile Ala Ser Gly Met Glu His Ala Arg Trp Trp Val
                 85                  90                  95

Gln Lys Asn Val Lys Asp Phe Trp Pro Asp Val Lys Ile Lys Tyr Ile
             100                 105                 110

Ala Val Gly Asn Glu Ile Ser Pro Val Thr Gly Thr Ser Tyr Leu Thr
         115                 120                 125

Ser Phe Leu Thr Pro Ala Met Val Asn Ile Tyr Lys Ala Ile Gly Glu
130                 135                 140

Ala Gly Leu Gly Asn Asn Ile Lys Val Ser Thr Ser Val Asp Met Thr
145                 150                 155                 160

Leu Ile Gly Asn Ser Tyr Pro Pro Ser Gln Gly Ser Phe Arg Asn Asp
                 165                 170                 175

Ala Arg Trp Phe Val Asp Pro Ile Val Gly Phe Leu Arg Asp Thr Arg
             180                 185                 190

Ala Pro Leu Leu Val Asn Ile Tyr Pro Tyr Phe Ser Tyr Ser Gly Asn
             195                 200                 205

Pro Gly Gln Ile Ser Leu Pro Tyr Ser Leu Phe Thr Ala Pro Asn Val
         210                 215                 220

Val Val Gln Asp Gly Ser Arg Gln Tyr Arg Asn Leu Phe Asp Ala Met
225                 230                 235                 240

Leu Asp Ser Val Tyr Ala Ala Leu Glu Arg Ser Gly Gly Ala Ser Val
                 245                 250                 255

Gly Ile Val Val Ser Glu Ser Gly Trp Pro Ser Ala Gly Ala Phe Gly
                 260                 265                 270

Ala Thr Tyr Asp Asn Ala Ala Thr Tyr Leu Arg Asn Leu Ile Gln His
             275                 280                 285

Ala Lys Glu Gly Ser Pro Arg Lys Pro Gly Pro Ile Glu Thr Tyr Ile
290                 295                 300

Phe Ala Met Phe Asp Glu Asn Asn Lys Asn Pro Glu Leu Glu Lys His
305                 310                 315                 320

Phe Gly Leu Phe Ser Pro Asn Lys Gln Pro Lys Tyr Asn Ile Asn Phe
                 325                 330                 335

Gly Val Ser Gly Gly Val Trp Asp Ser Ser Val Glu Thr Asn Ala Thr
             340                 345                 350

Ala Ser Leu Val Ser Glu Met
             355

(2) INFORMATION FOR SEQ ID NO:99:

(i) SEQUENCE CHARACTERISTICS:
        (A) LENGTH: 765 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:99:

```
AAATGACAAT TGAAATTTAT TAAAGTAATA TGATCTAATA TGTTCAAACA AGCTCAATCA      60
CAATTTAATT TAATTAATAT TGACCGCGCA TCGCGCGAGT ACGACTACTA GTTCAATTTA     120
GAAAGCTGGA GCCATTGCCG GAGTAATCAT GAAATTGGCG GAGTTGACTT CCGATTCCGG     180
TGATGGTGCG AGTATTCCCG AGCTTTTGAT CTCCGCCATT CCACGGCGTG CATTTCCACC     240
TTGTTCTTCA CACAATCTGG GAAGGTATAC ACCTTCTCCA GCAGCAAGGT TGAAGTAGAG     300
ATCAATAATA TTAGGGCAAT GTTTGTAGCA CTGAGGGGAG CACAGCTTCT GGGTAAAGTG     360
GCACTCGAGG AGAGAATCAG AAGAATTCCG AAAGTATTCC TATCAACACC GCAAGCCTGA     420
ATACACTGGT CGGTTTCAAT CCAGTCTTTG AGCTTATCAG CCTCAATTTC CGACGTCTTA     480
CATGTATATA CTTCTTCACC ACTCCTTTGG AGACGTTTCT CTAACACGCA ACGCTTCCCA     540
GTACTTGAAA TCGCAAAAGC GCATGAGTCC TTGTTTAGAT TCTCGCATGT TATGCTCCCT     600
AGAGTGACTT GAACACAGAA GACAAGTGCA CAAGCAACAA TAGCCAAAGT AAAGTTGTGG     660
AATGAAGCAA CCATGGTGAA AAATCTAGCA ACAATTGATC AGACTATAAA TTTTTTCTGA     720
GTATATATAG CTCCTTTTGG CTTTCGACTC TCCTTTTTTG TGGTT                    765
```

(2) INFORMATION FOR SEQ ID NO:100:

(i) SEQUENCE CHARACTERISTICS:
        (A) LENGTH: 1567 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:100:

```
GGCACGAGCA TTTTCCACAT CTTCTGCCAC TTCTAATTCC AAACTTCCAG TTCGAGAAAT      60
CCCAGGAGAC TATGGTTTCC CCTTTTGTGG AGCCATAAAA GATAGATATG ACTACTTCTA     120
CAACCTCGGC ACAGACGAAT TCTTTCTTAC CAAAATGCAA AAATACAACT CTACTGTCTT     180
TAGAACCAAC ATGCCACCAG GTCCATTCAT TGCTAAAAAT CCCAAAGTAA TTGTTCTCCT     240
CGATGCCAAA ACATTTCCCG TTCTTTTCGA CAACTCTAAA GTCGAAAAAA TGAACGTTCT     300
TGATGGCACG TACGTGCCAT CTACTGATTT CTATGGCGGA TATCGCCCGT GTGCTTATCT     360
TGATCCTTCT GAGTCAACTC ATGCCACACT TAAAGGGTTC TTTTTATCTT TAATCTCCCA     420
GCTTCATAAT CAATTKATTC CTTTATTTAG AACCTCAATT TCTGGTCTTT TCGCAAATCT     480
TGAGAATGAG ATTTCCCAAA ATGGCAAAGC GAACTTCAAC AATATCAGCG ACATTATGTC     540
ATTCGATTTT GTTTTTCGTT TGTTATGTGA CAAGACCAGT CCCCATGACA CAAATCTTGG     600
CTCTAATGGA CCAAAACTCT TTGATATATG GCTGTTGCCT CAACTTGCTC CATTGTTTAG     660
TCTAGGTCKT AAAATTGTG  CCGAACTTTC TGGAAGATTT AATGTTGCAT ACTTTTCCCT     720
TGCCATTTTT TCTAGTGAGA TCGAATTACC AGAAGCTTTA TGATGCTTTT AGCAAGCATG     780
CCGVAAGTAC ACTGAATGAA SCAGAGAAGA ATGGGRTCAC AAGAGACGAA GCATRCCACA     840
ACTTAGTTTT TCTTGCAGGT TTCAATGCTT ATGGTGGGAT GAAAGTTTTA TTCCCTGCAC     900
TGATAAAGTG GGTCGCCAAT GGAGGAAAGA GTTTACACAC TCGGCTGGCA AATGAAATCA     960
GGACANTTAT CAAAGAAGAA TGTGGGACCA TAACTCTATC AGCAATCAAC AAGATGAGTT    1020
TAGTAAAATC AGTAGTGTAT GAAGTATTAA GAATTGAACC TCCAGTTCCA TTCCAATATG    1080
GTAAAGCCAA AGAAGATATC ATAATCCAAA GCCATGATTC AACTTCTTA GTCAAGAAAG     1140
GTGAAATGAT CTTTGGATAT CAGCCTTTTG CTACAAAAGA TCCAAAGATT TTTGACAAAC    1200
```

```
CAGAGGAGTT TATTCCGGAG AGGTTCATGG CCGAAGGGGA AAAATTATTA AAGTATGTGT    1260

ATTGGTCAAA TGCAAGAGAG ACAGATGATC CAACGGTGGA CAACAAACAA TGCCCAGCGA    1320

AAAATCTTGT CGTGCTTTTG TGCAGGTTGA TGTTGGTGGA GGTTTTCATG CGTTACGACA    1380

CATTCACAGT GGAGTCAACY AAGCTCTTTC TTGGGTCATC AGTAACGTTC ACGACTCTGG    1440

AAAAAGCGAC ATGAGTTTCA GATATCTTAA TTGTAGGCTG CKAATAATAA TGTGGTCATT    1500

CTGCKAATTA TTGTACTTGT GCTGATGTAC TTGACTTCGA GTGGATATAA TAATGCACTG    1560

TTTTTAG                                                              1567

(2) INFORMATION FOR SEQ ID NO:101:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:101:

GGTCACTAAT ACCAAACCAA GATTCAGTTG GTTGAATGAT GATTTAACAG TTTAAGACAT      60

TAGACTATAC ATGTGATTAA GTACTAGTAC TTCCCCCACT CGCGAGGAAG TACATTCAAC     120

CAGAAGGAGA CCTCCAGAGT TAGTTCAGCA GNTCATTTAT CTACATAAAC TACAACTCTA     180

AGCAAGACAT AAGGGATAAA CAGGAGTATA CATATTATAC TACACATATT ACTGCGCAAT     240

AGCAAGTGGA CACAAAGGTA CCACTATTTG GTAGTGTTAG GGGCGTTCCC AAAAGGGGTT     300

CGGTCCCTTG AGTCATTGGA GGCTGTCTTG ATCTCTTGGC AGTTGGACAA TTCCACAATT     360

ACCTGAACTT CGCCAATTGG TTGAGATGTG AA                                   392

(2) INFORMATION FOR SEQ ID NO:102:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:102:

TGCCGCTTTA AGTGTGCTCG AACCTCCTAC TGGTAATGAG GATGATGATG ACCTGGAATT      60

TGAAAATGTC CACTGGAATG GTTCAGATAT GGCATCCGAT GATACTCAAA AATCTCATAG     120

ACCAAGGCAC CGCGTACATA AATCGTCTGG TTCCCACAAG GNCATGAGCC GCTCCCTTTC     180

ATGTGACTCG CAATCAAAAG GATCTATTTC TACACCTCGT GGGTCCATGG TTGACCTAAG     240

CAAACTCGAG ATGGCTGCAC TGTGGAGATA TTGGCGACAC TTTAACCTTA GGGAGGTATT     300

CCTAACCCTC GAAAGAGCAC TTATTGATGT GGTCAGAGCA TTCANATCTC AGAAATGGGC     360

GAGTGGAGGT ATTGTGGATT GGTCAAGCTG CAAGAG                               396

(2) INFORMATION FOR SEQ ID NO:103:

(i) SEQUENCE CHARACTERISTICS:
        (A) LENGTH: 653 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:103:

| | | | | | |
|---|---|---|---|---|---|
| CTTGTTTGGT | TGTTTGAGTT | ATTTTGCTTC | TAAGAACTTT | GTGAGAAATG | GCTGCTAACG | 60 |
| ATGCTACTTC | ATCCGAGGAG | GGACAAGTGT | TCGGCTGCCA | CAAGGTTGAG | GAATGGAACG | 120 |
| AGTACTTCAA | GAAAGGCGTT | GAGACTAAGA | AACTGGTGGT | GGTCGATTTT | ACTGCTTCAT | 180 |
| GGTGCGGSCC | TTGCCGTTTT | ATTGCCCCAA | TTCTTGCTGA | CATTGCTAAG | AAGATGCCCC | 240 |
| ATGTTATATT | CCTCAAGGTT | GATGTTGATG | AACTGAAGAC | TGTTTCAGCG | GGAATGGAGT | 300 |
| GTGGAGGCAA | TGCCAACTTT | TGTCTTCATT | AAAGATGGAA | AGAAGTGGA | CAGAGTTGTT | 360 |
| GGTGCCAAGA | AAGAGGAGTT | GCAGCAGACC | ATAGTGAAGC | ATGCTGCTCC | TGCTACTGTC | 420 |
| ACTGCTTGAA | TCTCCTTAAT | CAAGGGGATG | ATATCCCATA | TTTAGTAGTA | TTGTCTTTTG | 480 |
| TAATAACCAA | GTAACTTGTT | CGAATTTCAC | ACTATGGATC | ACTGTATGGT | TGTACTATCC | 540 |
| ACCATGTTTT | TATTGCTTTT | GTGAACCTTG | TCTTGTTGCT | TGGAATCTGA | TTTGTGCATT | 600 |
| ACTGGTGTAA | GGCTATATGC | CCAATTCYAC | AAAAAGACTA | CTTTTAGATT | TCT | 653 |

(2) INFORMATION FOR SEQ ID NO:104:

(i) SEQUENCE CHARACTERISTICS:
        (A) LENGTH: 1697 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:104:

| | | | | | |
|---|---|---|---|---|---|
| ATTCAAAATT | ATTGGATCCT | AGTTTTAAGT | GGAACTCCTA | ATTAATCAAT | CATTTCATGA | 60 |
| TCAACCTTTA | CTAACATCAC | CATTTTCCTT | GACAACATTA | TTTTCCGACT | TACCATTTTC | 120 |
| CTTAACACCA | TTACCCTCTG | GATTTTCCTT | GACAATATTA | CTCTCCGACT | TCTCATTTTC | 180 |
| GTTCACTTTA | TCAGTAATCT | TGGCTTCTTC | AGCAGCTGCT | TCTTTCTCTT | TCTCTTTCTC | 240 |
| TTTCTCAGCC | CTTTCTCTTT | CTTCTTCCTC | AGCCTTCAAT | TTTGGCTCCT | CCTTTGCAGT | 300 |
| TTCAAGAGCT | TTAATCAGTC | TCTCCAAACA | AGTGTTTGCA | TTTTCCTTAG | AAGACTTGGG | 360 |
| CATTAAATTC | TCAGCAACAT | CAGCAGGAGT | AATATTAGTT | TCCCCCAATA | AATGACGAAT | 420 |
| CTCAGGAAAA | TGATCATGAG | ACTCAATATC | TAGATAATTA | TTTGCAAGCA | CCTTGAAGGA | 480 |
| GTCAAAGCAA | CAGTATGATA | ACACAATGTG | TTTATCCATC | CTCCCCCTCC | GAATTAAAGC | 540 |
| AGGGTCAAGC | TTTTCCACAA | AGTTGGTAGT | GAAAACAATA | AGCCTTTCAC | CACCAATAGC | 600 |
| TGACCATAAC | CCATCAATAA | AGTTCAAAAG | CCCAGATAAA | GTCACCTCGC | TTTGCTTTTT | 660 |
| CTCCTCTCGA | TTTTTCATCT | TCTCCTTGAC | GGCATCTTTC | TCGTCTTTTA | CTTCCTCTTC | 720 |
| CTTGTCGTCT | TTCTTCTTCT | CCCTTTGGCC | GGTAAGGTCA | AGCGAACAGT | CGATGTCTTC | 780 |
| AATCACAATG | ATAGACTTAC | TAGTAGTATC | TATTAATAAC | TTTCTTAGCT | CGGTGTTGTC | 840 |
| CTTAACCGCT | GTCAATTCAA | GATCATAGAC | ATCATATTGT | AAGAAGTTAG | CCATTGCAGC | 900 |
| AATCATGCTA | GACTTACCGG | TTCCTGGAGG | ACCATATAGA | AGATAACCAC | GCTTCCATGC | 960 |
| CTTGCCAATC | TTGGCATAAT | AGTCTTTTGA | CTTGCTAAAT | GTTTGAAGGT | CATCCATAAT | 1020 |
| CTCTTGTTTC | TTGTTTGGCT | CCATGGCTAA | AGTATCAAAT | GTTGATGGAT | GTTCAAACAC | 1080 |
| TACTTGGCTC | CACATTCTCC | TCCTGTATCC | ATACCCACCA | TCTCCCTTAC | TGTTTGTGTA | 1140 |
| CAACTTTCTC | TGCCTTTCTC | TTACTGAAAT | TGCCTTCCCT | TCGTCCAATA | CATACTTCAA | 1200 |
| GTATGAAGCG | GTGATAAGCT | CGCGGTTCTT | TCTGTGAAAC | TTGAGTTTGA | AATACCTCTT | 1260 |
| CTCATCCTCC | CTAGGGTACC | AAGAAATTGT | CTGTCTGCTG | GCTACTTGTT | GGCTAGAAAT | 1320 |

```
CCACCAGACT TTCTCGCCTT TATATTCATC GGTTACCTCC TCATGATCAT CCATGGTTAG      1380

TACAAGAGAT TGGCCATCTT TCACTACATT GGCTTTGAGA CGCTTAGCTT GTGTGGAGGA      1440

GTTCTTGCTT AGGTACCTTT CAATTGCTAC ATAAGCTTTG CTACGCTCGA ACCAGCCATC      1500

AGTTTCATAC TCATGAAAAA TAATGTGCAT ATAAGGGTAG AAATAGCTCA CGAGTTTATC      1560

GGTATACCTC CTAATATGAC CACGAAGTTC GTGAGGAAAA TAGTTCTGGT ACATGGTCCA      1620

GGCAAACATG ATTGTTGCAA TAGCTGGACC CAACTGAGTC CAAACATCTT GCATCATCAT      1680

CATCATCTAA TTTCTCT                                                    1697
```

(2) INFORMATION FOR SEQ ID NO:105:

(i) SEQUENCE CHARACTERISTICS:
        (A) LENGTH: 654 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:105:

```
TTAACCTTGA GATAAGCATT AAAAAAACTC AATGGCAGGG AAGGTTGAGA AAGTGCTTGC        60

AGTACTGATG CTTGCAATGC TTCTGTTTTC GGAGCATTTC ATGGCTGCTA ATCATGAAAT       120

TAAAACAACT GAAGATAACT CTATTAGCCC TTTCTGCTTA ATAAAATGTT TATATGGATG       180

CAGGGGGTTG CCACCTGCAA AAGCAGCCAT TTGTGCAGCT CAATGTTTGT TTAAGTGCGC       240

TGTCCAAGAT GAGGCCAATA TAGCTGAAAC TAAGGGCATA ATAGGTGAGA CTGCATACAA       300

CCAGTATGAT GTTGGATGTG CCCTTGGCTA CTGCTCTGAG TTCCTGTTGA ATTATGATGA       360

GAGGAGGTTC AACTGCTGCA TGGAATACTG TCGCGAGGGC AAAATGACCT GTCCTGTTGA       420

GGCTGCACCT TGAAGAAATG GTTGCCCTAA AATTATCGCC TCATCAAATG GAAGTACACT       480

GCTTTTTCTA CTTCCGGTGT TTAGTAGTAG TAGTAAATAA GTGAGGCATG TTACGTACTC       540

TTATGTTTTG TAATAATTAT GCTTTTTAAT AATGTAATCT GTCTGTGTGC ATACAATGCA       600

CACGACGCTA GCTACTACTT TTTATCTACT AAAAACGAAA AGTAACTTAT TTCT            654
```

(2) INFORMATION FOR SEQ ID NO:106:

(i) SEQUENCE CHARACTERISTICS:
        (A) LENGTH: 1031 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:106:

```
GAGACAAATA CCTATAATAA GCCATTCATA ATCTTCTTGC TTCTTGTTCA GAATAATGGG        60

GAATCTTTTC TGTTGCGTGC TTGTGAAGCA ATCAGATGTT GCGGTCAAGG AGAGATTTGG       120

CAAATTCCAA AAAGTACTTA ATCCAGGTCT CCAATTTGTT CCATGGGTCA TCGGTGATTA       180

CGTCGCCGGT ACACTGACCC TTCGTCTTCA GCAACTCGAT GTTCAGTGTG AAACCAAAAC       240

AAAGGACAAT GTGTTTGTGA CAGTGGTTGC ATCCATACAA TACAGAGTCT TAGCTGACAA       300

GGCAAGTGAT GCTTTTTACA GACTCAGCAA TCCAACCACC CAAATCAAAG CCTACGTCTT       360

TGATGTGATC AGAGCATGTG TTCCAAAGCT GAACTTGGAC GATGTGTTCG AGCAGAAGAA       420

TGAAATTGCC AAATCTGTGG AAGAAGAGCT AGACAAAGCC ATGACTGCTT ATGGTTACGA       480

AATCCTTCAA ACCCTAATTA TCGACATTGA GCCTGATCAA CAGGTTAAAC GTGCCATGAA       540
```

```
CGAAATCAAC GCCGCGGCGA GGATGAGAGT GGCAGCGAGC GAAAAAGCAG AGGCTGAGAA    600

AATCATTCAG ATCAAAAGAG CAGAGGGTGA AGCAGAGTCA AAGTACCTGT CGGGACTCGG    660

AATCGCTCGG CAGAGACAAG CGATCGTGGA CGGTCTTGAG AGACAGTGTT CTTGGGTTCG    720

CAGGAAACGT GCCAGGGACG TCAGCGAAGG ATGTGTTGGA CATGGTGATG ATGACTCAGT    780

ACTTTGACAC AATGAGAGAT ATCGGAGCAA CTTCTAAATC CTCTGCGGTG TTTATCCCTC    840

ACGGTCCAGG CGCCGTCTCT GACGTGGCAG CGCAGATTCG AAATGGATTA TTACAGGCCA    900

ACAATGCCTC CTAATCACTC AAGTCAAATT GTCTTGGTCG TCTCTTTATA TATTTTCGTA    960

TCTTCTTATT AAAAAGGTAA ATTTGACTTT TAATATAATG GTGTGCTTAT TGCGAAAAAA   1020

AAAAAAAAA A                                                        1031

412
```

(2) INFORMATION FOR SEQ ID NO:107:

(i) SEQUENCE CHARACTERISTICS:
       (A) LENGTH: 95 amino acids
       (B) TYPE: amino acid
       (D) TOPOLOGY: linear (ii) MOLECULE TYPE: protein (xi) SEQUENCE DESCRIPTION: SEQ ID NO:107:

```
Met Phe Ser Lys Thr Asn Leu Phe Leu Cys Leu Ser Leu Ala Ile Leu
 1               5                  10                  15

Val Ile Val Ile Ser Ser Gln Val Asp Ala Arg Glu Met Ser Lys Ala
                20                  25                  30

Pro Ala Ser Ile Thr Gln Ala Met Asn Ser Asn Ile Ile Thr Asp Gln
            35                  40                  45

Lys Met Gly Ala Gly Ile Thr Arg Lys Ile Pro Gly Trp Ile Arg Lys
        50                  55                  60

Gly Ala Lys Pro Gly Gly Lys Ile Ile Gly Lys Ala Cys Lys Ile Cys
65                  70                  75                  80

Ser Cys Lys Tyr Gln Ile Cys Ser Lys Cys Pro Lys Cys His Asp
                85                  90                  95
```

(2) INFORMATION FOR SEQ ID NO:108:

(i) SEQUENCE CHARACTERISTICS:
       (A) LENGTH: 94 amino acids
       (B) TYPE: amino acid
       (D) TOPOLOGY: linear (ii) MOLECULE TYPE: protein (xi) SEQUENCE DESCRIPTION: SEQ ID NO:108:

```
Met Phe Ser Lys Thr Ile Leu Phe Leu Cys Phe Ser Leu Ala Ile Leu
 1               5                  10                  15

Val Met Val Ile Ser Ser Gln Ala Asp Ala Arg Glu Met Ser Lys Ala
                20                  25                  30

Ala Ala Pro Ile Thr Gln Ala Met Asn Ser Asn Ile Ile Thr Asp Gln
            35                  40                  45

Lys Thr Gly Ala Gly Ile Ile Arg Lys Ile Pro Gly Trp Ile Arg Lys
        50                  55                  60

Gly Ala Lys Gly Gly Asn Ile Ile Gly Lys Ala Cys Lys Ile Cys Ser
65                  70                  75                  80

Cys Lys Tyr Gln Ile Cys Ser Lys Cys Pro Lys Cys His Asp
                85                  90
```

(2) INFORMATION FOR SEQ ID NO:109:

(i) SEQUENCE CHARACTERISTICS:
        (A) LENGTH: 95 amino acids
        (B) TYPE: amino acid
        (D) TOPOLOGY: linear (ii) MOLECULE TYPE: protein (xi) SEQUENCE DESCRIPTION: SEQ ID NO:109:

Met Phe Ser Lys Thr Asn Leu Phe Leu Cys Leu Ser Leu Ala Ile Leu
1               5                   10                  15

Leu Ile Val Ile Ser Ser Gln Ala Asp Ala Arg Gln Ile Ser Lys Ala
            20                  25                  30

Ala Ala Pro Ile Thr His Ala Met Asn Ser Asn Asn Ile Thr Asn Gln
        35                  40                  45

Lys Thr Gly Ala Gly Ile Ile Arg Lys Ile Pro Gly Trp Ile Arg Lys
    50                  55                  60

Gly Ala Lys Pro Gly Gly Lys Val Ala Gly Lys Ala Cys Lys Ile Cys
65                  70                  75                  80

Ser Cys Lys Tyr Gln Ile Cys Ser Lys Cys Pro Lys Cys His Asp
                85                  90                  95

(2) INFORMATION FOR SEQ ID NO:110:

(i) SEQUENCE CHARACTERISTICS:
        (A) LENGTH: 95 amino acids
        (B) TYPE: amino acid
        (D) TOPOLOGY: linear (ii) MOLECULE TYPE: protein (xi) SEQUENCE DESCRIPTION: SEQ ID NO:110:

Met Phe Ser Lys Thr Asn Leu Phe Leu Cys Leu Ser Leu Ala Ile Leu
1               5                   10                  15

Leu Ile Val Ile Ser Ser Gln Ala Asp Ala Arg Glu Met Ser Lys Ala
            20                  25                  30

Ala Val Pro Ile Thr Gln Ala Met Asn Ser Asn Asn Ile Thr Asn Gln
        35                  40                  45

Lys Thr Gly Ala Gly Ile Ile Arg Lys Ile Pro Gly Trp Ile Arg Lys
    50                  55                  60

Gly Ala Lys Pro Gly Gly Lys Val Ala Gly Lys Ala Cys Lys Ile Cys
65                  70                  75                  80

Ser Cys Lys Tyr Gln Ile Cys Ser Lys Cys Pro Lys Cys His Asp
                85                  90                  95

(2) INFORMATION FOR SEQ ID NO:111:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO:111:

Met Phe Ser Lys Thr Asn Leu Phe Leu Cys Leu Ser Leu Ala Ile Leu
1               5                   10                  15

Leu Ile Val Ile Ser Ser Gln Ala Asp Ala Arg Glu Thr Ser Lys Ala
            20                  25                  30

Thr Ala Pro Ile Thr Gln Glu Met Asn Ser Asn Asn Thr Thr Asp Gln

```
                    35                  40                  45

Lys Ile Pro Lys Arg Pro Lys Pro Gly Gly Asn Ile Phe Gly Lys Ala
        50                  55                  60

Cys Lys Ile Cys Pro Cys Lys Tyr Gln Ile Cys Ser Lys Cys Pro Lys
 65                  70                  75                  80

Cys Asp Asp Gln Asn Ile Ala Gly Lys Phe Cys Lys Ile Cys Ser Cys
                    85                  90                  95

Lys Thr Gln Ile Cys Ser Lys Cys Pro Lys Cys His Asn Gln Asn
                100                 105                 110
```

INDUCIBLE HERBICIDE RESISTANCE

CROSS-REFERENCE TO RELATED U.S. PATENT APPLICATIONS

This application is a continuation of application Ser. No. 08/457,364, filed May 31, 1995, now U.S. Pat. No. 5,847,258 which is a divisional of application Ser. No. 08/181,271, filed Jan. 13, 1994, issued as U.S. Pat. No. 5,614,395, which is a continuation-in-part of abandoned application Ser. No. 08/093,301, filed Jul. 16, 1993, which is a continuation of abandoned application Ser. No. 07/973,197, filed Nov. 6, 1992, which is a continuation of abandoned application Ser. No. 07/678,378, filed Apr. 1, 1991, which is a continuation of abandoned application Ser. No. 07/305,566, filed Feb. 6, 1989, which is a continuation-in-part of abandoned application Ser. No. 07/165,667, filed Mar. 8, 1988. Said application Ser. No. 08/181,271 (U.S. Pat. No. 5,614,395) is also a continuation-in-part of abandoned application Ser. No. 08/042,847, filed Apr. 6, 1993, which is a continuation of abandoned application Ser. No. 07/632,441, filed Dec. 21, 1990 which is a continuation-in-part of abandoned application Ser. Nos. 07/425,504 and 07/165,667, filed Oct. 20, 1989 and Mar. 8, 1988, respectively. Said application Ser. No. 08/181,271 (U.S. Pat. No. 5,614,395) is also a continuation-in-part of abandoned application Ser. No. 07/848,506, filed Mar. 6, 1992, which is a continuation-in-part of abandoned application Ser. No. 07/768,122, filed Sep. 27, 1991, which is a continuation-in-part of abandoned application Ser. No. 07/580,431, filed Sep. 7, 1990, which is a continuation-in-part of abandoned application Ser. No. 07/425,504, filed Oct. 20, 1989, which is a continuation-in-part of abandoned application Ser. No. 07/368,672, filed Jun. 20, 1989, which is a continuation-in-part of abandoned application Ser. No. 07/329,018, filed Mar. 24, 1989. Said application Ser. No. 08/181,271 (U.S. Pat. No. 5,614,395) is also a continuation-in-part of abandoned application Ser. No. 08/045,957, filed Apr. 12, 1993.

FIELD OF THE INVENTION

One aspect of the present invention relates to the chemical regulation of gene expression. In particular, this aspect relates to non-coding DNA sequences which, in the presence of chemical regulators, regulate the transcription of associated DNA sequences in plants. Another aspect of the invention relates to DNA molecules encoding proteins capable of conferring plant disease and/or plant pest resistance. Both aspects of the invention relate, in part, to genes associated with the response of plants to pathogens.

BACKGROUND OF THE INVENTION

Advances in recombinant DNA technology coupled with advances in plant transformation and regeneration technology have made it possible to introduce new genetic material into plant cells, plants or plant tissue, thus introducing new traits, e.g., phenotypes, that enhance the value of the plant or plant tissue. Recent demonstrations of genetically engineered plants resistant to pathogens (EP-A 240 332 and EP-A 223 452) or insects (Vaeck, M. et al., *Nature* 328: 33 (1987)) and the production of herbicide tolerant plants (DeBlock, M. et al., *EMBO J.* 6: 2513 (1987)) highlight the potential for crop improvement. The target crops can range from trees and shrubs to ornamental flowers and field crops. Indeed, it is clear that the "crop" can also be a culture of plant tissue grown in a bioreactor as a source for some natural product.

A. General Overview of Plant Transformation Technology

Various methods are known in the art to accomplish the genetic transformation of plants and plant tissues (i.e., the stable introduction of foreign DNA into plants). These include transformation by Agrobacterium species and transformation by direct gene transfer.

1. Agrobactedum-mediated Transformations

*A. tumefaciens* is the etiologic agent of crown gall, a disease of a wide range of dicotyledons and gymnosperms, that results in the formation of tumors or galls in plant tissue at the site of infection. Agrobacterium, which normally infects the plant at wound sites, carries a large extrachromosomal element called the Ti (tumor-inducing) plasmid.

Ti plasmids contain two regions required for tumorigenicity. One region is the T-DNA (transferred-DNA) which is the DNA sequence that is ultimately found stably transferred to plant genomic DNA. The other region required for tumorigenicity is the vir (virulence) region which has been implicated in the transfer mechanism. Although the vir region is absolutely required for stable transformation, the vir DNA is not actually transferred to the infected plant. Transformation of plant cells mediated by infection with *Agrobacterium tumefaciens* and subsequent transfer of the T-DNA alone have been well documented. See, for example, Bevan, M. W. and Chilton, M-D., *Int. Rev. Genet.* 16: 357 (1982).

After several years of intense research in many laboratories, the Agrobacterium system has been developed to permit routine transformation of a variety of plant tissue. Representative species transformed in this manner include tobacco, tomato, sunflower, cotton, rapeseed, potato, soybean, and poplar. While the host range for Ti plasmid transformation using *A. tumefaciens* as the infecting agent is known to be very large, tobacco has been a host of choice in laboratory experiments because of its ease of manipulation.

*Agrobacterium rhizogenes* has also been used as a vector for plant transformation. This bacterium, which incites hairy root formation in many dicotyledonous plant species, carries a large extrachromosomal element called an Ri (root-inducing) plasmid which functions in a manner analogous to the Ti plasmid of *A. tumefaciens*. Transformation using *A. rhizogenes* has developed analogously to that of *A. tumefaciens* and has been successfully utilized to transform, for example, alfalfa, *Solanum nigrum L.*, and poplar.

2. Direct Gene Transfer

Several so-called direct gene transfer procedures have been developed to transform plants and plant tissues without the use of an Agrobacterium intermediate (see, for example, Koziel et al., *Biotechnology* 11: 194–200 (1993); U.S. Appln. Ser. No. 08/008,374, filed Jan. 25, 1993, herein incorporated by reference in its entirety). In the direct transformation of protoplasts the uptake of exogenous genetic material into a protoplast may be enhanced by use of a chemical agent or electric field. The exogenous material may then be integrated into the nuclear genome. The early work was conducted in the dicot tobacco where it was shown that the foreign DNA was incorporated and transmitted to progeny plants, see e.g. Paszkowski, J. et al., *EMBO J.* 3: 2717 (1984); and Potrykus, I. et al., *Mol. Gen. Genet.* 199: 169 (1985).

Monocot protoplasts have also been transformed by this procedure in, for example, *Triticum monococcum, Lolium multiflorum* (Italian ryegrass), maize, and Black Mexican sweet corn.

Alternatively exogenous DNA can be introduced into cells or protoplasts by microinjection. A solution of plasmid DNA is injected directly into the cell with a finely pulled glass needle. In this manner alfalfa protoplasts have been transformed by a variety of plasmids, see e.g. Reich, T. J. et al., *Bio/Technology* 4: 1001 (1986).

A more recently developed procedure for direct gene transfer involves bombardment of cells by microprojectiles carrying DNA, see Klein, T. M. et al., *Nature* 327: 70 (1987). In this procedure tungsten particles coated with the exogenous DNA are accelerated toward the target cells, resulting in at least transient expression in the example reported (onion).

B. Regeneration of Transformed Plant Tissue

Just as there is a variety of methods for the transformation of plant tissue, there is a variety of methods for the regeneration of plants from plant tissue. The particular method of regeneration will depend on the starting plant tissue and the particular plant species to be regenerated. In recent years it has become possible to regenerate many species of plants from callus tissue derived from plant explants. The plants which can be regenerated from callus include monocots, such as corn, rice, barley, wheat and rye, and dicots, such as sunflower, soybean, cotton, rapeseed and tobacco.

Regeneration of plants from tissue transformed with *A. tumefaciens* has been demonstrated for several species of plants. These include sunflower, tomato, white clover, rapeseed, cotton, tobacco, and poplar. The regeneration of alfalfa from tissue transformed with *A. rhizogenes* has also been demonstrated. Plant regeneration from protoplasts is a particularly useful technique, see Evans, D. A. et al., in: "Handbook of Plant Cell Culture", Vol. 1, MacMillan Publ. Co., 1983, p. 124. When a plant species can be regenerated from protoplasts, then direct gene transfer procedures can be utilized, and transformation is not dependent on the use of *A. tumefaciens*. Regeneration of plants from protoplasts has been demonstrated for rice, tobacco, rapeseed, potato, eggplant, cucumber, poplar, and corn.

Various plant tissues may be utilized for transformation with foreign DNA. For instance, cotyledon shoot cultures of tomato have been utilized for Agrobacterium mediated transformation and regeneration of plants (see European application 0249432). Further examples include Brassica species (see WO 87/07299) and woody plant species, particularly poplar (see U.S. Pat. No. 4,795,855, incorporated by reference herein in its entirety).

The technological advances in plant transformation and regeneration technology highlight the potential for crop improvement via genetic engineering. There have been reports of genetically engineered tobacco and tomato plants which are resistant to infections of, for example, tobacco mosaic virus (TMV) and resistant to different classes of herbicides. Insect resistance has been engineered in tobacco and tomato plants.

C. Cell Cultures

The potential for genetic engineering is not limited to field crops but includes improvements in ornamentals, forage crops and trees. A less obvious goal for plant biotechnology, which includes both genetic engineering and tissue culture applications, is the enhanced production of a vast array of plant-derived chemical compounds including flavors, fragrances, pigments, natural sweeteners, industrial feedstocks, antimicrobials and pharmaceuticals. In most instances these compounds belong to a rather broad metabolic group, collectively denoted as secondary products. Plants may produce such secondary products to ward off potential predators, attract pollinators, or combat infectious diseases.

Plant cell cultures can be established from an impressive array of plant species and may be propagated in a bioreactor. Typical plant species include most of those that produce secondary products of commercial interest. It has been clearly demonstrated in a number of agriculturally important crop plants that stable genetic variants arising from the tissue culture of plant somatic cells (somaclonal variation) can be induced and selected. Numerous advantages flow from plant tissue culture production of secondary compounds. These include (1) the possibility of increased purity of the resultant product, (2) the conversion of inexpensive precursors into expensive end products by biotransformation, and (3) the potential for feeding substrate analogs to the culture to create novel compounds.

D. Advantages of Controlled Gene Expression

Whether the target of genetic engineering of plants is a field crop, ornamental shrub, flower, tree or a tissue culture for use in a bioreactor, a principal advantage to be realized is the control of expression of the chimeric gene so that it is expressed only at the appropriate time and to the appropriate extent, and in some situations in particular parts of the plant. For example, in order to achieve a desirable phenotype the chimeric gene may need to be expressed at levels of 1% of the total protein or higher. This may well be the case for fungal resistance due to chimeric chitinase expression or insect resistance due to increased proteinase inhibitor expression. In these cases the energy expended to produce high levels of the foreign protein may result in a detriment to the plant whereas, if the gene were expressed only when desired, for instance when a fungal or insect infestation is imminent, the drain on energy, and therefore yield, could be reduced.

Alternatively, the phenotype expressed by the chimeric gene could result in adverse effects to the plant if expressed at inappropriate times during development. For example, if the chimeric gene product were a plant hormone that induced pod abscission, early expression could bring about abscission of the fruit from the plant before the seed had matured, resulting in decreased yield. In this case it would be much more advantageous to induce the expression of this type of gene to a time when pod abscission is preferred, or least injurious to the plant.

For tissue in culture or in a bioreactor the untimely production of a secondary product could lead to a decrease in the growth rate of the culture resulting in a decrease in the yield of the product. Therefore, it would be advantageous to allow the culture to grow without expressing the secondary product and then induce the chimeric gene at an appropriate time to allow for an optimized expression of the desired product.

In view of considerations like these, as well as others, it is clear that control of the time, extent and/or site of expression of the chimeric gene in plants or plant tissues would be highly desirable. Control that could be exercised easily in a field, a greenhouse or a bioreactor would be of particular commercial value.

E. Known Regulatable Gene Expression Systems in Plants

Several plant genes are known to be induced by various internal and external factors including plant hormones, heat shock, chemicals, pathogens, lack of oxygen and light. While few of these systems have been described in detail, in the best characterized, an increased accumulation of mRNA leads to an increased level of specific protein product.

As an example of gene regulation by a plant hormone, abscissic acid (ABA) has been shown to induce the late embryogenesis abundant mRNAs of cotton, see Galau, G. A. et al., *Plant Mol. Biol.* 7: 155 (1986). In another example, gibberellic acid (GA3) induces malate synthase transcripts in castor bean seeds and alpha-amylase isozymes in barley aleurone layers, see Rodriguez, D. et al., *Plant Mol. Biol.* 9: 227 (1987); Nolan, R. C. et al., *Plant Mol. Biol.* 8: 13 (1987).

The regulation of heat shock protein genes of soybean has been studied in detail. Treatment of plants for several hours at 40° C. results in the de novo synthesis of several so-called heat shock proteins (Key, J. et al., *Proc. Natl. Acad. Sci. USA*, 78: 3526 (1981)). Several such genes have been isolated and their regulation studied in detail. The expression of these genes is primarily controlled at the level of transcription. The promoter of the hsp70 gene has been fused to the neomycin phosphotransferase II (NptII) gene and the chimeric gene has been shown to be induced by heat shock (Spena, A. et al., *EMBO J.* 4: 2736 (1985)) albeit at a lower level than the endogenous heat shock genes.

Another class of inducible genes in plants include the light regulated genes, most notably the nuclear encoded gene for the small subunit of ribulose 1,5-bisphosphate carboxylase (RUBISCO). Morelli, G. et al., *Nature* 315: 200 (1985)) and Hererra-Estrella, L. et al., *Nature* 310: 115 (1984)) have demonstrated that the 5' flanking sequences of a pea RUBISCO gene can confer light inducibility to a reporter gene when attached in a chimeric fashion. This observation has been extended to other light inducible genes such as the chlorophyll a/b binding protein.

The alcohol dehydrogenase (adh) genes of maize have been extensively studied. The adh1-s gene from maize was isolated and a portion of the 5' flanking DNA was shown to be capable of inducing the expression of a chimeric reporter gene (e.g., chloramphenicol acetyl transferase, CAT) when the transiently transformed tissue was subjected to anaerobic conditions (Howard, E. et al., *Planta* 170: 535 (1987)).

A group of chemicals known as safeners have been developed to protect or "safen" crops against potentially injurious applications of herbicides. While a general mechanism for the action of such compounds has not been fully developed, regulation of naturally regulatable genes by such compounds is one possible mechanism. It has recently been reported that higher levels of a glutathione-S-transferase (GST) are induced in maize treated with the safener 2-chloro-4-(trifluoromethyl)-5-methyl-thiazolecarboxylic acid benzyl ester, see Wiegand, R. C. et al., *Plant Mol. Biol.* 7: 235 (1986). Although the level of GST mRNA is elevated upon treatment with the safener, the mechanism leading to the elevation was not reported.

Many plants, when reacting hypersensitively toward various pathogens, are stimulated to produce a group of acid-extractable, low molecular weight pathogenesis-related (PR) proteins (Van Loon, L. C., *Plant Mol. Biol.* 4: 111 (1985)). Of particular interest, however, is the observation that these same PR proteins accumulate to high levels in plants treated with chemicals such as polyacrylic acid and acetylsalicylic acid (Gianinazzi, S. et al., *J. Gen. Virol.* 23: 1 (1974); White, R. F., *Virology* 99: 410 (1979)). The presence of PR proteins has been correlated with the induction of both a local and systemic resistance against a broad range of pathogens. An interspecific tobacco hybrid resistant to tobacco mosaic virus (TMV) was shown to express the PR-proteins constitutively (Ahl, P. et al., *Plant Sci. Lett.* 26: 173 (1982)). Furthermore, immunoprecipitation of in vitro translation products using mRNA from either TMV-infected or chemically treated tobacco (Cornelissen, B. J. C. et al., *EMBO J.* 5: 37 (1986); Carr, J. P. et al., *Proc. Natl. Acad. Sci. USA* 82: 7999 (1985)) indicated that the increased level of PR-protein was a result of RNA accumulation. Therefore, induction of PR protein genes by chemicals or pathogens provides a method to address the problem of chemically regulating gene expression in plants and plant tissue.

F. Chemical Regulation of Expression

In some cases it will be desirable to control the time and/or extent of the expression of introduced genetic material in plants, plant cells or plant tissue. An ideal situation would be the regulation of expression of an engineered trait at will via a regulating intermediate that could be easily applied to field crops, ornamental shrubs, bioreactors, etc. This situation can now be realized by the present invention which is directed to, among other things, a chemically regulatable chimeric gene expression system comprising a chemically regulatable, non-coding DNA sequence coupled, for example, to a gene encoding a phenotypic trait, such that the expression of that trait is under the control of the regulator, e.g. such that expression from the regulated gene is determined by the presence or absence of a chemical regulator. This system is the first demonstration of the concept of chemical regulation of chimeric gene expression in plants or plant tissue. As such it enables the production of transgenic plants or plant tissue and the control of traits expressed as a function of a chemical regulator.

The present invention also teaches the external manipulation of the expression of endogenous genes which contain chemically regulatable sequences by the application of a chemical regulator (see Ward, E. et al., *Plant Cell* 3: 1085–1094 (1991); Williams et al., *Bio/Technology* 10: 540–543 (1992); and Uknes, S. et al., *Plant Cell* 5: 159–169 (1993). The control provided is somewhat limited, however, due to the responsiveness of such sequences to endogenous chemical metabolites and cell signals as well as externally applied chemical regulators. In yet another aspect of the invention, alterations are taught which block the responsiveness of these genes to endogenous signals while maintaining responsiveness to externally applied chemical regulators.

G. Insect Resistance

Pest infestation of crop plants causes considerable loss of yield throughout the world and most crops grown in the U.S. suffer infestation, particularly from insects. Major insect pests in the U.S. include the European Corn Borer (*Ostrinia nubilalis*) in maize, the cotton bollworm *Heliothis zea*) and the pink bollworm (*Pectinophora gossypiella*) in cotton and the tobacco budworm (*Heliothis virescens*) in tobacco. Resistance to pests is difficult to achieve using conventional breeding programs and typically pests have been controlled using chemical pesticides.

Recent advances in molecular biology and plant transformation technology have demonstrated the possibility of expressing in transgenic plants genes encoding insecticidal proteins; this represents a novel approach in the production of crop plants resistant to pests. Most notably, the expression of genes encoding the *Bacillus thuringiensis* δ-endotoxin has been successful in a wide range of plant species, and the analysis of transgenic lines expressing such genes has been well documented (Vaeck et al., *Nature* 328: 33–37 (1987); Fischoff et al., *Biotechnology* 5: 807–813 (1987); Carozzi et al., *Plant Mol. Biol.* 20: 539–548 (1992); Koziel et al., *Biotechnology* 11: 194–200 (1993)). Other insecticidal genes have been used successfully in generating insect resistant transgenic plants.

One approach has been the overexpression of genes encoding insect enzyme inhibitors such as trypsin inhibitors or seed proteins with known insecticidal activity, such as lectins (Hilder et al., *Nature* 330: 160–163 (1987)). Indeed, plants expressing both the cowpea trypsin inhibitor and pea lectin were shown to have additive effects in providing insect resistance (Boulter et al., *Crop Protection* 9: 351–354 (1990)). In cases where pests are able infest parts of the plant or tissues not readily accessible to conventional pesticides, a transgenic approach may be more successful than the use of conventional pesticides.

For example, the tobacco budworm Heliothis is well known to be difficult to control using pesticides because it burrows deep into the plant tissue. Additionally, some pests of roots, such as nematodes, are not readily controlled by foliar applications of pesticides. An advantage in the use of transgenic plants expressing insecticidal proteins is the controlled expression of the proteins in all desired tissues.

Chitinases catalyze the hydrolysis of chitin, a β-1,4-linked homopolymer of N-acetyl-D-glucosamine. Several different plant chitinases have been described and the cDNA sequences for some of these have been reported (Meins et al., *Mol. Gen. Genet.* 232: 460–469 (1992)). Based on structural characteristics, three classes have been distinguished. Class I chitinases have two structural domains, a cysteine-rich amino-terminal hevein domain and a carboxy-terminal catalytic domain separated from the former by a variable spacer. Class II chitinases lack the cysteine-rich hevein domain and all or part of the variable spacer, but retain the catalytic domain. Class III chitinases lack the hevein domain and contain a catalytic domain that shares no significant homology with that of the class I or class II enzymes.

Class I chitinase gene expression is induced by ethylene, whereas class II and class III chitinase gene expression is induced in the SAR response. The chitinase/lysozyme disclosed in abandoned U.S. application Ser. No. 07/329,018 and the chitinase/lysozymes disclosed in U.S. application Ser. No. 07/580,431 abandoned (provided herein as SEQ ID Nos. 29 and 30, respectively) are class III chitinases. It is well known that the level of chitinase activity of plants increases dramatically after pathogen invasion (Mauch et al., *Plant Physiol.* 76: 607–611 (1984)) and this is presumably due to the host plant's attempts to degrade the chitin of the fungal cell wall. Furthermore, chitinase has been shown in vitro to inhibit fungal and insect growth, and in transgenic plants a bacterial chitinase has been shown to exhibit inhibitory effects towards numerous pathogens and pests including insects (Suslow & Jones WPO 90-231246; U.S. Pat. Nos. 4,940,840 and 4,751,081; herein incorporated by reference in their entirety).

H. Resistance Response of Plants to Pathogen Infection

For over 90 years, scientists and naturalists have observed that when plants survive pathogen infection they develop an increased resistance to subsequent infections. In 1933, a phenomenon termed "physiological acquired immunity" was described in an extensive literature review by Chester, K. S., *Quart. Rev. Biol.* 8: 275–324 (1933). At that time, scientists believed they were investigating a phenomenon analogous to the immune response in mammals. In retrospect, at least three different processes were being called "aquired immunity": viral cross protection, antagonism (or biocontrol), and what we now refer to as systemic acquired resistance (SAR).

1. Systemic Acquired Resistance (SAR)

The first systematic study of SAR was published by A. Frank Ross in 1961. Using tobacco mosaic virus (TMV) on local lesion hosts, Ross demonstrated that infections of TMV were restricted by a prior infection. This resistance was effective against not only TMV, but also tobacco necrosis virus and certain bacterial pathogens. Ross coined the term "systemic acquired resistance" to refer to the inducible systemic resistance (Ross, A. F., *Virology* 14: 340–358 (1961)) and "localized acquired resistance" (LAR) to describe the resistance induced in inoculated leaves (Ross, A. F., *Virology* 14: 329–339 (1961)). It is still unclear whether SAR and LAR are aspects of the same response or distinct processes.

In the past 30 years, SAR has been demonstrated in many plant species and the spectrum of resistance has been broadened to include not only viruses and bacteria, but also many agronomically important phytopathogenic fungi (see Kuc, J., *BioScience* 32: 854–860 (1982). However, understanding of the biochemical events leading to the establishment of SAR had not progressed substantially until the past dozen years. In 1982, the accumulation of a group of extracellular proteins called pathogenesis-related (PR) proteins were reported to correlate with the onset of SAR (Van Loon, L. C. et al., *Neth. J. Plant. Path.* 88: 237–256 (1982)). In 1979, salicylic acid (SA) and certain benzoic acid derivatives were reported to be able to induce both resistance and the accumulation of PR proteins (White, R. F., *Virology* 99: 410–412 (1979). As a result, SA was considered as a possible endogenous signal molecule (Van Loon, L. C. et al., *Neth. J. Plant. Path.* 88: 237–256 (1982)). However, progress slowed through the 1980's and the involvement of PR proteins and salicylic acid in SAR was questioned.

With the advent of genetic engineering and recombinant DNA technology, the possibility of manipulating genetic material to improve the phenotype of plants has arisen. The present invention is based in part upon the discovery of the identity and role of genes involved in SAR which has allowed the application of modern molecular biological techniques for improved plant disease and plant pest resistance.

SUMMARY OF THE INVENTION

There are two major aspects of the present invention. The first aspect relates to chemically regulatable DNA sequences and the chemicals which regulate them. The second aspect relates to plant pathogenesis-related proteins. Both aspects of the invention have arisen, in part, from the inventors' identification and characterization of cDNAs and corresponding genes involved in the plant response to pathogen infection.

A principal object of the present invention is to provide a means for chemically regulating the expression of a desired gene in a plant, seed, or plant tissue.

To meet this objective, the first aspect of the present invention includes: (a) chemically regulatable DNA sequences, preferably in substantially pure form; (b) one or more chemically regulatable DNA sequences in combination with one or more parts but not all of any coding DNA sequences with which the regulatable sequences are associated in naturally occurring genes; (c) chimeric genes containing one or more chemically regulatable DNA sequences; (d) vectors containing sequences or genes of (a), (b) and/or (c); (e) plants, seeds, and plant tissue containing the chemically regulatable chimeric genes; and (f) chemical regulation of chemically regulatable chimeric genes in plant tissue. The invention further includes a signal peptide, a DNA sequence coding for the signal peptide, and the substantially pure forms of several naturally occurring chemically inducible genes.

The first aspect of the invention further embraces several uses of the chemically regulatable DNA sequences: (a) regulation of chimeric genes in cells propagated in a bioreactor, (b) an assay for chemical regulators, (c) developmental regulation of the plant, (d) regulation of plant sterility and (e) regulation of chimeric and/or heterologous gene expression in a transformed plant. Other uses and advantages will be apparent from the following detailed description of the invention.

Another principal object of the present invention is to provide transgenic plants expressing levels of plant pathogenesis-related proteins, or substantially homologous proteins, which confer an enhanced disease-resistant and/or pest-resistant phenotype with respect to wild-type plants.

Accordingly, to meet this objective and others, the second aspect of the present invention disclosed herein provides for the isolation, cloning and identification of novel cDNA clones coding for plant pathogenesis-related (PR) proteins. These cDNAs, or their genomnic counterparts, or DNA molecules with substantial homology to either (all of the above collectively referred to herein as "anti-pathogenic sequences"), can be engineered for expression of the encoded PR proteins or anti-sense RNA and transformed into plants to confer enhanced resistance or tolerance to various diseases and/or pests as described herein. These DNA molecules may be engineered for constitutive expression, expression in particular tissues or at certain developmental stages, or induced expression in response to an inducer, for example in response to a chemical inducer as described herein.

The present invention further provides novel methods for differential screening and enriching for induced cDNAs, particularly those cDNAs induced in response to pathogen infection or a chemical inducer which triggers a response mimicking pathogen infection.

The present invention is further drawn to a method of exogenously controlling the regulation of gene expression in plants. The method involves altering a plant to inactivate a predetermined signal transduction cascade, and subsequently treating the thus-modified plant with a chemical regulator that is capable of inducing expression of the gene or genes which is regulated by the native, non-modified signal transduction cascade. The plant may further be altered by transformation with a heterologous gene of interest which is expressed upon treatment of the plant with the chemical regulator. The method is useful in controlling or altering traits such as height, shape, development, male sterility, female sterility, and the ability of a plant to withstand cold, salt, heat, drought, disease or pest infestation. The method is especially useful when constitutive expression of gene(s) involved in manifestation of these traits might be deleterious to the growth or health of the plant. The method has further usefulness in rendering plants capable of functioning as bioreactors for the production of industrial or pharmaceutical biomaterials and precursors thereof. In the alternative, the altered plant containing the inactivated signal transduction cascade can be used in an assay to identify downstream-acting chemical regulators. That is, the chemical is not dependent upon the signal cascade and is capable of regulating, e.g., inducing expression of the gene or genes regulated endogenously by the native, functional cascade.

BRIEF DESCRIPTION OF THE FIGURES

FIG. 39. A DNA sequence comparison of five SAR8.2 cDNAs; SAR8.2a, b, c, d and e. Bases identical to the SAR8.2a sequence are represented by a dot. Mismatches are represented by a capital letter. Gaps are represented by dashes. The length of each cDNA is given in brackets at the 3' end of the sequence. Alignments were done using the MacVector (IBI) software, with larger gaps being determined by visual inspection.

FIG. 40. An amino acid sequence comparison of the five SAR8.2 cDNA open reading frames. Amino acids identical to the SAR8.2a sequence are represented by a dot. Mismatches are given by capital letters, and gaps are represented by dashes. An asterisk indicates a stop codon. The SAR8.2e sequence is continued on the next line to show its alignment with homologous segments of the other proteins and itself.

BRIEF DESCRIPTION OF THE SEQUENCES IN THE SEQUENCE LISTING

Figure 1:
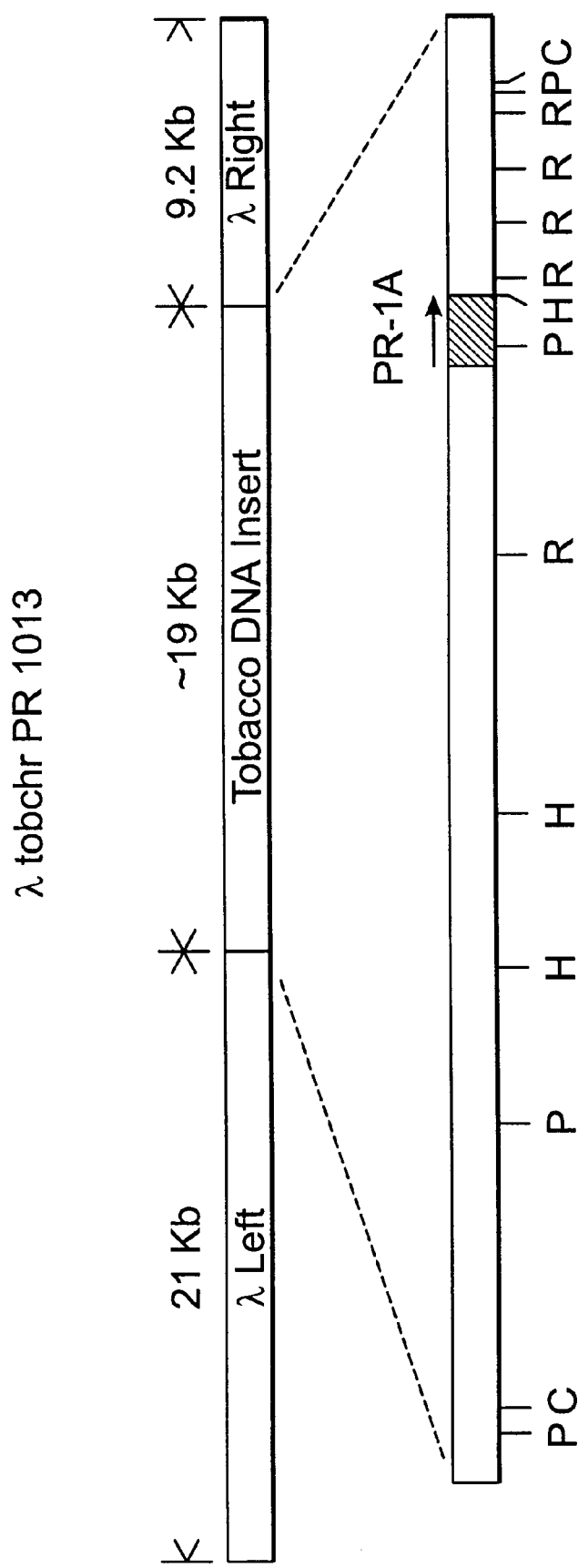
FIG. 1. Partial restriction endonuclease map of lambda tobchrPR1013. The 49 kb recombinant phage genome is depicted with the right and left arms of lambda designated. The 19 kb tobacco insert is enlarged below the lambda map. The location of the PR-1a gene (crosshatched box) and the direction of transcription (arrow) are designated. P=Pst, H=HindIII, C=ClaI, R=EcoRI.

SEQ ID No. 1: The genomic DNA sequence of the 2 kb pair fragment between the XhoI and BglII sites of the tobacco PR-1a gene. The transcription start site occurs at about nucleotide 903. The polypeptide sequence encoded by the coding portion of the gene is disclosed in SEQ ID No. 45.

SEQ ID No. 2: The genomic DNA sequence of the tobacco PR-1' gene. The amino acid sequence of the polypeptide which is coded by the coding region of this gene is disclosed in SEQ ID No. 46.

SEQ ID No. 3: The cDNA sequence encoding a cucumber chitinase/lysozyme protein cloned into the plasmid pBScucchi/chitinase.

SEQ ID No. 4: The cDNA sequence encoding a PR-R major protein cloned into the plasmid pBSPRR-401.

SEQ ID No. 5: The genomic DNA sequence of the tobacco basic β-1,3 glucanase gene contained in the clone pBSGluc39.1.

SEQ ID NO. 6: The genomic DNA sequence of the tobacco basic β-1,3-glucanase gene contained in the clone pBSGluc39.3.

SEQ ID No. 7: The cDNA sequence encoding a PR-Q protein cloned into the plasmid pBScht15.

SEQ ID No. 8: The DNA sequence of an isolated cDNA contained in the plasmid pBSGL6e. The cDNA encodes the acidic form of β-1,3-glucanase.

SEQ ID No. 9: The cDNA sequence encoding a PR-1a protein cloned into the plasmid pBSPR1-207.

SEQ ID No. 10: The cDNA sequence encoding a PR-1b protein cloned into the plasmid pBSPR1-1023.

SEQ ID No. 11: The cDNA sequence encoding a PR-1c protein cloned into the plasmid pBSPR1-312.

SEQ ID NO. 12: The cDNA sequence encoding a PR-P protein cloned into the plasmid pBScht28.

SEQ ID No. 13: A partial cDNA sequence encoding a PR-O' protein cloned into the plasinid pBSGL6e.

SEQ ID No. 14: The full length cDNA sequence encoding a PR-O' protein cloned into the plasmid pBSGL5B-12.

SEQ ID No. 15: The cDNA sequence encoding a SAR8.2a protein cloned into the plasmid pCIB/SAR8.2a.

SEQ ID No. 16: The cDNA sequence encoding a SAR8.2b protein cloned into the plasniid pCIB/SAR8.2b.

SEQ ID No. 17: The cDNA sequence encoding a SAR8.2c protein.

SEQ ID No. 18: The cDNA sequence encoding a SAR8.2d protein.

SEQ ID No. 19: The cDNA sequence encoding a SAR 8.2e protein.

SEQ ID No. 20: The cDNA sequence encoding a basic β-1,3-glucanase protein cloned into the plasmid pGLN17. The encoded amino acid sequence is provided in SEQ ID No. 98.

SEQ ID No. 21: The cDNA sequence encoding a PR-2 protein cloned into the plasmid pBSGL117.

SEQ ID No. 22: The cDNA sequence encoding a basic cucumber peroxidase protein cloned into the plasmid pBSPER1.

SEQ ID No. 23: The cDNA sequence encoding a PR-O protein cloned into the plasmid pBSGL134.

SEQ ID No. 24: The cDNA sequence encoding a PR-N protein cloned into the plasmid pBSGL167.

SEQ ID No. 25: The cDNA sequence encoding a PR-O-related tobacco β-1,3-glucanase protein, designated PR-2', cloned into the phage lambda tobcDNAGL161.

SEQ ID No. 26: The cDNA sequence encoding a PR-O-related tobacco β-1,3-glucanase protein, designated PR-2", cloned into the phage lambda tobcDNAGL153.

SEQ ID No. 27: The cDNA sequence encoding a cucumber peroxidase protein cloned into the plasmid pBSPERB24.

SEQ ID No. 28: The cDNA sequence encoding another cucumber peroxidase protein cloned into the plasmid pBSPERB25.

SEQ ID No. 29: The cDNA sequence encoding a basic tobacco chitinase/lysozyme protein cloned into the plasmid pBSCL2.

SEQ ID No. 30: The cDNA sequence encoding an acidic tobacco chitinase/lysozyme protein cloned into the plasmid pBSTCL226.

SEQ ID No. 31: The cDNA sequence encoding a PR-4a protein cloned into the plasmid pBSPR-4a.

SEQ ID No. 32: The cDNA sequence encoding a PR-4b protein cloned into the plasmid pBSPR-4b.

SEQ ID No. 33: The cDNA sequence encoding an Arabidoipsis PR-1 protein cloned into plasmid pAPR1C-1.

SEQ ID No. 34: The cDNA sequence encoding an Arabidopsis PR-4 protein cloned into pSLP-1.

SEQ ID No. 35: The cDNA sequence encoding an Arabidopsis PR-R protein cloned into pATL12a.

SEQ ID No. 36: The full sequence of a cucumber chitinase EcoR1 genomic clone.

SEQ ID No. 37: The cDNA sequence encoding an Arabidopsis class IV chitinase with a hevein domain (pChit4-TA).

SEQ ID No. 38: The cDNA sequence encoding an Arabidopsis class IV chitinase without a hevein domain (pChit4-TB).

SEQ ID No. 39: The cDNA sequence of the wheat gene WCI-1.

SEQ ID No. 40: The partial cDNA sequence of the 5' end of the wheat gene WCI-2 which encodes a lipoxygenase isozyme. The partial sequence of the 3' end of this cDNA is provided in SEQ ID No. 41.

SEQ ID No. 41: The partial cDNA sequence of the 3' end of the wheat gene WCI-2 which encodes a lipoxygenase isozyme. The partial sequence of the 5' end of this cDNA is provided in SEQ ID No. 40.

SEQ ID No. 42: The cDNA sequence of the wheat gene WCI-3.

SEQ ID No. 43: The cDNA sequence of the wheat gene WCI-4.

SEQ ID No. 44: The cDNA sequence of the wheat gene WCI-5.

SEQ ID No. 45: The amino acid sequence encoded by the coding portion of SEQ ID No. 1.

SEQ ID No. 46: The amino acid sequence encoded by the coding portion of SEQ ID No. 2.

SEQ ID No. 47: A representative molecular adaptor sequence.

SEQ ID NO. 48: Oligonucleotide primer for the PR-1 gene.

SEQ ID NO. 49: Oligonucleotide primer for GUS gene.

SEQ ID NO. 50: Oligonucleotide primer for the AHAS gene.

SEQ ID NO. 51: Oligonucleotide primer for the BT gene.

SEQ ID No. 52: Amino acid s equ e nce of PR-R Major.

SEQ ID No. 53: Amino acid sequence of PR-R Minor.

SEQ ID No. 54: The Pst/BamHI olignucleotide adaptor used in Example 25.

SEQ ID No. 55: The oligonucleotide primer used in Example 27.

SEQ ID No. 56: The oligonucleotide primer used in Example 30.

SEQ ID Nos. 57–58: Oligonucleotides used in Example 35.

SEQ ID Nos. 59–60: Oligonucleotides used in Exarnple 36.

SEQ ID Nos. 61–62: Oligonucleotides used in Example 42.

SEQ ID No. 63: Oligonucleotide used in Example 44.

SEQ ID No. 67: Oligonucleotide used in Example 46.

SEQ ID Nos. 68–69: Oligonucleotides used in Example 48.

SEQ ID Nos. 68–67: Oligonucleotides used in Example 49.

SEQ ID No. 70: Oligonucleotide used in Example 49.

SEQ ID Nos. 71–72: Oligonucleotides used in Example 51.

SEQ ID No. 73: Oligonucleotide used in Example 53.

SEQ ID No. 74: Oligonucleotide used in Example 55.

SEQ ID No. 75: Amino acid sequence recited in Example 55.

SEQ ID Nos. 76,78, 80: Oligonucleotides used in Example 58.

SEQ ID Nos. 77, 79, 81: Amino acid sequence recited in Example 58.

SEQ ID Nos. 82–83: Oligonucleotides used in Example 62.

SEQ ID Nos. 84–85: Oligonucleotides used in Example 72.

SEQ ID Nos. 86–89: Oligonucleotides used in Example 73.

SEQ ID Nos. 90–91: Oligonucleotides used in Example 79.

SEQ ID No. 92: Nucleotide sequence recited in Example 80.

SEQ ID Nos. 93–96: Oligonucleotides recited in Example 81.

SEQ ID No. 97: Oligonucleotide used in Example 84.

SEQ ID No. 98: Amino Acid sequence encoded by the coding sequence within SEQ ID No. 20.

SEQ ID No. 99: A tobacco protein-synthesis independent gene involved in the regulation of the systemic acquired resistance response designated p1.1.1.

SEQ ID No. 100: A tobacco protein-synthesis independent gene involved in the regulation of the systemic acquired resistance response designated p11.3.8.

SEQ ID No. 101: The 5' DNA sequence of a tobacco protein-synthesis independent gene involved in the regulation of the systemic acquired resistance response designated p11.30.13.

SEQ ID No. 102: The DNA sequence of the 3'end of the same protein-synthesis independent gene described in Seq. ID. No. (iii) cloned from tobacco and involved in the regulation of the systemic acquired resistance response designated p 11.30.13. This sequence is derived from the non-coding strand (i.e. the "bottom" strand). The first base listed is therefore located in the furthest 3' position.

SEQ ID No. 103: A tobacco protein-synthesis independent gene involved in the regulation of the systemic acquired resistance response designated p1.4.3. This sequence is identical to the thioredoxin gene published by Brugidou et al., *Mol. Gen. Genet.* 238: 285–293 (1993).

SEQ ID No. 104: A protein-synthesis dependent SAR gene cloned from tobacco designated p66B1.

SEQ ID No. 105: A protein-synthesis dependent SAR gene cloned from tobacco designated p14.22.3.

SEQ ID No. 106: An Arabidopsis protein-synthesis independent gene involved in the regulation of the systemic acquired resistance response designated pDPA2.

SEQ ID No. 107: Amino Acid sequence of an SAR8.2a protein.

SEQ ID No. 108 Amino Acid sequence of an SAR8.2b protein.

SEQ ID No. 109 Amino Acid sequence of an SAR8.2c protein.

SEQ ID No. 110 Amino Acid sequence of an SAR8.2d protein.

SEQ ID No. 111 Amino Acid sequence of an SAR8.2e protein.

DETAILED DESCRIPTION OF THE INVENTION

A. Definitions

In order to provide a clear and consistent understanding of the specification and the claims, including the scope given to such terms, the following definitions are provided:

Anti-pathogenic Sequence: A DNA molecule encoding a plant pathogenesis-related (PR) protein, or a DNA molecule with substantial homology thereto, which is capable of conferring enhanced resistance or tolerance to disease and/or pests when expressed in a plant, seed, or plant tissue.

Anti-sense Mechanism: A mechanism for regulation of gene expression based on the presence in a cell of a RNA molecule complementary to at least a portion of the mRNA encoded by the gene. This mechanism is thought to involve controlling the rate of translation of mRNA to protein due to the presence in a cell of an RNA molecule complementary to at least a portion of the mRNA being translated.

Associated DNA Sequence: A DNA sequence whose cellular activity either (1) regulates the activity of another DNA sequence or (2) is regulated by another DNA sequence. This definition specifically embraces, but is not limited to, sequences which are physically adjacent in a continuous DNA strand or which are physically separated. Physical separation includes, for example, separation within the same DNA strand, location within different DNA strands, or discontinuous interspersed sequences (e.g., alternating regulatable and coding sequences) in one strand.

Chemically Regulatable DNA Sequence:

A DNA sequence which is capable of regulating the transcription of an associated DNA sequence where the regulation is dependent on a chemical regulator. The sequences may be of natural or synthetic origin.

Chemically Regulatable Gene: A gene containing at least one non-coding chemically regulatable DNA sequence and at least one associated coding DNA sequence. The genes may be of natural, synthetic or partially natural/partially synthetic origin.

Chemical Regulator (for a chemically regulatable DNA sequence): An elemental or molecular species which controls (e.g., initiates, terminates, increases or reduces), by direct or indirect action, the activity of a chemically regulatable DNA sequence in a system in which the chemical regulator is not normally found in an active form in an amount sufficient to effect regulation of transcription, to the degree and at the time desired, of a transcribable DNA sequence associated with the chemically regulatable DNA sequence. This terminology is intended to embrace situations in which no or very little regulator is present at the time transcription is desired or in which some regulator is present but increased or decreased regulation is required to effect more or less transcription as desired.

Thus, if the system containing the chemically regulatable DNA sequence is a plant, for example a transgenic plant, a chemical regulator is a species not naturally found in the plant in an amount sufficient to effect chemical regulation, and thus transcription of an associated gene, to the desired degree at the time desired.

By "direct action" it is intended that the chemical regulator action result from the direct interaction between the chemical regulator and the DNA sequence. By "indirect action" it is meant that the regulator action results from the direct interaction between the chemical regulator and some other endogenous or exogenous component in the system, the ultimate result of that direct interaction being activation or suppression of the activity of the DNA sequence. By "active form" it is intended that the chemical regulator be in a form required to effect control.

Chimeric Sequence or Gene: A DNA sequence containing at least two heterologous parts, e.g., parts derived from naturally occurring DNA sequences which are not associated in their naturally occurring states, or containing at least one part that is of synthetic origin and not found in nature.

Coding DNA Sequence: A DNA sequence which, when transcribed and translated, results in the formation of a cellular polypeptide.

Constitutive transcription: Transcription of substantially fixed amounts of a DNA sequence, irrespective of environmental conditions.

Gene: A discrete chromosomal region which is responsible for a discrete cellular product.

Inducers: Molecules that cause the production of larger amounts of macromolecules, compared to the amounts found in the absence of the inducer.

Inducible Protein: Proteins whose rate of production can be increased by the presence of inducers in the environment.

Non-coding DNA Sequence:

A DNA sequence, which is not transcribed and translated, resulting in the formation of a cellular polypeptide when associated with a particular coding DNA sequence. A sequence that is non-coding when associated with one coding sequence may actually be coding when associated with another coding or non-coding sequence.

Phenotypic Trait: An observable property resulting from expression of a gene.

Plant Tissue: Any tissue of a plant in planta or in culture. This term includes, but is not limited to, whole plants, plant cells, plant organs, plant seeds, protoplasts, callus, cell cultures and any groups of plant cells organized into structural and/or functional units. The use of this term in conjunction with, or in the absence of, any specific type of plant tissue as listed above or otherwise embraced by this definition is not intended to be exclusive of any other type of plant tissue.

PR, or Pathogenesis-Related Proteins: Proteins expressed in plants reacting hypersensitively towards pathogens. This term embraces, but is not limited to, SAR8.2a and SAR8.2b proteins, the acidic and basic forms of tobacco PR-1a, PR-1b, PR-1c, PR-1', PR-2, PR-2', PR-2", PR-N, PR-O, PR-O', PR-4, PR-P, PR-Q, PR-S, and PR-R major proteins, cucumber peroxidases, basic cucumber peroxidase, the chitinase which is a basic counterpart of PR-P or PR-Q, and the beta-1,3-glucanase (glucan endo-1,3-β-glucosidase, EC 3.2.1.39) which is a basic counterpart of PR-2, PR-N or PR-O, the pathogen-inducible chitinase from cucumber, class IV chitinases with and without a hevein domain, and the WCI ("Wheat Chemically Induced") gene proteins from wheat. A hypersensitive reaction is characterized by a local necrosis of the tissues immediately surrounding the infection site of the pathogen and a subsequent localization of the pathogen, which is in contrast to a sensitive reaction wherein the pathogen spreads throughout the plant. Pathogens are, for example, viruses or viroids, e.g. tobacco or cucumber mosaic virus, ringspot virus or necrosis virus, pelargonium leaf curl virus, red clover mottle virus, tomato bushy stunt virus, and like viruses, fungi, e.g. *Phythophthora parasitica* or *Peronospora tabacina*, bacteria, e.g. *Pseudomonas syringae* or *Pseudomonas tabaci* or aphids, e.g. *Myzus persicae*. This list is not limiting in any respect.

Regulation:

The increasing (inducing) or decreasing (repressing) of the level of expression of a gene or the level of transcription of a DNA sequence. The definition is not intended to embrace any particular mechanism.

Substantially Pure DNA Sequence: A DNA molecule (sequence) isolated in substantially pure form from a natural or non-natural source. Such a molecule may occur in a natural system, for example, in bacteria, viruses or in plant or animal cells, or may be provided, for example, by synthetic means or as a cDNA. Substantially pure DNA sequences are typically isolated in the context of a cloning vector. Substantially pure means that DNA sequences other than the ones intended are present only in marginal amounts, for example less than 5%, less than 1%, or preferably less than 0.1%. Substantially pure DNA sequences and vectors containing may be, and typically are, provided in solution, for example in aqueous solution containing buffers or in the usual culture media.

Substantial Sequence Homology: Substantial sequence homology means close structural relationship between sequences of nucleotides or amino acids. For example, substantially homologous DNA sequences may be 80% homologous, preferably 90% or 95% homologous, and substantially homologous amino acid sequences may typically be 50% homologous, or more. Homology also includes a relationship wherein one or several subsequences of nucleotides or amino acids are missing, or subsequences with additional nucleotides or amino acids are interdispersed.

B. Abbreviations

The following abbreviations are used herein:

| | |
|---|---|
| AHAS | acetohydroxyacid synthase |
| ATCC | American Type Culture Collection |
| ATP | adenosine triphosphate |
| bp | base pair |
| BT | *Bacillus thuringiensis* endotoxin |
| CAT | chloramphenicol acetyltransferase |
| CETAB | hexadecyltrimethylammonium bromide |
| 2,4-D | 2,4-dichlorophenoxyacetic acid |

-continued

| | |
|---|---|
| DTT | dithiothreitol |
| dicamba | 3,6-dichloro-2-methoxybenzoic acid |
| EDTA | ethylendiamine N,N,N',N'-tetraacetic acid |
| GUS | beta-1,3-glucuronidase |
| kb | kilo base pair |
| LUX | luciferase |
| MES | 2-(N-morpholino)ethanesulfonic acid |
| MU | 4-methyl umbelliferyl glucuronide |
| NOS | nopaline synthase |
| NPT | neomycin phosphotransferase |
| NRRC | designation for deposits made with the Agricultural Research Culture Collection, International Depositing Authority, 1815 N. University Street, Peoria, Illinois 61604 |
| OCS | octopine synthase |
| PEG | polyethylene glycol |
| picloram | 4-amino-3,5,6-trichloropicolinic acid |
| PR protein | Pathogenesis-related protein |
| SAR | Systemic Acquired Resistance |
| SDS | sodium dodecyl sulfate |
| TFA | trifluoroacetic acid |
| TMV | tobacco mosaic virus |
| Tris-HCl | tris(hydroxymethyl)methylamine hydrochloride |
| WCI | Wheat Chemically Induced (gene nomenclature designation) |

C. Introduction

The present invention describes the identification, isolation, and cloning of DNA sequences which are capable of regulating the taanscription in plant tissue of an associated DNA sequence where the regulation is dependent upon a chemical regulator. These DNA sequences can be utilized to construct chimeric genes in which the expression of the gene can be regulated by such regulators. The ability to regulate the expression of a chimeric gene in a transgenic plant by a chemical method is useful to obtain suitable expression of the phenotypic trait with minimal adverse effect on the growth and development of the plant. This regulation is important in the production of secondary products or other cloned products in plant tissue in culture or bioreactors. The regulation of the cloned sequence is also important in the regulation of other gene products by an anti-sense mechanism.

The expression of a given coding sequence at any specific time can be regulated by use of a chemical regulator, typically applied to the plant tissue. Genes involved in the control of distinct developmental transition stages can also be regulated by associating a chemically regulatable DNA sequence with an appropriate coding DNA sequence. In this manner the development of a plant can be halted at a specific stage until, or accelerated at a specific rate when, the level of a chemical regulator is increased or reduced.

The chemically regulatable DNA sequences can be utilized to drive the expression of foreign genes which, for example, confer herbicide resistance or tolerance (e.g., atrazine tolerance in soybean), confer insect resistance (e.g., Bacillus thuringiensis crystal protein in cotton) or require selective expression (such as male or female sterility). The chemically regulatable DNA sequences can also be utilized to drive the transcription of a DNA sequence which will control the expression of a second coding sequence by an anti-sense mechanism.

The present invention further provides a) anti-pathogenic sequences derived from novel cDNA clones coding for plant pathogenesis-related proteins; b) chimeric DNA constructions useful for producing transgenic disease-resistant plants which comprise a first DNA sequence which promotes in a plant the constitutive transcription of the second DNA sequence, and a second DNA sequence which is a coding sequence of an inducible plant pathogenesis-related protein or a coding sequence having substantial sequence homology to a coding sequence of an inducible plant pathogenesis-related protein; c) vectors containing such chimeric DNA constructions; and c) transgenic plants, transgenic plant tissue, propagules and seeds of transgenic plants containing the chimeric DNA constructions for producing disease-resistant plants.

Also provided is a novel method for differential screening and enriching cDNA populations comprising a) providing single-stranded cDNA from induced and uninduced cDNA populations, the single-stranded cDNA from the induced and uninduced populations having opposite DNA polarity, and the cDNA from the uninduced population having a biotin-affinity tag; b) hybridizing the single-stranded cDNA populations of step a) with each other; and c) separating the hybridized mixture of step b) by biotin- avidin chromatography to enrich for single-stranded cDNAs from the induced population which are not hybridized to the cDNA from the uninduced population.

Further provided herein is a method for cloning cDNA's encoding disease-resistance proteins comprising a) providing tissue induced to systemic acquired resistance or localized acquired resistance using biological inducers or chemical inducers, and b) isolating cDNA clones including disease-resistance proteins. Although cDNA's have been produced previously from RNA isolated from pathogen-infected material, this is the first example of producing cDNA's from RNA isolated from uninfected portions of the plant that have been induced to resistance by pathogens. That is, the tissue is uninfected by pathogens, but is demonstrating acquired resistance. This method also encompasses the use of chemical inducers.

The production of transgenic plants which are disease resistant can now be realized by the present invention which is directed to, among other things, chimeric DNA constructions useful for producing transgenic disease- resistant plants. The chimeric DNA constructions contain a coding DNA sequence which encodes a plant pathogenesis-related protein which is normally pathogen-induced in a wild type plant, and a promoter DNA sequence which provides for the constitutive expression of pathogenesis-related proteins or anti-sense mRNA for PR-proteins in a transgenic plant containing the chimeric DNA construction.

Accordingly, the present invention includes, but is not limited to, the following:

a. A chimeric gene whose expression in plant tissue is regulated by a chemical regulator.

b. A substantially pure chemically regulatable DNA sequences capable of controlling genetic activity in plant tissue of other DNA sequences in response to a chemical regulator.

c. Chemically regulatable DNA sequences in combination with part but not all of any coding DNA sequence with which they are associate in naturally occurring genes.

d. Vectors containing the chemically regulatable DNA sequences with or without other parts of naturally occurring genes in which they may occur.

e. Vectors containing the chimeric genes of (a).

f. Plant tissue, plants and seeds derived from cells transformed by these vectors.

g. A process for chemically regulating the expression of DNA coding sequences associated with the chemically regulatable DNA sequences, for example to regulate a phenotypic trait.

h. A process for identifying new chemical regulators using chimeric genes of this invention and plant tissue containing them.

i. Signal peptide sequences in proteins encoded by chemically regulated genes.

j. Substantially pure pathogenesis-related protein genes and cDNAs.

k. Transgenic plants constitutively expressing pathogenesis-related protein genes providing an enhanced disease-resistant phenotype with respect to wild-type plants.

l. Transgenic plants constitutively transcribing sense or anti-sense mRNA strands of DNA sequences encoding plant pathogenesis-related proteins, or transcribing sense or anti-sense mRNA strands of DNA sequences substantially homologous to genomic or cDNA sequences encoding plant pathogenesis-related proteins, such transgenic plants thus having an enhanced disease-resistant phenotype with respect to wild-type plants.

Other aspects of the present invention are discernible from the following description.

D. Chemically Regulatable DNA Sequences

The present invention is concerned with non-coding DNA sequences which are capable of regulating, under the influence of a chemical regulator, the transcription of an associated DNA sequence in a plant or plant tissue. Specifically, the present invention embraces a non-coding DNA sequence capable of regulating the transcription of an associated DNA sequence in a plant or plant tissue wherein this regulation is dependent upon a chemical regulator. Preferably the DNA sequences exist in substantially pure form relative to the gene and genome in which they occur if they come from a natural source, or relative to a DNA mixture if they occur in a synthetic mixture.

Preferably the non-coding chemically regulatable DNA sequences of this invention are those which, when associated with a coding DNA sequence, regulate the expression of the coding sequence in plant tissue, the extent of regulation being dependent upon a chemical regulator. Such sequences can be synthesized de novo or derived (for example, isolated or cloned) from a naturally occurring chemically regulatable gene. The occurrence of chemically regulatable DNA sequences of the invention is not limited to plant tissue; i.e., the chemically regulatable DNA sequences may be derived from a variety of natural sources, e.g., bacterial, viral or animal sources. It may be isolated, for example, from the 5' flanking region or from the 3' flanking region of a naturally occurring chemically regulatable gene. Alternatively, the non-coding DNA sequence may be chemically synthesized or enzymatically synthesized as cDNA identical to, or having substantial sequence homology to, the isolated sequence. By cloning the chemically regulatable, non-coding DNA sequence, the sequence can be separated from other sequences which are adjacent to it in the naturally occurring gene. In this manner a substantially pure DNA sequence can be obtained.

In the context of the present invention, regulation embraces chemical regulators which are either inducing or repressing regulators. Examples of chemically repressible genes, that is, genes which are repressed by a repressing chemical, include, for example, genes like TrpR or AroH where the addition of the tryptophan repressor or tryptophan itself represses the expression from these genes. Many other genes exist that are regulated by this type of end-product repression and in each case the end-product acts as a chemical regulator that can be used to repress the expression of the gene. The present invention embraces the regulatable sections of such genes by themselves or as part of chimeric constructions which can be chemically regulated for transcription of an associated DNA sequence in a plant or plant tissue.

Examples of chemically inducible genes, that is, genes which are induced by an inducing chemical regulator, are the PR protein genes, especially the tobacco PR protein genes, for example the PR-1a, PR-1b, PR-1c, PR-1', PR-Q, PR-R and PR-S genes, the cucumber chitinase gene, and the basic and acidic tobacco β-1,3-glucanase genes. In a particular aspect the present invention comprises a substantially pure DNA sequence which is, or has substantial sequence homology to, a non-coding chemically regulatable DNA sequence which is part of a naturally occurring chemically regulatable gene, for example of a naturally occurring chemically regulatable gene in a plant or plant tissue from a monocot, dicot or gymnosperm. Preferably such a DNA sequence is capable of regulating the transcription of an associated DNA sequence in a plant or plant tissue wherein said associated DNA sequence is a coding sequence. The transcription of said DNA sequence may be regulated by a repressing chemical regulator or an inducing chemical regulator. DNA sequences particularly considered are those wherein the chemically regulatable gene is a PR protein gene, for example from a dicotyledonous plant, e.g. tobacco or cucumber. Most preferred are DNA sequences wherein the chemically regulatable gene is a tobacco PR-1a, PR-1b, PR-1c, PR-1', PR-Q or PR-R gene, a cucumber chitinase gene, or a basic or acidic β-1,3-glucanase gene, in particular the tobacco PR-1a and PR-1' gene, but also the cucumber chitinase gene and the basic and acidic tobacco β-1,3-glucanase genes. Foremost considered are DNA sequences wherein the chemically regulatable gene is a tobacco PR-1a or basic β-1,3-glucanase gene.

The chemically inducible DNA sequences of the preferred PR and related genes of the invention apparently occur in the non-coding sequences of the adjacent region 5' flanking to the coding sequences. As a representative example, in a sequence isolated from an approximately 6500 base pair fragment of the tobacco PR-1a gene containing part of the coding region, the region with about 900 to about 1200 base pairs, naturally adjacent to the transcriptional start site, has been found to be chemically inducible. Inducibility is retained in a fragment thereof containing about 500 to about 700 base pairs naturally adjacent to the transcriptional start site. Most preferred are therefore DNA sequences which are located in the 5' flanking region of said PR and related genes, for example in the 1200 base pairs adjacent to the transcriptional start site.

The invention further embraces a process for the preparation of a non-coding DNA sequence capable of regulating the transcription of an associated DNA sequence in a plant or plant tissue wherein this regulation is dependent upon a chemical regulator, and of DNA sequences having substantial homology to said non-coding sequences, characterized in that the DNA is isolated from a naturally occurring gene in substantially pure form or is synthesized chemically or enzymatically.

In particular, the invention embraces a process for the preparation of a substantially pure chemically regulatable DNA sequence from a chemically regulatable gene in a naturally occurring system containing that gene, which process comprises the steps of (a) activating expression in said system of RNA from the chemically regulatable gene;

(b) isolating said RNA;

(c) differentially screening a genomic library for clones corresponding to RNA isolated from said activated system that is less abundant or absent in RNA isolated from a control system that is not activated;

(d) isolating a genomic clone;

(e) subcloning the chemically regulatable gene from said genomic clone; and (f) isolating the desired chemically regulatable DNA sequence.

Moreover the invention embraces such a process wherein said system is a plant, which process comprises the steps of:

(a) activating expression in said plant of polyA+ RNA from the chemically regulatable gene;

(b) isolating said polyA+ RNA;

(c) constructing a cDNA library from said polyA+ RNA;

(d) differentially screening said cDNA library with cDNA generated from RNA in a control plant that is not activated;

(e) isolating cDNA clones that are chemically regulatable from the population of clones in (d) that do not correspond to cDNA clones generated from RNA in a control plant that is not activated;

(f) isolating a genomic clone from a genomic library of said plant using as a probe the cDNA clone of step (e);

(g) subcloning the chemically regulatable gene from said genomic clone; and (h) isolating the desired chemically regulatable DNA sequence.

Preferred is such a process wherein said chemically regulatable gene is a chemically inducible gene, for example a PR protein gene. Further preferred is such a process wherein said PR protein gene is activated in step (a) by a chemical inducer or a pathogen.

The invention further embraces substantially pure DNA prepared by the mentioned processes.

E. Chemically Regulatable DNA Sequences with Parts of Naturally Occuring Coding Sequences In addition to the entirely non-coding chemically regulatable DNA sequences described above in Part D, this invention also provides for the non-coding DNA sequence of a naturally occurring chemically regulatable DNA sequence in combination with part but not all of a coding sequence with which the regulatable sequence is associated in a naturally occurring gene. More specifically, the present invention embraces, preferably in substantially pure form, a DNA sequence which comprises a first DNA component sequence which is, or has substantial sequence homology to, a non-coding chemically regulatable DNA sequence of a naturally occurring chemically regulatable gene, this first component sequence being capable of regulating the transcription of an associated DNA sequence in a plant or plant tissue, wherein this regulation is dependent upon a chemical regulator, and a second DNA component sequence which is, or has substantial sequence homology to, part but not all of a transcribable DNA sequence with which the first component is associated in the naturally occurring chemically regulatable gene. The naturally occurring chemically regulatable gene may be of plant origin, for example occurring in a monocotyledonous or dicotyledonous plant, and may be regulated by a repressing or an inducing chemical regulator. The second DNA component sequence will typically be a coding sequence. A preferred second DNA sequence for the present invention is a sequence which codes for the signal peptide of any protein expressed by the naturally occurring chemically regulatable gene.

In particular the invention embraces such a DNA sequence comprising a first non-coding chemically regulatable DNA sequence and a second coding DNA sequence from a PR protein gene, for example a PR protein gene from a dicotyledenous or monocotyledenous plant. Preferred is a DNA sequence from a PR protein gene wherein the transcription is regulated by an inducing chemical regulator. In particular the invention embraces a DNA sequence wherein the first non-coding DNA sequence is located in the 5' flanking region of one of the PR protein genes, for example located in the approximately 2000 base pairs adjacent to the transcriptional start site of the PR protein gene. Most preferred is a DNA sequence comprising a preferred first non-coding sequence as mentioned above and a second coding DNA sequence coding for a signal peptide as mentioned above.

Most preferred are substantially pure DNA sequences as shown in SEQ ID Nos. 1, 2, 5 and 6, and substantially pure DNA sequences having substantial sequence homology to the sequences shown in any one of these figures. These sequences are examples of chemically regulatable DNA sequences comprising a first non-coding and a second coding DNA sequence and are derived from the PR protein genes tobacco PR-1a, PR-1', and from two forms of basic tobacco β-1,3-glucanase, respectively. SEQ ID No. 1 shows the sequence of the representative PR-1a gene from tobacco. Nucleotides 1 to about 1150 are the non-coding, 5' flanking chemically inducible DNA sequence and part of the PR-1a coding sequence which is naturally occurring in a tobacco plant. In this case the chemically inducible component sequence is adjacent to the coding sequence. Those nucleotides which code for the first thirty amino acids constitute the coding sequence for the signal peptide of the PR-1a protein. The coding sequence can be removed from the non-coding sequence to generate the non-coding, chemically inducible DNA sequence free of any coding sequence described above in Part A. Such removal can be accomplished by conventional techniques, such as restriction enzyme digestions.

The invention further embraces a method for the preparation of a DNA sequence which comprises a first DNA component sequence which is, or has substantial sequence homology to, a non-coding chemically regulatable DNA sequence of a naturally occurring chemically regulatable gene, this first component sequence being capable of regulating the transcription of an associated DNA sequence in a plant or plant tissue, wherein this regulation is dependent upon a chemical regulator, and a second DNA component sequence which is, or has substantial sequence homology to, part but not all of a transcribable DNA sequence with which the first component is associated in the naturally occurring chemically regulatable gene, characterized in that the DNA is isolated from a naturally occurring gene in substantially pure form or is synthesized chemically or enzymatically. Preferred are the particular processes mentioned in Part D above and the substantially pure DNA sequences obtained thereby.

F. Chemeric Genes Containing Chemically Regulatable DNA Sequences

A further aspect of the present invention is a chimeric DNA sequence (chimeric gene) containing at least one chemically regulatable DNA sequence. Two types of such chimeric sequences are provided as examples. The simpler, or two-part type chimeric DNA sequence comprises a chemically regulatable DNA sequence and a transcribable DNA sequence such that the chimeric gene is capable of being expressed in plant tissue under the proper conditions of chemical regulation. More specifically, the invention embraces a chemically regulatable chimeric DNA sequence comprising a first non-coding, chemically regulatable DNA component sequence which is capable of regulating the transcription of an associated DNA sequence in a plant or plant tissue, wherein this regulation is dependent upon a chemical regulator, and a second DNA component sequence capable of being transcribed in a plant or plant tissue. The DNA component sequences may be derived from natural sources or be prepared synthetically.

The second DNA sequence may be transcribed as an RNA which is capable of regulating the expression of a phenotypic trait by an anti-sense mechanism. Alternatively, the second DNA sequence in the chimeric DNA sequence may be transcribed and translated, i.e. coded, in the plant tissue to produce a polypeptide resulting in a phenotypic trait. The chimeric gene is constructed such that the second DNA sequence is properly associated with, typically in an adjacent orientation to, the chemically regulatable DNA sequence to ensure transcription. Association is effected with conventional techniques.

Preferred is a chimeric DNA sequence comprising a first non-coding chemically regulatable DNA component and a second transcribable DNA component wherein the first non-coding DNA sequence is one of the preferred DNA sequences mentioned above under Part D. The first DNA component sequence may be regulated by a repressing or by an inducing chemical regulator. A particular sequence of the invention is a chimeric DNA sequence wherein the first DNA component sequence has substantial sequence homology to a chemically regulatable DNA sequence in a naturally occurring chemically regulatable gene from a plant.

Preferred is a chimeric DNA sequence wherein the first DNA component sequence is, or has substantial sequence homology to, a chemically regulatable DNA sequence in a naturally occurring chemically regulatable gene from a plant and the second DNA component sequence is a coding sequence that is capable of being transcribed and translated to produce a polypeptide resulting in a phenotypic trait. Preferably this second DNA component sequence is adjacent to the first DNA coding sequence. Particularly preferred is such a chimeric DNA sequence wherein the first DNA component sequence is, or has substantial sequence homology to, the chemically inducible DNA sequence in a PR protein gene, for example a PR protein from a dicotyledonous plant, such as tobacco or cucumber. Examples thereof are mentioned above in Part D.

A second exemplified type of chimeric DNA sequence contains three DNA component sequences, originating from two or more sources. In the simplest embodiment this chimeric DNA sequence comprises the two-part DNA sequence as described above in Part E and a third DNA sequence originating from at least one different source. More specifically, this type of chimeric DNA sequence comprising a first DNA component sequence which is, or has substantial sequence homology to, a non-coding, chemically regulatable DNA sequence of a naturally occurring chemically regulatable gene, this first DNA component sequence being capable of regulating the transcription of an associated DNA sequence in a plant or plant tissue, wherein this regulation is dependent upon a chemical regulator, a second DNA component sequence which is, or has substantial sequence homology to, part but not all of a transcribable DNA sequence with which the first component is associated in the naturally occurring chemically regulatable gene, and a third DNA component sequence capable of being transcribed in a plant or plant tissue. Preferably, the naturally occurring chemically regulatable gene is a plant gene.

The second and third DNA component sequences will typically be coding sequences. The third DNA component may be derived from more than one natural or synthetic source. The first two DNA components will typically be natural in origin. If the origin is a plant, it may be a monocot, a dicot or a gymnosperm. In a preferred embodiment the second DNA sequence will include the nucleotide sequence which codes for the signal peptide of the chemically regulatable gene in which the first two DNA sequences occur. If the chemically regulatable DNA sequence is associated with part of the coding sequence of the gene from which it was derived, the third DNA sequence must not only be in the proper orientation, but must also be in the proper reading frame with the second DNA sequence. This orientation can be achieved by techniques well known in the art.

Preferred are chimeric DNA sequences wherein the first and the second DNA sequence components are those mentioned as preferred in Part E above. For example a preferred chimeric DNA sequence is one wherein the first DNA component sequence is, or has substantial sequence homology to, the chemically inducible DNA sequence in a PR protein gene from a dicotyledonous plant, for example from tobacco or cucumber. Examples of PR protein genes are mentioned above.

The chimeric genes described above embrace a variety of possible constructions. A chemically regulatable non-coding sequence can be associated with a gene controlling flowering or fruit ripening; a gene effecting tolerance or resistance to herbicides or to many types of pests, for example fungi, viruses, bacteria, insects, nematodes, or arachnids; a gene controlling production of enzymes or secondary metabolites; male or female sterility; dwarfness; flavor; nutritional qualities; and the like. Using the present invention such traits can be enhanced by the farmer and gardener, which is no longer dependent on natural factors alone. A phenotypic trait of particular interest for control is the production of metabolites in tissue culture or a bioreactor.

A preferred chimeric DNA sequence is a two or three component sequence wherein the coding DNA component sequence codes for a phenotypic trait, for example a trait selected from the group consisting of tolerance or resistance to a herbicide, fungus, virus, bacterium, insect, nematode or arachnid; production of secondary metabolites; male or female sterility; and production of an enzyme or other reporter compound. Particularly preferred is a two or three component chimeric DNA sequence wherein the coding component sequence codes for tolerance or resistance to herbicides, for example codes for wild-type or herbicide resistant acetohydroxyacid synthase (AHAS), or wherein the coding component sequence codes for resistance to insects, for example codes for *Bacillus thuringiensis* endotoxin (BT).

If the chimeric sequence is to be used as an assay for chemical regulators, the phenotypic trait is preferably an assayable marker. Suitable markers include, but are not limited to, luciferase (LUX), chloramphenicol acetyltransferase (CAT), neomycin phosphotransferase (NPT), nopaline synthase (NOS), octopine synthase (OCS), beta-1,3-glucuronidase (GUS), acetohydroxyacid synthase (AHAS), and *Bacillus thuringiensis* endotoxin (BT). Preferred markers are beta-1,3-glucuronidase (GUS), acetohydroxyacid synthase (AHAS), and *Bacillus thuringiensis* endotoxin (BT).

A representative example of such a chimeric DNA sequence, described in detail in the examples, is a two-part chimeric DNA sequence which contains the 5' flanking, non-coding sequence of the PR-1a gene. While one of the exemplified marker is the coding sequence for the GUS gene, any of the above mentioned markers could be used. The analogous three-part chimeric sequence contains part of the coding sequence of the PR-1a gene. These constructions are particularly useful because the effect of the chemical induction, i.e. beta-glucuronidase enzyme activity, is easily detectable in plant cells or extracts thereof. Other particular embodiments, for example those which comprise the non-coding sequence of one of the tobacco β-1,3-glucanase genes and those which comprise the coding sequence for wild-type or herbicide resistant acetohydroxyacid synthase or for *Bacillus thuringiensis* endotoxin, are described in Part O, Examples.

Preferred chimeric DNA sequence are two component or three component chimeric DNA sequences wherein the first DNA component sequence is the 5' flanking region of the tobacco PR-1a gene and contains more than about 300, for example between 300 and 2000, preferably between 600 and 1000, base pairs adjacent to the transcriptional start site.

Further preferred is a chimeric DNA sequence comprising three components wherein the second DNA component sequence codes for a signal peptide, for example wherein the second DNA component sequence codes for a peptide which is, or has substantial sequence homology to, the signal peptide from a PR protein gene, preferably the PR-1a gene.

The invention further embraces a method for the preparation of a chemically regulatable chimeric DNA sequence comprising a first non-coding, chemically regulatable DNA component sequence which is capable of regulating the transcription of an associated DNA sequence in a plant or plant tissue, wherein this regulation is dependent upon a chemical regulator, and a second DNA component sequence capable of being transcribed in a plant or plant tissue, characterized in that the DNA component sequences are ligated. Likewise, the invention embraces a method for the prepartion of a chimeric DNA sequence comprising a first DNA component sequence which is, or has substantial sequence homology to, a non-coding, chemically regulatable DNA sequence of a naturally occurring chemically regulatable gene, this first DNA component sequence being capable of regulating the transcription of an associated DNA sequence in a plant or plant tissue, wherein this regulation is dependent upon a chemical regulator, a second DNA component sequence which is, or has substantial sequence homology to, part but not all of a transcribable DNA sequence with which the first component is associated in the naturally occurring chemically regulatable gene, and a third DNA component sequence capable of being transcribed in a plant or plant tissue, characterized in that the DNA component sequences are ligated concurrently or consecutively.

G. Vectors

Vectors, produced by standard techniques and comprising either the chemically regulatable DNA sequences described in part D or E or the chimeric DNA sequences described in Part F above, represent an additional feature of the invention. Vectors are recombinant DNA sequences which may be used for isolation and multiplication purposes of the mentioned DNA sequence and for the transformation of suitable hosts with these sequences. Preferred vectors for isolation and multiplication are plasmids which can be propagated in a suitable host microorganism, for example in *E. coli*.

Preferred vectors for transformation are those useful for transformation of plant cells or of Agrobacteria. For Agrobacterium-mediated transformation, the preferred vector is a Ti-plasmid derived vector. For the direct DNA transfer into protoplasts, any of the mentioned vectors may be used. Appropriate vectors which can be utilized as starting materials are known in the art. Suitable vectors for transforming plant tissue and protoplasts have been described by deFramond, A. et al., *Bio/Technology* 1: 263 (1983); An, G. et al., *EMBO J.* 4: 277 (1985); Potrykus, I. et al., supra; Rothstein, S. J. et al., *Gene* 53: 153 (1987). In addition to these, many other vectors have been described in the art which are suitable for use as starting materials in the present invention.

The vectors which contain only the chemically regulatable DNA sequence as described in Part D or E above can be used as intermediates for the preparation of a vector containing the chimeric DNA sequence as described in Part F above. The insertion of an appropriate sequence, which is capable of transcription, into such an intermediate vector results in a vector comprising a chimeric DNA sequence of the invention that can then be used to transform the desired plant tissue, protoplast or other host. Alternatively, a chimeric DNA sequence can be prepared and inserted into a suitable vector which is then used to transform the desired plant tissue or other host.

The construction and multiplication of the vectors can be performed in a suitable host, for example, in *E. coli*. Suitable *E. coli* strains include HB101, JM83, DH1, DH5, LE392 and the like. The vectors of the invention may be used as such in a direct gene transfer or a micro-injection technique. In certain instances it may be preferable to linearize the vector before use. Alternatively the vectors may be transferred to an Azrobacterium host This transfer is accomplished by conventional techniques including biparental mating (Simon, R. et al., *Bio/Technology* 1: 74 (1983)), triparental mating (Ditta, G. et al., *Proc. Natl. Acad. Sci. USA* 77.: 7347 (1980)) or transformation (Holsters, M. et al., *Mol. Gen. Genet.* 163: 181 (1978)). Suitable strains of Agrobacterium include but are not limited to *A. tumefaciens* LBA4404, CIB542 and C58Z707.

Preferred vectors are those comprising the preferred DNA sequences mentioned in Parts D, E and F above. Furthermore a preferred vector is one that is functional in plant cells or in Agrobacterium, or both. Particularly preferred are the vectors described in Part H, Examples.

H. Plant Tissues, Plants and Seeds

A further aspect of the invention are plant tissue, plants or seeds containg the chimeric DNA sequences described above. Preferred are plant tissues, plants or seeds containing those chimeric DNA sequences which are mentioned as being preferred.

The cells of plant tissue are transformed with the vectors described above by any technique known in the art, including those described in the references discussed above and by techniques described in detail in the examples which follow. These techniques include direct infection or co-cultivation of plants or plant tissue with Agrobacterium. A very suitable technique is the leaf disk transformation described by Horsch, R. B. et al., *Science* 225: 1229 (1985). Alternatively, the vector can be transferred directly, for example by electroporation, by microinjection or by transformation of protoplasts in the presence of polyethylene glycol (PEG), calcium chloride or in an electric field, as more fully described above.

The cells transformed may originate from monocotyledenous or dicotyledonous plants and may contain one or more of the chemically regulatable chimeric genes of this invention. Thus, genes which, for example, code for resistance or tolerance to herbicides and a variety of insect, viral, bacterial, fungal and other pests, for sterility, for size, for flowering and fruit ripening, are introduced in the plant tissue, and these cells or protoplasts ultimately regenerated into plants in which these traits can be controlled by manipulations with a chemical regulator. Alternatively cells can be propagated in tissue culture or in a bioreactor to produce enzymes or secondary matabolites. If an enzyme assay is desired, the coding section of the chimeric gene may, for example, comprise a LUX, CAT, NPT, NOS, OCS, GUS, AHAS or BT gene, as identified previously. Such chimeric genes containing a chemically inducible sequence from a PR gene are a preferred embodiment of the invention because of the ease of application of the regulator and the ease of detection of the enzyme product.

Following transformation, the transformed cell or plant tissue is selected or screened by conventional techniques. The transformed cell or plant tissue contains the chimeric DNA sequence discussed above and is then regenerated, if desired, by known procedures, including those described in the reference discussed above and in the examples which follow for both monocot and dicot plants. The species which can be regenerated by these techniques include, but are not limited to, maize, sunflower, rapeseed, clover, tobacco, carrot, cotton, alfalfa, rice, potato, eggplant and cucumber. The regenerated plants are screened for transformation by standard methods. Progeny of the regenerated plants is continuously screened and selected for the continued presence of the integrated DNA sequence in order to develop improved plant and seed lines. The DNA sequence can be moved into other genetic lines by a variety of techniques, including classical breeding, protoplast fusion, nuclear transfer and chromosome transfer.

I. Advantages and Uses
1. Chemical Regulation of Expression

The present invention offers a number of advantages and uses stemming from the easily controlled regulatable expression in plants or plant tissue of the chimeric genes containing chemically regulatable DNA sequences. Regulation of genes acting by an anti-sense mechanism or of genes whose expression results in the production of a phenotypic trait is possible. Of particular importance are the ability to control the time and rate of gene expression and the ease of effecting this control, either uniformly throughout the plant or in localized parts of the plant.

Effecting the control may be accomplished simply by applying the chemical regulator to the plant tissue, or to the plant or part of the plant in such a manner and in such an amount to regulate the chimeric gene(s) whose expression in plant cells, plant tissues or plants is desired. For example, if the trait to be expressed is preferably expressed only in the leaves, then spraying or dusting the leaves at a time which optimizes that expression in the leaves, and before any migration to other parts of the plant, may accomplish that objective easily and efficiently. Alternatively uniform expression throughout that part of the plant above ground may result from application to the entire plant (i.e., stem and both sides of the leaves). If expression in the roots is desired, application to the seeds or the soil around the seeds or roots is a possible method of regulation. Expression in a bioreactor is accomplished quite easily, for example, by applying the chemical regulator to the medium contacting the cells.

The ability to control the time, rate and/or gene expression of novel phenotypic traits in transgenic plants offers a number of useful advantages. For example, if tolerance by a detoxification mechanism to a herbicide or other pesticide is introduced into a plant, that trait can be maximized by proper timing of the the application of the chemical regulator. Thus, the regulator can be applied before, with or after application of a herbicide or other pesticide, depending on which method gives optimal tolerance. It is also possible now to regulate the production of compounds whose biosynthesis is controlled by endogenous or foreign genes. Upon chemical induction the production of such products can be started at the desired time. The induced process could be a multi-step biosynthesis or a one-step conversion of a metabolite.

Another advantage of the present invention arises from the ability to regulate the developmental processes in plants at a desired time by the application of a regulating chemical. For example, the synchronization of plant development (germination, tillering, sprouting, flower formation, anthesis, fruit ripening, dry down, abscission etc.) can be accomplished. In addition, normal plant development can be prevented. This can be accomplished by introducing, for example, a toxin gene which would interfere with the desired developmental stage, a DNA sequence which would block the developmental stage through an anti-sense mechanism, or a gene whose expression blocks the transition to a new developmental stage and which can be chemically repressed to allow development to proceed. One suitable utility is the induction of male or female sterility for the controlled hybridization of crops.

Additional advantages of the present invention are novel assay procedures, preferably enzyme assay procedures. For example, identification of new chemical regulators can now be accomplished quite easily. Such assay methods involve the use of transformed plants or plant cells which contain a chimeric DNA sequence of this invention. A chemical is applied to the transformed host and the transcription of the transcribable DNA sequence is measured against a control; transcription is usually detected in the form of a translation product or as an effect of such a product. The assay may be performed in a variety of ways, but is typically carried out using whole, regenerated plants (by applying the chemical to the plant) or to cultured cells or tissue (by applying the chemical to the cells or tissue) and subsequently supplying a substrate for the enzyme activity. The product of enzyme activity is then detected by standard methods, e.g., spectrophotometric measurement.

In particular the invention embraces a process for identifying a chemical regulator which comprises transforming a host with a chimeric DNA sequence as described above in Part C or with a vector containing said chimeric DNA sequence, applying a putative chemical regulator to the transformed host, and measuring the expression of the phenotypic trait. A preferred process is such a process wherein the transformed host is plant tissue or plant cells. Further preferred is a process wherein the chimeric DNA sequence is a sequence mentioned above as being preferred, for example wherein the first DNA component sequence of said chimeric DNA is a chemically inducible sequence which is, or has substantial sequence homology to, a chemically inducible sequence of a PR protein gene, and wherein the phenotypic trait coded for by the chimeric DNA is an assayable enzyme marker.

Another feature of the invention is the development of novel methods to identify other chemically regulatable DNA sequences. A vector containing a putative chemically regulatable DNA sequence is prepared, for example, from a host-selectable marker and a selectable or assayable marker. Suitable selectable markers include antibiotic resistance genes and herbicide resistance genes. Representative antibiotic resistance genes includes those for hygromycin, kanamycin, chloramphenicol, bleomycin, puromycin, lincomycin, G418 and methotrexate. A particularly suitable gene for resistance to hygromycin is aminoglycoside phosphotransferase IV. Suitable vectors for the transformation of plants containing the hygromycin resistance gene have been described by Rothstein, S. J. et al., *Gene* 53: 153 (1987). Examples of herbicide resistance genes encode resistance to, for example, sulfonylureas, glyphosate, phosphinotricin and atrazine.

Suitable assayable markers include genes for enzymes, antigens, immunoglobulins and the like, as well as antibiotic resistance genes. Suitable enzyme markers include LUX, CAT, NPT, NOS, OCS, GUS, AHAS and BT. A particularly suitable enzyme is beta-1,3-glucuronidase (GUS) because of the ease of enzyme assay. The DNA sequence coding for the assayable marker can be inserted into the vector using conventional techniques.

The putative regulatable DNA sequence is typically inserted adjacent to the assayable marker gene so that the expression of the assayable marker is under the control of the putative DNA sequence. The vector is then used to transform plant tissue or another appropriate host. Transformed plant tissue or host is selected on the basis of the plant selectable marker, typically antibiotic resistance. A chemical regulator is then applied to the plant tissue or other host following selection or following regeneration of the transformed tissue. Induction or repression of the assayable marker following the application of the chemical regulator identifies the putative DNA sequence as one which is capable of regulating the transcription of an adjacent DNA sequence wherein the regulation is dependent on a chemical regulator. The assay can be performed on whole, regenerated or transformed plants, for example, by applying the chemical regulator to the leaves or other plant tissue, and measuring the expression of the assayable marker. Alternatively the assay can be performed on transformed callus tissue or other host in cell culture, by applying the putative chemical regulator to the callus or other culture and measuring the expression of the assayable marker.

In particular the invention embraces a process for identifying a chemically regulatable DNA sequence which comprises the steps of:

(a) transforming a host with a putative chemically regulatable DNA sequence or a vector containing said sequence, a second DNA sequence which is a host-selectable gene marker and a third DNA sequence which codes for a phenotypic trait;

(b) applying a chemical regulator to said transformed host; and (c) measuring the expression or selecting for change in expression of the phenotypic trait coded for by the third DNA sequence.

Preferred is such a process wherein said third DNA sequence is a host-selectable or an assayable gene marker, and a process wherein the second or third DNA sequence is a gene marker for herbicide resistance or antibiotic resistance, for example selected from the group consisting of hygromycin, kanamycin, chloramphenicol, bleomycin, puromycin, lincomycin and methotrexate resistance genes, e.g. an aminoglycoside phosphotransferase IV hygromycin resistance gene.

Also preferred is such a process wherein the putative chemically regulatable DNA sequence is associated with, and preferably adjacent to, the third DNA sequence. Further preferred is a process wherein the transformed host is plant tissue or plant cells.

Further preferred is such a process wherein the third DNA sequence codes for an assayable enzyme marker selected from the group consisting of luciferase (LUX), chloramphenicol acetyltransferase (CAT), neomycin phosphotransferase (NPT), nopaline synthase (NOS), octopine synthase (OCS), beta-1,3-glucuronidase (GUS), acetohydroxyacid synthase (AHAS), and *Bacillus thuringiensis* endotoxin (BT).

A further aspect of the invention are substantially pure chemically regulatable DNA sequence identified by the mentioned processes.

The present invention also provides a method for selecting transformed plant material. Plant material exposed to an exogenous DNA sequence containing a chemically regulatable DNA sequence for which a chemical regulator is known and a second DNA sequence for a phenotypic trait is treated with the regulator and expression of the phenotypic trait sought. Observation of the trait confirms that transformation of the putative transformants has indeed occurred. Typical phenotypic traits for purposes of this method include the host selectable markers and assayable markers previously described.

In particular the invention embraces a method for selecting transformed plant cells or tissue which have been subjected to transforming DNA comprising a first DNA component sequence that is chemically regulatable by a known chemical regulator and an associated second DNA sequence coding for a phenotypic marker, which process comprises the steps of (a) treating putative transformants with said known chemical regulator and (b) selecting transformants according to expression of the phenotypic trait coded for by the second DNA sequence. A preferred method is such a method wherein said phenotypic trait is antibiotic resistance, for example resistance to hygromycin, kanomycin, chloroamphenicol, bleomycin, puromycin, lincoymcin, G418 and methotrexate, or an assayable enzyme marker, for example selected from the group consisting of luciferase (LUX), chloramphenicol acetyltransferase (CAT), neomycin phosphotransferase (NPT), nopaline synthase (NOS), octopine synthase (OCS), beta-1,3-glucuronidase (GUS), acetohydroxyacid synthase (AHAS), and *Bacillus thuringiensis* endotoxin (BT).

2. Disease Resistance or Tolerance

With regard to the anti-pathogenic sequences described in part K below, the present invention provides a means for enhancing the ability of a plant, plant tissue or seed to withstand challenge by a pathogen. Thus the present invention makes it possible to genetically engineer plants for enhanced resistance or tolerance to pathogens including, but not limited to, viruses or viroids, e.g. tobacco or cucumber mosaic virus, ringspot virus or necrosis virus, pelargonium leaf curl virus, red clover mottle virus, tomato bushy stunt virus, and like viruses, fungi, e.g. *Phythoihthora iparasitica* or *Peronosisora tabacina*, bacteria, e.g. *Pseudomonas syringae* or *Pseudomonas tabaci*, or aphids, e.g. *Myzus persicae*.

3. Enhanced Exogenous Regulation via Inactivation of Endogenous Regulation

The present invention provides a method for exogenous regulation of gene expression in plants wherein the corresponding, native, endogenous regulation mechanism of the genes in the plant is rendered non-functional. In general, the method is applicable to any plant capable of being altered in a manner described herein, and is particularly applicable to agronomically important plants such as maize, wheat, soybean, cotton, rapeseed, barley, rice, sorghum, sunflower, bean, beet and tobacco.

Certain genes in plants are regulated endogenously by at least one corresponding signal transduction cascade (pathway), that is, the production in the plant cell of various regulating chemicals; e.g., signal molecules. These molecules often are produced via a biosynthetic pathway in response to an external stimulus such as, for example, a necrotizing pathogen. In turn, these signal molecules regulate; i.e., induce or repress, the expression of various genes in the plant. For instance, treatment of a plant such as tobacco by a necrogenic pathogen; e.g., TMV, or salicylic acid or 2-chloroethylphosphonic acid (Ethephon, Signa Chemicals, St. Louis, Mo.) initiates a process that leads to the accumulation of high concentrations of salicylic acid (SA) in other, non-infected parts of the plant. SA is bound by receptors in or on the target cells. The signal is transduced intra-cellularly. SA then activates the coordinate induction of the expression of a set of at least nine systemic acquired resistance (SAR) gene families, which include the ten pathogenesis-related (PR) proteins of tobacco. The expression products of these gene families causes the plant target cells to become resistant to attack by a side variety of agronomically important bacterial, fungal and viral pathogens. For example, transgenic tobacco expressing high levels of PR-1a have reduced disease symptoms following infection by oomycete fungi, including *Peronospora tabacina* (downy mildew) and *Phytophora parasitica* (black shank disease) (see Examples 148–168).

Applicants have discovered that inactivating an endogenous signal transduction cascade such that the expression of the target gene(s) is effectively eliminated affords the exclusive exogenous control of these genes. For example, Applicants, having confirmed that SA is the endogenous signal molecule that mediates SAR in plants such as Arabidolsis, tobacco and cucumber, have discovered that this signal cascade can be controlled; i.e., inactivated, disarmed or rendered dysfunctional, such that the induction of the target genes by SA is essentially eliminated. That is, the resultant concentration of the signal molecule in the plant cell is insufficient to activate the promoters of the signal-regulated genes. In turn, they have discovered that expression of the target genes can be induced by exogenous application of a chemical which acts downstream of the signal transduction cascade, or otherwise acts independently of the SA pathway.

The signal cascade can be rendered non-functional in a number of ways. First, the plant cell can be stably transformed with a gene encoding an enzyme capable of metabolizing or inactivating the plant cell signal. The gene encoding such an enzyme may be derived from any organism; e.g., microbe, plant or animal, or may be a truncated or synthetic gene, provided, however, that the gene is functional in plants. The gene can be linked to a promoter functional in plants and which allows expression at high levels in those cell types in which the subsequent exogenous chemical regulation is intended to be effected. In the alternative, a promoter may be used which drives expression at high levels in all or nearly all cell types. The promoter must be capable of functioning independently of the signal; i.e., expression of the operably linked gene(s) does not depend on the signal, and the exogenous chemical. Examples of suitable promoters include constitutive promoters such as the CaMV 35S promoter, small subunit of RUBISCO, an enhanced 35S promoter such as that described in Kay et al., *Science* 236: 1299–1302 (1987), a double 35S promoter such as that cloned into pCGN2113 (ATCC 40587), and any other constitutive promoter capable of functioning in the plant tissue of interest.

In a preferred embodiment, a plant is transformed with nahG, a gene which encodes salicylate hydroxylase (SH). SH (E.C. 1.14.13.1) catalyzes the conversion of salicylate to catechol. Yamamoto et al., *J. Biol. Chem.* 240(8): 3408–3413 (1965). This gene can be obtained from any soil microbe capable of growth on salicylate as sole carbon source. Examples include Pseudomonas sp., e.g., ATCC 29351 and 29352, *Pseudomonas cepacia* and *Trichosporon cutaneum* (Einarsdottir et al., *Biochemistry* 27: 3277–3285 (1988)). A preferred source is *Pseudomonas putida* PpG7 TCC 17485), wherein nahG on the 83 kilobase plasmid NAH7 is on of two operons involved in the conversion of naphthalene to pyruvate and acetaldehyde (Yen et al, *Proc. Natl. Acad. Sci. USA* 79: 874–878 (1982)). The 1305 base paid nucleotide sequence of the nahG coding region and approximately 850 base pairs of the 3' flanking sequence have been determined (You et al., Biochemistry 30: 1635–1641 (1991)). Approximately 200 base pairs of the 5' flanking sequence also have been determined. See Schell, *Proc. Natl. Acad. Sci. USA* 83: 369–373 (1986). Methods of transforming plants are known, and are disclosed herein and in co-owned pending application Ser. No. 07/583,892, filed Sep. 14, 1990, the relevant disclosure of which is incorporated herein by reference. Those skilled in the art could select an appropriate transformation method depending upon the type of target plant.

Those skilled in the art will appreciate that other means can be employed to achieve the same effect. For instance, a second method involves the expression or overexpression in a transformed plant of a gene encoding an enzyme which catalyzes the modification; e.g., degradation, of a metabolic precursor of the signal molecule so that the plant is rendered incapable of producing the signal molecule. A third method involves the external application to the plant of antagonists of the target cell signal. Such antagonists compete with the cell signal for the cell signal target site, but do not activate the response generated by the cell signal. Instead, inhibition of the cell signal response is effected. In the case of salicylic acid, o-trimethylsilyl benzoic acid exhibits such an antagonistic effect when applied exogenously to a plant. Further, aminoethoxyvinyl glycine and aminooxyacetic acid have been found to inhibit the ethylene cascade in plants, and that the ethylene response was restored upon subsequent, exogenous application of ethylene. See, Yang and Hoffman, Ann. Rev. Plant Physiol. 35:155–189 (1984).

Yet a fourth method involves the selection of plant mutants which fail to respond to the selected cell signal, but which are responsive to the predetermined exogenous chemical regulator. Methods of selecting mutants for a predetermined trait are known in the art. These include EMS, gamma-rays, T-DNA transposon insertion, and the like. A fifth method involves the expression of antisense RNA to any gene involved in the signal transduction cascade. This may include the expression of antisense RNA to a gene involved in the biochemical pathway leading to the synthesis of the cell signal, or in the alternative, to a gene encoding a receptor or other component of the pathway. See, Oeller et al., Science 254: 437–439 (1991). In either case, the cell signal which is regulating particular genes or sets of genes is significantly reduced. The cell signal also can be effectively rendered non-functional by overexpressing sense transcripts of any gene involved in the transduction cascade (pathway) utilizing a promoter functional in plant cells. This stratagem is based on the observation that the attempted overexpression of a gene in transgenic plants or plant cells can lead to a down-regulation of the homologous gene in the host plant as well as the transgene. See, van der Krol et al., *Plant Cell* 2: 291–299 (1990).

In cases where two or more endogenous signal transduction cascades can regulate at least gene or gene family of interest, techniques to deactivate all cascades can be used, thereby rendering the genes of interest regulatable only by exogenous application of a chemical regulator.

There are several signal transduction cascades known in plants. Representative examples include the phytohormones such as ethylene which affects fruit ripening and other responses (Guzman and Ecker, *Plant Cell* 2: 513–523 (1990); light (Chong et al., *Cell* 58: 991–999 (1990); touch (Braam and Davis, *Cell* 60: 357 (1990); and gravity (Okada et al., *Cell* 70: 369–372 (1992).

Once inactivation of the cell signal is achieved, the genes which are natively regulated by the signal can be regulated exclusively by the exogenous application to the plant of a chemical regulator. In general, the chemical regulator, which can be naturally or non- naturally occurring in plants, functions "downstream" of the signal in the transduction pathway, or functions completely independently; e.g., is not involved in the pathway. In the case of the SA pathway, for example, representative chemical regulators capable of inducing expression of PR genes include benzo-1,2,3-thiodiazole-7-carboxylate, n-propyl benzo-1,2,3-thiodiazole-7-carboxylate, methyl benzo-1,2,3-thiodiazole-7-carboxylate, benzyl benzo-1,2,3-thiodiazole-7-carboxylate, and benzo-1,2,3-thiodiazole-7-carboxylic acid N-secbutylhydrazide. These compounds are non-naturally occurring in plants.

Other chemicals encompassed by the present invention can be determined by assaying the test chemical in the presence of a plant modified in a manner described above, which plant also contains an endogenous or heterologous reporter gene operably linked to a promoter regulatable by the signal molecule. Since the modified plant is incapable of producing the signal molecule in sufficient amounts to include expression of the reporter gene, no difference will be observed upon application to the plant with the chemical unless the chemical is capable of regulating expression of the reporter gene. Examples of reporter genes include luciferase (LUX), chloramphenicol acetyltransferase (CAT), neomycin phosphotransferase (NPT), nopaline synthase (NOS), octopine synthase (OCS), beta-1,3-glucuronidase (GUS), acetohydroxyacid synthase (AHAS) and *Bacillus thuringiensis* endotoxin (Bt) (Williams et al., *Bio/Technology,* 10: 540–543 (1992). The assay can be performed using whole plants or with plant tissue in an in vitro assay.

In certain situations, it would be desirable to regulate the expression of various heterologous genes (transgenes) in transgenic plants. For example, the effectiveness of disease- or insect resistance in trarsgenic plants transformed with genes encoding disease- or insect-resistant proteins, respectively, could be enhanced if the timing of the expression could be controlled. See, e.g., Uknes, *Plant Cell,* 4: 645–656 (1992); Ward et al., *Plant Cell* 3:1085–1094 (1991); Gould, *Bioscience* 38: 26–33 (1988); and Gould, *TIBTECH* 6: S15–S18 (1988). Also, the chemical regulation o developmental processes such as homeosis, germination, tillering, sprouting, flowering, anthesis, fruit ripening, and abscission offers several advantages such as the facilitated production of hybrid seed, greater reduction of crop loss, and more generally, control of the growth and development of the plant by the farmer. Thus, the present invention applies equally to transgenic plants containing heterologous genes, e.g., disease resistance genes including PR and SAR genes, insect resistance genes such as Bt genes, and genes involved in developmental processes such as those described above. It also includes genes encoding industrial or pharmaceutical biomaterials such as plastics and precursors thereof, perfumes, additives, enzymes and other proteins, and pharmaceutical, wherein the plant effectively would be used as a bioreactor, e.g., the two genes encoding production of polyhydroxybutyrate, a thermoplastic (Poirer et al., *Science* 256: 520–523 (1992). To practice this embodiment of the present invention, the heterologous gene of interest should be fused to a promoter capable of being regulated by the exogenous chemical regulator (eg. containing a chemically regulatable DNA sequence) and for which activity, the signal is not required exclusively. In other words, the promoter can be regulatable by the signal, provided that it can be regulated by a chemical regulator in the absence of a functional, endogenous signal. Examples include the PR-1a promoter such as those disclosed herein and in Williams et al., *Bio/Technology* 10: 540–543 (1992); Uknes et al., *The Plant Cell* 5: 159–169 (1993); and Van de Rhee et al., *Plant Cell* 2: 357–366 (1990), and other promoters isolated from chemically regulated plant genes such as those described herein and in Payne et al., *Plant Mol. Biol.* 11:89–94 (1988).

J. Signal Peptides

A signal peptide or a signal sequence is a special N-terminal amino acid sequence in a protein entering the endoplasmic reticulum. Such a sequence in eukaryotic cells typically contains about 15 to 40 amino acid residues, many of which are hydrophobic. The sequence is eventually cleaved from the mature protein.

In the context of the present invention the signal peptide of a chemically regulatable gene is useful in the construction of three-part chimeric constructions as described above. Such chimeric constructions contain a first chemically regulatable sequence, a second DNA sequence coding for a signal peptide in proteins, and a third sequence which codes for a phenotypic trait. Preferably the phenotypic trait is one that is easily detected, for example in an assay procedure. Inclusion in the chimeric construction of the DNA sequence which codes for a signal peptide allows the product expressed by the third DNA sequence to be directed away from the endoplasmic reticulum of the host cell to its ultimate target site.

Therefore, an additional feature of the invention is a signal peptide from the tobacco PR-1a protein, and a protein with an amino acid sequence having substantial sequence homology to this peptide. The amino acid sequence for that peptide is as follows:

MetGlyPheValLeuPheSerGlnLeuProSerPheLeuLeuVal-SerThrLeuLeuLeuPheLeuValIleSerHisSerCysArgAla.

The present invention also embraces the DNA sequence which codes for this peptide (see nucleotides 932–1021 of SEQ ID No. 1) and DNA sequences having substantial sequence homology to this sequence. As noted previously, the invention also embraces (1) DNA sequences containing the chemically regulatable sequence in combination with the sequence coding for the signal peptide and (2) three-part chimeric DNA sequences containing the chemically regulatable component, the coding section for a signal peptide and a DNA sequence that is transcribed, preferably with translation.

K. Anti-Pathogenic Sequences

The present invention also embraces anti-pathogenic DNA sequences which are capable of conferring enhanced disease resistance or disease tolerance when expressed in a plant or plant tissue. This includes coding sequences for plant pathogenesis-related (PR) proteins as described herein and sequences with substantial homology to these coding sequences.

Included within the scope of the present invention, in addition to the sequences exemplified specifically below and enumerated in the sequence listing, are cDNA sequences which are equivalent to the enumerated Sequences which encode the given plant pathogenesis-related protein, and cDNA sequences which hybridize with the enumerated Sequences and encode a polypeptide having some degree of disease-resistant activity of the given plant pathogenesis-related protein (i.e. an anti-pathogenic sequence).

Equivalent cDNA sequences are those which encode the same protein even though they contain at least one different nucleotide from the enumerated sequence. As is well known in the art, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Amino Acid | Codon | Amino Acid | Codon |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thy) | ACL | Trytophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet codon corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence as follows:
A=adenine; G=guanine; C=cytosine; T=thymine
X=T or C if Y is A or G
X=C if Y is C or T
Y=A, G, C or T if X is C
Y=A or G if X is T
W=C or A if Z is A or G
W=C if Z is C or T
Z=A, G, C or T if W is C
Z=A or G if W is A
QR=TC if S is A, G, C or T;
    QR=AG if S is T or C
J=A or G
K=T or C
L=A, T, C or G
M=A, C or T The above shows that the amino acid sequence of the instant plant pathogenesis-related proteins can be prepared using different nucleotide sequences encoding the same amino acid sequence of the proteins. Accordingly, the scope of the present invention includes such "equivalent nucleotide sequences."

cDNA sequences that hybridize with a given enumerated sequence and encode a polypeptide or protein having at least some degree of activity of the corresponding plant pathogenesis-related protein are those which exhibit substantial sequence homology, as defined hereinabove, with the enumerated Sequence such that it hybridizes with the latter under low stringency conditions. Such conditions are described in Examples 46 and 51–58, below. Proteins translated from these hybridizable cDNA sequences have different primary structures from proteins translated from the enumerated Sequences. However, their respective secondary structures are the same.

Also included as part of the present invention are plant tissues, plants and seeds comprising anti-pathogenic sequences analogous to those plant tissues, plants and seeds comprising chemically regulatable sequences described in part H above.

L. Differential Cloning and Screening Technology

A method has been conceived and developed which will allow efficient enrichment of sequences present in one population of molecules in greater amounts than in another population. The method's greatest utility is in situations where the populations are very similar and the differentially present sequences represent a very small proportion of the population.

If two populations of clones are similar and one wishes to isolate those clones which are present in one population in higher amounts (i.e. "induced" or differentially regulated), past techniques involved screening with probes from the two populations (+/− screening; St. John and Davis, *Cell* 16:443–452 (1979)), or enrichment of probes or mRNAs by hybridization and hydroxy-apatite (HAP) chromatography (Davis, et al., *Proc. Natl. Acad. Sci, USA* 81: 2194–2198 (1984)). The first method has a demonstrated sensitivity limitation in that only clones present in greater than about one in 2,000 will be detected. The second is laborious, technically difficult, and achieves enrichments of 20–50 fold at best.

The present method involves exploiting two recent developments in molecular technology: the polymerase chain reaction (Saiki et al., *Science* 239:487–491 (1988)) and biotin-avidin chromatography [Stahl, et al., *Nuc. Acids. Res.* 16: 3026–3038 (1988)). The polymerase chain reaction (PCR) allows simple synthesis of large amounts of DNA of specified sequence. Biotin-avidin chromatography allows the efficient separation of molecules bearing a biotin affinity tag from those molecules which do not bear the tag.

In its general form, the technique consists of isolating single strands of cDNA representing two different populations ("induced" vs "uninduced"), but of opposite cDNA polarity for the two populations, i.e. one of "sense" polarity relative to mRNA's, and the other its complement, or "anti-sense", polarity relative to mRNA's. The isolated strands from the "induced" population would have no affinity tag, while the strands of opposite polarity from the "uninduced" populations would have stable affinity tags. When these two populations are hybridized together, hybrids will form between complementary strands present in the two populations. Those strands from the "induced" population which have no counterparts, or many fewer counterparts, in the "uninduced" population, remain single stranded.

Due to the presence of the affinity tag (in essence a handle) on the strands of the "uninduced" population molecules, those strands and, most importantly, any hybrid molecules can be removed from the mixture by affinity chromatography. This leaves only those "induced" molecules which are not significantly represented in the uninduced population. These "induced" molecules can then be cloned by standard means and serve as an enriched population from which to isolate "induced" clones; alternatively, the enriched molecules can be amplified individually and sequenced directly.

An alternate scheme is the same as described above except that it involves incorporating a labile affinity tag only on the "induced" population molecules, while the affinity tag on the "uninduced" population is stable. "Labile" in this case means that the affinity tag can be removed at will, or be altered at will in such a way that it no longer serves as an affinity tag. In this scheme all the molecules in the hybridization mixture could bind to the affinity matrix, but only those "induced" molecules that are not hybridized to a complementary "uninduced" counterpart could be selectively recovered from the matrix for subsequent cloning.

The advantage of the methods of the invention described above over those previously described is the ability to isolate those genes which are turned on only to low levels, in specific circumstances, and which may play a causative role in some important biological phenomenon.

The present invention teaches the cloning of SAR genes by differential screening of tissues induced and non-induced to the systemic acquired response. SAR induction causes the transcription of genes in a protein synthesis-dependent fashion and also a protein synthesis-independent fashion. Two methods were used to clone specifically genes whose induced transcription is protein-synthesis independent. Firstly, cDNAs which were cloned by standard differential screening techniques were further screened on SAR-induced RNA isolated with and without cycloheximide (CHX) pre-treatment. Secondly, a PCR-based "differential display" technique was used to identify SAR-induced, but protein synthesis independent cDNAs directly. Differential display RNAs were prepared with and without SAR induction and CHX treatment. The use of CHX as an inhibitor of protein synthesis is well known in the art and is described by Greenberg et al., *Mol. Cell Biol.* 6: 1050–1057 (1986), Lau and Nathans, *Proc. Natl. Acad. Sci.* 84: 1182–1186 (1987), and Uknes et al., *Plant Cell* 5: 159–169 (1993). Thus, a number of genes were cloned which were induced by the SAR response, yet expressed independently of protein synthesis. These cloned genes are likely signal transducers in the pathway leading from induction to the development of the resistant state.

M. Chemical Regulators

A chemical regulator is defined as a substance which regulates expression of a gene through a chemically regulatable DNA sequence under certain circumstances as indicated in the definition of the term. The substance, in ionic or neutral form, with or without solvating or other complexing molecules or anions, will usually be exogenous relative to the system containing the chemically regulatable gene at the time regulation is desired. The use of exogenous chemical regulators is preferred because of the ease and convenience of controlling the amount of regulator in the system. However, the invention also includes the use of endogenous regulators, e.g., chemicals whose activities or levels in the system are artificially controlled by other components in, or acting on, the system.

Chemical regulators include chemicals known to be inducers for PR proteins in plants, or close derivatives thereof. These include benzoic acid, salicylic acid, polyacrylic acid and substituted derivatives thereof; suitable substituents include lower alkyl, lower alkoxy, lower alkylthio and halogen. When applied to plant tissue, typically to the leaves of whole plants, increased levels of mRNA and PR proteins develop in the plant tissue.

An additional group of regulators for the chemically regulatable DNA sequences and chimeric genes of this invention is based on the benzo-1,2,3-thiadiazole structure and includes, but is not limited to, the following types of compounds: benzo-1,2,3-thiadiazolecarboxylic acid, benzo-1,2,3-thiadiazolethiocarboxylic acid, cyanobenzo-1,2,3-thiadiazole, benzo-1,2,3-thiadiazolecarboxylic acid amide, benzo-1,2,3-thiadiazolecarboxylic acid hydrazide, and derivatives thereof.

A preferred group of regulators includes, but is not limited to, benzo-1,2,3-thiadiazole-7-carboxylic acid, benzo-1,2,3-thiadiazole-7-thiocarboxylic acid, 7-cyanobenzo-1,2,3-thiadiazole, benzo-1,2,3-thiadiazole-7-carboxylic acid amide, benzo-1,2,3-thiadiazole-7-carboxylic acid hydrazide, and derivatives thereof.

Suitable derivatives encompass but are not limited to representatives of said types of compounds wherein the benzo-1,2,3-thiadiazole moiety is unsubstituted or substituted by small substituents normally used in aromatic ring systems of agrochemicals such as lower alkyl, lower alkoxy, lower haloalkyl, lower haloalkoxy, lower alkylthio, cyano, nitro and halogen. Suitable derivatives further encompass, but are not limited to, representatives of said benzo-1,2,3-thiadiazole compounds wherein either the carboxylic acid, the thiocarboxylic acid, the carboxylic acid amide or the carboxylic acid hydrazide functional group is unsubstituted or substituted by aliphatic, araliphatic or aromatic residues. Suitable residues encompass, but are not limited to, alkyl (especially lower alkyl), alkoxy (especially lower alkoxy), lower alkoxyalkyl, alkoxyalkoxyalkyl, cycloalkyl, cycloalkylalkyl, phenylalkyl (especially benzyl), naphthylalkyl, phenoxyalkyl, alkenyl, and alkinyl, wherein the alkyl part of the substituent is unsubstituted or substituted by hydroxy, halogen, cyano or nitro, and the aromatic part of the substituent is unsubstituted or substituted by small substituents normally used in aromatic ring systems in agrochemicals such as lower alkyl, lower alkoxy, lower haloalkyl, lower haloalkoxy, lower alkylthio, cyano, nitro and halogen.

Regulators based on the benzo-1,2,3-thiadiazole structure encompass all molecular systems capable of releasing the molecule actually acting as the regulator.

A preferred group of regulators based on the benzo-1,2, 3-thiadiazole structure includes benzo-1,2,3-thiadiazolecarboxylic acid, alkyl benzo-1,2,3-thiadiazolecarboxylate in which the alkyl group contains one to six carbon atoms, and substituted derivatives of these compounds. Suitable substituents include lower alkyl, lower alkoxy, lower alkylthio and halogen. In particular, benzo-1, 2,3-thiadiazole-7-carboxylic acid and its alkyl esters, e.g. methyl benzo-1,2,3-thiadiazole-7-carboxylate, are preferred inducers for the chimeric DNA sequences comprising chemically regulatable DNA sequences isolated from PR protein genes. The syntheses of the mentioned chemical regulators and their utility as biocides may be discerned from British Patent 1,176,799 and Kirby, P. et al., J. Chem. Soc. C 2250 (1970).

Derivatives of benzo-1,2,3-thiadiazole that may further be used as regulators according to the present invention are described in U.S. patent application Ser. No. 234,241 filed Aug. 18, 1988, which is hereby incorporated by reference.

Among the preferred species based on the benzo-1,2,3-thiadiazolestructure there may be mentioned, for example, benzo-1,2,3-thiadiazole-7-carboxylic acid, methyl benzo-1, 2,3-thiadiazole-7-carboxylate, n-propyl benzo-1,2,3-thiadiazole-7-carboxylate, benzyl benzo-1,2,3-thiadiazole-7-carboxylate, benzo-1,2,3-thiadiazole-7-carboxylic acid sec-butylhydrazide, and the like.

An additional group of regulators for the chemically regulatable DNA sequences of this invention is based on the pyridine carboxylic acid structure, such as the isonicotinic acid structure and preferably the haloisonicotinic acid structure. Preferred are dichloroisonicotinic acids and derivatives thereof, for example the lower alkyl esters. Suitable regulators of this class of compounds are, for example, 2,6-dichloroisonicotinic acid, and the lower alkyl esters thereof, especially the methyl ester.

A further aspect of the invention is therefore a process for regulating transcription of a chemically regulatable gene, which process comprises applying such a chemical regulator to plant tissue, plant or seed containing a chemically regulatable DNA sequence as described in Part A, B or C above. Preferred is such a process wherein the plant tissue, plant or seed contains a chemically regulatable DNA sequence mentioned above as being preferred.

The chemical regulators may be applied in pure form, in solution or suspension, as powders or dusts, or in other conventional formulations used agriculturally or in bioreactor processes. Such formulations may include solid or liquid carriers, that is, materials with which the regulator is combined to facilitate application to the plant, tissue, cell or tissue culture, or the like, or to improve storage, handling or transport properties. Examples of suitable carriers include silicates, clays, carbon, sulfur, resins, alcohols, ketones, aromatic hydrocarbons, and the like. If formulated as a conventional wettable powder or aqueous emulsion, the regulator formulation may include one or more conventional surfactants, either ionic or non-ionic, such as wetting, emulsifying or dispersing agents.

The regulators may also be applied to plants in combination with another agent which is desired to afford some benefit to the plant, a benefit related or unrelated to the trait controlled by any chimeric gene which is regulated by the regulator. For example, a regulator can be admixed with a fertilizer and applied just before the expression of a transgenic trait unrelated to fertilization is desired. Or it can be combined with a herbicide and applied to mitigate the effect of the herbicide at the time when such effect would otherwise be at a maximum.

As a liquid formulation the regulator may be applied as a spray to plant leaves, stems or branches, to seeds before planting or to the soil or other growing medium supporting the plant. Regulators can also be used in bioreactor systems, regulation being achieved by a single addition of regulator formulation to the reaction medium or by gradual addition over a predetermined period of time.

The regulator is applied in an amount and over a time sufficient to effect the desired regulation. A preferred regulator is one which shows no, or only minimal phytotoxic or other deleterious effect on the plant, plant tissue or plant cells to which it is applied in the amount applied.

Preferred DNA sequences among those described above in Part D or E and preferred chimeric DNA sequences among those described above in Part F are in particular those wherein the transcription is regulated by a chemical regulator mentioned above, for example selected from the group consisting of benzoic acid, salicylic acid, acetylsalicylic acid, polyacrylic acid and substituted derivatives thereof, or selected from the group consisting of benzo-1,2,3-thiadiazolecarboxylic acid, benzo-1,2,3-thiadiazolethiocarboxylic acid, cyanobenzo-1,2,3-thiadiazole, benzo-1,2,3-thiadiazolecarboxylic acid amide, benzo-1,2,3-thiadiazolecarboxylic acid hydrazide, and derivatives thereof, or dichloroisonicotinic acid or a derivative thereof. Most preferred are those DNA sequences wherein the transcription is regulated by the mentioned preferred chemical regulators, for example by benzo-1,2,3-thiadiazole-7-carboxylic acid, methyl benzo-1,2,3-thiadiazole-7-carboxylate, n-propyl benzo-1,2,3-thiadiazole-7-carboxylate, benzyl benzo-1,2,3-thiadiazole-7-carboxylate, benzo-1,2,3-thiadiazole-7-carboxylic acid sec-butylhydrazide, 2,6-dichloroisonicotinic acid, or methyl 2,6-dichloroisonicotinate, in particular methyl benzo-1,2,3-thiadiazole-7-carboxylate.

N. Deposits with the ATCC and NRRC

The following deposits have been made with the American Type Culture Collection (ATCC), Rockville, Md.:

1) Plasmid pCGN783, ATCC number 67868, deposited Dec. 22, 1988.
2) Plasmid pCGN1540, ATCC number 40586, deposited Mar. 22, 1989.
3) Plasmid pCGN2113, ATCC number 40587, deposited Mar. 22, 1989.
4) Plasmid pCIB/SAR8.2a, ATCC number 40584, deposited Mar. 22, 1989.
5) Plasmid pCIB/SAR8.2b, ATCC number 40585, deposited Mar. 22, 1989.
6) Plasmid pBScht28, ATCC number 40588, deposited Mar. 24, 1989.
7) Plasmid pBSGL117, ATCC number 40691, deposited Oct. 19, 1989.
8) Plasmid pBSPER1, ATCC number 40686, deposited Oct. 19, 1989.
9) Plasmid pBSGL134, ATCC number 40690, deposited Oct. 19, 1989.
10) Plasmid pBSGL167, ATCC number 40834, deposited Jul. 3, 1990.
11) Phage lambda tobcDNAGL153, ATCC number 40694, deposited Oct. 19, 1989.
12) Phage lambda tobcDNAGL161, ATCC number 40695, deposited Oct. 19, 1989.
13) Plasmid pBSPERB24, ATCC number 40687, deposited Oct. 19, 1989.
14) Plasmid pBSPERB25, ATCC number 40688, deposited Oct. 19, 1989.
15) Plasmid pBSCL2, ATCC number 40835, deposited Jul. 3, 1990.
16) Plasmid pBSTCL226, ATCC number 40838, deposited Jul. 3, 1990.
17) Plasmid pBSPR-4a, ATCC number 75016, deposited Jun. 5, 1991.
18) Plasmid pBSPR-4b, ATCC number 75015, deposited Jun. 5, 1991.
19) Plasmid pAGL2, ATCC number 75048, deposited Jul. 12, 1991.
20) Plasmid pAPR1C-1, ATCC number 75049, deposited Jul. 12, 1991.
21) Plasmid pSLP1, ATCC number 75047, deposited Jul. 12, 1991.
22) Plasmid pATL12a, ATCC number 75050, deposited Jul. 12, 1991.
23) Plasmid pBSGL125, ATCC number 40692, deposited Oct. 19, 1989.
24) Plasmid pBSGL148, ATCC number 40689, deposited Oct. 19, 1989.
25) Plasmid pBSGL135, ATCC number 40685, deposited Oct. 19, 1989.

26) Phage lambda tobcDNAGL162, ATCC number 40693, deposited Oct. 19, 1989.
27) Plasmid pBSPER25, ATCC number 40692, deposited Oct. 19, 1989.
28) *E. coli* HB101/pTJS75-Km, ATCC number 67628, deposited Feb. 11, 1988.
29) Plasmid pBS-PR1013Cla, ATCC number 40426, deposited on Feb. 11, 1988.
30) Plasmid pBS-PR1019, ATCC number 40427, deposited on Feb. 11, 1988.
31) Zea mays suspension culture 6-2717-GC, ATCC number 40326, deposited on May 20, 1987.
32) Plasmid pBS-Gluc39.1, ATCC number 40526, deposited on Dec. 29, 1988.
33) Plasmid pBS-Gluc39.3, ATCC number 40527, deposited on Dec. 29, 1988.
34) Plasmid pBScucchi/chitinase, ATCC number 40528, deposited on Dec. 29, 1988.
35) Plasmid pBSGL6e, ATCC number 40535, deposited on Jan. 18, 1989.
36) Plasmid pCIB2001/BamChit, ATCC number 40940, deposited on Dec. 20, 1990.
37) Plasmid pBScucchrcht5, ATCC number 40941, deposited on Dec. 20, 1990.

The following deposits have been made with the Agricultural Research Culture Collection, International Depositing Authority, 1815 N. University Street, Peoria, Ill. 61604:
38) Plasmid pWCI-1, NRRL number NRRL-B21097, deposited on May 24, 1993.
39) Plasmid pWCI-2, NRRL number NRRL-B21098, deposited on May 24, 1993.
40) Plasmid pWCI-3, NRRL number NRRL-B21099, deposited on May 24, 1993.
41) Plasmid pWCI-4, NRRL number NRRL-B21100, deposited on May 24, 1993.
42) Plasmid pAtPR1-P, NRRL number NRRL B-21169, deposited on Jan. 5, 1994.

The deposits have been made in accordance with the Budapest Treaty. In addition, Applicants declare that all restrictions on the availability of the deposits to the public will be irrevocably removed upon the granting of a U.S. patent.

O. Summary of Experimental Protocols for Chemically Regulatable Sequences

The chimeric genes of the present invention contain chemically regulatable DNA sequences from any source, natural or synthetic, in combination with one or more transcribable DNA sequences; usually at least part of the transcribable sequence will be translated into a phenotypic trait, although the invention also embraces chimeric genes which operate through an anti-sense mechanism. While the following description and many of the examples are directed to chemically regulatable DNA sequences found naturally in a plant genome, this invention applies equally to such sequences which occur in other natural systems, for example, bacterial, viral and animal systems, since techniques are well known to isolate such sequences from their natural systems. Furthermore, sequences derived from synthetic or other non-natural systems are similarly embraced.

A chemically regulatable DNA sequence is isolated from the source in which it exists naturally or synthetically and, if necessary, characterized by conventional methods. If the DNA sequence is isolated from a naturally occurring gene, this gene is activated by an appropriate regulator, either by a chemical or other known regulator for the gene. RNA resulting from that activation is isolated and is used to construct a cDNA library. This library is used for differential screening using radiolabelled cDNA generated both from (1) RNA isolated from the activated system and (2) RNA isolated from a second system not activated by the regulator. This differential screening is a particular aspect of the present invention, as mentioned above. The clones containing the chemically regulated cDNA are then isolated and are preferably sequenced at this point. The cDNA clones are then used to identify and isolate a genomic clone from a genomic library which genomic clone comprises the chemically regulatable DNA sequence. This gene is preferably sequenced and the chemically regulatable DNA sequence is functionally mapped by subcloning fragments of this gene, ligating them to a reporter gene and evaluating their activity in transgenic plant material or in transient plant expression systems.

For the PR protein genes of tobacco a lambda genomic library is constructed using standard techniques, and clones comprising chemically regulatable DNA sequences are identified and purified. One of these clones is characterized. Restriction fragments carrying the chemically regulatable DNA sequence are identified; for the PR-1a gene these gene fragments include a ClaI fragment of about 20,000 base pairs, a 6500 base pair HindIII fragment, and a 3600 base pair EcoRI fragment. The HindIII fragment contains about 500 coding base pairs and about 6000 non-coding bases in the 5' flanking region adjacent to the transitional start site. Some of these fragments are subcloned into plasmids for use as sources of DNA for further subcloning and full characterization, i.e., restriction mapping, DNA sequencing and identification of the transcriptional start site of the gene. For the PR-1a gene the 3600 base pair EcoRI fragment is directly subcloned from a lambda genomic clone and subsequently subcloned to a final clone of about 1200 base pairs flanked by XhoI and PstI sites. This clone contains a chemically inducible DNA sequence from the PR-1a gene and a portion of the adjacent coding region for that gene; this portion includes the coding sequence for the signal peptide of the PR-1a protein gene.

Likewise genomic clones are isolated which code for the basic form of beta-1,3-glucanase. Two clones named 39.1 and 39.3 are characterized, and restriction fragments comprising chemically regulatable DNA sequences identified.

Using the vectors of this invention, these clones can then be used for the preparation of chimeric genes containing three parts as discussed previously. These chimeric DNA sequences contain the chemically regulatable sequence, part of the transcribable DNA and a third DNA sequence from a foreign source. Alternatively the clones can be further manipulated, e.g., by site directed mutagenesis, to remove all or most of any coding fragment from the parent gene prior to attachment to a coding sequence from a foreign source to prepare a two-part chimeric gene as described above. In a preferred embodiment that part of the chimeric gene which is not the chemically regulatable sequence constitutes a reporter gene for an easily observed or detected phenotypic trait. The following examples illustrate the genes for beta-1,3-glucuronidase, wild-type and herbicide resistant acetohydroxyacid synthase, and *Bacillus thuringiensis* endotoxin, but a variety of other reporter genes can be envisioned as described above. In a further preferred embodiment the coding component DNA sequence of the chimeric gene codes for tolerance or resistance to herbicides or for resistance to insects. This embodiment is exemplified by the mentioned genes for acetohydroxyacid synthase and for *Bacillus thuringiensis* endotoxin.

The chimeric genes and vectors containing these genes can be introduced into plant cells by a variety of techniques which give rise to transformed cells, tissue and plants or to cell cultures useful in bioreactors. Several techniques are described in detail in the examples which follow, directed to both monocotyledons and dicotyledons. Some of these methods, included here for enabling purposes, are the subject of other patent applications, in particular the U.S. patent application Ser. No. 056,506, filed May 29, 1987, now abandoned, and the U.S. patent application Ser. No. 165,665, filed Mar. 8, 1988, now abandoned (incorporated by reference herein in their entirety).

The transformed plant material can then be treated with a chemical regulator and the expression of the phenotypic reporter gene observed and/or measured. This kind of system provides an easy screening device to identify the regulatory activity of particular chemicals. The invention also concerns an improved assay of beta-1,3-glucuronidase (GUS) enzymatic activity which allows the screening of a large number of samples with high precision and in a short period of time. In particular this assay comprises reaction of plant tissue extracts in samples of less than 0.5 ml containing 1.5 to 3 mM 4-methyl umbelliferyl glucuronide at around 37° C. for 1 to 5 hours and determining the concentration of the fluorescent indicator released.

The quantitative determination of steady-state levels of RNA is an essential step in the analysis of gene expression. To that end a primer extension assay has been developed. This method of the invention involves labeling a gene specific oligonucleotide to high specific radioactivity, hybridizing the oligonucleotide to an RNA sample and extending the hybrid with reverse transcriptase. The extension products are separated on denaturing acrylamide gels and visualized by autoradiography. The benefits of this method over previous assays include ease of probe preparation, simplicity of the assay protocol and the time required to carry out the assay. This primer extension assay is as sensitive and quantitative as S1 mapping.

The primer extension assay as applied under the particular reaction conditions described below in the examples is optimized for the determination of the level of PR-1 mRNA in total RNA extracted from TMV infected tobacco leaves. The PR-1 mRNA is expressed as 1% of the mRNA in these leaves based on quantitative analysis of the primer extension data and the frequency of cDNA clones in a cDNA library derived from this RNA. The improvements of the method of the invention relative to those previously described comprise the labelling of the oligonucleotide to a high specific activity, the decreased molar amount of probe used in the assay (typically about 0.01 to 0.05 pmol), optimized hybridization and elongation time, and optimized nucleotide triphospsphate concentrations.

The invention therefore embraces a method for the determination of the amount of a specific RNA in a solution of RNA comprising
 (a) labeling a RNA specific primer oligonucleotide of a length of between 12 and 18 nucleotides to high specific radioactivity,
 (b) hybridizing the RNA with the labeled oligonucleotide at a concentration of between 0.1 and 20 nM for between 2 minutes and 24 hours at a temperature around 37° C.,
 (c) elongating the primer oligonucleotide with reverse transcriptase in the presence of nucleotide triphosphates at a concentration of between 0.003 and 1 mM for between 1 and 120 minutes, and
 (d) separating and visualizing the elongation products with autoradiography.

EXAMPLES

A. Introduction

The following examples further illustrate the present invention. They are in no way to be construed as a limitation in scope and meaning of the claims.

Enzyme reactions are conducted in accordance with the manufacturer's recommended procedures unless otherwise indicated. The chimeric genes and vectors of the present invention are constructed using techniques well known in the art. Suitable techniques have been described in Maniatis, T. et al., "Molecular Cloning", Cold Spring Harbor Laboratory, New York (1982); *Methods in Enzymology*, Volumes 68, 100, 101 and 118 (1979, 1983, 1983 and 1986, respectively); and "DNA Cloning", Glover, D. M. Ed. IRL Press, Oxford (1985). Medium compositions have been described in Miller, J. H., "Experiments in Molecular Genetics", Cold Spring Harbor Laboratory, New York (1972), as well as the references previously identified.

1. Media Used in the Examples

SH-0 medium: Medium of Schenk, R. U. et al., *Can. J. Bot.*, 50: 199–204 (1972); without hormones. SH medium can be liquid or solidified with 0.8% agar or with 0.5% GelRite$^R$. The medium is normally sterilized by heat in an autoclave at 230–250° F for 15–20 mins.

SH-30 medium: SH-0 medium containing 30 m Dicamba.

SH-45 medium: SH-0 medium containing 45 m Dicamba.

RY-2 medium: Medium of Yamada, Y. et al., *Plant Cell Reports*, 5: 85–88 (1986).

OMS medium: Medium of Murashige, T. and Skoog, F., *Physiologia Plantarum* 9: 473 (1968). The medium can be solidified with 0.8% agar or agarose or with 0.5% GelRite$^R$.

TABLE I

Macroelements[a], microelements[a] and Fe-EDTA are as given in the literature: KM medium according to Kao, K. N. et al., Planta 126: 105–110 (1965); N6 medium according to Chu et al., Scientia Sinica 18: 659 (1975).
Composition of Media Used

|  | KM-8p[b,c,d] | N6 |
|---|---|---|
| Organics and vitamins[e] [mg/l]: | | |
| biotin | 0.01 | |
| pyridoxine-HCl | 1.00 | 0.5 |
| thiamine-hcl | 10.00 | 0.1 |
| nicotinamide | 1.00 | |
| nicotinic acid | 0.10 | 0.5 |
| folic acid | 0.40 | |
| D-Ca-pantothenate | 1.00 | |
| p-aminobenzoic acid | 0.02 | |
| choline chloride | 1.00 | |
| riboflavin | 0.20 | |
| Vitamin B 12 | 0.02 | |
| glycine | 0.10 | 2.0 |
| Sugars and sugar alcohols [g/l]: | | |
| sucrose | 0.25 | 30.0 |
| glucose | 68.40 | |
| mannitol | 0.25 | |
| sorbitol | 0.25 | |
| cellobiose | 0.25 | |
| fructose | 0.25 | |
| mannose | 0.25 | |
| rhamnose | 0.25 | |
| ribose | 0.25 | |
| xylose | 0.25 | |
| myo-inositol | 0.10 | |

TABLE I-continued

Macroelements[a], microelements[a] and Fe-EDTA are as given in the literature: KM medium according to Kao, K. N. et al., Planta 126: 105–110 (1965); N6 medium according to Chu et al., Scientia Sinica 18: 659 (1975).
Composition of Media Used

| | KM-8p[b,c,d] | N6 |
|---|---|---|
| Final pH | 5.8 | 5.6 |
| Sterilization | filter | autoclaved |

Footnotes:
[a]Macroelements are usually made up as a 10 X concentrated stock solution, and microelements as a 1000 X concentrated stock solution.
[b]Citric, fumaric and malic acid (each 40 mg/l final concentration) and sodium pyruvate (20 mg/l final concentration) are prepared as a 100 X concentrated stock solution, adjusted to pH 6.5 with $NH_4OH$, and added to this medium.
[c]Adenine (0.1 mg/l final concentration), and guanine, thymidine, uracil, hypoxanthine and cytosine (each 0.03 mg/l final concentration) are prepared as a 1000 X concentrated stock solution, adjusted to pH 6.5 with $NH_4OH$, and added to this medium.
[d]The following amino acids are added to this medium using a 10 X stock solution (pH 6.5 with $NH_4OH$) to yield the given final concentrations: glutamine (5.6 mg/l), alanine, glutamic acid (each 0.6 mg/l), cysteine (0.2 mg/l), asparagine, aspartic acid, cystine, histidine, isoleucine, leucine, lysine, methionine, phenylalanine, proline, serine, threonine, tryptophan, tyrosine and valine (each 0.1 mg/l).
[e]Vitamin stock solution is normally prepared 100 X concentrated.

2. Materials Used in the Examples

Agarose: Preparation and purification of agarose are described by Guiseley and Renn, "The Agarose Monograph", Marine Colloids Division FMC Corp., 1975. Agarose is one of the constituents of agar. Commercially available agar normally consists of a mixture of neutral agarose and ionic agaropectin with a large number of side groups. Usually a certain number of of side chains remains intact and determines the physicochemical properties of the agarose such as gel formation and melting temperature. Low-melting agarose, especially SeaPlaque[R] agarose, is a preferred solidifying agent.

Casein hydrolysate: Casein Hydrolysate—Enzymatic Hydrolysate from bovine milk, Type 1, Sigma Co., PO. Box 14508, St. Louis, Mo. 63178, USA.

Cellulase RS: Cellulase RS, Yakult Honsha Co. Ltd., 1.1.19 Higashi-Shinbashi, Minato-ku, Tokyo, 105 Japan.

GelRite[R]: GelRite Gellan Gum, Scott Laboratories Inc., Fiskerville, R.I. 02823, USA.

GeneScreen plus[R]: Cat. No. NEF 976, NEN Research Products, 549 Albany St., Boston, Mass. 02118, USA.

IBI Random primer kit: 'Prime Time' random primer kit, International Biotechnologies Inc., PO. Box 1565, New Haven, Conn. 07606, USA.

Nalgene[R] filter: Nalge Co., Division of Sybron Corp. Rochester, N.Y. 14602, USA.

Pectolyase $Y_{23}$[R]: Seishin Pharmaceutical Co. Ltd., 4-13 Koami-cho, Nihonbashi, Tokyo, Japan.

Parafilm[R]: ParafilmR laboratory film—American Can Co. Greenwich, Conn. 06830, USA.

SSC: 1.54 mM NaCl, 0.154 mM sodium citrate.

Spin column: Sephadex[R] G25 prepacked column, Cat.No. 100402, Boehringer Mannheim Biochemicals, Piscataway, N.J., USA.

TAE buffer and TBE buffer: Tris-acetate buffer and Tris-borate buffer, respectively—common buffers for electrophoresis, see Maniatis et al., supra.

B. General Techniques

This group of examples describes general manipulations used to carry out the following detailed examples.

EXAMPLE 1

Ligation in Agarose

Following restriction digestion of plasmid DNA and electrophoretic separation of the fragments on a low melting TAE gel, the bands containing appropriate fragments are precisely excised and heated to 65° C. to melt the agarose. 2–5 l are added to 15 l water and the solution is left at 65° C. for 10 minutes. This solution is cooled to 37° C. and left for five minutes to equilibrate to temperature. 2 l of 10× ligase buffer (200 mM Tris, pH 8.0, 100 mM $MgCl_2$, 100 mM DTT, 10 mM ATP) are added along with 1 l T4 DNA ligase (New England BioLabs), and this solution is allowed to solidify and incubate at 15° C. overnight.

EXAMPLE 2

Transformation from Agarose

The agarose containing the appropriate DNA is melted by incubating at 65° C. for 10 minutes. 10 l of this solution are added to 30 l of TE buffer (10 mM Tris pH 7.5, 1 mM EDTA), mixed and allowed to stand at room temperature. Frozen competent cells (*E. coli* strain DH5) are placed on wet ice to thaw. The diluted DNA solution is added to 200 l of cells and allowed to stand on ice for 20 minutes. The cells containing the DNA are then heat-shocked for 90 seconds at 41° C. The cells are then left at room temperature for 10 minutes. 0.8 ml of SOC medium (Hanahan, D., *J. Mol. Biol.* 166: 557–580 (1983)) is added and the culture is incubated at 37° C. for one hour. 100 l of the culture is plated on LB plates (Miller, supra) containing 100 g/ml ampicillin (L-amp) and the plates are incubated overnight at 37° C. Positive colonies are picked and restreaked to a second L-amp plate and the plates are incubated overnight at 37° C.

EXAMPLE 3

Labelling DNA Restriction Fragments

DNA is treated with the appropriate restriction enzymes and fragments are separated by electrophoresis on a low-gelling temperature agarose gel. A band containing the fragment of interest is excised and the DNA purified by standard techniques. 50 ng of the DNA fragment is labelled ysing the IBI Random primer kit "Prime time" according to the manufacturers directions.

EXAMPLE 4

Southern Blotting 3 g of tobacco DNA is digested with various restriction enzymes under the conditions suggested by the supplier. The DNA is extracted with phenol, precipitated with ethanol and then resuspended in gel loading buffer (15% ficoll, 0.025% bromophenol blue, 10 mM EDTA, pH 8). Samples are loaded and electrophoresed on a 0.5% agarose gel at 5 V/cm until the bromophenol blue dye reaches the end of the gel. The DNA is transferred to Gene-Screen Plus (DuPont) using the alkaline transfer procedure as described by the supplier. Pre-hybridization, hybridization and washing are according to the manufacturer's recommendation. Hybridization is detected by autoradiography.

EXAMPLE 5

Molecular Adaptors

A typical molecular adaptor is the sequence 5'-GGGATCCCTGCA-3' (SEQ ID No. 47) for the conversion of a PstI site to a BamHI site. This molecule is synthesized on an Applied Biosystems Synthesizer using B-cyanoethylphosphoramidite chemistry and purified by reverse-phase HPLC. About 2 g of this oligonucleotide is kinased according to Maniatis et al., supra, p. 125. The oligonucleotide solution is heated to 65° C. in a water bath and allowed to cool to room temperature over a period of about 30 minutes. An approximately 10-fold molar excess of this annealed adapter is added to the digested DNA along with 10× ligase buffer, T4 DNA ligase, and an appropriate amount of water. A typical reaction is:

DNA to be adapted: 1–2 l (~1 pmol)

Adapter: 1 l (~10 pmol)

10× ligase buffer: 1 l

T4 DNA ligase: 1 l

Water: 5–6 l

This solution is incubated at 12–15° C. for 30 minutes, and heated to 65° C. for 30 minutes to inactivate the ligase. The salt concentration and volume are adjusted for the appropriate restriction digest and the adapted DNA is digested to expose the adapted "sticky end." Unincorporated adapters are removed either by electrophoresis on an agarose gel or by sequential isopropanol precipitations.

EXAMPLE 6

Primer Extension Mapping

A. Synthesis and 5' End Labeling of Primers for Primer Extension

The following primer oligomers are synthesized using an Applied Biosystems Synthesizer and β-cyanoethylphosphoramidite chemistry:

PR-1: 5'-ATAGTCTTGTTGAGAGTT-3' (SEQ ID No. 48)

GUS: 5'-TCACGGGTTGGGGTTTCTAC-3' (SEQ ID No. 49)

AHAS: 5'-AGGAGATGGTTTGGTGGA-3' (SEQ ID No. 50)

BT: 5'-ATACGTTCTACTATCATAGT-3' (SEQ ID No. 51)

The oligonucleotides are purified by reverse-phase high pressure liquid chromatography (HPLC). 5 pmol of each oligo is kinased (Maniafis, T. et al., supra, at p. 125) using 200 C of $^{32}$P-ATP (6000 Ci/mmol, 10 Ci/l). After incubation at 37° C. for 30 minutes, the reaction is diluted to 100 l, extracted with phenol/chloroform and then precipitated three times with 50 g carrier RNA. The final precipitate is resuspended in 1× reverse-transcriptase buffer (50 mM Tris-HCl, pH 7.5, 40 mM KCl, 3 mM MgCl$_2$) at a concentration of 2 nM. The specific activity of the labeled oligonucleotide is determined to be about 3×10$^6$ Cvcpm/pmol.

B. Total RNA Preparation

Total RNA is prepared essentially as described by Lagrimini, L. M. et al., *Proc. Natl. Acad. Sci. USA* 84: 7542 (1987). Tissue is ground under liquid nitrogen in a mortar and pestle. The ground tissue is added to grinding buffer (Lagrimini et al., supra) using 2.5 ml per gram tissue. An equal volume of phenol is then added and the emulsion is homogenized in a Brinkman polytron. A one-half volume of chloroform is added and the emulsion is gently mixed for 15 minutes. The phases are separated by centrifugation and the aqueous phase is removed. RNA is precipitated by the addition of sodium acetate to 0.3 M and 2.5 volumes ethanol. The precipitate is collected by centrifugation and resuspended in 2 ml sterile water. Lithium chloride is added to a final concentration of 3 M and left at 4° C. overnight. The precipitate is collected by centrifugation and the pellet is washed with ice-cold 80% ethanol. The pellet is dried and resuspended in 500 l sterile water. The concentration of this total RNA preparation is determined spectrophotometrically.

Alternatively, RNA is extracted from callus as described above except that the callus tissue is cut into cubes approximately 3 mm in size, and added to pre-chilled mortars and pestles for grinding in liquid nitrogen prior to the polytron step.

C. Primer Extension 50 g of total RNA is lyophilized in a 500 l Eppendorf tube. The RNA is resuspended in 30 l of radiolabeled probe solution and heated to 70' C. for 10 minutes. The tube is slowly cooled to 37° C. and allowed to incubate overnight. Without removing the tube from the 37° C. water bath, 2 l of 10× reverse-transcriptase buffer (500 mM Tris-HCl, pH 7.5, 400 mM KCl, 30 mM MgCl$_2$), 1 l 5 mg/ml bovine serum albumin, 5 l 100 mM dithiothreitol, 5 l 10× dNTPs (10 mM of each dNTP in H$_2$O), 3 l H$_2$O, 2 l RNasin (80 units), and 2 l reverse transcriptase (400 units) are added and the reaction is incubated at 37° C. for 30 minutes. To stop the reaction, 5 l of 3 M sodium acetate, pH 5, and 150 l absolute ethanol are added. The tube is left at −20° C. for 30 minutes, the precipitate is collected by centrifugation, washed with 80% ethanol and allowed to air-dry. The precipitate is resuspended in 10–20 l of loading dye (90% formamide, 0.05% bromophenol blue, 0.05% xylene cyanol, 1 mM EDTA) and the extension products are separated on a 6% sequencing gel (Maniatis, T. et al., supra). Extension products are visualized by autoradiography.

EXAMPLE 7

S1 Nuclease Mapping

The plasmid pBS-PR1013Cla is digested with SfaNI, dephosphorylated with calf intestinal phosphatase and kinased with $^{32}$P-ATP. Following phenol extraction and ethanol precipitation, the DNA is digested with BstEI and the 300 bp fragment from 750 to 1035 of FIG. 1 is isolated after electrophoresis on a low gelling temperature agarose gel. The probe is resuspended in formamide hybridization buffer (Berk, A. J. et al., Cell 12, 721 (1977)) at a concentration of about 2 nM. The specific activity of the probe is about 5×10 Cvcpm/pmol.

Lyophilized, total RNA (50 g) is dissolved in 30 l of the probe solution, and the tubes are heated to 65° C. for 10 minutes, then allowed to hybridize overnight at 48° C. S1 nuclease treatment and gel electrophoresis are essentially as described, using an S1 concentration of 400 units/mil and an incubation temperature of 30° C. The appropriate S1 nuclease concentration is determined in pilot experiments.

EXAMPLE 8

Mapping the Transcriptional Start Site

The transcriptional start site for the PR-1a gene is determined by a combination of S1 nuclease mapping and primer extension analysis. An autoradiogram of a primer extension experiment using either RNA isolated from TMV-infected leaves or an mp19 subclone of the XhoI-PstI fragment as a template and a 17 base oligonucleotide complementary to positions 1025 to 1042 of the PR-1a sequence as a specific primer is examined. The primer itself is labeled at the 5' phosphate, therefore the size of the extension product will be identical to the size of the corresponding band in the sequencing lanes. The appearance of two strong bands corresponding to positions 902 and 903 and a weak band at position 901 of the genomic clone suggests transcription initiating at either of these positions. However, primer extension analysis alone cannot be used to identify the 5' end of a mRNA. For instance, the mRNA may contain a 5' end that has been spliced from an upstream location.

To determine conclusively the 5' end, high resolution S1 nuclease mapping is used in conjunction with primer extension. An SfaNI fragment is labeled at the 5' end and digested with BstEII to yield a strand specific probe extending from position 759 to 1040. This probe is used to map the 5' end of PR-1a transcripts in RNA isolated from TMV-infected tobacco leaves. A major band of 137 ±2 bases is found which corresponds to positions 901 to 905 of the genomic clone. In high resolution S1 experiments, where the digestion products are electrophoresed along with a size standard of sequencing reactions performed on the probe, three bands are visualized corresponding to positions 901, 902 and 903. These results confirm the primer extension analysis and place the 5' end of the PR-1 mRNA at either position 901, 902 or 903. With regard to transcription initiation, one possible interpretation of these results is that RNA polymerase begins transcription at either base 901, 902 or 903 with more or less equal probability. However, since eukaryotic transcription favors initiation at an A, a more likely explanation for the apparent multiple 5' ends is that the PR-1a mRNA begins at position 903 (an A) and the PR-1b and -1c mRNAs begin each at one of the other positions on their corresponding genes.

C. Protein Identification and Characterization

The PR proteins relevant to these examples are isolated, purified and sequenced, for the first time in some cases and in accordance with literature procedures in other, for the purpose of allowing the isolation of the corresponding cDNA's and ultimately for confirming the identities of their cDNA's and chemically inducible genes.

EXAMPLE 9

General Techniques for Peptide Generation, Purification, and Automated Sequencing

A. Reduction and Alkylation

Purified, lyophilized protein is dissolved in 6 M guanidine-HCl containing 1 M Tris-HCl, pH 8.6, 10 mM EDTA. Dithiothreitol is added to 20 mM and 4-vinylpyridine is added to a final concentration of 50 mM. The sample is then incubated for 1.5 hours under nitrogen. The pyridylethylated material is desalted on HPLC using an Aquapore phenyl column (2.1×10 cm, Brownlee). The column is eluted with a linear, 5–80% gradient of acetonitrile/isopropanol (1:1) in 0.1% trifluoroacetic acid (TFA).

B Cyanogen Bromide Cleavage and Removal of Pyroglutamate

Cyanogen bromide cleavage is performed in situ according to Simpson, R. J. et al., *Biochem. Intl.* 8: 787 (1984). Digestion of PR-1 protein with pyroglutamate aminopeptidase (Boehringer Mannheim) is carried out according to Allen, G., *Plant Sci. Lett.* 26: 173 (1982).

C. LysC digestion

Protein is digested with endoproteinase Lys-C (Boehringer Mannheim) in 0.1 M Tris-HCl, pH 8.5, for 24 hours at room temperature using an enzyme:substrate ratio of 1:10. Resulting peptides are isolated by HPLC using an Aquapore C-8 column (1×22 cm, Brownlee) eluted with a linear acetonitrile/isopropanol (1:1 ratio) gradient (0 to 60%) in 0.1% TFA.

D. Trypsin Digestion

Digestion with trypsin (Cooper) is performed in 0.1 M ammonium bicarbonate, pH 8.2, containing 0.1 M calcium chloride for five hours at 37° C. using an enzyme:substrate ratio of 1:100. Peptides generated are separated on HPLC using the same conditions as with the Lys-C peptides or performed in 0.1 M Tris-HCl pH 8.5 for 24 hours at 37° C. using an enzyme to substrate ratio of 1:50. Peptides are isolated by HPLC using a Vydac C-18 column (2.1×150 mm) with a linear 0 to 60% acetonitrile:isopropanol (1:1) gradient in 0.1% TFA.

E. Sequencing

Automated Edman degradations are performed with an Applied Biosystems 470A gas-phase sequencer. Phenylthiohydantoin (PTH) amino acids are identified using an Applied Biosystems 120A PTH analyzer.

EXAMPLE 10

Purification of PR-1a and PR-1b Protein

Plants of *Nicotiana tabaccum* cv. Xanthi are grown in a glasshouse and infected when eight weeks old by gently rubbing the leaves with a suspension of a common strain (UI) of TMV (0.5 g/ml). Leaves are harvested seven days after infection and the intracellular fluid (ICF) is washed out of the leaves and collected according to Parent, J. G. et al., *Can. J. Bot.* 62: 564 (1984). 250 ml of ICF are concentrated to 50 ml by lyophilization and loaded on an Ultragel ACA54 column equilibrated with Tris-HCl, pH 8.0, and 1 mM EDTA. Eluates are analyzed by electrophoresis on 10% polyacrylamide gels. Fractions containing PR-1 proteins are pooled, lyophilized, resuspended in 3 ml water and then dialyzed overnight against water. This preparation is further purified by HPLC anion exchange chromatography on a TSK-DEAE 5PN column. The column is eluted with a 0–0.6 M NaCl gradient in 50 mM Tris-HCl, pH 8.0, 1 mM EDTA. Fractions are analyzed by polyacrylamide gel electrophoresis (PAGE). PR-1b elutes first from the column at 0.18 M NaCl and PR-1a elutes at 0.28 M NaCl. Fractions containing each protein are pooled, dialyzed against water and lyophilized. The purity of the PR-1a and PR-1b protein preparation is confirmed by reverse-phase HPLC using an Aquapore phenyl column (2.1×100 mm, Brownlee) and eluting with a linear acetonitrile/isopropanol (1:1) gradient (5–80%) in 0.1% TFA.

EXAMPLE 11

Protein Sequence Determination

Purified, lyophilized PR-1a protein is dissolved in 6 M guanidine-HCl containing 1 M Tris-HCl, pH 8.6, 10 mM EDTA. Dithiothreitol is added to 20 mM and 4-vinylpyridine is added to a final concentration of 50 mM. The sample is then incubated for 1.5 hours under nitrogen. The pyridylethylated material is desalted on HPLC using an Aquapore phenyl column (2.1×10 cm, Brownlee). The column is eluted with a linear, 5–80% gradient of acetonitrile/isopropanol (1:1) in 0.1% trifluoroacetic acid (TFA).

Automated Edman degradations are performed with an Applied Biosystems 470A gas-phase sequencer. Phenylthiohydantoin (PTH) amino acids are identified by an Applied Biosystems 120A PTH analyzer.

Cyanogen bromide cleavage is performed in situ according to Simpson, R. J. et al., *Biochem. Intl.* 8: 787 (1984). Digestion of PR-1 with pyroglutamate aminopeptidase (Boehringer Mannheim) is carried out according to Allen, G., *Plant Sci. Lett.* 26: 173 (1982).

PR-1a is digested with endoproteinase Lys-C (Boehringer Mannheim) in 0.1 M Tris-HCl, pH 8.5, for 24 hours at room temperature using an enzyme to substrate ratio of 1:10. Peptides are isolated by HPLC using an Aquapore C-8 column (1×22 cm, Brownlee) by a linear acetonitrile/isopropanol (1:1 ratio) gradient (0 to 60%) in 0.1% TFA.

Digestion of the N-terminal Lys-C peptide with trypsin (Cooper) is performed in 0.1 M ammonium bicarbonate, pH 8.2, containing 0.1 M calcium chloride for five hours at 37° C. using an enzyme to substrate ratio of 1:100. The two peptides generated are separated on HPLC using the same conditions as with the Lys-C peptides.

EXAMPLE 12

Purification and Sequence of PR-1a and PR-1b Protein

A correlation of the DNA sequence of three cDNA clones with the PR-1a, -1b and -1c proteins is originally made by Cornelissen, B. J. C. et al., supra, based on a comparison of the published protein sequence data of three peptides derived from PR-1a (Lucas, J. et al., *EMBO J.* 4: 2745 (1985)) and the primary structure of the protein deduced from the cDNA clones. However, the cDNA clone designated as PR-1a is truncated at the 5' end and can be compared to only two of the three peptides with a mismatch of one residue. The encoded amino acid sequence deduced from cDNA as prepared and analyzed in the example below, and the PR-1a cDNA sequence from Pfitzner, U. M. et al., supra, mismatch the published protein sequence at the tryptophan residue as reported. They also do not match at three other positions of the amino-terminal protein sequence. This anomaly places the previous identification of the PR-1 clones in question.

In order to confirm the identity of our cDNA clones as either PR-1a, PR-1b or PR-1c, a large portion of the primary structure of the purified PR-1a and PR-1b protein and peptides derived from the proteins is determined by amino acid sequencing. This data is then compared to the protein sequence deduced from the nucleotide sequence of the cDNA's in order to identify which of the cDNA clones corresponds to which protein. Plants of *Nicotiana tabacum* cv. Xanthi are grown in a glasshouse and when eight weeks old are infected by gently rubbing the leaves with a suspension of a common strain (UI) of TMV (0.5 g/ml). Leaves are harvested seven days after infection and the intracellular fluid (ICF) is washed out of the leaves and collected according to Parent, J. G. et al., *Can. J. Bot.* 62: 564 (1984). 250 ml of ICF are concentrated to 50 ml by lyophilization and loaded on an Ultragel ACA54 column equilibrated with Tris-HCl, pH 8.0, and 1 mM EDTA. Eluates of this column are analyzed by electrophoresis on 10% native polyacrylaride gels. Fractions containing PR-1 proteins are pooled, lyophilized, resuspended in 3 ml water and then dialyzed overnight against water. This preparation is further purified by HPLC anion exchange chromatography on a TSK-DEAE 5PN column. The column is eluted with a 0–0.6 M NaCl gradient in 50 mM Tris-HCl, pH 8.0, 1 mM EDTA. Fractions are analyzed by polyacrylamide gel electrophoresis (PAGE).

PR-1b elutes first from the column at 0.18 M NaCl and PR-1a elutes at 0.28 M NaCl. Fractions containing each protein are pooled, dialyzed against water and lyophilized. The purity of the PR-1a and PR-1b protein preparation is confirmed by reverse-phase HPLC using an Aquapore phenyl column (2.1×100 mm, Brownlee) and eluting with a linear acetonitrile/isopropanol (1:1) gradient (5–80%) in 0.1% TFA.

Protein sequence is derived from either the deblocked amino terminus of the intact protein, from peptides derived from cyanogen bromide cleavage of the proteins, from peptides derived from LysC digestion of the proteins or from peptides derived from trypsin digestion of the protein using techniques detailed above or using other methods known in the art. Using standard techniques, the amino acid sequence of several peptides derived from either PR-1a or PR-1b was determined.

EXAMPLE 13

Purification and Sequence of PR-R Major and PR-R Minor

Plants of *Nicotiana tabacum* cv. Xanthi are grown in a glasshouse and infected when eight weeks old by gently rubbing the leaves with a suspension of a common strain (U1) of TMV (0.5 g/ml). Leaves are harvested seven days after infection and the intracellular fluid (ICF) is washed out of the leaves and collected according to Parent, J. G. et al., *Can. J. Bot.* 62: 564 (1984). 250 ml of ICF are concentrated to 50 ml by lyophilization and loaded on an Ultragel ACA54 column equilibrated with Tris-HCl, pH 8.0, and 1 mM EDTA. Eluates are analyzed by electrophoresis on 10% polyacrylamide gels. Fractions containing the PR-R protein and several minor contaminating proteins are pooled, lyophilized, resuspended in 3 ml water and then dialyzed overnight against water. This preparation is further purified by HPLC reverse phase chromatography using a Brownlee Aquapore phenyl column (2.1×100 mm). The column is eluted with a linear gradient of 20 to 80% acetonitrile:isopropanol (1:1) in 0.1% trifluoroacetic acid using a flow rate of 50 l/minute over 80 minutes. It is found that the major proteins present are isoforms of PR-R which are given the names PR-R major, for the most abundant protein eluting at 46 minutes and PR-R minor for the less abundant protein eluting at 47.5 minutes. The peaks containing PR-R major and PR-R minor are collected and the samples are reduced to dryness. The proteins are then resuspended in 6M guanidine-HCl, 1M Tris-HCl, reduced and alkylated as described above and subjected to automated sequencing as described above.

A summary of the data obtained is presented below.

PR-R Major: ATFDIVNKCTYTVWAAASPGGGRR (SEQ ID No. 52)

PR-R Minor: ATFDIVNQCTYTVWAAASPGGGRQLN (SEQ ID No. 53)

EXAMPLE 14

Purification and Sequence of PR-P and PR-Q

Plants of *Nicotiana tabacum* cv. Xanthi are grown in a glasshouse and infected when eight weeks old by gently rubbing the leaves with a suspension of a common strain (UI) of TMV (0.5 g/ml). Leaves are harvested seven days after infection and the intracellular fluid (ICF) is washed out of the leaves and collected according to Parent, J. G. et al., *Can. J. Bot.* 62: 564 (1984). 250 ml of ICF are concentrated to 50 ml by lyophilization and loaded on an Ultragel ACA54 column equilibrated with Tris-HCl, pH 8.0, and 1 mM EDTA. Eluates are analyzed by electrophoresis on 10% polyacrylamide gels. Fractions from the Ultragel ACA54 chromatography containing PR-O, PR-P, PR-Q and PR-R are pooled and concentrated by lyophilization. The proteins are further purified by polyacrylamide gel electrophoresis followed by electroblotting onto PVDF membrane (Matsudaira, P., 1987, *J. Biol. Chem.* 261: 10035–10038). The blotted protein bands containing PR-P and PR-Q are excised and treated with 0.5% PVP-40 in 100 mM acetic acid according to the Applied Biosystems User Bulletin No. 36, Mar. 21, 1988. Deblocking of the protein is carried out with pyroglutamate aminopeptidase as described and the protein is sequenced from the PVDF by automated Edman degradation as described above.

The sequences of the amino terminus of the PR-P and PR-Q proteins are described below.

To obtain protein sequence from peptides derived from PR-P and PR-Q, the fractions from the Ultragel column, which contain PR-proteins, are pooled, lyophilized, dissolved in water and then dialyzed against water prior to chromatography on DEAE-Sephacel. The DEAE-Sephacel column is equilibrated with 50 mM Tris-HCl (pH 8.0), 1 mM EDTA and eluted with a linear, 0 to 0.4 M gradient of sodium chloride. Fraction 6, which contains a mixture of PR-R major, PR-R minor, PR-P, PR-Q, PR-O and several minor contaminants is lyophilized and then resuspended in distilled water.

The proteins from Fraction 6 are further purified by HPLC using a reverse phase phenyl column and eluted with a linear 20–80% gradient of acetonitrile:isopropyl alcohol (1:1) in 0.1% trifluoroacetic acid (TFA). PR-P and PR-Q proteins co-eluted as a single peak which is collected and concentrated almost to dryness in vacuo, resuspended in 10 mM ammonium acetate, pH 7.0 and applied to a Brownlee Labs AX-300 HPLC ion-exchange column (2.1 mm×10 cm) equilibrated in 10 mM ammonium acetate (pH7.0). The proteins are eluted from this column using a linear gradient of 10 to 250 mM ammonium acetate (pH 7.0). PR-P and PR-Q elute as single distinct peaks at ca. 75 mM and ca. 95 mM ammonium acetate, respectively. The protein is resuspended in 6M guanidine-HCl, 1M Tris-HCl and reduced and alkylated as described above. Peptides are generated by trypsin digestion, separated and sequenced as described above.

EXAMPLE 16

Purification and Protein Sequence of PR-2, PR-N and PR-O

Plants of *Nicotiana tabacum* cv. Xanthi.nc are grown in a glasshouse and infected when eight weeks old by gently rubbing the leaves with a suspension of of a common strain (U1) of TMV (0.5 g/ml). Leaves are harvested seven days after infection and the intercellular fluid (ICF) is washed out of the leaves and collected according to Parent, J. G. et al., *Can. J. Bot.* 62: 564 (1984). 250 ml of ICF are concentrated to 50 ml by lyophilization and loaded on an Ultragel ACA54 column equilibrated with Tris-HCL, pH 8.0 and 1 mM EDTA. Eluates are analyzed by electrophoresis on 10% polyacrylamide gels. Fractions containing PR-proteins as determined by gel electrophoresis are pooled, lyophilized, dissolved in water and dialyzed against water prior to chromatography on DEAE-Sephacel. The DEAE-Sephacel column is equilibrated with 50 mM Tris-HCl (pH 8.0), 1 mM EDTA and eluted with a linear 0 to 0.4 M gradient of sodium chloride. Fraction 6, which contains a mixture of PR-Rmajor, PR-Rminor, PR-P, PR-Q, PR-O and several minor contaminants, is lyophilized. Fraction 3, which contains a mixture of PR-2, PR-N and several minor contaminants, is also collected separately and concentrated by lyophilization.

PR-O is further purified from other Fraction 6 proteins by first resuspending Fraction 6 in 2 mls water and then separating the proteins by HPLC reverse phase chromatography using a Vydac phenyl column (4.6×250 mm). Proteins are eluted using a linear 20–80% gradient of acetonitrile:isopropanol (1:1) in 0.1% triflouroacetic acid. The results of this purification step reveal that the mixture contained at least nine proteins. One of these proteins, eluting in one run at 51 minutes is PR-O as determined by gel electrophoresis. The peak containing PR-O is collected and concentrated by lyophilization. The protein is resuspended in 6 M guanidine-HCl, 1M Tris-HCl and reduced and alkylated as described above. Peptides are generated by trypsin and LysC digestion and are purified as described above. Protein sequence is determined as described in Example 9, above. A summary of the sequencing data is provided below.

The proteins PR-2 and PR-N are purified from Fraction 3 using a Brownlee Aquapore AX-300 (2.1×100 mm) anion exchange column. The proteins are eluted from the column using a linear gradient of 10 mM to 350 mM ammonium acetate pH 7.0. PR-N eluted at 37.5 minutes and PR-2 eluted at 50.0 minutes as single, uniform peaks. The identity of the proteins is confirmed by gel electrophoresis. The proteins are collected, concentrated by lyophilization and then reduced and alkylated as described above. Peptides are generated by trypsin digestion, purified and sequenced as described in Example 9 above.

EXAMPLE 17

Purification and Sequencing of PR4

Plants of *Nicotiana tabacum* cv. Xanthi.nc are grown in a glasshouse and infected when eight weeks old by gently rubbing the leaves with a suspension of a common strain (U1) of TMV (0.5 g/ml). Leaves are harvested seven days after infection and the intercellular fluid (ICF) is washed out of the leaves and collected according to Parent et al., *Can. J. Bot.*, 62: 564 (1984). 250 ml of ICF is concentrated to 50 ml by lyophilization and loaded on an Ultragel ACA54 column equilibrated with Tris-HCl, pH 8.0 and 1 mM EDTA. Eluates are analyzed by electrophoresis on 10% polyacrylamide gels. Fractions containing PR-proteins as determined by gel electrophoresis are pooled, lyophilized, dissolved in water and dialyzed against water prior to chromatography on DEAE-Sephacel. The DEAE-Sephacel column is equilibrated with 50 mM Tris-HCl (pH 8.0), 1 mM EDTA, and eluted with a linear 0 to 0.4 M gradient of sodium chloride. Fraction 5, which contains PR-4 and several minor contaminants, is lyophilized.

PR-4 is further purified from other Fraction 5 proteins by first resuspending Fraction 5 in 2 mls water and then separating the proteins by HPLC reverse phase chromatography using a Vydac phenyl column (4.6×250 mm). Proteins are eluted using a linear 20–80% gradient of acetonitrile:isopropanol (1:1) in 0.1% trifluoroacetic acid. A peak eluting at approximately 24 minutes is determined by gel electrophoresis to contain PR-4 protein. This peak is collected and lyophilized and resuspended in 0.1 M Tris-HCl, pH 8.0. The protein is digested with trypsin for 48 hours at 30° C., then incubated with 3 M guanidine-HCl, 1 M Tris-HCl, and 20 mM dithiothreitol for 30 minutes at room temperature. (The protein is not reduced and pyridylethylated prior to digestion.) Tryptic peptides are purified and sequenced as described above.

Alternatively, PR-4 is purified by directly fractionating ICF on the Vydac phenyl reverse phase column as described above. PR-4 co-elutes with PR-1a, b, and c. This fraction is concentrated almost to dryness under vacuum, and resuspended in 10 mM ammonium acetate (pH 7.0). PR-4 is separated from PR-1 isoforms on a Brownlee Labs AX-300 HPLC ion exchange column (2.1 mm×10 cm), equilibrated with 10 mM ammonium acetate (pH 7.0). PR-4 is not retained on the column, while PR-1a, b, and c did bind. The purified PR-4 is incubated in 6 M guanidine-HCl, 1 M Tris-HCl (pH 8.6), 10 mM EDTA, 20 mM dithiothreitol for 1 hour at 37° C. 4-vinyl pyridine is added and the incubation continued at room temperature for 1 hour. The modified protein is desalted on a Brownlee labs PH-300 column with a linear gradient of 0–80% acetonitrile:isopropanol in 0.1% trifluoroacetic acid. Digestion with endoprotease Asp-N is carried out in 0/1 M Tris-HCl pH 8.0 for 4.5 hours at room temperature. Peptides are purified and sequenced as described above.

EXAMPLE 18

Purification and Protein Sequence of Cucumber Chilinase/Lysozyme

A pathogen-inducible chitinase protein is isolated from infected cucumber leaves as described (Metraux, J. P. et al., *Physiological and Molecular Plant Pathology*, 33: 1–9 (1988)). Peptides are generated from this homogeneous protein preparation and sequenced essentially as described above.

EXAMPLE 19

Purification and Protein Sequence of the Cucumber Peroxidase

The pathogen-induced, acidic, cucumber peroxidase protein is purified as described by Smith, J. A., Ph. D. Thesis, Department of Botany and Plant Pathology, Michigan State University, Lansing, Mich. (1988), from the uninfected leaves of cucumber plants that had been infected seven days previously with a spore suspension of *Colletotrichum lagenarium*. The purified protein is reduced and alkylated and amino acid sequence from the amino terminus and from peptides derived from either LysC or trypsin digestion is determined as described in Example 9 above.

D. Production of Clones Related to Chemically Regulated Sequences

This group of examples describes clones prepared as a result of gene isolation and identification of the chemically regulatable sequences and chimeric genes containing those sequences.

EXAMPLE 20

Preparation of tobchrPR1013

Nuclei are isolated from leaves of *Nicotiana tabaccum* by first freezing 35 grams of the tissue in liquid nitrogen and grinding to a fine powder with a mortar and pestle. The powder is added to 250 ml of grinding buffer (0.3 M sucrose, 50 mM Tris, pH 8, 5 mM magnesium chloride, 5 mM sodium bisulfite, 0.5% NP40) and stirred on ice for 10 minutes. This mixture is filtered through six layers of cheesecloth, and the liquid is transferred to centrifuge bottles and subjected to centrifugation at 700×g for 10 minutes. The pellets are resuspended in grinding buffer and recentrifuged. The pellets are again resuspended in grinding buffer and recentrifuged. The pellets are again resuspended in grinding buffer and this suspension is layered over a 20 ml cold sucrose cushion containing 10 mM Tris, pH 8, 1.5 mM magnesium chloride, 140 mM sodium chloride, 24% sucrose, 1% NP40. These tubes are centrifuged at 17,000×g for 10 minutes. The pellets at this stage contain mostly nuclei and starch granules. High molecular weight DNA is isolated from the nuclei essentially according to Maniatis, T. et al., supra. The DNA is partially digested with MboI and ligated into the BamHI site of the EMBL3 cloning vector. Approximately 300,000 plaques are screened with a labeled PR-1b cDNA probe. Fifty positive clones are isolated and characterized. Positive plaques are purified and characterized by restriction analysis. These clones are classified into eight distinct groups by restriction mapping. One of the clones is identified as tobchrPR1013. A partial restriction map of tobchrPR1013 is shown in FIG. 1. Isolation of DNA and DNA manipulations are essentially as described by Maniatis, T. et al., supra.

EXAMPLE 21

Preparation of pBS-PR1013Cla

Figure 2:
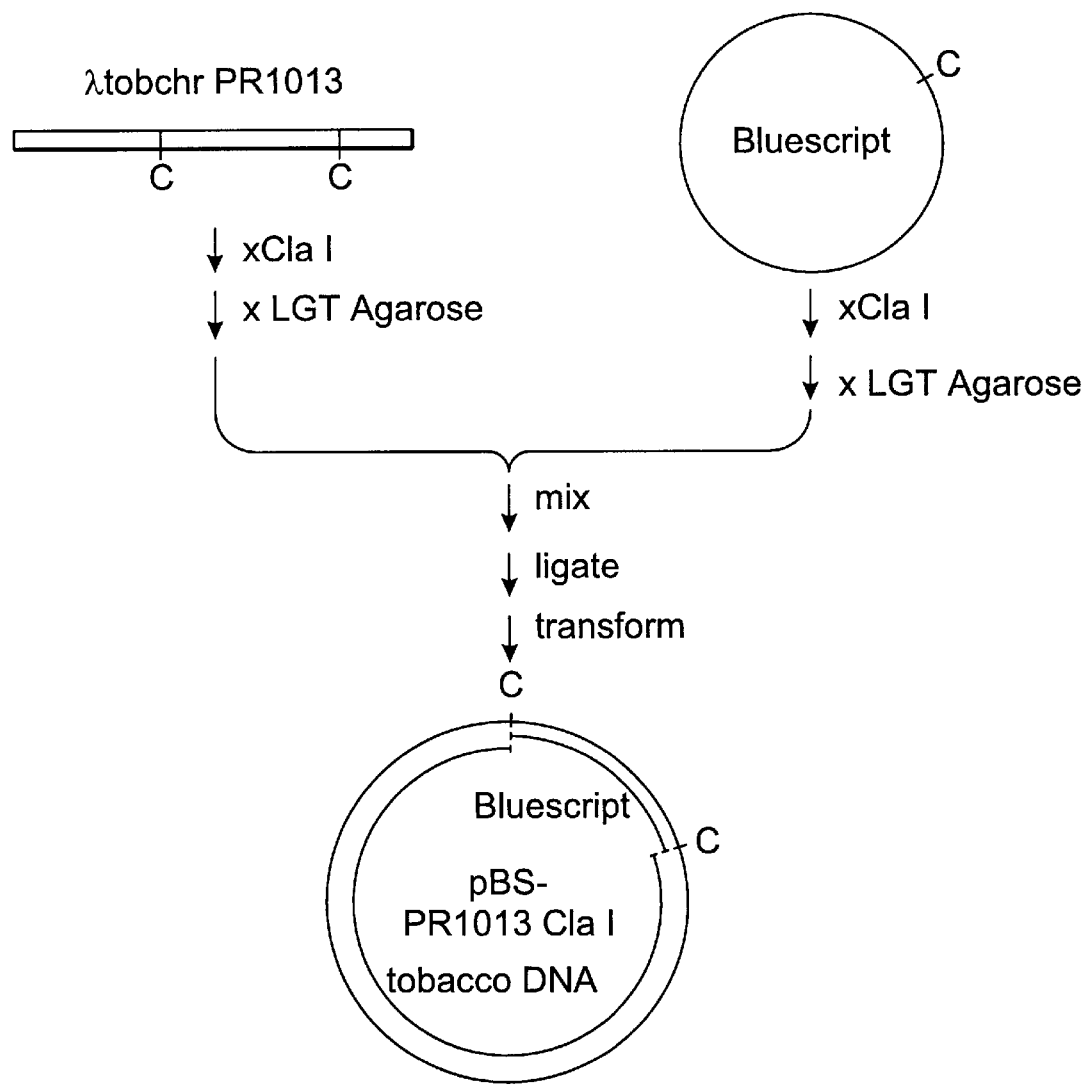
FIG. 2. The construction of pBS-PR1013Cla from lambda tobchrPR1013 is shown. The 19 kb DNA fragment between the two ClaI sites was subcloned into the bluescript plasmid. C=ClaI, LGT agarose=low-gelling temperature agarose.

A ClaI fragment from the clone tobchrPR1013 is subcloned into the Bluescript plasmid (Stratagene Cloning Systems), resulting in pBS-PR1013Cla (see FIG. 2). The 2 kb XhoI-BglII fragment from pBS-PR1013Cla is sequenced and positions 913 to 1711 (see SEQ ID No. 1) are found to match perfectly the sequence of a cDNA clone clone for PR-1a isolated by Pfitzner, U. M. et al., supra. Possible rearrangements of the tobacco DNA during the cloning procedure are ruled out by analyzing predicted restriction fragments from genomic DNA. Based on sequence information and a restriction map of pBS-PR1013Cla, digestion of genomic tobacco DNA with either EcoRI, HindIII, XhoI+BglII, or HindIII+PstI should generate fragments of 3.2 kb, 6.7 kb, 2.0 kb or 6.4 kb, respectively, which contain the PR-1a gene. To test this prediction, 3 g of tobacco chromosomal DNA is digested with the appropriate enzymes and electrophoresed on a 0.7% agarose gel. The DNA is transferred to a nylon membrane and probed with a labeled XhoI-BstEII restriction fragment from the PR-1a gene. As a control, pBS-PR1013Cla DNA is digested and electrophoresed on the same gel. As predicted, the EcoRI, HindIII, XhoI+BglII, and HindIII+PstI digests produce bands of the expected molecular weight which comigrate with the control bands. Therefore, the DNA contained in the tobchrPR1013 clone represents a contiguous piece of DNA in the tobacco genome.

EXAMPLE 22

Preparation of pBS-PR1013Eco

Figure 3:
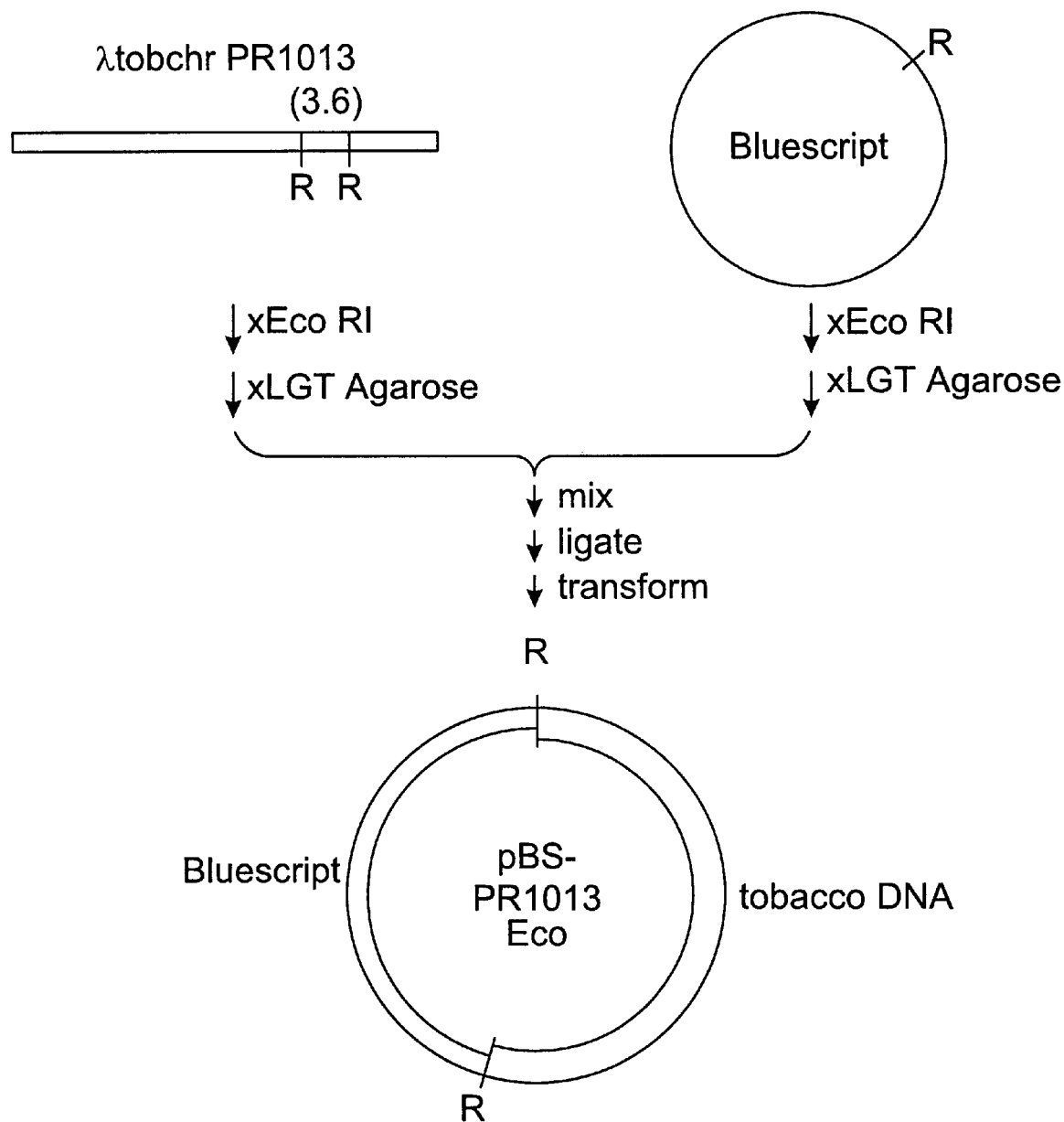
FIG. 3. The construction of pBS-PR1013Eco from lambda tobchrPR1013 is depicted. The 3.6 kb EcoRI fragment containing the PR-1A gene from lambda tobchrPR1013 is subcloned into Bluescript. R=EcoRI, LGT agarose=low-gelling temperature agarose.

A. The plasmid pBS-PR1013Eco is constructed by subcloning the 3.6 kb EcoRI fragment containing the PR-1a gene from tobchrPR1013 (Example 11) into the unique EcoRI site of the bluescript plasmid. Bluescript plasmid (catalog no. 21203) is obtained from Stratagene Cloning Systems, La Jolla, Calif. The structure of pBS-PR1013Eco is confirmed by both restriction mapping and DNA sequencing. This construction of the plasmid is shown in FIG. 3.

Figure 4:
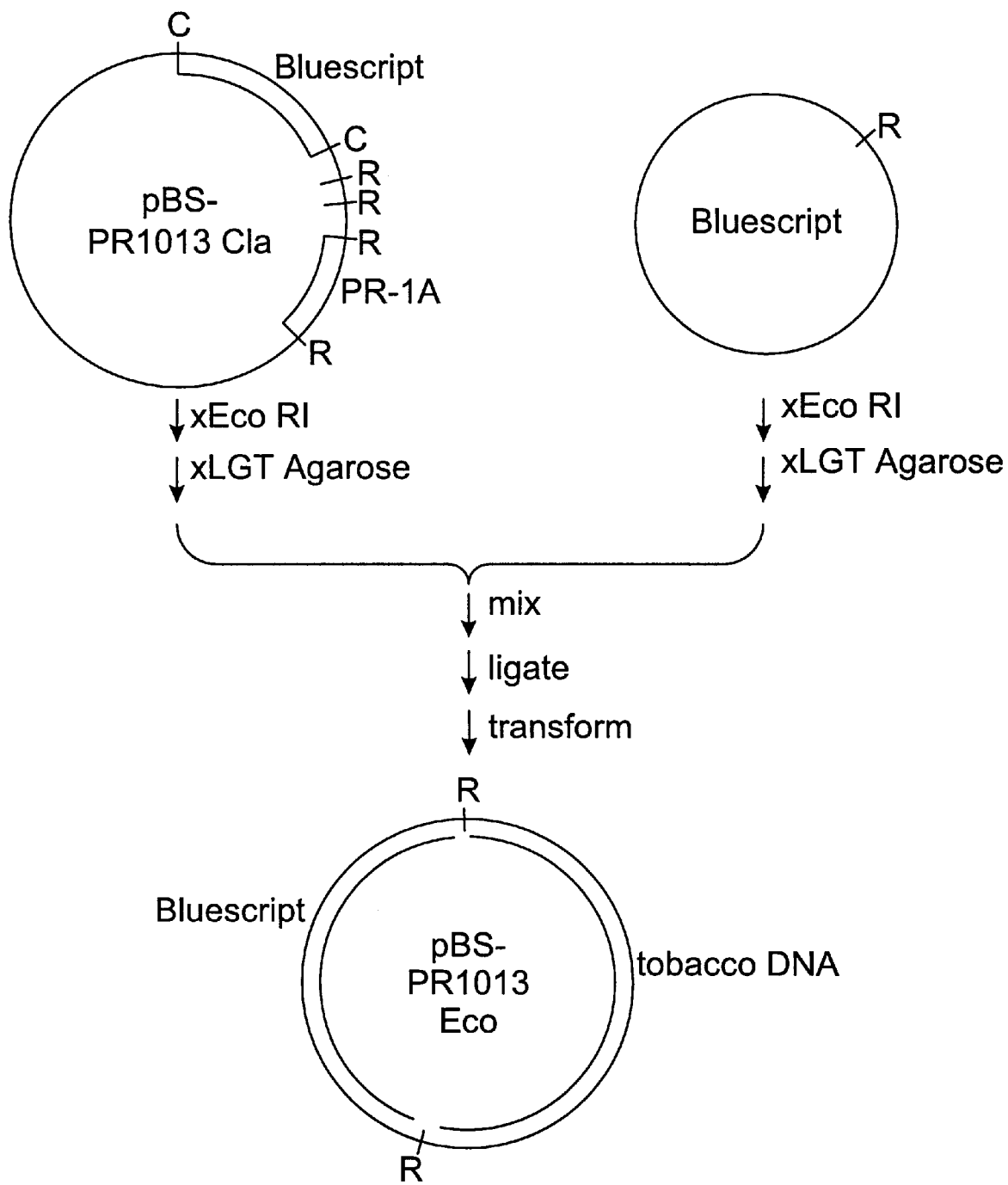
FIG. 4. The construction of pBS-PR1013Eco from pBS-PR1013Cla is shown. The 3.6 kb EcoRI fragment containing the PR-1a gene is subcloned into the EcoRI site of the bluescript plasmid, C=ClaI, R=EcoRI, LGT=low-gelling temperature agarose.

B. Alternatively, the plasmid pBS-PR1013Cla is digested with EcoRI and the 3.6 kb fragment containing the PR-1a gene is isolated. The pBluescript is digested with EcoRI, mixed with and ligated to the previously isolated 3.6 kb EcoRI fragment. This construction of the plasmid is shown in FIG. 4.

EXAMPLE 23

Preparation of pBS-PR1013Eco Pst

Figure 5:
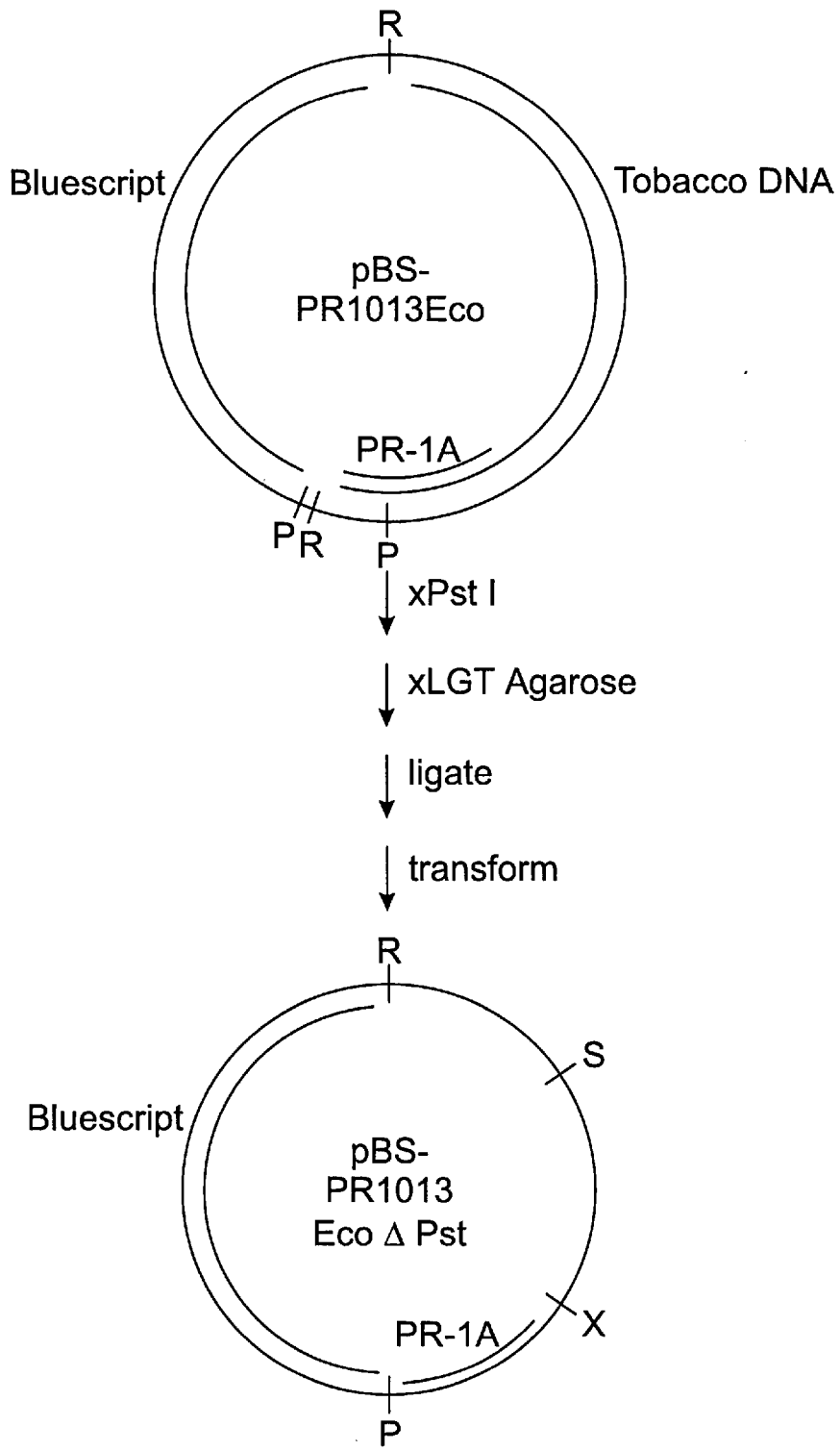
FIG. 5. The construction of pBS-PR1013Eco Pst from pBS-PR1013Eco is shown. The 600 bp PstI fragment is deleted from pBS-PR1013Eco. P=PstI, R=EcoRI, X=XhoI, S=SalI, LGT agarose=low-gelling temperature agarose.

The plasmid pBS-PR1013Eco is digested with PstI and the DNA fragments separated on a 2.5% low-gelling temperature agarose gel. The large fragment containing the bluescript vector and a 3.0 kb fragment of the tobacco DNA are precisely excised and heated to 65° C. to melt the agarose. One of these plasmids is selected as the plasmid pBS-PR1013Eco Pst. The structure of this subclone is verified by sequence analysis. The construction of this plasmid is shown in FIG. 5.

EXAMPLE 24

Preparation of pBS-PR1013Eco Pst Xho

Figure 6:
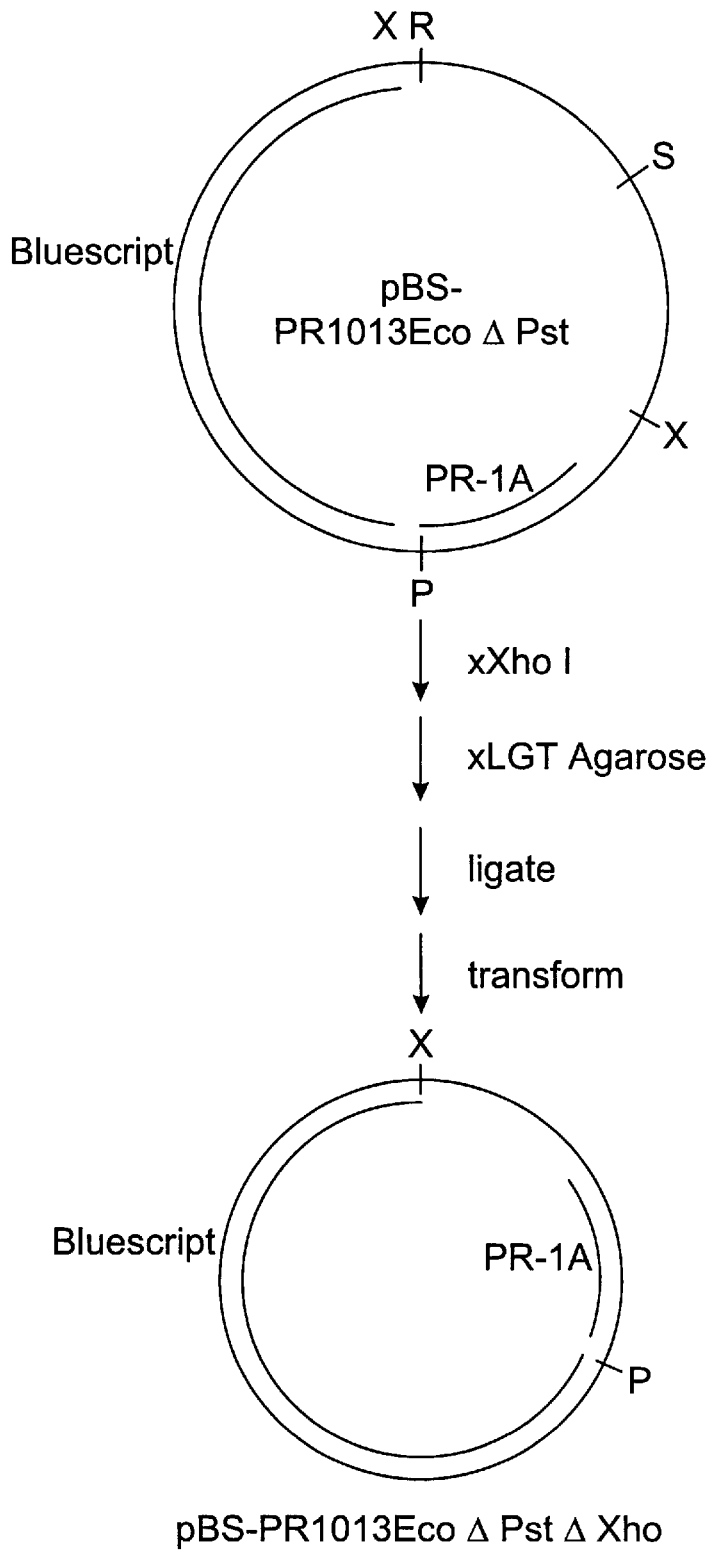
FIG. 6. The construction of pBS-PR1013Eco Pst Xho from pBS-PR1013Eco Pst is shown. The 2 kb XhoI fragment is deleted from the plasmid pBS-PR1013Eco Pst. R=EcoRI, P=PstI, X=XhoI, S=SalI, LGT agarose=low-gelling temperature agarose.

A preliminary restriction map of pBS-PR1013Eco is established. An XhoI restriction site is located ~1200 bp upstream from the PstI site. The plasmid pBS-PR1013Eco Pst is digested with XhoI and the fragments are separated on 0.9% low-gelling temperature agarose gel. Two fragments are visualized with sizes of 3.9 kb and 1.7 kb. The band containing the 3.9 kb fragment is carefully excised from the gel and ligated in agarose essentially as described above. The agarose is melted and the DNA transformed into competent *E. coli* strain HB101 as described above. Cells are plated onto LB-amp plates and incubated as described. One putative positive colony is inoculated into LB-amp media and DNA is isolated essentially as described. The structure of this new subclone pBS-PR1013Eco Pst Xho is verified by restriction analysis and DNA sequencing. FIG. 6 shows the construction of this plasmid.

EXAMPLE 25

Preparation of pCIB270

Figure 7:
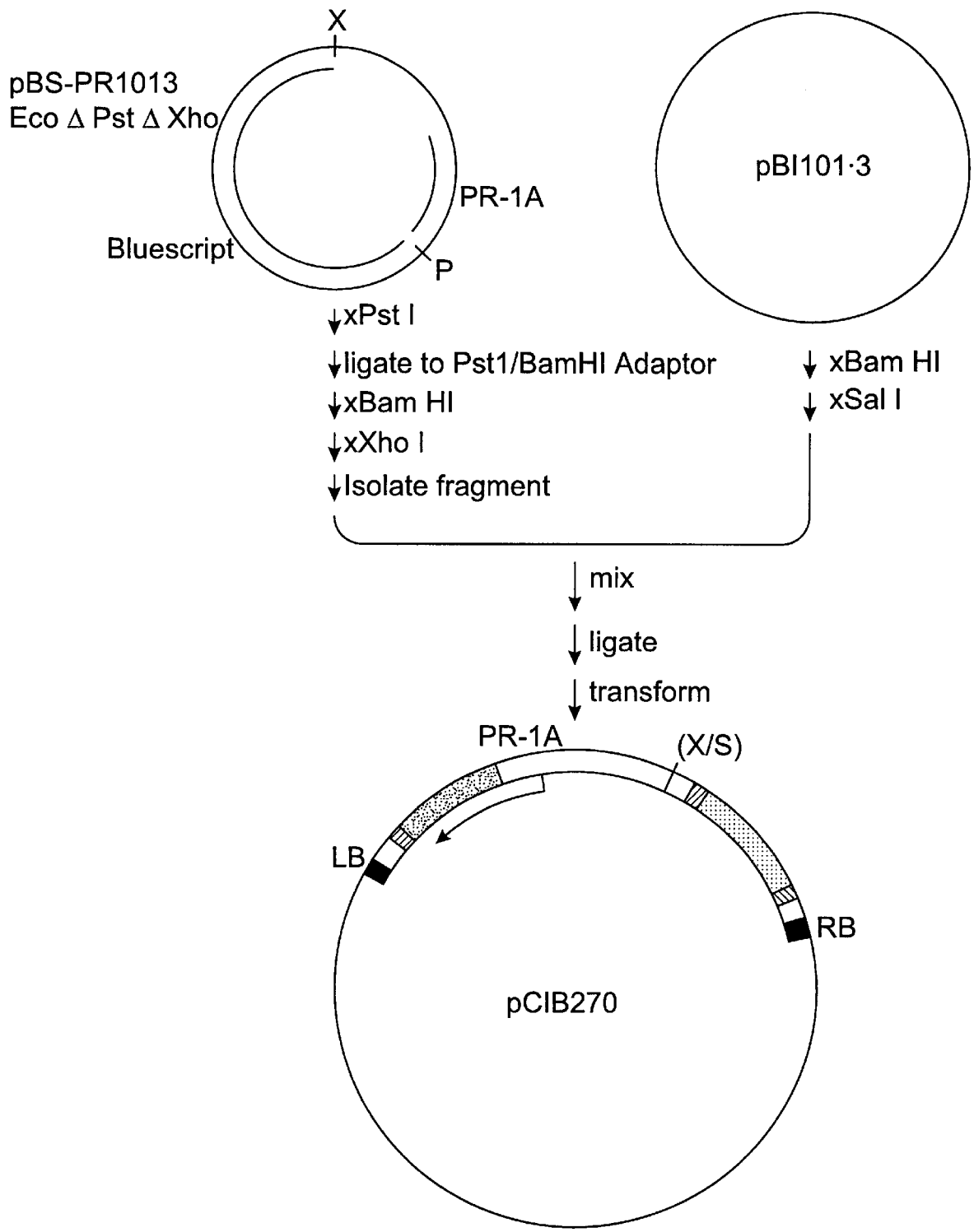
FIG. 7. The construction of pCIB270 from pBI101.3 and pBS-PR1013Eco Pst Xho is illustrated. The PstI-XhoI fragment containing part of the PR-1a gene and 5' flanking sequence is subcloned into SalI-BamHI digested pBI101.3. The XhoI and SalI sites are compatible and when ligated destroy both restriction sites. The PstI site is adapted to a BamHI site using a molecular adapter. X=XhoI, P=PstI, (X/S)=site of XhoI and SalI fusion. Neither enzyme will now cut at this (X/S) site. LB=T-DNA left border, RB=T-DNA right border. Direction of transcription from the PR-1a inducible region is shown by the arrow on pCIB270. The crosshatched area on pCIB270 represents the 3'-processing site of the NOS gene. The shaded area of pCIB270 represents the beta-glucuronidase gene. The stippled area of pCIB270 represents the neomycin phosphotransferase II gene. The striped area of pCIB270 represents the NOS promoter.

Plasmid pBI101.3 (Catalog no. 6024.1) is obtained from Clonetech Labs, Palo Alto, Calif. This plasmid is first digested with BamHI and then with SalI. The plasmid pBS-PR1013Eco Pst Xho is digested with PstI. A PstI/BamHI adaptor having the sequence 5'-GGGATCCCTGCA-3' (SEQ ID No. 54) is prepared as described in Example 5 and ligated to the PstI- digested pBS-PR1013Eco Pst Xho. The resulting material is first digested with BamHI and then with XhoI. The BamHI/XhoI fragment is isolated, mixed with and ligated to the digested pBI101.3, and transformed. A putative positive clone of pCIB270 is isolated and verified by restriction and DNA sequence analysis. The preparation of this plasmid is shown in FIG. 7.

EXAMPLE 26

Preparation of M13mp18- or mp19-PR1013Eco Pst Xho

Figure 8:
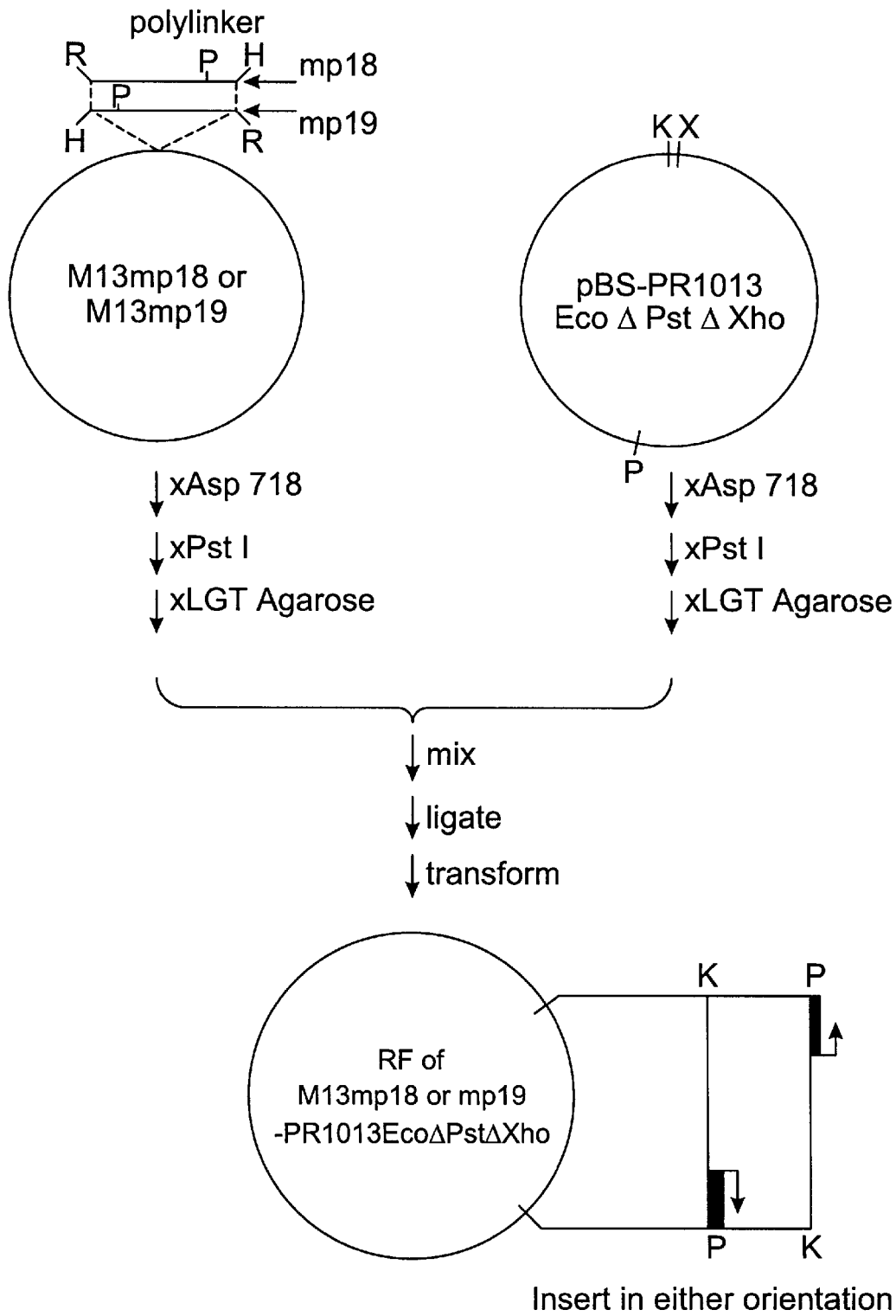
FIG. 8. The construction of M13mp18-PR1013Eco Pst Xho and M13mp19-PR1013Eco Pst Xho is shown. The PstI-Asp718 fragment containing part of the PR-1a coding sequence and the 5' flanking sequence is subcloned from pBS-PR1013Eco Pst Xho into Asp718-PstI digested M13mp18 or 19. R=EcoRI, H=HindIII, P-PstI, K=KpnI (Asp718 is an isoschizomer of KpnI), LGT agarose=low-gelling temperature agarose.

The plasmid pBS-PR1013Eco Pst Xho is digested with PstI and Asp718. The 1.1 kb Asp718/PstI fragment is isolated after electrophoresis on a 1% TAE low-gelling agarose gel. The replicative form (RF) of the coli phage M13mp18 or M13mp19 is prepared according to Messing, J., *Meth. Enzymol.* 101: 20 (1983). Alternatively, these vectors can be obtained from Bethesda Research Labs., Gaithersburg, Md. Either vector is digested first with Asp718 and then with PstI. After removal of the polylinker piece by electrophoresis on 0.7% TAE low-gelling agarose, the resulting vector RF is mixed and ligated in agarose with the 1.1 kb fragment prepared above. The DNA is transformed, putative positive plaques are isolated and their structure is verified by analysis of the RF DNA. The constructions of M13mp18- and mp19-PR1013Eco Pst Xho are shown in FIG. 8.

EXAMPLE 27

Preparation of M13mp18- or mp19-PR1013Eco Pst Xho.Nco and pCIB 268

Figure 9:
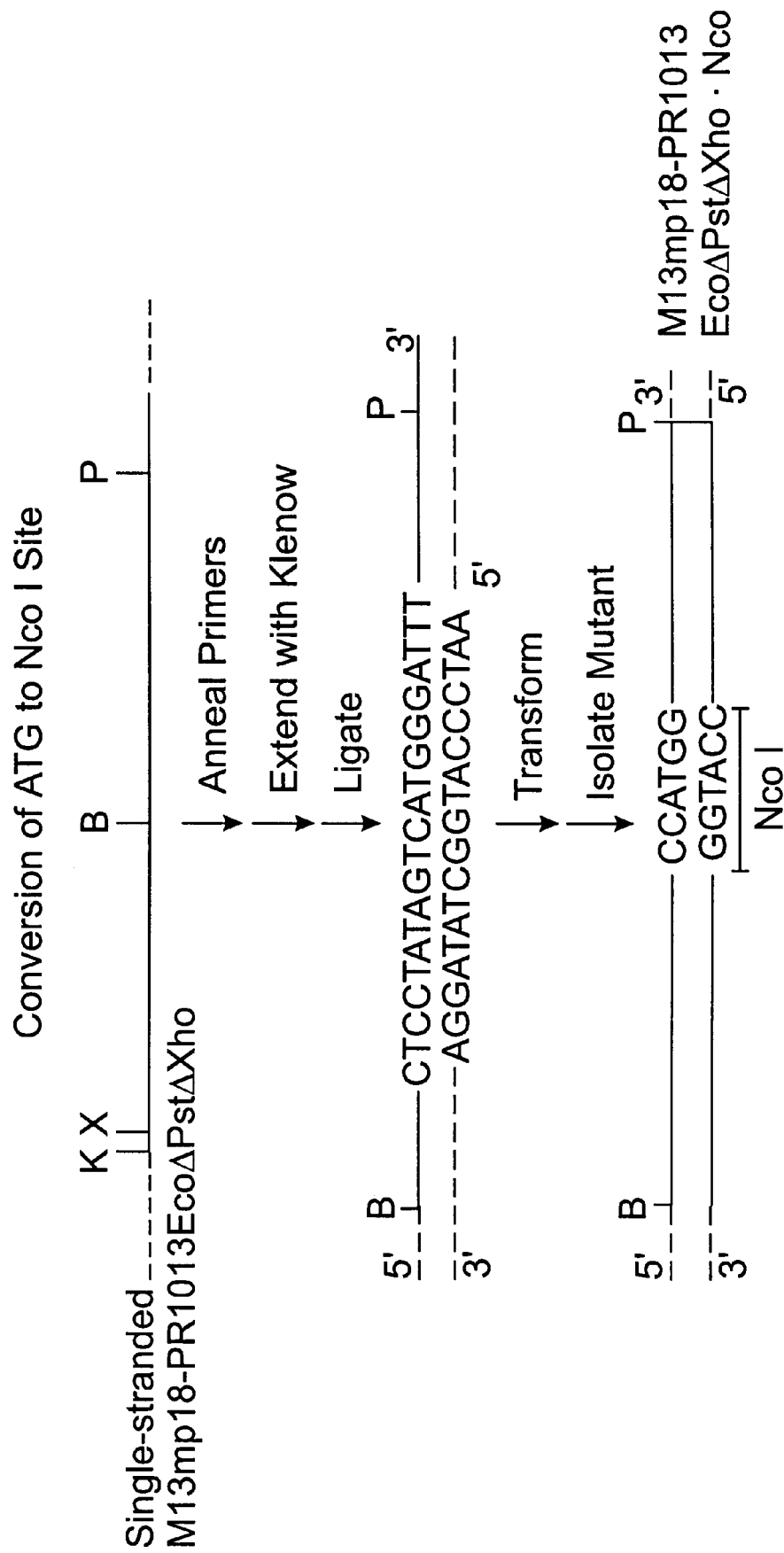
FIG. 9. Flow diagram depicting the conversion of the ATG codon of PR-1a to a NcoI site. The single stranded DNA of M13mp18-PR1013Eco Pst Xho is shown with a solid line. The sequence TCATGG is converted to CCATGG by site-directed mutagenesis. K=KpnI, X=XhoI, B=BstEII, P=PstI.

Single stranded M13mp18-PR1013Eco Pst Xho phage DNA is isolated according to Messing, supra. An 18 bp oligonucleotide primer of the sequence 5'-AATCCCATGGCTATAGGA-3' (SEQ ID No. 55) is synthesized as described above. The primer is phosphorylated with T4 polynucleotide kinase (Maniatis, T. et al., supra at p. 125) using unlabeled ATP. After incubation at 37° C. for 60 minutes the reaction is heated to 68° C. for 15 minutes and then placed on ice. This primer and the M13-40 forward sequencing primer (New England Biolabs #1212) are annealed to single stranded M13mp18-PR1013Eco Pst Xho DNA after mixing in a 1:1:1 molar ratio, by slow cooling after heating for 10 minutes at 68° C. The annealed mixture is placed on ice and 1/10 volume of 10× elongation buffer (20 mM Tris buffer pH 7.5, 6 mM $MgCl_2$, 1 mM DTT, 1 mM dATP, 1 mM dCTP, 1 mM dGTP, and 1 mM dTTP) is added. 10 units of DNA Polymerase I large fragment (Klenow fragment, New England Biolabs #210) and 0.1 unit of T4 DNA Ligase (NEB #202) are added and the reaction is allowed to proceed 14 hours at 15° C. At that time an additional aliquot of each enzyme is added and the reaction is carried out for an additional 2 hours at 25° C. before the mixture is used to transform competent JM101 *E. coli*. A general flow diagram of this procedure is presented in FIG. 9.

To identify the mutated phage, the plaques are lifted to Gene Screen Plus (DuPont) and processed according to the manufacturer's recommendations. The filters are prehybridized for four hours, and hybridized overnight at 42° C., in the manufacturer's hybridization solution containing 0.9 M NaCl. The filters are then sequentially washed at a NaCl concentration of 0.9 M and monitored by autoradiography increasing the wash temperature by 5° C. at each step. Phages identified by hybridization to have been mutated are sequenced to confirm the base change.

Figure 10:
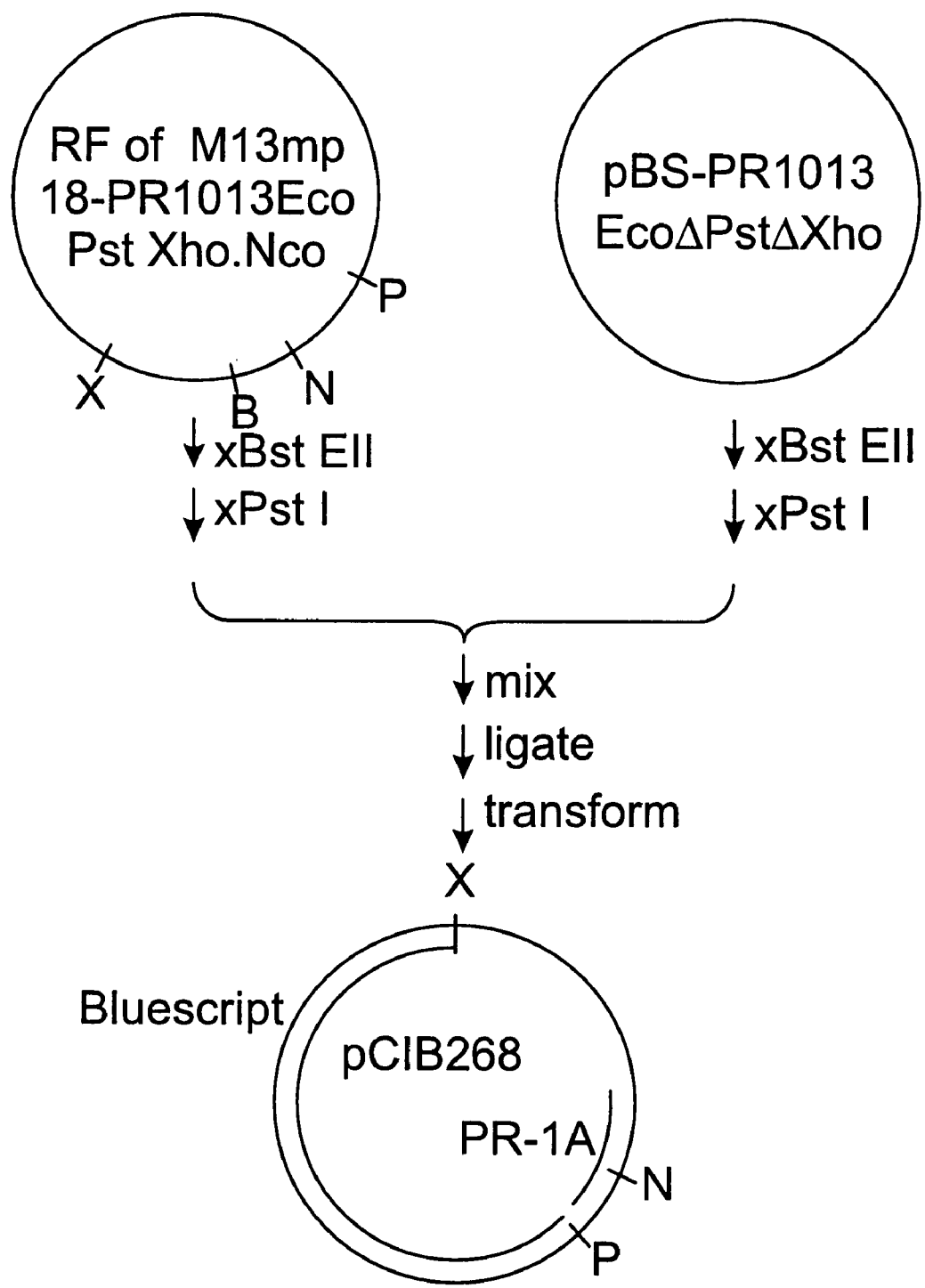
FIG. 10. The construction of pCIB268 is shown. The BstEII-PstI fragment derived from the replicative form of M13mp18-PR1013Eco Pst Xho.Nco is subcloned into BstEII-PstI digested pBS-PR1013Eco Pst Xho to form pCIB268. X=XhoI, B=BstEII, N=NcoI, P=PstI.

The replicative form of one such candidate (M13mp18-PR1013Eco Pst Xho.Nco) is isolated and digested with PstI and BstEII to produce a 394 bp fragment which is used to replace the corresponding non-mutated 394 bp fragment in pBS-PR1013Eco Pst Xho as illustrated in FIG. 10. This results in the preparation of pCIB268 which has an NcoI site at position 930 followed by 217 bp of the coding sequence for the PR-1a gene. The structure of this plasmid is confirmed by sequence analysis.

EXAMPLE 28

Preparation of Chimeric Genes Containing GUS and Variable Lengths of the PR Promoter Sequence A. Construction of pCIB269

Figure 11:
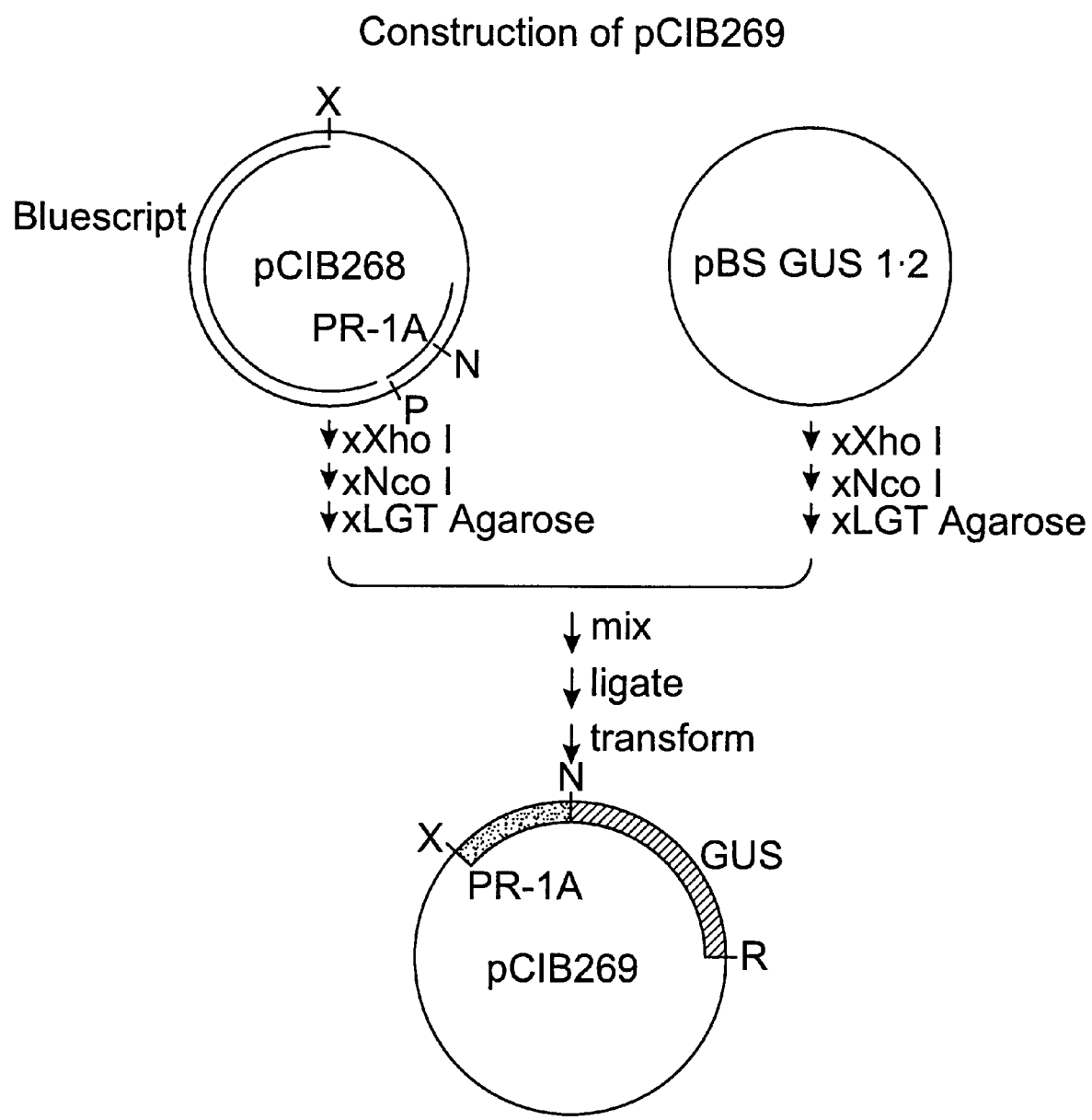
FIG. 11. The construction of pCIB269 from pBS-GUS1.2 and pCIB268 is shown. X=XhoI, N=NcoI, P=PstI. The crosshatched box of pCIB269 depicts the GUS gene sequences, and the shaded box depicts the sequences derived from the PR-1a gene.

A fragment of 930 bp is isolated after electrophoresis of XhoI and NcoI digested pCIB268 on a 1.0% low gelling temperature agarose TAE gel. This fragment is then ligated into pBS-GUS1.2 (see part B below) which had been digested with XhoI and NcoI. Transformants are isolated and analyzed by restriction analysis and DNA sequencing. One positive plasmid is chosen and named pCIB269. The construction of this plasmid is shown in FIG. 11.

Figure 12:
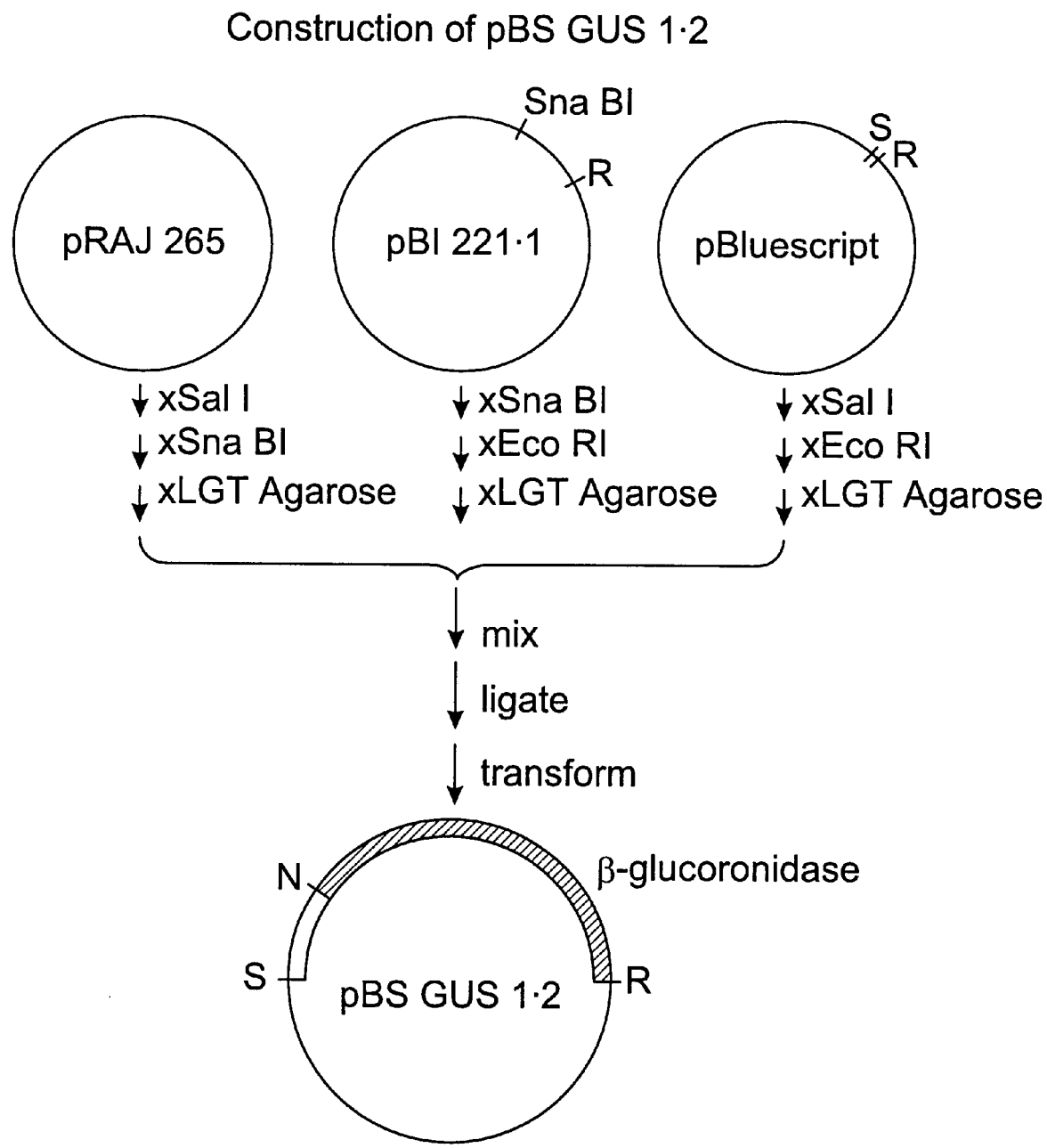
FIG. 12. The construction of pBS-GUS1.2 is shown. pBS-GUS1.2 is made via a three-way ligation from fragments derived from pRAJ265, pBI221.1 and pBluescript. S=SalI, R=EcoRI, N=NcoI.

B. Construction of pBS-GUS1.2 pBS-GUS1.2 is created by three part ligation of a 391 bp SalI/SnabI fragment from pRAJ265 (Jefferson, R. A. et al., *EMBO J.* 6: 3091–3907 (1987) and GUS User Manual, Clonetech Labs., Palo Alto, Calif.) with a 1707 bp SnabI/EcoRI fragment from pBI221 (Jefferson, R. A. et al., *EMBO J.* supra) and pBS digested with SalI and EcoRI (see FIG. 12). Transformants are isolated and analyzed by restriction digestion and DNA sequencing. One verified clone is named pBS-GUS1.2.

C. Construction of pCIB200

TJS75Kan is first created by digestion of pTJS75 (Schmidhauser and Helinski, *J. Bacteriol.* 164: 446–455 (1985)) with NarI to excise the tetracycline gene, followed by insertion of an AccI fragment from pUC4K (Messing, J. and Vierra, J., *Gene* 19: 259–268 (1982)) carrying a NptI gene. pCIB 200 is then made by ligating XhoI linkers to the EcoRV fragment of pCIB7 (containing the left and right T-DNA borders, a plant selectable nos/nptII chimeric gene and the pUC polylinker, Rothstein, S. J. et al., *Gene* 53: 153–161 (1987)) and cloning XhoI digested fragment into SalI digested TJS75Kan.

D. Construction of pCIB271

Figure 13:
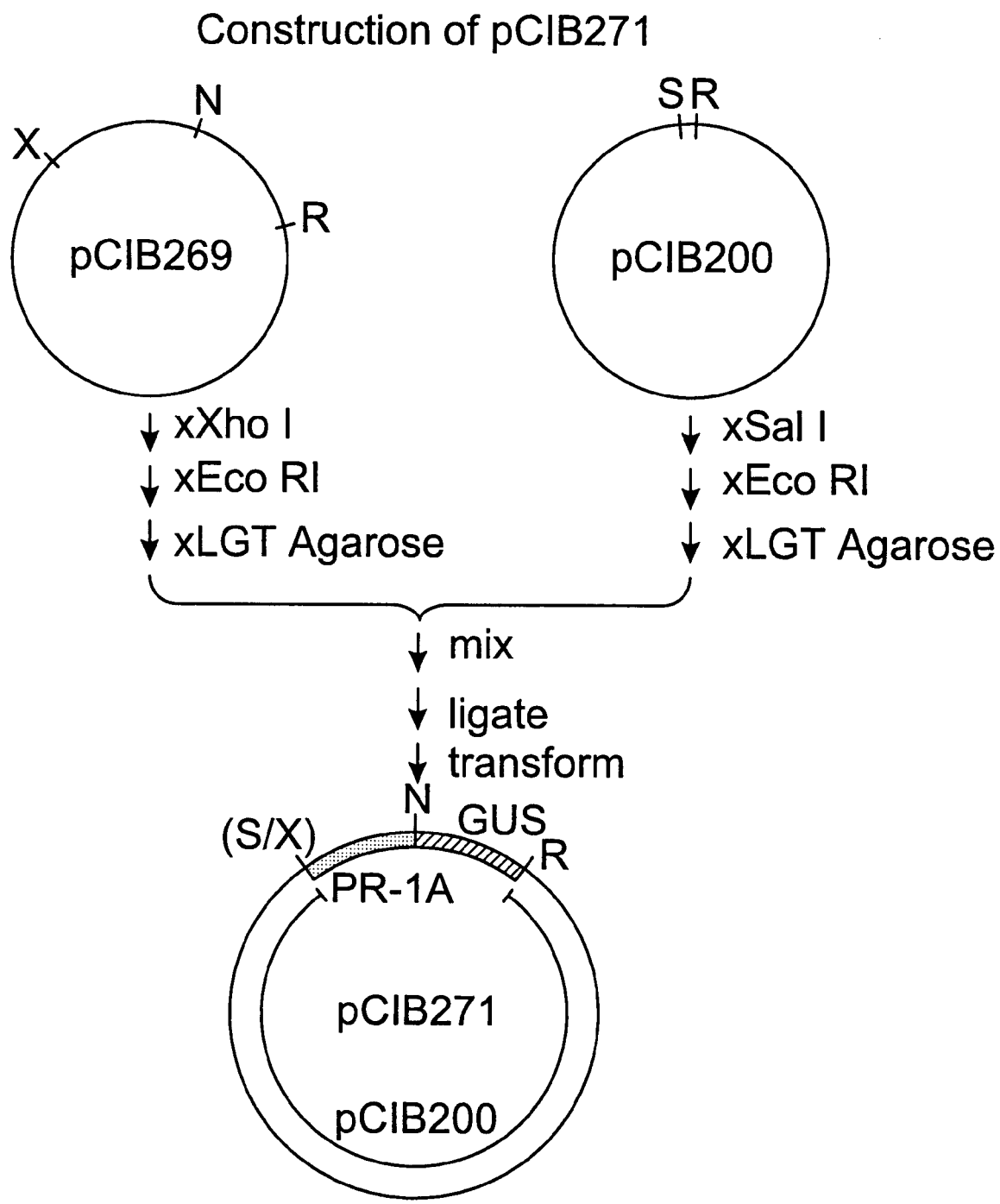
FIG. 13. The construction of pCIB271 from pCIB269 and pCIB200 is shown. X=XhoI, N=NcoI, R=EcoRI, S=SalI, (S/X)=fusion of SalI and XhoI sites, LGT agarose=low-gelling temperature agarose.

The plasmid pCIB269 (part A above) is digested with XhoI and EcoRI and the 3023 bp fragment carrying the PR-1a promoter linked to the GUS gene with a nos 3' end is isolated following electrophoresis on a 1.0% low gelling agarose TAE gel. This fragment is then ligated into a broad host range vector pCIB200 which has been digested with SalI and EcoRI. Transformants are isolated and analyzed by restriction analysis. One verified clone is named pCIB271. The construction of this clone is shown in FIG. 13.

E. Construction of pCIB272 pCIB268 (Example 27) is digested with AluI plus NcoI and an 833 bp fragment is isolated after electrophoresis on a 1× TAE 0.7% agarose gel. This fragment is ligated to the β-glucuronidase gene with the nos 3' end in pBS-GUS1.2 (part B above). The promoter and GUS are then excised from this plasmid named pCIB282 as an Asp718I/BamHI fragment and ligated into pCIB200 which has been digested with Asp718I and BamHI before transformation into *E. coli* strain DH5. Transformants are isolated and analyzed by restriction analysis. One verified clone is named pCIB272.

F. Construction of pCIB273 pCIB268 is digested with HaeIII plus NcoI and a 603 bp fragment is isolated after electrophoresis on a 1× TAE 0.7% agarose gel. This fragment is placed in front of the β-glucuronidase gene with the nos 3' end in pBS-GUS1.2. The promoter and GUS are then excised from this plasmid named pCIB283 as an Asp718I/BamHI fragment and ligated into pCIB200 which has been digested with Asp718I and BamHI before transformation into *E. coli* strain DH5. Transformants are isolated and analyzed by restriction analysis. One verified clone is named pCIB273.

EXAMPLE 29

Figure 14:
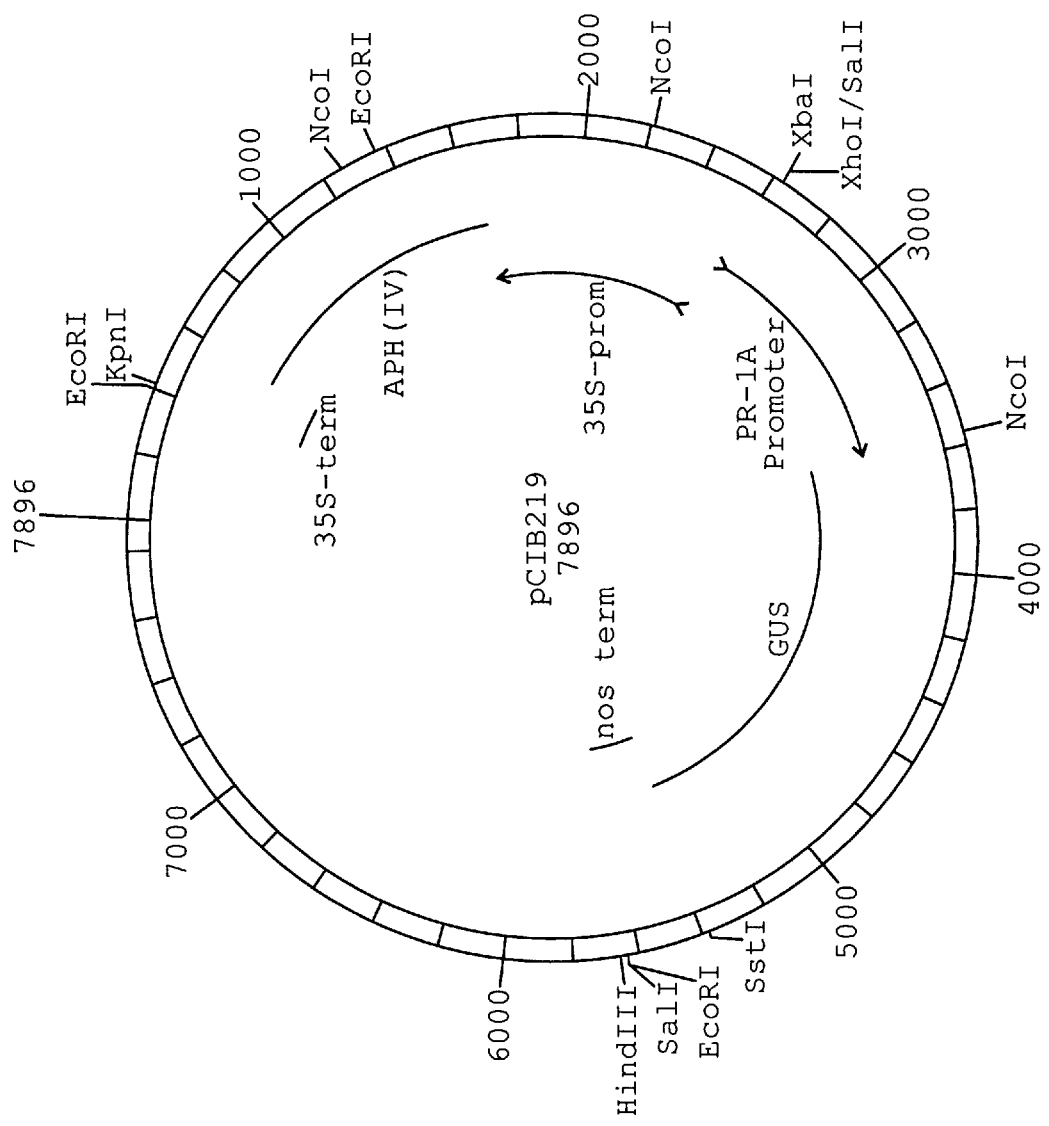
FIG. 14. Restriction endonuclease map of pCIB219. This plasmid is constructed by adding an EcoRI/XhoI adapter to the pCIB269 XhoI/EcoRI fragment containing the PR-1 and GUS gene and ligating it into SalI restricted pCIB712.
Figure 15:
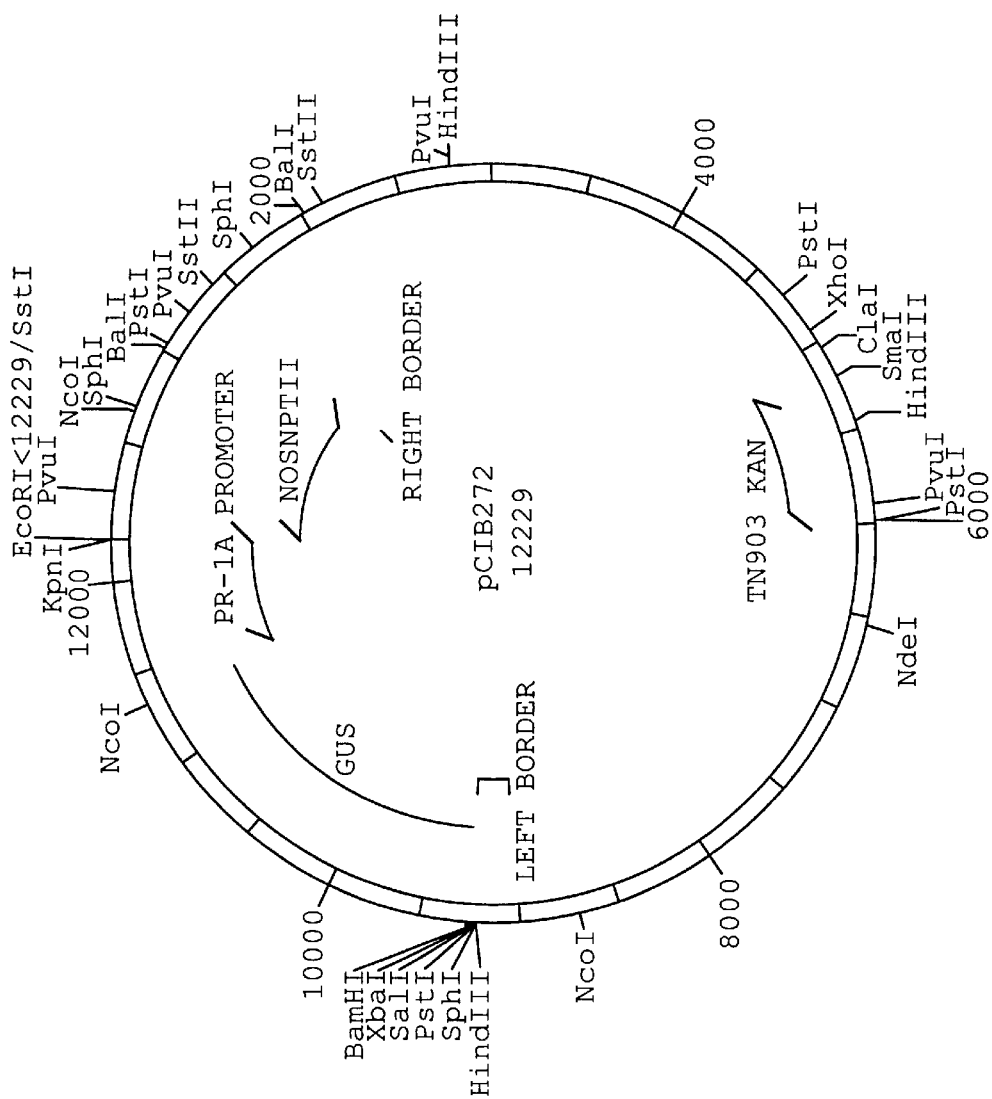
FIG. 15. Restriction endonuclease map of pCIB272. This plasmid is constructed by ligating an Asp718I/BamHI fragment from pCIB282 containing a PR-1/GUS gene (−833 to +1 of PR-1a) into Asp718I/BamHI restricted pCIB200.
Figure 16:
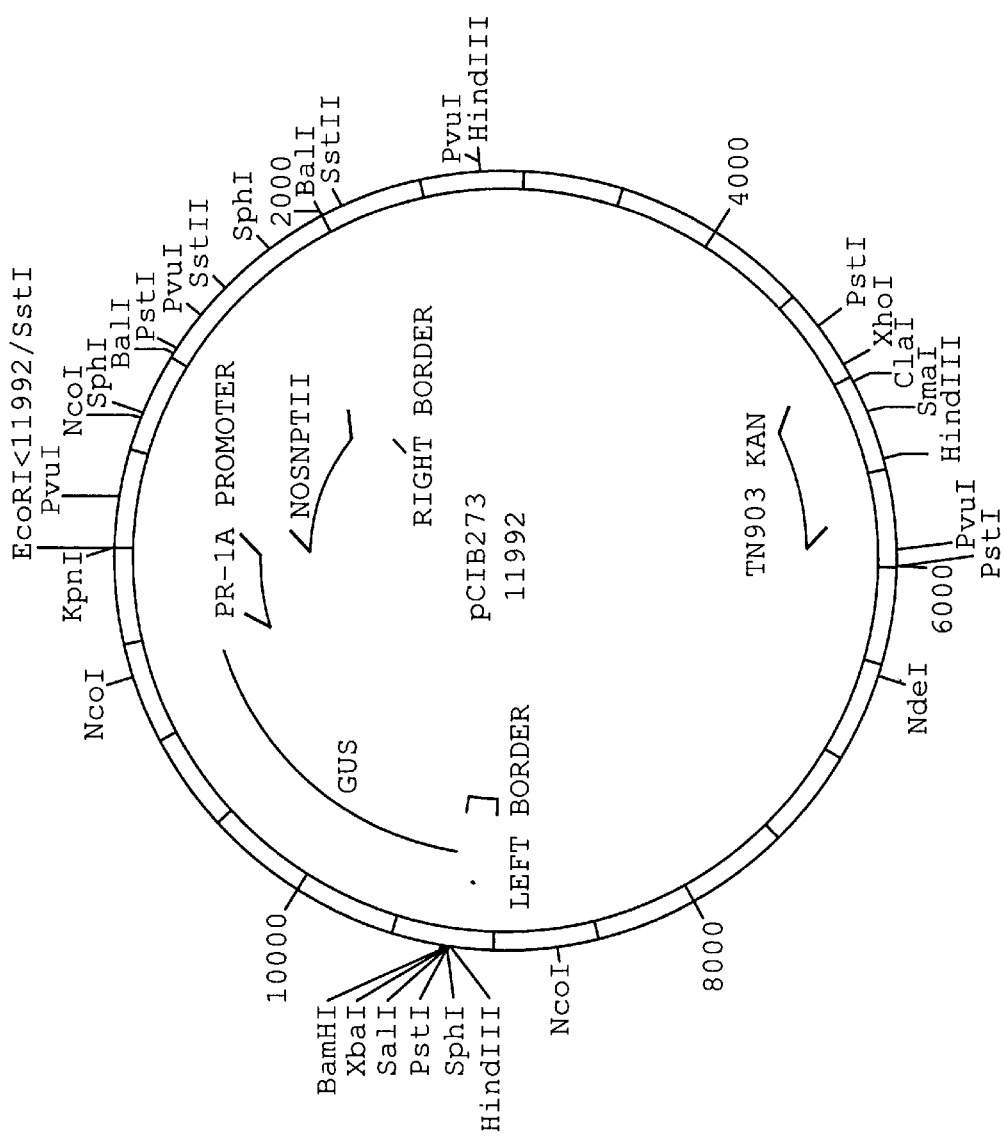
FIG. 16. Restriction endonuclease map of pCIB273. This plasmid is constructed by ligating an Asp718I/BamHI fragment from pCIB283 containing a PR-1/GUS gene (−603 to +1 of PR-1a) into Asp718I/BamHI restricted pCIB200.
Figure 17:
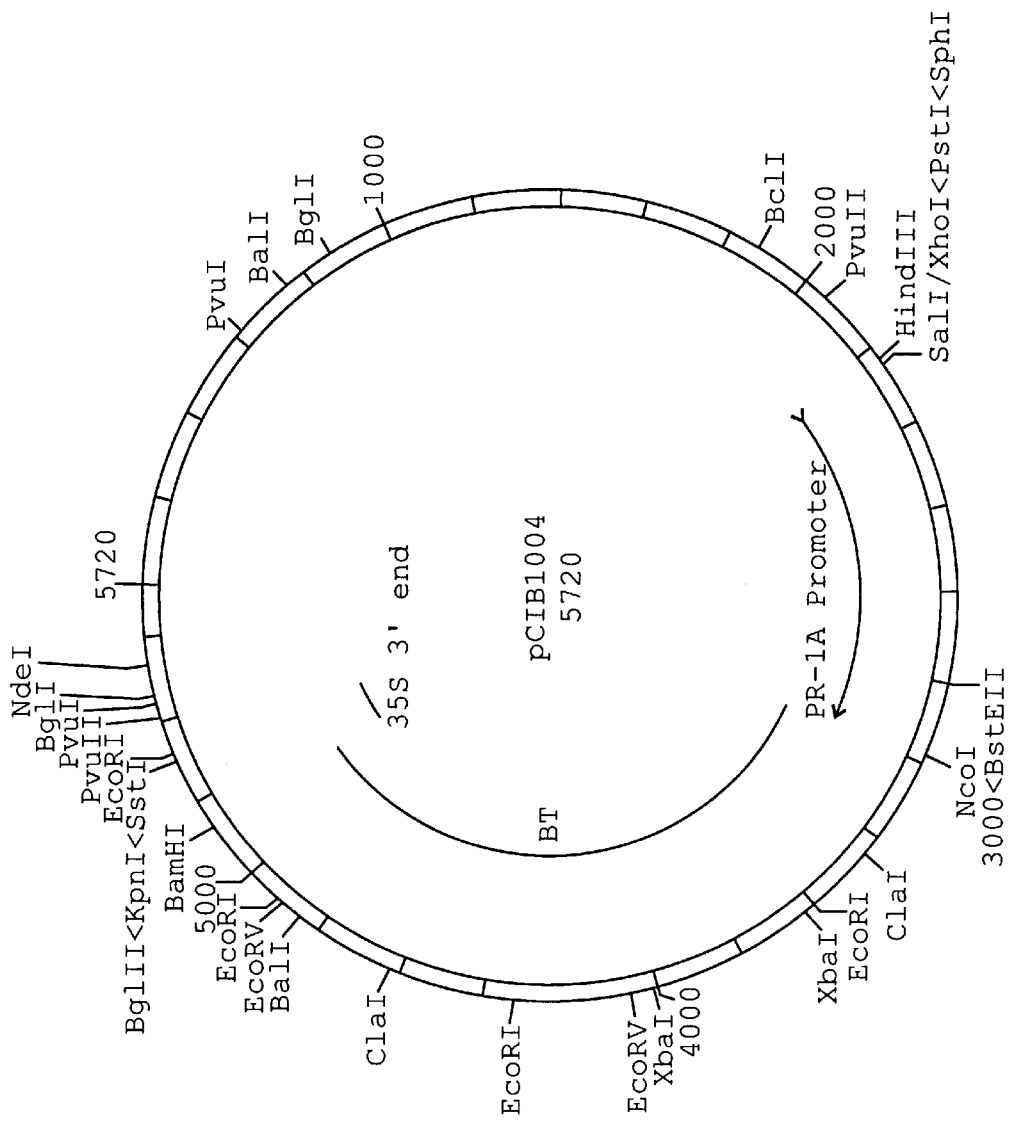
FIG. 17. Restriction endonuclease map of pCIB1004. This plasmid is constructed by ligating a XhoI/NcoI fragment from pCIB269 (containing the PR-1a promoter) with the BT gene excised from pCIB10/35Bt(607) as a NcoI/BamHI fragment and SalI/BamHI digested pCIB710.
Figure 18:
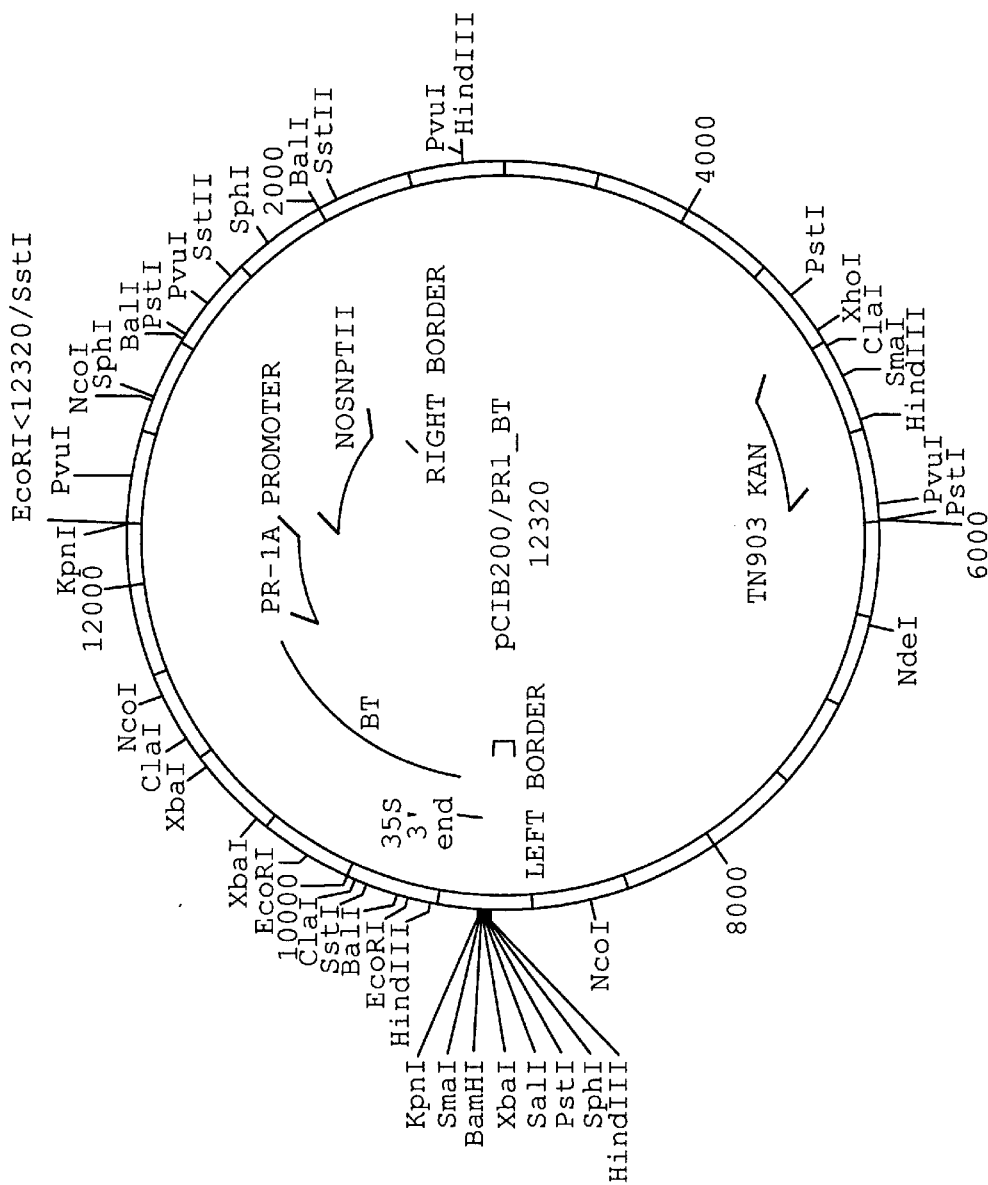
FIG. 18. Restriction endonuclease map of pCIB200/PR1-BT. This plasmid is constructed from pCIB1004 and pCIB200.
Figure 19:
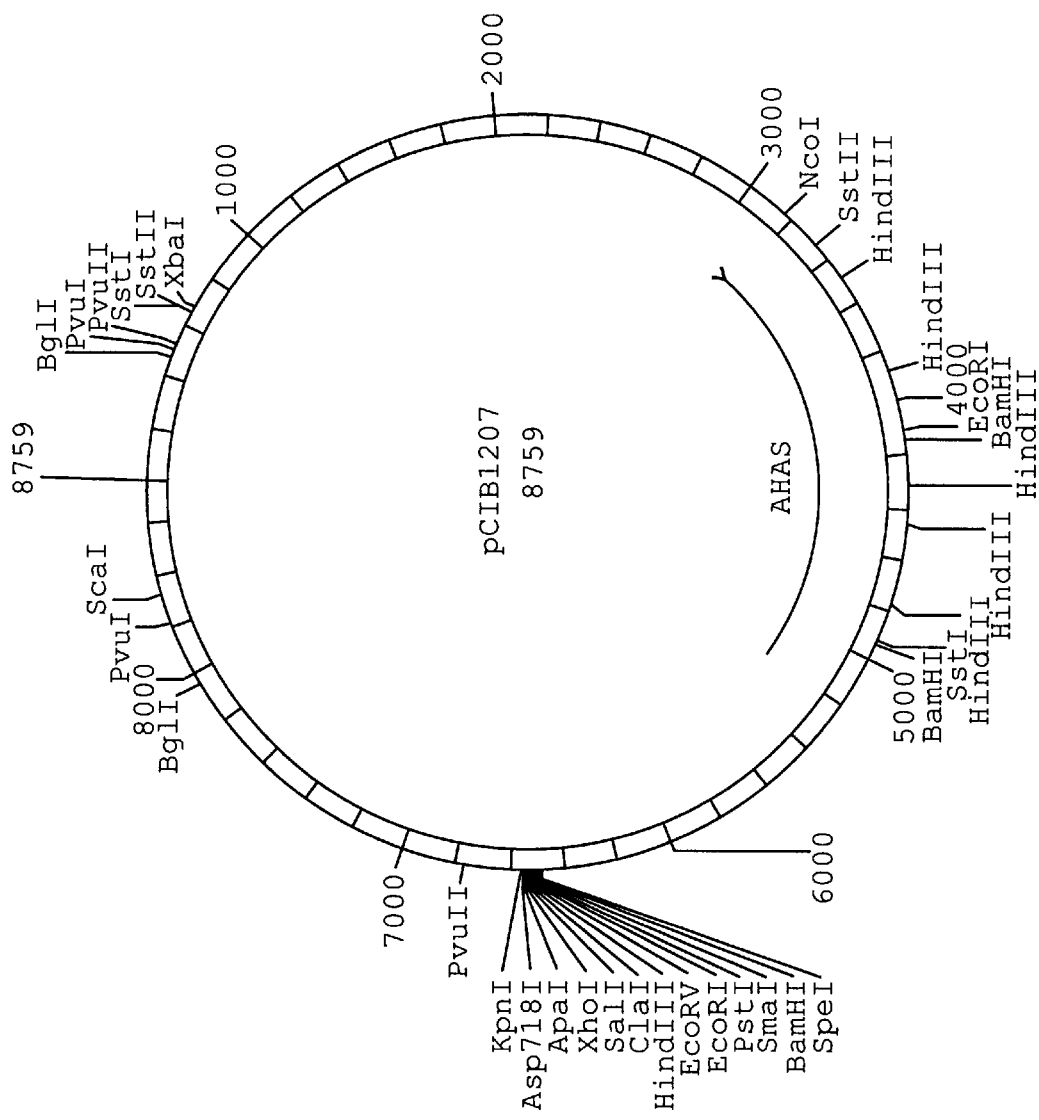
FIG. 19. Restriction endonuclease map of pCIB1207. A 5.8 kb XbaI fragment of the lambda genomic clone containing the Arabidopsis AHAS gene is cloned into XbaI restricted Bluescript.
Figure 20:
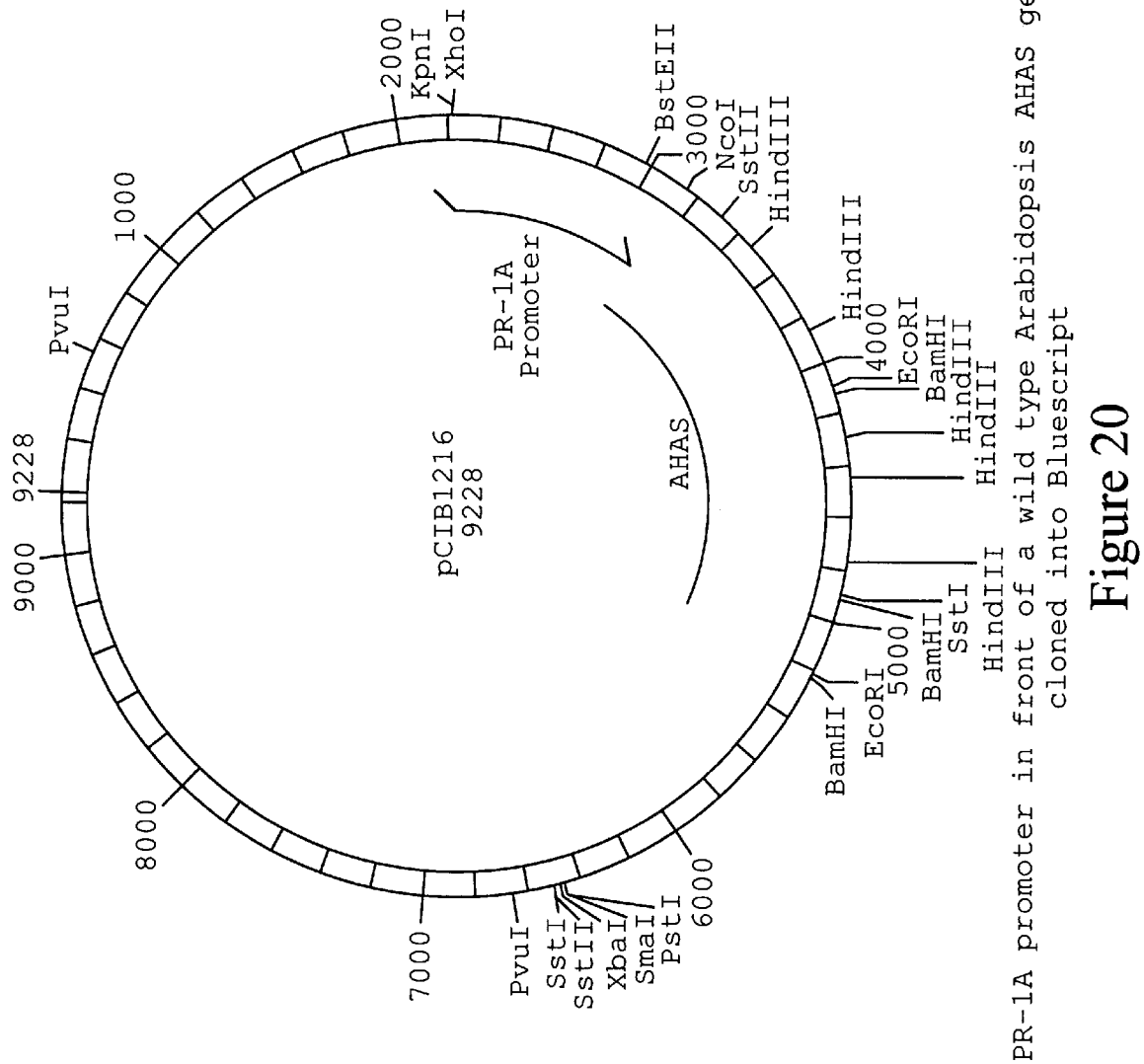
FIG. 20. Restriction endonuclease map of pCIB1216. A 3.3 kb NcoI/XbaI fragment from pCIB 1207 is cloned into pCIB269 which had been restricted with NcoI and XbaI to remove the GUS gene.
Figure 21:
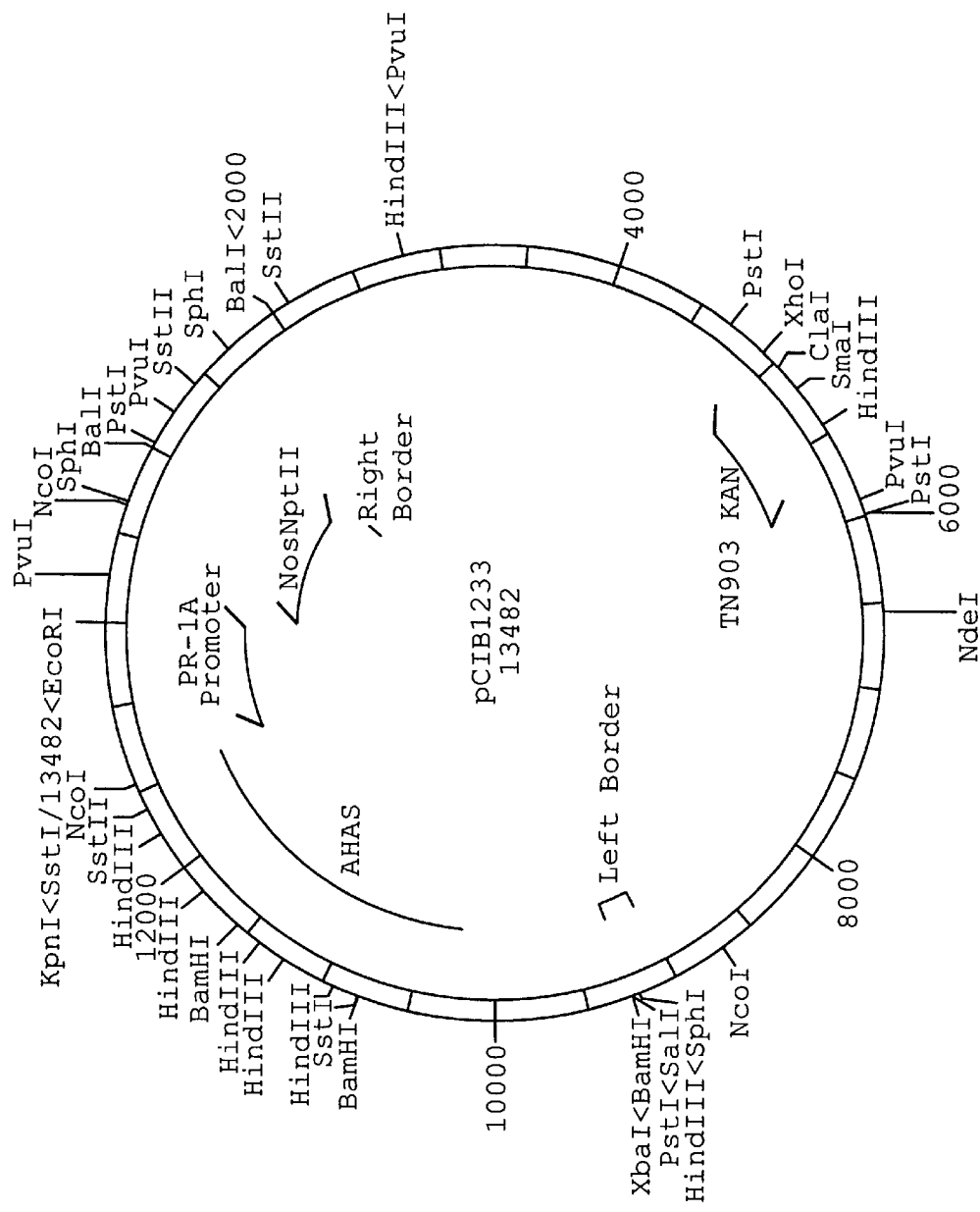
FIG. 21. Restriction endonuclease map of pCIB1233. A 4.2 kb KpnI/XbaI fragment is isolated from pCIB1216 and ligated into pCIB200 which had been restricted with KpnI and XbaI.
Figure 22:
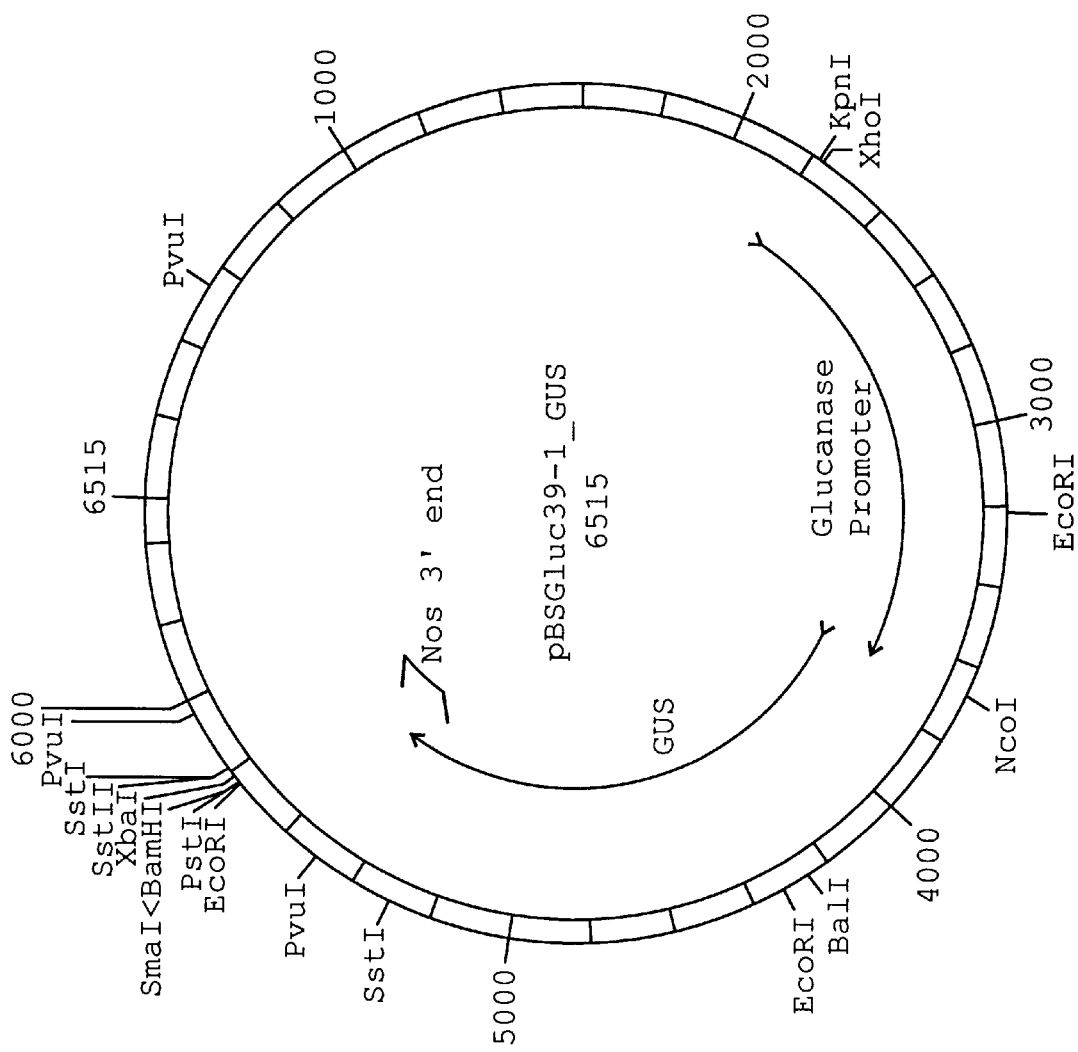
FIG. 22. Restriction endonuclease map of pBSGluc39.1/GUS. A 1462 bp fragment of pBSGluc39.1 is cloned into pBS-GUS1.2 which had been restricted with NcoI and KpnI.
Figure 23:
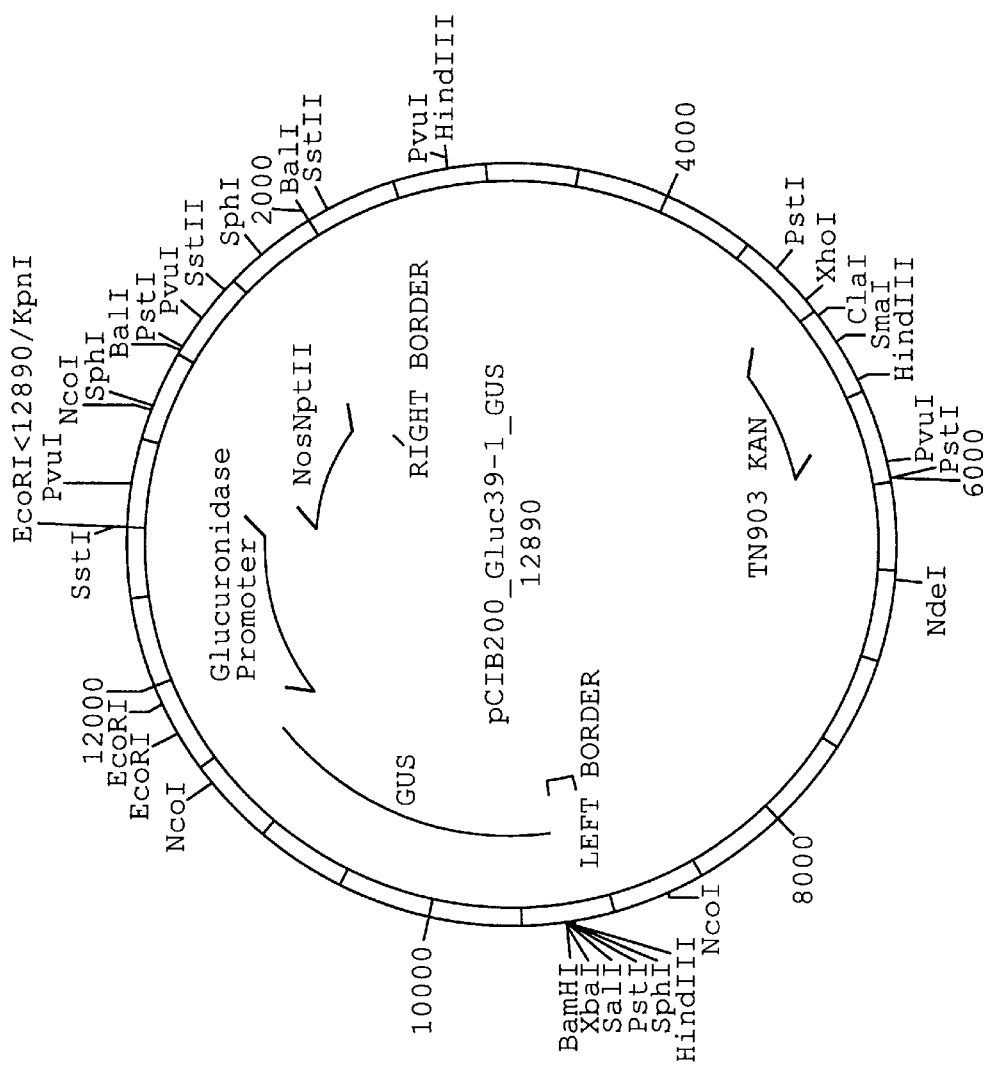
FIG. 23. Restriction endonuclease map of pCIB200/Gluc39.1-GUS. A KpnI/XbaI fragment containing the β-glucanase promoter and the GUS gene is isolated from pBSGluc39.1/GUS and ligated into pCIB200 restricted with KpnI and XbaI.
Figure 24:
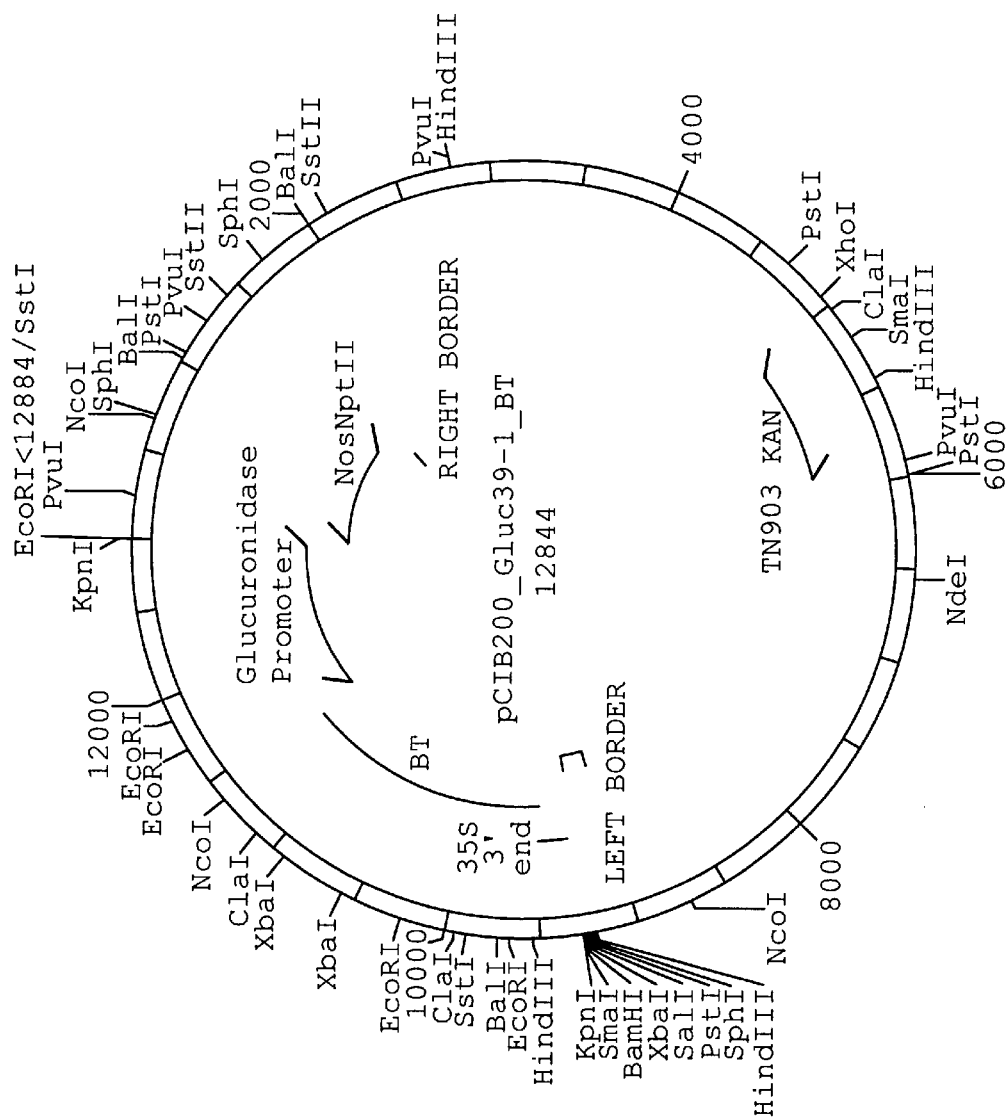
FIG. 24. Restriction endonuclease map of pCIB200/Gluc39.1-BT. A KpnI/NcoI fragment from pCIB1004 containing the BT gene, a KpnI/NcoI fragment from pBSGluc39.1/GUS, and pCIB200 restricted with KpnI and treated with calf thymus alkaline phosphatase are ligated.
Figure 25:
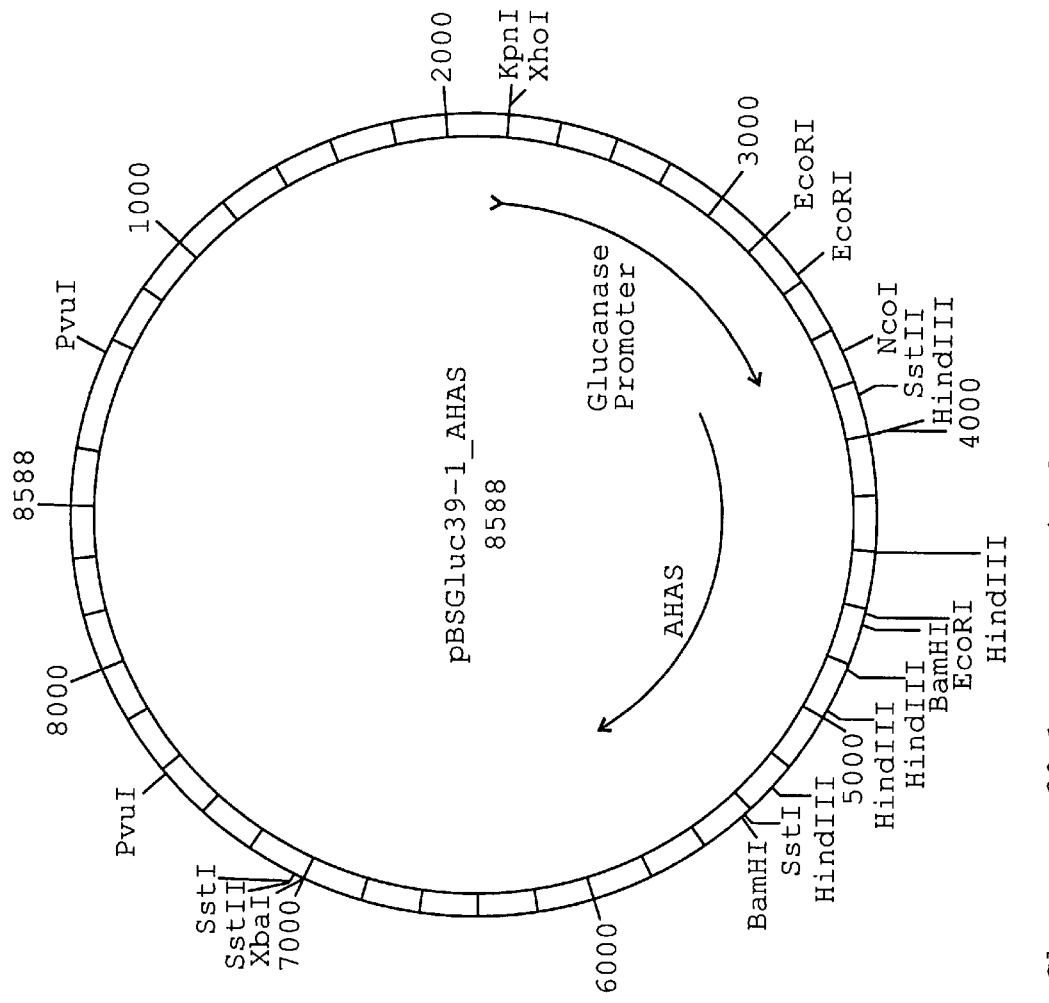
FIG. 25. Restriction endonuclease map of pBSGluc39.1/AHAS, constructed from a NcoI/XbaI fragment of pBSGluc39.1/GUS and a 3.3 kb NcoI/XbaI fragment from pCIB1207 containing the AHAS gene.
Figure 26:
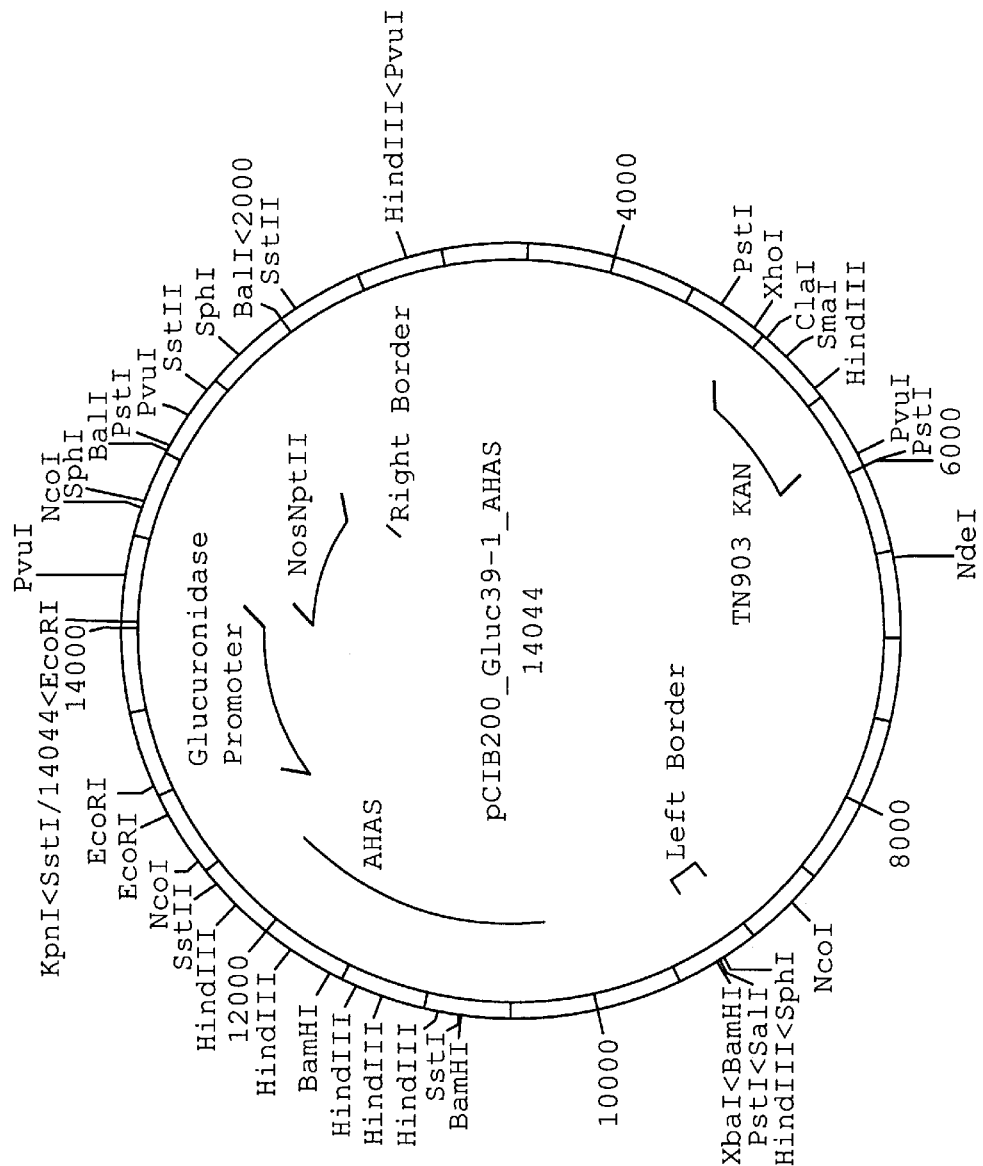
FIG. 26. Restriction endonuclease map of pCIB200/Gluc39.1-AHAS. A KpnI/XbaI fragment containing the β-glucanase promoter and the AHAS gene is isolated from pBSGluc39.1/AHAS and ligated into pCIB200 restricted with KpnI and XbaI.
Figure 27:
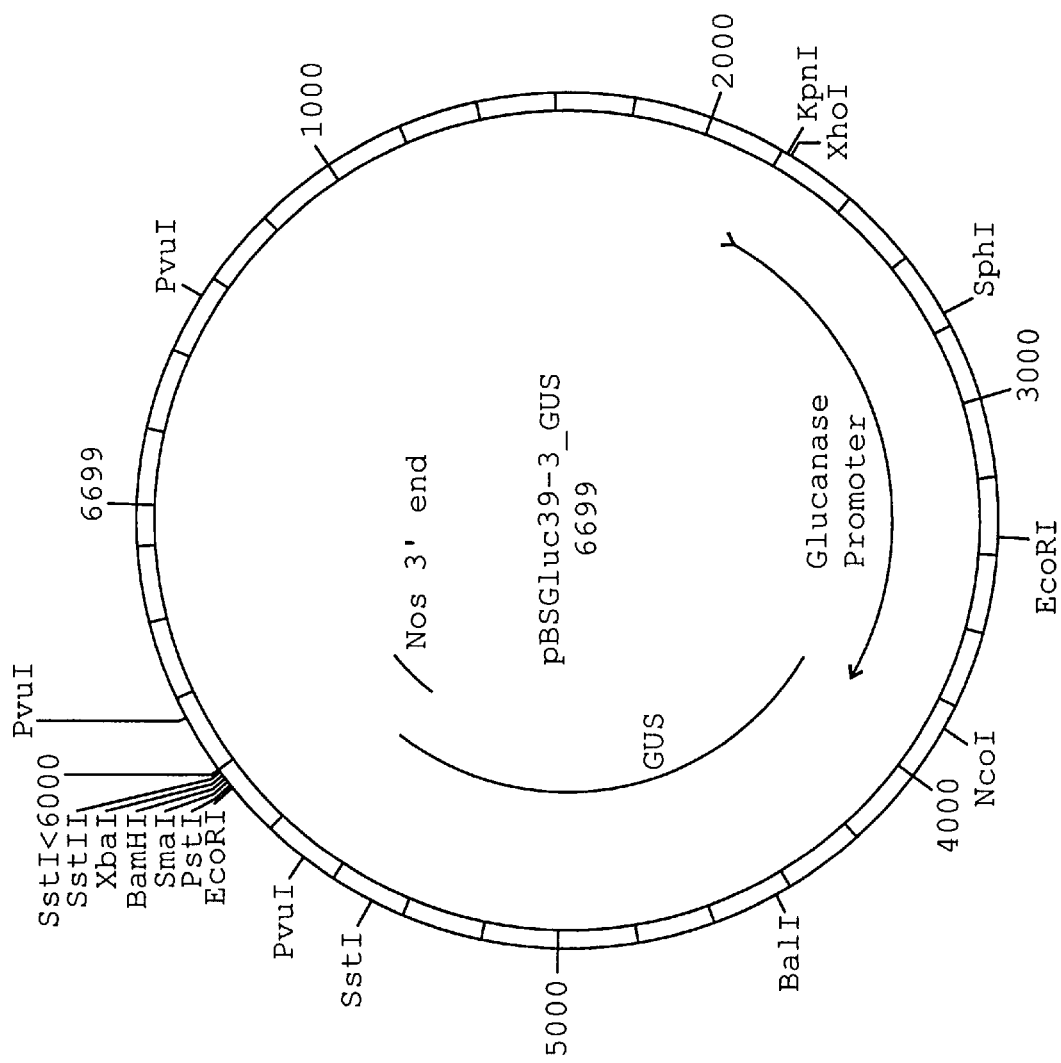
FIG. 27. Restriction endonuclease map of pBSGluc39.3/GUS. A 1677 bp fragment of pBSGluc39.3 is cloned into pBS-GUS1.2 which had been restricted with NcoI and KpnI.
Figure 28:
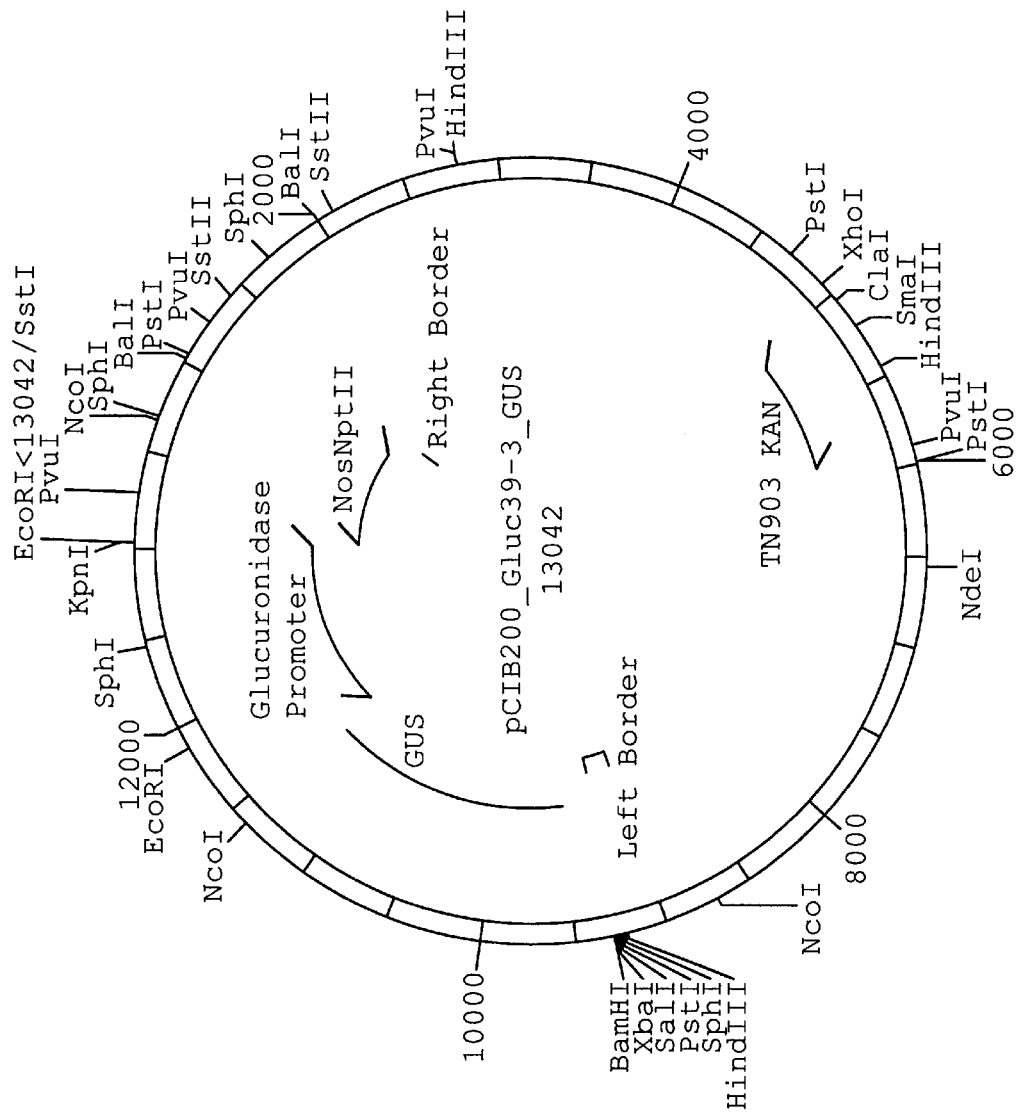
FIG. 28. Restriction endonuclease map of pCIB200/Gluc39.3-GUS. A KpnI/XbaI fragment containing the β-glucanase promoter and the GUS gene is isolated from pBSGluc39.3/GUS and ligated into pCIB200 restricted with KpnI and XbaI.
Figure 29:
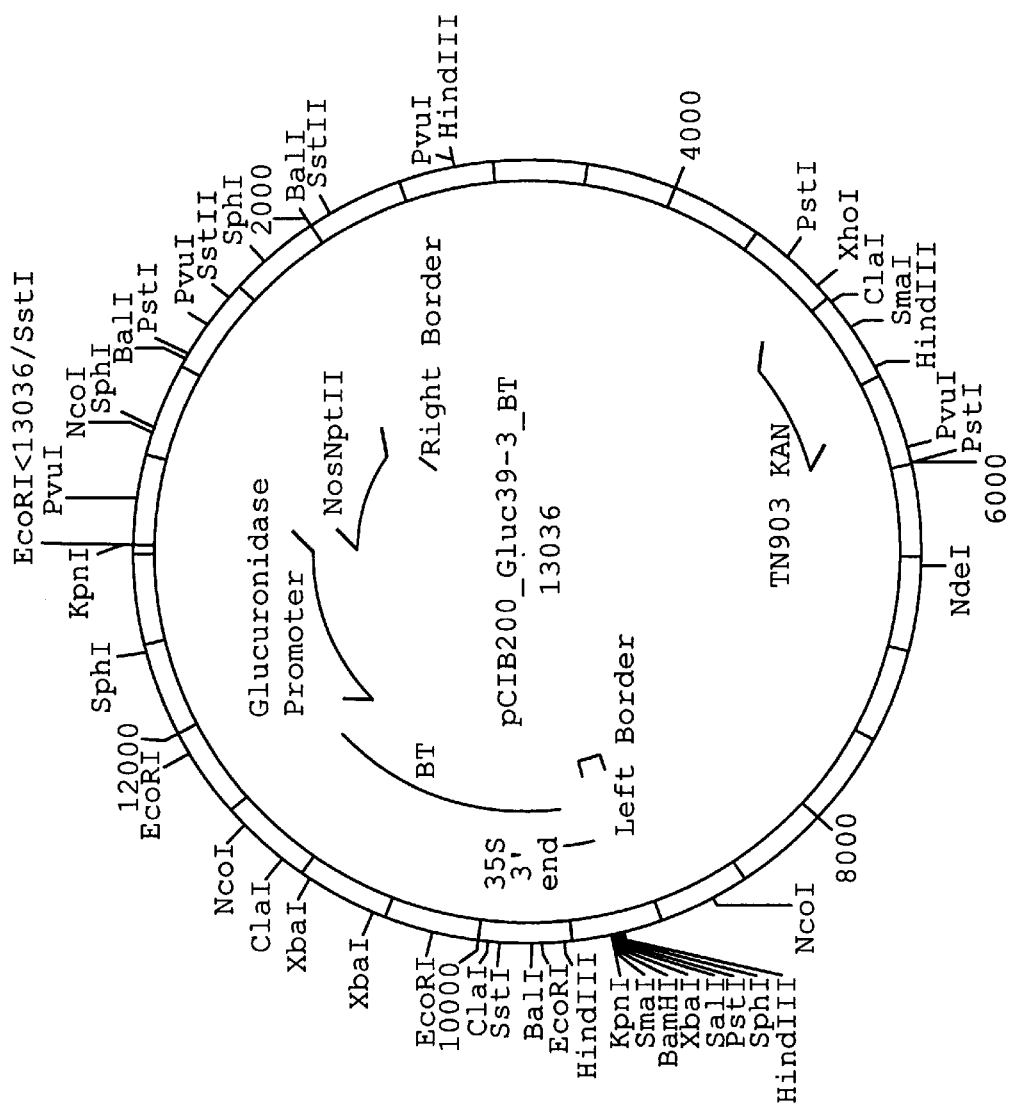
FIG. 29. Restriction endonuclease map of pCIB200/Gluc39.3-BT. A KpnI/NcoI fragment from pCIB1004 containing the BT gene, a KpnI/NcoI fragment from pBSGluc39.3/GUS, and pCIB200 restricted with KpnI and treated with calf thymus alkaline phosphatase are ligated.
Figure 30:
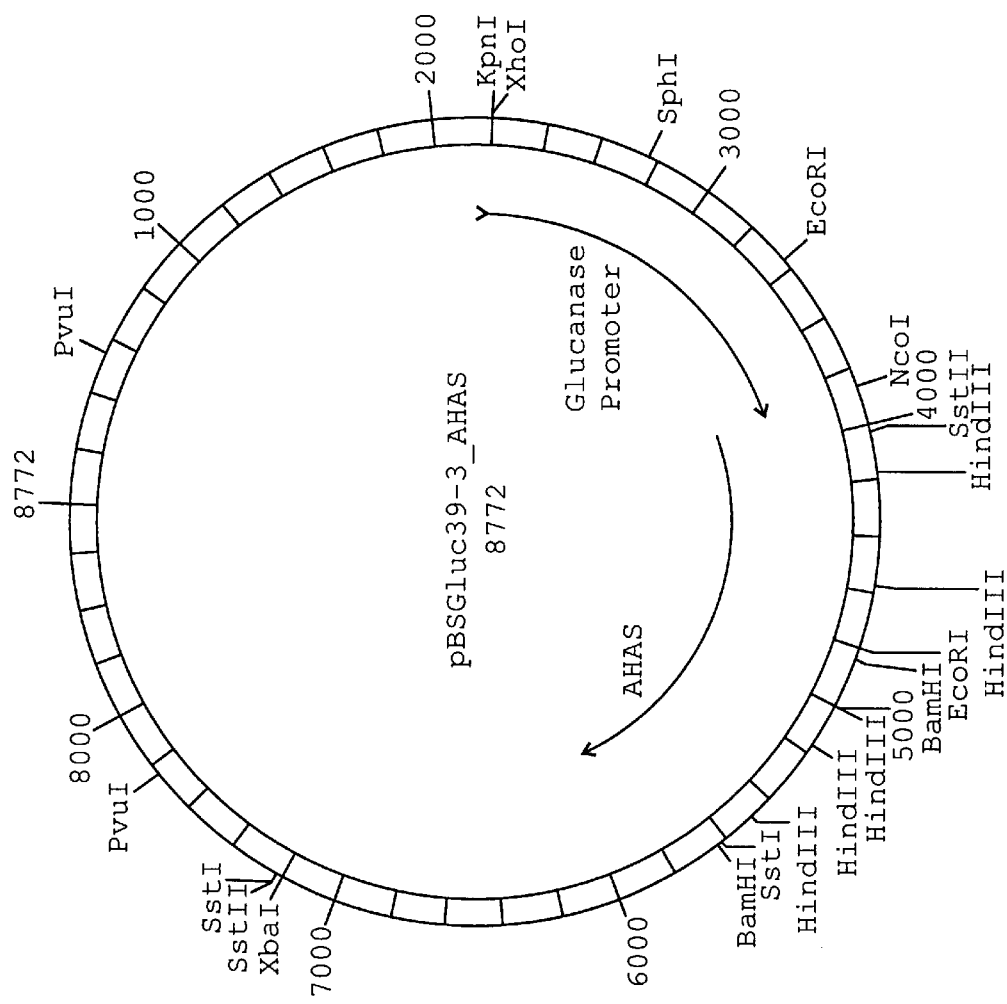
FIG. 30. Restriction endonuclease map of pBSGluc39.3/AHAS, constructed from a NcoI/XbaI fragment of pBSGluc39.3/GUS and a 3.3 kb NcoI/XbaI fragment from pCIB 1207 containing the AHAS gene.
Figure 31:
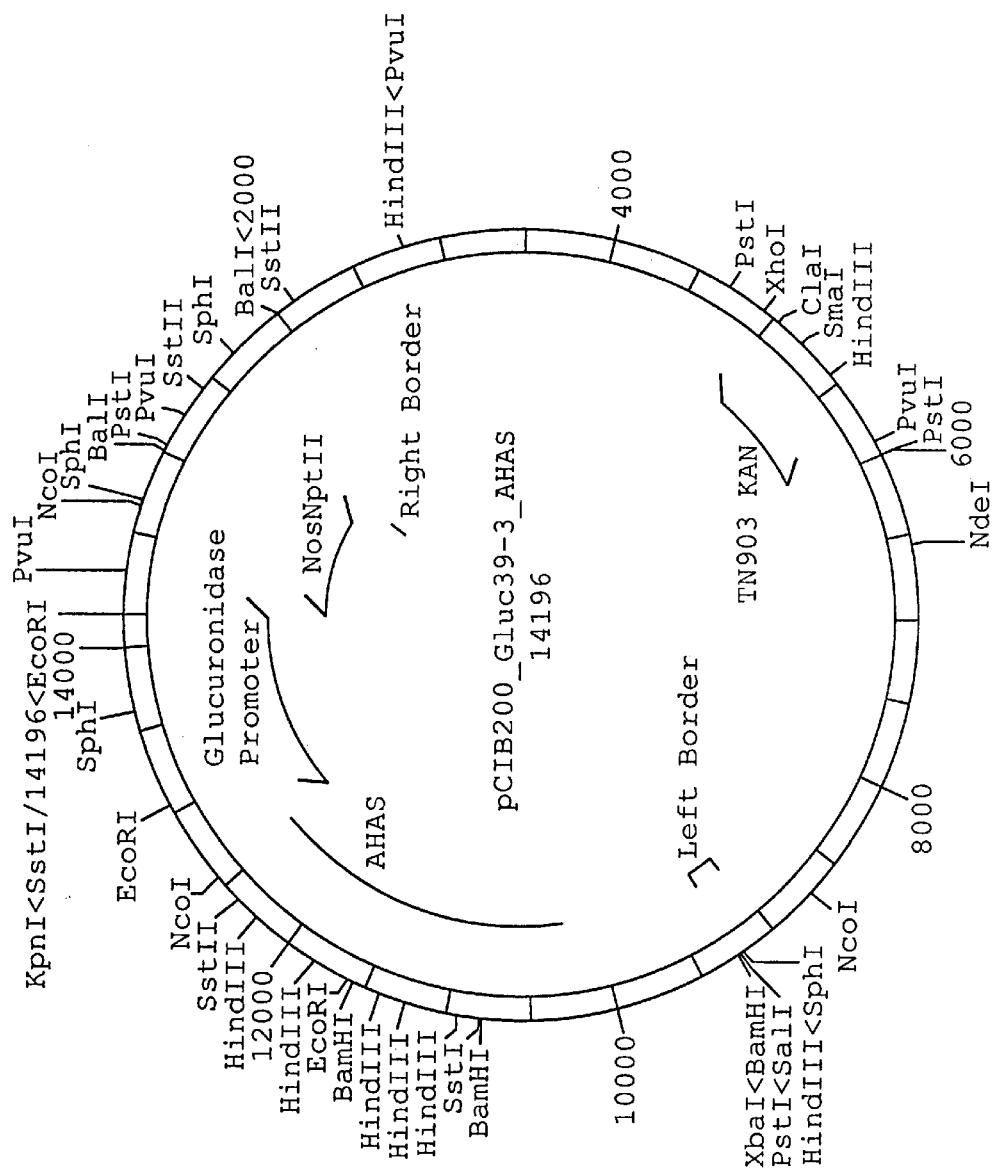
FIG. 31. Restriction endonuclease map of pCIB200/Gluc39.3-AHAS. A KpnI/XbaI fragment containing the β-glucanase promoter and the AHAS gene is isolated from pBSGluc39.3/AHAS and ligated into pCIB200 restricted with KpnI and XbaI.
Figure 32:
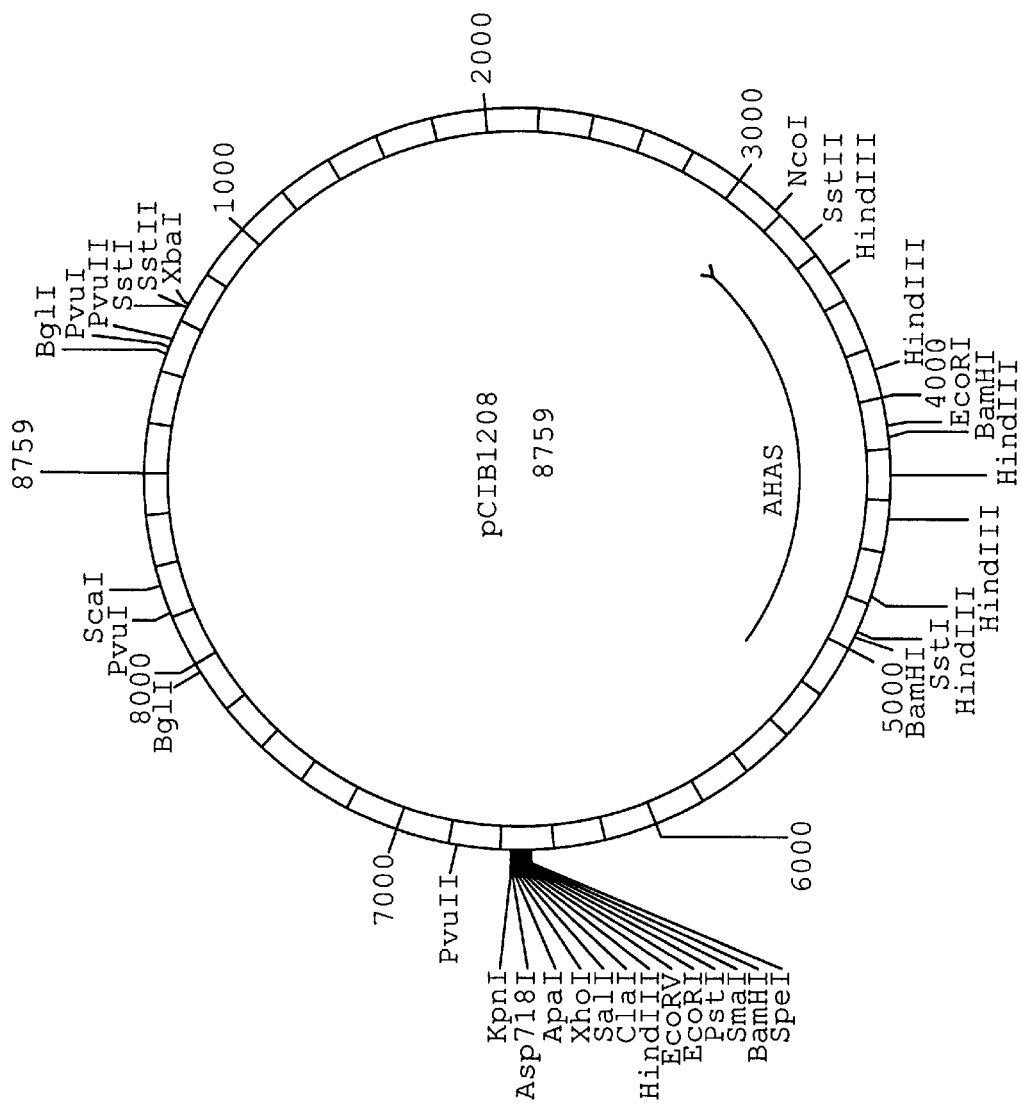
FIG. 32. Restriction endonuclease map of pCIB1208. A 5.8 kb XbaI fragment of the lambda genomic clone containing a mutated Arabidopsis AHAS gene is cloned into XbaI restricted Bluescript.
Figure 33:
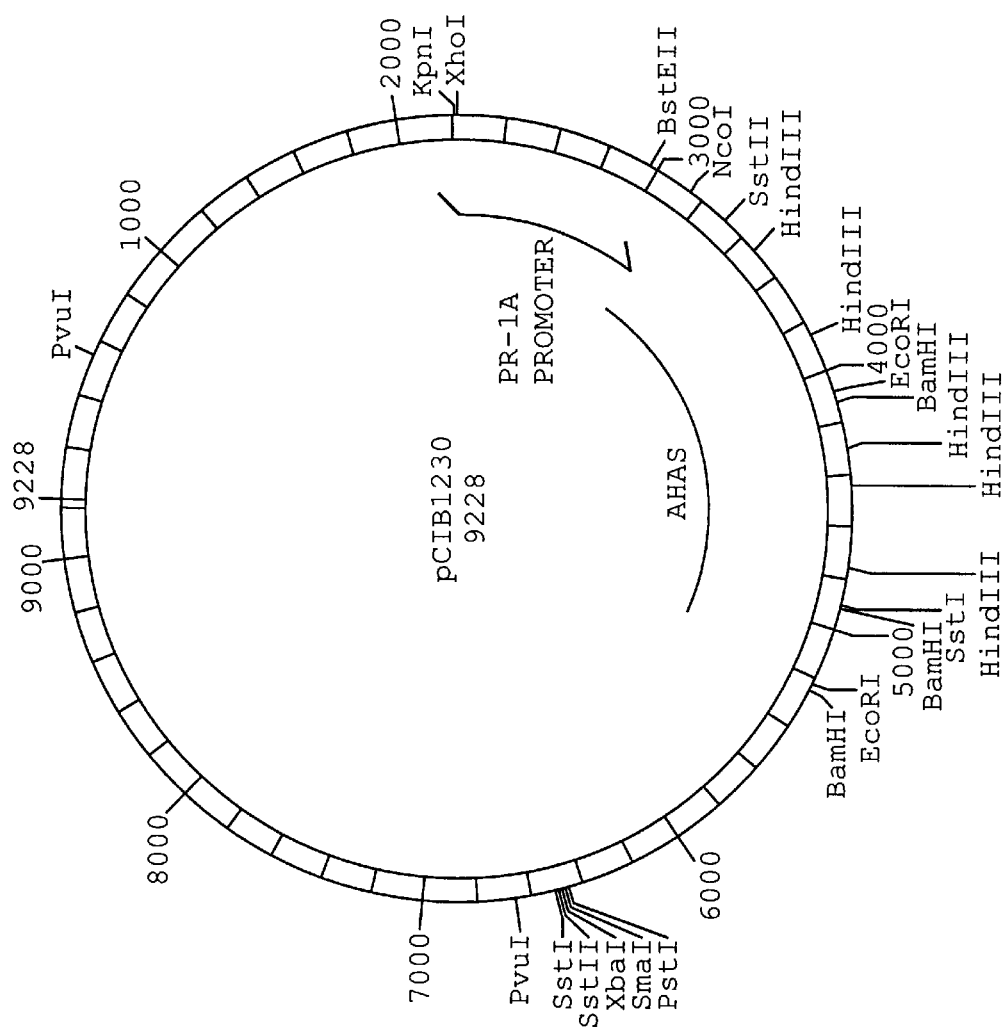
FIG. 33. Restriction endonuclease map of pCIB1230. A 3.3 kb NcoI/XbaI fragment from pCIB1208 is cloned into pCIB269 which had been restricted with NcoI and XbaI to remove the GUS gene.
Figure 34:
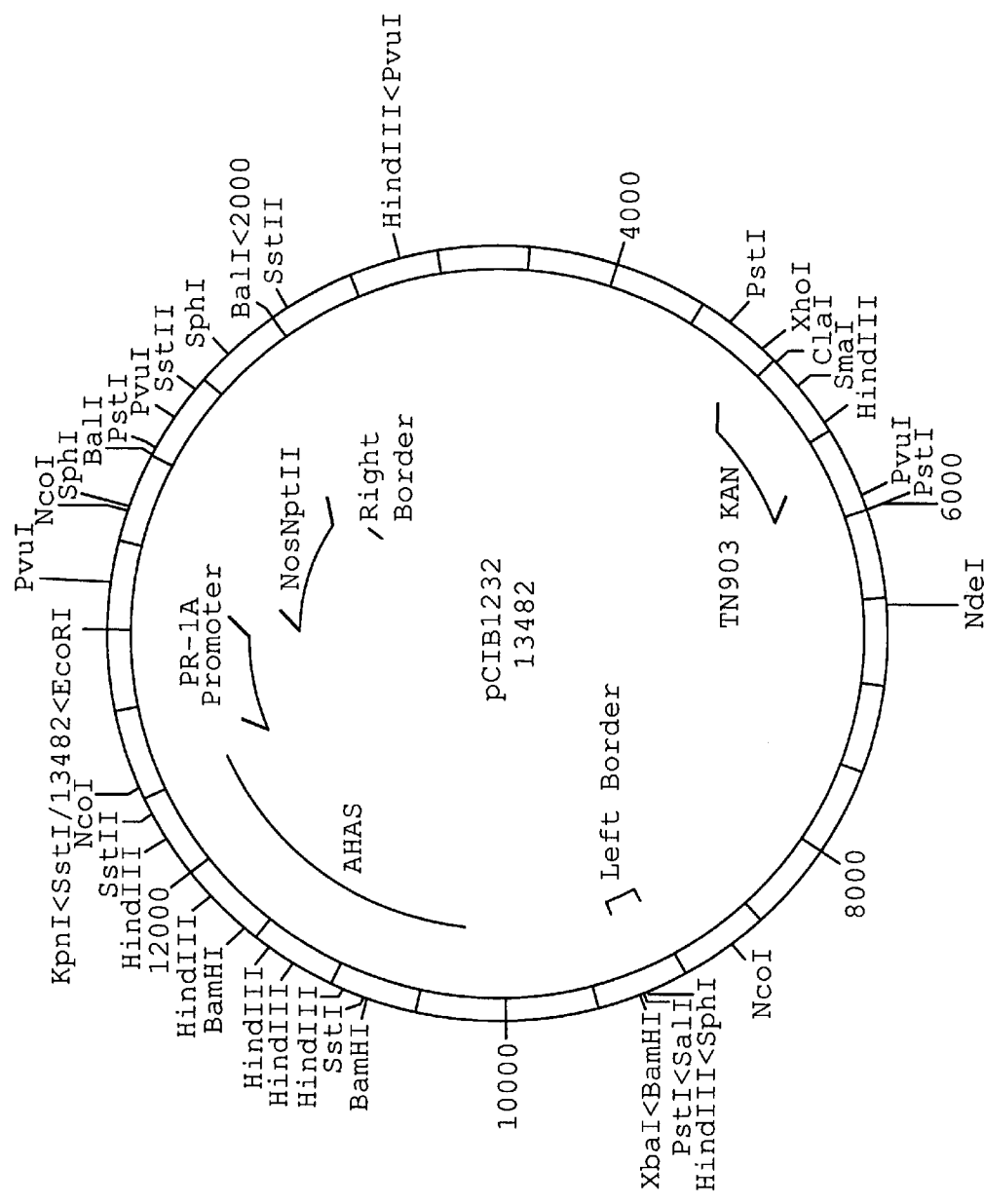
FIG. 34. Restriction endonuclease map of pCIB1232. A 4.2 kb KpnI/XbaI fragment is isolated from pCIB 1230 and ligated into pCIB200 which had been restricted with KpnI and XbaI.
Figure 35:
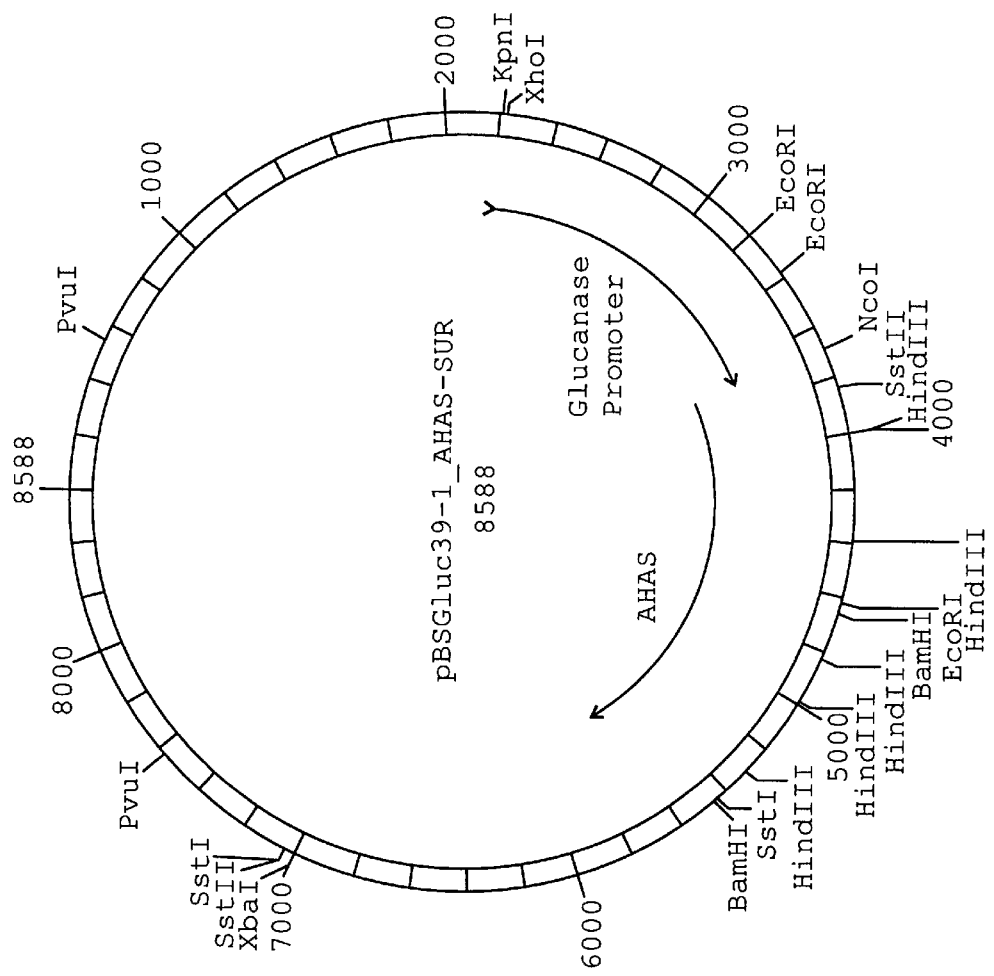
FIG. 35. Restriction endonuclease map of pBSGluc39.1/AHAS-SuR, constructed from a NcoI/XbaI fragment of pBSGluc39.1/GUS and a 3.3 kb NcoI/XbaI fragment from pCIB1208 containing the AHAS gene.
Figure 36:
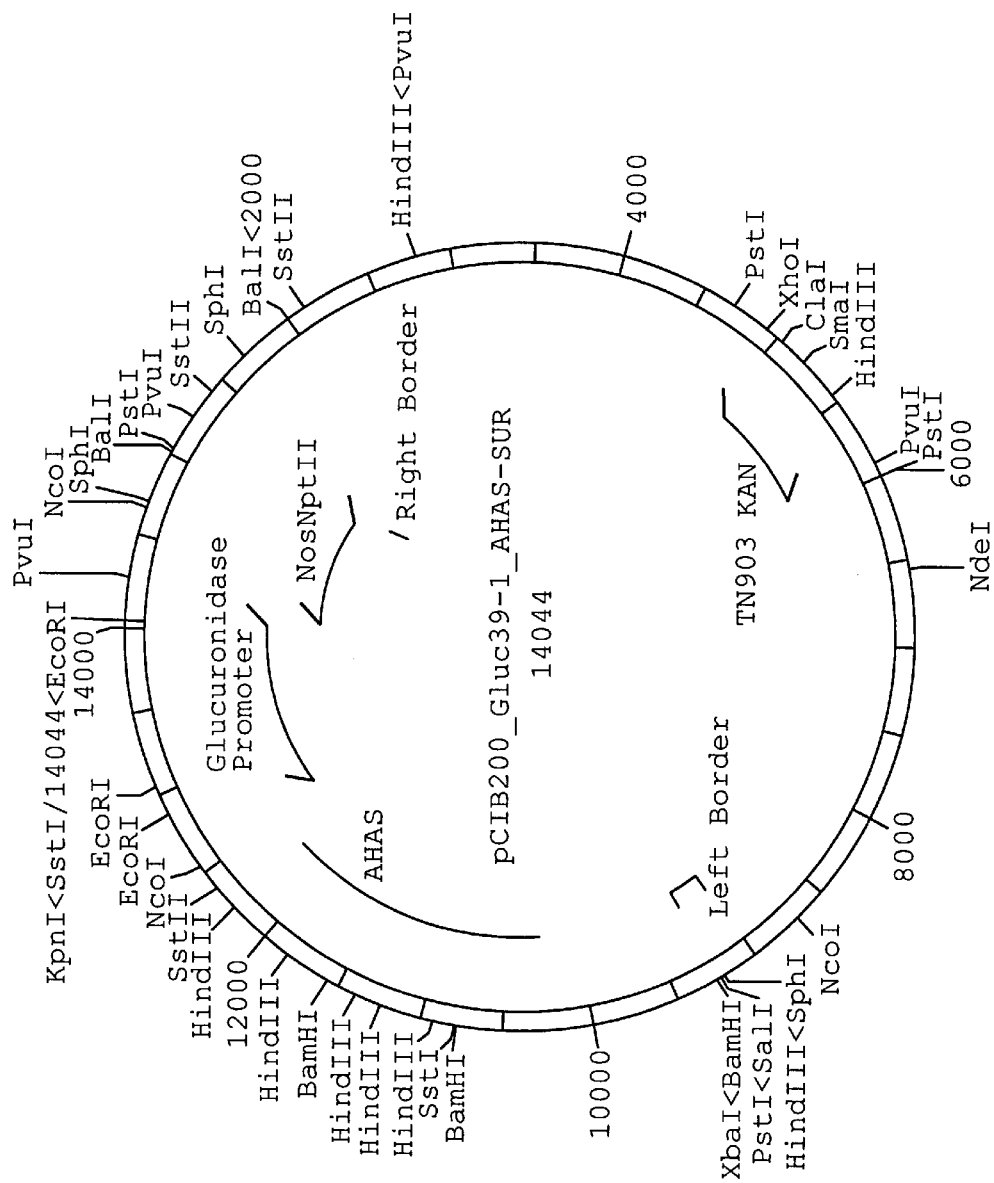
FIG. 36. Restriction endonuclease map of pCIB200/Gluc39.1-AHAS-SuR. A KpnI/XbaI fragment containing the β-glucanase promoter and the AHAS gene is isolated from pBSGluc39.1/AHAS-SuR and ligated into pCIB200 restricted with KpnI and XbaI.
Figure 37:
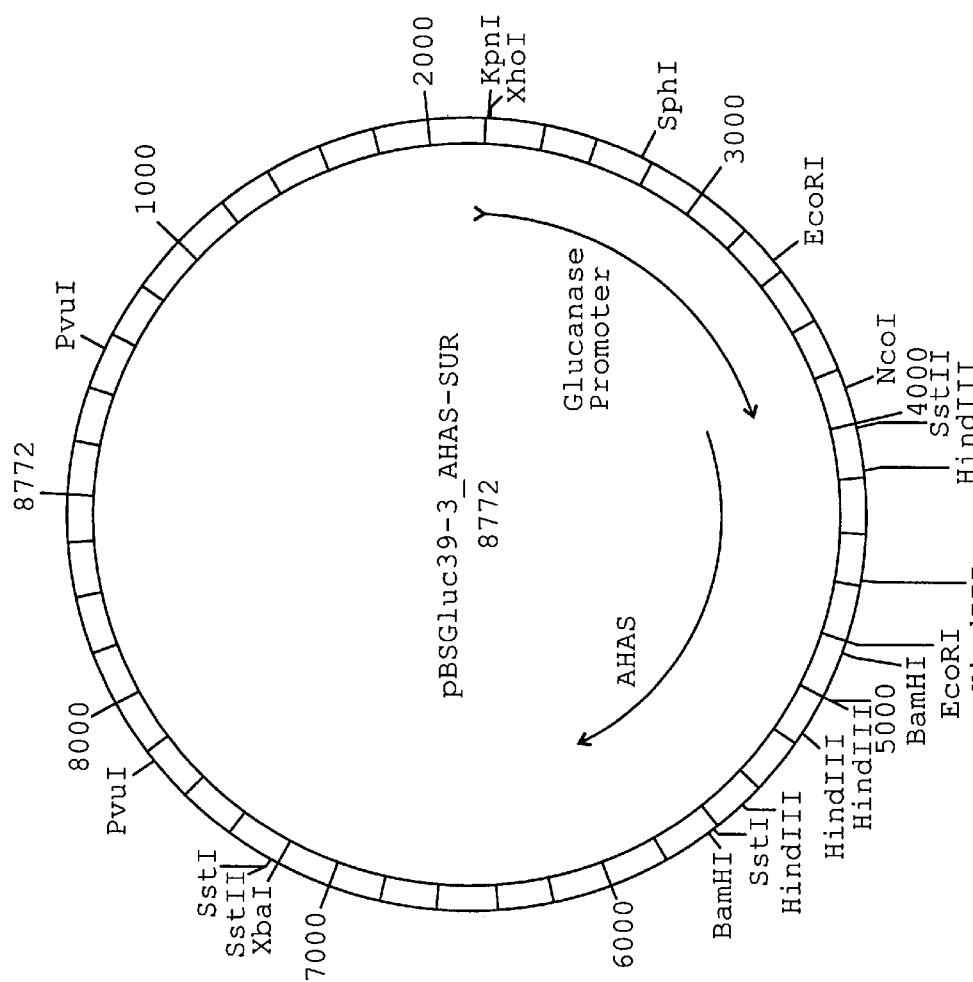
FIG. 37. Restriction endonuclease map of pBSGluc39.3/AHAS-SuR, constructed from a NcoI/XbaI fragment of pBSGluc39.3/GUS and a 3.3 kb NcoI/XbaI fragment from pCIB1208 containing the AHAS gene.
Figure 38:
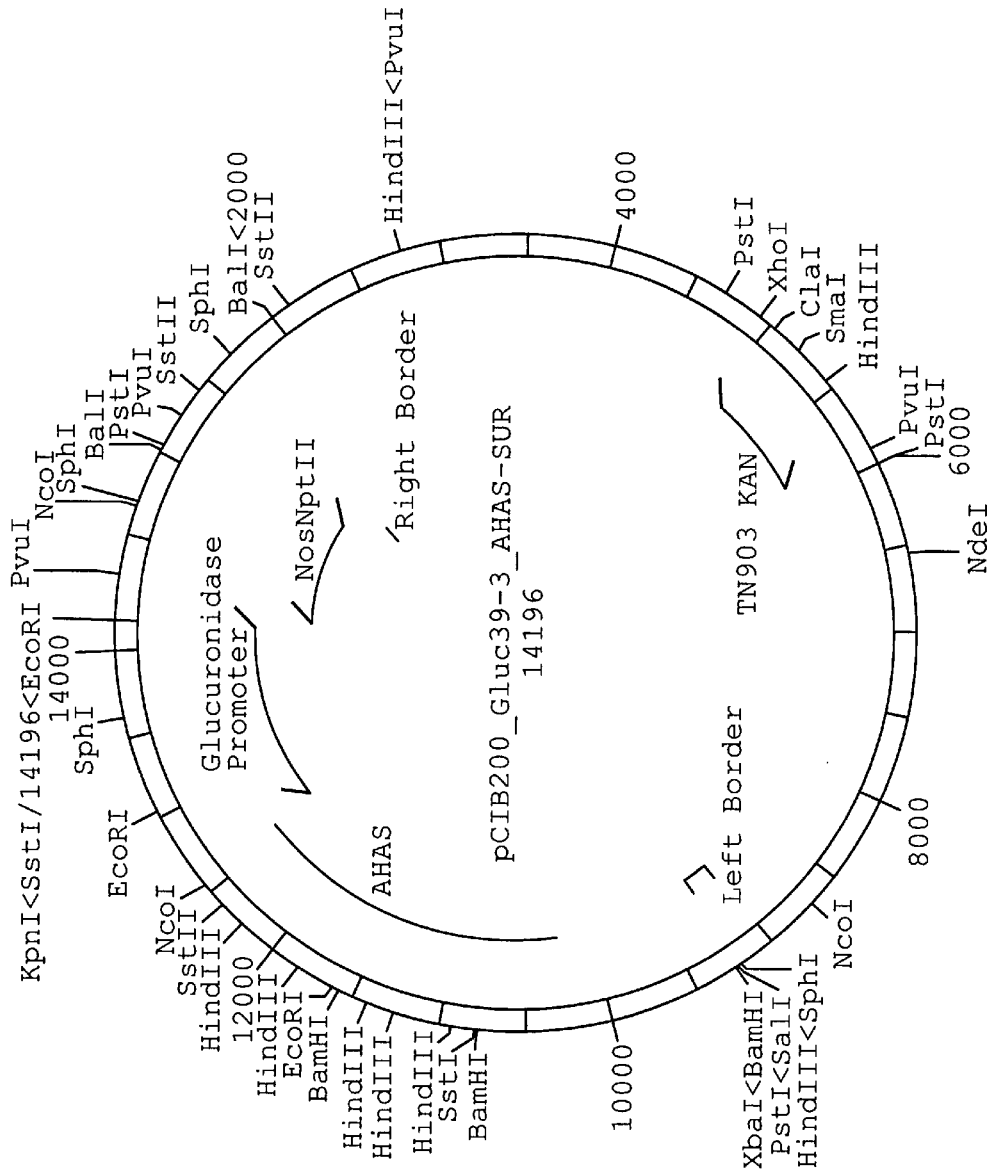
FIG. 38. Restriction endonuclease map of pCIB200/Gluc39.3-AHAS-SuR. A KpnI/XbaI fragment containing the β-glucanase promoter and the AHAS gene is isolated from pBSGluc39.3/AHAS-SuR and ligated into pCIB200 restricted with KpnI and XbaI.

Preparation of a Chimeric Gene in a Hygromycin Vector pCIB269 is digested with XhoI and EcoRI and the 3023 bp fragment carrying the PR-1a promoter linked to the GUS gene with a nos 3' end is isolated following electrophoresis on a 1.0% low gelling agarose TAE gel. This fragment is then converted to a XhoI/SalI fragment by ligation with a EcoRI/SalI adapter having the sequence 5'-AATTCGTCGACG-3'. The XhoI/SalI fragment is ligated into SalI digested pCIB712 (Rothstein, S. J. et al., supra) to create pCIB219, see FIG. 14.

EXAMPLE 30

Preparation of pCIB200/PR1-BT

A. Ligation with pCIB200

The plasmid pCIB1004 (see below) is digested with SphI, phenol extracted, ethanol precipitated and resuspended. An oligonucleotide with the sequence 5'-CCGGTACCGGCATG-3' (SEQ ID No. 56) is synthesized, purified, kinased, and ligated to the SphI digested plasmid pCIB 1004. After ligation, the ligase is inactivated and the DNA digested with KpnI. This DNA is run on a 0.8% low gelling temperature agarose gel. The plasmid pCIB200 (Example 28, part C) is digested with KpnI and treated with calf-intestinal alkaline phosphatase and run on a 0.8% low gelling temperature agarose gel. The band containing the pCIB200 vector and the band containing the PR-1 5' flanking sequence/BT fusion are mixed and the DNA ligated to form the plasmid pCIB200/PR1-BT.

B. Preparation of pCIB1004

The plasmid pCIB10/35Bt(607) is digested with NcoI and BamHI and run on a 0.8% low gelling temperature agarose gel. The plasmid pCIB269 (Example 28, part A) is digested with NcoI and XhoI and run on a 0.8% low gelling temperature agarose gel. The plasmid pCIB710 (Rothstein, S. J. et al., supra) is digested with SalI and BamHI and run on a 0.8% low gelling temperature agarose gel. The band with the SalI and BamHI digested vector containing a CaMV 35S promoter 3' end cloned into pUC19, the band containing the BT gene and the band containing the PR-1 5' flanking region are excised, mixed and the DNA ligated to form the plasmid pCIB1004.

C. Preparation of pCIB10/35Bt(607)

pCIB10/35Bt(607), a deleted protoxin gene containing a sequence coding for approximately 607 amino acids, is prepared from plasmid pCIB10/35Sbt, a plasmid containing the protoxin gene from *Bacillus thuringiensis* endotoxin. *E. coli* MC1061 containing pCIB10/35Sbt was deposited at the American Type Culture Collection, ATCC No. 67329, Feb. 27, 1987. A deleted protoxin gene is made by introducing a BamHI cleavage site (GGATCC) following nucleotide 1976 in the BT gene sequence. This is done by cloning the BamHI fragment containing the protoxin sequence from pCIB10/35Sbt into mp18, and using standard oligonucleotide mutagenesis procedures. After mutagenesis, double-standard replicative form DNA is prepared from the M13 clone, which is then digested with BamHI. The approximately 1.9 kb fragment containing the deleted protoxin gene is inserted into BamHI-cleaved pCIB10/710. The resulting plasmid is selected for on kanamycin. A detailed description for the preparation is given in U.S. patent application Ser. No. 122,109, filed Nov. 18, 1987, which is incorporated by reference herein in its entirety.

EXAMPLE 31

Preparation of pCIB1233 (pCIB200/PR1-AHAS)

A. Ligation with pCIB200

The plasmid pCIB200 is digested with KpnI and XbaI and run on a 0.8% low gelling temperature agarose gel. The plasmid pCIB1216 is digested with KpnI and XbaI and run on a 0.8% low gelling temperature agarose gel. The ~4.3 kb band containing the PR-1 5' flanking sequence fused to the AHAS coding sequence and the band containing the pCIB200 vector are excised, mixed and the DNA ligated to form pCIB1233.

B. Preparation of pCIB1216

The plasmid pCIB269 (Example 28, part A) is digested with XbaI and NcoI and run on a 0.8% low gelling temperature agarose gel. The plasmid pCIB1207 (see below) is digested with XbaI and NcoI and run on a low gelling temperature agarose gel. The band containing the bluescript vector with the PR-1 5' flanking sequence and the 3.3 kb band containing the AHAS coding sequence are excised, mixed and the DNA ligated to form the plasmid pCIB 1216.

C. Preparation of Plasmid pCIB1207 Containing the Arabidopsis AHAS Gene

Total plant DNA is isolated from 5 weeks old *Arabidopsis thaliana* ecotype Columbia. 250 g of this DNA is digested with 4000 units of the restriction enzyme XbaI for 4 hours. The digest is fractionated by electrophoresis on a 0.8% agarose gel. The DNA fragments between 6.5 kb and 4.36 kb (based upon HindIII-digested lambda DNA size markers) are isolated from the gel using NA-45 DEAE membrane (Schleicher and Schuell, Keene, N.H., USA) following the manufacturer's recommended procedures. XbaI digested and phosphatase-treated lambda ongC (longC) arm preparation is obtained from Stratagene Cloning Systems (La Jolla, Calif., USA). 0.1 g of the Arabidoosis XbaI insert DNA is ligated to 1.0 g of the longC arms according to procedures recommended by Stratagene. 2.5 l of the ligation reaction is packaged in lambda phage heads using the Gigapack Plus kit (Stratagene Cloning Systems) following procedures recommended by the manufacturer. The activity of the library is titered on *E. coli* VCS257 (Stratagene Cloning Systems).

50 g of pE16/8-c4 plasmid DNA (J. Polaina, Carlsberg Res. Comm. 49, 577–584) are digested with EcoRI, and the digest products are resolved on a 0.8% agarose gel. The 2 kb EcoRI fragment containing the coding sequence for the yeast AHAS gene is isolated from the gel using NA45 DEAE membrane following procedures recommended by the manufacturer. Radiolabeled probes to the 2 kb fragment are synthesized on the day of the hybridization reaction with the random priming reaction using Prime Time kit (International Biotechnologies Inc., New Haven, Conn., USA), following procedures recommended by the manufacturer.

250,000 recombinant phages are plated on VCS257. Duplicate membrane lifts of the phage plaques are made using Colony/Plaque Screen membranes (NEN Research Products, Du Pont, Boston, Mass., USA) following procedures recommended by the manufacturer. The membranes are prehybridzed in LS hybridization buffer, then transferred to 150 ml of fresh LS hybridization buffer containing 0.25 g of $^{32}$P-labelled yeast AHAS gene probe prepared as described above. The membranes are incubated for 16 hours at 42° C. with gentle shaking, washed twice at room temperature with 2× SSC for 15 minutes per wash, washed three times at 42° C. in LS wash buffer (25% formamide, 5× SSC, 1% SDS) for 2 hours per wash, and washed twice at in rinse buffer (0.1× SSC, 0.1% SDS) for 30 minutes per wash. The membranes are mounted and fluorographed with Cronex Lightening Plus Sceens (Du Pont, Wilmington, Del., USA) and XAR-5 film (Kodak). The plaques from regions of the plates that gave positive film signals on both membrane lifts are picked and replated at a low density of 300 plaques per 150 mm plate, and the screening process is repeated until single hybridizing plaques are isolated.

Miniprep of phage DNA from the plaque-purified phage is carried out following procedures accompanying the LambdaSorb Phage Adsorbent kit (Promega, Madison, Wis., USA). The phage DNA is cut with restriction enzyme XbaI and the 5.8 kb insert fragment is cloned into the XbaI site of pBS(-) plasmid (Stratagene Cloning Systems). The identity of the cloned fragment with the XbaI fragment containing the Arabidopsis AHAS gene is verified by comparing its restriction map and DNA sequence with those published for the gene by Haughn et al., *Mol. Gen. Genet*. 211: 266 (1988), and Mazur et al., *Plant Physiol*. 85: 1110 (1987). This plasmid is designated pCIB1207.

EXAMPLE 32

Preparation of pCIB1232 (pCIB200/PR1-AHAS-SuR)

A. Ligation with pCIB200

The plasmid pCIB200 (Example 28, part C) is digested with KpnI and XbaI and run on a 0.8% low gelling temperature agarose gel. The plasmid pCIB1230 is digested with KpnI and XbaI and run on a 0.8% low gelling temperature agarose gel. The ~4.3 kb band containing the PR-1 5' flanking seqeunce fused to the AHAS-SuR coding sequence and the band containing the pCIB200 vector are excised, mixed and the DNA ligated to form pCIB1232.

B. Preparation of pCIB1230

Plasmid pCIB 1208 (see below) is digested with XbaI and NcoI and the fragments are separated by electrophoresis on a 1× TAE 0.8% low gelling temperature agarose gel. The plasmid pCIB269 (Example 28, part A) is digested with NcoI and XbaI and run on a 1× TAE 0.8% low gelling temperature agarose gel. The pCIB269 fragment containing the bluescript vector and the PR-1 promoter and the 3.3 kb fragment containing the mutated AHAS gene (identified by cross homology and by restriction fragment analysis with the gene decribed Mazur et al., *Plant Physiol*. 85: 1110–1117 (1987)) are excised, melted and ligated together to create a clone designated as pCIB1230.

C. Preparation of pCIB1208

A genomic DNA library is constructed as described in Example 31, part C using DNA isolated from Arabidoysis plants selected for resistance to sulfonylurea herbicide as described by Haughn and Somerville, *Mol. Gen. Genet*. 204: 430–434 (1986). Plaques containing genes encoding acetohydroxy acid synthase (AHAS) are identified by cross hybridization with a yeast acetohydroxy acid synthase gene probe (see Example 31, part C). The recombinant DNA is subcloned into Bluescript (Stratagene) creating a clone designated as pCIB1208. This plasmid contains a gene encoding a mutated acetohydroxyacid synthase that is resistant to inhibition by sulfonylurea herbicides.

EXAMPLE 33

Isolation of a Genomic Clone Encoding the Basic Fonn of β-1,3-Glucanase (Glucan Endo-1,3-β-glucosidase) from *Nicotiana Tabacum*

High molecular weight DNA is prepared from leaves of *Nicotiana tabacum* cv. Havana 425 by the CETAB procedure (Murray and Thompson, *Nucleic Acid Res.* 8: 4321 (1980)). 100 g of DNA is digested to completion with SacI. This DNA is separated by electrophoresis on a 0.8% agarose gel. The region of the gel corresponding to a molecular weight range of 3 to 7 kb is cut into 6 equally sized strips and the DNA is electroeluted from these strips and precipitated as separate fractions. The DNA is resuspended and an aliquot from each fraction is run on an agarose gel and analyzed by Southern blotting. The fraction that contains DNA which hybridizes to a β-1,3-glucanase cDNA probe (Shinshi, H. et al., *Proc. Natl. Acad. Sci. USA* 85: 5541–5545 (1988)) is pooled and used in constructing libraries.

The cloning vector lambdaOngC purchased from Stratagene Corp. is digested with SacI. 1 g of this DNA is mixed with 0.1 g of the SacI digested tobacco DNA, and the DNA is ligated with T4 DNA ligase according to the manufacturer's suggestions. The ligated DNA is then packaged into phage particles using an in vitro packaging procedure according to Stratagene. The phages are plated with bacteria as suggested in the lambda manual. About 75,000 plaques are screened using a 32-P labeled β-1,3-glucanase cDNA probe. 11 positive plaques are identified. These plaques are purified by successive rounds of plating and screening.

DNA is isolated from the purified clones and the clones are analyzed by restriction digestion using HindIII, EcoRI, and SacI. The clones are of two types, one represented by the clone 39.1 and the other represented by the clone 39.3. The 4.5 and 4.7 kb inserts in clone 39.1 and 39.3, respectively, are subcloned into the bluescript plasmid digested with SacI, and the subclones pBSGluc39.1 (SacI fragment derived from the lambda clone 39.1) and pBSGluc39.3 (SacI fragment derived from the lambda clone 39.3) are isolated. The sequence of the DNA in the SacI fragments contained in the subclones pBSGluc39.1 and pBSGluc39.3 is determined by DNA sequencing and shown in SEQ ID Nos. 5 and 6, respectively. The coding sequence is found and a large intervening sequence is located near the 5' end of the coding sequence.

EXAMPLE 34

Identification of the Transcriptional Start Site for the β-1,3-Glucanase Gene

A. Primer Extension Mapping

A synthetic DNA primer is synthesized which is complementary to bases 2399 to 2416 and used in primer extension experiments as described in Example 6. The RNA for these experiments is isolated from *Phytophthora parasitica* var. nicotiana infected tobacco. The primer extension products are run against a molecular weight standard in which the labeled primer is used in dideoxy DNA sequencing reactions with the subclone pBSGluc39.1 used as a template. Extension products are identified, after gel electrophoresis and autoradiography as described in Example 6, that correspond to positions 1432, 1446 and 1447 of the β-1,3-glucanase 39.1 sequence, SEQ ID No. 5. Since a large intron exists between positions 1554 and 2345 of the pBSGluc39.1 sequence, the molecular weight ladder might not reflect the correct molecular weight of the extension products. Therefore, a second primer extension mapping experiment is conducted using a primer that is complementrary to positions 1530 to 1547. Using this primer, three 5' ends of the glucanase mRNA are mapped to A residues at positions 1434, 1448 and 1449.

B. S1 Nuclease Mapping

A synthetic oligonucleotide complementary to positions 1415 to 1504 is synthesized for use as a probe in S1 nuclease mapping. The oligonucleotide is kinased at the 5' end using 32P-ATP and T4 polynucleotide kinase according to the supplier's recommendation. Following phenol extraction and ethanol precipitation the labeled oligonucleotide is resuspended in formamide hybridization buffer (see Example 7) at a concentration of about 2 nM. The RNA used in these experiments is isolated from *Phytophthora parasitica* infected tobacco as in the previous example. S1 mapping is conducted on this RNA using the labeled oligonucleotide as described in Example 7. After gel electrophoresis three bands are detected that correspond to positions 1434, 1448 and 1449 on the pBSGluc39.1 DNA sequence.

C. Determination of the Transcriptional Start Site

Primer extension and S1 nuclease mapping procedures both place the 5' ends of the mRNA at positions 1434, 1448 and 1449. Therefore these sites, which are all adenine residues, correspond to the transcriptional start site of the β-1,3-glucanase gene.

EXAMPLE 35

Preparation of pBSGluc39.1/GUS

Oligonucleotides with the sequences

A) 5'-GTTTATGTGAGGTAGCCATGGTGGG-AAGACTTGTTGGG-3' (SEQ ID No. 57); and

B) 5'-GATCGCGGTACCGAGCTCCTCTAGGGGG-CCAAGG-3' (SEQ ID No. 58) are synthesized, purified and used in a polymerase catalyzed reaction (PCR) according to the supplier's directions (Perkin Elmer Cetus, DNA thermal cycler; and Perkin Elmer Cetus, GeneAmp Reagent Kit) to amplify a 1494 bp fragment of DNA from pBSGluc39.1. The oligos are designed to add a KpnI site immediately 5' to the SacI site at base-pair 1 of the 39.1 glucanase sequence and to generate a new NcoI site at base-pair 1462. The DNA derived from the PCR amplification procedure is phenolchloroform extracted and ethanol precipitated. The DNA is resuspended and digested with both NcoI and KpnI and run on a 0.8% low-gelling temperature agarose gel. The 1462 bp band is excised and used in the following ligation. The plasmid pBS-GUS1.2 (Example 28, part B) is digested with NcoI and KpnI and run on a 0.8% agarose gel and the band containing the vector is excised. The band containing the pBS-GUS1.2 vector and the 1462 bp band from the PCR reaction are ligated and used to transform *E. coli*. Positive colonies are picked and screened for those that contain the 1462 bp insert. The plasmids containing inserts are putative clones of pBSGluc39.1/GUS, however, since the mutation rate in this procedure is relatively high (~1/1000 bases), several clones have to be sequenced throughout the 1462 bp fragment. One clone which has the expected sequence is chosen as the clone pBSGluc39.1/GUS.

EXAMPLE 36

Preparation of pBSGluc39.3/GUS

Oligonucleotides with the sequences

A) 5'-GTTTATCTGAGGTAGCCATGGTGAGAA-GACTTGTTGGA-3' (SEQ ID No. 59); and

B) 5'-GATCGCGGTACCGAGCTCCCTTGGGGGG-CAAG-3' (SEQ ID No. 60) are synthesized, purified and used in a PCR reaction to amplify a 1677 bp fragment from pBSGluc39.3. The oligonucleotides are designed to introduce a new KpnI site immediately adjacent to the SacI site at position 1 of the glucanase 39.3 sequence and a new NcoI site at position 1646. The DNA from the PCR amplification is phenol/chloroform extracted, ethanol precipitated, resuspended, digested with both NcoI and KpnI and run on a 0.8% low-gelling temperature agarose gel. The band at 1646 bp is excised and used in the following ligation. pBS-GUS1.2 is digested with NcoI and KpnI and run on a 0.8% low gelling temperature agarose gel. The band containing the vector is excised, mixed with the 1646 bp band from the PCR reaction and ligated to form the plasmid pBSGluc39.3/GUS. As before, several putative plasmids are isolated and sequenced and one with the expected sequence is picked as the plasmid pBSGluc39.3/GUS.

EXAMPLE 37

Preparation pCIB200/Gluc39.1-GUS and pCIB200/Gluc39.3-GUS

A. pCIB200 (Example 28, part C) is digested with KpnI and XbaI and run on a 0.8% low gelling temperature agarose gel. The plasmid pBSGluc39.1/GUS (Example 35) is digested with KpnI and XbaI and the fragments are separated on a 0.8% low gelling temperature gel. The bands containing the pCIB200 vector and the KpnI-XbaI band containing the 5' flanking sequence of the glucanase 39.1 gene fused to the GUS gene are excised and the DNA ligated to form the plasmid pCIB200/Gluc39.1-GUS.

B. Likewise, plasmid pBSGluc39.3/GUS (Example 36) is digested and ligated with digested pCIB200 to form the plasmid pCIB200/Gluc39.3-GUS.

EXAMPLE 38

Preparation of pCIB200/Gluc39.1-BT and pCIB200/Gluc39.3-BT

A. pCIB200/Gluc39.1-BT

The plasmid pBSGluc39.1/GUS is digested with KpnI and NcoI and run on a 0.8% low gelling temperature agarose gel. The plasmid pCIB1004 (Example 30, part B) is digested with KpnI and NcoI and run on a 0.8% low gelling temperature agarose gel. The plasmid pCIB200 (Example 28, part C) is digested with KpnI, dephosphorylated using calf-intestine alkaline phosphatase and run on a 0.8% low gelling temperature agarose gel. The band containing the pCIB200 vector, the band containing the glucanase 5' flanking region, and the band containing the BT gene are excised, mixed together and ligated to form the plasmid pCIB200/Gluc39.1-BT.

B. pCIB200/Gluc39.3-BT

Likewise, plasmid pBSGluc39.3/GUS is digested and ligated with digested pCIB1004 and digested pCIB200 to form the plasmid pCIB200/Glu39.3-BT.

EXAMPLE 39

Preparation of pCIB200/Gluc39.1-AHAS and pCIB200/Gluc39.3-AHAS

A. Ligation with pCIB200

The plasmid pBSGluc39.1/AHAS is digested with KpnI and XbaI and run on a 0.8% low gelling temperature agarose gel. The plasmid pCIB200 (Example 28, part C) is digested with KpnI and XbaI and run on a 0.8% low gelling temperature agarose gel. The band containing the glucanase/AHAS fusion and the band containing the pCIB200 expression vector are excised, mixed and the DNA ligated to form the plasmid pCIB200/Gluc39.1-AHAS.

Likewise, plasmid pBSGlu39.3/AHAS is digested and ligated with digested pCIB200 to form the plasmid pCIB200/Glu39.3-AHAS.

B. Preparation of plasmids pBSGlu39.1/AHAS and pBSGlu39.3/AHAS

The plasmid pBSGluc39.1/GUS (Example 35) is digested with NcoI and XbaI and run on a 0.8% low gelling temperature agarose gel. The plasmid pCIB1207 (Example 31, part C) is digested with NcoI and XbaI and run on a 0.8% low gelling temperature agarose gel. The band containing the glucanase 5' flanking sequence and vector and the band containing the AHAS coding sequence are excised, mixed and the DNA ligated to produce the plasmid pBSGluc39.1/AHAS.

Likewise, plasmid pBSGlu39.3/GUS (Example 36) is digested and ligated with digested pCIB1207 to form the plasmid pBSGlu39.3/AHAS.

EXAMPLE 40

Preparation of pCIB200/Gluc39.1-AHAS-SuR and pCIB200/Gluc39.3-AHAS-SuR

A. Ligation with pCIB200

The plasmid pBSGluc39.1/AHAS-SuR is digested with KpnI and XbaI and run on a 0.8% low gelling temperature agarose gel. The plasmid pCIB200 (Example 28, part C) is digested with KpnI and XbaI and run on a 0.8% low gelling temperature agarose gel. The band containing the glucanase/AHAS-SuR fusion and the band containing the pCIB200 expression vector are excised, mixed and the DNA ligated to form the plasmid pCIB200/Gluc39.1-AHAS-SuR.

Likewise, plasmid pBSGluc39.3/AHAS-SuR is digested and ligated with digested pCIB200 to form the plasmid pCIB200/Gluc39.1-AHAS-SuR.

B. Preparation of plasmids pBSGluc39.1/AHAS-SuR and pBSGluc39.3/AHAS-SuR

The plasmids pBSGluc39.1/GUS (Example 35) and pBSGluc39.3/GUS (Example 36) are digested with NcoI and XbaI and the restriction fragments are separated on a 1× TAE 0.8% low gelling temperature agarose gel. pCIB1208 (Example 32, part C) is digested with XbaI and NcoI and the 3.3 kb fragment containing the mutated AHAS gene (sulfonylurea herbicide resistant, SuR) is isolated by agarose gel electrophoresis. The fragments containing the glucuronidase promoter and pBS vector are excised, melted and ligated with the AHAS fragment to create clones designated pBSGluc39.1/AHAS-SuR and pBSGluc39.3/AHAS-SuR, respectively.

EXAMPLE 40A

Cloning of cDNAs Corresponding to SAR CHX-independent Genes from Tobacco

A number of cDNAs were cloned by differential screening from cDNA prepared from induced and non-induced tissue. The induced cDNA was prepared from tobacco leaves which had been pre-treated with methyl benzo-1,2,3-thiadiazole-7-carboxylate (BTH), whereas the non-induced cDNA was prepared from tissue which had not been pre-treated with BTH. cDNA libraries were prepared in λZAP II (STRATAGENE). A standard differential screening technique was used. Plaques carrying induced cDNA were plated at low density and transferred to two sets of hybridization filters. Known SAR gene sequences (from previous cloning experiments) were hybridized to the first filter and unreduced cDNA to the second. The second filter was then stripped and hybridized with induced cDNA. Plaques which hybridized with the induced cDNA probe, but not with the unreduced cDNA probe or with known SAR gene sequences were potential novel SAR genes and were picked directly for further analysis. Plating had been at a plaque density which was sufficiently low to enable these plaques to be picked as nearly pure plaques. Multiple candidates for each plaque were in vivo excised, according to the manufacturer's recommended conditions, for further screening by Northern hybridization to RNA isolated from either untreated or BTH-treated tobacco plants. Individual clones chosen from the secondary screen were further analyzed by Northern hybridization to RNA isolated from tobacco plants which had been pre-treated with salicylic acid (3 mM), IAN (1 mM), and BTH (1 mg/ml), all in the presence or absence of cycloheximide (CHX; 1 mg/ml). Inducer pre-treatments were done at 2 h, one day, and eight days before the isolation of RNA, whereas CHX treatment was done at one day before isolation of RNA. Four cDNAs were found induced in a protein synthesis independent fashion. The genes corresponding to these cDNAs have been designated 1.1.1, 11.3.8, 11.30.13, and 1.4.3 (see SEQ. ID Nos. 99–103) and are likely signal transducers of the SAR response. Gene 1.4.3 has previously been disclosed as a thioredoxin (Brugidou et al., Mol. Gen. Genet. 238: 285–293 (1993)). However, this is the first disclosure of the gene's likely involvement in the systemic acquired response. Two cDNAs were found to be expressed in a protein synthesis dependent fashion. These were designated 66B1 and 14.22.3 and are listed as SEQ. ID Nos. 104 and 105.

EXAMPLE 40B

Cloning of cDNAs Corresponding to SAR CHX-independent Genes from Arabidopsis

Total RNA was isolated from the following Arabidopsis lines: (1) untreated, (2) INA treated (0.25 mg/ml), (3) CHX treated (1 mg/ml), and (4) INA & CHX. Treatments were made 1 day before RNA isolation. RNA thus isolated was was subjected to "differential display" using the protocol described by Liang and Pardee, Science 257: 967–971 (1992). Amplified fragments which were found in both the INA as well as the INA & CHX treated RNA samples were gel-purified as used as probes on Northern blots carrying similarly induced RNA samples. Fragments for which Northern hybridization confirmed the induction profile apparent from differential display were subcloned into a plasmid vector. Using the cloned fragment it was possible to isolate near full-length cDNAs from a cDNA library produced by BTH induction (see Example 54). The cDNA cDPA2 was cloned using this technique and is induced by the SAR response in a protein synthesis independent fashion. Its sequence is listed in Seq. ID No. 106.

E. Isolation of Novel cDNA Clones Encoding PR Proteins

This group of Examples describes the isolation of novel cDNA clones encoding plant PR proteins. It is divided into 3 sections: Section A covers the construction of libraries used in the isolation of clones. Section B covers the identification and purification of clones thus isolated. Section C covers the development of a novel cDNA cloning technology. We have found that cDNAs isolated from uninoculated tissue of inoculated plants express messenger RNAs that encode proteins which are involved in manifestation of the plant's systemic acquired resistance to a variety of plant pathogens, such as bacteria, viruses and fungi. These are distinguished from those mRNAs expressed in inoculated tissue, which are often related to generalized stress conditions, such as pathogen attack and cell death. We also have found that this same set of systemic acquired resistance genes is also involved in the expression of proteins in chemically induced resistance.

1. Construction of cDNA Libraries

EXAMPLE 41

Preparation of cDNA Library From TMV-Infected Tobacco Leaves

*Nicotiana tabacum* cv. Xanthi-nc leaves are infected with tobacco mosaic virus and harvested five days post-infection. Total RNA is prepared as described above and poly A+RNA is isolated using standard techniques. A cDNA library is constructed using this poly A+RNA in the Lambda ongC cloning vector (Stratagene) essentially as described (Gubler, U. and Hoffman, B. J., Gene 25: 263 (1983)).

EXAMPLE 42

Preparation of a cDNA Library From Uninfected Leaves of TMV Inoculated Tobacco Using a Novel cDNA Cloning Vector pCGN1703, a plasmid cDNA cloning vector of the vector-primer type described by Okayama and Berg, Mol. and Cell Biol. 2:161–170 (1982), is constructed as an improved vector to simplify the cloning process and allow easy shuttling of libraries into a phage vector, as well as to provide additional functions that are outside the present use.

A. Construction of the pCGN1703 Cloning Vector

Bluescribe M13- (Stratagene, Inc.) is used as a starting plasmid. The BamHI site is deleted by BamHI digestion and mungbean nuclease treatment, followed by ligation with T4

DNA ligase to yield pCGN1700. This plasmid is digested with EcoRI and SacI and then ligated with a double stranded synthetic polylinker created by annealing two oligonucleotides of the sequence

[oligo #47] 5'-AATTTCCCGGGCCCTCTAGACT-GCAGTGGATCCGAGCT-3' (SEQ ID No. 61)

[oligo #46] 5'-CCGATCCACTGCAGTCTAGAGGG-CCCGGGA-3' (SEQ ID No. 62) The resulting plasmid thus has additional restriction sites for SmaI, ApaI, XbaI, PstI, and BamHI, and is designated pCGN1702. Note that the EcoRI site is not reconstructed. pCGN1702 is digested to completion with HindIII and made blunt ended with T4 polymerase. The resultant DNA is subjected to partial digestion with PvuII and then ligated with T4 DNA ligase. A transformant is selected that had deleted the 214 bp HindIII-PvuII fragment which included the lac operator-promoter region; this plasmid is designated pCGN1703. Use of vector-primer plasmids such as pCGN1703 is described previously (D. Alexander, *Methods in Enzymology* 154:41–64(1987)). As described in the ADDENDUM section of that work, the present vector is a monomer vector. The T-tracts used to prime cDNA synthesis are present on both ends of the vector during the reverse transcriptase and terminal transferase (G-tailing) reactions, and the linker DNA used to circularize the final products of cDNA cloning with pCGN1703 have the generalized structure as follows: T7 promoter, a multiple cloning site (SmaI, ApaI, XbaI, PstI, BamHI, NotI, EcoRI, SacI), C:G homopolymer tract (10–15 residues), cDNA insert (5'-3' of mRNA-sense strand), A:T homopolymer tract (40–100 residues), and another multiple cloning site (KpnI, SmaI, XbaI, SalI, PstI and SphI), all contained within the plasmid backbone derived from Bluescribe M13- as described above.

B. Construction of the cDNA Library Using pCGN1703

Xanthi.nc tobacco plants are grown in a phytotron until they are approximately 10–12 inches tall. Two leaves near the bottom of each plant are inoculated with either a mock buffer-only sample (10 mM sodium phosphate, pH7.0) or a sample of TMV (10 g/ml in the same buffer). Eleven days later 3–4 upper leaves, which had not been inoculated, are harvested and frozen in liquid nitrogen. Poly-A+mRNA is isolated by methods previously described (Hall et al., *PNAS USA* 75: 3196–3200 (1978); Maniatis et al., "Molecular Cloning", p. 297–209 (1982)). A cDNA library is constructed, using the poly-A+ RNA isolated from TMV-induced leaves, in the cDNA vector pCGN1703 by methods previously described (D. Alexander, *Methods in Enzymology* 154:41–64 (1987)).

Plasmid DNA of the amplified cDNA library (D. C. Alexander, 1987, supra) is digested to completion with EcoRI and sub-cloned into the EcoRI site of gt-10 (Stratagene, Inc.). Note that the plasmid vector remains attached to the cDNAs and is also cloned into the phage vector. Therefore, using this process, two cDNA libraries are constructed, one in which the library is contained in a plasmid vector and the other in which the cDNA library is contained in a phage vector.

EXAMPLE 43

Preparation of a cDNA Library From TNV Infected Cucumber Leaves

Cucumber leaves are infected with Tobacco Necrosis Virus (TNV) and RNA is isolated 5 days after infection as described above. Poly A+ RNA is isolated by standard techniques and a cDNA library is constructed in the lambda Zap cloning vector (Stratagene), essentially as described (Gubler, U. and Hoffman, B. J., *Gene* 25: 263 (1983)).

2. Identification, Isolation and Characterization of cDNA Clones Encoding PR Proteins The Examples below describe the identification, isolation and characterization of cDNA clones encoding PR proteins.

EXAMPLE 44

Isolation of cDNA's Encoding PR-1a, PR-1b and PR-1c

About 300,000 plaques from the cDNA library prepared above are screened with an oligonucleotide of the sequence:

5' CAAAACTCTCAACAAGACTATTTGGATGCCC 3' (SEQ ID No. 63). 25 positive plaques axe purified by standard techniques and DNA is prepared from the phage. A fragment of the recombinant phage which contains the cDNA is subcloned into the bluescript plasmid. A partial cDNA sequence of each clone is determined by DNA sequencing. It is found that the 26 clones can be typed into three classes of cDNA's. Class 1 is represented by the clone pBSPR1-207 (see SEQ ID No. 9), class 2 is represented by the clone pBSPR1l-1023 (see SEQ ID No. 10) and class 3 is represented by the clone pBSPR1-312 (see SEQ ID No. 11). In order to determine the identity of the three clones relative to the known PR-1 proteins, the amino acid sequence data for the PR-1a and PR-1b proteins determined above is compared to the amino acid sequences deduced from the three representative cDNA clones.

When the protein sequence for PR-1a was compared to the deduced amino acid sequence derived from pBSPR1-207 there was agreement at every residue. However, when the deduced amino acid sequence derived from the pBSPR1-1023 or pBSPR1-312 peptides was compared to the protein sequence for PR-1a there were seven and six mismatches, respectively. Thus, the sequence data clearly demonstrates that the clone pBSPR1-207 encodes the PR-1a protein.

When the amino acid sequence for the PR-1b protein was compared to the deduced amino acid sequence derived from the pBSPR1-1023 protein there was agreement at every residue. However, in comparisons to the sequence derived from pBSPR1-207 or pBSPR1-312, there were three or six mismatches, respectively. Thus, the data clearly demonstrates that the clone pBSPR1-1023 encodes the PR-1b protein. Further, by default, the clone pBSPR1-312 is determined to encode the PR-1c protein. The sequences of the cDNA's encoding PR-1a, PR-1b and PR-1c are included in SEQ ID Nos. 9, 10 and 11, respectively.

EXAMPLE 45

Isolation of cDNA Clones Encoding PR-R Major and PR-R Minor

About 300,000 plaques from the library constructed above are screened with an oligonucleotide probe of the sequence 5'-GAACTTCCTAAAAGCTTCCCCTITIATGCC-3' (SEQ ID No. 64). Fifteen positive plaques are purified by standard techniques and DNA is prepared from the phage. A fragment of the recombinant phage which contains the cDNA is subcloned into the bluescript plasmid. Partial DNA sequence of the cDNA insert reveals that the clones can be typed into two classes.

The sequence of one of these clones, pBSPRR-401, which encodes the major form of PR-R (Pierpoint, W. S. et al., *Physiol. Plant Pathol.* 31: 291 (1987) and above) is presented in SEQ ID No. 4. The identity of this cDNA as encoding the major form of PR-R major is confirmed by comparing the encoded protein sequence to the amino terminal sequence determined experimentally above and by comparing to the sequence presented for the PR-R major isoform by Pierpoint, et al., supra. This encoded protein has a very strong homology to a known trypsin/alpha-amylase inhibitor isolated from maize (Richardson, M. et al., *Nature* 327: 432 (1987)). The cloned PR-R may be an inhibitor of either proteases or alpha-amylases and as such may confer insecticidal, viricidal or fungicidal activity to plants when expressed transgenically.

EXAMPLE 46

Isolation of cDNA Clones Encoding PR-P and PRQ

About 300,000 plaques of the cDNA library prepared above are screened using a labeled cDNA probe encoding the tobacco basic chitinase gene (Shinshi et al., *Proc. Natl. Acad. Sci. USA* 84: 89–93 (1987)) and washing filters at 50° C. in 0.125 mM NaCl, 1% SDS, 40 mM sodium phosphate (pH 7.2), 1 mM EDTA. 24 positive plaques are purified and the DNA sequence of one clone named pBScht15 is determined. This sequence is presented in SEQ ID No. 7.

The protein encoded in the clone of this sequence is determined to be the pathogenesis-related protein Q based on: 1) limited structural homology to the the basic tobacco chitinase and 2) identity to the amino-terminal protein sequence of PR-Q and identity to the sequence of a number of internal peptides derived from PR-Q as determined by protein sequencing (see above). The isolated clone appears to be a truncated cDNA. In order to isolate the 5' end of the cDNA, the end of the mRNA is first determined.

An oligonucleotide primer of the sequence:

5' CAGCAGCTATGAATGCAT 3' (SEQ ID No. 65), referred to as oligo A, is synthesized by β-cyanoethylphosphoramidite chemistry and purified by standard techniques. This primer is used in a primer extension experiment as above using RNA isolated from TMV infected leaves. Two extension products are visualized by autoradiography corresponding to mRNA end points that are 43 bp and 53 bp longer than the pBScht15 cDNA.

In order to isolate the 5' end of the PR-Q cDNA, a novel method of cloning is developed based on Polymerase-catalyzed Chain Reaction (PCR) technology. Essentially, two primers are used to amplify and then clone the 5' end of the cDNA clone from the cDNA library. One primer (oligo A) which is complementary to the sense-strand of the cDNA and located about 160 bases into the pBScht15 cDNA and a second primer (either oligo B or Oligo C, below) which will prime into the cDNA from either side of the lambda cloning vector are used in this procedure.

Oligo A is complementary to the PR-Q mRNA and contains a sequence recognized by the endonuclease NsiI. Two other oligo nucleotides with the sequence 5' GGCAGGGATATFCTGGC 3' (SEQ ID No. 66) and 5' TGCAAAGCTTGCATGCC 3' (SEQ ID No. 67) are synthesized, purified and named oligo B and oligo C. Oligo B has the same sequence as part of the lambda OngC cloning vector and Oligo C is complementary to the polylinker of the Lambda OngC cloning vector.

In order to clone the 5' end of the PR-Q cDNA, two PCR reactions are carried out, one using oligos A and B and the other using oligos A and C. An aliquot of the cDNA library is used as a template for the reaction. The two reactions are necessary to amplify clones that had been ligated into the lambda OngC vector in either direction. As a control, reactions are also performed on aliquots of the purified phage lysate using the chitinase 15 isolate.

After amplification, the DNA is purified and digested with NsiI and EcoRI and runs on a 1.5% LGT agarose gel. Gel slices containing DNA fragments longer than the control are excised and ligated into pBluescript which is digested with both EcoRI and PstI as described above.

After transformation, positive colonies are isolated and the DNA insert analyzed by DNA sequencing. It is found that several inserts contain the 5' end of the PR-Q cDNA and others contain the 5' end of PR-P (as determined by comparing the amino acid sequence deduced from the clones to the protein sequence determined above).

The 3' end of PR-P is then isolated from the cDNA library by screening about 100,000 clones of the cDNA library with a probe from one of the 5' isolates of PR-P, pBScht5'-5. Positive phage are isolated and purified and the insert is subcloned into pBluescript. Several inserts are sequenced and one, pBSCht28, is determined to encode PR-P. The cDNA sequence of PR-P and PR-Q are shown in SEQ ID Nos. 12 and 7, respectively.

EXAMPLE 47

Isolation of cDNA Clones Encoding PR-O'

About 300,000 plaques of the cDNA library described above are screened using a labeled cDNA probe encoding the basic form of β-1,3-glucanase (Shinshi, H.et al., *Proc. Natl. Acad. Sci. USA* 85: 5541–5545 1988) and washing filters at 50° C. in 0.125 M NaCl, 1% SDS, 40 mM sodium phosphate (pH 7.2), 1 mM EDTA. 15 positive plaques are isolated and the insert is subcloned into the bluescript plasmid. Partial DNA sequencing reveals that pBSGL5 and pBSGL6e encode identical cDNA's which have about 55% homology to the known DNA sequence of the basic form of β-1,3 glucanase. The sequence of the cDNA in clone 5 and 6 is determined and shown in SEQ ID No. 13 for the cDNA in the plasmid pBSGL6e.

It is concluded that this cDNA encodes the PR-O' protein (an acidic form of β-1,3 glucanase) based on the comparison to the amino acid sequence of peptides derived from the PR-O' protein. In dot matrix comparison to the basic β-1, 3-glucanase it is found that the cDNA sequence in SEQ ID No. 13 is probably missing about 80 bases from the 5' end.

In order to isolate the full-length form of the PR-O' cDNA, the library is rescreened with a labeled EcoRI restriction fragment derived from the pBSGL6e plasmid. Six positive clones are isolated, purified and subcloned into the bluescript plasmid. The sequence of the inserts in the plasmids are determined by DNA sequencing. One clone, pBSGL5B-12, is 87 base pairs longer than the cDNA in pBSGL6e. The sequence of this cDNA is shown in SEQ ID No. 14.

EXAMPLE 48

Isolation of cDNA Clones Encoding PR-2, PR-N, PR-O, PR-2' and PR-2"

About 300,000 plaques of the cDNA library prepared as described from RNA isolated from TMV infected tobacco leaves are screened with a probe comprising a mixture of labelled oligonucleotides (JR138) of the formula:

5' ATGTTYGAYGARAAYAA 3' (SEQ ID No. 68), wherein each Y is independently selected from a pyrimidine C or T and each R is independently selected from a purine G or C. This probe is 17 bases long with 16 fold redundancy in the mixture. The probe design is based on an analysis of the protein data in Example 16. The probe will recognize clones containing the PR-2, PR-N or basic β-1,3-glucanase but not PR-O' or PR-O.

30 positively hybridizing plaques are isolated and purified and their inserts are subcloned into the bluescript plasmid. The sequence of the inserts is determined by DNA sequencing and the results indicate that at least three distinct cDNA's have been isolated. When comparing to the protein data in Example 16, it is clear that one type of clone contains a full-length cDNA that encodes the PR-2 protein (pBSGL117, ATCC 40691), one type encodes the PR-O protein (pBSGL134, ATCC 40690), one type encodes the PR-N protein (pBSGL125, ATCC 40692; pBSGL148, ATCC 40689) and one type encodes a highly related protein which is neither PR-2, PR-N or PR-O. This type of cDNA is named PR-2'(pBSGL135, ATCC 40685).

In order to isolate a cDNA clone encoding PR-O and also to isolate more full-length cDNA clones, the library is screened for a second time with a PstI restriction fragment from pBSGL125. pBSGL125 is a 600 base pair clone encoding a PR-N, which is truncated at the 5' end. About 300,000 plaques of the library are screened and 17 positive plaques are isolated, purified and the inserts are subcloned into bluescript. The sequence of the inserts are determined by DNA sequencing.

To insure that full-length clones are isolated from all of the acidic glucanases, two final strategies are employed. First, a final round of screening is carried out using a 210 base pair, PvuII-TaqI, restriction fragment derived from pBSGL117 as a probe. In this screen, 17 clones are isolated, purified, subcdoned into bluescript and their sequence is determined by DNA sequencing.

The second strategy is to amplify the 5' end of the cDNA out of the library by a PCR strategy described in Example 46 above. In this case, the two oligonucleotides B and C are used along with a third oligonucleotide JR209 which is complementary to positions 152 to 169 of the PR-2 cDNA sequence. In this experiment, two PCR reactions are carried out; one containing an aliquot of the cDNA library as a template and the primers JR209 and DP01 (oligo B from Example 46) and the other using an aliquot of the cDNA library as a template and using JR209 and GP38 (Oligo C from Example 46) as primers. The sequence of JR209 is as follows:

JR209 5' AACATCTTGGTCTGATGG 3' (SEQ ID No. 69).

A positive control in the amplification experiment is an aliquot of the purified GL117 clone encoding the full-length PR-2 cDNA amplified with JR209 and DP01. A negative control in the experiment is an amplification using JR209 and GP38.

Aliquots of the PCR reactions are analyzed by agarose gel elctrophoresis and it is found that a band about the size of the positive control amplified from the library for each set of primers. This result suggests that the procedure is successful and so the remaining DNA is purified and then treated with the Klenow fragment of DNA polymerase I in the presence of all four dNTP's, as described by Maniatis, et al, to make the ends of the DNA molecules "flush". The Klenow enzyme is inactivated by heating to 65° C. for 15 minutes and the DNA is then restricted with EcoRI.

The DNA is purified and then electrophoresed on a 1.5% LGT agarose gel. The band of DNA of the correct size is excised from the gel and used to ligate into the bluescript plasmid, which has been restricted with both EcoRI and EcoRV. The ligation is used to transform bacteria and positive colonies are selected and analyzed by DNA sequencing.

The result of the preceding procedures is the isolation of clones comprising the full-length cDNAs for PR-2, PR-N, PR-O, a fourth type of glucanase designated PR-2' which encodes an unknown protein, and a fifth type of glucanase designated PR-2" which encodes an unknown protein.

pBSGL117 is the isolated plasmid containing a cDNA insert encoding a PR-2 protein. The sequence of PR-2 is included as SEQ ID No. 21.

pBSGL134 is the isolated plasmid containing a cDNA insert encoding a PR-O protein. The sequence of PR-O is included as SEQ ID No. 23.

pBSGL167 is the isolated plasmid containing a cDNA insert encoding a PR-N protein. The sequence of PR-N is included as SEQ ID No. 24.

The phage lambda tobcDNAGL161 is a clone containing the full-length PR-2' cDNA. The sequence of PR-2' is included as SEQ ID No. 25.

The phage lambda tobcDNAGL153 is a clone containing the full-length PR-2' cDNA. The sequence of PR-2' is included as SEQ ID No. 26.

The determination of the protein encoded in the cDNA insert is based on a comparison between the protein data in Example 16 and the deduced protein sequence encoded by the cDNA insert.

pBSGL117, pBSGL125, pBSGL148, pBSGL134 and pBSGL135 have all been deposited in the American Type Culture Collection, Rockville, Md. as noted in the list of deposits provided above in section N of the DETAILED DESCRIPTION.

EXAMPLE 49

Isolation of cDNA Clones Encoding PR4

Approximately 300,000 plaques of the cDNA library described in Example 41 are screened with a probe comprising a mixture of labelled oligonucleotides (LF30) of the formula:

5' GGYTTRTCXGCRTCCCA 3' (SEQ ID No. 70) wherein each Y is independently selected from a pyrimidine C or T, each R is independently selected from a purine G or A, and each X is independently selected from a purine or pyrimidine A, C, G, or T. This probe is 17 bases long with 32 fold redundancy in the mixture. The probe design is based on an analysis of the protein data in Example 17.

Positively hybridizing plaques are purified and the DNA sequences of seven inserts determined. Three of the isolates had the same DNA sequence which was called PR-4a.

The sequence of PR-4a is presented as SEQ ID No. 31 and the plasmid pBSPR-4a that contains the insert shown in the Sequence was deposited in the ATCC (accession no. 75016).

The sequence of PR-4b is presented as SEQ ID No. 32 and the plasmid pBSPR-4b that contains the sequence was deposited in the ATCC (accession no. 75015).

PR-4a and PR-4b are structurally similar; they may be collectively referred to as "PR-4 proteins." Other cDNA sequences which hybridize with either of the aforementioned PR-4 encoding cDNAs have been found to be hybridize with the other, and are said to encode a polypeptide having PR-4 activity. See, e.g. Examples 51–58, below.

EXAMPLE 50

Isolation of a Distinct Family of cDNA Clones Encoding SAR8.2 Proteins

Figure 39:
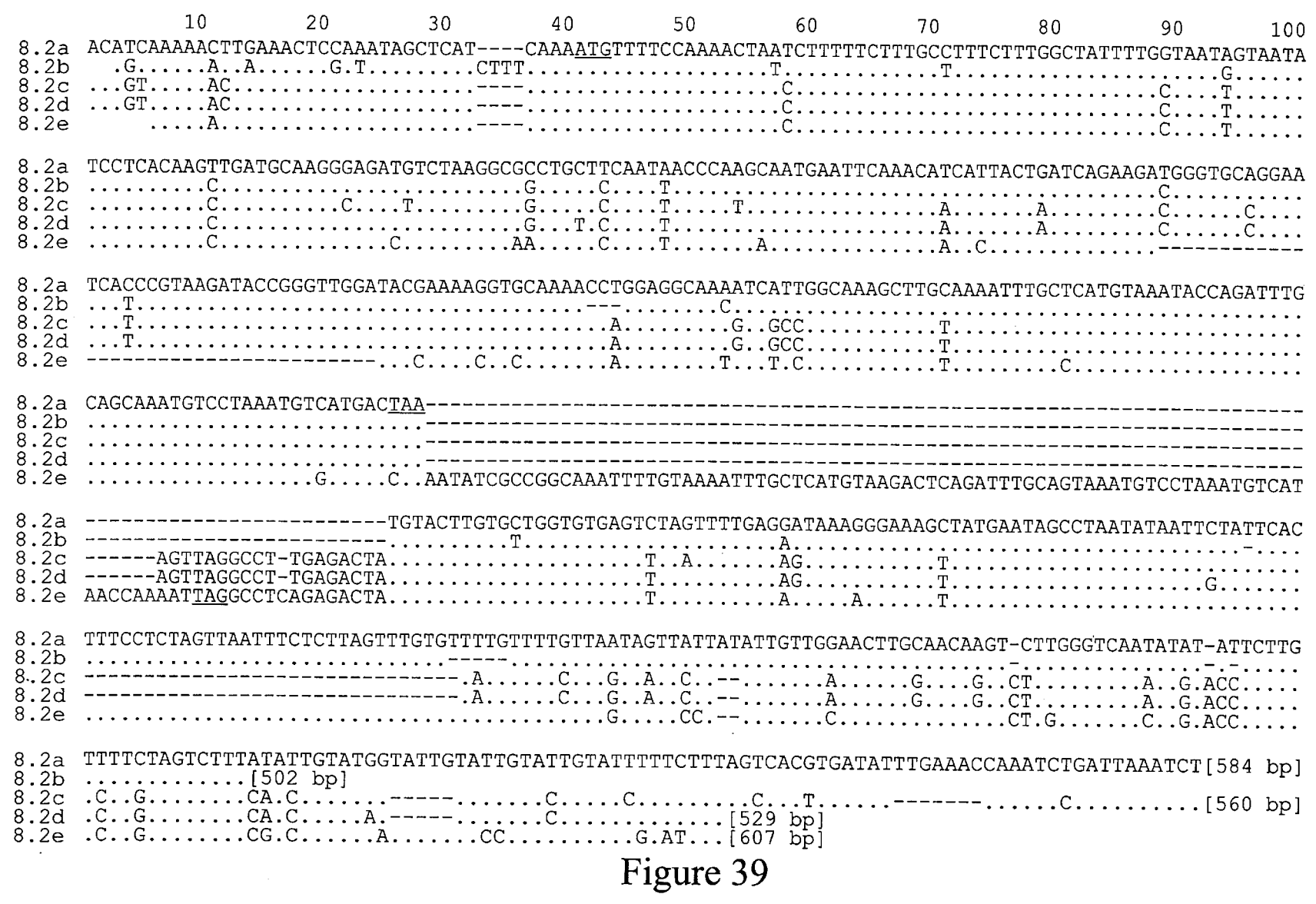

The cDNAs designated SAR8.2a, SAR8.2b, SAR8.2c, SAR8.2d, and SAR8.2e share no significant homology with any known group published DNA sequence, and are therefore considered a group of sequences distinct from cDNA sequences that encode other plant pathogenesis-related related proteins. Amongst themselves, they share DNA sequence identity ranging from 70 to 91% and are therefore considered to be members of a single distinct family of cDNA clones, called the SAR8.2 encoding DNA sequences. See FIG. 39. Their predicted protein products contain putative signal peptides. Assuming cleavage of the signal peptides in a fashion consistent with the rules of von Heijne, *Nuc. Acids. Res*. 14: 4683–4690 (1986), the mature proteins encoded by SAR8.2a-SAR8.2d have molecular weights of 7500–7700. SAR8.2e, due to a duplication of 25 amino acids at its carboxy terminus compared to SAR8.2a-SAR8.2d, has a predicted mature molecular weight of 9655. All of the predicted proteins have calculated isoelectric points greater than or equal to 10.

Transgenic tobacco plants expressing an SAR8.2 cDNA are demonstrably resistant to the fungal pathogen *Phytophthora narasitica*, the causative agent of black shank disease (see Example 165. Thus, an SAR8.2 protein is one encoded by a DNA sequence that hybridizes to any of the disclosed SAR8.2 cDNA sequences under low stringency conditions (as laid out in Example 46), and which is capable of conferring resistance to fungal diseases in plants in which it has been expressed.

Filter lifts of the sub-cloned library prepared above are screened with labeled cDNA probes in a method described previously (St. John and Davis (1979) *Cell*, 16:443–452 (1979)) except that the same filter lifts are screened sequentially rather than by screening replicate lifts. The first probe is synthesized as described, using reverse transcriptase and [$^{32}$P]-dCTP, from mRNA of the mock-induced RNA sample isolated above; following probing and exposure to X-ray film the same filters are probed again (without stripping) using probe synthesized as above but from the TMV-induced RNA sample isolated above.

Following exposure the two X-ray films are compared using a computerized digital image analysis system (Biological Vision, Inc., San Jose, Calif.) according to the manufacturer's specifications, and plaques are selected that yield an increased signal when probed with the TMV-induced probe.

The selected plaques are purified by a second round of probing at a selected plaque density of approximately 100/plate, and the cDNA inserts are recovered from the phage as follows: a small amount of isolated phage DNA is digested with EcoRI followed by inactivation of the restriction enzyme, dilution, re-ligation with T4 DNA ligase, and transformation into *E. coli* strain DH-5, (Bethesda Research Laboratories, Bethesda, Md.) followed by selective growth on ampicillin-containing culture plates.

This procedure allows direct recovery of the cDNA contained in the plasnid vector from the phage vector. The DNA sequence of a clone thus isolated, designated SAR8.2a, is shown as SEQ ID No. 15. Further clones that cross-hybridize with SAR8.2a are isolated by using SAR8.2a as a probe and re-screening the library under high or low stringency conditions. Appropriate conditions are those described in Example 46.

A total of 24 phage plaques are identified by this method and their DNA sequences are determined. These 24 clones are found to fall into five classes based on DNA sequence identity: 5 of the 24 clones are designated type SAR8.2a, 8 are type SAR8.2b, 4 are type SAR8.2c, 6 are type SAR8.2d, and one is type SAR8.2e. The sequences of longest member of each class of clone, appear as SEQ ID Nos. 15–19.

SAR8.2a, b, c, and d are greater than 91% identical to each other in DNA sequence in their open reading frames. As shown in FIG. 40, the predicted protein products from these same clones are between 88 and 96% identical to each other in amino acid sequence. SAR8.2e is 71% identical to SAR8.2d in DNA sequence, and 72% identical in amino acid sequence.

Hybridization of tobacco SAR8.2 cDNAs to genomic DNA from other plants is detected by genomic Southern blot analysis (see Example 4) under low stringency hybridization and washing conditions. Appropriate conditions are hybridization at 42° C. in 30% formamide, 5× SSC 0.1% SDS, 5 mM EDTA, 10× Denhardt's solution, 25 mM sodium phosphate pH 6.5, and 250 g/ml sheared salmon sperm DNA; washing at 42° C. in 2× SSC, 0.1% SDS (where 1× SSC is 150 mM NaCl, 15 mM Na citrate). Alternatively, the low stringency conditions described in Example 46 can be used. Positive hybridization to multiple discrete bands is detected in genomic DNA from several Solanaceae, including *Lycopersicon esculentum*, as well as Brassica, Ricinus, and Arabidopsis.

SAR8.2-encoding DNA sequences can be isolated from other plants by using the tobacco SAR8.2a, b, c, d or e cDNA sequence as a probe for screening cDNA or genomic libraries of the plant of interest under low stringency conditions, as described in the present Example or in Example 46.

Analysis of RNA from mock-induced vs TMV-induced tobacco leaves, using Northern analysis and Primer extension assay confirms that steady-state levels of the pSAR8.2 family mRNA's are increased by TMV induction.

EXAMPLE 51

Isolation of cDNA Clones Encoding the Chitinase/Lysozyme From Cucumber

Two regions of the protein sequence determined in Example 18, above, are selected and oligonucleotide probes are synthesized that are complementary to all possible combinations of messenger RNA capable of encoding the peptides. The sequences of the probes are:

```
                        G T    A
Probe 1: 5'-CCATTCTGNCCCCAGTA-3' (SEQ ID No. 71)

G G G G C
Probe 2: 5'-GGATTATTATAAAATTGNACCCA-3' (SEQ ID No. 72).
```

About 300,000 plaques are plated from the library constructed above and duplicate plaque lifts are probed either with $^{32}$P labeled oligonucleotide mixture 1 (probe 1) or mixture 2 (probe 2). Plaques are isolated that show positive results when screened with either probe. Isolation of phage and automatic excision are carried out as described in the Stratagene Lambda Zap laboratory manual.

Once the chitinase cDNA clones are isolated in the bluescript plasmid they are sequenced by dideoxy sequencing. The sequence of the chitinase cDNA contained in the plasmid pBScucchi/chitinase is presented in SEQ ID No. 3.

EXAMPLE 52

Isolation of cDNA Clones Encoding Chitinase/Lysozymes from Tobacco

About 300,000 plaques of the TMV-infected tobacco cDNA library described in Example 41 are screened using a labeled cDNA probe encoding the cucumber chitinase/lysozyme cDNA and washing filters at 50° C. in 0.125 mM NaCl, 1% SDS, 40 mM sodium phosphate (pH 7.2), 1 mM EDTA. Positive plaques are purified and the DNA sequence of two clones, named pBSCL2 and pBSTCL226 are determined. These are presented in SEQ ID Nos. 29 and 30, respectively. The proteins encoded in the clones of these sequences are determined to be chitinase/lysozymes based on structural homology to the cucumber chitinase/lysozyme.

In addition, a protein is purified from intercellular fluid of TMV-infected tobacco as described in Example 16. Peptides are generated and sequenced as described in Example 9.

The protein encoded by pBSTCL226, corresponding to an acidic isoform of chitinase/lysozyme, was found to match the deduced peptide sequences exactly.

EXAMPLE 53

Cucumber Peroxidase cDNA

An oligonucleotide probe is designed to isolate cDNA's encoding the cucumber peroxidase based on the protein data presented in Example 50. The sequence of the mixture of oligonucleotides is as follows:

JR74 5' ACRAARCARTCRTGRAARTG 3' (SEQ ID No. 73), wherein each R is independently selected from a purine G or C. This oligonucleotide mixture is 20 bases long and contains 64 species.

A cDNA library is prepared from RNA isolated from leaves of cucumber plants five days after infection with tobacco necrosis virus as described in Example 43. This library is constructed in the Lambda ZAP cloning vector.

About 300,000 plaques of this cDNA library are screened with the oligonuleotide probe and 25 plaques are isolated. These are rescreened several times and purified. As a result of this process only six plaques remained as still positive after many rounds of purification. The inserts contained in these clones are excised using the automatic excision protocol described in the Stratagene Lambda ZAP laboratory manual. The inserts are sequenced by double stranded dideoxy sequencing and then the structures are analyzed by dot matrix analysis comparing to the sequence of an acidic, lignin-forming peroxidase isolated from tobacco (Lagrimini, et al., *Proc. Natl. Acad. Sci. USA* 84: 7542–7546 (1987)).

Two of the clones, Per1 and Per25, show some limited homology to the tobacco cDNA and are chosen for further analysis. Upon complete sequencing of the clones, it is found that they encode the same protein.

A probe derived from the cucumber peroxidase is then used to rescreen to cucumber library and about 30 plaques are isolated. After purification the inserts are excised from the phage as plasmids and then the sequence is determined by DNA sequencing. The results of this analysis is the isolation of two types of peroxidase cDNA clones from cucumber. One encoding a basic protein encoded by the plasmid pBSPERI, the nucleotide sequence which is shown in SEQ ID No. 22, and the other encoding a related peroxidase contained in the plasmids, pBSPER24 and pBSPER25.

Plasmids pBSPERI, pBSPER24 and pBSPER25 have all been deposited in the American Type Culture Collection as noted in the list of deposits provided above in section N of the DETAILED DESCRIPTION.

As disclosed above, also included within the scope of the present invention are cDNA sequences that hybridize with the enumerated Sequences and encode a polypeptide having the activity of the plant PR protein encoded by the enumerated Sequence with which it hybridizes. The representative Examples set forth below describe a protocol sufficiently detailed to guide or instruct one of ordinary skill in the art to isolate other cDNA's encoding plant PR proteins within the scope of the invention without undue experimentation.

EXAMPLE 54

Construction of a Chemically-Induced Arabidopsis cDNA Library

Mature *Arabidopsis thaliana* ecotype Columbia (Lehle Seeds, Tucson, Ariz.) plants are sprayed with a 0.5 mg/ml suspension of a wettable powder formulation of methylbenzo-1,2,3-thiadiazole-7-carboxylate consisting of 25% active ingredient. Seven days later, the leaf tissue is harvested and frozen in liquid $N_2$. Total RNA is isolated as described in Example 6 and Poly (A)$^+$ RNA is isolated using a Poly (A) Quik™ mRNA isolation kit from Stratagene (La Jolla, Calif.). This Poly (A)$^+$ RNA is then used to make a cDNA library in the uni-zap™ XR vector (Stratagene) using a ZAP-cDNA™ Gigapack$^R$ II Gold cloning kit from Stratagene. A portion of the cDNA library is amplified as described in the Stratagene kit.

EXAMPLE 55

Isolation of an Acidic beta-1,3-glucanase cDNA from Arabidovsis

*Arabidopsis thaliana* ecotype Columbia plants are sprayed with a 1 mg/ml suspension of a wettable powder formulation of 2,6-dichloroisonicotinic acid methyl ester, consisting of 25% active ingredient. After seven days, the leaves are harvested and the intercellular fluid (ICF) collected as described in Example 12.

The proteins contained in the ICF are fractionated on a 20% polyacrylamide native gel (Phast system, Pharmacia). Two predominant chemically-induced protein bands are detected. The slower migrating (top) band is designated band 1. The faster migrating band (band 2) is excised from the gel and the protein eluted. Peptides are generated with lysyl endopeptidase and sequenced as described in Example 9.

The deduced peptide sequences were found to align with a high degree of similarity with the sequence of several known beta-1,3-glucanases from tobacco. An oligonucleotide of sequence:

5' ATG TTY GAY GAR AAY AA 3' (SEQ ID No. 74) that corresponds to the amino acids MFDENN (SEQ ID No. 75), which are highly conserved among acidic, extracellular beta-1,3-glucanases (Ward et al., *Plant Physiol.*

96: 390–397 (1991), is used as a hybridization probe to isolate cDNA clones from the A. thaliana library described in Example 54. The clones are purified, plasmids excised in vivo as described by the manufacturer of the cloning vector (Stratagene), and their nucleotide sequences determined. The partial DNA sequence of the longest of these was cloned into pAGL2, (ATCC No. 75048).

EXAMPLE 56

Isolation of a PR-1-related cDNA Clone from Arabidopsis

Approximately 200,000 plaques from the Arabidopsis cDNA library are screened with a combination of PR-1a and PR-1 basic cDNAs from tobacco as probes at low stringency, as described in Example 46.

Three purified positive clones are in vivo excised (as per Stratagene) and plasmid DNA is isolated and sequenced. All 3 cDNAs share sequence identity and one cDNA clone appears to be full length (clone pAPR1C-1, ATCC No. 75049) as determined by comparison to the tobacco PR-1 sequences. The DNA sequence appears as SEQ ID No. 33.

Proteins from the ICF described in Example 55 are separated by SDS polyacrylamide gel electrophoresis on an 8–25% acrylamide gradient gel (Phast system, Pharmacia). A third abundant chemically-induced protein is identified that migrates at an apparent molecular weight similar to that of the PR-1 proteins of tobacco. The protein band is excised from the gel, and is separated from a closely migrating protein by reverse phase HPLC. Peptides from the chemically-induced protein are generated with tyypsin, and their sequences determined as described in example 9.

Peptides are also generated with lysyl endopeptidase as described in Example 9. The sequence of one peptide is determined as described in Example 9.

The predicted protein encoded by the C-1 clone was found to match the deduced peptide sequences exactly, indicating that the C-1 clone encodes the extracellular Arabidopsis protein related to PR-1 from tobacco.

EXAMPLE 57

Isolation of a PR4-Related cDNA Clone from Arabidopsis

Approximately 200,000 plaques from the Arabidopsis cDNA library are probed with the tobacco PR-4 cDNA clone at low stringency as described in Example 46. Four purified positive clones are in vivo excised and the resultant plasmid inserts are sequenced. The DNA sequence of one of these clones, designated pSLP1 (ATCC #75047) appears as SEQ ID No. 34. The clone is found to have substantial sequence homology to the win1 and win2 genes of potato (Sanford et al., *Mol. Gen. Genet.* 215: 200–208 (1988)). Specifically, it contains the "hevein" domain at its predicted N-terminus, which is also found in the tobacco basic chitinase (Shinshi et al., *Plant Mol. Biol.* 14:357–368 (1990)). The clone has homology to PR-4 from tobacco at the predicted C-terminus.

EXAMPLE 58

Isolation of a PR-S-Related cDNA Clone from Arabidopsis

The band 1 protein described in Example 55 is eluted from a native polyacrylamide gel and peptide generated and their sequences determined as described in example 9.

The peptide sequences from the band 1 protein were found to have a significant level of similarity to osmotin and PR-R (a.k.a. PR-5) of tobacco. Using these peptide sequences, oligos SU01, SU02, and EW59 were designed. SU01 is a 128-fold degenerate oligonucleotide mixture 17 bases in length having sequence:

5' AAY AAY TGY CCN ACN AC 3' (SEQ ID No. 76)
(where Y=C or T; N=C or T or A or G)

which is derived by reverse translation from the amino acid sequence NNCPTT SEQ ID No. 77), which occurs in the N-terminus of the protein. SU02 is a 32-fold degenerate oligonucleotide mixture of sequence:

5' AC RTC RTA RAA RTC YTT 3' (SEQ ID No. 78)
(where R=A or G) which is the antisense strand of a sequence derived by reverse translation from the amino acid sequence KDFYDV (SEQ ID No. 79).

EW59 is a 64-fold degenerate oligonucleotide mixture 17 bases in length having the sequence:

5' CK RCA RCA RTA YTG RTC 3' (SEQ ID No. 80)
(where K=T or G) which is the antisense strand of a sequence derived by reverse translation from the amino acid sequence DQYCCR (SEQ ID No. 81).

A polymerase chain reaction is carried out using double-stranded cDNA (used for constructing the library described in Example 54) as template, and SU01 and EW59 as primers. The 50 ul reaction contains approximately 20 ng cDNA, 12 uM SU01, 6uM EW59, 200 uM each dATP, dCTP, dGTP, and dTTP, 1× PCR buffer (Perkin-Elmer Cetus), and 2.5 u Amplitaq polymerase. The reaction is cycled 30 times through a temperature profile of 94° C. for 30 sec., 44° C. for 45 sec., and 72° C. for 30 sec in a DNA thermal cycler (Perkin Elmer Cetus, Norwalk, Conn.).

A band approximately 450 bp in length is amplified that also hybridizes to SU02, which is predicted to lie between SU01 and EW59, based on alignment of the peptides with the osmotin and PR-R sequences. The fragment is gel purified, labeled by random priming, and used to probe the cDNA library. Four positively-hybridizing clones are purified, in vivo excised, and their DNA sequences determined.

The sequence of one clone, designated pATL12a (ATCC #75050), appears as SEQ ID No. 35. This clone appears to be a full-length clone based on identification of the N-terminal peptide sequence in the predicted protein coding sequence near the 5' end of the clone.

EXAMPLE 58A

Cloning of Class IV Chitinase cDNAs from Arabidopsis

Class specific degenerate oligonucleotides were designed from areas of homology between bean PR4 chitinase (Margis-Pinheiro et al., *Plant Mol. Biol.* 17: 243–253 (1991)) and sugar beet chitinase 4 (Mikkelsen et al., in Advances in Chitin and Chitosan, ed. by Brine et al., pub. by Elsevier, Amsterdam (1992)): oligonucleotides were designed degenerate for the peptide sequences HFCYIEE (forward, spanning nucleotides 406–426), and IRAING (reverse, spanning nucleotides 705 to 675). DNA was extracted from two-week old plants of Arabidopsis thaliana ecotype Landsberg and amplified using a Perkin-Elmer thermal cycler 480 at the following cycle settings: 94° C. for 5 minutes; 35 cycles at 94° C., 1 minute, 43° C. or 45° C., 1 minute, and 72° C., 2 minutes; followed by 5 minutes at 72° C. The amplified fragment was gel purified, collected by centrifugation through Whatman paper, ethanol precipitated, resuspended in TE, digested with BamHI and NsiI and subcloned into pTZ18U (Pharmacia). Four clones of the fragment were sequenced; they differed only within the oligo-derived sequence as could be expected from amplification with degenerate oligonucleotides.

Two different cDNAs were isolated simultaneously by screening a leaf tissue cDNA library (Uknes et al., *Plant Cell* 4: 645–656 (1992)) at high stringency with the PCR amplified genomic fragment described above. Duplicate plaque lifts were taken with nitrocellulose filters (Schleicher & Schuell, Keene, N.H.) (Ausubel et al., in Current Protocols in Molecular Biology, pub. by J. Wiley & Sons, New York (1987)). Probes were labelled by random priming (using the labeling system supplied by Gibco BRL, Gaithersburg, Md.). Hybridization and washing were done at 65° C. according to Church and Gilbert, *Proc. Natl. Acad. Sci.* 81: 1991–1995 (1984). Positive plaques were purified and plasmids containing the cDNA inserts were in vivo excised for DNA sequence determination. Of the six positive clones two contained an insert with structural homology to previously characterized class IV chitinases and were designated class IV chitinase type A and four clones were divergent in that they lacked the class IV chitinase hevein domain; these were designated class IV chitinase type B. As none of the cDNA inserts was full-length, an additional 29 bp of class IV chitinase type A and 17 bp of class IV chitinase type B, both containing a methionine initiation codon were amplified from ethephon-induced RNA using the 5' RACE system for rapid amplification of cDNA ends (Gibco BRL, Gaithersburg, Md.). Sequence comparisons were performed using the GAP and PILEUP features of the Genetics Computer Group software (Genetics Computer Group, Madison, Wis.).

Class IV chitinase type A is a 1079 base pair cDNA with an open reading frame of 264 amino acids containing the characteristic cysteine-rich hevein and chitinolytic domains and the three short deletions typically found in class IV chitinases (see SEQ ID No. 37). The cDNA for class IV chitinase type B is 952 base pairs in length and encodes a protein of 214 amino acids which lacks a hevein domain and contains a fourth deletion (see SEQ ID No. 38). The cDNAs are 71% identical overall and 80% identical over coding sequence. The predicted protein encoded by Arabidopsis class IV chitinase type A is 89% homologous to the basic Brassica napus (rapeseed) class IV chitinase, 61% homologous to basic Beta vulgaris (sugar beet) class IV chitinase, 57% homologous to basic Zea mays class IV chitinase B, 58% homologous to acidic Phaseolis vulgaris (bean) PR4 class IV chitinase, and 55% homologous to acidic Dioscorea japonica (yam) class IV chitinase. It is 42% homologous to Arabidopsis thaliana basic class I chitinase.

The predicted mature protein encoded by Arabidopsis class IV chitinase type A has a molecular weight of 25695 D and a pI of 7.8; whereas the protein encoded by Arabidopsis class IV chitinase type B has a molecular weight of 20553 D and a pI of 10 assuming the removal of a signal peptide based on homology to tobacco PR-Q.

Northern analysis showed that both chitinases were induced by TCV infection, confirming their classification as PR-proteins.

Using techniques well known in the art, these cDNAs can be cloned into expression cassettes and vectors for transfer to transgenic plants. Typical techniques used in the art are described in section 6 (examples 64 to 82), section 7 (examples 83 to 108) and section 8 (examples 109 to 133).

EXAMPLE 58B

Isolation of Wheat cDNAs Specifically Induced by Treatment with benzo-1,2,3-thiodiazole-7-carboxylic Acid Thiomethyl Ester, Using the Method of Differential Plaque Filter Hybridization Samples of winter wheat (cultivar Kanzler) were harvested 2–3 days after treatment with either water or 200 ppm of the plant activator compound benzo-1,2,3-thiodiazolecarboxylic acid. Total RNA was prepared from frozen tissue samples using a standard phenol extraction/LiCl precipitation procedure (Lagrimini et al., *Proc. Natl. Acad. Sci.* 84: 7542–7546 (1987)). PolyA (+) RNA was purified from total RNA using the Poly(A) Quik mRNA purification kit (Stratagene Cloning Systems, LaJolla, Calif.). A bacteriophage lambda ZAP II cDNA library was prepared from the benzo-1,2,3-thio-diazolecarboxylic acid treated polyA(+) sample using the Uni-Zap XR Gigapack II Gold cloning kit (Stratagene) as described by the manufacturer. The phage library was plated at a density of approximately 5000 plaques on a 10 cm petri dish and grown for 6–8 hours at 37° C. Duplicate filter lifts of the plaques were made using nitrocellulose membranes (Schleicher & Schuell, Keene, N.H.). Labelled first strand cDNA probes were prepared from polyA of both the water control and the benzo-1,2,3-thiodiazolecarboxylic acid-treated samples using 32P-dCTP and the AMV reverse transcriptase (GibcoBRL, Gaithersburg, Md.) under the manufacturer's conditions. Each probe was hybridized (>106 cpm/ml) with one set of the duplicate lifts overnight at 65 deg C. Hybridization and wash conditions were as described in Church and Gilbert, *Proc. Natl. Acad. Sci.* 81: 1991–1995 (1984). Hybridization was detected by autoradiography.

Plaques appearing to hybridize preferentially to the chemically treated cDNA were purified and their cDNA inserts were amplified using the GeneAmp Polymerase Chain Reaction (PCR) kit (Perkin Elmer, Norwalk, Conn.) and primers homologous to the flanking lambda Zap II sequences. The amplified inserts were excised from a low melting temperature SeaPlaque GTG agarose gel (FMC BioProducts, Rockland, Me.) and labelled using 32P-dCTP and the Random Primers DNA Labeling System (Gibco BRL). These probes were hybridized with total RNA blots (Ausubel et al., in Current Protocols in Molecular Biology, pub. by J. Wiley & Sons, New York (1987)) of control and benzo-1,2,3-thiodiazolecarboxylic acid treated RNAs to verify that they contained chemically induced cDNAs.

The induced clones were in vivo excised into pBluescript plasmids according to the manufacturer's instructions (Stratagene) and plasmid DNAs were purified using Magic Miniprep columns (Promega Biotech, Madison, Wis.). The cDNA sequences were determined by the chain termination method using dideoxy terminators labelled with fluorescent dyes (Applied Biosystems, Inc., Goster City, Calif.). The DNA and the predicted amino acid sequences were compared to available databases using the GAP (Deveraux et al., *Nucl. Acids Res.* 12: 387–395 (1984)) and the BLAST (Altschul et al., *J. Mol. Biol.* 215: 403–410 (1990)) programs.

The nucleotide sequence of one apparently full length induced clone is set forth in SEQ ID No. 39. This clone, denoted WCI-1 (Wheat Chemical Induction), was found to share limited homology with two rice cDNAs, one expressed specifically in the shoot apical meristem (De Pater and Schilperoort, *Plant Mol. Biol.* 18: 161–164 (1992)), the other inducible by salt stress (Claes et al., *Plant Cell* 2: 19–27 (1990)). The function of these proteins is unknown.

The predicted amino acid sequence of a second highly induced cDNA, WCI-2, clearly identified it as an isozyme of wheat lipoxygenase, based on its homology to other plant lipoxygenases in the database. The DNA sequence of this cDNA is shown in SEQ ID No. 40.

A third class of induced cDNA (WCI-3) was isolated which to date shows no significant homology to sequences in the databases. The DNA sequence of this apparently full-length clone is set forth in SEQ ID No. 42.

Using techniques well known in the art, these cDNAs can be cloned into expression cassettes and vectors for transfer to transgenic plants. Typical techniques used in the art are described in section 6 (examples 64 to 82), section 7 (examples 83 to 108) and section 8 (examples 109 to 133).

EXAMPLE 58C

Isolation of Wheat cDNAs Specifically Induced by Treatment with benzo-1,2,3-thiodiazolecarboxylic acid, Using the Method of Differential cDNA Display The total and polyA(+) samples described in Example 1 were used for PCR differential display of the mRNA from water and benzo-1,2,3-thiodiazolecarboxylic acid treated wheat tissue essentially as described in Liang and Pardee, Science 257: 967–971 (1992). Amplified cDNA fragments that appeared to be present only in the chemically treated sample were excised from the dried sequencing gel and electroeluted using a Centrilutor device and Centricon-30 Microconcentrators (Amicon, Beverly, Mass.). The purified fragments were PCR amplified using primers that consisted of the original differential display 10-mers plus an additional 10 bases of unique sequence added to their 5' ends. After 8 PCR cycles at low annealing temperature (42–45° C.), the annealing temperature was raised to 60° C. for an additional 30 cycles. Essentially 100% of the fragments could then be visualized by EtBr staining and were excised from a Sea-Plaque GTG agarose gel (FMC).

These gel fragments were labelled and used to probe RNA blots as previously described. Fragments that hybridized only with chemically treated RNA were TA-cloned into the plasmid vector pCR II using a TA Cloning Kit (Invitrogen Corporation, San Diego, Calif.). Inserts from the plasmids were screened again against control/chemical RNA blots to verify that the inducible gene fragment had been subcloned. Induced fragments were then labelled by random priming and hybridized against filter lifts of the chemically induced cDNA library as described in Example 58A. Hybridizing plaques were purified, sequenced, and analyzed as previously described in order to obtain full length clones corresponding to the original small (200–400 bp) fragments, and to identify the induced gene product where possible.

The nucleotide sequence of one clone obtained by this procedure is set forth in SEQ ID No. 43. This clone, WCI-4, has some homology to known thiol protease sequences from a variety of sources and may therefore be a thiol protease.

Partial sequences of an additional induced gene that was isolated using differential display is set forth in SEQ ID No. 44. This fr-agment shows no database homology and has been designated WCI-5.

Using techniques well known in the art, these cDNAs can be cloned into expression cassettes and vectors for transfer to transgenic plants. Typical techniques used in the art are described in section 6 (examples 64 to 82), section 7 (examples 83 to 108) and section 8 (examples 109 to 133).

EXAMPLE 59

Isolation of the cDNA Encoding the Acidic Form of β-1,3-glucanase

About 300,000 plaques of the tobacco cDNA library described above are screened using a labeled cDNA probe encoding the basic form of β-1,3-glucanase (Shinshi, H. et al., supra) and washing filters at 50° C. in 0.125 M NaCl, 1% SDS, 40 mM sodium phosphate (pH 7.2), 1 mM EDTA. 15 positive plaques are isolated and the insert is subcloned into the bluescript plasmid. Partial DNA sequencing reveals that clone 5 and 6 encode identical cDNA's which have about 55% homology to the known DNA sequence of the basic form of β-1,3 glucanase. The sequence of the cDNA in clone 5 and 6 is determined and shown in SEQ ID No. 8. It is concluded that this cDNA encodes the acidic form of β-1,3 glucanase based on the limited amino acid sequence homology and the more acidic isoelectric point of the encoded protein.

3. A Novel, Differential Cloning and Screening Technology

EXAMPLE 60

Differential Enrichment Scheme

The following is a specific example of the differential cloning and screening technique described above in section L of the "DETAILED DESCRIPTION" using cDNA populations in phage cloning vectors. The "induced" and "unreduced" cDNA populations (constructed from mRNA from TMV-induced or mock-induced tobacco leaves in this case) are cloned in two different phages so that the primers used for amplifying the clone inserts will be different (and thus not hybridize in later steps).

The "induced" cDNA bank is constructed in GEM-4 (Promega, Inc.) and the "unreduced" or "mock-induced" DNA bank is constructed in ZAP-II (Strategene, Inc.). For each vector specific oligonucleotide primers are synthesized such that they represent sequences in the phage vector immediately adjacent to the cDNA cloning site, and that, when used in the polymerase chain reaction in the presence of the corresponding phage, the DNA cloned into the cDNA cloning site will be amplified.

A population of phages representing all the members of each bank are amplified together, producing a population of cDNA inserts representing the bank. One of the oligonucleotide primers in each case is biotinylated so that a specific strand of each amplified bank DNA can be positively selected by avidin affinity chromatography and strand separation, followed by release and recovery of the biotin-selected strand.

Importantly, the primers used for biotinylation are selected such that strands of opposite polarity are selected from the "induced" vs "uninduced" cDNA banks. The biotin tag in the case of the "induced" DNA is a labile one in that the spacer arm through which the biotin moiety is attached contains a disulfide linkage, and the tag in the "uninduced" DNA is a stable one. In this case the single strand from the "induced" population is released by dithiotreitol treatment, losing its biotin tag, and the single strand from the "uninduced" population is released by denaturation of the avidin molecule, while retaining its biotin tag.

When the recovered "target" DNA (single strand from the "induced" library) is hybridized to the recovered "driver" DNA (single strand from the "mock-induced" or "uninduced" library), the complexes that are formed, and the excess "driver" DNA can be removed by avidin affinity chromatography.

The remaining "target" DNA still bears the primer sequences, making its recovery, by subsequent repair or amplification and cloning, very simple.

In the alternate scheme also described above in section L of the "DETAILED DESCRIPON", both the "target" and "driver" single stranded DNAs are recovered by denaturation of the avidin on the affinity matrix, and both retain their biotin tags. After hybridization all the molecules are bound to the affinity matrix and following washing, the non-hybridized "target" DNA, bearing the "liable" affinity tag, is selectively eluted from the matrix by dithiothreitol. This modification allows a positive selection for the single stranded "target" DNA, avoiding potential problems with less-than-quantitative binding of the hybridization mix to the affinity matrix.

The advantage of this technique over those previously described is the ability to isolate those genes which are turned on only to low levels, in specific circumstances, and which may play a causative role in some important biological phenomenon.

In both forms of the technique described above, the "target" and "driver" single stranded DNA is generated by biotin-avidin affinity chromatography.

An alternative method for generating these single-stranded populations is a method described as "asymmetric" PCR (Gyllensten, U. and Erlich, H., Proc. Natl. Acad. Sci. USA. 85: 7652–7656 (1988)). This consists of multiple cycles of polymerase extension and denaturation, as in PCR, but in the presence of only one of the primers. The primer chosen determines the polarity of the resultant DNA, thus allowing the selective polarity critical to the technique as described above. Asymmetric PCR in this case is most easily accomplished using as template a small amount of double-stranded PCR products of the relevant population, from which the excess primers have been removed.

F. Isolation of Novel PR Protein Genes

The following examples disclose the isolation and characterization of novel genomic clones encoding PR proteins.

EXAMPLE 61

Isolation of a Genomic Clone Encoding PR-1'

A genomic library is constructed and screened with a PR-1 cDNA probe as described in Example 20. A clone is isolated and designated lambda tobchrPR1019. A preliminary restriction map is established. A ClaI fragment is subcloned into bluescript and then a restriction map of plasmid, pBS-PR1019Cla, is established. A large XhoI fragment is deleted from pBS-PR1019Cla resulting in the plasmid pBS-PR1019Cla Xho. This plasmid contains about 2.7 kb of tobacco DNA containing the PR1Oi9 gene. Deletions are made in this plasmid and the set of deletions are used for DNA sequencing.

The DNA sequence for 2256 bp of this gene is shown in SEQ ID No. 2. The protein encoded in the PR1019 (SEQ ID No. 46) is found to be about 65% homologous to PR-1a, PR-1b, or PR-1c; therefore, this new gene is named PR-1'.

EXAMPLE 62

Isolation of a Genomic Clone Encoding the Cucumber Chitinase Gene

A. Preparation of Cucumber Genomic DNA

Nuclei are isolated from leaves of Cucumis sativus cv. Long Marketer by first freezing 35 grams of the tissue in liquid nitrogen and grinding to a fine powder with a mortar and pestle. The powder is added to 250 ml of grinding buffer (0.3 M sucrose, 50 mM Tris, pH 8, 5 mM magnesium chloride, 5 mM sodium bisulfite, 0.5% NP40) and stirred on ice for 10 minutes. This mixture is filtered through six layers of cheesecloth, and the liquid is centrifuged at 700×g for 10 minutes. The pellets are resuspended in grinding buffer and recentrifuged. The pellets are again resuspended in grinding buffer and this suspension is layered over a 20 ml cold sucrose cushion containing 10 mM tris, pH 8, 1.5 mM magnesium chloride, 140 mM sodium chloride, 24% sucrose, 1% NP40. These tubes are centrifuged at 17,000×g for 10 minutes. The pellets at this stage contain mostly nuclei and starch granules. High molecular weight DNA is isolated from the nuclei essentially according to Maniatis, T. et al., Molecular Cloning, Cold Spring Harbor Laboratory, New York (1982) using cesium chloride ethidium bromide gradients.

B. Preparation of Genomic Library

Three ug of the purified DNA is digested with EcoRV, EcoRI, BamHI or HinDIII and the fragments are separated on a 0.5% agarose gel. The gel is blotted to nylon membrane (GeneScreen Plus, NEN Research Products, Boston, Mass.) in 0.4 M NaOH as described by Reed et al., Nucleic Acids Res. 13: 7207–7221 (1985). The gel blot is hybridized to a probe of the cucumber chitinase cDNA (SEQ ID No. 3) labeled with 32P by random priming using the PrimeTime kit (International Biotechnologies, New Haven, Conn.). A single band of about 12 kb is detected in the EcoRI digest; thus it is decided to isolate the cucumber chitinase gene using a total EcoRI digest and ligating into a lambda replacement-type cloning vector.

Ten ug of this DNA is digested to completion using EcoRI and the DNA is then extracted with phenol, precipitated with ethanol and ligated into the EcoRI site of EMBL 4. About 100,000 plaques are screened with the 32P-labeled cDNA probe of cucumber chitinase. Ten positive plaques are picked and purified and insert DNA is prepared using LambdaSorb Immunoaffinity Adsorbent according to the manufacturer's instructions (Promega, Madison, Wis.). The insert DNA is analyzed by preliminary restriction digest mapping which shows that the inserts are identical. One clone is picked for further analysis; the 12 kb insert (SEQ ID No: 36) is subcloned into the pBluescript vector (Stratagene, LaJolla, Calif.) to give the plasmid pBScucchrcht5 (ATCC accession no. 40941).

C. Preparation of Clones for Sequencing

A restriction map is established for pBScuccrcht5 and fragments of the genomic DNA insert are subcloned into pBluescript. The clones generated are designated D1-3, D-Cla1, D-Cla2, D-BamCla, and D-XbaI. The D1-3 clone is made from a gel-purified EcoRI fragment of pBScuccrcht5. This fragment is digested with EcoRV and the EcoRV insert is gel-purified away from the vector piece. Low melting point agarose for gel-purification is from BRL (Gaithersburg, Md.). EcoRI linkers (BRL) are kinased and ligated with the EcoRV piece, and then the piece is digested with EcoRI and gel-purified again. The purified fragment is ligated with pBluescript that has been digested with EcoRI and treated with calf intestinal alkaline phosphatase (Boehringer Mannheim Biochemicals, Indianapolis, Ind.).

pBScucchrcht5 is digested with ClaI to generate two ClaI fragments containing insert DNA. These pieces are gel-purified and cloned separately into pBluescript that has been digested with ClaI and treated with calf intestinal alkaline phosphatase. The resulting plasmids are called D-Cla1 and D-Cla2. The plasmid D-BamCla is made by isolating the BamHI/ClaI fragment of pBScucchrcht5 and cloning it into pBluescript digested with BamHI and ClaI. The plasmid D-XbaI is made by isolating the insert XbaI fragment of pBScucchrcht5 and cloning it into pBluescript digested with XbaI and treated with calf intestinal alkaline phosphatase.

The ligation reactions for each of the constructs are melted by incubating at 65° C. for 10 minutes. 10 ul of this solution are added to 30 ul of TE buffer (10 mM Tris, pH 7.5, 1 mM EDTA), mixed and allowed to stand at room temperature. The diluted DNA solution is added to 200 ul of thawed frozen competent cells (*E. coli* strain DH5) and allowed to stand on ice for 20 minutes. The cells are then heat-shocked for 90 seconds at 42° C., followed by a 10 minute room temperature incubation. 0.8 ml of SOC medium [Hanahan, D., J. Mol. Biol. 166, 557–580 (1983)] is added and the culture is incubated at 37° C. for one hour. 100 ul of the culture is plated on LB plates [Miller, *Experiments in Molecular Genetics*, Cold Spring Harbor Laboratory, New York (1972)] containing 100 ug/ml ampicillin (L-amp) and the plates are incubated overnight at 37° C. Positive colonies are picked and restreaked to a second L-amp plate and the plates are incubated overnight at 37° C.

Plasmid DNA for each of the clones is prepared essentially according to Maniatis et al., *Molecular Cloning*, Cold Spring Harbor Laboratory, New York (1982). The DNA sequences of the plasmid inserts are determined by the dideoxy method using the Sequenase kit (United States Biological, Cleveland, Ohio). The -20 and reverse primers for the pBluescript vector are used in the sequencing reactions as well as internal primers synthesized by automated phosphoramidite synthesis on an Applied Biosystems Synthesizer (Foster City, Calif.). The DNA Star (Madison, Wis.) sequence compilation software is used to compile the sequences of the subclones. The total EcoRI genomic clone is shown in SEQ ID No. 36.

The compiled sequence revealed the existence of three open reading frames within the total 12 kb genomic clone (pBScucchrcht5). The open reading framed included in the plasmid D-Cla1 potentially encodes for a protein of about 31,000 Daltons, with a pI=4.69. The sequence found in the plasmid D-BamCla corresponds to the sequence of the cDNA (SEQ ID No. 3) isolated by Metraux et al., *PNAS USA*, 86: 896–900 (1989). This open reading frame codes for a protein of about 28,000 Daltons with a pI of about 4.13. The last open reading frame is included in the plasmid D-Cla2 and potentially codes for a protein of about 29,000 Daltons and a pI of about 3.88. These three open reading frames share about 90% DNA sequence homology, but their flanking sequences have diverged.

D. Preparation of Constructs Containing Cucumber Chitinase Gene

1. Construction of pCIB2001

TJS75Kan is first created by digestion of pTJS75 [Schmidhauser et al., *J. Bacteriol.* 164: 446–455 (1985)] with NarI to excise the tetracycline gene, followed by insertion of an AccI fragment from pUC4K [Messing et al., *Gene* 19: 259–268 (1982)] carrying a NptI gene. pCIB200 is then made by ligating XhoI linkers to the EcoRV fragment of pCIB7 (containing the left and right T-DNA borders, a plant selectable nos/NptII chimeric gene and the pUC polylinker [Rothstein et al., *Gene* 53: 153–161 (1987)] and cloning the XhoI-digested fragment into SalI-digested TJS75Kan. pCIB2001 is made by cloning a new polylinker into the multiple cloning site of pCIB200 to give more unique restriction enzyme sites.

2. Construction of pCIB2001/BamChit

The plasmid pCIB2001/BamChit is constructed by digesting the plasmid DBamCla (section C, above) with BamHI and KpnI and cloning into pCIB2001 that has been digested with BglII and KpnI. pCIB2001/BamChit contains 2613 bp of the promoter region from the cucumber chitinase genomic clone, the chitinase gene and approximately 2.1 kb of 3' sequence.

3. Construction of pCIB2001/SalChit

The plasmid pCIB2001/SalChit is constructed by digesting DBamCla with SalI and cloning into pCIB2001 that has been digested with SalI and treated with calf intestinal alkaline phosphatase. pCIB2001/SalChit contains 1338 bp of the promoter region from the cucumber chitinase genomic clone, the chitinase gene and approximately 2.1 kb of 3' sequence.

4. Construction of pCIB2001/NcoChit

The plasmid pCIB2001/NcoChit is constructed by digesting DBamCla with NcoI, ligating with an NcoV/BamHI adapter, then digesting with BamHI and KpnI, and cloning into pCIB2001 that has been digested with BglII and KpnI. pCIB2001/NcoChit contains 222 bp of the promoter region from the cucumber chitinase genomic clone, the chitinase gene and approximately 2.1 kb of 3' sequence.

5. Verification of Clones

Plasmid DNA for each of the constructs is prepared essentially according to Maniatis et al., *Molecular Cloning* Cold Spring Harbor Laboratory, New York (1982). The purified DNA is used in restriction analysis and DNA sequencing across the cloning sites to verify the clones. The insert of pCIB2001/SalChit is in the same orientation as pCIB2001/BamChit and pCIB2001/NcoChit, whose orientation is forced by the cloning method used.

E. Preparation of a Chimeric Construct

1. Construction of pBSGus1.2 pBSGus1.2 is created by a three part ligation of a 391 bp SalI/SnaBI fragment from pRAJ265 [Jefferson et al., *EMBO J.* 6: 3091–3907 (1987) and GUS User Manual, Clonetech Labs (Palo Alto, Calif.)] with a 1707 bp SnaBI/EcoRI fragment from pBI221 [Jefferson et al., Id.] and pBS digested with SalI and EcoRI. Transformants are isolated and analyzed by restriction digestion and DNA sequencing. One verified clone is named pBSGus1.2.

2. Construction of pBSChit/GUS

The 2613 bp cucumber chitinase promoter region in pCIB2001/BamChit is isolated using PCR with the Gene-Amp kit from Perkin-Elmer/Cetus (Norwalk, Conn.) according to the manufacturer's recommendations and using the following primers:

5'-GCCTCGAGGATCCTATTGAAAAAG-3' (SEQ ID No. 82) and

5'-GCCTCGAGTGCTTAAAGAGCTTTC-3' (SEQ ID No. 83). The PCR product consists of the 2613 bp promoter with XhoI restriction enzyme sites on both ends of the sequence due to the design of the primers. This amplified product is then digested with XhoI and the piece is gel-purified. The purified fragment is ligated with pBSGus1.2 that has been digested with XhoI and treated with calf intestinal alkaline phosphatase. Transformants are isolated and analyzed by DNA sequencing. One verified clone, containing the cucumber promoter in its correct orientation in front of the GUS gene, is named pBSChit/GUS.

3. Construction of pCIB2001/Chit/GUS

The plasmid pBSChit/GUS is digested with KpnI and XbaI, and the insert piece containing the chitinase promoter and GUS gene with its flanking 3' sequences is gel-purified. The purified fragment is ligated with pCIB2001 (section D, above) that has been digested with KpnI and XbaI. Transformants are isolated on L-kan plates and plasmid DNA is analyzed by restriction digestion and DNA sequencing across the cloning sites. One verified clone is named pCIB2001/Chit/GUS.

EXAMPLE 63

Isolation of a Genomic Clone Encoding Acidic β-1, 3-glucanase

A genomic library is constructed as described in Example 20 and screened with a cDNA clone for the acidic β-1,3-glucanase, Example 59. A lambda clone is isolated, and a 1 kb EcoRI fragment of this lambda clone subcloned into Bluescript as described above in Example 61. The bluescript clone is named pBSGL6e.

EXAMPLE 63A

Isolation of a Genomic Clone for Arabidopsis PR-1

The Arabidopsis PR-1 cDNA cloned in pAPR1C-1 (sequence 33) was used as a hybridization probe in screening an Arabidopsis λEMBL 3 genomic library (purchased from Clontech). Four hybridizing plaques were plaque purified using conventional techniques and λ DNA was isolated from each one with lambdasorb (Promega). The λ DNA thus isolated was digested with XhoI, electrophoresed, transferred to hybridization membrane for hybridization with the PR-1 cDNA. A fragment of 7 kb was found to hybridize to the cDNA. DNA from one of the four purified plaques was then redigested with XhoI and ligated into the XhoI site of pBluescript (Stratagene). A colony carrying the promoter fragment was identified by probing with oligonucleotide DC21 from the PR-1 coding sequence (position +110 to +84) and the plasmid contained therein was designated pAtPR1-P and deposited Jan. 5, 1994 with the the Agricultural Researech Culture Collection, International Depositing Authority, 1815 N. University Street, Peoria, Ill. 61604 (NRRL deposit no. NRRL B-21169. Restriction analysis identified the 7 kb XhoI fragment as extending 4.2 kb upstream of the ATG of the PR1 gene.

G. Chemeric Genes Containing Anti-Pathogenic Sequences

This section describes combinations of cDNA sequences with sequences that promote transcription of the cDNA's and with those that facilitate processing of the 3' end of the mRNA in the plant cells.
1. Construction of plasmids containing plant expression cassettes.

This first set of examples covers the construction of plasmids which contain expression cassettes.

EXAMPLE 64

Construction of pCGN1509 (tobacco RUBISCO small subunit promoter cassette)

pCGN1509 is an expression cassette plasmid containing the 5' regulatory region and promoter from a tobacco ribulose-bis-phosphate carboxylase (RuBISCO) small subunit gene, and the 3' region from the octopine synthase (ocs) gene of the Ti plasmid of *Agrobacterium tumefaciens*, with unique restriction sites between these two parts. The 5' regulatory region is ultimately derived from a 3.4 kb EcoRI fragment containing tobacco RuBISCO small subunit gene TSSU3-8 (O'Neal et al., *Nucl. Acids Res.* 15:8661–8677 (1987)).

The 3.4 kb EcoRI fragment of TSSU3-8 is cloned into the EcoRI site of M13 mp18 (Yanisch-Perron et al., *Gene* 53:103–119 (1985)) to yield an M13 clone 8B. Single-stranded DNA is used as a template to extend oligonucleotide primer "Probe 1" (O'Neal et al., *Nucl. Acids Res.* 15:8661–8677 (1987)) using the Klenow fragment of DNA polymerase I. Extension products are treated with mung bean nuclease and then digested with HindIII to yield a 1450 bp fragment containing the small subunit promoter region; the fragment is cloned into HindII-SmaI digested pUC18 (Yanisch-Perron et al., Gene 53:103–119 (1985)) to yield pCGN625.

The BamHI-EcoRI fragment of pCGN625 is cloned into the large BamHI-EcoRI fragment (plasmid backbone) of BamHI-EcoRI digested pCGN607 in which the SmaI site at position 11207 (Barker et al., *Plant Mol Biol* 2: 335:350 (1983)) of the ocs 3' region is converted to a BglII site by ligation of a synthetic BglII linker (Facciotti et al., *Bio/Technology* 3:241–246 (1985)). This yields plasmid pCGN630. The BamHI site of pCGN630 is deleted by digestion with BamHI and treatment with the Klenow fragment of DNA polymerase I to create pCGN1502. The KpnI site of pCGN1502 is replaced by a BamHI site by digestion of pCGN1502 with KpnI, treatment with Klenow enzyme, and ligation of a synthetic BamHI linker. The resulting construction is pCGN1509.

EXAMPLE 65

Double CAMV 35S Promoter/Terminator Cassette Containing Ampicillin Resistance and pCGN1431 (A Double CAMV 35S Promoter/Terminator Cassette Containing Chloramphenicol Resistance)

pCGN1761 contains a double CaMV 35S promoter and the tml-3' region with an EcoRI site between contained in a pUC-derived plasmid backbone. The promoter-EcoRI-3' processing site cassette is bordered by multiple restriction sites for easy removal. The plasmid is derived by a series of steps (see below) from an initial double-35S plasmid, pCGN2113, which itself is derived from pCGN164, and pCGN638. The plasmid pCGN2113 is deposited with ATCC March (accession number 40587).

pCGN1431 also contains the double CAMV 35S promoter and the tml 3' region with a multiple cloning site between them. This promoter/terminator cassette is contained in a pUC-derived vector which contains a chloramphenicol rather than ampicillin resistance gene. The cassette is bordered by multiple restriction sites for easy removal.

A. Construction of pCGN986.

pCGN986 contains a cauliflower mosaic virus 35S (CaMV35) promoter and a T-DNA tml-3' -region with multiple restriction sites between them. pCGN986 is derived from another plasmid, pCGN206, containing a CaMV35S promoter and a different 3' region, the CaMV region VI 3'-end. The CaMV 35S promoter is cloned as an AluI fragment (bp 7144–7734) (Gardner et al., *Nucl. Acids Res.* 9: 2871–2888 (1981)) into the HincII site of M13mp7 (Messing et al., *Nucl. Acids Res.* 9:309–321 (1981)) to create C614. An EcoRI digest of C614 produced the EcoRI fragment from C614 containing the 35S promoter which is cloned into the EcoRI site of pUC8 (Vieira and Messing, *Gene* 19:259–268 (1982)) to produce pCGN147.

pCGN148a containing a promoter region, selectable marker (Kanamycin with 2 ATG's) and 3' region, is prepared by digesting pCGN528 with BglII and inserting the BamHI- BglII promoter fragment from pCGN147. This fragment is cloned into the BglII site of pCGN528 so that the BglII site is proximal to the kanamycin gene of pCGN528.

The shuttle vector, pCGN528, used for this construct is made as follows: pCGN525 is made by digesting a plasmid containing Tn5 which harbors a kanamycin gene (Jorgensen et al., *Mol. Gen. Genet.* 177:65 (1979)), with HindIII-BamHI and inserting the HindIII-BamHI fragment containing the kanamycin resistance gene into the HindIII-BamHI sites in the tetracycline gene of pACYC184 (Chang and Cohen, *J. Bacteriol.* 134:1141–1156 (1978)) pCGN526 is made by inserting the BamHI fragment 19 of pTiA6 (Thomashow et al., *Cell* 19:729–739 (1980)) modified with XhoI linkers inserted into the SmaI site, into the BamHI site of pCGN525. pCGN528 is obtained by deleting the small XhoI and religating.

pCGN149a is made by cloning the BamHI Kanamycin gene fragment from pMB9KanXXI into the BamHI site of pCGN148a. pMB9KanXXI is a pUC4K variant (Vieira and Messing, Gene 19:259–268 (1982)) which has the XhoI site missing but contains a function kanamycin gene from Tn903 to allow for efficient selection in Agrobacterium.

pCGN149a is digested with HindIII and BamHI and ligated to pUC8 digested with HindIII and BamHI to produce pCGN169. This removes the Tn903 kanamycin marker. pCGN565 and pCGN169 are both digested with HindIII and PstI and ligated to form pCGN203, a plasmid containing the CaMV 35S promoter and part of the 5'-end of the TN5 kanamycin gene (up to the PstI site, (Jorgensen et al. *Mol. Gen. Genet.* 177: 65 (1979)). A 3' regulatory region is added to pCGN203 from pCGN204 (an EcoRI fragment of CaMV (bp 408–6105) containing the 3' region of gene VI subcloned into pUC18 (Gardner et al., *Nucl. Acids Res.* 9: 2871–2888 (1981)) by digestion with HindIII and PstI and ligation. The resulting cassette, pCGN206, is the basis for the construction of pCGN986.

The pTiA6 T-DNA tml 3'-sequences are subcloned from the Bam19 T-DNA fragment (Thomashow et al., *Cell* 19:729–739 (1980)) as a BamHI-EcoRI Fragment (nucleotides 9062 to 12, 823, numbering as in (Barker et al., *Plant Mo. Biol.* 2: 335–350 (1983)) and combined with the pACYC184 (Chang and Cohen, *J. Bacteriol.* 134:1141–1156 (1978)) origin of replication as an EcoRI-HindII fragment and a gentamycin resistance marker (from plasmid pLB41), (D. Figurski) as a BamHI-HindII fragment to produce pCGN417.

The unique SmaI site of pCGN417 (nucleotide 11,207 of the Bam19 fragment) is changed to a SacI site using linkers and the BamHI-SacI fragment is subcloned into pCGN565 to give pCGN971. The BamHI site of pCGN971 is changed to an EcoRI site using linkers to yield pCGN971E. The resulting EcoRI-SacI fragment of pCGN971E, containing the tml 3' regulatory sequences,was joined to pCGN206 by digestion with EcoRI and SacI to give pCGN975. The small part of the Tn5 kanamycin resistance gene is deleted from the 3'-end of the CaMV 35S promoter by digestion with SalI and BglII, blunting the ends and ligation with SalI linkers. The final expression cassette pCGN986 contains the CaMV 35 promoter followed by two SalI sites, an XbaI site, BamHI, SmaI KpnI and the tml 3'region (nucleotides 11207–9023 of the T-DNA).

B. Construction of pCGN164

The AluI fragment of CaMV (bp 7144–7735) (Gardner et al., *Nucl. Acids Res.* 9: 2871–2888 (1981)) is obtained by digestion with AluI and cloned into the HincII site of M13mp7 (Vieira and Messing, *Gene* 19: 259–268 (1982)) to create C614. An EcoRI digest of C614 produces the EcoRI fragment from C614 containing the 35S promoter which is cloned into the EcoRI site of pUC8 (Vieira and Messing, *Gene* 19: 259–268 (1982)) to produce pCGN146. To trim the promoter region, the BglII site (bp7670) is treated with BglII and Bal31 and subsequently a BglII linker is attached to the Bal31 treated DNA to produce pCGN147. pCGN147 is digested with EcoRI HphI and the resultant EcoRI-HphI fragment containing the 35S promoter is ligated into EcoRI-SmaII digested M13mp8 (Vieira and Messing, *Gene* 19:259–268 (1982)) to create pCGN164.

C. Construction of pCGN638

Digestion of CaMV10 (Gardner et al., *Nucl. Acids Res.* 9: 2871–2888 (1981)) with BglII produces a BglII fragment containing a 35S promoter region (bp 6493–7670) which is ligated into the BamHI site of pUC19 (Norrander et al., Gene 26:101–106 (1983)) to create pCGN638.

D. Construction of pCGN2113 pCGN164 is digested with EcoRV and BamHI to release a EcoRV-BamHI fragment which contained a portion of the 35S promoter (bp 7340–7433); pCGN638 is digested with HindIII and EcoRV to release a HindIII-EcoRV fragment containing a different portion of the 35S promoter (bp 6493–7340). These two fragments are ligated into pCGN986 which has been digested with HindIII and BamHI to remove the HindIII-BamHI fragment containing the 35S-promoter; this ligation produces pCGN639, which contains the backbone and tm1-3' region from pCGN986 and the two 35S promoter fragments from pCGN164 and pCGN638. pCGN638 is digested with EcoRV and DdeI to release a fragment of the 35S promoter (bp 7070–7340); the fragment is treated with the Klenow fragment of DNA polymerase I to create blunt ends, and is ligated into the EcoRV site of pCGN639 to produce pCGN2113 having the fragment in the proper orientation.

E. Construction of pCGN1761 pCGN2113 is digested with EcoRI and the plasmid is ligated in the presence of a synthetic DNA adaptor containing an XbaI site and a BamHI site (the adaptor contains EcoRI sticky ends on either end, but the adjacent bases are such that an EcoRI site is not reconstructed at this location) to produce pCGN2113M. pCGN2113M is digested to completion with SacI and then subjected to partial digestion with BamHI. This DNA is then treated with T4 DNA polymerase to create blunt ends and an EcoRI linker is ligated into the blunt-ended plasmid. After transformation a plasmid clone which contains a unique EcoRI site between the promoter and the intact tm1-3' region is selected and designated pCGN1761.

F. Construction of pCGN1431

The SalI-EcoRI fragment of pCGN2113, which contains the entire promoter-polylinker-3' cassette, is removed by SalI-EcoRI digestion and cloned into SalI-EcoEl digested pCGN565 to create pCGN2120; pCGN565 is a cloning vector based on pUC8-Cm (K. Buckley, PH.D. Thesis, UC San Diego 1985), but containing the polylinker from pUC18

(Yanisch-Perron et al., Gene 53: 103–119 (1985)). pCGN2120 is digested to completion with PstI and then religated. A clone is selected which had deleted only the 858 bp PstI-PstI fragment (9207–10065, Barker et al., 1983, supra) from the tml 3' region to create pCGN1431.

2. Chimeric Genes

This second section describes the subcloning of cDNA's into the cassettes in both sense and anti-sense orientation.

EXAMPLE 66

Construction of pCGN1752A and pCGN1752B (SSU Promoter/PR-1A Expression Cassette; Sense and Anti-Sense Orientation))

The 807 bp EcoRI fragment of pBSPR1-207 is subcloned into EcoRI digested pCGN1509 and plasmids bearing the cDNA in each of the two possible orientations are selected; a plasmid in which the tobacco RuBISCO small subunit promoter would be expected to generate a transcript with the mRNA sense strand of PR1a is designated pCGN1752A, and a plasmid in which the tobacco RuBISCO small subunit promoter would be expected to generate a transcript with the anti-sense strand (i.e. complementary sequence of the mRNA) of PR1a is designated pCGN1752B.

EXAMPLE 67

Construction of pCGN1753A and pCGN1753B (SSU Promoter/PR-1B Expression Cassette; Sense and Anti-Sense Orientation)

The 717 bp EcoRI fragment of pBSPR1-1023 is subcloned into EcoRI digested pCGN1509 and plasmids bearing the cDNA in each of the two possible orientation are selected; a plasmid in which the tobacco RuBISCO small subunit promoter would be expected to generate a transcript with the mRNA sense strand of PR-1b is designated pCGN1753A, and a plasmid in which the tobacco RuBISCO small subunit promoter would be expected to generate a transcript with the antisense strand (i.e. complementary sequence of the mRNA) of PR-1b is designated pCGN1753B.

EXAMPLE 68

CAMV 35S Promoter/PR-1A Expression Cassette (Sense and Anti-Sense Orientation))

A 807 bp EcoRI fragment bearing a tobacco PR1a cDNA is released from pBSPR1-207 by EcoRI digestion and subcloned into EcoRI digested pCGN565 to yield pCGN1750. A 717 bp EcoRI fragment bearing the entire coding region of a tobacco PR-1b cDNA is released from pBSPR1-1023 by digestion with EcoRI and subdloned into EcoRI digested pCGN565 to yield pCGN1751. These two plasmids are constructed to facilitate subsequent subcloning experiments.

The 807 bp EcoRI fragment of pCGN1750 is subcloned into EcoRI digested pCGN1761 and plasmids bearing the cDNA in each of the two possible orientation are selected; a plasmid in which the double 35S promoter would be expected to generate a transcript with the mRNA sense strand of PR-1a is designated pCGN1762A, and a plasmid in which the double 35S promoter would be expected to generate a transcript with the anti-sense strand (i.e. complementary sequence of the mRNA) of PR-1a is designated pCGN1762B.

EXAMPLE 69

Construction of pCGN1763A and pCGN1763B (Double CaMV 35S Promoter/PR-1b Expression Cassette; Sense and Anti-Sense Orientation)

The 717 bp EcoRI fragment of pCGN1751 (see above) is subcloned into EcoRI digested pCGN1761 and plasmids bearing the cDNA in each of the two possible orientation are selected; a plasmid in which the double 35S promoter would be expected to generate a transcript with the mRNA sense strand of PR-1b is designated pCGN1763A, and a plasmid in which the double 35S promoter would be expected to generate a transcript with the anti-sense strand (i.e. complementary sequence of the mRNA) of PR-1b is designated pCGN1763B.

EXAMPLE 70

Construction of pCIB1002 and pCIB1003 (Double CAMV 35S Promoter/PR-R major Expression Cassettes; Sense and Anti-Sense Orientation)

The plasmid pBSPRR-401 is partially digested with EcoRI and the resulting DNA fragments are separated on a 1.0% low-gelling temperature agarose gel. A band at about 900 base pairs, which contains the full length PR-R cDNA insert, is excised and ligated to pCGN1761 which had been digested to completion with EcoRI and dephosphorylated using calf intestine alkaline phosphatase. The DNA is ligated and transformed as described above, positive colonies are screened and their plasmids are analyzed. One plasmid which contains the PR-R cDNA in a sense orientation relative to the double CAMV 35S promoter, is selected and designated as pCIB 1002. A second plasmid, in which the PR-R cDNA is in an anti- sense orientation relative to the double CAMV 35S promoter is selected and designated pCIB1003.

EXAMPLE 71

Construction of pCIB1020 and pCIB1021 (Double CAMV 35S Promoter/PR-P Expression Cassette; Sense and Anti-Sense Orientation)

The plasmid pBScht28 (see above) is digested with EcoRI and fragments are separated on a 0.5% LGT agarose gel. The band containing the PR-P cDNA is excised and mixed with pCGN1761 (see above) which had been digested with EcoRI, treated with calf intestinal alkaline phosphatase (CIAP) and purified on a 0.5% low gelling temperature (LGT) agarose gel. The mixture is ligated and transformed as described. Plasmids are screened for insertion of the PR-P cDNA in either orientation. One plasmid, in which the PR-P cDNA is inserted in a sense orientation relative to the double CAMV 35S promoter, is designated pCIB1020. A plasmid in which the PR-P cDNA is inserted in an anti-sense orientation relative to the double CAMV 35S promoter is designated pCIB1021.

The plasmid pBScht28 is deposited with ATCC (accession number 40588).

EXAMPLE 72

Construction of pCIB1022 and pCIB1023 (Double CAMV 35S Promoter/PR-Q Expression Cassette; Sense and Anti-Sense Orientation)

The full-length cDNA sequence for PR-Q is contained on two different plasmids, PBScht15 contains the 3' end of the cDNA and pBScht5'-4 contains the 5' end of the cDNA. Because of this situation, the plasmids pCIB1022 and pCIB1023 are constructed in a three way ligation and differ by their orientation in the pCGN1761 vector. pCGN1761 is digested with EcoRI, treated with CIAP and purified on a 0.5% LGT agarose gel. pBScht15 (see above) is digested with NsiI and EcoRI and the fragments are separated on a 0.5% LGT agarose gel. A PCR reaction using pBScht5'-4 (see above) as a template and oligonucleotides:

1) 5' CTATGAATGCATCATAAGTG 3' (SEQ ID No. 84); and 2) 5' GCGGAATTCAAAAAAAAAAAAAAAACATAAG 3' (SEQ ID No. 85) as primers is performed to amplify the 5' end of the PR-Q cDNA. The PCR product is purified and digested with NsiI and EcoRI and the 210 bp product is purified from a 1.0% LGT agarose gel. The purified pCGN1761 vector, the 810 bp NsiI/EcoRI fragment from pBScht15 and the NsiV/EcoRI digested PCR fragment are ligated and transformed as described above. Transformants are screened and selected which include the entire cDNA in either orientation.

One plasmid which has the full-length PR-Q cDNA in a sense orientation relative to the double CAMV 35S promoter is designated as pCIB1022. A plasmid in which the full-length PR-Q cDNA is inserted in the anti-sense orientation relative to the promoter is designated pCIB1023.

EXAMPLE 73

Construction of pCIB1024 and pCIB1025 (Double CAMV 35S PromoterIPR-O' Expression Cassette; Sense and Anti-Sense Orientation)

The plasmid pBSGL6e is deposited with ATCC (accession number 40535). The PR-O' cDNA cloned into pBSGL6e is truncated at the 5' end and is missing almost all of the complete signal sequence. This sequence is necessary for extracellular transport of the protein and should be replaced in order to engineer transgenic plants that secrete the protein. This example describes the subcloning of the PR-O' cDNA into the double CAMV 35S expression cassette in such a way that a signal peptide from PR-1a is added to the PR-O' protein.

This construction is carried out as a complicated three-way ligation. First a fusion of the PR-1a leader and signal peptide and the coding sequence of the mature PR-O' is made by a PCR gene fusion method. Then this piece is ligated along with the 3' end of the PR-O' cDNA into the pCGN1761 vector and transformants are selected with the insert in either orientation relative to the promoter.

A gene fusion technique based on PCR amplification has been developed by Ho, S. et al, *Gene* 77: 51–59 (1989). In this technique a gene fusion is made by creating two fragments with overlapping ends by PCR. In a subsequent reaction these two fragments are then fused also by PCR to generate a perfect fusion between the two molecules. This strategy is used to fuse the PR-1a signal peptide and leader to the PR-O' cDNA. Four oligonucleotides are synthesized with the following sequences:

```
GP50 - 5' CCATAACAAACTCCTGCTTGGGCACGGCAAGAGTGGGATA 3' (SEQ ID
No. 86)

GP51 - 5' TATCCCACTCTTGCCGTGCCCAAGCAGGAGTTTGTTATGG 3' (SEQ ID
No. 87)

GP52 - 5' GATCGAATTCATTCAAGATACAACATTTCT 3' (SEQ ID No. 88)

GP53 - 5' CATTCTCAAGGTCCGG 3' (SEQ ID No. 89).
```

The GP50 and GP51 oligonucleotides are complementary to each other and contain the DNA sequence desired for the fusion between the PR-1a leader and signal and the PR-O' mature coding sequence. This is diagrammed below:

```
GP51 5' TATCCCACTCTTGCCGTGCCCAAGCAGGAGTTTGTTATGG 3'
     3' ATAGGGTGAGAACGGCACGGGTTCGTCCTCAAACAATACC 5'
GP50
        |   PR-1A    ||   PR-O'     |
```

The oligonucleotide GP52 is the same sequence as the 5' end of the PR-1a cDNA and it contains on the 5' end a sequence encoding an EcoRI site:

```
GP52 - 5' GATCGAATTCATTCAAGATACAACATTTCT 3'(SEQ ID No. 88)
          |EcoRI|    PR-1a        |
```

The oligonucleotide GP53 serves as a primer and is complementary to positions 180 to 195 of the PR-O' sequence in SEQ ID No. 13.

In order to fuse the two pieces of DNA two PCR reactions are set up. One uses the plasmid pBSPR1-207 as a template and the two primers GP52 and GP50; the other uses pBSGL6e as a template and the primers GP51 and GP53. The PCR products are analyzed by gel electrophoresis and it is determined that the reactions are successful.

The PCR products are then purified and an aliquot of each is used in a second stage PCR reaction. In this reaction the templates are both of the products from the first two reactions and the primers are GP52 and GP53. A modified PCR reaction is established such that in the first round of synthesis the DNA templates are added without the primers and the templates are heated and allowed to cool and then extended at 65° C. The two primers are then added and the PCR reaction is carried out normally.

An aliquot of the PCR reaction is analyzed by gel electrophoresis and it is determined that the reaction is successful. The remaining DNA is then purified and digested with SacI and EcoRI and the digest is electrophoresed on a 1.5% LGT agarose gel. The band corresponding to the correct PCR product is excised and used for ligation.

The plasmid pBSGL6e is digested with both SacI and EcoRI and the digest is electrophoresed on a 0.5% LGT agarose gel. The 1.0 kb band containing the large PR-O' fragment is excised and ligated with the SacI-EcoRI PCR product from above and the plasmid pCGN1761 which had been digested with EcoRI and CIAP and purified on a 0.5% LGT agarose gel. The fragments are ligated and transformed as described above. Transformants are screened for the correct construct.

A plasmid in which the PR-1a leader and signal has been fused to the PR-O' mature coding sequence and is in the sense orientation relative to the promoter is designated pCIB1024; this construct is confirmed by DNA sequencing.

A plasmid with the correct fusion but in the opposite orientation relative to the promoter is designated pCIB1025. This construct is also verified by DNA sequencing.

EXAMPLE 74

Construction of pCIB1024A and pCIB1025A (Double 35S PromoterIPR-O' Expression Cassette; Sense and Anti-Sense Orientation)

The plasmid pBSGL5B-12, which contains a full-length cDNA encoding the PR-O' protein is digested with EcoRI and the fragments are separated on a 0.5% LGT agarose gel. The 1.2 kb band is excised and ligated with pCGN1761 which is digested with EcoRI, treated with CIAP and purified on a 0.5% LGT agarose gel as described above. The ligation mixture is transformed as described and transformants are screened for a clone containing the PR-O' cDNA in either orientation. One plasmid, in which the cDNA is inserted in a sense orientation relative to the double CAMV 35S promoter, is designated pCIB1024. A plasmid in which the cDNA is inserted in an anti-sense orientation relative to the promoter is designated as pCIB1025A.

EXAMPLE 75

Construction of pCIB1032 and pCIB1033 (Double 35S Promoter/PR-2 Expression Cassette; Sense and Anti-Sense Orientation)

The plasmid pBSGL117 contains a full-length cDNA encoding the PR-2 protein. The PR-2 cDNA from pBSGL117 is subcloned into the pCGN1761 expression plasmid in either orientation to create pCIB1032 and pCIB1033. However, the cDNA contains an internal EcoRI site and so the cDNA has to be excised by a partial EcoRI digest.

The plasmid pBSGL117 is digested with EcoRI under conditions in which a partial digest resulted. The digestion products are separated on a 0.5% LGT agarose gel and the 1.2 kb band containing the full-length cDNA for PR-2 is excised and ligated to pCGN1761 which had been digested with EcoRI, treated with CLAP and purified on a 0.5% LGT agarose gel. The ligation and transformation are carried out as previously described. Positive transformants are isolated and screened for the presence of the large PR-2 cDNA fragment inserted in either orientation. One plasmid, with the PR-2 cDNA subcloned in a sense orientation relative to the transcriptional start site is designated as pCIB1032 and a plasmid with the fragment in an anti-sense orientation is designated as pCIB1033. The structure of these constructs is verified by DNA sequencing.

EXAMPLE 76

Construction of pCIB1034 and pCIB1035 (Double 35S Promoter/PR-N Expression Cassette; Sense and Anti-Sense Orientation)

A plasmid containing a full-length cDNA encoding the PR-N protein is used as a source to subclone the PR-N cDNA into the pCGN1761 expression plasmid in either orientation. The resulting plasmids are designated as pCIB1034 and pCIB1035. However, the cDNA contains an internal EcoRI site and so the cDNA has to be excised by a partial EcoRI digest.

The plasmid containing the full-length PR-N cDNA is digested with EcoRI under conditions in which a partial digest results. The digestion products are separated on a 0.5% LGT agarose gel and the 1.2 kb band containing the full-length cDNA for PR-N is excised and ligated to pCGN1761 which has been digested with EcoRI, treated with CIAP and purified on a 0.5% LGT agarose gel. The ligation and transformation is carried out as previously described.

Positive transformants are isolated and screened for the presence of the large PR-N cDNA fragment inserted in either orientation. One plasmid, with the PR-N cDNA subcloned in a sense orientation relative to the transcriptional start site is designated as pCIB1034 and a plasmid with the fragment in an anti-sense orientation is designated as pCIB1035. The structure of these constructs is verified by DNA sequencing.

EXAMPLE 77

Construction of pCIB1036 and pCIB1037 (Double 35S Promoter/PR-O Expression Cassette; Sense and Anti-Sense Orientation)

A plasmid containing a full-length cDNA encoding the PR-O protein is used as a source to subclone the PR-O cDNA into the pCGN1761 expression plasmid in either orientation. The resulting plasmids are designated as pCIB1036 and pCIB1037. However, the cDNA contains an internal EcoRI site and so the cDNA has to be excised by a partial EcoRI digest.

The plasmid containing the full-length PR-O cDNA is digested with EcoRI under conditions in which a partial digest results. The digestion products are separated on a 0.5% LGT agarose gel and the 1.2 kb band containing the full-length cDNA for PR-O is excised and ligated to pCGN1761 which has been digested with EcoRI, treated with CIAP and purified on a 0.5% LGT agarose gel. The ligation and transformation is carried out as previously described. Positive transformants are isolated and screened for the presence of the large PR-O cDNA fragment inserted in either orientation. One plasmid, with the PR-O cDNA subcloned in a sense orientation relative to the transcriptional start site is designated as pCIB1036 and a plasmid with the fragment in an anti-sense orientation is designated as pCIB1037. The structure of these constructs is verified by DNA sequencing.

EXAMPLE 78

Construction of pCIB1038 and pCIB1039 (Double 35S promoter/PR-2' Expression Cassette; Sense and Anti-Sense Orientation)

A plasmid (pBSGL135 from Example 48) containing a full-length cDNA encoding the PR-2' protein is used as a source to subclone the PR-2' cDNA into the pCGN1761 expression plasmid in either orientation. The resulting plasmids are designated as pCIB1038 and pCIB1039. However, the cDNA contains an internal EcoRI site and so the cDNA has to be excised by a partial EcoRI digest.

The plasmid containing the full-length PR-2' cDNA is digested with EcoRI under conditions in which a partial digest results. The digestion products are separated on a 0.5% LGT agarose gel and the 1.2 kb band containing the full-length cDNA for PR-2' is excised and ligated to pCGN1761 which has been digested with EcoRI, treated with CIAP and purified on a 0.5% LGT agarose gel. The ligation and transformation is carried out as previously described. Positive transformants are isolated and screened for the presence of the large PR-2' cDNA fragment inserted in either orientation. One plasmid, with the PR-2' cDNA subcloned in a sense orientation relative to the transcriptional start site is designated as pCIB1036 and a plasmid with the fragment in an anti-sense orientation is designated as pCIB1039. The structure of these constructs is verified by DNA sequencing.

The foregoing methods can be used to construct a double 35S promoter-driven expression cassette for any other cDNA sequence isolated, including, but not limited to, those cDNAs presented in SEQ ID No. 26 (PR-2"), SEQ ID No. 29 (basic tobacco chitinase/lysozyme), SEQ ID No. 30 (acidic tobacco chitinase/lysozyme), and SEQ ID Nos. 31 and 32 (PR-4a and PR-4b).

EXAMPLE 79

Construction of pCIB1005B and pCIB1006B (Double CAMV 35S Promoter/Basic Glucanase Expression Casseue; Sense and Anti- Sense Orientation)

The plasmid pGLN17 is a hybrid cDNA encoding the basic β 1,3 glucanase from Nicotiana tabacum (Shinshi, H. et al., 1988 supra) constructed by fusing the 5' end of the pGL31 clone and the 3' end of the pGL36 clone. The sequence encoded in this hybrid cDNA is shown in SEQ ID No. 20. It is found that this cDNA is truncated at the 5' end and does not encode the entire signal peptide. In order to make transgenic plants in which this protein is properly targeted (ie, the central vacuole), it is necessary to add this sequence back on to the truncated cDNA. Therefore, the double CAMV 35S expression cassette is constructed in a two step process. In the first step the signal peptide of the cDNA is replaced by a signal peptide encoded in the genomic clone. In the second step, this "repaired cDNA" is moved into the expression vector.

The plasmid pSGL2 is a subclone of the pGLN17cDNA. This plasmid is digested with ClaI and EcoRI and the 1 kb fragment containing the glucanase cDNA is isolated from a LGT agarose gel. The pBluescript plasmid is digested with EcoRI, treated with CIAP and purified on a LGT agarose gel.

The plasmid pBS-Gluc 39.1 (ATCC accession no. 40526) contains a 4.4 kb insert which includes the glucanase coding sequence, about 1.5 kb of 5' flanking sequence, a 600 bp intron, and about 1 kb of 3' flanking sequence. This plasmid is used as a template in a PCR experiment containing the following two primers:

A. 5' CATCTGAATTCTCCCAACAAGTMTCCC 3' (SEQ ID No. 90)

B. 5' AACACCTATCGATTGAGCCCCTGCTAT-GTCAATGCTGGTGGC3' (SEQ ID No. 91)

The result of this amplification is to produce a fragment to replace the truncated 5' end of the glucanase cDNA. A single-base mutation creating an EcoRI site is introduced to facilitate cloning experiments. The PCR product is digested with EcoRI and ClaI and fragments are separated on a 2.0% LGT agarose gel. A 120 bp band is excised, mixed with the 1 kb ClaI-EcoRI fragment from pSGL2 and the purified, EcoRI digested bluescript vector, ligated and transformed as described above. Transformants are screened for the presence of the insert and one plasmid with the proper structure is designated pCIB1009.

The plasmid pCIB1009 is digested with EcoRI and the 1.2 kb fragment is purified on a LGT agarose gel. The plasmid pCGN1761 is digested with EcoRI, treated with CIAP, purified on a LGT agarose gel, mixed with the 1.2 kb EcoRI fragment, and then ligated and transformed. Transformants are screened for the presence of the insert. One plasmid, in which the glucanase cDNA is in a sense orientation relative to the CAMV promoter is designated as pCIB1005B. Another plasmid, with the cDNA insert in an anti-sense orientation is designated pCIB 1006B.

EXAMPLE 80

35S Promoter/Basic Chitinase Expression Cassette (Sense and Anti-Sense Orientation)

The plasmid pSCH10 contains a cDNA insert of the tobacco basic chitinase which is similar to the insert in pCHN50 (Shinshi, H. et al., supra) but with an extension of 81 base pairs on the 5' end. The 80 extra base pairs are:

```
5'GGATCCGTTTGCATTTCACCAGTTTACTACTACATTAAAATGAGGCTTTGTAAATTC
 |    |    |    |    |    |
 1    10   20   30   40   50

5' ACAGCTCTCTCTTCTCTACTATTT 3' (SEQ ID No. 92)
            |    |    |
            60   70   80
``` pSCH10 is digested with BamHI and then ligated with a molecular adaptor with the sequence 5' GATCCGGAAT-TCCG 3' as described in Example 5 above. The ligation product is then purified and digested with EcoRI and the 1.2 kb fragment containing the adapted chitinase cDNA is purified from a LGT agarose gel. This fragment is mixed with EcoRI digested, CIAP treated pCGN1761 which is also purified from a LGT agarose gel and the mixture is ligated and transformed. Transformants are screened for the chitinase cDNA insert and one plasmid which contains the chitinase cDNA in a sense orientation relative to the CAMV promoter is designated as pCIB1007. A plasmid with the chitinase cDNA in an anti-sense orientation with respect to the promoter is designated as pCIB1008.

EXAMPLE 81

Construction of PCGN1788A and pCGN1788B (Double CAMV 35S Promoter/SAR8.2 Expression Cassette; Sense and Anti-Sense Orientation)

The plasmids pCIB/SAR8.2a and pCIB/SAR8.2b are deposited with ATCC, accession numbers 40584 and 40585 respectively. The pSAR8.2a cDNA (see above) is subcloned into the double CAMV 35S promoter/3'tml terminator cassette pCGN1431 (see above) using a PCR amplification method. Four oligonucleotides, two for each of the sense and anti-sense constructions and each one 33 nucleotides in length, are synthesized for use as primers to generate the cDNA sequence of pSAR8.2a by PCR using the plasmid pSAR8.2a as template. The primers contained additional sequences at their 5' ends that generated new restriction sites upon completion of PCR amplification.

For the sense construction the sequence of oligonucleotide 1167 is

5'-GTGACCGAGCTCAAAGAAAAATACAGTAC-AATA-3' (SEQ ID No. 93)

which generates an SstI site proximal to the 3' end of the cDNA sequence. The sequence of oligonucleotide 1168 is 5' ACCGTGGGATCCACAGTAAAAAACTGAAA-CTCC-3' (SEQ ID No. 94)

and generates a BamHI site proximal to the 5' end of the cDNA.

For the anti-sense construction, the sequence of oligonucleotide 1224 is

5'-GTGACCGGATCCAAAGAAAAATACAGTAC-AATA-3' (SEQ ID No. 95)

which generates a BamHI site proximal to the 3' end of the cDNA. The sequence of oligonucleotide 1225 is 5'-ACCGTGGAGCTCACAGTAAAAAACTGAAA-CTCC-3' (SEQ ID No. 96)

and generates an SstI site proximal to the 5' end of the cDNA.

Oligonucleotide 1167 and 1168 are used in a PCR reaction in which the plasmid pSAR8.2a served as a DNA template. The purified PCR product generated in this reaction is digested with SstI and BamHI and cloned into pCGN1431 which is digested with SstI and BaniHI. The DNA is transformed and plasmids are screened for the presence of the pSAR8.2a cDNA insert in a sense orientation relative to the double CAMV 35S promoter. Putative plasmids are then subjected to DNA sequencing and one, which has the proper orientation and contains no introduced mutations, is designated pCGN1788A.

For the anti-sense construct, oligonucleotides 1224 and 1225 are used in a PCR reaction as described above. After digestion with SstI and BamHI the DNA is cloned into SstI and BamHI digested pCGN1431. Putative positive plasmids are screened for the insertion of the cDNA in an anti-sense orientation relative to the promoter and the constructs are verified by sequencing the entire cDNA. One plasmid, in which the cDNA is inserted in the correct orientation and the DNA sequence is correct, is designated pCGN1788B.

EXAMPLE 82

Construction of PCIB1000 and PCIB1001 (Double CAMV 35S Promoter/Cucumber Chitinase/ Lysozyme Expression Cassette (Sense and Anti-Sense Orientation)

The plasmid pBScucchi/chitinase (ATCC accession number 40528) is digested with EcoRI and the fragments are separated on a 0.5% LGT agarose gel. The 1.2 kb band is excised and ligated with pCGN1761 which had been digested with EcoRI, treated with CIAP and purified on a 0.5% LGT agarose gel as described above. The ligation mixture is transformed as described and transformants are screened for containing the chitinase/lysozyme cDNA in either orientation. One plasmid, in which the cDNA is inserted in a sense orientation relative to the double CAMV 35S promoter, is designated pCIB1000. A plasmid in which the cDNA is inserted in an anti-sense orientation relative to the double CAMV 35S promoter is designated pCIB1001.

EXAMPLE 82A

Fusion of the Arabidopsis PR-1 Promoter to the Firefly Luciferase Gene

Plasmid pDO432 containing a gene encoding luciferase (LUC) from firefly was received from Dr David Ow (University of California, San Diego; se Ow et al., 1986; Science 234: 856). The LUC gene was excised from pDO432 by digestion with XbaI (at position +45 relative to the ATG) and SstI (approximately 1.8 kb downstream of the ATG and outside the LUC coding region). Additionally, an EcoRI-XbaI promoter fragment was excised from pAtPR1-P; this fragment was 1.4 kb in size and delineated by an XbaI site 2.8 kb upstream of the PR-1 ATG and an EcoRI site in the pBluescript polylinker distal to the 5' end of the cloned promoter fragment (at −4.2 kb relative to the ATG). These two fragments were cloned by threeway ligation into EcoRI/ SacI cleaved pBluescript thus orienting the LUC gene adjacent to the upstream PR-1 promoter fragment (pAtPR1-Q).

Subsequently, pAtPR1-P was cleaved with XbaI (at the −2.8 kb position and within the pBluescript polylinker) and religated to generate a PR-1 genomic construct without the upstream 1.4 kb promoter fragment and which thus ended 2.8 kb upstream of the PR-1 ATG (pAtPR1-R). This plasmid was used as a template in PCR with a left-to-right "topstrand" primer extending from positions −237 to −214 (DC39) upstream of the PR-1 ATG (oligo A) and a right-to-left "bottomstrand" primer comprising 15 bp of LUC coding sequence extending up to the LUC ATG and a further 19 bp of PR-1 sequence extending from the ATG into the PR-1 untranslated leader (oligo B: sequence: TTT GGC GTC TTC CAT TTT TCT AAG TTG ATA ATG G). This PCR reaction was undertaken for five cycles at 94_C (30 s), 40_C (60 s), and 72_C (30 s) followed by 25 cycles at 94_C (30 s), 55_C (60 s) and 72_C (30 s) and this generated a product of 245 bp through annealing of the homologous PR-1 sequences; the fragment included a BglII site at its left end from the PR-1 promoter. A second PCR reaction was done using plasmid pDO432 as a template and using a left-to-right "topstrand" oligonucleotide which comprised 15 bp of PR-1 untranslated leader up to the PR-1 ATG and a further 12 bp of LUC sequence from the ATG into the LUC coding sequence (oligo C: sequence: TAT CAA CTT AGA AAA ATG GAA GAC GCC AAA) and a right-to-left "bottom strand" oligonucleotide extending from positions 332 to 312 (DC53) into the LUC coding sequence (oligo D). This PCR reaction was done under the same conditions as the one described above and generated a fragment of approximately 300 bp through annealing of the homologous LUC sequences; this fragment included a PstI site at its right end, derived from the LUC sequence amplified.

The two PCR fragments generated above were gel purified using standard procedures to remove oligonucleotides and were then themselves mixed in a further PCR reaction ("inside-outside PCR") with oligonucleotides A and D as primers. Conditions for this reaction were the same as described above. The amplified fragment was a fusion of the PR-1 promoter fragment from the first PCR reaction described above and the LUC 5' coding sequence from the second PCR reaction described above and had a BglII site at its left end and a PstI site at its right end. The fragment was gel purified and cleaved with BglII and PstI to yield a product of 545 bp in size which was cloned into pAtPR1-R which had previously been cleaved with the same enzymes. Cleavage of the resultant plasmid (pAtPR1-S) with XbaI released a PR-1 promoter fragment extending from −2.8 kb to the XbaI site downstream of the LUC ATG, the fusion point between the PR-1 promoter and the LUC coding sequence being at the ATG. This fragment was cloned into XbaI cleaved pAtPR1-Q regenerating the full-length PR-1 promoter (4.2 kb) in operational fusion to LUC (pAtPR1-R).

A. Transfer of the Arabidopsis PR-1 Promoter—Firefly Luciferase Gene Fusion to pCIB200 pAtPR1-R was cleaved with XhoI and SacI and transferred to SalI/SacI cleaved pCIB200 to create a binary vector construction (pAtPR1-S) suitable for Arabidopsis transformation (see example 28). pAtPR1-S was then transferred to *Agrobacterium tumefaciens* strain A136/pCIB542 for transfer to Arabidopsis Dijon-0 using the method described by Wen-jun and Forde, *Nucl. Acids Res.* 17: 8385–8386 (1989). T2 or T3 lines carrying the PR1-LUC transgene in the homozygous state were generated for chemical induction analysis.

H. Vectors Containing Anti-Pathogenic Sequences

This section details the construction of binary vectors containing all of the chimeric genes.
1. Binary vectors
This section explains the development of the binary vectors to be used.

EXAMPLE 83

Construction of pCGN783 pCGN783 is a binary plasmid containing the left and right T-DNA borders of *Agrobacterium tumefaciens* octopine Ti-plasmid pTiA6 (Currier and Nester, *J. Bact* 126:157–165 (1976)) the gentamycin resistance gene of pPh1JI (Hirsch and Beringer, *Plasmid* 12: 139–141 (1984)), the 35S promoter of cauliflower mosaic virus (CaMV) (Gardner et al., *Nucl. Acids Res.* 9: 2871–2888 (1981)), the kanamycin resistance gene of Tn5 (Jorgensen et al., *Mol. Gen Genet.* 177: 65 (1979)), and the 3' region from transcript 7 of pTiA6 (Currier and Nester, *J. Bact.* 126: 157–165 (1976)). The vector is constructed in a multi-step process detailed below.

The plasmid pCGN783 is deposited with ATCC, accession number 67868.

A. Construction of pCGN739

To obtain the gentamicin resistance marker, the resistance gene is isolated from a 3.1 kb EcoRI-PstI fragment of pPhIJI (Hirsch et al. 1984, supra) and cloned into pUC9 (Vieira and Messing, *Gene* 19: 259–268 (1982)), yielding pCGN549. The pCGN549 HindIII-BamHI fragment containing the gentamicin resistance gene replaces the HindIII-BglII fragment of pCGN587 (for above) constructing pCGN594. The pCGN594 HindIII-BamHI region which contains an ocs-kanamycin-ocs fragment is replaced with the HindIII-BamHI polylinker region from pUC18 (Yanisch-Perron et al., *Gene* 53: 103–119 (1985)) to make pCGN739.

B. Construction of pCGN726C pCGN566 contains the EcoRI-HindIII linker of pUC18 Yanisch-Perron et al., *Gene* 53: 103–119 (1985), inserted into the EcoRI-HindIII sites of pUC13-cm (K. Buckley, Ph.D. Thesis, UC San Diego 1985). The HindIII-BglII fragment of pNW3 lc-8, 29-1 (Thomashow et al., *Cell* 19: 729–739 (1980)) containing ORF1 and 2 (Barker et al., *Plant Mol. Biol.* 2: 335–350 (1983)) is subcloned into the HindIII-BamHI sites of pCGN566 producing pCGN703. The Sau3A fragment of pCGN703 containing the 3' region of transcript 7 from pTiA6 (corresponding to bases 2396–2920 of pTi15955; Barker et al., *Plant Mo. Biol.* 2:335–350 (1983)) is subcloned into the BamHI site of pUC18 (Yanisch-Perron al., *Gene* 53:103–119 (1985)) producing pCGN709.

The EcoRI-SmaI polylinker region of pCGN709 is replaced with the EcoRI-SmaI fragment from pCGN587 (for production see infra) which contains the kanamycin resistance gene (APH3 'II) producing pCGN726.

The EcoRI-SalI fragment of pCGN726 plus the BglII-EcoRI fragment of pCGN734 are inserted into the BamHI-SalI sites of pUC8-pUC13-cm (chloramphenical resistant, K. Buckley, PH.D. Thesis, UC San Diego 1985) producing pCGN738. To construct pCGN734, the HindIII-SphI fragment of pTiA6 corresponding to bases 3390–3241 (Barker et al., *Plant Mo. Biol.* 2:335–350 (1983)) is cloned into the HindIII-SphI site of M13mp19 (Yanisch-Perron et al., *Gene* 53: 103–119 (1985); Norrander et al. *Gene* 26: 101–106 (1983)). Using an oligonucleotide corresponding to bases 3287 to 3300, DNA synthesis is primed from this template. Following S1 nuclease treatment and HindIII digestion, the resulting fragment is cloned in the HindIII-SmaI site of pUC19 (Yanisch-Perron et al., *Gene* 53: 103–119 (1985)). The resulting EcoRI-HindIII fragment corresponding to bases 3287–3390 (Barker et al., *Plant Mo. Biol.* 2: 335–350 (1983)), is cloned with the EcoRI-HindIII fragment of pTiA6 (corresponding to bases 3390–4494) into the EcoRI site of pUC8 (Vieira and Messing, *Gene* 19: 259–268 (1982)) resulting in pCGN374. pCGN726c is derived from pCGN738 by deleting the 900 bp EcoRI-EcoRI fragment.

C. Construction of pCGN766C

The HindIII-BamHI fragment of pCGN167 (see infra) containing the CAMV-35S promoter, 1 ATG-kanamycin gene and the BamHI fragment 19 of pTiA6 is cloned into the BamHI-HindIII sites of pUC19 (Norrander et al. *Gene* 26:101–106 (1983); Yanisch-Perron et al., *Gene* 53: 103–119 (1985)) constructing pCGN976.

The 35S promoter and 3' region from transcript 7 is developed by inserting a 0.7 kb HindIII-EcoRI fragment of pCGN976 (35S promoter) and the 0.5kB EcoRI-SalI fragment of PCGN709 (transcript 7:3') into the HindIII-SalI sites of pCGN566 constructing pCGN766c. To construct pCGN167, the AluI fragment of CAMV (bp 7144–7735) (Gardner et al., *Nucl. Acids Res.* 9: 2871–2888 (1981)) is obtained by digestion with AluI and cloned into the HincII site of M13mp7 (Vieira and Messing, *Gene* 19: 259–268 (1982) to create C614. An EcoRI digest of C614 produces the EcoRI fragment from C614 containing the 35S promoter which is cloned into the EcoRI site of pIC8 (Vieira and Messing, *Gene* 19: 259–268 (1982)) to produce pCGN146. To trim the promoter region, the BglII site (bp 7670) is treated with BglII and Bal31 and subsequently a BglII linker is attached to the Bal3l treated DNA to produce pCGN147. pCGN148a containing a promoter region, selectable marker (KAN with 2 ATG's) and 3' region is prepared by digesting pCGN528 (see below) with BglII and inserting the BamHI-BglII promoter fragment from pCGN147. This fragment is cloned into the BglII site of pCGN528 so that the GglII site is proximal to the kanamycin gene of pCGN528.

The shuttle vector used for this construct, pCGN528, is made as follows. pCGN525 is made by digesting a plasmid containing Tn5 which harbors a kanamycin gene (Jorgenson et al., *Mol. Gen. Genet.* 177: 565 (1979)) with HindIII-BamHI and inserting the HindIII-BamHI fragment containing the kanamycin gene into the HindIII-BamHI sites in the tetracycline gene of pACYC184 (Chang and Cohen, *J. Bacteriol.* 134: 1141–1156 (1978)). pCGN526 is made by inserting the BamHI fragment 19 of pTiA6 (Thomashow et al., *Cell* 19:729–739 (1980)) into the BamHI site of pCGN525. pCGN528 is obtained by deleting the small XhoI fragment from pCGN526 by digesting with XhoI and relegating.

pCGN149a is made by cloning the BamHI kanamycin gene fragment from 9MB9KanXXI into the BamHI site of pCGN148a.

pMB9KanXXI is a pUC4k variant (Vieira and Messing, *Gene* 19:259–268 (1982)) which has the XhoI site missing but containing a functional kanamycin gene from Tn903 to allow for efficient selection in Agrobacterium.

pCGN149a is digested with BglII and SphI. This small BglII-SphI fragment of pCGN149A is replaced with the BamHI-SphI fragment from MI (see below) isolated by digestion with BamHI and SphI. This produces pCGN167, a construct containing a full length CaMV promoter, lATG-Kanamycin gene, 3' end and the bacterial Tn903-type kanamycin gene. MI is an EcoRI fragment from pCGN550 (see construction of pCGN587) and is cloned into the EcoRI cloning site of M13mp9 in such a way that the PstI site in the 1ATG-kanamycin gene is proximal to the polylinker region of M13mp9.

D. Construction of pCGN451 pCGN451 contains the ocs5'-ocs3' cassette cloned into a derivative of pUC8 (Vieira and Messing, *Gene* 19: 259–268 (1982)). The modified vector is derived by digesting pUC8 with HincII and ligating in the presence synthetic linker DNA, creating pCGN416, and then deleting the EcoRI site of pCGN416 by EcoRI digestion followed by treatment with Klenow enzyme and self ligation to create pCGN426.

The ocs5'-ocs3' cassette is constructed by a series of steps from DNA derived from the octopine Ti-plasmid pTiA6 (Currier and Nester, *J. Bact.* 126: 157–165 (1976)). An EcoRI fragment of pTiA6 (bp 13362–16202; the numbering is by Barker et al., *Plant Mol. Biol.* 2: 335–350 (1983), for the closely related Ti plasmnid pTi 15955) is removed from pVK232 (Knauf and Nester, *Plasmid* 8: 45 (1982)) by EcoRI digestion and cloned into EcoRI digested pACYC184 (Chang and Cohen, *J. Bacteriol.* 134: 1141–1156 (1978)) to generate pCGN15. The 2.4 kb BamHI-EcoRI fragment (bp 13774–16202) of pCGN15 is cloned into EcoRI-BamHI digested pBR322 (Bolivar et al., *Gene* 2: 95–113 (1977)) to yield pCGN429. The 412 bp EcoRI-BamHI fragment (bpl3362–13774) of pCGN1S is cloned into EcoRI-BamHI digested pBR3322 (Bolivar et al., *Gene* 2: 95–113 (1977)) to yield pCGN407. The cut-down promoter fragment is obtained by digesting pCGN407 with XmnI (bp 13512), followed by resection with Bal31 exonuclease, ligation of synthetic EcoRI linkers, and digestion with BamHI. Resulting fragments of approximately 130 bp are gel purified and cloned into M13mp9 (Vieira and Messing, *Gene* 19: 259–268 (1982)) and sequenced. A clone, I-4, in which the EcoRI linker had been inserted at bp 13642 between the transcription initiation point and the translation initiation codon is identified by comparison with the sequence of de Greve et al., *J. Mol. Appl. Genet.* 1: 499–512 (1982)); the EcoRI cleavage site is at position 13639, downstream from the mRNA start site. The 141 bp EcoRI-BamHI fragment of I-4, containing the cut-down promoter, is cloned into EcoRI-BamHI digested pBR322 (Bolivar et al., *Gene* 2: 95–113 (1977)) to create pCGN428. The 141 bp EcoRI-BamHI promoter piece from pCGN428, and the 2.5 kb EcoRI-BamHI ocs 5' piece from pCGN429 are cloned together into EcoRI digested pUC9 (Vieira and Messing, *Gene* 19: 259–268 (1982)) to generate pCGN442, reconstructing the ocs upstream region with a cut-down promoter section.

The HindIII fragment of pLB41 (D. Figurski) containing the gentamycin resistance gene is cloned into HindIII digested pACYC184 (Chang and Cohen, *J. Bacteriol.* 134: 1141–1156 (1978)) to create pcDNA413b. The 4.7 kb BamHI fragment of pTiA6 (Currier and Nester, *J. Bact.* 126: 157–165 (1976)) containing the osc 3' region, is cloned into BamHI digested pBR325 (F. Bolivar, *Gene* 4: 121–136 (1978)) to create 33c-19. The SmaI site a position 11207 of 33c-19 is converted to an XhoI suite using synthetic XhoI linker DNA, generating pCGN401.2. The 3.8 kb BamHI-EcoRI fragment of pCGN401.2 is cloned into BamHI-EcoRI digested pCGN413b to create pCGN419.

The ocs5'-osc3' cassette is generated by cloning the 2.64 kb EcoRI fragment of pCGN442, containing the 5' region, into EcoRI digested pCGN419 to create pCGN446. The 3.1 kb XhoI fragment of pCGN446, having the ocs 5' region (bpl3639–15208) and ocs 3' region (bp 11207–12823), is cloned into the XhoI site of pCGN426 to create pCGN451.

E. Construction of pCGN587.

The HindIII-SmaI fragment of Tn5 containing the entire structural gene for APH3'II (Jorgensen et al., *Mol. Gen. Genet.* 177: 65 (1979)) is cloned into pUC8 (Vieira and Messing, *Gene* 12: 259–268 (1982)) this converts the fragment into HindIII-EcoRI fragment, since there is an EcoRI site immediately adjacent to the SmaI site. The PstI-EcoRI fragment of pCGN300, containing the 3'-portion of the APH3'II gene, is then combined with an EcoRI-BamHI-SalI-PstI linker into the EcoRI site of pUC7 to make pCGN546W]. An ATG codon is upstream from and out of reading frame with the ATG initiation codon of APH3'II. The undesired ATG is avoided by inserting a Sau3A-PstI fragment from the 5'-end of APH3'II, which fragment lacks the superfluous ATG, into the BamHI-PstI site of pCGN546W to provide plasmid pCGN550. The EcoRI fragment of pCGN550 containing the APH3'II gene is then cloned into the EcoRI site of pUS8-pIC13-cm (K. Buckley (1985), sura) to give pCGN551. The plasmid pCGN451 (described above) having the ocs 5' and the ocs 3' in the proper orientation is digested with EcoRI and the EcoRI fragment from pCGN551 containing the intact kanamycin resistance gene is inserted into the EcoRI site to provide pCGN552 having the kanamycin resistance gene in the proper orientation.

This ocs/KAN gene is used to provide a selectable marker for the trans type binary victor pCGN587.

The 5' portion of the engineered octopine synthase promoter cassette consists of pTiA6 DNA from the XhoI at bp 15208–13644 (Barker et al., *Plant Mo. Biol.* 2: 335–350 (1983)), which also contains the T-DNA boundary sequence (border) implicated in T-DNA transfer. In the plasmid pCGN587, the ocs/KAN gene form pCGN552 provides a selectable marker as well the right border. The left boundary region is first cloned in M13mp9 as a HindIII-SmaI piece (pCGN502) (base pairs 602–2212) and recloned as a KpnI-EcoRI fragment in pCGN565 to provide pCGN580. pCGN565 is a cloning vector based on pUC-pUC13-Cm, (K. Buckley, Ph.D. Thesis, UC San Diego 1985 but containing pUC18 linkers; Yanisch-Perron et al., Gene 53:103–119 (1985)) pCGN580 is linearized with BamHI and used to replace the smaller BalI fragment of pVCK102 (Knauf and Nester, *Plasmid* 8: 45 (1982)), creating pCGN585. By replacing the smaller SalI fragment of pC GN585 with the XhoI fragment from pCGN552 containing the ocs/KAN gene, pCGN587 is obtained.

E. Final construction of pCGN783

The 0.7 kb HindIII-EcoRI fragment of pCGN766c (CaMV-35S promoter) is ligated to the 1.5 kb EcoRI-SalI fragment of pCGN726c (2 ATG-KAN-3' region) into the HindIII-SalI sites of pUC 119 (J. Vieira, Rutgers University, N.J.) to produce pCGN778. The 2.2 kb region of pCGN778, HindIII-SalI fragment containing the CaMV 35S promoter (1-ATG-KAN-3' region) replaces the HindIII-SalI polylinker region of pCGN739 to produce pCGN783.

EXAMPLE 84

Construction of pCGN1539 and pCGN1540

CGN1539 and pCGN1540 are binary plant transformation vectors containing the left and right T-DNA borders of Agrobacterium tumefaciens octopine Ti-plasmid pTiA6 (Currier and Nester, *J. Bact.* 126: 157–165 (1976)), the gentamycin resistance gene of pPHiJI (Hirsch and Beringer, *Plasmid* 12: 139–141 (1984)), an agrobacterium rhizogenes Ri plasmid origin of replication from pLJB11 (Jouanin et al., *Mol. Gen. Genet.* 201: 370–374 (1985)), the mas promoter region and mas 3' region of pTiA6 with the kanamycin resistance gene of Tn5 (Jorgensen et al., *Mol. Gen. Genet.* 177: 65 (1979)) a ColE1 origin of replication from pBR322 (Bolivar et al., *Gene* 2: 95–113 (1977)), and a lacZ' screenable marker gene from pUC18 (Norrander et al., *Gene* 26: 101–106 (1983)). The backbone of pCGN1539-1540, containing the gentamycin resistance gene and the Ri and ColE1 origins, is derived from pCGN1532 (see below). The Ti borders and plant selectable marker gene (mas 5'-kan-mas3'), are from pCGN1537; the plant selectable marker cassette is in turn taken from pCGN1536, while the right border and the lacZ' fragments are derived from pCGN565RBx2X, and the left border is derived from pCGN65.

A. pCGN1532 construction

The 3.5 kb EcoRI-PstI fragment containing the gentamycin resistance gene is removed from pPhlJI (Hirsch and Beringer, Plasmid 12: 139–141 (1984)) by EcoRI-PstI digestion and cloned into EcoRI-PstI digested pUC9 (Vieira and Messing, *Gene* 19: 259–268 (1982)) to generate pCGN549. HindIII-PstI digestion of pCGN549 yields a 3.1 kb fragment bearing the gentamycin resistance gene, which is made blunt ended by the Klenow fragment of DNA polymerase I and cloned into PvuII digested pBR322 (Bolivar et al., *Gene* 2: 95–113 (1977) to create pBR322GM. pBR322Gm is digested with DraI and SphI, treated with Klenow enzyme to create blunt ends, and the 2.8 kb fragment cloned into the Ri origin containing plasmid pLJbB11 (Jouanin et al., ol. *Gen. Genet*. 201: 370–374 (1985)) which had been digested with ApaI and made blunt ended with Klenow enzyme, creating pLHbB11Gm. The extra ColE1 origin and the kanamycin resistance gene are deleted from pLJvB11GM by digestion with BamHI followed by self closure to create pGMB11. The HindII site of pGmB11 is deleted by HindII digestion followed by treatment with Klenow enzyme and self closure, creating pGmB11-H. The Psti site of pGmB11-H is deleted by PstI digestion followed by treatment with Klenow enzyme and self closure, creating pCGN1532.

B. pCGN1536 construction

The 5.4 kb EcoRI fragment is removed from pVK232 (Knauf and Nester, *Plasmid* 8: 45 (1982)) by EcoRI digestion and cloned into EcoRI digested pACYC184 (Chang and Cohen, *J. Bacteriol.* 134: 1141–1156 (1978)) to create pCGN14. The 1434 bp ClaI-SphI fragment of pCGN14, containing the mas 5' region (bp20128–21562 according to numbering of (Barker et al., *Plant Mo. Biol.* 2: 335–350 (1983)) is cloned into AccI-SphI digested pUC19 (Yanisch-Perron et al., *Gene* 53: 103–119 (1985)) to generate pCGN50. A 746 bp EcoRV-NaeI fragment of the mas 5' region is replaced by an XhoI site by digesting pCGN40 with EcoRV and NaeI followed by ligation in the presence of a synthetic XhoI linker DNA to create pCGN1036. The 765 bp SstI-HindIII fragment (bp 18474–19239) of pCGN14, containing the mas 3' region, is cloned into SstI-HindIII digested pUC18 (Norrander et al., *Gene* 26: 101–106 (1983)) to yield pCGN43. The HindIII site of pCGN43 is replaced with an EcoRI site by digestion with HindIII, blunt ending with Klenow enzyme, and ligation of synthetic EcoRI linker DNA to create pCGN1034.

The 767 bp EcoRI fragment of pCGN 1034 is cloned into EcoRI-digested pCGN1036 in the orientation that placed bp 19239 of the mas 3' region proximal to the mas 5' region to create pCGN1040. pCGN1040 is subjected to partial digestion with SstI, treated with T4 DNA polymerase to create blunt ends, and ligated in the presence of synthetic XhoI linker DNA; a clone is selected in which only the SstI site at the junction of bp 18474 and vector DNA (constructed in pCGN43 and carried into pCGN1040) is replaced by an XhoI site to generate pCGN1047.

pCGN565 (see above) is digested with EcoRI and HindIII, treated with Klenow enzyme to create blunt ends, and ligated in the presence of synthetic XhoI linker DNA to create pCGN1003; this recreates the EcoRI site adjacent to the XhoI linker. pCGN1003 is digested with EcoRI, treated with Klenow enzyme to create blunt ends, and ligated in the presence of synthetic PstI linker DNA to create pCGN1007. The 1.5 kb XhoI fragment of pCGN1047, containing the mas 5' region and the mas 3' region with a multiple cloning site between, is cloned into XhoI digested pCGN1007 to construct pCGN1052. A portion of the multiple cloning site of pCGN1052 is deleted by digestion with XbaI and SstI, treated with Klenow enzyme to make blunt ends, and ligated to generate pCGN1052deltaXS.

The 1 kb EcoRI-SmaI fragment of pCGN550 (pCGN783 description), containing the 1 ATG-kanamycin resistance gene, is cloned into EcoRI-SmaI digested Bluescript M13-KS (Strategene, Inc.) to create pBSKm; this plasmid contains an M13 region allowing generation of single stranded DNA. Single stranded DNA is generated according to the supplier's recommendations, and in vitro mutagenesis is performed (Adelman et al., *DNA* 2: 183–193 (1983)) using a synthetic oligonucleotide with the sequence 5'GAACTC-CAGGACGAGGC3' (SEQ ID No. 97) to alter a PstI site within the kanamycin resistance gene and make it undigestable, creating pCGN1534. pCGN1534 is digested with SmaI and ligated in the presence of synthetic EcoRI linker DNA to generate pCGN1535.

The 1 kb EcoRI fragment of pCGN1536 is cloned into EcoRI digested pCGN1052deltaXS to create the mas5'-kan mas3' plant selectable marker cassette pCGN1536.

C. pCGN565RAx2X construction pCGN451 (pCGN783 description) is digested with HpaI and ligated in the presence of synthetic SphI linker DNA to generate pCGN55. The XhoI-SphI fragment of pCGN55 (bp13800–15208, including the right border, of *Agrobacterium tumefaciens* T-DNA; (Barker et al., *Gene* 2: 95–113 (1977)) is cloned into SalI-SphI digested pUC19 (Yanisch-Perron et al., *Gene* 53: 103–119 (1985)) to create pCGN60. The 1.4 kb HindIII-BamHI fragment of pCGN60 is cloned into HindIII-BamHi digested pSP64 (Promega, Inc.) to generate pCGN1039. pCGN1039 is digested with SmaI and NruI (deleting bp14273–15208; Barker et al., *Gene* 2: 95–113 (1977)) and ligated in the presence of synthetic BglII linker DNA creating pCGN1039deltaNS The 0.47 kb EcoRI-HindIII fragment of pCGN1039deltaNS is cloned into Eco-RI-HindIII digested pCGN565 (described in pCFN783 description) to create pCGN565RB. The HindIII site of pCGN565RB is replaced with an XhoI site by HindHIII digestion, treatment with Klenow enzyme, and ligation in the presence of synthetic XhoI linker DNA to create pCGN565RB-H+X. pUC18 (Norrander et al. *Gene* 26: 101–106 (1983) is digested with HaeII to release the lacZ' fragment, treated with Klenow enzyme to create blunt ends, and the lacZ'-containing fragment ligated into pCGN565RB-H+X, which had been digested with AccI and SphI and treated with Klenow enzyme,in such an orientation that the lacZ' promoter is proximal to the right border fragment; this construct, pCGN565RBx2x is positive for lacZ' expression when plated on an appropriate host and contains bp 13990–14273 of the right border fragment (Barker et al., *Plant Mo Biol.* 2: 335–350 (1983)) having deleted the AccI-SphI fragment (bp 13800–13990).

D. pCGN65 construction pCGN501 is constructed by cloning a 1.85 kb EcoRI-XhoI fragment of pTiA6 (Currier and Nester, *J. Bact.* 126: 157–165 (1976)) containing bases 13362–15208 (Barker et al., *Plant Mol. Biol.* 2: 335–350 (1983)) of the T-DNA (right border), into EcoRI-SalI digested M13mp9 (Vieira and Messing, *Gene* (1982) 19: 259–268 (1982). PCGN502 is constructed by cloning a 1.6 kb HindIII-SmaI fragment of pTiA6, containing bases 602–2212 of the T-DNA (left border), into HindIII-SmaI digested M13mp9. pCGN501 and pCGN502 are both digested with EcoRI and HindIII and both T-DNA-containing fragments cloned together into HindIII digested pUC9 (Vieira and Messing, *Gene* 19: 259–268 (1982)) to yield pCGN503, containing both T-DNA border fragments. pCGN503 is digested with HindIII and EcoRI and the two resulting HindIII-EcoRI fragments (containing the T-DNA borders) are cloned into EcoRI digested pHC79 (Hohn and Collins, *Gene* 11: 291–298 (1980)) to generate pCGN518. The KpnI-EcoRI fragment from pCGN518, containing the left T-DNA border, is cloned into KpnI-EcoRI digested pCGN565 to generated pCGN580. The BamHI-BglII fragment of pCGN580 is cloned into the BamHI site of pACYC184 (Chang and Cohen, *J. Bacteriol.* 134: 1141–1156 (1978)) to create pCGN51. The 1.4 kb BamHI-SphI fragment of pCGN60 (see pCGN65x2X section above) containing the T-DNA right border fragment, is cloned into BamHI-SphI digested pCGN51 to create pCGN65.

E. pCGN1537 construction pCGN65 is digested with KpnI and XbaI, treated with Klenow enzyme to create blunt ends, and ligated in the presence of synthetic BglII linker DNA to create pCGN65deltaKX. pCGN65deltaKX is digested with SalI, treated with Klenow enzyme to create blunt ends, and ligated in the presence of synthetic XhoI linker DNA to create pCGN65deltaKX-S+X. The 728 bp BglII-XhoI fragment of pCGNRBx2X, containing the T-DNA right border piece and the lacZ' gene, is cloned into BglII-XhoI digested pCGN65deltaKX-S+X, replacing pCGN65x2X. The ClaI fragment pCGN65x2X is deleted and replaced with an XhoI linker by digesting with ClaI, treating with Klenow enzyme to create blunt ends, and ligating in the presence of synthetic XhoI linker DNA to create pCGN65delta2XX.

pCGN65delta2XX is digested with BglII and fused with BglII digested pCGN549 (see pCGN1532 section above) to create pCGN1530 which contained both plasmid backbones. pCGN1530 is digested with XhoI and religated, then a gentamycin-resistant cholramphenicol-sensitive clone is chosen which had deleted the pACYC184-derived backbone, creating pCGN1530A. The 2.43 kb XhoI fragment of pCGN1536, containing the mas5'-kan-mas3' cassette, is cloned into XhoI digested pCGN1530A to create pCGN1537.

F. Final assembly of pCGN1540

The BglII fragment of pCGN1537, containing the plant selectable marker gene and the lacZ' screenable marker gene (with multiple cloning site), all between the T-DNA borders, is cloned into BamHI digested pCGN1532. A clone of the orientation bearing the T-DNA right border adjacent to the pBR322 origin of replication is designated pCGN1539, and the orientation bearing the T-DNA right border adjacent to the Ri plasmid origin of replication is designated pCGN1540. This binary vectors has several advantageous features, including a minimal amount of DNA between the T-DNA borders, high stability in Agrobacterium hosts, high copy number in *E. coli* hosts, and a blue/white screen with multiple restriction enzyme sites for ease of cloning target DNA.

The plasmid pCGN1540 has been deposited with ATCC, accession number 40586.

2. Binary Vectors Containing Chimeric Genes

This section details the subcloning of the expression cassette into the binary vector. In the previous section the construction of pCGN783 and pCGN1540 are detailed. These are binary vectors which can be used in Agrobacterium mediated transformation experiments to transform plants. The vectors are designed to cotransform a chimeric gene of interest into a plant. However, the chimeric gene first must be subcloned into the binary vector. The following section details the subcloning of the chimeric genes constructed in Section 6 into either the pCGN783 or the pCGN1540 binary vectors. The resulting vectors are capable of transforming plants with the chimeric gene.

EXAMPLE 85

Construction of pCGN1754 and pCGN1760
(pCGN783 Containing the Empty SSU Promoter Cassette in Either Orientation)

The BamHI site of pCGN783 lies near the right T-DNA border, with the plant selectable marker gene lying between the left T-DNA border and the BamHI site. Cloning a chimeric gene construct into the BamHI site places the chimeric gene between the plant selectable marker gene and the right T-DNA border. The unique BglII site of pCGN1509 lies in a non-essential portion of the ocs 3'region.

pCGN1509 is digested with BglII and the entire vector is cloned into the BamHI site of pCGN783, and both possible orientations are recovered. A plasmid in which the RuBISCO small subunit promoter and ocs 3' regions are proximal to the right T-DNA border of pCGN783 is designated pCGN1754, and a plasmid in which the RuBISCO small subunit promoter and ocs 3' regions are proximal to the plant selectable marker gene of pCGN783 is designated pCGN1760.

EXAMPLE 86

Construction of pCGN1755A, pCGN1755B, pCGN1755C, and pCGN1755D (pCGN783 Containing the SSU/PR-1a (Sense and And-Sense) Expression Cassette in Either Orientation)

pCGN1752A is digested with BglII and the entire vector is cloned into BamHI digested pCGN783, and both possible orientations are recovered. A plasmid in which the RuBISCO small subunit promoter-PR1-ocs 3' regions are proximal to the right T-DNA border of pCGN783 is designated pCGN1755C, and a plasmid in which the RuBISCO small subunit promoter-PR1-ocs 3' regions are proximal to the plant selectable marker gene of pCGN783 is designated pCGN1755A.

pCGN1752B is digested with BglII and the entire vector is cloned into BamHI digested pCGN783, and both possible orientations are recovered. A plasmid in which the RuBISCO small subunit promoter-PR1-ocs 3' regions are proximal to the right T-DNA border of pCGN783 is designated pCGN1755B, and a plasmid in which the RuBISCO small subunit promoter-PR1-ocs 3' regions are proximal to the plant selectable marker gene of pCGN783 is designated pCGN1755B.

EXAMPLE 87

Construction of pCGN1756A, pCGN1756B, pCGNI756C, and pCGN1756D (pCGN783 Containing the SSU Promoter/PR-1b (Sense and Anti-Sense) Expression Cassette in Either Orientation)

pCGN1753A is digested with BglII and the entire vector is cloned into BamHI digested pCGN783, and both possible orientations are recovered. A plasmid in which the RuBISCO small subunit promoter-PR1-ocs 3' regions are proximal to the right T-DNA border of pCGN783 is designated pCGN1756C, and a plasmid in which the RuBISCO small subunit promoter-PR1-ocs 3' regions are proximal to the plant selectable marker gene of pCGN783 is designated pCGN1756A.

pCTN1753B is digested with the Bg1II and cloned into BamHI digested pCGN783, and both possible orientations are recovered. A plasmid in which the RuBISCO small subunit promoter-PR1-ocs 3' regions are proximal to the right T-DNA border of pCGN783 is designated pCGN1756D, and a plasmid in which the RuBISCO small subunit promoter-PR1-ocs 3 regions are proximal to the plant selectable marker gene pCGN783 is designated pCGN1756B.

EXAMPLE 88

Construction of pCGN1766 and pCGN1767 (pCGN783 Containing an Empty Double CAAMV 35S Promoter Cassette in Either Orientation)

pCGN1761 is digested with BamHI and the entire vector is cloned into BamHI digested pCGN783, and both possible orientations are recovered. A plasmid in which the double CAMV 35S promoter and tml 3' regions are proximal to the plant selectable marker gene of pCGN783 is designated pCGN1767, and a plasmid in which the double 35S promoter and tml 3' regions are proximal to the right T-DNA border of pCGN783 is designated pCGN1766.

EXAMPLE 89

Construction of pCGN1764A, pCGN1764B, pCGN1764C, and pCGN1764D (Double CAMV 35S Promoter/PR-1a (Sense and Anti-Sense) into pCGN783)

pCGN1762A is digested with BamHI and cloned into BamHI digested pCGN783, and both possible orientations are recovered. A plasmid in which the double 35S-PR1-tml3' regions are proximal to the plant selectable marker gene of pCGN783 is designated pCGN1764A, and a clone in which the double35S-PR1-tml3' regions are proximal to the right T-DNA border of pCGN783 is designated pCGN1764C.

pCGN1762B is digested with BamHI and cloned into BamHI digested pCGN783, and both orientations are recovered. A plasmid in which the double 35S promoter is proximal to the plant selectable marker is designated pCGN1764B. A plasmid in the opposite orientation is designated pCGN1764D.

EXAMPLE 90

Construction of pCGN1765A, pCGN1765B, pCGN1765C, and pCGN1765D (Double CAMV 35S Promoter/PR-1b (Sense and And-Sense) into pCGN783 in Either Orientation)

pCGN1763A is digested with BamHI and cloned into BamHI digested pCGN783, and both possible orientations are recovered. A plasmid in which the double 35S-PR1-tml3' regions are proximal to the plant selectable marker gene of pCGN783 is designated pCGN1765A, and a plasmid in which the double35S-PR1-tml3' regions are proximal to the right T-DNA border of pCGN783 is designated pCGN1765C.

pCGN1763B is digested with BailrI and cloned into BamHI digested pCGN783 and both possible orientations are recovered. A plasmid in which the double 35S-PR1-tml3' regions are proximal to the plant selectable marker gene of pCGN783 is designated pCGN1765B, and a plasmid in which the double35S-PR1-tml3' regions are proximal to the right T-DNA border of pCGN783 is designated pCGN1765D.

EXAMPLE 91

Construction of pCGN1780A, PCGN1780B, pCGN1780C, PCGN1780D (Double CAMV35S Promoter/Cucumber Chidnase/Lysoyme (Sense and Anti-Sense) into pCGN783 in Either Orientation)

pCIB1000 is digested with BamHI and cloned into BamHI site in pCGN783, and both possible orientations are recovered. A plasmid in which the double 35S-chitinase-tml3' regions are proximal to the plant selectable marker gene of pCGN783 is designated pCGN1780A, and a plasmid in which the double 35S-chitinase-tml3' regions are proximal to the right T-DNA border of pCGN783 is designated pCGN1780C.

pCIB1001 is digested with BamHI and cloned into BamHI digested pCGN783 in either orientation. A plasmid in which the double 35S-chitinase-tml3' regions are proximal to the plant selectable marker gene of pCGN783 is designated pCGN1780B. A plasmid in which the double 35S-chitinase-tml3' regions are proximal to right T-DNA border of pCGN783 is designated pCGN1780D.

EXAMPLE 92

Construction of pCGN1789 (Double CAMV 35S Promoter Empty Cassette into pCGN1540 in Either Orientation)

The 2.36 kb XbaI-PstI fragment of pCGN1431 is subcloned into XbaI-PstI digested pCGN1540 to create the plasmid pCGN1789. This plasmid has the insert oriented in a direction such that the double 35S CAMV promoter is proximal to the plant selectable marker.

EXAMPLE 93

Construction of pCGN1774A, pCGN1774B, pCGN1774C, and pCGN1774D (Double CAMV 35S Promoter/PR-1a (Sense and Anti-Sense) into pCGN1540 in Either Orientation)

The 4.2 kb XbaI fragment of pCGN1762A is subcloned into XbaI digested pCGN1540, and both possible orientations are recovered. A plasmid in which the double 35S promoter fragment is proximal to the right T-DNA border of pCGN1540 is designated pCGN1774A, and a plasmid in which the double 35S promoter fragment is proximal to the plant selectable marker gene of pCGN1540 is designated pCGN1774C.

The 4.2 kb XbaI fragment of pCGN1762B is cloned into XbaI digested pCGN1540, and both possible orientations are recovered. A plasmid in which the double 35S promoter fragment is proximal to the right T-DNA border of pCGN1540 is designated pCGN1774B, and a plasmid in which the double 35S promoter fragment is proximal to the plant selectable marker gene of pCGN1540 is designated pCGN1774D.

EXAMPLE 94

Construction of pCGN1775A, pCGN1775B, pCGN1775C, and pCGN1775D (Double CAMV 35S Promoter/PR-1b (Sense and Anti-Sense) into pCGN1540 in Either Orientation)

The 4.1 kb XbaI fragment of pCGN1763A is cloned into XbaI digested pCGN1540, and both possible orientations are recovered. A plasmid in which the double 35S promoter fragment is proximal to the right T-DNA border of pCGN1540 is designated pCGN1775A, and a plasmid in which the double 35S promoter fragment is proximal to the plant selectable marker gene of pCGN1540 is designated pCGN1775C.

The 4.1 kb XbaI fragment of pCGN1763B is cloned into XbaI digested pCGN1540, and both possible orientations are recovered. A plasmid in which the double 35S promoter fragment is proximal to the right T-DNA border of pCGN1540 is designated pCGN1775B, and a clone in which the double 35S promoter fragment is proximal to the plant selectable marker gene of pCGN1540 is designated pCGN1775D.

EXAMPLE 95

Construction of pCGN1783C and PCGN1783D (Double CAMV 35S Promoter/PR-R major (Sense and And-Sense) into pCGN1540 in Either Orientation)

The 4.5 kb XbaI fragment of pCIB1002 is subcloned into XbaI digested pCBN1540 in such an orientation that the double 35S promoter is proximal to the plant selectable marker gene of 1540. This plasmid is designated as pCGN1783C.

The 4.5 kb XbaI fragment of pCIB1003 is subcloned into XbaI digested pCGN1540 in such an orientation that the double 35S promoter fragment is proximal to the plant selectable marker gene of pCGN1540 to create pCGN1783D.

EXAMPLE 96

Construction of pCIB1026 and pCIB1027 (Double CAMV 35S Promoter/PR-P (Sense and And-Sense) into pCGN1540 in Either Orientation)

The XbaI fragment of pCIB1020, which contains the chimeric PR-P gene, is subcloned into XbaI digested pCGN1540 in such an orientation that the promoter fragment is proximal to the plant selectable marker gene. This plasmid is designated as pCIB 1026.

The XbaI fragment of pCIB1021, which contains the chimeric PR-P anti-sense gene, is subcloned into XbaI digested pCGN1540 in such an orientation that the promoter fragment is proximal to the plant selectable marker gene. This plasmid is designated as pCIB1027.

EXAMPLE 97

Construction of pCGN1791C and pCGN1791D (Double CAMV 35S Promoter/PR-Q (Sense and And-Sense) into pCGN1540 in Either Orientation)

The XbaI fragment from pCIB1022, which contains the chimeric PR-Q gene, is subcloned into XbaI digested pCGN1540 in an orientation such that the promoter fragment is proximal to the plant selectable marker. This plasmid is designated as pCGN1791C.

The XbaI fragment from pCIB1023, which contains the chimeric PR-Q anti-sense gene, is subcloned into XbaI digested pCGN1540 in such an orientation that the promoter fragment is proximal to the plant selectable marker. The plasmid is designated pCGN1791D.

EXAMPLE 98

Construction of pCIB1030 and pCIB1031 (Double CAMV 35S Promoter/PR-O' (Sense and Anti-Sense) into pCGN1540 in Either Orientadon)

The XbaI fragment of pCIB1024, which contains the chimeric PR-O' gene is subcloned into XbaI digested pCGN1540 in such a way that the 35 S promoter is proximal to the plant selectable marker. The plasmid is designated pCIB1030.

The XbaI fragment of pCIB1025, which contains the chimeric PR-O' anti-sense gene, is subcloned into XbaI digested pCGN1540 in a similar orientation as pCIB1030. The new plasmid is designated pCIB1031.

EXAMPLE 99

Construction of pCIB1030A and pCIB1031B (double CAMV 35S Promoter/PR-O' (Sense and Anti-Sense) into pCGNI540)

The XbaI fragment of pCIB1024A, which contains the chimeric PR-O' gene, is subcloned into XbaI digested pCGN1540 in such a way that the 35S promoter is proximal to the plant selectable marker. This plasmid is designated as pCIB1030A.

The XbaI fragment of pCIB1025A, which contains the chimeric PR-O' gene in an anti-sense orientation, is subcloned into XbaI digested pCGN1540 in such a way that the 35S promoter is proximal to the plant selectable marker. The resulting plasmid is designated pCIB1031A.

EXAMPLE 100

Construction of pCIB1042 and pCIB1043 (Double CAMV 35S Promoter/PR-2 (Sense and Anti-Sense) into pCGN1540)

The XbaI fragment of pCIB1032, which contains the chimeric PR-2 gene, is subcloned into XbaI digested pCGN1540 in such a way that the 35S promoter is proximal to the plant selectable marker. This plasmid is designated as pCIB1042.

The XbaI fragment of pCIB1033, which contains the chimeric PR-2 gene in an anti-sense orientation, is subcloned into XbaI digested pCGN1540 in such a way that the 35S promoter is proximal to the plant selectable marker. The resulting plasmid is designated pCIB1043.

EXAMPLE 101

Construction of pCIB1044 and pCIB1045 (Double CAMV 35S Promoter/PR-N (Sense and Andi-Sense) into pCGN1540)

The XbaI fragment of pCIB1034, which contains the chimeric PR-N gene, is subcloned into XbaI digested pCGN1540 in such a way that the 35S promoter is proximal to the plant selectable marker. This plasmid is designated as pCIB1044.

The XbaI fragment of pCIB1035, which contains the chimeric PR-N gene in an anti-sense orientation, is subcloned into XbaI digested pCGN1540 in such a way that the 35S promoter is proximal to the plant selectable marker. The resulting plasmid is designated pCIB1045.

EXAMPLE 102

Construction of pCIB1046 and pCIB1047 (Double CAMV 35S Promoter/PR-O (Sense and And-Sense) into pCGN1540)

The XbaI fragment of pCIB1036, which contains the chimeric PR-O gene, is subcloned into XbaI digested pCGN1540 in such a way that the 35S promoter is proximal to the plant selectable marker. This plasmid is designated as pCIB1046.

The XbaI fragment of pCIB1037, which contains the chimeric PR-O gene in an anti-sense orientation, is subcloned into XbaI digested pCGN1540 in such a way that the 35S promoter is proximal to the plant selectable marker. The resulting plasmid is designated pCIB1047.

EXAMPLE 103

Construction of pCIB1048 and pCIB1049 (Double CAMV 35S PromoterlPR-2' (Sense and And-Sense) into pCGN1540)

The XbaI fragment of pCIB1038, which contains the chimeric PR-2' gene, is subcloned into XbaI digested pCGN1540 in such a way that the 35S promoter is proximal to the plant selectable marker. This plasmid is designated as pCIB1048.

The XbaI fragment of pCIB1039, which contains the chimeric PR-2' gene in an anti-sense orientation, is subcloned into XbaI digested pCGN1540 in such a way that the 35S promoter is proximal to the plant selectable marker. The resulting plasmid is designated pCIB1049.

The foregoing methods can be used to insert any double 35S/cDNA expression cassette, constructed as described in Example 73, into pCGN1540. Such a sense or antisense expression cassette includes, but is not limited to, double 35S/PR-2", double 35S/tobacco basic chitinase/lysozyme, and double 35S/tobacco acidic chitinase/lysozyme, double 35S/PR-4a and double 35S/PR-4b.

EXAMPLE 104

Construction of pCGN1781C and PCGN1781D (Double CAMV 35S Promoter/Basic Glucanase (Sense and Anti-Sense) into pCGN1540 in Either Orientation)

The 4.9 kb XbaI fragment of pCIB1005B is subcloned into XbaI digested pCGN1540 in such an orientation that the double 35S promoter fragment is proximal to the plant selectable marker gene of pCGN1540 to create pCGN1787C.

The 4.5 kb XbaI fragment of pCIB1006B is subcloned into XbaI digested pCGN1540 in such an orientation that the double 35 S promoter fragment is proximal to the plant selectable gene of pCGN1540 to create pCGN1787D.

EXAMPLE 105

Construction of pCGN1782C and PCGN1782D (Double CAMV 35S Promoter/Basic Chitinase (Sense and Anti-Sense) into pCGN1540 in Either Orientation)

The 4.8 kb XbaI fragment of pCGN1007 is cloned into XbaI digested pCGN1540 in such an orientation that the double 35S promoter fragment is proximal to the plant selectable marker gene of pCGN1540 to create pCGN1782C.

The 4.8 kb fragment of pCIB 1008 is cloned into XbaI digested pCGN1540, similarly, to create pCGN1782D.

EXAMPLE 106

Construction of PCGN1790C and PCGN1790D (Double CAMV 35S Promoter/SAR8.2 (Sense and Anti-Sense) into pCGN1540 in Either Orientation)

The 2.89 kb XbaI-PstI fragment of pCGN1788A is subcloned into XbaI-PstI digested pCGN1540 to create pCGN1790C. The orientation of the double 35S promoter in these construct is the same as the other C type constructs in the examples above.

The 2.89 kb fragment of pCGN1788B is subcloned into XbaI-PstI digested pCGN1540 to create pCGN1790D. The orientation of the promoter in the construct is the same as in pCGN1790C.

EXAMPLE 107

Construction of pCGN1779C, and PCGN1779D (Double CAMV35S Promoter/Cucumber ChitinaselLysozyme (Sense and Anti-Sense) into pCGN1540 in Either Orientation)

The 4.6 kb XbaI fragment of pCIBl000 is cloned into XbaI digested pCGN1540 in such an orientation that the double 35S promoter fragment is proximal to the plant selectable marker gene of pCGN1540 to crete pCGN1779C. The 4.6 kb XbaI fragment of pCIB1001 is cloned into XbaI digested pCGN1540 in such an orientation that the double 35S promoter fragment is proximal to the plant selectable marker gene of pCGN1540 to create pCGN1779D.

EXAMPLE 108

Vectors having Hygromycin-Resistance as the Plant-selectable Marker Gene

Plant transformation vectors having the hygromycin-resistance gene instead of the kanamycin gene as used above are constructed (Rothstein, et al., *Gene* 53: 153–161(1987)). The vector pCIB743 is one such vector. The chimeric gene for expression in the plant is cut from any of the vectors described above using a suitable restriction enzyme, for example XbaI, and inserted into the polylinker of pCIB743. This constructs the chimeric gene(s) for plant expression in the broad host range transformation vector conferring hygromycin-resistance to transformed plant tissue. This allows one skilled in the art to utilize either hygromycin-resistance, or kanamycin-resistance, or both, as selection for transformed plant tissue.

I. Stable Transformation and Regeneration of Plants

Plant tissue is transformed with the vectors described above by any technique known in the art. Such methods used for transfer of DNA into plant cells include, for example, the direct infection of or co-cultivation of plants, plant tissue or cells with *A. tumefaciens* (Horsch, R. B. et al., *Science* 225: 1229 (1985); Marton, L., *Cell Culture and Somatic Cell Genetics of Plants* 1: 514–521, 1984), treatment of protoplasts with exogenous DNA by methods such as those described in the following publications: Paszkowski, J. et al., *EMBO J.* 3: 2717 (1984); EP-A 0 164 575; Shillito, R. D. et al., *Bio/Technology* 3: 1099 (1985); Potrykus, I. et al., supra; Loerz, H. et al., *Mol. Gen. Genet.* 199: 178 (1985); Fromm, M. et al., supra; GB 2,140,822; and Negrutiu, I. et al., *Plant Mol. Biol.* 8: 363 (1987); incubation with polyethylene glycol (PEG) (Negrutiu, I. et al., suPra); micro-injection (Reich, T. J. et al., *Bio/Technology* 4: 1001–1004 (1986); Reich, T. J. et al., *Can. J. Bot.* 64: 1259–1267 (1986)), microprojectile bombardment (Klein, T. M. et al., *Nature* 327: 70 (1987)).

EXAMPLE 109

Transformation of Agrobacterium with Constructs Containing Chemically Regulatable Sequences pCIB270 (Example 25), pCIB271, pCIB272 and pCIB273 (Example 28) plasmid DNA is purified on cesium chloride ethidium bromide gradients and is used to transform *A. tumefaciens* strain A136 containing the helper plasmid pCIB542 by the procedure of Holsters, M. et al., *Mol. Gen. Genet.* 163: 181–187 (1978) resulting in the strains CIB270, CIB271, CEB272 and CIB273.

Using the same procedure, plasmids pCIB271, pCIB272, and pCIB273 are transformed into the virulent *A. tumefaciens* strains 15955, A208, A281, and the *A. rhizogenes* strain A4, creating strains designated as pCIB271×15955, pCIB271× A208, pCIB271× A281, pCIB271× A4, pCIB272×15955, pCIB272× A208, pCIB272× A281, pCEB272× A4, pCIB273×15955, pCIB273× A208, pCIB273× A281, and pCIB273× A4.

Purified pCIB2001, pCIB2001/BamChit, pCIB2001/SalChit and pCIB2001/NcoChit DNA (Example 62) is used to transform *Agrobacterium tumefaciens* strain CIB542 by the procedure of Holsters et al., *Mol Gen Genet.* 163: 181–187 (1978). Agrobacterium strain CIB542 is strain EHA101 (Hood et al., *J. Bacteriol.* 168: 1291–1301 (1986)) in which the kanamycin marker of the plasmid has been replaced by the spectinomycin/streptomycin portion of Tn7.

EXAMPLE 110

Transformation of *Agrobacterium tumefaciens* with Binary Vectors Containing Anti-pathogenic Sequences The binary vectors described in Section 7 are transformed into *Agrobacterium tumefaciens* strain LB4404 by the following method. The Agrobacterium strain is grown at 30° C. overnight in 5 ml of MG/L medium (50% L broth, 50% mannitol-glutamate medium (Holsters et al., *Mol. Gen. Genet.* 163: 4181–4187 (1978)). The 5 ml culture is added to 250 ml of MG/L and shaken vigorously until the culture density reaches an OD=0.6 at 600 nm wavelength. The cells are then collected by centrifugation at 8000×g and resuspended in 5 ml of MG/L. 200 1 of cells are added to 0.2 to 1[B g of binary plasmid DNA in MG/L and the mix is frozen immediately in a dry ice/ethanol bath. After 5 minutes the tube is placed in a 37° C. water bath for 5 minutes and then 2 ml of MG/L is added. The suspension is kept in a 30° C. water bath for 2–3 hours and then cell are collected by centrifugation. The cells are resuspended in a minimal volume of MG/L and then plated on selective media (MG/L plates with 100 g/ml gentamycin. Colonies appear after 2–3 days at 30° C.

EXAMPLE 111

General Method for *Axrobacterium tumefaciens*-Mediated Transformation of *Nicotiana tabacum*

Explants roughly 5–10 mm are cut from young leaves 3–5 cm long and third to sixth from the apex of *Nicotiana tabacum* cv 'Xanthi nc' grown under axenic conditions (Facciotti and Pilet, *Plant Science Letters* 15: 1–7 (1979)) in solid MS medium (Murashige and Skoog, *Physiol. Plant.* 15:473–497 (1962)) containing 0.7% phytagar (Gibco-BRL), 1 mg/L IAA, 0.15 mg/L kinetin. These explants are plated on solid MS medium containing 0.6% phytagar, 40 mg/L adenine sulfate, 2 mg/L IAA, and 2 mg/L kinetin on the surface of which is placed a #1 Whatman filter and incubated for 24 hrs in the dark at 24° C. Agrobacterium strains (bearing chimeric gene constructions described above) are grown overnight in MG/L broth (Garfinkel and Nester, *J. Bact.* 144: 732–743 (1980)) at 30° C. on a shaker at 180 rmp. Explants are dipped into a bacterial suspension of $3.3 \times 10^8$ cells/ml for approximately 5 minutes, blotted on sterile paper towels, and re-plated on the same plates.

After 48 hours explants are placed on selection medium containing the same plate medium as above plus 350 mg/L cefotaxime and 100 mg/L kanamycin. Co-cultivated control tissue is placed on the same medium but without kanamycin. The explants are transferred to fresh media every two weeks. Shoots are harvested 4–8 weeks after co-cultivation, placed on 50 ml culture tubes with 25 ml of solid MS medium containing 0.6% phytagar, 1 mg/L IBA, 350 mg/L coefotaxime, and 100 mg/L kanamycin. All tissue is grown at 24–28° C., 12 hours light, 12 hours dark, light intensity 80–100 Einstein. Shoots rooted in 1–2 weeks and are then transplanted to planting mix in 4" pots and placed in the "transgenic plant phytotron".

EXAMPLE 112

Leaf Disk Transformation of Tobacco

Agrobacterium strains containing the vectors described above are grown 18–24 hours in glutamate salts media adjusted to pH 5.6 and supplemented with 0.15% mannitol, 50 g/ml kanamycin, 50 g/ml spectinomycin and 1 mg/ml streptomycin before they are diluted to an $OD_{600}$ of 0.2 in the same media without the antibiotics. The bacteria are then grown for three to five hours before dilution to an OD600 of 0.2–0.4 for inoculation of discs of 5–7 mm punched from leaves of *Nicotiana tabacum* cv. xanthi that have been grown aseptically in GA7 containers, following a modification of the method of Horsch, R. et al., *Science* 227: 1229–1232 (1985).

The leaf disks are maintained on 0.7% agar containing Murashige and Skoogs major and minor salts (MS), 1 mg/l benzyladenine and 1 mg/ml -naphthaleneacetic acid for two days before transfer to the same media containing 50 g/ml kanamycin, 100 g/ml carbenicillin and 100 g/ml mefoxin. Shoots which form on the discs are excised and propagated until six plantlets are obtained by subculturing the shoot tips on MS media containing 50 g/ml kanamycin in GA7 containers.

The plantlets are rooted on medium containing no hormones and 50 g/ml kanamycin, transferred to soil and hardened in a phytotron before transfer to the greenhouse for induction treatment with chemical regulators. At flowering time flowers are induced to selfpollinate. Seeds are harvested following maturation.

EXAMPLE 113

Production of Transgenic Tobacco Callus and Plants

Agrobacterium strains containing the appropriate vectors are used to transform callus forming from the leaf disks (Example 112). Callus forming on kanamycin-containing MSBN selection medium is maintained on a callus growth medium comprised of MS major, minor salts and Fe-EDTA (Gibco # 500-1117; 4.3 g/l), MS vitamins, 100 mg/l myo-inositol, 20 g/l sucrose, 2 mg/l naphthaleneacetic acid and 0.3 mg/l kinetin.

The callus can be used to regenerate transgenic plants by transferring callus pieces to MSBN medium and following methods described in Examples 111 and 112. The callus is also used to measure gene induction following application of inducing chemicals and to screen for gene inducing chemicals.

EXAMPLE 114

Transformation of Carrot

Agobacterium strains containing the appropriate vectors as described above (e.g. CEB270, CIB271, CIB272, CIB273, pCIB271x15955, pCIB271x A208, pCIB271x A281, pCIB271x A4, pCIB272x15955, pCIB272x A208, pCIB272x A281, pCIB272x A4, pCIB273x15955, pCIB273x A208, pCIB273x A281, and pCIB273x A4) are grown as described in Example 112. The bacteria, diluted to an $OD_{600}$ of 0.2–0.4, are then used for inoculation of discs cut from surface sterilized carrots.

To surface sterilize the carrots they are peeled and then soaked 20 minutes in a 10% solution of chlorox. The carrots are rinsed with sterile water, sliced into 5 mm pieces and placed basal side up onto water agar. 20–50 l of bacteria are then applied to the upper surface of the discs. After 7 days the discs are transferred to 0.7% agar containing MS salts, 3% sucrose, 0.1 mg/l 2,4-D, 50 g/ml kanamycin, 100 g/ml carbenicillin, and 100 g/ml mefoxin. Callus forming around the cambial ring is excised and placed on 0.7% MS agar supplemented with 3% sucrose, 0.1 mg/l 2,4-D, 50 g/ml kanamycin, 100 g/ml carbenicillin, and 100 g/ml mefoxin. After the callus has been grown it is cut into small pieces and randomized onto four plates of the same media.

For induction experiments, when the callus has filled the plate three of the plates are sprayed with water, 50 mM sodium salycilate pH 5.6, or 250 g/l methyl benzo-1,2,3-thiadiazole-7-carboxylate to induce the expression of the chimeric PR-1a/GUS gene.

EXAMPLE 115

Transformation of Sunflower

Agrobacterium strains containing the appropriate vectors as described above (e.g. CIB270, CIB271, CIB272, CIB273, pCIB271x15955, pCIB271x A208, pCIB271x A281, pCIB271x A4, pCIB272x15955, pCIB272x A208, pCIB272x A281, pCIB272x A4, pCIB273x15955, pCIB273x A208, pCIB273x A281, and pCIB273x A4) are grown as described in Example 112. The bacteria, diluted to an $OD_{600}$ of 0.2–0.4, are then used for inoculation of stems of sunflower plants prepared as follows:

Sunflower seeds are soaked 10 min in 10% captan followed by 10 min in 10% chlorox and rinsing with sterile water. The seed coats are removed and the seeds are germinated on 0.7% water agar in the dark for three days, after which they are placed into a labline incubator set at 23° C. with a 12 hour day and night. The seedlings are grown for one week before decapitation and inoculation of the bacteria onto the cut stem surface.

After one week the stems inoculated with CIB270, CIB271, CIB272 or CIB273 are cut and placed on 0.7% agar containing MS salts, 3% sucrose, 2 mg/ml -napthaleneacetic acid, 1 mg/ml 6-benzylaminopurine, 100 g/ml carbenicillin, 100 g/ml mefoxim and 50 g/ml kanamycin. Stems inoculated with pCIB271x15955, pCIB271x A208, pCIB271x A281, pCIB271x A4, pCIB272x15955, pCIB272x A208, pCIB272x A281, pCIB272x A4, pCIB273x15955, pCIB273x A208, pCIB273x A281, and pCIB273x A4 are cut and placed on 0.7% agar containing MS salts, 3% sucrose, 100 g/ml carbenicillin, and 100 g/ml mefoxim. The callus is transferred to fresh media every two weeks until sufficient quantity is obtained for 4 plates. Half of the callus growing from the virulent Agrobacterium strains is transferred to media without hormones containing 50 g/ml kanamycin. After sufficient callus grown in the presence or absence of kanamycin is obtained, it is treated for induction as described above for transformed carrot callus.

EXAMPLE 116

Transformation of Tomato

Agrobacterium strains containing the appropriate vectors as described above (e.g. CIB270, CIB271, CIB272, CIB273, pCIB271x15955, pCIB271x A208, pCIB271x A281, pCIB271x A4, pCIB272x15955, pCIB272x A208, pCIB272x A281, pCIB272x A4, pCIB273x15955, pCIB273x A208, pCIB273x A281, and pCIB273x A4) are grown as described in Example 112. The bacteria, diluted to an $OD_{600}$ of 0.2–0.4, are then used for inoculation of stems of tomato seedlings prepared as described below.

Tomato seeds are soaked 20 min in 10% chlorox and rinsed with sterile water. The seeds are germinated on 0.7% water agar in the dark for three days, after which they are placed into a labline incubator set at 23° C. with a 12 hour day and night. The seedlings are grown for one week before decapitation and inoculation of the bacteria onto the cut stem surface.

After one week the inoculated stems are cut and placed on 0.7% agar containing MS salts, 3% sucrose, 2 mg/ml -napthaleneacetic acid, 1 mg/ml 6-benzylaminopurine, 100 g/ml carbenicillin, 100 g/ml mefoxim, and 50 g/ml kanamycin. For stems inoculated with pCIB271×15955, pCIB271× A208, pCIB271× A281, pCIB271× A4, pCIB272×15955, pCIB272× A208, pCIB272× A281, pCIB272× A4, pCIB273×15955, pCIB273× A208, pCIB273× A281, and pCIB273× A4 the plating media used is 0.7% agar containing MS salts, 3% sucrose, 100 g/ml carbenicillin, and 100 g/ml mefoxim. The callus is transferred to fresh media every two weeks until sufficient quantity is obtained for 4 plates.

For induction experimenta, half of the callus growing from the virulent Agrobacterium strains is transferred to media without hormones containing 50 g/ml kanamycin. After sufficient callus grown in the presence or absence of kanamycin is obtained, it is treated for induction as described above for transformed carrot callus.

EXAMPLE 117

Transformation of Cotton

Agrobacterium strains containing the appropriate vectors (e.g. pCIB271×15955, pCIB271× A208, pCIB271× A281, pCIB271× A4, pCIB272×15955, pCIB272× A208, pCIB272× A281, pCIB272× A4, pCIB273×15955, pCIB273× A208, pCIB273× A281, and pCIB273× A4) are grown as described in Example 112. The bacteria, diluted to an $OD_{600}$ of 0.2–0.4, are then used for inoculation of cotton cotyledons prepared as described below.

The cotton seeds are soaked 20 min in 10% chlorox and rinsed with sterile water. The seeds are germinated on 0.7% water agar in the dark. The seedlings are grown for one week before inoculation of the bacteria onto the cotyledon surface.

The inoculated cotyledons are allowed to form callus before they are cut and placed on 0.7% agar containing MS salts, 3% sucrose, 100 g/ml carbenicillin, and 100 g/ml mefoxim. The callus is transferred to fresh media every three weeks until sufficient quantity is obtained for 4 plates. Half of the callus growing from the virulent Agrobacterium strains is transferred to media without hormones containing 50 g/ml kanamycin. For induction experiments, after sufficient callus grown in the presence or absence of kanamycin is obtained, it is treated for induction as described above for transformed carrot callus.

EXAMPLE 118

Preparation of a Special Type of Callus of Zea Mays, Elite Inbred Line Funk 2717

Zea mays plants of the inbred line Funk 2717 are grown to flowering in the greenhouse, and self pollinated. Immature ears containing embryos approx. 2–2.5 mm in length are removed from the plants and sterilized in 10% Clorox solution for 20 minutes. Embryos are aseptically removed from the kernels and plated with the embryo axis downwards on OMS medium containing 0.1 mg/l 2,4-D, 6% (w/v) sucrose and 25 mM L-proline solidified with 0.24% (w/v) Gelrite$^R$ (initiation medium). After two weeks' culture in the dark at 27° C., the callus developing on the scutellum is removed from the embryo and plated on B5 medium, (Gamborg, O. L. et al., *Experimental Cell Research* 50: 151–158 (1968)), containing 0.5 mg/l 2,4-D and solidified with 0.24% (w/v) Gehrite$^R$.

The callus is subcultured every two weeks to fresh medium. After a total of eight weeks after placing the embryos on the initiation medium, the special type of callus is identified by its characteristic morphology. This callus is subcultured further on the same medium. After a further period of two months, the callus is transferred to, and serially subcultured on, N6 medium containing 2 mg/l 2,4-D and solidified with Gelrite$^R$.

EXAMPLE 119

Preparation of a Suspension Culture of Zea Mays, Elite Inbred Funk 2717

The callus described in Example 118 is subcultured for a total of at least six months. The type of callus chosen for subculture is relatively non-mucilaginous, granular and very friable, such that it separated into small individual cell aggregates upon placing into liquid medium. Cultures containing aggregates with large, expanded cells are not retained. Approximately 500 mg aliquots of the special callus of Zea mays elite inbred funk 2717 are placed into 30 ml of N6 medium containing 2 mg/l 2,4-D in 125 ml Delong flasks. After one week of culture at 26° C. in the dark on a gyratory shaker (130 rpm, 2.5 cm throw), the medium is replaced with fresh medium. The suspensions are again subcultured in this way after another week. At that time, the cultures are inspected, and those which did not show large numbers of expanded cells are retained. Suspension cultures containing aggregates with large, expanded cells are discarded.

The preferred tissue consisted of densely cytoplasmic dividing cell aggregates which had a characteristically smoother surface than the usual type of cell aggregates. The cultures retained had at least 50% of the cells represented in these small aggregates. This is the desired morphology. These suspensions also had a rapid growth rate, with a doubling time of less than one week.

The suspension cultures are subcultured weekly by transferring 0.5 ml PCV (packed cell volume: settled cell volume in a pipette) into 25 ml of fresh medium. After four to six weeks of subculture in this fashion, the cultures increased two- to three-fold per weekly subculture. Cultures in which more than 75% of the cells are of the desired morphology are retained for further subculture. The lines are maintained by always choosing for subculture the flask whose contents exhibited the best morphology. Periodic filtration through 630 m pore size stainless steel sieves every two weeks is used in some cases to increase the dispersion of the cultures, but is not necessary.

EXAMPLE 120

Preparation of Protoplasts from Suspension Cultures of Zea Mays

1–1.5 ml PCV of the suspension culture cells prepared as in Example 119 are incubated in 10–15 ml of a filter-sterilized mixture consisting of 4% (w/v) cellulase RS with 1% (w/v) Rhozyme in KMC (8.65 g/l KCl, 16.47 g/l $MgCl_2 \cdot 6H_2O$ and 12.5 g/l $CaCl_2 \cdot 2H_2O$, 5 g/l MES, pH 5.6) salt solution. Digestion is carried out at 30° C. on a slow rocking table for a period of 3–4 hours. The preparation is monitored under an inverted microscope for protoplast release.

The protoplasts which are released are collected as follows. The preparation is filtered through a 100 m mesh sieve, followed by a 50 m mesh sieve. The protoplasts are washed through the sieves with a volume of KMC salt solution equal to the original volume of enzyme solution. 10 ml of the protoplast preparation is placed in each of several disposable plastic centrifuge tubes, and 1.5–2 ml of 0.6 M sucrose solution (buffered to pH 5.6 with 0.1% (w/v) morpholinoethane sulfonic acid (MES and KOH)) layered underneath. The tube is centrifuged at 60–100×g for 10 minutes, and the protoplasts banding at the interface collected using a pipette and placed in a fresh tube.

The protoplast preparation is resuspended in 10 ml of fresh KMC salt solution, and centrifuged for five minutes at 60–100×g. The supernatant is removed and discarded, and the protoplasts resuspended gently in the drop remaining, and then 10 ml of a 13/14 strength KMC solution gradually added.

After centrifuging again for five minutes, the supernatant is again removed and the protoplasts resuspended in a 6/7 strength KMC solution. An aliquot is taken for counting, and the protoplasts again sedimented by centrifugation.

The protoplasts are resuspended at $10^7$ (ten million) per ml in KM-8p medium (Table I) or in 0.5 M mannitol containing 6 mM $MgCl_2$ or other suitable medium for use in transformation as described in the following examples. This protoplast suspension is used for transformation and is cultured as described below in Examples 121 and 122.

EXAMPLE 121

Transformation of *Zea Mays* Protoplasts by Electroporation

A. All steps except the heat shock are carried out at room temperature (22–28° C.). The protoplasts are resuspended in the last step of Example 120 in 0.5 M mannitol containing 0.1% (w/v) MES and 6 mM $MgCl_2$. The resistance of this suspension is measured in the chamber of a Dialog Electroporator (DIA-LOG G.m.b.H., D-4000 Duesseldorf 13, Federal Republic of Germany) and adjusted to 1–1.2 kOhm using a 300 mM $MgCl_2$ solution. The protoplasts are heat-shocked by immersing the tube containing the sample in a water bath at 45° C. for five minutes, followed by cooling to room temperature on ice. 4 g of linearized plasmid containing a plant-selectable hygromycin resistance gene such as described by Rothstein, S. J. et al., supra, or chimeric gene constructs as described in previous Examples, and 20 g of calf thymus carrier DNA are added to aliquots of 0.25 ml of this suspension. 0.125 ml of a 24% (w/v) polyethylene glycol (PEG) solution (MW 8000) in 0.5 M mannitol containing 30 mM $MgCl_2$ are added to the protoplasts. The mixture is mixed well but gently, and incubated for 10 minutes. The sample is transferred to the chamber of the electroporator and samples pulsed three times at 10 second intervals, at initial voltages of 1500, 1800, 2300 or 2800 Vcm-1, and an exponential decay time of 10 sec.

The protoplasts are cultured as follows. The samples are plated in 6 cm petri dishes at room temperature. After a further 5–15 minutes, 3 ml of KM-8p medium (Table I, supra) containing 1.2% (w/v) SeaPlaque agarose and 1 mg/l 2,4-D are added. The agarose and protoplasts are mixed well and the medium allowed to gel.

B. Part A above is repeated with one or more of the following modifications:

(1) The resistance of the protoplast preparation is adjusted to 0.5–0.7 kOhm.

(2) The PEG used is PEG with a molecular weight of 4000.

(3) No PEG is added, or one-half volume of 12% (w/v) PEG is added.

(4) The pulses are applied at intervals of three seconds.

(5) The protoplasts are plated after the electroporation in dishes placed on a plate cooled to a temperature of 16° C.

(6) The protoplasts are placed in tubes after the electroporation step, washed with 10 ml of 6/7 strength KMC solution or with W5 solution (comprised of 380 mg/l KCl, 18.375 g/l $CaCl_2.2H_2O$, 9 g/l NaCl; 9 g/l glucose, pH 6.0), then collected by centrifugation at 60 g for 10 minutes, resuspended in 0.3 ml of KM medium, and plated as in A.

(7) The calf thymus carrier DNA is not added.

EXAMPLE 122

Transformation of *Zea Mays* Protoplasts by Treatment with Polyethylene Glycol (PEG)

A. The protoplasts are resuspended at the last step of Example 120 in a 0.5 M mannitol solution containing 12–30 mM $MgCl_2$. A heat shock of 45° C. for five minutes is given as described in Example 43. The protoplasts are distributed in aliquots for transformation in centrifuge tubes, 0.3 ml of suspended protoplasts per tube. During the next 10 minutes the following are added: DNA (as for Example 43) and polyethylene glycol (PEG) solution (MW 6000, 40% (w/v); containing 0.1 M $Ca(NO_3)_2$ and 0.4 M mannitol; pH 8–9 with KOH) to give a final concentration of 20% PEG. The aliquots are incubated for 30 minutes with occasional gentle shaking, and then the protoplasts are placed in petri dishes (0.3 ml original protoplast suspension per 6 cm diameter dish) and cultured as described in Example 121.

B. Part A above is repeated and the protoplasts are washed after 30 minutes of incubation in the PEG solution of part A, by adding 0.3 ml of W5 solution five times at two- to three-minute intervals. The protoplast suspension is centrifuged, the supernatant removed, and the protoplasts are cultured as for Example 121, part A.

C. Parts A and B above are repeated with the modification that the final concentration of PEG is between 13 and 25% (w/v).

EXAMPLE 123

Regeneration of Callus from Protoplasts

The plates containing the protoplasts in agarose are placed in the dark at 26° C. After 14 days, colonies arise from the protoplasts. The agarose containing the colonies is transferred to the surface of a 9 cm diameter petri dish containing 30 ml of N6 medium (Table I, supra) containing 2 mg/l 2,4-D, solidified with 0.24% w/v Gehrite$^R$. This medium is referred to as 2N6. The callus is cultured further in the dark at 26° C. and callus pieces subcultured every two weeks onto fresh solid 2N6 medium.

EXAMPLE 124

Selecton of Transformed Callus of *Zea Mays*

Example 123 is repeated with the modification that 100 mg/l or 200 mg/l hygromycin B is added to the 2N6 medium in order to select for transformed cells.

EXAMPLE 125

Regeneration of Corn Plants

A. Callus is placed on 2N6 medium for maintenance and on ON6 (comprising N6 medium lacking 2,4-D) and N61 medium (comprising N6 medium containing 0.25 mg/l 2,4-D and 10 mg/l kinetin) to initiate regeneration. Callus growing on ON6 and N61 media is grown in the light (16 hours/day light of 10–100 Einsteins/m²sec from white fluorescent lamps). Callus growing on N61 medium is transferred to ON6 medium after two weeks, as prolonged time on N61 medium is detrimental. The callus is subcultured every two weeks even if the callus is to be transferred again on the same medium formulation.

Plantlets appear in about four to eight weeks. Once the plantlets are at least 2 cm tall, they are transferred to ON6 medium in GA7 containers. Roots form in two to four weeks, and when the roots look well-formed enough to support growth, the plantlets are transferred to soil in peat pots, under a light shading for the first four to seven days. It is often helpful to invert a clear plastic cup over the transplants for two to three days to assist hardening off. Once the plants are established, they are treated as normal corn plants and grown to maturity in the greenhouse. In order to obtain progeny plants are self pollinated or crossed with wild type.

B. Part A above is repeated with the modification that 100 mg/l or 200 mg/l hygromycin B is added to the medium used to maintain the callus.

EXAMPLE 126

Preparation of Embryogenic Suspensions from Tissue of *Dactylis Glomerata L.* (Orchardgrass)

A. Embryogenic callus is initiated from basal sections of the youngest leaves of greenhouse-grown orchardgrass plants (*Dactylis glomerata L.*) as described by Hanning, G. E. et al., *Theor. Appl. Genet.*, 63: 155–159 (1982). The leaves are surface sterilized by immersion in a 1:10 dilution of Clorox solution (5.25% (w/v) sodium hypochlorite; The Clorox Company, Oakland, Calif.) for about 10 minutes and then cut aseptically into small segments of 1 to 5mm in length or in diameter. These segments are plated on sterile SH-30 medium containing 0.8% (w/v) agarose as a gelling agent. Callus and/or embryogenic structures appear within 2 to 6 weeks after plating, upon culture at about 25° C. Embryogenic callus is maintained by subculturing onto fresh SH-30 medium every 2 to 4 weeks and culturing in the dark at 25° C.

B. Embryogenic suspension cultures are initiated by placing approximately 0.5 g fresh weight of embryogenic callus into 50 ml of liquid medium described by Gray, D. J. et al., *Plant Cell Tissue Organ Cult.*, 4: 123–133 (1985) containing 45 M dicamba and 4 gtliter casein hydrolysate. The suspension cultures are grown at 27° C. under a 16 hours light (40 E/m² sec), 8 hours dark photoperiod on a gyratory shaker at about 130 rpm in 125 ml Delong flasks sealed with a metal cap and parafilm$^R$. After approximately four weeks the large clumps are allowed to settle for about 30 seconds and 10 ml aliquots of the supernatant medium containing small cell clusters are removed and transferred to 50 ml of fresh medium. This process is repeated every 3 to 4 weeks using the most successful cultures as judged by smaller clump size and better quality based on the presence of small, cytoplasmic cells. After 5 to 8 transfers the suspensions are essentially free of non embryogenic cells and the majority of the embryogenic cell clusters are quite small (150 to 2000 m).

EXAMPLE 127

Isolation and Purification of *Dactylis Glomerata L.* Protoplasts

Protoplasts are prepared from embryogenic suspension cultures of Example 126 by aseptically filtering the cells on a Nalgene$^R$ 0.2 m filter unit and then adding 0.5 g fresh weight cells to each 12.5 ml of protoplast enzyme mixture in a petri dish. The enzyme mixture consists of 2% (w/v) Cellulase RS, 7 mM CaCl$_2$×H$_2$O, 0.7 mM NaH$_2$PO$_4$×H$_2$O, 3 mM MES (pH 5.6), glucose (550 mOs/kg H$_2$O of pH 5.6), and is filter sterilized. The mixture is swirled on an orbital shaker at about 50 rpm in dim (<5 E/m ²sec) light for about 4 to 5 hours. The digest is then sieved through a stainless steel sieve (100 m mesh size) and distributed into 12 ml centrifuge tubes which are centrifuged at about 60 to 100 g for about 5 minutes. The protoplast-containing sediment is then washed three times with protoplast culture medium KM-8p adjusted to 550 mOs/kg H$_2$O with glucose. At this point a flotation step may be included for further purification of the protoplasts. In this case, the washed protoplasts are layered atop 10 ml of KM-8p culture medium adjusted 700 mOs/kg H$_2$O with sucrose. After centrifugation at 60–100×g for about 10 minutes, protoplasts banding at the interface are collected using a fine pipette. Finally, the protoplasts are resuspended in 1 to 2 ml KM-8p culture medium and sieved through a stainless mesh screen (20 m mesh size). The protoplasts released are collected and washed and resuspended in KM-8p medium for culture or in osmotically adjusted medium suitable for transformation according to the Examples below.

EXAMPLE 128

*Dactylis Glomerata L.* Protoplast Culture and Growth of Callus

A. The purified protoplasts are plated at a density of about 5×10$^5$ protoplasts per ml in KM-8p culture medium containing 1.3% (w/v) SeaPlaque$^R$ agarose (FMC Corp., Marine Colloids Division, Rockland, Me., USA) and 30 to 40% (w/v) of conditioned medium (obtained from 3 to 4 week-old *Dactylis glomerata L.* embryogenic suspension cultures by filtering the medium through a sterile Nalgene$^R$ 0.2 m filter, making the medium 550 mOsrnAcg H$_2$O by addition of glucose, and again filter sterilizing). The plates are then placed in the dark at a constant temperature of 28° C. After 10 to 14 days the agarose is cut into wedges and placed into 'bead culture' as described by Shillito, R.D. et al., *Plant Cell Reports*, 2: 244–247 (1983) using 20 ml SH-45 suspension culture medium with 3% (w/v) sucrose per 3 ml original agarose embedded culture. The plates are put on a platform shaker and agitated at about 50 rpm in light at 8 E/m ²sec. New suspension cultures are formed as the colonies grow out of the agarose and release cells into the liquid medium. The resultant suspension cultured cells are plated onto agar-solidified SH-30 medium and placed in the dark at 25° C. until callus is formed.

B. Protoplasts are cultured as described in part A above except that the culture media contains no conditioned medium.

EXAMPLE 129

Transformation of *Dactylis Glomerata L.* Protoplasts by Means of Electroporation A. Immediately after purification of the protoplasts, electroporation is performed according to Shillito, R. D. et al., *Bio/Technology* 3: 1099–1103 (1985) using linearized plasmid such as that as described in Example 29. The protoplasts are resuspended after the last wash at a density of about 7×10$^6$ protoplasts per ml in the electroporation buffer (0.4 M mannitol, 6 mM MgCl$_2$). The protoplasts are placed in 0.7 ml aliquots in 10 ml plastic centrifuge tubes.

Plasmid DNA, such as that described in Example 29, and sonicated calf thymus DNA (Sigma) to give final concentrations of 10 g/ml and 50 g/ml respectively is added to the tubes. Then 0.38 ml polyethylene glycol (PEG) solution [24% (w/v) PEG 6000 in 0.4 M mannitol 30 mM $MgCl_2$, 0.1% (w/v) MES (pH 5.6)] is added and the solution gently mixed. The protoplast suspension is transferred into the chamber of a Dialog$^R$ Electroporator and 10 pulses of 3250 V/cm initial voltage and exponential decay constant of 10 sec applied at 30 sec intervals. The sample is removed from the chamber, and placed in a 10 cm diameter petri dish. 10 ml of KM-8p medium containing 1.2% (w/v) SeaPlaque$^R$ agarose is added, the protoplasts distributed evenly throughout the medium, and the agarose allowed to gel.

B. Part A above is repeated except that the initial voltage used is 3500 V/cm, 4000 V/cm, 5000 V/cm, 3000 V/cm, or 2500 V/cm.

C. Parts A and B above are repeated except that PEG of MW 4000 or PEG of MW 8000 is used.

D. Parts A to C are repeated except that the final PEG concentration is between 10% and 30% (w/v).

EXAMPLE 130

Transformation of *Dactylis Glomerata L.* Protoplasts by Treatment with Polyethylene Glycol (PEG)

A. PEG mediated direct gene transfer is performed according to Negrutiu, I. et al., supra. The DNA used is linearized plasmid such as that described in Example 29.

The protoplasts are suspended following the last wash in 0.5 M mannitol containing 15 mM $MgCl_2$ at a density of about $2 \times 10^6$ per ml. The protoplast suspension is distributed as 1 ml aliquots into 10 ml plastic centrifuge tubes. The DNA is added as described in Example 51 above, and then 0.5 ml of the PEG solution added (40% (w/v) PEG 4000 in 0.4 M mannitol, 0.1 M $Ca(NO_3)_2$, pH 7.0). The solutions are mixed gently and incubated for 30 minutes at room temperature (about 24° C.) for 30 minutes with occasional shaking. 1.4 ml of the wash solution is then added, and the contents of the tube gently mixed. The wash solution consists of 87 mM mannitol, 115 mM $CaCl_2$, 27 mM $MgCl_2$, 39 mM KCl, 7 mM Tris-HCl and 1.7 g/l myo-inositol, pH 9.0. Four further 1.4 ml aliquots of wash solution are added at 4 minute intervals, with mixing after each addition. The tube is then centrifuged at about 60×g for about 10 minutes, and the supernatant discarded. The sedimented protoplasts are taken up in 1 ml KM-8p culture medium, and placed in a 10 cm petri dish. 10 ml of KM-8p medium containing 1.2% (w/v) SeaPlaque$^R$ agarose is added. The protoplasts are evenly distributed throughout the medium, and the agarose allowed to gel.

B. Part A is repeated with one or more of the following modifications:

(1) The pH of the wash solution is adjusted to 5.6 or 7.0.
(2) The PEG used is PEG of MW 6000, PEG of MW 2000 or PEG of MW 8000.
(3) The wash medium consists of 154 mM NaCl, 125 mM $CaCl_2$, 5 mM KCl, 5 mM glucose, pH to 6.0 with KOH, of 0.2 M $CaCl_2$, 0.1% (w/v) MES, pH 6.0 with KOH, or of 0.2 M $CaCl_2$, 7 mM Tris/HCl, pH 9.0 with KOH.

EXAMPLE 131

Transformation of *Daetylis Glomerata L.* Protoplasts by Electroporation or PEG Treatment Transformation is carried out as described in Examples 129 or 130, except that the protoplasts are treated at 45° C. for about 5 minutes prior to distribution of the aliquots into tubes for transformation or after distribution of the aliquots, and before addition of the PEG.

EXAMPLE 132

Selection of Transformed Colonies

A. The culture plates (petri dishes) containing the protoplasts from Examples 129 to 131 are incubated for 10 days in the dark at about 25° C. and then cut into 5 equal slices for 'bead cultures' (Shillito, R. D. et al., *Plant Cell Reports* 2: 244–247 (1983)). Four of the slices are placed each into 20 ml SH-45 culture medium with 4 g/l casein hydrolysate and 20 g/ml hygromycin B. The fifth slice is put into 20 ml of the same medium but without hygromycin B as a non-selected control. After 4 to 5 weeks the putative transformed protoplast-derived cell colonies growing in hygromycin B are cut out of the agarose and placed into a 19 mm petri dish with 2 ml of liquid SH-45 medium containing 20 g/ml hygromycin B, which is agitated at about 50 rpm on an orbital shaker. After another 4 to 5 weeks all colonies which grow to make new suspensions are transferred into 125 ml Erlenmeyer flasks and grown in a manner similar to the parent suspension culture, except that 20 g/ml hygromycin B is included in the medium.

The new suspensions are subcultured every 1 to 3 weeks using SH-45 medium containing 4 gl casein hydrolysate and 20 g/ml hygromycin B. Cells from these suspensions are also plated on solidified SH-30 medium containing 20 g/ml hygromycin B and incubated at about 25° C. in the dark. Calli grown from the plated cells are subcultured every two weeks onto fresh medium. The cells which grow in the presence of hygromycin B are presumed to be transformants.

B. Selection is carried out as described in part A except that the protoplast-derived cell colonies growing in hygromycin B containing medium are placed on agar plates of SH-30 medium containing 20 g/ml hygromycin B and incubated at about 25° C. in the dark.

EXAMPLE 133

Regeneration of Transformed *Dactylis Glomerata L.* Plants

A. *Dactylis Glomerata L.* callus (obtained as described in Example 132) derived from protoplasts is grown on solidified SH-30 medium, and subcultured every two weeks. Any embryos which form are removed and plated on germination medium (SH-0) and placed in the light (45 to 55 E/m $^2$sec). Germination of these embryos occurs in 1 to 4 weeks and the resultant plantlets are placed on SH-0 medium in the light to form root systems. They are moved into the greenhouse at the six to twelve leaf stage, and hardened off gradually.

B. Callus (obtained as described in Example 132) derived from protoplasts is grown on SH-0 medium solidified with 0.24% (w/v) Gelrite$^R$ in the light (45 to 55 E/m $^2$sec), and subcultured every two weeks. The resultant plantlets are placed on a 1:1 mixture of SH-0 and OMS media solidified with a combination of 0.12% (w/v) Gehrite$^R$ and 0.4% (w/v) agar in the light to form root systems. They are moved to the greenhouse at the six to twelve leaf stage, and hardened off gradually.

C. Small plantlets are obtained as described in Example 125, parts A and B, and are placed on OMS medium solidified with 0.8% (w/v) agar in the light to form root systems. They are moved to the greenhouse at the six to twelve leaf stage, and hardened off gradually.

D. Small plantlets are obtained as described in Example 125, part A and are placed on a 1:1 mixture of SH-0 and OMS media solidified with a combination of 0.12% (w/v) GelRite$^R$ and 0.4% (w/v) agar in the light to form root systems. They are moved to the greenhouse at the six to twelve leaf stage, and hardened off gradually.

J. Transient Gene Expression

The following examples describe how the chimeric genes can be introduced and utilized without the gene necessarily being stably incorporated into the genome of the plant.

EXAMPLE 134

Introduction of DNA into Protoplasts of N. Tabacum by Treatment with PEG

A. Preparation of protoplasts of N. tabacum can be carried out in accordance with the methods described in the following publications: Paszkowski, J. et al., *EMBO J.* 3: 2717 (1984); GB patent application 2 159 173, European Patent Application EP 0 129 668; Shillito, R. D. and Potrykus, I., *Methods in Enzymology* 153: 313–306, (1987) or by other methods known in the art.

B. DNA is introduced into protoplasts by a modification of the method of Negrutiu, I. et al., *Plant Mol. Biol.* 8: 363 (1987). The protoplasts prepared as described in part A are resuspended following the last washing step in a solution consisting of 0.4 M mannitol, 15–30 mM CaCl$_2$, 0.1% w/v MES at a density of 1.6–2×10$^6$ per ml. The protoplast suspension is distributed as 0.5 ml aliquots into 10 ml plastic centrifuge tubes. DNA such as that described in Examples 28 to 40 is added in 10 l sterile distilled water, sterilized as described by Paszkowski, J. et al., *EMBO J.* 3: 2717 (1984), and then 0.5 ml of the PEG solution (40% (w/v) PEG MW 8000 in 0.4 M mannitol, 0.1 M Ca(NO$_3$)$_2$, pH 7.0) is added. The solutions are mixed gently and incubated for 30 minutes at room temperature (about 24° C.) with occasional shaking. 1 ml of the wash solution is then added, and the contents of the tube gently mixed. The wash solution consists of 154 mM NaCl, 125 mM CaCl2, 5 mM KCl, 5 mM glucose, pH to 6.0 with KOH. Further aliquots of 2 ml, 3 ml and 4 ml of wash solution are added sequentially at 5 minute intervals, with mixing after each addition. The tube is then centrifugated at about 10–100×g for about 10 minutes, and the supernatant discarded. The pelleted protoplasts are taken up in sufficient K3 culture medium with 0.3 M glucose as the osmoticum, and no sucrose, to achieve a final density of 100,000 per ml and cultured in a 10 cm petri dish.

C. Part B is repeated with one or more of the following modifications:

(1) The pH of the wash solution is adjusted to 5.6 or 7.0.
(2) The PEG used is PEG with a molecular weight of 4000.
(3) The wash medium consists of 0.2 M CaCl$_2$, 0.1% w/v MES, pH 6.0 with KOH, or of 0.2 M CaCl$_2$, 7 mM Tris/HCl, pH 9.0 with KOH.
(4) 50 g of sheared calf thymus DNA in 25 l sterile water is added together with the plasmid DNA.
(5) The plasmid DNA is linearized before use by treatment with an appropriate restriction enzyme (e.g. BamHI).

EXAMPLE 135

Introduction of DNA into Protoplasts of N. Tabacum by Electroporation.

A. Introduction of DNA into protoplasts of N. tabacum is effected by treatment of the protoplasts with an electric pulse in the presence of the appropriate DNA, in a modification of the methods of Fromm, M. E., *Methods in Enzymology* 153: 307, (1987); and Shillito R. D and Potrykus I., ibid., p. 283–306.

Protoplasts are isolated as described in Example 134, part A. The protoplasts are resuspended following the last wash in the following solution: 0.2 M mannitol, 0.1% w/v MES/ 72 mM NaCl, 70 mM CaCl$_2$, 2.5 mM KCl, 2.5 mM glucose, pH to 5.8 with KOH, at a density of 1.6–2×10$^6$ per ml. The protoplast suspension is distributed as 1 ml aliquots into plastic disposable cuvettes and 10 g of DNA added as described in Example 134, parts B and C. The resistance of the solution at this point when measured between the electrodes of the 471 electrode set of the electroporation apparatus described below is in the range of 6 Ohms.

DNA such as that described in Examples 28 to 40 is added in 10 1 sterile distilled water, sterilized as described by Paszkowski, J. et al., *EMBO J.* 3: 2717 (1984). The solution is mixed gently and then subjected at room temperature (24–28° C.) to a pulse of 400 V/cm with an exponential decay constant of 10 ms from a BTX-Transfector 300 electroporation apparatus using the 471 electrode assembly. The protoplasts are left undisturbed for 5 minutes, and then placed in a petri dish and K3 medium as described in Example 56 A added to bring the density of protplasts to 100,000 per ml.

B. Part A is repeated with one or more of the following modifications:

(1) The voltage used is 200 V/cm, or between 100 V/cm and 800 V/cm.
(2) The exponential decay constant is 5 ms, 15 ms or 20 ms.
(3) 50 g of sheared calf thymus DNA in 25 1 sterile water is added together with the plasmid DNA.
(4) The plasmid DNA is linearized before use by treatment with an appropriate restriction enzyme (e.g. BamHI).

EXAMPLE 136

Introduction of DNA into Protoplasts of Zea Mays Line 2717

Protoplasts of maize inbred line Funk 2717 are prepared as described in Examples 118 to 125 above, and resuspended in in either of the solutions described for resuspension of the N. tabacum protoplasts in Examples 134 and 135 above at a density of 10$^7$ per ml. Transformation is carried out essentially as described in Examples 134 and 135. The protoplasts are cultured following transformation at a density of 2×106 per ml in KM-8p medium with no solidifying agent added and containing 1 mg/l 2,4-D.

EXAMPLE 137

Introduction of DNA into Protoplasts of Sorghum Bicolor

Protoplasts of sorghum suspension FS 562 are prepared essentially as described for Zea mays in Example 118 above, and resuspended in in either of the solutions described for resuspension of the N. tabacum protoplasts in Examples 134 and 135 above at a density of 10$^7$ per ml. Transformation is carried out essentially as described in Example 136. The protoplasts are cultured following transformation at a density of 2×10$^6$ per ml in KM-8p medium, with no solidifying agent added.

EXAMPLE 138

Introduction of DNA into Protoplasts of *Nicotiana Plumbaginifolia, Petunia Hybrida* and *Lolium Multiflorum*

Protoplasts of *N. ylumbaginifolia, P. hybrida* or *L. multiflorum* are prepared as described in Shillito and Potrykus, supra, and treated as described in Examples 134 and 135. They are cultured in the medium described by Shillito and Potrykus, supra, without addition of agarose or any other gelling agent.

EXAMPLE 139

Introduction of DNA into Protoplasts of *Glycine Max*

Protoplasts of *Glycine max* are prepared by the methods as described by Tricoli, D. M. et al., *Plant Cell Reports* 5: 334–337 (1986), or Chowhury, V. K. and Widholm, J. M., *Plant Cell Reports* 4: 289–292 (1985), or Klein, A. S. et al., *Planta* 152: 105–114 (1981). DNA is introduced into these protoplasts essentially as described in Examples 134 and 135. The protoplasts are cultured as described in Klein, A. S. et al., supra, Chowhury V. K. and Widholm, J. M. supra, or Tricoli, D. M. et al., supra, without the of addition of alginate to solidify the medium.

K. Chemical Regulation of Transgenic Plant Tissue

The following examples describe procedures for the chemical regulation of chemically regulatable genes in representative transgenic plant tissue. While the following examples are directed to induction, similar procedures would be applicable for systems operating by repression.

A variety of techniques are available for the treatment of transgenic cells with a chemical regulator. For example, cells may be suspended in liquid medium containing the regulator. Callus may be grown on, or transferred to medium containing the regulator, or the regulator may be applied to callus with a sterile paint brush or plant mister. Likewise plants or parts of plants are treated with a solution or a suspension of the regulator by the way of a paint brush or, preferably, a plant mister.

Expression of the phenotypic trait in transgenic plants containing a chemically regulatable chimeric gene is proportional to the amount of the regulator applied to the plant or plant tissue.

EXAMPLE 140

Chemical Induction in Transgenic Callus Cultures

A. Callus obtained according to previously described procedures is assayed for chemical induction by applying with a sterile paint brush or a plant mister a filter sterilized solution of 0.1 to 50 mM salicylic acid which has been adjusted to a pH between 6.0 and 8.0 by the addition of NaOH.

After induction the callus is allowed to incubate for two days and then harvested, frozen in liquid nitrogen and stored at −80° C. until they are assayed for gene induction as described in Example 65 and/or Example 66.

B. Alternatively, the following solutions are used for induction:
(1) 0.1 to 50 mM benzoic acid which has been adjusted to a pH between 6.0 and 8.0 by the addition of NaOH.
(2) 0.1 to 50 mM polyacrylic acid which has been adjusted to a pH between 6.0 and 8.0 by the addition of NaOH.
(3) Methyl benzo-1,2,3-thiadiazole-7-carboxylate. The solution is made by resuspending a wettable powder containing the chemical in sterile water for several minutes at a concentration of 1 mg/ml. Insoluble solid is removed from the solution by filter sterilizing.
(4) 0.1 to 50 mM benzo-1,2,3-thiadiazole-7-carboxylic acid, pH between 6.0 and 8.0. The compound is dissolved in a minimum of dimethyl sulfoxide (DMSO), then diluted with sterile water to the desired concentration. The obtained suspension is applied without filtering.
(5) 0.1 to 50 mM n-propyl benzo-1,2,3-thiadiazole-7-carboxylate, prepared as in (4).
(6) 0.1 to 50 mM benzyl benzo-1,2,3-thiadiazole-7-carboxylate, prepared as in (4).
(7) 0.1 to 50 mM benzo-1,2,3-thiadiazole-7-carboxylic acid N-sec- butylhydrazide, prepared as in (4).
(8) 0.1 to 50 mM 2,6-dichloroisonicotinic acid, pH between 6.0 and 8.0, prepared as in (4).
(9) 0.1 to 50 mM methyl 2,6-dichloroisonicotinate, prepared as in (4).

EXAMPLE 141

Chemical Induction in Transgenic Plants

A. Gene expression is induced in plants obtained according to previously described procedures by applying a fine spray of a solution of 0.1 to 50 mM salicylic acid which has been adjusted to a pH between 6.0 and 8.0 with NaOH, to the leaves using a plant mister.

The plants are allowed to continue to grow for two days and are then harvested, frozen in liquid nitrogen and stored at −80° C. until they are assayed as described in Example 65 and/or Example 66.

B. Alternatively, the following solutions are used for induction:
(1) 0.1 to 50 mM benzoic acid which has been adjusted to a pH between 6.0 and 8.0 by the addition of NaOH.
(2) 0.1 to 50 mM polyacrylic acid which has been adjusted to a pH between 6.0 and 8.0 by the addition of NaOH.
(3) Methyl benzo-1,2,3-thiadiazole-7-carboxylate. The solution is made by resuspending a wettable powder containing the chemical in sterile water for several minutes at a concentration of 1 mg/ml. Insoluble solid is removed from the solution by filter sterilizing.
(4) 0.1 to 50 mM benzo-1,2,3-thiadiazole-7-carboxylic acid, pH between 6.0 and 8.0. The compound is dissolved in a minimum of dimethyl sulfoxide (DMSO), then diluted with sterile water to the desired concentration. The obtained suspension is applied without filtering.
(5) 0.1 to 50 mM n-propyl benzo-1,2,3-thiadiazole-7-arboxylate, prepared as in (4).
(6) 0.1 to 50 mM benzyl benzo-1,2,3-thiadiazole-7-carboxylate, prepared as in (4).
(7) 0.1 to 50 mM benzo-1,2,3-thiadiazole-7-carboxylic acid N-sec-butylhydrazide, prepared as in (4).
(8) 0.1 to 50 mM 2,6-dichloroisonicotinic acid, pH between 6.0 and 8.0, prepared as in (4).
(9) 0.1 to 50 mM methyl 2,6-dichloroisonicotinate, prepared as in (4).

EXAMPLE 142

Induction of Expression of the Introduced DNA in Protoplasts of *N. Tabacum, Zea Mays, N. Plumbaginifolia P. Hybrida, L. Multiflorum* and *Sorzhum Bicolor*

The protoplasts treated as described in Examples 134 to 139 above are cultured at 26° C. in the dark for 2 days. After this time salicylic acid is added to a concentration of between 0.1 to 50 mM as a neutralized solution, pH between 6.0 and 8.0. The protoplasts are cultured for a further 2 days, harvested by centrifugation, quick frozen and assayed as described in the following Examples.

B. Alternatively, neutralized solutions or suspensions of the following compounds are added to the protoplasts to give a final concentration of between 0.1 and 50 mM:
(1) benzoic acid
(2) polyacrylic acid
(3) methyl benzo 1,2,3-thiadiazole-7-carboxylate
(4) benzo-1,2,3-thiadiazole-7-carboxylic acid
(5) n-propyl benzo-1,2,3-thiadiazole-7-carboxylate
(6) benzyl benzo-1,2,3-thiadiazole-7-carboxylate
(7) benzo-1,2,3-thiadiazole-7-carboxylic acid N-sec-butylhydrazide
(8) 2,6-dichloroisonicotinic acid
(9) methyl 2,6-dichloroisonicotinate C. Alternatively, induction is carried out as described in parts A and B except that the protoplasts are cultured for 1 day, 3 days or 5 days before induction.

D. Induction is carried out as described in Examples parts A, B or C except that the protoplasts are cultured for 1 day, 3 days or 5 days after induction and before being harvested.

EXAMPLE 143

Assay for Chemically Inducible DNA Sequence: mRNA Production

Plant materials induced and harvested as in Examples 140 to 142 are assayed for the induction of mRNA species by the isolation of RNA and the primer extension assay as described in Example 6.

Callus or regenerated plant material derived from transgenic plants containing chemically regulatable chimeric genes coding for GUS, AHAS or BT and induced by salicylic acid, methyl benzo-1,2,3-thiadiazole-7-carboxylate, benzo-1,2,3-thiadiazole-7-carboxylic acid, n-propyl benzo-1,2,3-thiadiazole-7-carboxylate, benzyl benzo-1,2,3-thiadiazole-7-carboxylate, benzo-1,2,3-thiadiazole-7-carboxylic acid N-sec-butylhydrazide, 2,6-dichloroisonicotinic acid, methyl 2,6-dichloroisonicotinate, or TMV demonstrates elevated levels of mRNA upon assay with the GUS, AHAS or BT primer, respectively, in the primer extension assay. The level of mRNA is proportional to the amount of regulator applied.

EXAMPLE 144

Assay for Chemically Inducible DNA Sequences: β-Glucuronidase Enzymatic Activity

A. ELISA Assay

Frozen leaf tissue is ground in a mortar with a pestle in the presence of liquid nitrogen to produce a fine powder. Leaf extracts are prepared by mixing a given weight (g) with an equal volume (ml) of GUS extraction buffer (50 mM sodium phosphate buffer pH 7.0, 0.1% Triton-X 100, 0.1% sarkosyl, 10 mM β-mercaptoethanol) as described by Jefferson, R. A. et al., *Proc. Natl. Acad. Sci. USA* 83: 8447–8451 (1986).

The reactions are carried out in the wells of ELISA plates by mixing 5–25 l extract with 120–100 l GUS assay buffer (50 mM sodium phosphate buffer pH 7.0, 0.1% Triton X-100, 10 mM β-mercaptoethanol) containing 4-methyl umbelliferyl glucuronide (MU) at a final concentration of 2 mM in a total volume of 125 l. The plate is incubated at 37° C. for 1–5 hours and the reaction is stopped by the addition of 150 l 3 M $Na_2CO_3$. The concentration of fluorescent indicator released is determined by reading the plate on a Flow Labs Fluoroskan II ELISA plate reader.

B. Results

TABLE II

| | Specific Activity nKat MU/mg protein | | | | |
|---|---|---|---|---|---|
| Plant[a] | A | B | C | D | E[b] |
| H 1 | 5.39 ± 1.9 | 13.9 ± 1.2 | 13.5 ± 0.8 | 20.1 ± 5.1 | 33.6 ± 2.6 |
| H 3 | 0.21 ± 0.02 | 6.92 ± 0.88 | 11.95 ± 0.85 | 1.66 ± 0.02 | 6.54 ± 1.43 |
| H 4 | 8.39 ± 1.31 | 27.5 ± 0.7 | 18.52 ± 1.07 | 2.28 ± 0.78 | 25.1 ± 0.9 |
| H 6 | 0.10 ± 0.04 | 4.08 ± 0.58 | 2.58 ± .01 | 0.09 ± 0.06 | 2.8 ± 1.2 |
| H 9 | 0.23 | 10.8 | 9.1 | 0.5 | 7.5 |
| Alu 1 | 5.6 | 20.0 | 206.9 | 20.5 | 70.5 |
| Alu 2 | 2.0 | 6.6 | 83.2 | 8.9 | 155.3 |
| Alu 3 | 0.1 ± .07 | 2.8 ± .9 | 2.0 ± .9 | 2.0 ± .5 | 5.8 ± 3.8 |
| Alu 4 | 2.1 ± 1 | 43.0 ± 19 | 7.1 ± 2.6 | 6.1 ± 3.2 | 7.5 ± 3.5 |
| Alu 5 | 0.6 ± .2 | 4.4 ± 2.3 | 1.2 ± .6 | 0.5 ± .3 | 8.3 ± 3.7 |
| Alu 6 | 0.8 | 28.8 | 67.0 | 3.1 | 36.4 |
| Alu 7 | 1.7 | 38.7 | 29.1 | 21.7 | 63.0 |
| Alu 8 | 0.6 | 0.4 | 0.4 | 0.6 | 0.2 |
| Alu 9 | 0.9 | 0.6 | 0.4 | 0.3 | nd |
| Alu 10 | 4.0 | 39.2 | 52.0 | 8.1 | 37.9 |
| Alu 11 | 1.6 ± .8 | 1.9 ± .9 | 2.8 ± 1.3 | 2.2 ± 2.6 | 2.8 ± 2.9 |
| Alu 12 | 0.7 ± .4 | 57.1 ± 22 | 73.4 | 2.3 ± 1.2 | 78.0 ± 41.4 |
| Alu 13 | 0.1 | 19.1 | 13.2 | 1.9 | 10.6 |
| Hae 1 | 0.6 | 1.6 | 2.6 | 1.7 | 3.9 |
| Hae 2 | 2.3 | 8.8 | 11.8 | 0.4 | 0.8 |
| Hae 3 | 1.7 | 11.1 | 11.2 | 3.0 | 1.6 |
| Hae 4 | 2.0 | 8.1 | 10.8 | 1.7 | 0.82 |
| Hae 5 | 18.1 | 59.4 | 132.5 | 36.6 | 14.0 |
| Hae 8 | 0.4 | 30.6 | 28.9 | 0.6 | 29.0 |
| Hae 9 | 2.6 | 63.9 | 129.7 | 12.5 | 55.2 |
| Hae 10 | 1.6 | 70.5 | 98.2 | 13.5 | 94.5 |
| Hae 11 | 2.6 | 81.8 | 58.5 | 3.9 | 46.0 |
| Hae 12 | 0.2 | 2.5 | 5.8 | 0.6 | 14.5 |
| Hae 13 | 0.01 | 0.7 | 0.1 | nd | nd |
| Hae 14 | 0.1 | 1.8 | 8.6 | 0.1 | 3.3 |
| Hae 15 | 0.1 | 6.4 | 7.2 | 3.4 | 7.4 |
| Hae 16 | 0.1 | 2.3 | 4.3 | 0.8 | 2.7 |

Footnotes
[a]H 1–9 are tobacco plants obtained by transformation of leaf disks by strain CIB271
Alu 1–13 are tobacco plants obtained by transformation of leaf disks by strain CIB272
Hae 1–16 are tobacco plants obtained by transformation of leaf disks by strain CIB273
[b]A Water
B Salicylic acid
C Methyl benzo-1,2,3-thiadiazole-7-carboxylate
D Buffer
E TMV Transformed tobacco callus (Example 113): The following GUS activities are obtained from samples of transformed callus which has been harvested 21 hours after treatment. Transformed with CIB271: $H_2O$ spray: 1.8 nKat MU/mg protein; 50 mM sodium salicylate spray: 3.8 nKat MU/mg protein.

Transformed with CIB271 (different experiment): $H_2O$ spray: 2.8 nKat MU/mg protein; 250 g/l methyl benzo-1,2, 3-thiadiazole-7-carboxylate spray: 13.7 nKat MU/mg protein. Transformed with CIB273: $H_2O$ spray: 0.46 nKat MU/mg protein; 250 g/l methyl benzo-1,2,3-thiadiazole-7-carboxylate spray: 31.2 nKat MU/mg protein.

Transformed carrot (Example 114): The following GUS activities are obtained from samples of callus transformed by pCIB271 which has been harvested 21 hours after treatment. H$_2$O spray: 5.2 pKat MU/mg protein. 50 mM sodium salicylate spray: 11.6 pKat MU/mg protein. 250 g/l methyl benzo-1,2,3-thiadiazole-7-carboxylate spray: 22.1 pKat MU/mg protein.

Transformed tomato (Example 116): The following GUS activities are obtained from samples of transformed callus which has been harvested 21 hours after treatment. Transformed with CIB271: H$_2$O spray: 17.2 pKat MU/mg protein; 250 g/l methyl benzo-1,2,3-thiadiazole-7-carboxylate spray: 56.1 pKat MU/mg protein. Transformed with CIB273 X A4: H$_2$O spray: 4.6 pKat MU/mg protein; 250 g/l methyl benzo-1,2,3-thiadiazole-7-carboxylate spray: 22.1 pKat MU/mg protein.

Transient expression in tobacco protoplasts (Example 134) treated with pCIB269: H$_2$O: 30.6 13 pKat MU/mg protein; methyl benzo-1,2,3-thiadiazole-7-carboxylate: 66.6 20 pKat MU/mg protein.

EXAMPLE 145

Assay for Chemical Induction of the Endogenous Gene

As a control procedure, tobacco plant materials induced as described in Examples 139–141 by salicylic acid, methyl benzo-1,2,3-thiadiazole-7-carboxylate and TMV are assayed for transcription of mRNA from the endogenous PR-1a gene by the methods described in Example 6. Elevated levels of mRNA are detected after induction by all three inducers.

EXAMPLE 146

Assay for Chemically Inducible DNA Sequences: Acetohydroxyacid Synthase (AHAS) Enzymatic Activity A. Sample preparation for AHAS assay The weight of the leaf and/or root tissue material to be assayed is determined, the tissue is placed into liquid nitrogen and macerated to a fine powder. One volume (in ml) of cold homogenization buffer (50 mM NaH$_2$PO$_4$ buffer pH 7.0, 0.5 mM EDTA pH 7.0, 0.5 mM MgCl$_2$, 1 mM sodium pyruvate pH 7.0, 10 M flavine adenine dinucleotide, 1 mM phenylmethylsulfonyl fluoride, 10% glycerol) equal to two times the weight (in g) of tissue is added and the mixture is transferred to a French pressure cell. All subsequent steps are carried out keeping the material cold (about 4° C.). The cells are disrupted at 16,000 psi, collecting the cell exudate into a container on ice. Alternatively the tissue is ground with homogenization buffer in a mortar and pestle in place of the French pressure cell treatment. The exudate is centrifuged 5 min at 10,000 rpm to clear the cell debris. The volume of the supernate is measured and enzyme grade ammonium sulfate added to 25% saturation (144 mg (NH$_4$)$_2$SO$_4$/ml supernate). The mixture is stirred on ice for 15 min, then centrifuged for 5 min at 10,000 rpm. The pellet is discarded and the supernate adjusted to 50% saturation with ammonium sulfate (158 mg (NH$_4$)$_2$SO$_4$/ml supernate). After stirring on ice for 15 min, the pellet is collected by centrifugation at 10,000 rpm for 5 min. The pellet obtained is dissolved in 1 ml of column buffer for each 2 g of leaf or 5 g of root material. The extract is desalted by application to a Sephadex G50 column equilibrated with column buffer (50 mM NaH$_2$PO$_4$ buffer pH 7.0, 0.1 mM EDTA, 0.5 mM MgCl$_2$, 10 M flavine adenine dinucleotide, 1 mM phenylmethylsullfonyl fluoride, 10% glycerol). The sample is eluted with column buffer, collecting 2 ml of sample for each ml of sample applied to the column.

B. Tube Assay

5–50 1 of an extract prepared according to part A are dissolved in a total volume of 0.5 ml of reaction mixture (20 mM NaH$_2$PO$_4$ buffer pH 7.0, 20 mM sodium pyruvate pH 7.0, 0.5 mM thiamine pyrophosphate, 5 mM MgCl$_2$, 10 M flavine adenine dinucleotide). The mixture is incubated for 30 min at 37° C. The reaction is stopped by the addition of 50 1 of 6N H$_2$SO$_4$. The mixture is incubated for 15 min at 60° C., then treated with 625 l of -napthol reagent (500 1 5% -napthol in 2.5 M NaOH and 125 1 25 mg/ml creatine) and incubated another 15 min at 60° C. If a precipitate has formed, this is spun out, and the absorbance measured at 520 m. The pMoles acetoin formed are calculated from a standard curve developed using 0.4 g to 10 g acetoin. The specific activity is expressed as pKat/mg protein.

C. Elisa Plate Assay

1–20 1 of a sample are placed in an Elisa plate well with a total volume of 0.15 ml of reaction mixture. The mixture is reacted for 30 min at 37° C. The reaction is stopped by the addition of 50 1 of 2.4 M H$_2$SO$_4$ containing 1% creatine. The mixture is incubated for 30 min at 60° C. Any precipitate present is separated by centrifugation. 150 1 of the assay mixture are transferred to a new Elisa plate, treated with 100 l 10% -napthol in 5M NaOH and incubated another 20 min at 60° C. The absorbance is measured at 520 m, and the specific activity expressed as under part B.

EXAMPLE 147

Assay for Chemically Inducible DNA Sequences: *Bacillus thuringiensis* Endotoxin A. Plant Extraction Procedure About 100 mg plant tissue is homogenized in 0.1 ml extraction buffer (50 mM Na$_2$CO$_3$ pH 9.5, 10 mM EDTA, 0.05% Triton X-100, 0.05% Tween, 100 mM NaCl, 1 mM phenylmethylsulfonyl fluoride (added just prior to use), and 1 mM leupeptine (added just prior to use)). After extraction, 2 M Tris pH 7.0 is added to adjust the pH to 8.0–8.5. The extract is then centrifuged 10 minutes in a Beckman microfuge and the supernatant used for ELISA analysis.

B. ELISA

An ELISA plate is pretreated with ethanol. Affinity-purified rabbit anti-Bt antiserum (50 1) at a concentration of 3 g/ml in borate-buffered saline (100 mM boric acid, 25 mM sodium borate, 75 mM NaCl, pH 8.4–8.5) is added to the plate and this allowed to incubate overnight at 4° C. Antiserum is produced by immunizing rabbits with gradient-purified Bt (*Bacillus thuringiensis* endotoxin) crystals (Ang, B. J. & Nickerson, K. W., *Appl. Environ. Microbiol.* 36: 625–626 (1978)) solubilized with sodium dodecyl sulfate. The plate is washed with wash buffer (10 mM Tris-HCl pH 8.0, 0.05% Tween 20, 0.02% sodium azide), then treated 1 hour at room temperature with blocking buffer (10 mM sodium phosphate buffer pH 7.4, 140 mM NaCl, 1% bovine serum albumin, 0.02% sodium azide), and washed again. The plant extract is added in an amount to give 50 g of protein (typically ca. 5 l of extract; the protein is determined by the method of Bradford, M., *Anal. Biochem.* 72: 248 (1976) using a commercially available kit from Bio-Rad), and incubated overnight at 4° C. After washing, 50 l affinity-purified goat anti-Bt antiserum are added at a concentration of 3 g/ml protein in ELISA diluent (10 mM sodium phosphate buffer pH 7.4, 140 mM NaCl, 0.05% Tween 20, 1% bovine serum albumin, 0.02% sodium azide), and this allowed to incubate for 1 hour at 37° C. After washing, 50 l rabbit anti-goat antibody bound to alkaline phosphatase (Sigma Chemicals, St. Louis, Mo., USA) diluted 1:500 in ELISA diluent is added and allowed to incubate for 1 hour at 37° C. After washing, 50 l substrate (0.6 mg/ml p-nitrophenyl phosphate, 0.05 mg/ml $MgCl_2$, 10% diethanolamine, pH 9.8 adjusted with HCl) is added and allowed to incubate for 30 minutes at room temperature. The reaction is terminated by adding 50 l 3 M NaOH. The absorbance is read at 405 nm in a modified ELISA reader (Hewlett Packard, Stanford, Calif., USA).

EXAMPLE 147A

Analysis of Cucumber Chitinase Constructs

A. Transgenic Plant Treatments

Once the transgenic plants are transferred to soil, they are grown 4–5 weeks before treatment. The following solutions are applied to the leaves with sterile paintbrushes:
1. Sterile dH2O
2. 50 mM salicylic acid
3. Methyl benzo-1,2,3-thiadiazole-7-carboxylate. The solution is made by resuspending a wettable powder containing a formulation of the chemical with 25% active ingredient in sterile water at a concentration of 1 mg/ml.
4. Methyl 2,6-dichloroisonicotinate, prepared as above. Alternatively, 30 ul of 10 mM sodium phosphate buffer, pH 7.0, or 30 ul of the same buffer containing tobacco mosaic virus (50–100 pfu/30 ul) is applied to the leaves which have been sprinkled with carborundum. The buffers are distributed over the whole treated leaf by gentle rubbing.

The plants are allowed to continue to grow for seven days. The treated leaves are then harvested, frozen in liquid nitrogen and stored at −80° C. until they are assayed.

B. ELISA Assay

Frozen leaf tissue is ground in a mortar with a pestle in the presence of liquid nitrogen to produce a fine powder. 0.33 g of each tissue sample is added to 1 ml extraction buffer (50 mM Tris-HCl, pH 8.5, 0.2M 2-mercaptoethanol, 2 mM phenyl methyl sulfonyl fluoride, 2 mM benzamidine, 10 mM epsilon-aminocaproic acid, 1 mM leueptine) and the sample homogenized for one minute with an Ultra Turrax Mixer (shaft #S25N-8G, Tekmar Co. Cincinnati, Ohio). The samples are then centrifuged at 48,000×g for fifteen minutes at 4° C. and the supernatant removed from the pelleted material. The extracts are diluted at least 1:50 in ELISA diluent (10 mM sodium phosphate, pH 7.4, 140 mM sodium chloride, 0.05% Tween 20, 0.02% sodium azide, 1% BSA).

A microtiter plate is coated with monoclonal antibody specific to the cucumber chitinase protein at 2 ug/ml in borate-buffered saline (100 mM boric acid, 25 mM sodium borate, 75 mM sodium chloride; pH 8.5) using 50 ul per well. The plate is incubated overnight at 4° C. The plate is washed with ELISA wash buffer (10 mM Tris-HCl, pH 8.0, 0.05% Tween 20, 3 mM sodium azide) and BSA blocking solution (10 mM sodium phosphate, pH 7.4, 140 mM sodium chloride, 0.02% sodium azide, 1% BSA) is added to completely cover each well. Incubation is for at least 30 minutes at room temperature.

The microtiter plate is washed with ELISA wash buffer and 50 ul of extract is added to the appropriate well. 50 ul of each of 10 chitinase protein standards (ranging from 0 ng/ml to 31.64 ng/ml) was also added to the appropriate well and the plate is incubated for two hours at 4° C. The plate is washed with ELISA wash buffer and 50 ul of rabbit polyclonal antibody to the cucumber chitainase protein (diluted 1:15,000 in ELISA diluent) is added to the well and incubated for one hour at 37° C. After washing with ELISA wash buffer, 50 ul of goat anti-rabbit conjugated to alkaline phosphatase (1:500 in ELISA diluent) is added to each well and incubated at 37° C. for one hour. The plate is then washed and 50 ul alkaline phosphatase substrate solution (0.6 mg/ml p-nitrophenyl phosphate in 0.5 mM magnesium chloride and 10% diethanolamine) is added to each well. After a 30 minute incubation at room temperature, 50 ul of 3N sodium hydroxide is added to each well to stop the reaction.

The plate is read at 405 nm and 492 nm on an HP Genenchem ELISA plate reader. The output values are expressed as A(405 nm)-A(492 nm)-0.092 to allow for correction of p-nitrophenyl phosphate as substrate. The chitinase standards for each plate are graphed logarithmically. The amount of chitinase protein in each sample is determined from the standard curve. If the amount of chitinase in any sample is close to the upper limit of the curve, the sample is assayed again at a greater dilution. Final results are expressed in the table below in ug chitinase per gram tissue.

TABLE I

TRANSGENIC CHITINASE PLANTS - ELISA ASSAY RESULTS
(ug chitinase/g tissue)

| | TREATMENTS | | | | | |
|---|---|---|---|---|---|---|
| LINE | Water | Salicyl-ate | MBTH7C | Buffer | TMV | MDCINA |
| 2001/ BamChit | | | | | | |
| Bam-1 | 0.066 | — | 3.000 | — | 33.885 | — |
| Bam-3 | — | — | 0.504 | — | 4.227 | — |
| Bam-4 | — | — | — | — | — | — |
| Bam-8 | — | — | — | — | 2.244 | — |
| Bam-9 | — | 0.522 | 33.885 | — | 28.255 | — |
| Bam-10 | 0.059 | 0.093 | 25.182 | 0.084 | 102.436 | 2.378 |
| Bam-12 | — | — | 1.349 | — | 2.421 | — |
| Bam-14 | — | — | 0.541 | — | 7.818 | — |
| Bam-15 | — | — | 3.366 | — | 7.964 | — |
| Bam-16 | — | 0.690 | 18.849 | — | 17.803 | 0.864 |
| Bam-17 | — | — | 2.997 | — | 6.041 | — |
| Bam-19 | — | 0.760 | 0.998 | — | 28.255 | — |
| Bam-21 | — | — | — | — | 2.260 | — |
| Bam-23 | — | — | 0.782 | — | 2.421 | — |
| Bam-24 | — | — | 0.88 | — | 12.081 | — |
| Bam-25 | — | 0.522 | 18.145 | — | 3.389 | — |
| Bam-26 | — | — | 0.676 | — | 4.676 | — |
| 2001/ SalChit | | | | | | |
| Sal-2 | — | — | 0.117 | — | — | — |
| Sal-3 | — | — | 0.060 | — | 0.106 | 0.047 |
| Sal-4 | — | 0.047 | 0.537 | — | 4.740 | — |
| Sal-5 | — | — | 0.229 | — | 0.288 | — |
| Sal-7 | — | — | 0.377 | — | 0.600 | — |
| Sal-8 | — | — | — | — | 0.117 | — |
| Sal-9 | — | 1.052 | 0.553 | — | 5.478 | — |
| Sal-11 | — | — | — | — | — | — |

TABLE I-continued

TRANSGENIC CHITINASE PLANTS - ELISA ASSAY RESULTS
(ug chitinase/g tissue)

| | TREATMENTS | | | | | |
|---|---|---|---|---|---|---|
| LINE | Water | Salicyl-ate | MBTH7C | Buffer | TMV | MDCINA |
| Sal-12 | — | — | — | — | 0.189 | — |
| Sal-13 | — | — | — | — | 0.047 | — |
| Sal-14 | — | — | — | — | — | — |
| Sal-15 | — | — | 0.038 | — | 1.999 | — |
| 2001/ NcoChit | | | | | | |
| Nco-2 | — | — | — | — | — | — |
| Nco-3 | — | — | — | — | — | — |
| Nco-5 | — | — | — | — | — | — |
| Nco-8 | — | — | — | — | — | — |
| Nco-9 | — | — | — | — | — | — |
| Nco-10 | — | — | 0.047 | — | — | — |
| Nco-11 | — | — | — | — | — | — |
| Nco-15 | — | — | — | — | — | — |
| Nco-16 | 0.555 | 0.555 | 0.784 | 0.566 | 0.784 | 0.286 |
| Nco-17 | — | — | — | — | — | — |

—Indicates that sample has no detectable level of chitinase protein

C. Transformation of the Chimeric Construct

The plasmid pCIB2001/Chit/GUS is transformed into Agrobacterium as previously described in Example 109. Transformed Agrobacterium strains are prepared and transformed into tobacco leaf disks as previously described in Example 112. Transformed plants treatments and harvesting are as described in section A above.

D. Beta-Glucuronidase Enzyme Assay

Frozen leaf tissue is ground in a mortar with a pestle in the presence of liquid nitrogen to produce a fine powder. Leaf extracts are prepared in GUS extraction buffer (50 mM sodium phosphate pH7.0, 0.1% Triton-X 100, 0.1% sarkosyl, 10 mM beta-mercaptoethanol) as described by Jefferson, R. A. et al., *PNAS USA* 83, 8447–8451 (1986).

The reactions are carried out in the wells of microtiter plates by mixing 5–25 ul of extract with 120–100 ul of GUS assay buffer (50 mM sodium phosphate pH 7.0, 0.1% Triton X-100, 10 mM beta-mercaptoethanol) containing 4-methyl umbelliferyl glucuronide (MU) at a final concentration of 2 mM in a total volume of 125 ul. The plate is incubated at 37° C. for 1–5 hours and the reaction is stopped by the addition of 150 ul 3 M sodium carbonate. The concentration of fluorescent indicator released is determined by reading the plate on a Flow Labs Fluoroskan II ELISA plate reader.

The amount of protein in each extract is determined using the BCA Protein Assay (Pierce, Rockford, Ill.) according to the manufacturer's recommendations. The specific activity is determined for each sample and can be expressed in nKat MU/mg protein.

EXAMPLE 147B

Chemical Induction of the Arabidopsis PR-1 Promoter

Leaves of transgenic Arabidopsis lines carrying the PR-1 promoter-LUC gene fusion were treated by spraying with 0.15 g/ml INA (isonicotinic acid) for 48 h. Five days later, sprayed leaves were analyzed for luciferase activity using the Promega Luciferase Assay System (Cat. # E 1500). Transgenic lines showed 144-fold induction over controls. In other assays, luciferase activity was measured by imaging lines for bioluminescence using intensified cameras (VIM) and photon-counting image processors (ARGUS-50 or ARGUS-100) from Hamamatsu Photonic Systems (Bridgewater, N.J.). Leaves were sprayed with INA and subsequently with a 5 mM solution of D-luciferin (Analytical Bioluminescence Laboratories, San Diego, Calif.) 24 h before and then immediately before imaging. Transgenic plants carrying the PR1-LUC fusion had strongly induced bioluminescence when compared to water-treated controls.

L. Analysis of Transgenic Plants Containing Anti-Pathogenic Sequences

In the previous sections, the creation of transgenic plants expressing chimeric disease resistance genes has been described. In this section the development of transgenic seed lines and characterization of those lines with respect to chimeric gene expression is explained. Essentially, this characterization process comprises a preliminary screening of the transgenic plants for expression of the chimeric gene, segregation of the chimeric gene into stable homozygous lines and further characterization of the gene expression.

EXAMPLE 148

Development of Transgenic T3 Seed Lines

Genotype designations for transgenic plants are used herein according to the following convention: the initial plant resulting from a transformation event and having grown from tissue culture is designated a T1 plant. Plants resulting from self pollination of the natural flowers of the T1 plant, are designated T2, having acquired a new genotype during the normal meiotic process. Likewise, seeds borne from self-pollination of the natural flowers of T2 plants (i.e. grown from T2 seed) are designated T3, etc. Transgenic plants (T1) are grown to maturity. Flowers are allowed to self-pollinate and seed pods are collected after normal desiccation. Seeds from each individual plant are collected and stored separately. Each seed lot is tested by genetic segregation analysis to determine the number of Mendelian loci bearing the kanamycin resistance trait. T2 seeds are surface-sterilized by multiple washing in 2% hypochlorite containing 0.02% (v/v) Tween-20, followed by rinses in sterile water. Approximately 150 of the seeds are placed on filter paper saturated with 0.2× MS salts (Murashige and Skoog, *Physiol. Plant*. 15: 473–497 (1962)) containing 150 g/ml kanamycin. Following germination and expansion of the cotyledons to approximately, 5 mm, the ratio of normal-green (kan-r) versus bleached (kan-s) cotyledons is determined. Only those T2 seed lots exhibiting an approximately 3:1 (kan-r:kan-s) ratio are kept for further analysis; this segregation ratio is indicative of a single Mendelian locus bearing the kanamycin marker gene.

Four to ten plants are grown to maturity from each T2 seed lot (using the same conditions described above), and are allowed to self-pollinate. T3 seed collection, seed sterilization, and seed germination are as described above for the T2 seed. T3 seed lots in which 100% of the tested seeds (n=150) exhibited the kan-r phenotype are assumed to be homozygous for the trait (i.e. resulting from a homozygous T2 parent plant) and are kept for phenotypic analysis.

EXAMPLE 149

Expressing Sense or Anti-sense PR-1

The expression of PR-1a in either sense or anti-sense orientation is assayed in transgenic plant material using either an ELISA assay for PR-1a protein or a primer extension assay for PR-1 mRNA as described.

A. ELISA for PR1 Protein

Assays are performed in Immunolon II microtiter plates (Dynatech) which had been rinsed with ethanol and allowed to air dry. Tobacco leaf material is ground with a plastic tissue homogenizer (Kontes) in a buffer consisting of 50 mM Tris-HCl, pH 8.5, 200 mM 2-mercaptoethanol, 2 mM PMSF (Sigma), 2 mM BAM (Sigma), 10 mM ACA (Sigma), and 0.048% (w/v) Leupeptine (hemisulfate salt) (Sigma); three ml of extraction buffer are used per gram of leaf tissue. A sufficient sample of healthy-leaf (untreated tobacco) extract is made so that a 1/10 dilution of this extract could serve as a diluent for all the other samples. Extracts are centrifuged in a microcentrifuge in 1.5 ml polypropylene tubes at 12,000×g (max) for 15 minutes to remove debris. Wells are coated with a solution of a monoclonal antibody specific for PR1 protein (tobacco). Following washing the wells are blocked for 30–120 minutes with a solution of bovine serum albumin (1% w/v) and then washed again.

The unknown samples and the standard curve samples, diluted to appropriate concentrations in a 1/10 solution of healthy-plant extract, are added to the wells and incubated for 1 hour at 37° C. (A standard curve is performed using highly purified PR-1a protein). Following washing, a rabbit polyclonal antiserum (5 g/ml specific for PR1 is added to the wells and incubated for an additional hour at 37° C., and then the wells are washed again. A goat, anti-rabbit IgG antibody (133 ng/ml), to which is conjugated the indicator enzyme alkaline phosphatase (Promega), is added and the indicator reaction is developed according to the manufacturer's recommendations. The reaction is stopped after 30 minutes by the addition of NaOH and the absorbence is read at 405 nm.

B. Primer Extension Assay for PR1

RNA is extracted from tobacco leaf tissue by a method previously described (Ecler and Davis, *Proc. Natl. Acad. Sci, USA* 84: 5203–5206 (1987)). Primer extension assays are performed as described in Example 6 using a synthetic oligonucleotide of the sequence 5'GTAGGTGCATTGGT-TGAC3'. The complement of this sequence occurs in both PR-1a and PR-1b mRNA, resulting in priming of both types of mRNA in the assay.

The primer extension products of the chimeric gene product are distinguishable from the products of the endogenous PR-1 genes using polyacrylamide gel electrophoresis. The chimeric PR-1a transcript generated from the tobacco RuBISCO small subunit promoter of pCGN1509 derivatives results in a primer extension product which is 90 bp longer than that of the endogenous PR-1a gene. The chimeric PR-1b transcript generated from the tobacco RuBISCO small subunit promoter of pCGN1509 derivatives produces a primer extension product 95 bp longer than that of the endogenous PR-1b gene. The chimeric PR-1a transcript generated from the double 35S promoter of pCGN1761 derivatives yields a product 4 bp longer than that of the endogenous PR-1a gene. The chimeric PR-1b transcript generated from the double 35S promoter of pCGN1761 derivatives yields a product 10 bp longer than that of the endogenous PR1b gene.

EXAMPLE 150

Analysis of Seed Lines Derived from Transformation of Tobacco with PCGN1755 and PCGN1756 Series Vectors (RuBISCO SSU/PR-1a or PR-1blocs 3')

A leaf tissue sample is taken from T1 plants transformed with either: pCGN1754 or pCGN1760 (as empty cassette controls); one of the pCGN1755 binary vector series (SSU promoter/PR-1a in all orientations); or one of the pCGN1756 binary vector series (SSU promoter/PR-1b). The expression of PR-1 protein in this tissue is determined by ELISA for PR-1 protein and in some cases the RNA level is monitored by primer extension assay.

It is predicted that tissue transformed with the control plasmids, pCGN1754 and pCGN1760 (empty cassette) will result in a certain basal level of PR-1 protein which would be due to endogenous synthesis. Tissue transformed with the plasmids pCGN1755A, pCGN1755C, pCGN1756A or pCGN1756C (PR-1a or PR-1b in a sense orientation) should produce plants expressing PR-1 at a level significantly higher than the basal level. Tissue transformed with pCGN1755B, pCGN1755D, pCGN1756B or pCGN1756D (PR-1a or PR-1b in an anti-sense orientation) should produce significantly lower levels of PR-1 protein relative to the control. When the transformed T1 tissue is screened for PR-1 protein by ELISA those plants which conform to the expectation are promoted to T2 analysis. The intent in this screening is to eliminate transformants that do not cotransform the chimeric PR-1 gene with the antibiotic resistance gene. Many plants from each transformation do conform to the expectation and the protein result is confirmed by primer extension analysis of the RNA to make sure that the higher level of expression in sense plants is due to chimeric gene expression.

The assays are repeated at the T2 generation and at this point several lines are chosen for further characterization. The lines are chosen for based on: 1) a 3:1 segregation of the antibiotic resistance, which indicates a Mendelian inherited (single insertion event) trait; 2) high levels of expression of PR-1 for sense construct, low levels for anti-sense constructs and intermediate levels for control plants. The lines chosen for further study and the data for PR-1 expression and segregation are shown below.

| Seed Line | T2 Segregation Analysis (% Kan-R) | T2 PR-1 expression ELISA (ng/ml) |
| --- | --- | --- |
| 1754-12 | 77% | 300 |
| 1755A-4 | 75% | 175 (Av = 515 in T3) |
| 1755B-2 | 83% | ≦2 |
| 1755B-3 | 76% | ≦2 |
| 1760-1 | 93% | 240 |

The seed line nomenclature is designed such that the transforming plasmid is designated first and the individual transformant is designated second. For example, 1755A-4 represents a transgenic plant resulting from transformation with the plasmid pCGN1755A and this is the fourth individual transformant selected. In many of these experiments the control level of PR-1 expression seems artificially high (ie 1754–12 above at a level of 300 ng/ml is about 30 times higher than normal). This level decreases in the control, but not in the experimental, plants with successive generations.

The T2 seed lines above are mixed genotypes in respect to the chimeric PR-1 gene. For instance, some of the plants from a seed line are homozygous and some are heterozygous for the trait. In order to isolate homozygous seed lines, between four and ten plants of each line are allowed to self pollinate and set seed. This seed is collected and segregation is determined as explained above. These segregation data for several lines is shown below.

| T3 Seed Line | Segregation | (% Kan-R) |
|---|---|---|
| 1754-12-10 | 100 | |
| 1755A-4-2 | 100 | |
| 1755B-2-1 | 100 | |
| 1755B-3-1 | 100 | |
| 1760-1 | | ND |

These homozygous seed lines are then analyzed for generalized disease resistance as described below. The general conclusion from the analysis of this series of plants is that the sense constructs (both PR-1a and PR-1b) produce 6 to 150 times the amount of PR-1 in healthy tobacco tissue and anti-sense constructs usually produce much less PR-1 than in healthy tobacco.

EXAMPLE 151

Analysis of Seed Lines Derived from Transformation of Tobacco with pCGN1764, pCGN1765, PCGN1774 and PCGN1775 Series of Vectors (Double CAMV 35S Promoter/PR-1a)

The development of seed lines in this example include the transformations of tobacco with the double CAMV 35S promoter linked to PR-1a (pCGN1764 and pCGN1774 series) in sense and anti-sense orientation and the double CAMV 35S promoter linked to PR-1b (pCGN1765 and pCGN1775 series) in sense and anti-sense orientation. The difference between the pCGN1764/pCGN1765 and pCGN1774/pCGN1775 constructs is that the binary vector is different (see relevant examples above). Empty cassette controls for pCGN1764 and pCGN1765 are pCGN1766 and pCGN1767. The empty cassette control for pCGN1774 and pCGN1775 is pCGN1789.

PR1 protein expression in the "sense" T1 plants (all events) range from undetectable levels up to approximately 13,000 ng/ml extract; this maximum level is within two fold of the levels seen in a highly infected primary leaf bearing many lesions. The levels seen in secondary tissue, even under optimal conditions, is several fold lower than this. The average expression level for all the "sense" T1 plants is approximately, 4,200 ng/ml, which is more than 20-fold higher than the average for the small subunit-PR1 transgenic plants.

No significant differences are seen in the expression levels of the chimeric gene between the pCGN783 binary vector (pCGN1764 and pCGN1765 series). Both sets of plants have a wide range of expression levels, as is common in transgenic experiments of this type. The highest expression in both types is similar, and the number of plants expressing at a low level is about the same. The average for the pCGN783 binary plants is higher than the average for the small subunit-PR1 transgenic plants.

No significant differences are seen in the expression levels of the chimeric gene between the pCGN783 binary vector (pCGN1764 and pCGN17065 series) and the pCGN1540 binary vector (pCGN1774 and pCGN1775 series). The average for the pCGN783 binary plants is 3,955 ng/ml, and for the pCGN1540 binary plants is 4,415 ng/ml, but considering the variation, this difference is not significant. Similarly, the orientation of the genes in the binary has no major effect on expression. The "C" orientation (head to tail) gives three of the four highest expressing plants, but it also gives more low level expressing plants. The "A" (head to head) orientation plants tend to group more in the moderate expression range, but again the variation and the small sample size prevent the attachment of any statistical significance to these differences. Primer extension analysis of a limited number of samples shows that the chimeric gene mRNA is the dominant or the only PR1 mRNA present.

The conclusion from the T1 data is that the level of PR-1 protein in plants transformed with double CAMV 35S promoter/PR-1a or PR-1b sense constructs is several hundred fold higher than the level of control plants. The level of expression of PR-1 in plants transformed with the anti-sense construct is very low. The binary vector used for transformation (pCGN783 or pCGN1540) does not significantly effect the level of PR-1 expression in the transgenic plants. Likewise, the orientation of the expression cassette within the vector has no significant effect on the level of PR-1 expression. Therefore, one line is selected that produces high levels of PR-1a due to sense expression and one is selected that produces low levels of PR-1a due to anti-sense expression for further development. A control line with an empty cassette is included. The results of PR-1 expression and antibiotic segregation for the selected lines is shown below.

| T2 Seed Line | Segregation Analysis | (% Kan-R) | T2 PR-1 expression ELISA (ng/ml) |
|---|---|---|---|
| 1774A-10 | 409/553 | (74.0) | 9000 |
| 1774B-3 | 109/142 | (76.8) | ≦2 |
| 1789-10 | 371/459 | (80.8) | 5.6 |

Homozygous T3 seed lines are generated from each of the selected lines as described in the previous example. The results of segregation analysis are shown below.

| T3 Seed Line | Segregation (% Kan-R) |
|---|---|
| 1774A-10-1 | 100 |
| 1774B-3-2 | 100 |
| 1789-10-3 | 100 |

These homozygous seed lines are evaluated for PR-1 expression and disease resistance as described below.

EXAMPLE 152

Analysis of Seed Lines Derived from Transformation of Tobacco with the PCGN1779 Plasmid Series (Double CAMV 35S Promoter/ Cucumber Chitinase/Lysozyme)

A leaf tissue sample is taken from T1 plants transformed with either of the binary vectors pCGN1779C or pCGN1779D. The cucumber chitinase/lysozyme protein content is determined using an ELISA assay essentially as described above except that the monoclonal and polyclonal antibodies are directed against the cucumber chitinase/lysozyme protein.

Eight of thirteen T1 "sense" plants produce very high amounts (>10,000 ng/ml extract) of the cucumber chitinase foreign gene product Again a wide range, from undetectable up to 31,500 ng/ml extract, is observed, with an average of 12,500 ng/ml extract. The conclusion from the T1 data is that the transformed T1 plants produce several thousand times more of the transgenic protein than is present in control plants. T3 seed lines are derived from the high expressing T1 plants as described in Example 148 and these T3 seed lines maintain their high levels of chitinase/lysozyme expression.

EXAMPLE 153

Analysis of Seed Lines Derived from Transformation of Tobacco with the pCGN1782 Plasmid Series (Double CAMV 35S Promoter/ Tobacco Basic Chitinase)

A leaf tissue sample is taken from T1 plants transformed with either of the binary vectors pCGN1782C or pCGN1782D. The tobacco basic chitinase protein content is estimated by an immunoblot technique CTowbin, H., et al., *Proc. Natl. Acad. Sci. USA* 76: 4350–4354 (1979) as modified by Johnson, D., et al., *Gene Anal. Tech.* 1: 3–8 (1984)), following SDS-polyacrylamide gel electrophoresis (Laemnrli, E., Nature, 227: 680–685 (1970)). The antibodies used are raised against the tobacco basic chitinase protein by standard methods and are specific for the tobacco basic chitinase protein. T1 plants with the pCGN1782C plasmid (containing the sense expression cassette) showing high levels of expression relative to control and anti-sense plants, are advanced to T3 seed lines as described in Example 148. Homozygous T2 plants which yield these T3 seed continue to express the protein at high levels. T1 plants transformed by the pCGN1782D plasmid (containing the anti-sense expression cassette) which give low levels of expression are also advanced to T3 seed as described in Example 148.

EXAMPLE 154

Analysis of Seed Lines Derived from Transformation of Tobacco with the PCGNI 781 Plasmid Series (Double CAMV 35S Promoter/ Tobacco Basic Glucanase)

A leaf tissue sample is taken from T1 plants transformed with either of the binary vectors pCGN1781C or pCGN1781D. The tobacco basic glucanase protein content is estimated by an immunoblot technique as described in Example 153 above. The antibodies used are raised against the tobacco basic glucanase protein by standard methods and are specific for the tobacco basic glucanase protein. T1 plants with the pCGN1781C plasmid (containing the sense expression cassette), showing high levels of expression relative to control and anti-sense plants, are advanced to T3 seed lines as described in Example 148. Homozygous T2 plants which yield these T3 seed continue to express the protein at high levels. T1 plants transformed by the pCGN1781D plasmid (containing the anti-sense expression cassette) which give low levels of expression are also advanced to T3 seed as described in Example 148.

EXAMPLE 155

Analysis of Seed Lines Derived from Transformation of Tobacco with the pCGN1783 Plasmid Series (Double CAMV 35S Promoter/ Tobacco PR-R major)

A leaf tissue sample is taken from T1 plants transformed with either of the binary vectors pCGN1783C or pCGN1783D. The tobacco PR-R protein content is estimated by an immunoblot technique as described in Example 153 above. The antibodies used are raised against the tobacco PR-R protein by standard methods and are specific for the tobacco PR-R protein. T1 plants with the pCGN1783C plasmid (containing the sense expression cassette) showing high levels of expression relative to control and anti-sense plants, are advanced to T3 seed lines as described in Example 148. Homozygous T2 plants which yield these T3 seed continue to express the protein at high levels. T1 plants transformed by the pCGN1783D plasmid (containing the anti-sense expression cassette) which give low levels of expression are also advanced to T3 seed as described in Example 148.

EXAMPLE 156

Analysis of Seed Lines Derived from Transformation of Tobacco with the pCGN1790 Plasmid Series (Double CAMV 35S Promoter/SAR 82)

A leaf tissue sample is taken from T1 plants transformed with either of the binary vectors pCGN1790C or pCGN1790D. The SAR8.2 protein content as estimated by an immunoblot technique as described in Example 153 above. The antibodies used are raised against the SAR 8.2 protein by standard methods and are specific for the SAR 8.2 protein. T1 plants with the pCGN1790C plasmid (containing the sense expression cassette) showing high levels of expression relative to control and anti-sense plants, are advanced to T3 seed lines as described in Example 148. Homozygous T2 plants which yield these T3 seed continue to express the protein at high levels. T1 plants transformed by the pCGN1790D plasmid (containing the anti-sense expression cassette) which give low levels of expression are also advanced to T3 seed described in Example 148.

EXAMPLE 157

Analysis of Seed Lines Derived from Transformation of Tobacco with the p6CGN1791 Plasmid Series (Double CAMV 35S Promoter/PR-Q)

A leaf tissue sample is taken from T1 plants transformed with either of the binary vectors pCGN1791C or pCGN1791D. The PR-Q protein content is estimated by an immunoblot technique as described in Example 153 above. The antibodies used are raised against the PR-Q protein by standard methods and are specific for the PR-Q protein. T1 plants with the pCGN1791C plasmid (containing the sense expression cassette) showing high levels of expression relative to control and anti-sense plants, are advanced to T3 seed lines as described in Example 148. Homozygous T2 plants which yield these T3 seed continue to express the protein at high levels. T1 plants transformed by the pCGN1791D plasmid (containing the anti-sense expression cassette) which give low levels of expression are also advanced to T3 seed as described in Example 148.

EXAMPLE 158

Analysis of Seed Lines Derived from Transformed of Tobacco with the pCGN1792 Plasmid Series (Double CAMV 35S Promoter/PR-O')

A leaf tissue sample is taken from T1 plants transformed with either of the binary vectors pCGN1792C or pCGN1792D. The PRO' protein content is estimated by an immunoblot technique as described in Example 153 above. The antibodies used are raised against the PR-O' protein by standard methods and are specific for the PR-O' protein. T1 plants with the pCGN1792C plasmid (containing the sense expression cassette) showing high levels of expression relative to control and anti-sense plants, are advanced to T3 seed lines as described in Example 148. Homozygous T2 plants which yield these T3 seed continue to express the protein at high levels. T1 plants transformed by the pCGN1792D plasmid (containing the anti-sense expression cassette) which give low levels of expression are also advanced to T3 seed as described in Example 148.

EXAMPLE 159

Analysis of Seed Lines Derived from Transformation of Tobacco with the pCGN1793 Plasmid Series (Double CAMV 35S Promoter/PR-2)

A leaf tissue sample is taken from T1 plants transformed with either of the binary vectors pCGN1793C or pCGN1793D. The PR-2 protein content is estimated by an immunoblot technique as described in Example 153 above. The antibodies used are raised against the PR-2 protein by standard methods and are specific for the PR-2 protein. T1 plants with the pCGN1793C plasmid (containing the sense expression cassette) showing high levels of expression relative to control and anti-sense plants, are advanced to T3 seed lines as described in Example 148. Homozygous T2 plants which yield these T3 seed continue to express the protein at high levels. T1 plants transformed by the pCGN1793D plasmid (containing the anti-sense expression cassette) which give low levels of expression are also advanced to T3 seed as described in Example 148.

11. Evaluation of Phenotype

The development of stable, transgenic seed lines of tobacco which express chimeric pathogenesis-related protein genes in sense and anti-sense orientation is explained in Section 1 to 8. Once the seed lines are developed they are evaluated quantitatively for resistance to various diseases.

EXAMPLE 160

Evaluation of Transgenic Tobacco Expressing PR-1 in an Anti-Sense Orientation for Disease Resistance The seed lines 1755A42 and 1755B-2–1 are analyzed for resistance to TMV. The results of these experiments are that there is no significant difference in lesion size or lesion number due to either elevated or depressed levels of PR-1 protein.

The seed lines 1755A4–2 and 1755B-2–1 are analyzed for resistance to the fungal pathogen *Peronospora tabacina* (blue mold, or downy mildew) by spraying a spore suspension on the leaves of the plants and incubating under standard conditions for seven days. The plants are then scored for resistance to bluemold based on the percentage of leaf surface area infected by the pathogen. Six plants of the 1755A-4–2 line which are expressing an average of 1454 ng/ml PR-1 protein are showing 98 +/– 3% infected surface area. Six plants of the 1755B-2–1 line, which are expressing an average of 370 ng/ml PR-1 protein are showing 45% +/– 26% infected surface area. Six plants derived from untransformed Xanthi.nc tobacco which are producing 559 ng/ml PR-1 protein are showing 99% +/– 1% infected surface area. This result indicates that the anti-sense expression of PR-1a results in a significant and valuable resistance to downy mildew in transgenic plants.

EXAMPLE 161

Evaluation of Transgenic Tobacco Expressing PR-1 in a Sense Orientation for Disease Resistance The seed lines 1774A-10-1 and 1774B-3-2 are analyzed for resistance to TMV. The results of these experiments are that there is no significant difference in lesion size or lesion number due to either elevated or depressed levels of PR-1 protein.

The seed lines 1774A10-1 and 1774B-3-2 are analyzed for resistance to the fungal pathogen *Peronospora tabacina* (blue mold, or downy mildew) by spraying a spore suspension on the leaves of the plants and incubating under standard conditions for seven days. The plants are then scored for resistance to bluemold based on the percentage of leaf surface area infected by the pathogen. Six plants of the 1774A-10-1 line are showing 6.3% +/– 11% infected surface area. Six plants of the 1774B-3-2 line are showing 46% +/– 10% infected surface area. Six plants derived from untransformed Xanthi.nc tobacco are showing 55% +/– 5% infected surface area. This result indicates that the sense expression of PR-1a results in a significant and valuable resistance to downy mildew in transgenic plants.

EXAMPLE 162

Generation of F1 Plants Containing Two of the Above Chimeric Genes by Genetic Crossing Using standard techniques, T3 homozygous plants expressing different cDNAs are cross-pollinated in all possible combinations. The total number of pariwise gene combination is calculated from the expression $$(n^2-n)/2$$

where n=number of parental T3 lines. For instance, for the case of six separate T3 parental lines, each expressing a different cDNA, the number of crosses required to yield all possible combinations of two expressed cDNAs is 15. In addition, all crosses are performed reciprocally, i.e. each T3 parental line is used as both male (pollen) parent and female (ovule) parent for each cross.

EXAMPLE 163

Evaluation of Transgenic Tobacco Expressing Basic Chitinase in a Sense and Anti-Sense Orientation for Disease Resistance The seed lines 1782C (sense orientation) and 1782D (anti-sense orientation) are analyzed for resistance to the bacterial pathogen *Pseudomonas tabaci*. Suspensions of bacteria ($10^6-3\times10^6$/ml) are injected into the intercellular space of the leaves. The plants are incubated under 100% relative humidity at 20° C. for three days and then further incubated at 40% relative humidity. The symptoms caused by the bacteria are evaluated 3,4,5 and 6 days after the inoculation as follows:

0=no symptom
1=1% to 25% of the injected area shows symptoms (yellowing or necrosis)
2=26% to 50% of the injected area shows symptoms (yellowing or necrosis)
3=51% to 75% of the injected area shows symptoms (yellowing or necrosis)
4=76% to 99% of the injected area shows symptoms (yellowing or necrosis)

5=100% of the injected area shows symptoms (yellowing or necrosis)

1 test, 3×10⁶b/ml

| | disease severity | | | |
|---|---|---|---|---|
| Plant | 3 day | 4 day | 5 day | 6 day |
| non-transformed | 3.5 ± 1.2 | 3.6 ± 1.2 | 4.0 ± 1.3 | 4.5 ± 0.9 |
| empty cassette | 1.5 ± 1.4 | 2.3 ± 1.5 | 2.4 ± 1.4 | 2.5 ± 1.4 |
| chitinase sense | 1.0 ± 0.8 | 1.6 ± 1.1 | 1.4 ± 0.5 | 1.4 ± 1.0 |
| chitinase antisense | 3.9 ± 0.8 | 4.4 ± 0.7 | 4.5 ± 0.9 | 4.8 ± 0.4 |

As there is a high difference between the symptom severity on the chitinase sense and antisense transformed plants as well as between the non-transformed plants and empty cassette, the test is repeated.

2nd test, 3×10⁶b/ml

| | disease severity | | |
|---|---|---|---|
| Plant | 3 day | 4 day | 5 day |
| non-transformed | 3.8 ± 0.9 | 4.0 ± 1.0 | 4.1 ± 1.0 |
| empty cassette | 3.8 ± 0.7 | 4.2 ± 0.7 | 4.2 ± 0.8 |
| chitinase sense | 2.3 ± 1.0 | 3.2 ± 1.1 | 2.4 ± 1.3 |
| chitinase antisense | 4.8 ± 0.4 | 5.0 ± 0.0 | 5.0 ± 0.0 |

2nd, 10⁶b/ml

| | disease severity | | |
|---|---|---|---|
| Plant | 3 day | 4 day | 5 day |
| non-transformed | 1.7 ± 0.8 | 1.5 ± 0.8 | 1.5 ± 0.8 |
| empty cassette | 2.4 ± 1.0 | 2.2 ± 1.0 | 1.8 ± 1.1 |
| chitinase sense | 1.4 ± 0.5 | 1.4 ± 0.5 | 0.9 ± 0.2 |
| chitinase antisense | 3.8 ± 0.4 | 3.8 ± 0.4 | 3.4 ± 1.0 |

In this second test, the enhanced resistance of the chitinase-sense plants and the enhanced susceptibility of the chitinase antisense plants is clear.

EXAMPLE 164

Evaluation of Transgenic Tobacco Expressing Cucumber Chidnase or Tabacco Basic Chitinase for Disease Resistance The seed line 1779C (sense orientation) from Example 152 (tobacco transformed with pCGN1779 plasmid (Double CAMV 35S promoter/cucumber chitinase) is analyzed for resistance to damping off, a disease caused by the soil fungal pathogen *Rhizoctonia solani*. The following plants are grown:

a) control plants grown in uninfected soil
b) transgenic plants expressing the PR-Q
c) control plants transformed with an empty cassette
d) transgenic plants expressing the tobacco basic chitinase gene.
e) transgenic plants expressing cucumber chitinase.

The plants transformed with tobacco basic chitinase and cucumber chitinase exhibit enhanced resistance to damping off.

EXAMPLE 165

Evaluation of Transgenic Tobacco Expressing SAR8.2 in a Sense Orientation for Disease Resistance The seed lines 1790C (sense orientation) (Example 156) is analyzed for resistance to black shank, a disease caused by the fungal pathogen Phytopthora.

Four control plants are transformed with an empty expression cassette and are severely affected by black shank disease.

Four plants are transformed with the chimeric double 35S-SAR8.2 construct and exhibit appreciable enhanced resistance to black shank disease.

EXAMPLE 166

Analysis of Seed Lines Derived from Transformation of Tobacco with the Basic and Acidic Class III Tobacco Chitinase Genes Binary constructions carrying the tobacco basic and acidic class III chitinases were transformed into *Nicotiana tabacum* cv Xanthi-nc. Leaf tissue samples were taken from T1 plants and assayed for expression of either transgene protein (by Western analysis) or transgene RNA (by Northern analysis). T1 plants found to express the transgene at high levels were advanced to T3 seed lines as described above.

A. Analysis of Transgenic Plants Expressing Class III Chitinase for Pest Resistance Transgenic plant lines expressing one or more class III chitinase genes are assessed for resistance to numerous pests. Approximately six plants of each line are tested. Pests at the appropriate stage of their growth cycle (such as larvae) are introduced at the appropriate stage of plant development Plants are later assayed for % of leaf or tissue area eaten, % of introduced larvae surviving, and the weight of surviving larvae.

B. Analysis of Transgenic Tobacco Plants Expressing Class III Chitinase for Pest Resistance Transgenic tobacco plants expressing class III chitinase are assessed for resistance to numerous pests. Those tested include *Spodoptera exigua* (beet armyworm), the green peach tobacco aphid, *Manduca sexta*, and various nematodes, weevils, mites, and other pests.

C. Analysis of Transgenic Plants Expressing Basic Class III Chitinase for Resistance to *Heliothis virescens*

Transgenic tobacco lines expressing the tobacco basic class III chitinase gene were assessed for resistance to the insect *Heliothis virescens*. Eight plants of each line were tested. 50 mm leaf discs were cut from the youngest leaves of transgenic plants approximately six weeks after germination and 3 larvae (2nd stage) were allowed to feed on each disc for 3–7 days. After 3–7 days the leaf discs were assessed for area eaten, % of larval survivors and weight (in mg) of larval survivors. Results of three separate experiments are shown in the tables provided below.

The results show elevated resistance to Heliothis in basic class III chitinase overexpressing plants when compared to non-transformed control lines. *Heliothis virescens* (the tobacco budworm) causes considerable damage in tobacco crops and is particularly recalcitrant to control using pesticides as the larvae burrow deep within the plant. Furthermore, other Heliothis species cause similar damage to cotton and other crops.

| LARVAE Line | (1) % LEAF EATEN | (1) % SURV IVORS | (1) WT (mg) LARVAE | (2) % LEAF EATEN | (2) % SURV IVORS | (2) WT(mg) | (3) % LEAF EATEN | (3) % SURV IVORS | (3) WT (mg) LARVAE |
|---|---|---|---|---|---|---|---|---|---|
| Control | 72 | 100 | 23 | 77 | 100 | 26 | 65 | 100 | 53 |
| 3505 C-15-5 | 45 | 92 | 14 | 65 | 96 | 19 | | | |
| 3505 C-5-3 | 55 | 96 | 17 | 60 | 92 | 23 | | | |
| 3505 C-4-2 | 57 | 92 | 19 | 60 | 100 | 20 | | | |
| 3505 C-12-8 | — | — | — | 44 | 87 | 15 | 59 | 100 | 34 |

A summary of the two experiments detailed above is given below:

| | | | | | |
|---|---|---|---|---|---|
| (1) Line: | Control | 3505 C-15-5 | 3505 C-5-3505 | C-4-2 | |
| Resistance Index | 0 | 4 | 2.5 | 2 | |
| (2) Line: | Control | 3505 C-15-5 | 3505 C-5-3505 | C-4-2 | 3505 C-12-8 |
| Resistance Index | 0 | 2 | 3 | 3 | 4 |
| (3) Line: | Control | 3505 C-12-8 | | | |
| Resistance Index | 0 | 3 | | | |

Resistance Index:

S=significantly more susceptible than control plants (i.e. wild-type)

(S)=more susceptible than control plants, but not significantly in all evaluations 0=like wild type plants 1=some signs of resistance but not significantly different to controls 2=identified resistance, significant only in some evaluations 3=resistance with small significant differences in all evaluations 4=high resistance, but symptoms or damage can still be observed 5=total resistance. No symptoms or damage.

EXAMPLE 167

Alternative Methods for Introducing and Expressing more than One Ant-Pathogenic Sequence in Plant Tissue In addition to the possibility of expressing more than one transgene in transgenic lines by the sexual crossing of lines which are transgenic for one gene only (as described above), the skilled artisan will recognize that an equivalent way of generating lines transgenic for more than one gene is by the use of transformation plasmids which carry more than one gene. For example, the expression of two cDNAs in a transgenic line can be achieved by the transformation of the host plant with a vector carrying each cDNA under the independent regulation of two promoters i.e. the vector carries two expression cassettes in addition to sequences needed for antibiotic selection in vitro. Each expression cassette can also carry any signal sequence, vacuolar targeting sequence and transcriptional terminator so desired. Vectors carrying multiple expression cassettes can be constructed for use with Agrobacterium transformation or direct gene transfer transformation systems.

A further method for the expression of more than one transgene in a transgenic plant line is to firstly transform with a single gene (with appropriate regulatory signals) carried on a transformation vector and subsequently transform a line selected from this transformation with a further gene (with appropriate regulatory signals) carried on a different plasmid which utilizes a different antibiotic selection system. This method is obvious to those of skill in the art.

EXAMPLE 168

Synergistic Effect of Combined Anti-Pathogenic Sequences

Overexpression of two or more PR proteins in a transgenic plant gives rise to a synergistic anti-pathogen effect. The table below shows data from an experiment in which control and transgenic tobacco lines were inoculated with the pathogen *Peronospora tabacina*. 5 and 8 days after inoculation, percentage leaf area infected was assessed The left side of the table shows raw data from numerous lines of each phenotype, whereas the right side shows mean data for each phenotype. In addition to the mean values for percentage leaf area infected, the relative area compared as a percentage of the control (=100%) is presented. This enables a calculation of the expected value in the line expressing both PR-1a and SAR8.2 assuming that the individual components are additive in action. The observed values of 40.8 and 30.4% are well below the expected values of 63.4 and 62.4% for 5 and 8 days post-inoculation and therefore the disease resistance effects of PR-1a and SAR8.2 are synergistic in transgenic plants.

TABLE A

| | DAYS AFTER INOCULATION 5 | DAYS AFTER INOCULATION 8 | | MEAN DATA DAYS AFTER INOCULATION 5 | MEAN DATA DAYS AFTER INOCULATION 8 |
|---|---|---|---|---|---|
| Control (L6) | 36.1 | 42.2 | CONTROL | 40.2 | 49.4 |
| Control (L18) | 42.8 | 51.1 | | (100) | (100) |
| Control (L22) | 41.7 | 55.0 | | | |
| PR-1a (12) | 35.0 | 42.8 | PR-1a | 30.4 | 34.3 |
| PR-1a (L7) | 25.0 | 25.0 | | (75.6) | (69.4) |
| PR-1a (L13) | 31.1 | 35.0 | | | |
| SAR8.2 (L1) | 36.7 | 49.4 | SAR8.2 | 33.7 | 44.7 |
| SAR8.2 (L8) | 36.1 | 45.0 | | (83.8) | (89.9) |

TABLE A-continued

| | DAYS AFTER INOCULATION | | MEAN DATA DAYS AFTER INOCULATION | |
|---|---|---|---|---|
| | 5 | 8 | 5 | 8 |
| SAR8.2 (L11) | 26.7 | 45.0 | | |
| SAR8.2 (L21) | 35.6 | 46.1 | | |
| SAR8.2 (L25) | 33.3 | 37.8 | | |
| PR-1a/SAR8.2 (L17) | 16.1 | 15.0 | PR-1a/SAR8.2 | 16.1 (40.8) | 15.0 (30.4) |
| Expected Additive Values: | | | 63.4 | 62.4 |

EXAMPLE 168A

Expression of SAR/CHX-independent Genes in Transgenic Plants

The cDNAs described in examples 40A and 40B can be expressed in transgenic plants using techniques well known in the art. As components of the signal transduction pathway involved in SAR, the CHX-independent genes are useful for the manipulation of the SAR response. For example, the constitutive expression of key components in the SAR transduction pathway in transgenic plants will likely lead to the generation of plants with enhanced disease resistance characteristics and this will likely be achieved by the activation of components in the pathway downstream to the component being expressed transgenically and hence to the activation of anti-pathogenic end products. By way of illustration this may be achieved from the expression of the appropriate genes behind the constitutive 35S promoter. cDNAs may be transferred to the vector pCGN1761 or pCGN1761/ENX which carry the double 35S CaMV promoter and the tml transcriptional terminator on a pUC-derived plasmid. Colonies carrying the cDNA in sense are recovered and the cDNA carrying expression cassette is subsequently excised and cloned into pCIB200 for use in plant transformations using Agrobacterium. For direct gene transfer, the cDNA-carrying expression cassette is transferred to the vector pCIB3064. Transformation to transgenic plants is undertaken using techniques well known in the art. For transformation of dicotyledonous species using binary Agrobacterium vectors such as pCIB200 see Alexander et al., *Proc. Natl. Acad. Sci.* 90: 7327–7331 (1993), and for transformation of monocotyledonous species using direct gene transfer vectors such as pCIB3064 see Koziel et al., *Biotechnology* 11: 194–200 (1993). Transgenic plants are screened for high-level expression of the appropriate cDNA by Northern or Western analysis. Plants which express high levels of the gene product are found to have enhanced resistance to plant pathogens.

Other promoters are suitable for the expression of these cDNAs in transgenic plants. These include (but are not restricted to) constitutive promoters (such as those from the ubiquitin and actin genes) and cell and tissue-specific promoters.

For genes involved in the signal transduction of SAR which may cause negative regulation of the SAR pathway, increased disease resistance can be achieved from the constitutive expression of cDNA in antisense to the gene coding sequence. The cloning and transfer of antisense sequences is undertaken in the same way as described above, except that the orientation of the cDNA is inverted to effect expression of antisense transcripts.

M. Enhanced Chemical Regulation via Inactivation of Endogenous Regulation

EXAMPLE 169

Cloning of a DNA Fragment Encoding the *Pseudomonas putida* nahG Gene into the Plant Expression Vector pCIB200

Genes encoding enzymes involved in the metabolic pathway which converts naphthalene to pyruvate and acetaldehyde in the bacterium *Pseudomonas putida* PpG7 are organized in two operons on the plasmid NAH7. Salicylate hydroxylase, which catalyzes the conversion of salicylate to catechol, is encoded by nahG. pSR20, a plasmid NAH subclone obtained from M. Schell (University of Georgia), was digested with SspI and HpaI to obtain a ca 1.5 kb restriction fragment containing nahG. This SspI-HpaI fragment was ligated to EcoRI linkers, digested with EcoRI, and cloned into the EcoRI site of pCGN1761, a derivative of PCGN2113 (ATCC 40587) to add plant-recognized regulatory sequences.

PCGN1761 is prepared by digesting PCGN2113 with EcoRI and ligating the plasmid in the presence of a synthetic DNA adaptor containing an XbaI site and a BamHI site. The adaptor contained EcoRI sticky ends on either end, but the adjacent bases were such that an EcoRI site was not reconstructed at this location. PCGN1761 contains a double CaMV 35S promoter and the tml-3' region with an EcoRI site between contained in a pUC-derived plasmid backbone. The promoter-EcoRI-3' processing site cassette is bordered by multiple restriction sites for easy removal.

A PCGN1761 derivative was identified with the nahG gene oriented 5' to 3' behind a double 35S promoter from the Cauliflower Mosaic Cirus, and followed by the efficient 3' terminator tml. This plasmid was digested with XbaI to release a 4.7 kb restriction fragment containing the nahG construct, which was subsequently cloned into the IbaI site of the plant transformation vector pCIB200. See, Uknes et al., *Plant Cell* 5: 159–169 (1993).

EXAMPLE 170

Transformation of the nahG Containing Plant Expression Vector pCIB2001nahG into *Nicotiana tabacum* cv. Xanthi-nc pCIB200/nahG was first transferred from *E. coli* to *Agrobacterium tumefaciens* strain CIB542 (Uknes et al., supra.) using the electroporation method described by Wenjun and Forde, *Nucleic Acids Res.* 17: 8385 (1989). Transformed Agrobacterium colonies were selected on 25 ug/ml kanamycin.

*Agrobacterium tumefaciens*-mediated transformation of *Nicotiana tabacum* cv Xanthi-nc was undertaken essentially as described by Horsch et al., *Science* 227: 1229–1231 (1985). Leaf disks of *Nicotiana tabacum* cv Xanthi-nc were infected with the *Agrobacterium tumefaciens* strain carrying pCIB200/nahG and selected for callus growth on kanamycin. A single shoot was regenerated (T1 generation) from each leaf disk and grown in soil until seed set. Seed resulting from self-pollination (T2 generation) of the regenerated transformants was scored for antibiotic resistance on MS medium (Murashige and Skoog, *Physiol. Plant*: 473 (1962) containing 150 ug/ml kanamycin. Lines homozygous for the transgene were identified by allowing ten kanamycin resistant T2 progeny from each independent transformant to self-pollinate and set seed and screening for plants whose seed (T3 generation) were 100% kanamycin resistant.

Plants expressing nahG at high levels were not visually distinct from wild-type plants. They flowered and set seed normally.

EXAMPLE 171

Analysis of Transformants Expressing the nahG Gene

Independently transformed plants were screened by RNA blot analysis (Ausubel et al., Current Protocols in Molecular Biology, Vol. 1, Wiley & Sons, New York (1987)) for nahG MRNA accumulation and several transformants were selected (ah -1, -2, -3, -8, -9 and -10). These plants were allowed to set seed and homoxygous T3 seed for further analysis was generated as described above.

A. Effect of nahG Expression on the Accumulation of Salicylic Acid

To determine the effect of the expression of the nahG gene on the accumulation of salicylic acid, several plants from each of the lines selected above were inoculated with TMV. After 7 days, when lesions had formed on the infected leaves, leaf tissue was harvested and assayed for nahG mRNA, the salicylate hydroxylase protein, and salicylic acid. Assessment of mRNA abundance was undertaken by RNA blot analysis as described above.

Salicylate hydroxylase protein was determined by Western analysis using standard techniques. See, Pratt et al., *Modern Methods Plant Anal. New Series* 4: 51 (1986). Antiserum raised to salicylate hydroxylase was purified from expression of the nahG gene in the *E. coli* expression vector pGEX-2Tb.

Salicylic acid concentration was determined after extraction from leaf tissue using the technique essentially as described by Yalpani et al., *Plant Cell* 3: 809–818 (1991), except that samples were not allowed to overdry, and that the final samples were resuspended in 500 ul of 20% methanol. 10–100 ul were injected onto a Dynamax 60A, 8 uw, C-18 (4.6 mm×25 cm) column with guard column (Rainin Instruments Co., Emeryville, Calif.) maintained at 40° C. Isocratin separation was performed at 1 ml/min using 20% (v/v) methanol in 20 Mm sodium acetate, Ph 5.0. Fluorescence detection was done using a Model 980 detector (ABI/Kratos analytical, Forster City, Calif.) with a 5 ul flowcell, deuterium lamp with a 295 nm excitation setting and a 370 nm cutoff emission filter. The limit of detection was 500 pg SA in 50 ul. Quantification was determined versus a linear range (10–1000 ng/ml) of calibration standards for sodium salicylate.

The nahG-3, -8 and -10 lines expressed high levels of nahG mRNA and salicylate hydroxylase protein. These lines accumulated about 100 ng/g SA following TMV treatment (see Table 1, below) which represented approximately a 2–3 fold increase above the concentration in buffer-treated control plants. Lines nahG-1 and-2 expressed intermediate levels of mRNA and barely detectable levels of salicylate hydroxylase protein, but accumulated 2824 and 979 ng/g SA, respectively, following TMV treatment, representing an 80 and a 30-fold induction, respectively. Line nahG-9 did not have detectable levels of either nahG mRNA or salicylate hydroxylase protein and accumulated 6334 ng/g SA. Similarly, the accumulation of SA in the non-transformed control line was 5937 ng/g, representing a 180-fold induction.

These results showed a tight inverse correlation between expression of the nahG transgene and accumulation of SA. The presence of high levels of nahG mRNA and salicylate hydroxylase protein resulted in a significant block in SA accumulation in TMV-treated transgenic plants.

TABLE 1

| Salicylic Acid Levels (ng/g tissue) ± Standard Deviation | | | |
|---|---|---|---|
| Xanthi  | 32.1 ± 2.3  | 5937 ± 1011 | 185 |
| NahG-1  | 35.8 ± 2.2  | 2824 ± 1461 | 79  |
| NahG-2  | 38.8 ± 10.2 | 979 ± 113   | 25  |
| NahG-3  | 41.3 ± 5.6  | 107 ± 45    | 3   |
| NahG-8  | 36.2 ± 2.7  | 81 ± 22     | 2   |
| NahG-9  | 35.6 ± 3.0  | 6334 ± 765  | 179 |
| NahG-10 | 33.9 ± 3.5  | 112 ± 4     | 3   |

All results were the average standard deviation, after the results were corrected for recovery (57.1%). All values were based on triplicate assays, except for NahG/buffer, whose value was based on duplicate assay.

B. Effects of nahG Expression on Systemic Acquired Resistance (SAR)

To determine the effects of the reduced accumulation of SA on SAR, transgenic lines were challenge-inoculated with TMV. Lesion size was scored 7 days later and compared to lesion size on buffer treated controls (see Table 2, below). Control non-transgenic lines showed a reduction of lesion size of 63% relative to buffer-treated plants, which is typical of the SAR response to TMV. In the lines expressing high levels of nahG mRNA and salicylate hydroxylase protein, which were shown above not to accumulate SA, lesion size was reduced by only 5–9% (nahG-3, -8 and -10). Lines expressing intermediate levels of nahG mRNA and salicylate hydroxylase protein showed an intermediate reduction in lesion size (nahG-1, and -2). The nahG-9 line, which did not express detectable levels of nahG mRNA or salicylate hydroxylase protein, showed a 66W reduction in lesion size.

These results clearly demonstrate that SA is required for the onset of SAR and is a cell signal in the SAR transduction pathway which can be effectively eliminated.

TABLE 2

| Lesion Size (Average Standard Deviation) | | | | | |
|---|---|---|---|---|---|
| LINE | BUFFER | n | TMV | n | % REDUCTION |
| Xanthi  | 3.5 ± 0.4(d) | 3 | 1.3 ± 0.5(d) | 5 | 63 |
| NahG-1  | 4.1 ± 0.4(b) | 3 | 2.7 ± 0.6(c) | 5 | 34 |
| NahG-2  | 4.4 ± 0.4(a) | 3 | 3.8 ± 0.5(b) | 5 | 14 |
| MahG-3  | 4.4 ± 0.4(a) | 2 | 4.0 ± 0.5(b) | 5 | 9  |
| NahG-8  | 4.2 ± 0.4(b) | 2 | 4.1 ± 0.7(b) | 5 | 5  |
| NahG-9  | 3.8 ± 0.4(c) | 3 | 1.3 ± 0.7(d) | 5 | 66 |
| NahG-10 | 4.5 ± 0.4(a) | 3 | 4.2 ± 0.8(a) | 5 | 7  |

Three to five plants were analyzed per sample as indicated. Per plant, 10 lesions were measured on 3 leaves. The date were analyzed statistically by ANOVA II, followed by a Tukey-Kramer test. Within each treatment, statistically equivalent groups (p=0.05) are shown (a–d).

C. Benzo-1,2,3-thiodiazole-7-carboxylic Acid Indication of SAR in Plants Expressing nahG Three lines, nahG-3, -8 and -10, were shown above to express high levels of nahG mRNA and salicylate hydroxylase protein, and to be blocked in their SAR response to disease infection. Plants of these lines were treated with the inducing chemical benzo-1,2,3-thiodiazole-7-carboxylic acid, and were shown to possess the SAR response. This result demonstrated the position of benzo-1,2,3-thiodiazole-7-carboxylic acid downstream relative to SA in the SAR signal transduction pathway.

D. Chemical Regulation of Gene Expression in nahGO-expressing plants

The PR-1a promoter (Uknes et al., Plant Cell 5: 159–169 (1993) is chemically regulated by exogenously applied benzo-1,2,3-thiodiazole-7-carboxylic acid and derivatives thereof, as well as by SA. Plants possessing the PR-1a promoter fused to the GUS reporter gene are crossed to nahG-expressing lines nahG-3, -8 and -10. Progeny lines carrying both transgene constructions are found to express GUS when induced by Benzo-1,2,3-thiodiazole-7-carboxylic acid, but not when treated with SA. Further, there is not GUS expression in response to fluctuating endogenous levels of SA as would occur in plants not expressing the nahG gene prior to and during flowering, for example. Consequently, the chemical regulation of the PR-1a gene promoter can be utilized without the activation of the endogenous cell signal SA.

E. Chemical Regulation of a Gene Encoding the delta-endotoxin of *Bacillus thuringiensis* in nahG-expressing Plants Plants possessing the PR-1a promoter fused to a gene encoding the delta-endotoxin of *Bacillus thuringiensis* (Williams et al., *Bio/Technology* 10: 540–543 (1992) are crossed to nahG-expressing lines nahG-3, -8 and -10. Progeny lines carrying both transgene constructions are found to express the endotoxin gene when induced by benzo- 1,2,3-thiodiazole-7-carboxylic acid, but not when treated with SA. Further, there is no endotoxin gene expression in response to fluctuating endogenous levels of SA as would occur in plants not expressing the nahG gene prior to and during flowering, for example. Consequently, the chemical regulation of the PR-1a gene promoter can be utilized without the activation of the endogenous cell signal SA.

N. Exploitation of Disease Susceptibility Created by Inactivation of Endogenous Regulation Apart from their utility in chemical regulation, plants which are disrupted in the signal transduction cascade leading to the expression of PR-proteins and therefore systemic acquired resistance, have further utility for disease testing. Plants incapable of expressing PR proteins do not develop the systemic acquired resistance response and thus develop larger lesions more quickly when challenged by pathogens. These plants are useful as "universal disease susceptible" (UDS) plants by virtue of their being susceptible to many strains and pathotypes of pathogens of the host plant and also to pathogens which do not normally infect the host plant, but which infect other hosts. They provide useful indicators of evaluation of disease pressure in field pathogenesis tests where the natural resistance phenotype of so-called wild-type (i.e. non-transgenic) plants may vary and therefore not provide a reliable standard of susceptibility. Furthermore, these plants have additional utility for the the testing of candidate disease resistance transgenes. Using a nahG-expressing stock line as a recipient for transgenes, the contribution of the transgene to disease resistance is directly assessable over a base level of susceptibility. A further utility of nahG-expressing plants is as a tool in the understanding of plant-pathogen interactions. NahG-expressing host plants do not mount a systemic response to pathogen attack, and the unabated development of the pathogen is an ideal system in which to study its biological interaction with the host. As nahG-expressing host plants may also be susceptible to pathogens outside of whose host-range they normally fall, these plants also have significant utility in the molecular, genetic, and biological study of host-pathogen interactions. Furthermore, the UDS phenotype of nahG-expressing plants also renders them of utility for fungicide screening. Plants expressing nahG in a particular host have considerable utility for the screening of fungicides using that host and pathogens of the host. The advantage lies in the UDS phenotype of the nahG-expressing host which circumvents the problems encountered by hosts being differentially susceptible to different pathogens and pathotypes, or even resistant to some pathogens or pathotypes. nahG-expressing plants have further utility for the screening of fungicides against a range of pathogens and pathotypes using a heterologous host i.e. a host which may not normally be within the host species range of particular pathogens. Thus, the susceptibility of nahG-expressing host plants such as Arabidopsis, which are easily manipulable and have limited space requirements, to pathogens of other species (e.g. crop plant species) would facilitate efficacious fungicide screening procedures for compounds against important pathogens of crop plants.

In the situations described above the nahG gene can be expressed behind promoters which are expressible in plants using gene cloning techniques which are well known in the art. A preferred promoter would express nahG at the time of disease challenge. A particularly preferred promoter would be expressed constitutively e.g. the Cauliflower Mosaic Virus 35S promoter.

EXAMPLE 172

Use of nahG-Expressing Plant Lines in Disease Testing

Tobacco and Arabidopsis plants expressing the nahG gene constitutively were challenged with numerous pathogens and found to develop larger lesions more quickly than wild-type plants. This phenotype is referred to as UDS (i.e. universal disease susceptibility) and is a result of the plants being unable to express SAR genes to effect the plant defense against pathogens by virtue of the expression of salicylate hydroxylase protein, and the inactivation of salicylic acid as an endogenous cell signal in systemic acquired resistance. Table 2 (in example 5) shows a comparison of lesion size in plants expressing nahG and wild-type plants and table 6 (below) shows a comparison of the development of lesions over an eight-day period in wild-type tobacco and nahG-expressing tobacco.

TABLE 3

Lesion Growth Over a Period of Eight Days in NahG-transgenic and Non-transgenic Tobacco

| Xanthi | | NahG-10 | | |
|---|---|---|---|---|
| mean | SD | mean | SD | DPI |
| 50.8 | 12.4 | 47.5 | 12.6 | 2 |
| 102.2 | 19.3 | 113.4 | 26.7 | 3 |
| 138.0 | 25.6 | 186.4 | 29.0 | 4 |
| 170.8 | 29.7 | 227.3 | 27.1 | 5 |
| 199.0 | 34.7 | 276.5 | 35.3 | 6 |
| 220.9 | 39.8 | 332.4 | 38.0 | 7 |
| 234.2 | 47.5 | 376.4 | 42.5 | 8 |

Plants of nahG-expressing line NahG-10 (see tables 1 and 2) and wild-type tobacco cultivator Xanthi were inoculated with TMV and lesion size was monitored over a period of 8 days post inoculation (DPI). Mean values for lesion size are reported in 1/1000 inch with standard deviation (SD). The nahG-expressing line develops larger lesions more quickly than does wild-type Xanthi.

The UDS phenotype of these nahG expressing plants renders them useful as control plants for the evaluation of disease symptoms in experimental lines in field pathogenesis tests where the natural resistance phenotype of so-called wild-type lines may vary (i.e. to different pathogens and different pathotypes of the same pathogen). Thus, in a field environment where natural infection by pathogens is being relied upon to assess the resistance of experimental lines, the incorporation into the experiment of nahG expressing lines of the appropriate crop plant species would enable an assessment of the true level and spectrum of pathogen pressure, without the variation inherent in the use of non-experimental lines.

EXAMPLE 173

Assessment of the Utility of Transgenes for the Purposes of Disease Resistance Plants constitutively expressing nahG are used as host plants for the transformation of transgenes to facilitate their assessment for use in disease resistance. A stock of Arabidopsis or tobacco plants is created which express the nahG gene. This stock is used for subsequent transformations with candidate genes for disease resistance thus enabling an assessment of the contribution of an individual gene to resistance against the basal level of the UDS nahG expressing plants.

EXAMPLE 174

NahG-expressing Plants as a Tool in Understanding Plant-Pathogen Interactions Plants expressing nahG are useful for the understanding of plant pathogen interactions, and in particular for the understanding of the processes utilized by the pathogen for the invasion of plant cells. This is so because nahG-expressing host plants do not mount a systemic response to pathogen attack, and the unabated development of the pathogen is an ideal scenario in which to study its biological interaction with the host.

Of further significance is the observation that a host species expressing nahG may be susceptible to pathogens not normally associated with that particular host, but instead associated with a different host. Arabidopsis plants were transformed with nahG and those expressing the gene were characterized by the UDS phenotype. These plants are challenged with a number of pathogens which normally only infect tobacco, and found to be susceptible. Thus, the expression of nahG in a host plant and the accompanying UDS phenotype leads to a modification of pathogen-range susceptibility and this has significant utility in the molecular, genetic and biochemical analysis of host-pathogen interaction.

EXAMPLE 175

NahG-expressing Plants for Use in Fungicide Screening

Plants expressing nahG are particularly useful in the screening of new chemical compounds for fungicide activity. The advantage lies in the UDS phenotype of the nahG-expressing host plant which circumvents the problems encountered by the host being differentially susceptible to different pathogens and pathotypes, or even resistant to some pathogens or pathotypes. By way of example transgenic wheat expressing nahG could be effectively used to screen for fungicides to a wide range of wheat pathogens and pathotypes as the nahG-expressing line would not mount a resistance response to the introduced pathogen and would not display differential resistance to different pathotypes which might otherwise require the use of multiple wheat lines, each adequately susceptible to a particular test pathogen. Wheat pathogens of particular interest include (but are not limited to) *Erisyphe graminis* (the causative agent of powdery mildew), *Rhizoctonia solani* (the causative agent of sharp eyespot), *Pseudocercosporella hermotrichoides* (the causative agent of eyespot), *Puccinia* spp. (the causative agents of rusts), and *Septoria nodorum*. Similarly, corn plants or tobacco plants expressing nahG would be highly susceptible to their respective pathogens and would therefore be useful in the screening for fungicides.

nahG-expressing plants have further utility for the screening of a wide range of pathogens and pathotypes in a heterologous host i.e. in a host which may not normally be within the host species range of a particular pathogen and which may be particularly easily to manipulate (such as Arabidolpsis). By virtue of its UDS phenotype the heterologous host expressing nahG is susceptible to pathogens of other plant species, including economically important crop plant species. Thus, by way of example, the same Arabidonsis nahG-expressing line could be infected with a wheat pathogen such as *Erisyphe graminis* (the causative agent of powdery mildew) or a corn pathogen such as *Helminthosporium maydis* and used to test the efficacy of fungicide candidates. Such an approach has considerable improvements in efficiency over currently used procedures of screening individual crop plant species and different cultivars of species with different pathogens and pathotypes which may be differentially virulent on the different crop plant cultivars. Furthermore, the use of Arabidopsis has advantages because of its small size and the possibility of thereby undertaking more tests with limited resources of space.

While the present invention has been described with reference to specific embodiments thereof, it will be appreciated that numerous variations, modifications, and embodiments are possible, and accordingly, all such variations, modifications and embodiments are to be regarded as being within the spirit and scope of the present invention.

What is claimed is:

1. A chemically inducible plant gene expression cassette comprising a chemically inducible promoter operatively linked to a target gene which confers resistance to a herbicide, wherein said chemically inducible promoter is inducible by application of a benzo-1,2,3-thiadiazole, an isonicotinic acid compound, or a salicylic acid compound.

2. A plant cell containing a plant gene expression cassette according to claim 1.

3. A plant cell according to claim 2, wherein the plant gene expression cassette is stably incorporated into the plant's genome.

4. A plant tissue comprising a plant cell according to claim 2.

5. A plant comprising a plant cell according to claim 2.

6. A plant derived from a plant according to claim 5.

7. A seed derived from a plant according to claim 5.

8. A method of controlling herbicide resistance, comprising transforming a plant cell with the plant gene expression cassette of claim 1.

9. A method of selectively controlling weeds in a field of plants according to claim 5, comprising applying an effective amount of the herbicide and an exogenous inducer.

10. A chemically inducible plant gene expression cassette according to claim 1, wherein said inducible promoter is isolatable from the 5' flanking region of a chemically inducible plant gene by a process comprising the steps of:
   (a) activating expression in plant tissue of RNA from the chemically inducible plant gene by applying an exogenous inducing chemical to said plant tissue, wherein said inducing chemical is a benzo-1,2,3-thiadiazole, an isonicotinic acid compounds, or a salicylic acid compound;
   (b) isolating said RNA;
   (c) differentially screening a genomic library for a genomic clone that corresponds to said RNA and that is less abundant or absent in RNA isolated from control plant tissue that is not activated;
   (d) isolating said genomic clone;
   (e) subcloning the chemically inducible plant gene from said genomic clone; and
   (f) isolating the chemically inducible promoter from the 5' flanking region of said chemically inducible plant gene.

11. A chemically inducible plant gene expression cassette according to claim 10, wherein said inducing chemical is a benzo-1,2,3-thiadiazole.

12. A chemically inducible plant gene expression cassette according to claim 10, wherein said inducing chemical is an isonicotinic acid compound.

13. A chemically inducible plant gene expression cassette according to claim 10, wherein said inducing chemical is a salicylic acid compound.

14. A chemically inducible plant gene expression cassette according to claim 1, wherein said inducible promoter is isolatable from the 5' flanking region of a chemically inducible plant gene by a process comprising the steps of:
   (a) activating expression in plant tissue of poly A+ RNA from the chemically inducible plant gene by applying an exogenous inducing chemical to said plant tissue, wherein said inducing chemical is a benzo-1,2,3-thiadiazole, an isonicotinic acid compound, or a salicylic acid compound;
   (b) isolating said polyA+ RNA;
   (c) constructing a cDNA library from said polyA+ RNA;
   (d) differentially screening said cDNA library with cDNA generated from RNA in control plant tissue that is not activated;
   (e) isolating cDNA clones that are chemically inducible from the population of cDNA clones in step (d) that do not correspond to the cDNA clones generated from the RNA in the control plant tissue that is not activated;
   (f) isolating a genomic clone from a genomic library of said plant tissue by probing with the cDNA clones isolated in step (e);
   (g) subcloning the chemically inducible plant gene from said genomic clone; and
   (h) isolating the chemically inducible promoter from the 5' flanking region of said chemically inducible plant gene.

15. A chemically inducible plant gene expression cassette according to claim 14, wherein said inducing chemical is a benzo-1,2,3-thiadiazole.

16. A chemically inducible plant gene expression cassette according to claim 14, wherein said inducing chemical is a isonicotinic acid compound.

17. A chemically inducible plant gene expression cassette according to claim 14, wherein said inducing chemical is a salicylic acid compound.

18. A chemically inducible plant gene expression cassette according to claim 1, wherein said inducible promoter is an at least 603-bp fragment isolated from the 5' flanking region adjacent the coding region of a tobacco PR-1a gene.

19. A chemically inducible plant gene expression cassette according to claim 18, wherein said promoter is isolated from the region upstream of nucleotide number 932 of SEQ ID NO: 1.

20. A chemically inducible plant gene expression cassette according to claim 1, wherein said inducible promoter is isolated from the 5' flanking region adjacent the coding region of an Arabidopsis PR-1 gene.

21. A chemically inducible plant gene expression cassette according to claim 20, wherein said Arabidopsis PR-1 gene comprises a DNA sequence that specifically hybridizes to SEQ ID NO:33 or wherein said Arabidopsis PR-1 gene comprises a DNA sequence that encodes the protein encoded by SEQ ID NO:33.

22. A chemically inducible plant gene expression cassette according to claim 20, wherein said promoter is comprised within plasmid pAtPR1-P (NRRL B-21169).

23. A chemically inducible plant gene expression cassette according to claim 1, wherein said inducible promoter is isolated from the 5' flanking region upstream of the coding region of a cucumber chitinase/lysozyme gene.

24. A chemically inducible plant gene expression cassette according to claim 23, wherein said promoter is isolated from the region upstream of nucleotide number 6037 of SEQ ID NO:36.

25. A chemically inducible plant gene expression cassette according to claim 1, wherein said target gene encodes acetohydroxyacid synthase (AHAS).

26. A chemically inducible plant gene expression cassette according to claim 1, wherein said target gene encodes aminoglycoside phosphotransferase IV.

27. A chemically inducible plant gene expression cassette according to claim 1, wherein said herbicide is a sulfonylurea.

28. A chemically inducible plant gene expression cassette according to claim 1, wherein said herbicide is glyphosate.

29. A chemically inducible plant gene expression cassette according to claim 1, wherein said herbicide is phosphinotricin.

30. A chemically inducible plant gene expression cassette according to claim 1, wherein said herbicide is atrazine.

31. An isolated chemically inducible promoter isolatable from the 5' flanking region of a chemically inducible plant gene by a process comprising the steps of:
  (a) activating expression in plant tissue of RNA from the chemically inducible plant gene by applying an exogenous inducing chemical to said plant tissue, wherein said inducing chemical is a benzo-1,2,3-thiadiazole, an isonicotinic acid compound, or a salicylic acid compound;
  (b) isolating said RNA;
  (c) differentially screening a genomic library for a genomic clone that corresponds to said RNA and that is less abundant or absent in RNA isolated from control plant tissue that is not activated;
  (d) isolating said genomic clone;
  (e) subcloning the chemically inducible plant gene from said genomic clone; and
  (f) isolating the chemically inducible promoter from the 5' flanking region of said chemically inducible plant gene.

32. A chemically inducible promoter according to claim 31, wherein said inducing chemical is a benzo-1,2,3-thiadiazole.

33. A chemically inducible promoter according to claim 31, wherein said inducing chemical is an isonicotinic acid compound.

34. A chemically inducible promoter according to claim 31, wherein said inducing chemical is a salicylic acid compound.

35. A chemically inducible plant expression cassette, comprising the chemically inducible promoter of claim 31, operatively linked to a coding sequence of interest.

36. A chemically inducible plant expression cassette according to claim 35, wherein the coding sequence of interest confers herbicide tolerance.

37. A plant transformation vector comprising the chemically inducible plant expression cassette of claim 35.

38. A transgenic plant or plant tissue, each transformed with the plant transformation vector of claim 37.

39. An isolated chemically inducible promoter isolatable from the 5' flanking region of a chemically inducible plant gene by a process comprising the steps of:
  (a) activating expression in plant tissue of poly A+ RNA from the chemically inducible plant gene by applying an exogenous inducing chemical to said plant tissue, wherein said inducing chemical is a benzo-1,2,3-thiadizole, an isonicotinic acid compound, or a salicylic acid compound;
  (b) isolating said polyA+ RNA;
  (c) constructing a cDNA library from said polyA+ RNA;
  (d) differentially screening said cDNA library with cDNA generated from RNA in control plant tissue that is not activated;
  (e) isolating cDNA clones that are chemically inducible from the population of cDNA clones in step (d) that do not correspond to the cDNA clones generated from the RNA in the control plant tissue that is not activated;
  (f) isolating a genomic clone from a genomic library of said plant tissue by probing with the cDNA clones isolated in step (e);
  (g) subcloning the chemically inducible plant gene from said genomic clone; and
  (h) isolating the chemically inducible promoter from the 5' thanking region of said chemically inducible plant gene.

40. A chemically inducible promoter according to claim 39, wherein said inducing chemical is a benzo-1,2,3-thiadiazole.

41. A chemically inducible promoter according to claim 39, wherein said inducing chemical is an isonicotinic acid compound.

42. A chemically inducible promoter according to claim 39, wherein said inducing chemical is a salicylic acid compound.

43. A chemically inducible plant expression cassette, comprising the chemically inducible promoter of claim 39 operatively linked to a coding sequence of interest.

44. A chemically inducible plant expression cassette according to claim 43, wherein the coding sequence of interest confers herbicide tolerance.

45. A plant transformation vector comprising the chemically inducible plant expression cassette of claim 43.

46. A transgenic plant or plant tissue, each transformed with the plant transformation vector of claim 45.

* * * * *